(12) United States Patent
Amberg et al.

(10) Patent No.: US 9,650,334 B2
(45) Date of Patent: *May 16, 2017

(54) PYRROLIDINE DERIVATIVES, PHARMACEUTICAL COMPOSITIONS CONTAINING THEM, AND THEIR USE IN THERAPY

(71) Applicants: AbbVie Deutschland GmbH & Co. KG, Wiesbaden (DE); AbbVie Inc., North Chicago, IL (US)

(72) Inventors: Wilhelm Amberg, Ludwigshafen (DE); Frauke Pohlki, Ludwigshafen (DE); Udo Lange, Ludwigshafen (DE); Ying X. Wang, Libertyville, IL (US); Hongyu H. Zhao, Libertyville, IL (US); Huan-Qiu Li, Wilmette, IL (US); Jason T. Brewer, Zion, IL (US); Irini Zanze, Libertyville, IL (US); Justin Dietrich, Abbott Park, IL (US); Anil Vasudevan, Union Grove, WI (US); Stevan W. Djuric, Libertyville, IL (US); Yanbin Lao, Abbott Park, IL (US); Charles W. Hutchins, Green Oaks, IL (US)

(73) Assignees: AbbVie Inc., North Chicago, IL (US); AbbVie Deutschland GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/215,533

(22) Filed: Mar. 17, 2014

(65) Prior Publication Data
US 2014/0275086 A1    Sep. 18, 2014

Related U.S. Application Data
(60) Provisional application No. 61/788,538, filed on Mar. 15, 2013.

(51) Int. Cl.

| | | |
|---|---|---|
| *A61K 31/4025* | (2006.01) | |
| *A61K 31/44* | (2006.01) | |
| *A61K 31/4178* | (2006.01) | |
| *C07D 207/09* | (2006.01) | |
| *C07D 403/12* | (2006.01) | |
| *C07D 401/12* | (2006.01) | |
| *C07D 207/48* | (2006.01) | |
| *C07D 401/14* | (2006.01) | |
| *C07D 403/14* | (2006.01) | |
| *C07D 405/14* | (2006.01) | |
| *C07D 487/10* | (2006.01) | |
| *C07D 417/14* | (2006.01) | |
| *C07D 409/14* | (2006.01) | |
| *C07D 495/04* | (2006.01) | |
| *C07D 471/04* | (2006.01) | |
| *C07D 487/04* | (2006.01) | |

(52) U.S. Cl.
CPC ........ *C07D 207/09* (2013.01); *A61K 31/4025* (2013.01); *A61K 31/44* (2013.01); *C07D 207/48* (2013.01); *C07D 401/12* (2013.01); *C07D 401/14* (2013.01); *C07D 403/12* (2013.01); *C07D 403/14* (2013.01); *C07D 405/14* (2013.01); *C07D 409/14* (2013.01); *C07D 417/14* (2013.01); *C07D 471/04* (2013.01); *C07D 487/04* (2013.01); *C07D 487/10* (2013.01); *C07D 495/04* (2013.01)

(58) Field of Classification Search
None
See application file for complete search history.

(56) References Cited

U.S. PATENT DOCUMENTS

| | | | |
|---|---|---|---|
| 3,867,391 | A | 2/1975 | Holland |
| 4,927,838 | A | 5/1990 | Guthrie et al. |
| 5,506,246 | A | 4/1996 | Junge et al. |
| 5,519,034 | A | 5/1996 | Kozlik et al. |

(Continued)

FOREIGN PATENT DOCUMENTS

| | | |
|---|---|---|
| DE | 10315570 | 10/2004 |
| EP | 0091241 | 10/1983 |

(Continued)

OTHER PUBLICATIONS

Database Registry Chemical Abstracts Service, Columbus, Ohio, Accession No. RN 1057254-23-5, Entered STN: Oct. 5, 2008.*
Ito et al. [Ito, Nobuyuki. Cancer Science 94(1), (2003) 3-8.*
Database Registry Chemical Abstracts Service, Columbus, Ohio, Accession No. RN 267876-15-3, Entered STN: Jun. 2, 2000.*
Database Registry Chemical Abstracts Service, Columbus, Ohio, Accession No. RN 1381576-56-2, Entered STN: Jul. 5, 2012.*

(Continued)

*Primary Examiner* — Samantha Shterengarts
(74) *Attorney, Agent, or Firm* — Neal, Gerber & Eisenberg, LLP

(57) ABSTRACT

The present invention relates to pyrrolidine derivatives of the formula (I),

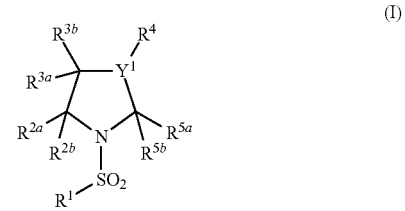

or a physiologically tolerated salt thereof.
The invention relates to pharmaceutical compositions comprising such pyrrolidine derivatives, and the use of such pyrrolidine derivatives for therapeutic purposes. The pyrrolidine derivatives are GlyT1 inhibitors.

20 Claims, No Drawings

(56) References Cited

U.S. PATENT DOCUMENTS

| | | |
|---|---|---|
| 5,545,755 A | 8/1996 | Lin et al. |
| 6,057,357 A | 5/2000 | Horwell et al. |
| 6,197,798 B1 | 3/2001 | Fink et al. |
| 6,331,636 B1 | 12/2001 | Romero et al. |
| 6,426,364 B1 | 7/2002 | Egle et al. |
| 7,189,850 B2 | 3/2007 | Ceccarelli et al. |
| 7,427,612 B2 | 9/2008 | Alberati-Giani et al. |
| 7,462,617 B2 | 12/2008 | Alberati-Giani et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 8,420,670 B2 | 4/2013 | Amberg et al. |
| 8,563,617 B2 | 10/2013 | Amberg et al. |
| 8,642,587 B2 | 2/2014 | Lange et al. |
| 8,653,100 B2 | 2/2014 | Ochse et al. |
| 2002/0169197 A1 | 11/2002 | Egle et al. |
| 2003/0083359 A1 | 5/2003 | Lee et al. |
| 2004/0026364 A1 | 2/2004 | Kihara et al. |
| 2005/0124627 A1 | 6/2005 | Schadt et al. |
| 2005/0153963 A1 | 7/2005 | Dargazanli et al. |
| 2005/0153980 A1 | 7/2005 | Schadt et al. |
| 2005/0159450 A1 | 7/2005 | Dargazanli et al. |
| 2005/0267152 A1 | 12/2005 | Bloomfield et al. |
| 2006/0074105 A1 | 4/2006 | Ware et al. |
| 2006/0223802 A1 | 10/2006 | Dargazanli et al. |
| 2006/0223861 A1 | 10/2006 | Dargazanli et al. |
| 2006/0223885 A1 | 10/2006 | Dargazanli et al. |
| 2006/0223886 A1 | 10/2006 | Dargazanli et al. |
| 2007/0021408 A1 | 1/2007 | Molino et al. |
| 2007/0155753 A1 | 7/2007 | Ye et al. |
| 2007/0185056 A1 | 8/2007 | Duan et al. |
| 2007/0214087 A1 | 9/2007 | Kawaguchi et al. |
| 2008/0045540 A1 | 2/2008 | Keil et al. |
| 2008/0070941 A1 | 3/2008 | Dargazanli et al. |
| 2008/0119486 A1 | 5/2008 | Jolidon et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2012/0040947 A1 | 2/2012 | Pohlki et al. |
| 2012/0040948 A1 | 2/2012 | Pohlki et al. |
| 2012/0077796 A1 | 3/2012 | Pohlki et al. |
| 2012/0088790 A1 | 4/2012 | Pohlki et al. |
| 2012/0295881 A1 | 11/2012 | Lange et al. |
| 2012/0316153 A1 | 12/2012 | Amberg et al. |
| 2013/0035323 A1 | 2/2013 | Amberg et al. |
| 2013/0131132 A1 | 5/2013 | Amberg et al. |
| 2013/0184238 A1 | 7/2013 | Amberg et al. |
| 2013/0203749 A1 | 8/2013 | Amberg et al. |
| 2013/0210880 A1 | 8/2013 | Amberg et al. |
| 2014/0031331 A1 | 1/2014 | Amberg et al. |
| 2014/0256701 A1 | 9/2014 | Pohlki et al. |
| 2014/0275087 A1 | 9/2014 | Amberg et al. |
| 2015/0111867 A1 | 4/2015 | Amberg et al. |
| 2015/0111875 A1 | 4/2015 | Amberg et al. |

FOREIGN PATENT DOCUMENTS

| | | |
|---|---|---|
| EP | 0258755 | 3/1988 |
| EP | 0303961 | 2/1989 |
| EP | 0420064 | 4/1991 |
| EP | 1199306 | 4/2002 |
| EP | 1254662 | 11/2002 |
| EP | 1284257 | 2/2003 |
| EP | 2246331 | 11/2010 |
| WO | WO 81/03491 | 12/1981 |
| WO | WO 90/15047 | 12/1990 |
| WO | WO 92/06967 | 4/1992 |
| WO | WO 92/19234 | 11/1992 |
| WO | WO 92/22533 | 12/1992 |
| WO | WO 93/13073 | 7/1993 |
| WO | WO 95/07271 | 3/1995 |
| WO | WO 97/10223 | 3/1997 |
| WO | WO 97/45115 | 12/1997 |
| WO | WO 98/04521 | 2/1998 |
| WO | WO 98/56757 | 12/1998 |
| WO | WO 00/07978 | 2/2000 |
| WO | WO 00/20376 | 4/2000 |
| WO | WO 01/09120 | 2/2001 |
| WO | WO 01/46155 | 6/2001 |
| WO | WO 02/076979 | 10/2002 |
| WO | WO 03/031435 | 4/2003 |
| WO | WO 03/045924 | 6/2003 |
| WO | WO 03/053942 | 7/2003 |
| WO | WO 03/055478 | 7/2003 |
| WO | WO 03/068220 | 8/2003 |
| WO | WO 03/076420 | 9/2003 |
| WO | WO 03/087086 | 10/2003 |
| WO | WO 03/089411 | 10/2003 |
| WO | WO 03/097586 | 11/2003 |
| WO | WO 2004/007468 | 1/2004 |
| WO | WO 2004/013100 | 2/2004 |
| WO | WO 2004/013101 | 2/2004 |
| WO | WO 2004/022528 | 3/2004 |
| WO | WO 2004/071445 | 8/2004 |
| WO | WO 2004/072034 | 8/2004 |
| WO | WO 2004/080968 | 9/2004 |
| WO | WO 2004/096761 | 11/2004 |
| WO | WO 2004/110149 | 12/2004 |
| WO | WO 2004/112787 | 12/2004 |
| WO | WO 2004/113280 | 12/2004 |
| WO | WO 2004/113301 | 12/2004 |
| WO | WO 2005/009996 | 2/2005 |
| WO | WO 2005/014563 | 2/2005 |
| WO | WO 2005/023260 | 3/2005 |
| WO | WO 2005/037781 | 4/2005 |
| WO | WO 2005/037782 | 4/2005 |
| WO | WO 2005/037783 | 4/2005 |
| WO | WO 2005/037785 | 4/2005 |
| WO | WO 2005/037792 | 4/2005 |
| WO | WO 2005/023261 | 5/2005 |
| WO | WO 2005/040166 | 5/2005 |
| WO | WO 2005/046601 | 5/2005 |
| WO | WO 2005/049023 | 6/2005 |
| WO | WO 2005/058317 | 6/2005 |
| WO | WO 2005/058882 | 6/2005 |
| WO | WO 2005/058885 | 6/2005 |
| WO | WO 2005/099353 | 10/2005 |
| WO | WO 2005/123681 | 12/2005 |
| WO | WO 2006/008754 | 1/2006 |
| WO | WO 2006/034235 | 3/2006 |
| WO | WO 2006/040177 | 4/2006 |
| WO | WO 2006/063709 | 6/2006 |
| WO | WO 2006/082001 | 8/2006 |
| WO | WO 2006/102760 | 10/2006 |
| WO | WO 2006/121767 | 11/2006 |
| WO | WO 2007/143823 | 12/2007 |
| WO | WO 2008/038053 | 4/2008 |
| WO | WO 2008/038841 | 4/2008 |
| WO | WO 2008/148755 | 12/2008 |
| WO | WO 2009/024611 | 2/2009 |
| WO | WO 2009/121872 | 10/2009 |
| WO | WO 2010/020548 | 2/2010 |
| WO | WO 2010/025856 | 3/2010 |
| WO | WO 2010/029180 | 8/2010 |
| WO | WO 2010/092181 | 8/2010 |
| WO | WO 2010/138901 | 12/2010 |
| WO | WO 2012/020130 | 2/2012 |
| WO | WO 2012/020131 | 2/2012 |
| WO | WO 2012/020133 | 2/2012 |
| WO | WO 2012/020134 | 2/2012 |
| WO | WO 2012/152915 | 11/2012 |

(56) References Cited

FOREIGN PATENT DOCUMENTS

| WO | WO 2013/020930 | 2/2013 |
|---|---|---|
| WO | WO 2013/072520 | 5/2013 |
| WO | WO 2013/120835 | 8/2013 |

OTHER PUBLICATIONS

Database Registry Chemical Abstracts Service, Columbus, Ohio, Accession No. RN 1394552-70-5, Entered STN: Sep. 18, 2012.*
Database Registry Chemical Abstracts Service, Columbus, Ohio, Accession No. RN 1394343-08-8, Entered STN: Sep. 17, 2012.*
Database Registry Chemical Abstracts Service, Columbus, Ohio, Accession No. RN 1381247-33-1, Jul. 4, 2012; RN 13811527-00-9, Jul. 5, 2012; RN 1381432-23-0, Jul. 4, 2012; RN 1413171-39-7, Dec. 10, 2012.*
ACS Database Accession No. 1381432-38-7 (Jul. 4, 2012).
ACS Database Accession No. 1394552-70-5 (Sep. 18, 2012).
ACS Database Accession No. 1410185-83-9 (Dec. 3, 2012).
ACS Database Accession No. 1434168-57-6 (Jun. 4, 2013).
ACS Database Accession No. 1434399-98-0 (Jun. 5, 2013).
ACS Database Accession No. 1506112-12-4 (Dec. 29, 2013).
ACS Database Accession No. 1515211-93-4 (Jan. 9, 2014).
ACS Database Accession No. 1521424-46-3 (Jan. 16, 2014).
ACS Database Accession No. 1530956-16-1 (Jan. 27, 2014).
ACS Database Accession No. 1535994-72-9 (Feb. 3, 2014).
Ashby, E.C. et al., "Single electron transfer in reactions of alkyl halides with lithium thiolates," J. Org. Chem. (1985) 50(25):5184-5193.
Barbasiewicz, M. et al., "Intermolecular reactions of chlorohydrine anions: acetalization of carbonyl compounds under basic conditions," Org. Lett. (2006) 8(17):3745-3748.
Baumann, M. et al., "Synthesis of a drug-like focused library of trisubstituted pyrrolidines using integrated flow chemistry and batch methods," ACS Comb. Sci. (2011) 13:405-413.
Belliotti, T.R. et al., "Structure-activity relationships of pregabalin and analogues that target the alpha(2)-delta protein," J. Med. Chem. (2005) 48(7):2294-2307.
Bermejo, A. et al., "Syntheses and antitumor targeting G1 phase of the cell cycle of benzoyldihydroisoquinolines and related 1-substituted isoquinolines," J. Med. Chem. (2002) 45:5058-5068.
Beylot, M. et al., "In vivo studies of intrahepatic metabolic pathways," Diabetes Metabolism (1997) 23(3):251257.
Bishop, D.C., "Analgetics based on the azetidine ring," Azetidine Analgetics (1968) 11:466-470.
Blagojevic, N. et al., "Role of heavy water in boron neutron capture therapy," Topics in Dosimetry and Treatment Planning for Neutron Capture Thearpy (1994) 125-134.
Blake, M.I. et al., "Studies with deuterated drugs," J. Pharm. Sci. (1975) 64(3):367-391.
Boulay, D. et al., "Characterization of SSR103800, a selective inhibitor of the glycine transporter-1 in models predictive of therapeutic activity in schizophrenia," Pharmacology, Biochemistry and Behavior (2008) 91:47-58.
Brickner, S.J. et al., "Synthesis and antibacterial activity of U-100592 and U-100766, two oxazolidinone antibacterial agents for the potential treatment of multidrug-resistant gram-positive bacterial infections," J. Med. Chem. (1996) 39(3):673-679.
Burn, D., "Alkylation with the vilsmeier reagent," Chem. and Industry (1973) 870-873.
Burns, N.Z. et al., "Total synthesis of haouamine A: the indeno-tetrahydropyridine core," Tetrahedron (2009) 65(33):6600-6610.
Butte, N.F. et al., "Measurement of milk intake: tracer-to-infant deuterium dilution method," Br. J. Nutrition (1991) 65:3-14.
Cheng, Y. et al., "Relationship between the inhibition constant (KI) and the concentration of inhibitor which causes 50 percent inhibition (I.sub.50) of an enzymatic reaction," Biochem. Pharmacol. (1973) 22:3099-3108.

Cheung, F.K. et al., "The use of a [4+2] cycloadditional reaction for the preparation of a series of 'tethered' Ru(II)diamine and aminoalcohol complexes," Org. & Biomol. Chem. (2007) 5(7):1093-1103.
Chrzanowska, M. et al., "Asymmetric synthesis of isoquinoline alkaloids," Chem. Rev. (2004) 104(7):3341-3370.
Clayden, J. et al., "2,3-Dihydroisoindolones by cyclisation and rearomatisation of lithiated benzamides," Tetra. Lett. (2003) 44(15):3059-3062.
Clezy, P.S. et al., "Preparation of a deuterated analogue of tetrahydropapaveroline suitable for use as an internal standard for G.C./M.S. analysis of this alkaloid: retro pictet-spengler condensation," Australian J. Chem. (1998) 41:483-491.
Colandrea, V.J. et al., "Synthesis and regioselective alkylation of 1.6- and 1.7-naphthyridines," Tetra. Lett. (2000) 41:8053-8057.
Coward, W.A. et al., "New method for measuring milk intakes in breast-fed babies," The Lancet (1979) 13-14.
Czajka, D.M. et al., "Effect of deuterium oxide on the reproductive potential of mice," Annals of the New York Academy of Sciences (1960) 84:770-779.
Czajka, D.M. et al., "Physiological effects of deuterium on dogs," Am. J. Physiology (1961) 201(2):357-362.
Denkewalter, R.G. et al., Progress of Pharmaceutical Research, Drug Research (1966) 10:223-226.
Di, L. et al., "Optimization of a higher throughput microsomal stability screening assay for profiling drug discovery candidates," J. Biomol. Screening (2003) 8(4):453-462.
Dohi, T. et al., "Glycine transporter inhibitors as a novel drug discovery strategy for neuropathic pain," Pharma. & Therapeutics (2009) 123(1):54-79.
Donohoe et al., Document No. 139:117274 retrieved from CAPLUS, "Product class 14:1H- and 2H-isoindoles" Sci of Synthesis (2001) 10:653-692.
Duan, Z.C. et al., "Highly enantioselective Rh-catalyzed hydrogenation of beta gamma-unsaturated phosphonates with chiral ferrocene-based monophosphoramidite ligands," J. Org. Chem. (2009) 74(23):9191-9194.
Erhunmwunse, M.O. et al., "A novel rearrangement reaction of beta-diaxo-alpha-ketoacetals," Tetra. Lett. (2009) 50:3568-3570.
Estieu, K. et al., "New alkylidenecyclo propane amino acid derivatives for an efficient construction of the 6H-pyrrolo[3,4-b]pyridine skeleton," J. Org. Chem. (1997) 62:8276-8277.
Ferles, M. et al., "Reduction of 1-isoquinolyl-dimethylmethanol and 1-(1-isoquinolyl)cyclohexanon," Collection of Czechoslovak Chem. Comm. (1981) 46(1):262-265.
Fiedler, H.B., "Lexikon der hilfsstoffe fur pharmazie, Kosmetik and angrenzende Gebiete," (1996) 4th Edition, Table of Contents.
Foster, A.B. et al., "Deuterium isotope effects in the metabolism of drugs and xenobiotics: implications for drug design," Advances in Drug Research (1985) 14:2-36.
Fraser, R.R. et al., "Effect of substituents on the chemical shift of benzylic protons. III," Canadian Journal of Chemistry (1971) 49(5):800-802.
Grant & Hackh's Chemical Dictionary, 5th Edition (1987), p. 148.
Green, G.M. et al., "Polystyrene-supported benzenesulfonyl azide: a diazo transfer reagent that is both efficient and safe," J. Org. Chem. (2001) 66(7):2509-2511.
Greene, T.W. et al., in Protective Groups in Organic Synthesis, 2nd Edition, John Wiley & Sons, Inc., (1991) Table of Contents.
Greene, T.W. et al., in Protective Groups in Organic Synthesis, 3rd Edition, John Wiley & Sons, Inc., (1999) Preface, Table of Contents and Abbreviations.
Guillonneau, C. et al., "Synthesis of 9-0-substituted derivatives of 9-hydroxy-5, 6-dimethy1-6H-pyrido[4,3- b]carbazole-1-carboxylic acid (2-(dimethylamino)ethyl)amide and their 10- and 11-methyl analogues with improved antitumor activity," J. Med. Chem. (1999) 42(12):2191-2203.
Gupta, A. et al., "Simple and efficient synthesis of steroidal hybrids of estrogen and vitamin D3," Synthetic Comm. (2009) 39:61-69.
Harsing, L.G. et al., "Glycine transporter Type-1 and its inhibitors," Curr. Med. Chem. (2006) 13:1017-1044.

(56) References Cited

OTHER PUBLICATIONS

Hashimoto, K. "Glycerine transport inhibitors for the treatment of schizophrenia," The Open Medicinal Chemistry Journal (2010) 4:10-19.

Hashimoto, K. et al., "Phencyclidine-induced cognitive deficits in mice are improved by subsequent subchronic administration of the glycine transporter-1 inhibitor NFPS and D-serine," Eurp. Neuropsychopharmacology (2008) 18:414-421.

Hashimoto, K., "Glycine transporter inhibitors as therapeutic agents for schizophrenia," Recent Patents on CNS Drug Discovery (2006) 1:43-53.

Hermanns, H. et al., "Differential effects of spinally applied glycine transporter inhibitors on nociception in a rat model of neuropathic pain," Neurosci Lett. (2008) 445:214-219.

Hillier, M.C. et al., "A one-pot preparation of 1,3-disubstituted azetidines," J. Org. Chem. (2006) 71(20):7885-7887.

Ikunaka, M. et al., "The highly selective equatorial hydride delivery by biocatalysis: chemoenzymatic synthesis of trans-2-(4-propylcyclohexyl)-1,3-propanediol via cis-4-propylcyclohexanol," Organic Process Research and Development (2004) 8(3):389-395.

Javitt, D.C., "Glutamate as a therapeutic target in psychiatric disorders," Mol. Psychiatry (2004) 9:984-997.

Jellimann, C. et al., "Synthesis of phenalene and acenaphthene derivatives as new conformationally restricted ligands for melatonin receptors," J. Med. Chem. (2000) 43(22):4051-4062.

Jensen, B.L. et al., "Total synthesis of 4,5,7a,8-tetrahydro-1,2-dimethoxyphenantluo[10,1-bc]-azepin-6(7H)-one: a photochemical approach," J. Heterocyclic Chem. (1986) 23:343-347.

Jetter, M.C. et al., "Heteroaryl beta-tetralin ureas as novel antagonists of human TRPV1," Bioorg. Med. Chem. Lett. (2007) 17(22):6160-6163.

Jutz, C. et al., "The Vilsmeier-Haackarnold acylations. C-C bond-forming reactions of chloromethyleniminium ions," Adv. Org. Chem. (1976) 9(1):225-342.

Kaiser, C. et al., "6,7-dichloro-1-(3,4,5-trimethyoxygenzyl)-1,2,3,4-tetrahydroisoquinoline. A structurally novel beta-adrenergic receptor blocking agent," J. Med. Chem. (1986) 29(11):2381-2384.

Kametani, T. et al., "Studies on the syntheses of heterocyclic compounds. Part DLXXVII. Synthesis of 2,3,4,5-tetrahydro-1H-benzazepine derivatives by phenolic cyclisation," Journal of the Chemical Society, Perkin Trans 1, (1974) 22:2602-2604.

Kato, S. et al., "Synthesis of deuterated mosapride citrate," J. Labelled Compounds and Radiopharmaceuticals (1995) 36(10):927-932.

King, F.D., editor "Bioisosteres, conformational restriction and pro-drugs—case history: an example of a conformational restriction approach," Medical Chemistry: Principles and Practice (1994), Chapter 14, 206-209.

Kinney, G.G. et al., "The glycerine transporter type 1 inhibitor N-[3-(4'-fluorophenyl)-3-(4'-phenylphenoxy) propyl] sarcosine potentiates NMDA receptor-mediated responses in vivo and produces an antipsychotic profile in rodent behavior," The Journal of Neurosci. (2003) 23(20):7586-7591.

Kocienski, P.J., Protective Groups, Georg Thieme Verlag Stuttgart, Germany, Table of Contents (1994).

Kreher, R.P., Hetarene II Georg Thieme Verlag Stuttgart, Germany (1991) 583-726.

Kuhakarn, C. et al., "Synthesis of alkylated indolizidine alkaloids via pummerer mediated cyclization: synthesis of indolizidine 167B, 5-butylindolizidine and monomorine I," Tetrahedron (2008) 64(8):1663-1670.

Kushner et al., "Pharmacological uses and perspectives of heavy water and deuterated compounds," Canadian J. Physiol. Pharmacol. (1999) 77(2):79-88.

Lindsley, C.W. et al., "Design, synthesis, and in vivo efficacy of glycine transporter-1 (GlyT1) inhibitors derived from a series of [4-phenyl-1-(propylsulfonyl)piperidin-4-yl]methyl benzamides," Chem. Med. Chem. (2006) 1(8):807-811.

Lindsley, C.W. et al., "Progress in the preparation and testing of glycine transporter type-1 (glyT1) inhibitors," Curr. Top. Med. Chem. (2006) 6:1883-1896.

Lindsley, C.W. et al., "Progress towards validating the NMDA receptor hypofunction hypothesis of schizophrenia," Cur. Top. Med. Chem. (2006) 6:771-785.

Lizondo, J. et al., "Linezolid: oxazolindinone antibacterial," Drugs of the Future (1996) 21(11):1116-1123.

Lowe, J. et al., "A novel-nonsubstrate-based series of glycine type 1 transporter inhibitors derived from high-throughput screening," Bioorg. Med. Chem. Lett. (2007) 17(6):1675-1678.

Maclennan, A.H. et al., "Neonatal body water turnover: a putative index of perinatal morbidity," Amer. J. Obstetrics & Gynecology (1981) 139(8):948-952.

Mai, K. et al., "A fast n-substituted alpha-aminonitrile synthesis," Synthetic Commun. (1985) 15(2):157-163.

Mallesham, B. et al., "Highly efficient cul-catalyzed coupline of aryl bromides with oxazolidinones using Buchwald's protocol: a short route to linezolid and toloxatone," Org. Left. (2003) 5(7):963-965.

Matsunaga, S. et al., "Linked-BINOL: an approach towards practical asymmetric multifunctional catalysis," Adv. Synth. Catal. (2002) 344(1):3-15.

McOmie, J.F.W., ed., Protective Groups in Organic Chemistry, Plenum Press (1973) Table of Contents.

Meek, J.S. et al., "Diels-Alder reactions of 9-substituted anthracenes.1 II. 9-cyanoanthracene," J. Amer. Chem. Soc. (1956) 78(20):5413-5416.

Memetzidis, G. et al., "Synthesis of aromatic chloroberbines," Heterocycles (1990) 31(2):341-351.

Mezler, M. et al., "Inhibitors of GlyT1 affect glycine transport via discrete binding sites," Mol. Pharmacol. (2008) 74(6):1705-1715.

Morita, K. et al., "Spinal antiallodynia action of glycine transporter inhibitors in muropathic pain models in mice," J. Pharm. Env. Therap. (2008) 326(2):633-645.

Munson, P.J. et al., "Ligand: a versatile computerized approach for characterization of ligand-binding systems," Anal. Biochem. (1980) 107(1):220-239.

Nunez, E. et al., "Differential effects of the tricyclic antidepressant amoxapine on glycine uptake mediated by the recombinant GLYT1 and CLYT2 glycine transporters," Br. J. Pharm. (2000) 129(1):200-206.

Obach, R.S., "Prediction of human clearance of twenty-nine drugs from hepatic microsomal intrinsic clearance data: an examination of in vitro half-life approach and nonspecific binding to microsomes," Drug Metabolism and Disposition (1999) 27(11):1350-1359.

Obach, R.S., "The prediction of human clearance from hepatic microsomal metabolism data," Curr. Opin. Drug Disc. & Development (2001) 4(1):36-44.

Paal, T.A. et al., "Lipase-catalyzed kinetic and dynamic kinetic resolution of 1,2,3,4-tetrahydroisoquinoline-1-carboxylic acid," Tetrahedron: asymmetry (2007) 18(12):1428-1433.

Papageorgiou, C. et al., "163 synthesis of hydroxy-and methoxy-substituted octahydrobenzo[g]isoquinolines as potential ligands for serotonin receptors," Helvetica Chimica Acta (1989) 72:1463-1470.

Pinard, E. et al., "Selective gly T1 inhibitors: discovery of [4-(3-fluoro-5-trifluoremethylpyridin-2-yl)piperazin-1-yl]-]-[5-methanesulfonyl-2-((S)-2,2,2-trifluoro-1-methylethoxy)phenyl)methanone (RG1678), a promising novel medicine to treat schizophrenia," J. Med. Chem. (2010) 53:4603-4614.

Pisaneschi, F. et al., "Diastereoselective cycloaddition of alkylidenecyclopropane nitrones from palladium(O)catalyzed nucleophilic substitution of asymmetric l-alkenylcyclopropyl esters by amino acids," Tetrahedron: Asymmetry (2000) 11:897-909.

Pitts, M.R. et al., "Indium metal as a reducing agent in organic synthesis," J. Chem Soc. Perkin Transactions (2001) 1:955-977.

Pons, G. et al., "Stable isotopes labeling of drugs in pediatric clinical pharmacology," Pediatrics (1999) 104(32):633-639.

Poornachandran, M. et al., "Synthesis of pyrrolo[3,4-b]pyrroles and perhydrothiazolo-[3',4'-2,3]pyrrolo[4,5- c]pyrroles," Tetrahedron (2008) 64:6461-6474.

Prout, F.S. et al., "3-Benzyl-3-Methylpentanoic acid," Organic Syntheses, Coll. (1963) 4:93; (1955) 35:6.

(56) References Cited

OTHER PUBLICATIONS

Quirante, J. et al., "Synthesis of diazatricyclic core of magangamines from Cis-perhydroisoquinolines," J. Org. Chem. (2008) 73(7):768-771.
Rand et al., "Indium (III) chloride-promoted rearrangement of epoxides: a selective synthesis of substituted benzylic aldehydes and ketones," J. Org. Chem. (1998) 8212-8216.
Reddy, K.S. et al., "Synthesis of a 9-fluorenone derived beta-amino alcohol ligand depicting high catalytic activity and pronounced non-linear stereochemical effects," Synthesis (2000) 1:165-176.
Reddy, M.P. et al., "Applications of the Vilsmeier reaction. 13. Vilsmeier approach to polycyclic aromatic hydrocarbons," J. Org. Chem. (1981) 46:5371-5373.
Registry No. 1025812-32-1; entered in STN Jun. 5, 2008, "4-morpholineacetamide, N-[2-[[1-[2,4-dihydroxy-5-(1-methylethyl)benzoyl]-2,3-dihydro-1H-isoindol-5-yl]oxy]ethyl]".
Reimann, E. et al., "A convenient synthesis of 1-benzyl-1,2,3,4-tetrahydroisoquinolines by combined Strecker/Bruylants reaction," Monatshefte fur Chemie/Chemical Monthly (2004) 135(10):1289-1295.
Rodewald, L.E. et al., "Deuterium oxide as a tracer for measurement of compliance in pediatric clinical drug trials," J. Pediatrics (1989) 114(5):885-891.
Schwarcz, H.P., "Use of stable isotopes to determine compliance," Controlled Clinical Trials (1984) 5(Supp 4):573-575.
Schwarz, J.B. et al., "Novel cyclopropyl beta-amino acid analogues of pregabalin and gabapentin that target the alpha2-delta protein," J. Med. Chem. (2005) 48(8):3026-3035.
Sharma, S.D. et al., "Phosphorous oxychloride (POCI3): a key molecule in organic synthesis," Indian J. Chem. (1998) 37B:965-978.
Sur, C. et al., "Glycine transporter 1 inhibitors and modulation of NMDA receptor-mediated excitatory neurotransmission," Curr. Drug Targets (2007) 8:643-649.
Taber, D.F. et al., "Enantioselective ring construction: synthesis of (+)-alpha-cuparenone," J. Amer. Chem. Soc. (1985) 107:196-199.
Tanabe, M. et al., "Glycine transporter inhibitors as a potential therapeutic strategy for chronic pain with memory impairment," Anesth. (2008) 108:929-937.
Tavares, F.X. et al., "Potent, selective, and orally efficacious antagonists of melanin-concentrating hormone receptor 1," J. Med. Chem. (2006) 49(24):7095-7107.
Thompson, H.W. et al., "Stereochemical control of reductions. 9. Haptophilicity studies with 1,1-disubstituted 2-methyleneacenaphthenes," J. Org. Chem. (2002) 67(9):2813-2825.
Thomson, J.F., "Physiological effects of D20 in mammals," Annals of the N.Y. Academy of Sci. (1960) 84:736-744.
Ting, P.C. et al., "The synthesis of substituted bipiperidine amide compounds as CCR3 antagonists," Bioorg. Med. Chem. Lett. (2005) 15(5):1375-1378.
Tsai, G. et al., "Gene knockout of glycine transporter 1: characterization of the behavioral phenotype," PNAS (2004) 101(22):8485-8490.
Ungureanu, I. et al., "The reactivity of N-tosylpheny-laziridine versus N-tosylphenylazetidine in heterocyclization reactions," Tetra. Lett. (2001) 42:6087-6091.
Vogel, S. et al., "Palladium-catalyzed intramolecular allylic alkylation of alpha-sulfinyl carbanions: a new asymmetric route to enantiopure gamma-lactams," Tetra. Lett. (2010) 51(11):1459-1461.
White, J.D. et al., "Catalyzed asymmetric diels-alder reaction of benzoquinone. Total synthesis of (-31 )-ibogamine," Org. Lett. (2000) 2(15):2373-2376.
Zhao, Z. et al., "Synthesis and SAR of GlyT1 inhibitors derived from a series of N-((4-(morpholine-4-carbonyl)-1-(propylsulfonyl) piperidin-4-yl) methyl) benzamindes," Bioorg. Med. Chem. Lett. (2006) 16(23):5968-5972.
Zhou, D. et al., "Studies toward the discovery of the next generation of antidepressants. Part 5: 3,4-dihydro-2H-benzo[1,4]oxazine derivatives with dual 5-HT1A receptor and serotonin transporter affinity," Bioorg. Med. Chem. Lett. (2006) 16(5):1338-1341.
United States Patent Office Notice of Allowance for U.S. Appl. No. 12/706,326 dated Jun. 11, 2013 (10 pages).
United States Patent Office Notice of Allowance for U.S. Appl. No. 12/706,326 dated Feb. 21, 2013 (9 pages).
United States Patent Office Action for U.S. Appl. No. 12/706,326 dated Sep. 21, 2012 (7 pages).
United States Patent Office Notice of Allowance for U.S. Appl. No. 12/666,629 dated Dec. 11, 2012 (5 pages).
United States Patent Office Action for U.S. Appl. No. 12/666,629 dated Jul. 5, 2012 (11 pages).
United States Patent Office Notice of Allowance for U.S. Appl. No. 12/706,321 dated Sep. 30, 2013 (10 pages).
United States Patent Office Action for U.S. Appl. No. 12/706,321 dated Jul. 19, 2012 (7 pages).
United States Patent Office Action for U.S. Appl. No. 12/706,321 dated Mar. 27, 2012 (11 pages).
United States Patent Office Notice of Allowance for U.S. Appl. No. 12/933,326 dated Jan. 9, 2014 (2 pages).
United Statse Patent Office Notice of Allowance for U.S. Appl. No. 12/933,326 dated Dec. 9, 2013 (4 pages).
United States Patent Office Notice of Allowance for U.S. Appl. No. 12/933,326 dated Oct. 1, 2013 (8 pages).
United States Patent Office Notice of Allowance for U.S. Appl. No. 12/933,326 dated Jan. 11, 2013 (5 pages).
United States Patent Office Action for U.S. Appl. No. 12/933,326 dated Oct. 29, 2012 (6 pages).
United States Patent Office Notice of Allowance for U.S. Appl. No. 13/206,937 dated Feb. 21, 2014 (9 pages).
United States Patent Office Action for U.S. Appl. No. 13/206,937 dated Aug. 28, 2013 (6 pages).
United States Patent Office Notice of Allowance for U.S. Appl. No. 13/206,937 dated May 15, 2014 (9 pages).
United States Patent Office Action for U.S. Appl. No. 13/206,750 dated Feb. 19, 2014 (6 pages).
United States Patent Office Notice of Allowance for U.S. Appl. No. 13/206,750 dated Nov. 7, 2014 (8 pages).
United States Patent Office Notice of Allowance for U.S. Appl. No. 13/207,030 dated Mar. 7, 2014.
United States Patent Office Notice of Allowance for U.S. Appl. No. 13/207,030 dated May 13, 2014 (9 pages).
United States Patent Office Notice of Allowance for U.S. Appl. No. 13/207,160 dated Mar. 17, 2014 (9 pages).
United States Patent Office Notice of Allowance for U.S. Appl. No. 13/207,160 dated Jun. 6, 2014 (9 pages).
United States Patent Office Action for U.S. Appl. No. 13/546,434 dated Apr. 14, 2014 (12 pages).
United States Patent Office Notice of Allowance for U.S. Appl. No. 13/546,434 dated Jan. 16, 2015 (9 pages).
United States Patent Office Action for U.S. Appl. No. 13/566,051 dated Sep. 16, 2013 (15 pages).
United States Patent Office Notice of Allowance for U.S. Appl. No. 13/566,051 dated May 29, 2014 (8 pages).
United States Patent Office Action for U.S. Appl. No. 13/680,488 dated Dec. 5, 2013 (17 pages).
United States Patent Office Action for U.S. Appl. No. 13/680,488 dated Jun. 21, 2013 (43 pages).
United States Patent Office Notice of Allowance for U.S. Appl. No. 13/680,488 dated Apr. 28, 2014 (13 pages).
United States Patent Office Corrected Notice of Allowance for U.S. Appl. No. 13/680,488 dated Jun. 12, 2014 (7 pages).
United States Patent Office Action for U.S. Appl. No. 13/789,967 dated Apr. 1, 2014 (11 pages).
United States Patent Office Action for U.S. Appl. No. 14/317,104 dated Nov. 5, 2014 (11 pages).
United States Patent Office Notice of Allowance for U.S. Appl. No. 14/317,104 dated Apr. 15, 2015 (9 pages).
United States Patent Office Action for U.S. Appl. No. 13/792,105 dated Apr. 16, 2014 (6 pages).
United States Patent Office Notice of Allowance for U.S. Appl. No. 13/792,105 dated Oct. 2, 2014 (10 pages).

(56) References Cited

OTHER PUBLICATIONS

United States Patent Office Action for U.S. Appl. No. 14/031,265 dated Apr. 15, 2014 (14 pages).
United States Patent Office Notice of Allowance for U.S. Appl. No. 14/031,265 dated Jan. 27, 2015 (11 pages).
United States Patent Office Action for U.S. Appl. No. 14/282,712 dated Oct. 3, 2014 (12 pages).
United States Patent Office Notice of Allowance for U.S. Appl. No. 14/282,712 dated Mar. 5, 2015 (9 pages).
United States Patent Office Action for U.S. Appl. No. 13/468,682 dated Sep. 10, 2014 (12 pages).
United States Patent Office Action for U.S. Appl. No. 13/468,682 dated Feb. 24, 2015 (7 pages).
United States Patent Office Action for U.S. Appl. No. 13/764,454 dated Sep. 30, 2014 (11 pages).
United States Patent Office Action for U.S. Appl. No. 13/764,454 dated Mar. 5, 2015 (8 pages).
United States Patent Office Action for U.S. Appl. No. 14/216,222 dated Jan. 2, 2015 (17 pages).
International Search Report for Application No. PCT/EP2010/051903, mailed May 26, 2010.
International Search Report for Application No. PCT/EP2008/061007 dated Aug. 10, 2009 (6 pages).
International Search Report for Application No. PCT/EP2009/053800 dated Nov. 20, 2009 (6 pages).
International Search Report for Application No. PCT/EP2012/058760 dated Aug. 27, 2012 (4 pages).
International Search Report for Application No. PCT/EP2012/065294 dated Sep. 21, 2012 (4 pages).
International Search Report and Writeen Opinion for Application No. PCT/EP2014/055159 dated Jun. 16, 2014.
International Search Report and Written Opinion for Application No. PCT/EP2014/072235 dated Dec. 15, 2014.
International Search Report and Written Opinion for Application No. PCT/EP2014/072233 dated Jan. 20, 2015.
Written Opinion for Application No. PCT/EP2010/051903, mailed Aug. 16, 2011.
Written Opinion for Application No. PCT/EP2008/061007 dated Aug. 10, 2009 (7 pages).
Written Opinion for Application No. PCT/EP2009/053 800 dated Nov. 20, 2009 (7 pages).
Written Opinion for Application No. PCT/EP2012/058760 dated Aug. 27, 2012 (4 pages).
Damasio, A.R., "Alzheimer's disease and related dementias," Cecil Textbook of Medicine, 20th Edition (1996) 2:1992-1996.
FDA mulls drug to slow late-stage Alzheimer's [online], retrieved on Sep. 23, 2003 from the Internet URL: http://www.cnn.com120031HEALTH/conditions/O91241alzheimers.drug.aplindexhtml.
Layzer, R.B., "Degenerative diseases of the nervous system," Section Five, Cecil Textbook of Medicine, 20th Edition (1996) 2:2050-2057.
United States Patent Office Action for U.S. Appl. No. 13/468,682 dated Jul. 24, 2015 (7 pages).
United States Patent Office Action for U.S. Appl. No. 13/764,454 dated Jun. 4, 2015 (12 pages).
United States Patent Office Action for U.S. Appl. No. 14/216,222 dated Jul. 6, 2015 (13 pages).
United States Patent Office Notice of Allowance for U.S. Appl. No. 13/468,682 dated Nov. 30, 2015 (5 pages).
United States Patent Office Notice of Allowance for U.S. Appl. No. 13/764,454 dated Jan. 7, 2016 (10 pages).
United States Patent Office Action for U.S. Appl. No. 14/216,222 dated Nov. 10, 2015 (16 pages).
United States Patent Office Notice of Allowance for U.S. Appl. No. 14/317,104 dated Sep. 3, 2015 (9 pages).
United States Patent Office Notice of Allowance for U.S. Appl. No. 14/282,712 dated Sep. 11, 2015 (9 pages).

* cited by examiner

PYRROLIDINE DERIVATIVES, PHARMACEUTICAL COMPOSITIONS CONTAINING THEM, AND THEIR USE IN THERAPY

CROSS-REFERENCE TO RELATED APPLICATIONS

This claims priority to U.S. Patent Application No. 61/788,538, filed on Mar. 15, 2013, the entire contents of which are fully incorporated herein by reference.

The present invention relates to pyrrolidine derivatives, pharmaceutical compositions comprising such pyrrolidine derivatives, and the use of such pyrrolidine derivatives for therapeutic purposes.

BACKGROUND OF THE INVENTION

The pyrrolidine motif is an important pharmacophore possessing biological activity against a number of different targets and thus has found use in various advanced pharmaceutical research compounds and clinical candidates (such as Factor Xa inhibitors, NK3 receptor antagonists, DPP-IV inhibitors, PDE-IV inhibitors, or MC4 receptorselective agonists).

A pyrrolidine compound already known in the art as type IV phosphodiesterase inhibitor (PDE-IV) is for example:

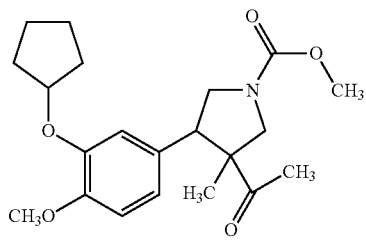

U.S. Pat. No. 5,665,754

WO 9508534, US 2006074123, WO 2001047915, US 20020169196, WO 2001047879 and WO 2001047914 describe further PDE-IV inhibitors having related structures.

Further, the synthesis of certain trisubstituted pyrrolidine derivatives has been reported in Baumann Marcus, et al., ACS Comb. Sci. 2011, 13, 405-413.

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the WO-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])-sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

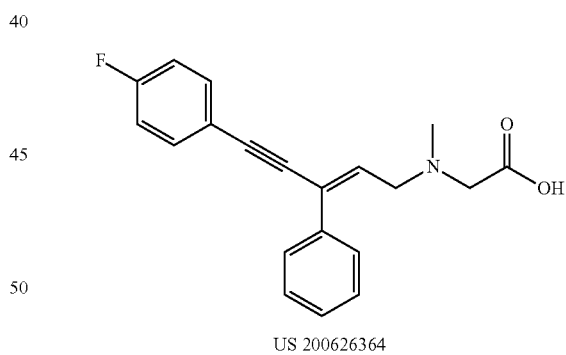

US 200626364

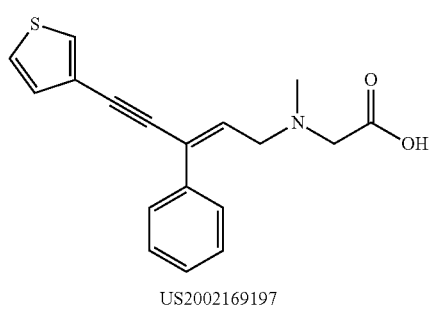

US2002169197

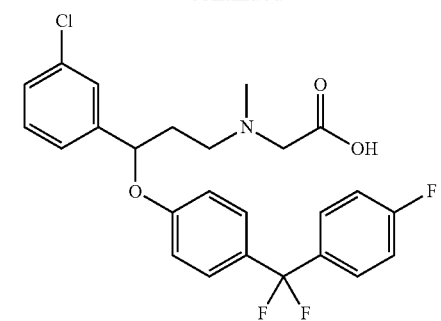
EP 1 284 257
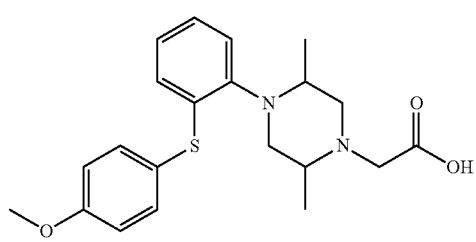
WO 2003053942
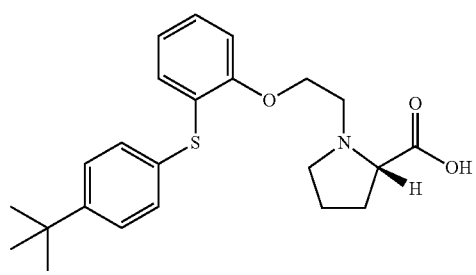
WO 2004096761
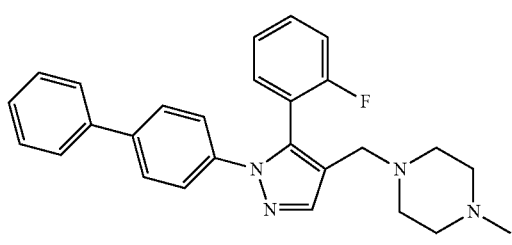
WO 2003031435
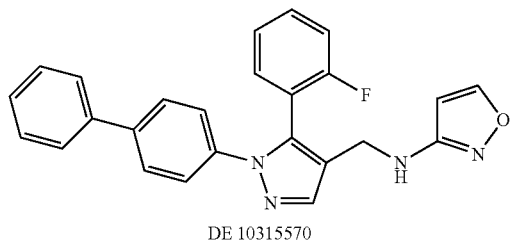
DE 10315570
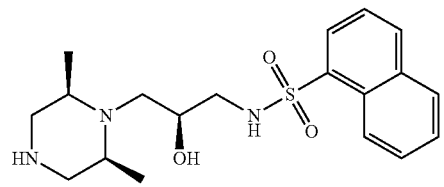
WO 2003055478
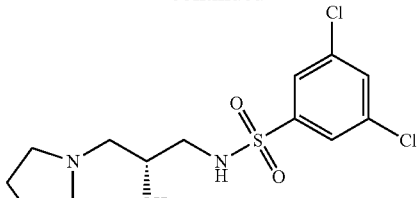
WO 2004113280
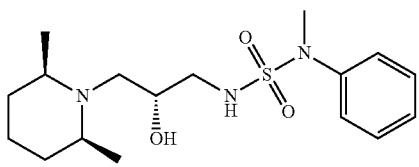
WO 2004112787
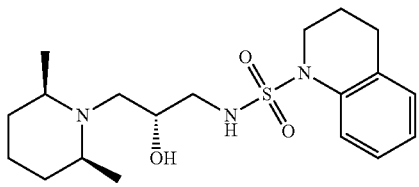
WO 2004113301
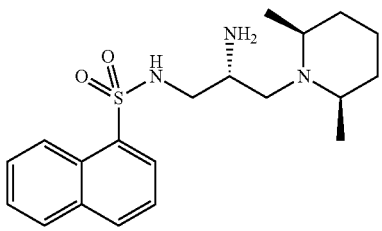
WO 2005049023
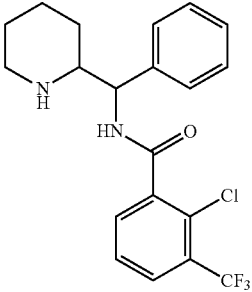
WO 2003089411
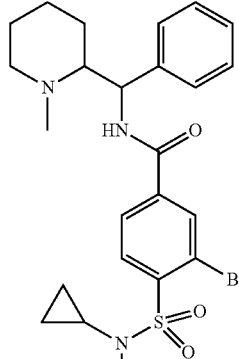
WO 2004013100

5
-continued
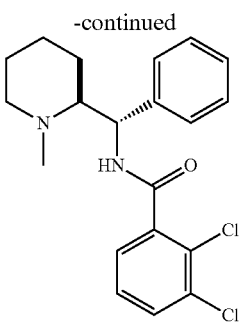
WO 2004013101
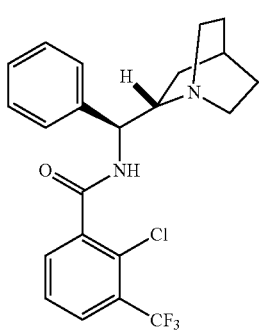
WO 2005037783
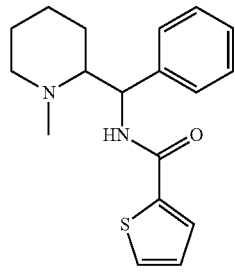
WO 2005037792
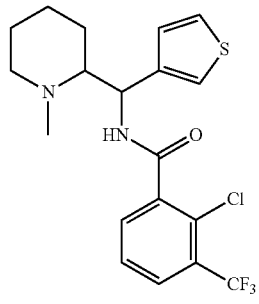
WO 2005037781
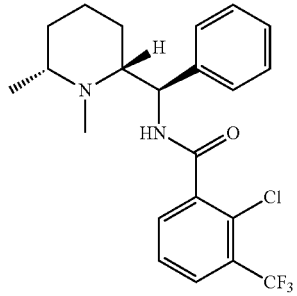
WO 2005037782
6
-continued
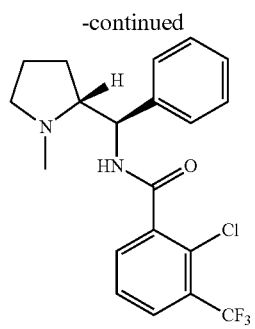
WO 2005037785
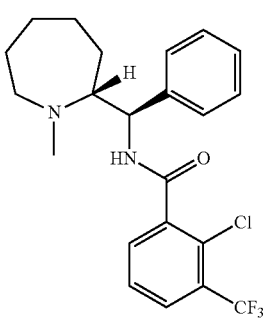
WO 2005037785
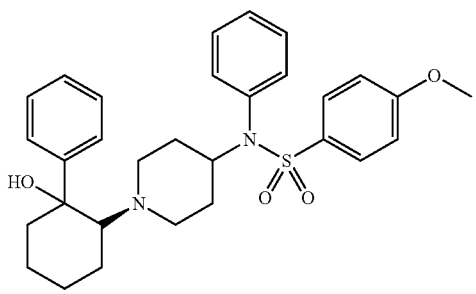
WO 2004072034
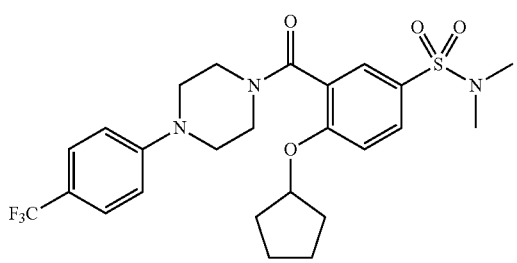
WO 2005014563
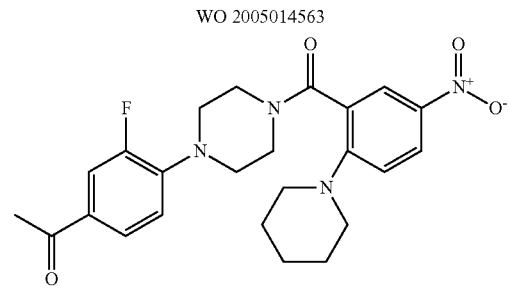
WO 2005023260

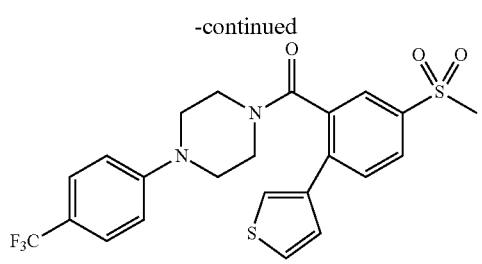

WO 2005023261

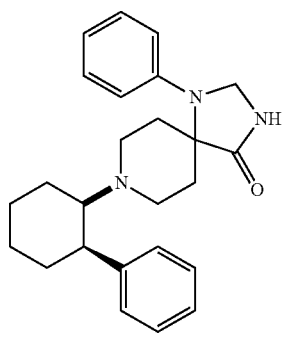

WO 2005040166

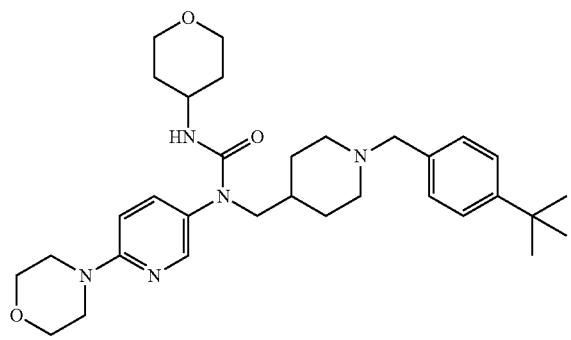

WO 2005058882

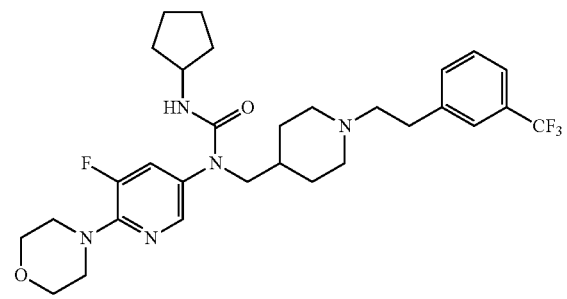

WO 2005058885

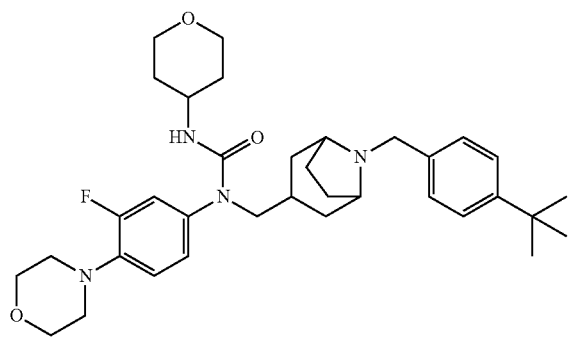

WO 2005058317

WO 2005046601

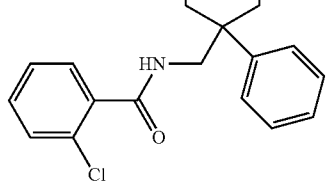

WO 2003087086

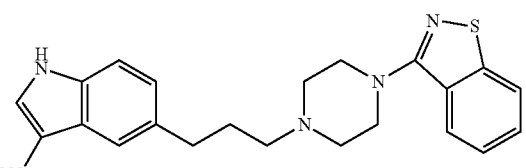

WO 2003076420

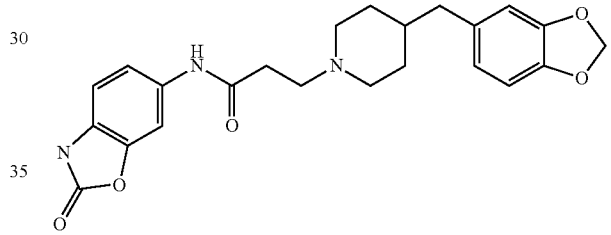

WO 2004022528

(see also Hashimoto K., Recent Patents on CNS Drug Discovery, 2006, 1, 43-53; Harsing L. G. et al., Current Medicinal Chemistry, 2006, 13, 1017-1044; Javitt D.C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

Further glycine transporter inhibitors are known from the following documents.

WO 2009024611 describes 4-benzylaminoquinolines of formula:

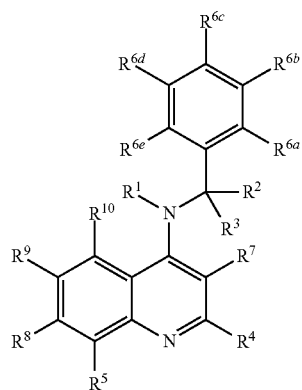

WO 2009121872 describes tetrahydroisoquinolines of formula:

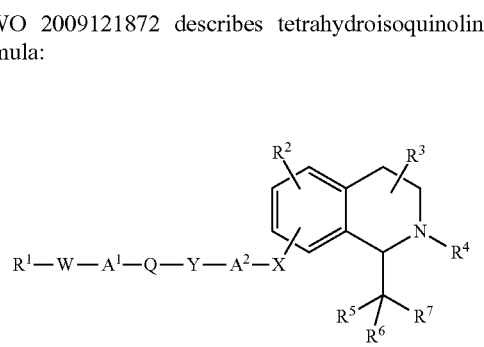

WO 2010092180 describes aminotetraline derivatives of formula:

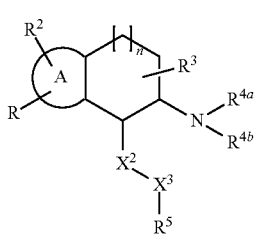

WO 2010092181 describes heterocyclic compounds of formula:

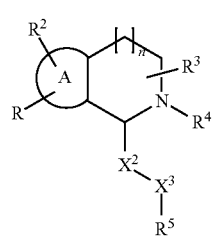

WO 2012020131 describes aminoindane derivatives of formula:

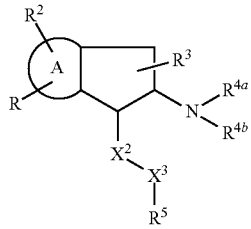

WO 2012020130 describes phenalkylamine derivatives of formula:

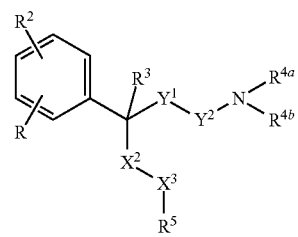

WO 2012020133 describes tetraline and indane derivatives of formula:

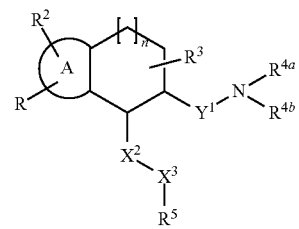

WO 2012152915 describes benzazepine derivatives of formula:

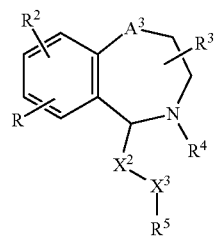

WO 2012020134 describes phenalkylamine derivatives of formulae:

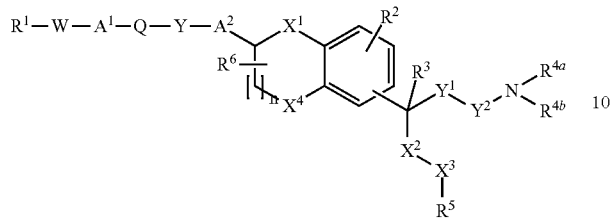

(I)

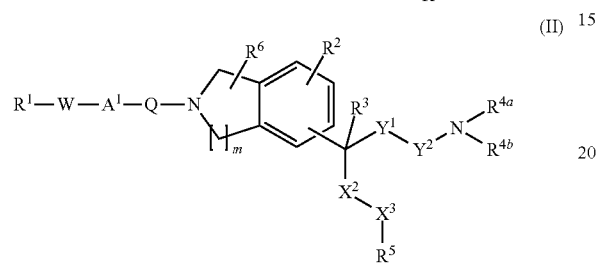

(II)

WO 2013020930 describes aminochromane, aminothiochromane and amino-1,2,3,4-tetrahydroquinoline derivatives of formula:

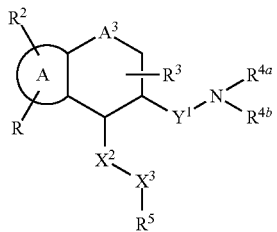

(I)

WO 2013072520 describes N-substituted aminobenzocycloheptene, aminotetraline, aminoindane and phenalkylamine derivatives of formula:

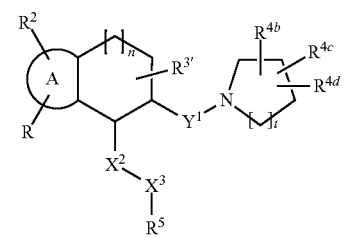

(I)

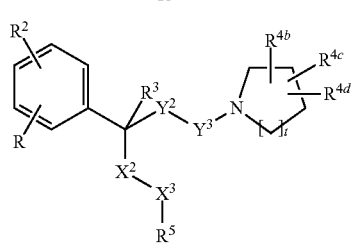

(II)

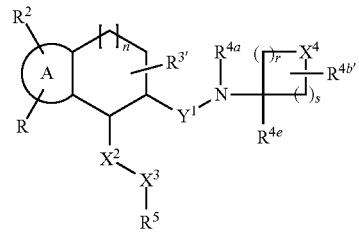

(III)

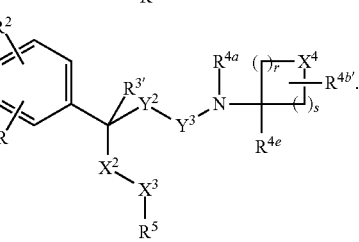

(IV)

WO 2013120835 describes isoindoline derivatives of formula

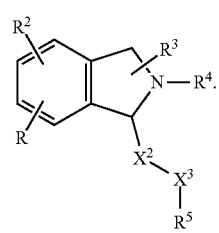

(I)

It was one object of the present invention to provide further glycine transporter inhibitors. It was a further object of the present invention to provide glycine transporter inhibitors which combine high stability with high affinity. It was a further object of the present invention to provide glycine transporter inhibitors which show favorable efflux properties. It was a further object of the present invention to provide glycine transporter inhibitors which combine high stability and high affinity with favorable efflux properties. It was a further object of the present invention to provide glycine transporter inhibitors which show good oral bioavailability.

SUMMARY OF THE INVENTION

The present invention relates to pyrrolidine derivatives of the formula (I)

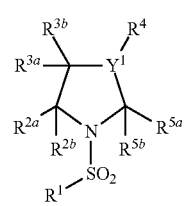

(I)

wherein $R^1$ is alkyl, (optionally substituted cycloalkyl)-alkyl, (optionally substituted aryl)-alkyl, (optionally substituted heterocyclyl)-alkyl, optionally substituted cycloalkyl, optionally substituted aryl, or optionally substituted heterocyclyl;

$R^{2a}$, $R^{2b}$
are independently hydrogen, halogen, or alkyl; or $R^{2a}$, $R^{2b}$
together with the carbon atom to which they are bound may form a C=O;

$R^{3a}$
is cycloalkyl, optionally substituted aryl, hydroxy, alkoxy, halogenated alkoxy, cycloalkyl-alkoxy, alkenyloxy, aryl-alkoxy, heterocyclyl-alkoxy, optionally substituted aryloxy, heterocyclyloxy, or optionally substituted heterocyclyl; or $R^{3a}$ and one of $R^{2a}$ or $R^{2b}$
together with the carbon atoms to which they are bound may form an optionally substituted anellated aryl;

$R^{3b}$ is hydrogen, alkyl, or hydroxy; or $R^{3a}$ and $R^{3b}$
together are optionally substituted alkylene;

$Y^1$ is >CR$^6$— or >N—;

$R^6$ is hydrogen, alkyl, halogenated alkyl, (optionally substituted aryl)-alkyl, hydroxy-alkyl, alkoxy-alkyl, or hydroxy; or $R^6$ and $R^{3a}$ or $R^{3b}$
together are optionally substituted alkylene; or $R^6$
is alkylene that is bound to a carbon atom in $R^{3a}$, and $R^{3a}$ is an optionally substituted aryl or an optionally substituted heterocyclyl;

$R^4$ is —(CR$^{7a}$R$^{7b}$)$_{n1}$OR$^{10}$, —(CR$^{7c}$R$^{7d}$)$_{n2}$NR$^{11a}$R$^{11b}$, —(CR$^{7e}$R$^{7f}$)$_{n3}$R$^{12}$, optionally substituted aryl, —NR$^{8a}$(—$^{9a}$R$^{9b}$)$_{n4}$R$^{13}$, —NR$^{8b}$COR$^{14}$, —NR$^{8c}$COOR$^{15}$, —NR$^{8d}$CONR$^{16a}$R$^{16b}$, —NR$^{8e}$SO$_2$R$^{17}$, —O(CR$^{9c}$R$^{9d}$)$_{n5}$R$^{18}$, —COR$^{19}$, —CONR$^{20a}$R$^{20b}$, —SO$_2$R$^{21}$, or optionally substituted heterocyclyl;

$R^{7a}$, $R^{7b}$
are independently hydrogen or alkyl;

n1 is 1, 2, 3, or 4;

$R^{10}$ is hydrogen, optionally substituted aryl, or optionally substituted heterocyclyl;

$R^{7c}$, $R^{7d}$
are independently hydrogen or alkyl;

n2 is 1, 2, 3, or 4;

$R^{11a}$ is alkyl, (optionally substituted cycloalkyl)-alkyl, alkoxy-alkyl, (optionally substituted aryl)-alkyl, (optionally substituted heterocyclyl)-alkyl, optionally substituted aryl, or optionally substituted heterocyclyl;

$R^{11b}$
is hydrogen or alkyl;

$R^{7e}$, $R^{7d}$
are independently hydrogen or alkyl;

n3 is 1, 2, 3, or 4;

$R^{12}$
is optionally substituted aryl or optionally substituted heterocyclyl;

$R^{8a}$, $R^{8b}$, $R^{8c}$, $R^{8d}$, $R^{8e}$
are independently hydrogen, alkyl, or alkylcarbonyl, or $R^6$ and one of $R^{8a}$, $R^{8b}$, $R^{8c}$, $R^{8d}$, or $R^{8e}$
together are optionally substituted alkylene, wherein one or more —CH$_2$— of alkylene may be independently replaced by a an oxygen atom or C=O; or $R^{3a}$ and one of $R^{8a}$ or $R^{8b}$
together are optionally substituted alkylene;

$R^{9a}$, $R^{9b}$
are independently hydrogen, halogen, alkyl, halogenated alkyl, hydroxy, or alkoxy;

n4 is 0, 1, 2, 3, or 4;

$R^{13}$ is hydrogen, alkyl, halogenated alkyl, (optionally substituted cycloalkyl)-alkyl, alkoxy-alkyl, optionally substituted cycloalkyl, alkenyl, optionally substituted cycloalkenyl, optionally substituted aryl, hydroxy, alkoxy, alkoxy-alkoxy, optionally substituted aryloxy, optionally substituted heterocyclyloxy, optionally substituted heterocyclyl, or tri-(alkyl)-silyloxy;

$R^{14}$ is alkyl, halogenated alkyl, (optionally substituted cycloalkyl)-alkyl, (optionally substituted aryl)-alkyl, hydroxy-alkyl, alkoxy-alkyl, (optionally substituted aryloxy)-alkyl, alkylcarbonyl-alkyl, alkoxycarbonyl-alkyl, alkylaminocarbonyl-alkyl, optionally substituted (heterocyclyl)-alkyl, optionally substituted cycloalkyl, optionally substituted aryl, or optionally substituted heterocyclyl;

$R^{15}$ is alkyl, optionally substituted aryl, or optionally substituted heterocyclyl;

$R^{16a}$ is (optionally substituted aryl)-alkyl, optionally substituted (heterocyclyl)-alkyl, optionally substituted aryl, or optionally substituted heterocyclyl;

$R^{16b}$ is hydrogen or alkyl;

$R^{17}$ is (optionally substituted aryl)-alkyl, (optionally substituted heterocyclyl)-alkyl, optionally substituted aryl, or optionally substituted heterocyclyl;

$R^{9c}$, $R^{9d}$
are independently hydrogen, halogen, or alkyl;

n5 is 0, 1, 2, 3, or 4;

$R^{18}$ is hydrogen, alkyl, optionally substituted cycloalkyl, alkylcarbonyl, alkoxycarbonyl, halogenated alkoxycarbonyl, aryloxycarbonyl, alkylaminocarbonyl, (halogenated alkyl)aminocarbonyl, arylaminocarbonyl, optionally substituted aryl, alkylamine, (cycloalkylalkyl)amino, (halogenated alkyl)amino, (alkoxy-alkyl)amino, (aryl-alkyl)amino, dialkylamine, optionally substituted arylamine, or optionally substituted heterocyclyl;

$R^{19}$ is optionally substituted aryl or optionally substituted heterocyclyl;

$R^{20a}$ is alkyl, (optionally substituted cycloalkyl)-alkyl, alkoxy-alkyl, (optionally substituted aryl)-alkyl, (optionally substituted heterocyclyl)-alkyl, optionally substituted aryl, or optionally substituted heterocyclyl;

$R^{20b}$ is hydrogen or alkyl;

$R^{21}$ is optionally substituted aryl, or optionally substituted heterocyclyl; and $R^{5a}$, $R^{5b}$
are independently hydrogen, halogen, or alkyl, or $R^{5a}$, $R^{5b}$
together with the carbon atom to which they are bound may form a C=O; or one of $R^{2a}$ or $R^{2b}$ and one of $R^{5a}$ or $R^{5b}$
together are optionally substituted alkylene, or a physiologically tolerated salt thereof.

Said compounds of formula (I), i.e., the pyrrolidine derivatives of formula (I) and their physiologically tolerated salts, are glycine transporter inhibitors and thus useful as pharmaceuticals. Compounds of formula (I) combine high metabolic stability with high affinity. Compounds of formula (I) show favorable efflux properties which may lead to enhanced oral bioavailability and/or increased brain availability. Compounds of formula (I) combine high metabolic stability and high affinity with favorable efflux properties.

The present invention thus further relates to the compounds of formula (I) for use in therapy.

The present invention also relates to pharmaceutical compositions which comprise a carrier and a compound of formula (I).

In particular, said compounds, i.e., the pyrrolidine derivatives and their physiologically tolerated salts, are inhibitors of the glycine transporter GlyT1.

The present invention thus further relates to the compounds of formula (I) for use in inhibiting the glycine transporter.

The present invention also relates to the use of the compounds of formula (I) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (I) for use in treating a neurologic or psychiatric disorder.

The present invention further relates to the compounds of formula (I) for use in treating pain.

The present invention also relates to the use of the compounds of formula (I) in the manufacture of a medicament for treating a neurologic or psychiatric disorder and corresponding methods of treating said disorders. The present invention also relates to the use of the compounds of formula (I) in the manufacture of a medicament for treating pain and corresponding methods of treating pain.

DETAILED DESCRIPTION OF THE INVENTION

Provided that the pyrrolidine derivatives of the formula (I) of a given constitution may exist in different spatial arrangements, for example if they possess one or more centers of asymmetry, polysubstituted rings or double bonds, or as different tautomers, the invention relates to the corresponding enantiomeric mixtures, in particular racemates, diastereomeric mixtures and tautomeric mixtures, as well as to the respective essentially pure enantiomers, diastereomers and tautomers of the compounds of formula (I) and/or of their salts.

According to one embodiment, an enantiomer of the pyrrolidine derivatives of the present invention has the following formula:

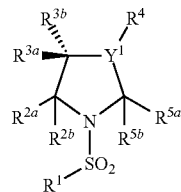

wherein $R^1$, $R^{2a}$, $R^{2b}$, $R^{3a}$, $R^{3b}$, $R^4$, $Y^1$, $R^{5a}$, $R^{5b}$ are as defined herein.

According to another embodiment, an enantiomer of the pyrrolidine derivatives of the present invention has the following formula:

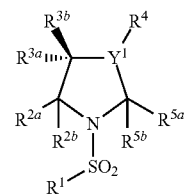

wherein $R^1$, $R^{2a}$, $R^{2b}$, $R^{3a}$, $R^{3b}$, $R^4$, $Y^1$, $R^{5a}$, $R^{5b}$ are as defined herein.

If $Y^1$ is >$CR^6$— it is preferred that $R^{3a}$ and $R^4$ are in trans position.

Accordingly, the invention relates in particular to an enantiomer of the pyrrolidine derivatives having the following formula:

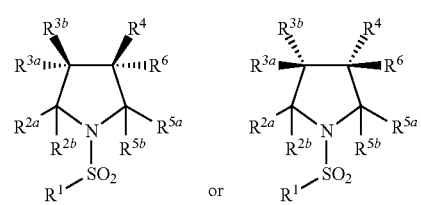

wherein $R^1$, $R^{2a}$, $R^{2b}$, $R^{3a}$, $R^{3b}$, $R^4$, $R^6$, $R^{5a}$, $R^{5b}$ are as defined herein.

Preferably, the invention relates to an enantiomer of the pyrrolidine derivatives having the following formula:

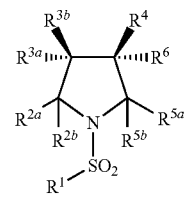

wherein $R^1$, $R^{2a}$, $R^{2b}$, $R^{3a}$, $R^{3b}$, R4, $R^6$, $R^{5a}$, $R^{5b}$ are as defined herein.

The physiologically tolerated salts of the pyrrolidine derivatives of the formula (I) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. The physiologically tolerated salts of the isoindoline derivatives also include salts of a physiologically tolerated anion with an isoindoline derivatives wherein one or more than one nitrogen atom is quaternized, e.g. with an alkyl residue (e.g. methyl or ethyl).

The present invention moreover relates to compounds of formula (I) as defined herein, wherein at least one of the atoms has been replaced by its stable, non-radioactive isotope (e.g., hydrogen by deuterium $^{12}$C by $^{13}$C, $^{14}$N by $^{15}$N, $^{16}$O by $^{18}$O) and preferably wherein at least one hydrogen atom has been replaced by a deuterium atom.

Of course, such compounds contain more of the respective isotope than this naturally occurs and thus is anyway present in the compounds (I).

Stable isotopes (e.g., deuterium, $^{13}$C, $^{15}$N, $^{18}$O) are non-radioactive isotopes which contain one or more additional neutron than the normally abundant isotope of the respective atom. Deuterated compounds have been used in pharmaceutical research to investigate the in vivo metabolic fate of the compounds by evaluation of the mechanism of action and metabolic pathway of the non-deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10): 927-932 (1995); Kushner et al., *Can. J. Physiol. Pharmacol.*, 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introclueing isotopic atoms to a chemical structure. Relevant procedures and intermediates are disclosed, for instance in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The organic moieties mentioned in the above definitions of the variables are—like the term halogen—collective terms for individual listings of the individual group members. The prefix $C_n$-$C_m$ indicates in each case the possible number of carbon atoms in the group.

Unless indicated otherwise, the term "substituted" means that a radical is substituted with 1, 2 or 3, especially 1, substituent which, according to a particular embodiment of the invention, are independently selected from the group consisting of halogen, $C_1$-$C_4$-alkyl, $C_3$-$C_6$-aryl-$C_1$-$C_4$-alkyl, halogenated-$C_1$-$C_4$-alkyl, hydroxy-$C_1$-$C_4$-alkyl, hydroxy-(halogenated $C_1$-$C_4$-alkyl), $C_1$-$C_4$-alkoxy-$C_1$-$C_4$-alkyl, amino-$C_1$-$C_4$-alkyl, $C_3$-$C_{12}$-heterocyclyl-$C_1$-$C_4$-alkyl, $C_3$-$C_7$-cycloalkyl, $C_2$-$C_4$-alkenyl, —CN, —$CO_2H$, $C_1$-$C_4$-alkoxycarbonyl, aminocarbonyl, $C_1$-$C_4$-alkylaminocarbonyl, (di-$C_1$-$C_4$-alkylamino)carbonyl, $C_6$-$C_{12}$-arylaminocarbonyl, $C_3$-$C_{12}$-heterocyclylaminocarbonyl, $C_6$-$C_{12}$-aryl, oxo (=O), OH, $C_1$-$C_4$-alkoxy, halogenated-$C_1$-$C_4$-alkoxy, $C_3$-$C_7$-cycloalkoxy, carboxy-$C_1$-$C_4$-alkoxy, $C_6$-$C_{12}$-aryl-$C_1$-$C_4$-alkoxy, $C_6$-$C_{12}$-aryloxy, $C_3$-$C_{12}$-heterocyclyl-$C_1$-$C_4$-alkoxy, SH, $C_1$-$C_4$-alkylthio, $C_1$-$C_4$-alkylsulfonyl, $C_1$-$C_4$-alkylaminosulfonyl, di-$C_1$-$C_4$-alkylaminosulfonyl, $C_3$-$C_6$-arylsulfonyl, aminosulfonyl, $C_3$-$C_6$-arylaminosulfonyl, $C_3$-$C_{12}$-heterocyclylaminosulfonyl, $NH_2$, $C_1$-$C_4$-alkylamino, di-$C_1$-$C_4$-alkylamino, $C_6$-$C_{12}$-aryl-$C_1$-$C_4$-alkylamino, $C_1$-$C_4$-alkylcarbonylamino, $C_3$-$C_6$-arylcarbonylamino, $C_3$-$C_{12}$-heterocyclylcarbonylamino, $C_1$-$C_6$-alkylsulfonylamino, $C_3$-$C_6$-arylsulfonylamino, $C_3$-$C_{12}$-heterocyclylsulfonylamino and $C_3$-$C_{12}$-heterocyclyl, wherein aryl and heterocyclyl may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy. Additional substituents may be independently selected from the group consisting of $C_1$-$C_4$-alkylamino-$C_1$-$C_4$-alkyl, di-$C_1$-$C_4$-alkylamino-$C_1$-$C_4$-alkyl, $C_1$-$C_4$-alkyl-carbonyl, halogenated $C_1$-$C_4$-alkyl-carbonyl, $C_3$-$C_{12}$-cycloalykyl-$C_1$-$C_4$-alkoxy, $C_1$-$C_4$-alkoxy-$C_1$-$C_4$-alkoxy, $C_1$-$C_4$-alkylamino-$C_1$-$C_4$-alkoxy, di-$C_1$-$C_4$-alkylamino-$C_1$-$C_4$-alkoxy, and $C_3$-$C_{12}$-heterocycloxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$-Alkyl is methyl or ethyl, $C_1$-$C_3$-alkyl is additionally n-propyl or iso-propyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_8$-Alkyl is a straight-chain or branched alkyl group having from 1 to 8 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, 1-methylhexyl, 2-methylhexyl, 3-methylhexyl, 4-methylhexyl, 5-methylhexyl, 1,2-dimethylpentyl, 1,2,3-trimethylbutyl 1-ethyl-2-methylbutyl, 1-methyl-2-ethylbutyl, octyl, 1-methyl-heptyl, 2-methylheptyl, 3-methyl-hepthyl, 4-methyl-heptyl, 5-methylheptyl, 6-methylheptyl, 1-methyl-2-ethylpentyl, 1,1-dimethylhexyl, 1,2-dimethylhexyl, 1,3-dimethylhexyl, 1,4-dimethylhexyl, 2,2-dimethylhexyl, 2,3-dimethylhexyl, 3,3-dimethylhexyl, 4,5-dimethylhexyl, 1,2,3-trimethylpentyl, 1,2-dimethyl-3-ethylbutyl, 1-ethyl-2-ethylbutyl and 1,3-dimethyl-2-ethylbutyl.

Halogenated $C_1$-$C_6$-alkyl is a straight-chain or branched alkyl group having 1 to 6 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, 1,1-dihalogenopentyl, 4,4-dihalogenopentyl etc. Particular examples include the fluorinated $C_1$-$C_4$ alkyl groups as defined, such as trifluoromethyl.

$C_3$-$C_{12}$-Cycloalkyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a cycloaliphatic radical having from 3 to 12 carbon atoms such as in cyclopropylmethyl, cyclobutylmethyl, cyclopentylmethyl and cyclohexylmethyl.

$C_1$-$C_6$-Alkylcarbonyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or 2 carbon atoms, wherein one hydrogen atom is replaced by a $C_1$-$C_6$-alkylcarbonyl group, in particular by a $C_1$-$C_4$-alkylcarbonyl group, such as in methylcarbonylmethyl, methylcarbonylethyl, methylcarbonylpropyl, ethylcarbonylmethyl, n-propylcarbonylmethyl, iso-propylcarbonylmethyl, n-butylcarbonylmethyl, 2-butylcarbonylmethyl or iso-butylcarbonylmethyl.

$C_1$-$C_6$-Alkoxycarbonyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkoxycarbonyl group, in particular by a $C_1$-$C_4$-alkoxycarbonyl group, such as in methoxycarbonylmethyl, methoxycarbonylpropyl, ethoxycarbonylmethyl, n-propoxycarbonylmethyl, n-butoxycarbonylmethyl, 2-butoxycarbonylmethyl or iso-butoxycarbonylmethyl.

$C_6$-$C_{12}$-Aryl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_6$-$C_{12}$-aryl, such as in benzyl.

Hydroxy-$C_1$-$C_6$-alkyl is a straight-chain or branched alkyl group having 1 to 6 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl, (R)-1-hydroxypentyl, (S)-1-hydroxypentyl, 2-hydroxypentyl and 4-hydroxypentyl.

Hydroxy-(halogenated $C_1$-$C_4$-alkyl) is a straight-chain or branched alkyl group having 1 to 4 carbon atoms, preferably 1 to 3 carbon atoms, more preferably 1 or 2 carbon atoms, wherein at least two, e.g. 2, 3, 4 or all of the hydrogen atoms are replaced by a number of identical or different halogen atoms and by one or two hydroxyl groups, such as in hydroxyhalogenomethyl, hydroxydihalogenomethyl, (R)-1-hydroxy-1-halogenoethyl, (S)-1-hydroxy-1-halogenoethyl, (R)2,2-dihalogeno-1-hydroxyethyl, (S)2,2-dihalogeno-1-hydroxyethyl, (R)2,2,2-trihalogeno-1-hydroxyethyl, (S)2,2,2-trihalogeno-1-hydroxyethyl (R)-1-hydroxy-1-halogenopropyl, (S)-1-hydroxy-1-halogenopropyl, (R)-2-halogeno-2-hydroxypropyl, (S)-2-halogeno-2-hydroxypropyl, 3-halogeno-2-hydroxypropyl, 1,1-dihalogeno-1-hydroxypropyl, 2,2-dihalogeno-1-hydroxypropyl, 3,3,3-trihalogeno-1-hydroxypropyl, (R)-2-halogeno-1-methyl-1-hydroxyethyl, (S)-2-halogeno-1-methyl-1-hydroxyethyl, (R)-2,2-dihalogeno-1-methyl-1-hydroxyethyl, (S)-2,2-dihalogeno-1-methyl-1-hydroxyethyl, (R)-2,2,2-trihalogeno-1-methyl-1-hydroxyethyl, (S)-2,2,2-trihalogeno-1-methyl-1-hydroxyethyl, (R)-1-(halogenomethyl)-1-hydroxyethyl, (S)-1-(halogenomethyl)-1-hydroxyethyl, (R)-1-(dihalogenomethyl)-1-hydroxyethyl, (S)-1-(dihalogenomethyl)-1-hydroxyethyl, (R)-1-(trihalogenomethyl)-1-hydroxyethyl, (S)-1-(trihalogenomethyl)-1-hydroxyethyl, etc. Particular examples include the hydroxyfluorinated $C_1$-$C_4$ alkyl groups as defined, such as 1-(trifluoromethyl)-1-hydroxyethyl.

$C_1$-$C_6$-Alkoxy-$C_1$-$C_6$-alkyl is a straight-chain or branched alkyl group having 1 to 6 carbon atoms, preferably 1 to 4 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, (R)-1-methoxypentyl, (S)-1-methoxypentyl, 2-methoxypentyl, 3-methoxypentyl, 4-methoxypentyl, (R)-1-methoxyhexyl, (S)-1-methoxyhexyl, 2-methoxyhexyl, 3-methoxyhexyl, 4-methoxyhexyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl, (R)-1-ethoxypentyl, (S)-1-ethoxypentyl, 2-ethoxypentyl, 3-ethoxypentyl, 4-ethoxypentyl, 5-ethoxypentyl, (R)-1-ethoxyhexyl, (S)-1-ethoxyhexyl, 2-ethoxyhexyl, 3-ethoxyhexyl and 6-ethoxybutyl.

$C_6$-$C_{12}$-Aryloxy-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a radical of the formula R—O—, wherein R is an aryl group having from 6 to 12, in particular 6 carbon atoms as defined herein. Examples include phenoxymethyl, (4-F-phenoxy)methyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in aminomethyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, iso-propylaminomethyl, n-butylaminomethyl, 2-butylaminomethyl, iso-butylaminomethyl or tert-butylaminomethyl.

Di-$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-Alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, iso-propylcarbonylaminomethyl, n-butylcarbonylaminomethyl, 2-butylcarbonylaminomethyl, iso-butylcarbonylaminomethyl or tert-butylcarbonylaminomethyl.

$C_1$-$C_6$-Alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylaminocarbonylamino group, in particular by a $C_1$-$C_4$-alkylaminocarbonylamino group, such as in methylaminocarbonylaminomethyl, ethylaminocarbonylaminomethyl, n-propylaminocarbonylaminomethyl, iso-propylaminocarbonylaminomethyl, n-butylaminocarbonylaminomethyl, 2-butylaminocarbonylaminomethyl, iso-butylaminocarbonylaminomethyl or tert-butylaminocarbonylaminomethyl.

Di-$C_1$-$C_6$-alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylaminocarbonylamino group, in particular by a di-$C_1$-$C_4$-alkylaminocarbonylamino group, such as in dimethylaminocarbonylaminomethyl, dimethylaminocarbonylaminoethyl, dimethylaminocarbonylamino-propyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethylsulfonylaminomethyl, n-propylsulfonylaminomethyl, iso-propylsulfonylaminomethyl, n-butylsulfonylaminomethyl, 2-butylsulfonylaminomethyl, iso-butylsulfonylaminomethyl or tert-butylsulfonylaminomethyl.

($C_6$-$C_{12}$-Aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl)amino group, in particular a ($C_6$-$C_{12}$-aryl-$C_1$-$C_2$-alkyl) amino group, such as in benzylaminomethyl.

$C_3$-$C_{12}$-Heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_3$-$C_{12}$-heterocyclyl, such as in N-pyrrolidinylmethyl, N-piperidinylmethyl, N-morpholinylmethyl, tetrahydropyran-2-yl-methyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is $>C=O$.

$C_1$-$C_6$-Alkylcarbonyl is a radical of the formula R—C(O)—, wherein R is an alkyl radical having from 1 to 6, preferably from 1 to 4, in particular 1 or 2 carbon atoms as defined herein. Examples include acetyl, propionyl, n-butyryl, 2-methylpropionyl, pivaloyl.

Halogenated $C_1$-$C_6$-alkylcarbonyl is $C_1$-$C_6$-alkylcarbonyl as defined herein, wherein at least one, e.g. 1, 2, 3, 4 or all of the hydrogen atoms are replaced by 1, 2, 3, 4 or a corresponding number of identical or different halogen atoms. Examples include fluoromethylcarbonyl, difluoromethylcarbonyl, trifluoromethylcarbonyl. Further examples are 1,1,1-trifluoroeth-2-ylcarbonyl, 1,1,1-trifluoroprop-3-ylcarbonyl.

$C_6$-$C_{12}$-Arylcarbonyl is a radical of the formula R—C(O)—, wherein R is an aryl radical having from 6 to 12 carbon atoms as defined herein. Examples include benzoyl.

$C_1$-$C_6$-Alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl and tert-butoxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl, 2-hexen-1-yl.

$C_3$-$C_6$-Cycloalkenyl is a carbocyclic radical having at least one carbon-carbon double bond and from 3 to 6 carbon atoms. In particular, 3 to 6 carbon atoms form the cyclic structure, such as 2-cyclopenten-1-yl, 2-cyclohexen-1-yl. The cyclic structure may be unsubstituted or may carry 1, 2, 3 or 4 $C_1$-$C_4$ alkyl radicals, preferably one or more methyl radicals.

$C_2$-$C_6$-Alkynyl is a singly unsaturated hydrocarbon radical having 2, 3, 4, 5 or 6 carbon atoms, e.g. ethynyl, 2-propyn-1-yl, 1-propyn-1-yl, 2-propyn-2-yl and the like. $C_3$-$C_5$-Alkynyl is, in particular, 2-propyn-1-yl, 2-butyn-1-yl, 3-butyn-1-yl, 2-pentyn-1-yl, 3-pentyn-1-yl, 4-pentyn-1-yl.

$C_1$-$C_5$-Alkylene is straight-chain or branched alkylene group having from 1 to 5 carbon atoms. Examples include methylene and ethylene. A further example is propylene. Another further example is butylene.

$C_2$-$C_4$-Alkenylene is straight-chain or branched alkenylene group having from 2 to 4 carbon atoms.

$C_2$-$C_4$-Alkynylene is straight-chain or branched alkynylene group having from 2 to 4 carbon atoms. Examples include propynylene.

$C_6$-$C_{12}$-Aryl is a 6- to 12-membered, in particular 6- to 10-membered, aromatic cyclic radical which can be a monocyclic aromatic ring, for example, phenyl etc., or a fused polycyclic aromatic ring comprising a first monocyclic aromatic ring and one or more carbocycles which are saturated, partially unsaturated or aromatic, for example, naphthyl, indenyl, tetrahydronaphthyl, indanyl.

$C_3$-$C_{12}$-Arylene is an aryl diradical. Examples include phen-1,4-ylene and phen-1,3-ylene. Hydroxy is —OH.

Oxo is =O.

$C_1$-$C_6$-Alkoxy is a radical of the formula R—O—, wherein R is a straight-chain or branched alkyl group having from 1 to 6, in particular 1 to 4 carbon atoms. Examples include methoxy, ethoxy, n-propoxy, iso-propoxy, n-butoxy, 2-butoxy, iso-butoxy (2-methylpropoxy), tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably from 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$-alkoxy is an alkoxy radical having from 1 to 4, preferably 1 or 2 carbon atoms as defined herein, wherein one hydrogen atom is replaced by an amino group. Examples include 2-aminoethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably 1 to 4 carbon atoms as defined herein. Examples include methylaminomethoxy, ethylaminomethoxy, n-propylaminomethoxy, iso-propylaminomethoxy, n-butylaminomethoxy, 2-butylaminomethoxy, iso-butylaminomethoxy, tert-butylaminomethoxy, 2-(methylamino)ethoxy, 2-(ethylamino)ethoxy, 2-(n-propylamino)ethoxy, 2-(iso-propylamino)ethoxy, 2-(n-butylamino)ethoxy, 2-(2-butylamino)ethoxy, 2-(iso-butylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a dialkylamino group having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, iso-propylcarbonylaminomethoxy, n-butylcarbonylaminomethoxy, 2-butylcarbonylaminomethoxy, iso-butylcarbonylaminomethoxy, tert-butylcarbonylaminomethoxy, 2-(methylcarbonylamino)ethoxy, 2-(ethylcarbonylamino)ethoxy, 2-(n-propylcarbonylamino)ethoxy, 2-(iso-propylcarbonylamino)ethoxy, 2-(n-butylcarbonylamino)ethoxy, 2-(2-butylcarbonylamino)ethoxy, 2-(iso-butylcarbonylamino)ethoxy, 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, iso-propoxycarbonylaminomethoxy, n-butoxycarbonylaminomethoxy, 2-butoxycarbonylaminomethoxy, iso-butoxycarbonylaminomethoxy, tert-butoxycarbonylaminomethoxy, 2-(methoxycarbonylamino)ethoxy, 2-(ethoxycarbonylamino)ethoxy, 2-(n-propoxycarbonylamino)ethoxy, 2-(iso-propoxycarbonylamino)ethoxy, 2-(n-butoxycarbonylamino)ethoxy, 2-(2-butoxycarbonylamino)ethoxy, 2-(iso-butoxycarbonylamino)ethoxy, 2-(tert-butoxycarbonylamino)ethoxy.

$C_2$-$C_6$-Alkenyloxy is a radical of the formula R—O—, wherein R is a straight-chain or branched alkenyl group having from 2 to 6, in particular 2 to 4 carbon atoms. Examples include vinyloxy, allyloxy (2-propen-1-yloxy), 1-propen-1-yloxy, 2-propen-2-yloxy, methallyloxy (2-methylprop-2-en-1-yloxy) and the like. $C_3$-$C_5$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methylbut-2-en-1-yloxy or 2-ethylprop-2-en-1-yloxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino)ethoxy, 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy, 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_6$-alkyl)sulfonylamino group, preferably by a ($C_6$-$C_{12}$-aryl-$C_1$-$C_2$-alkyl)sulfonylamino group. Examples include 2-(benzylsulfonylamino) ethoxy.

$C_3$-$C_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclylsulfonylamino group as defined herein. Examples include 2-(pyridin-3-yl-sulfonylamino)ethoxy.

$C_3$-$C_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclyl group as defined herein. Examples include 2-(N-pyrrolidinyl)ethoxy, 2-(N-morpholinyl)ethoxy and 2-(N-imidazolyl)ethoxy.

$C_1$-$C_2$-Alkylenedioxo is a radical of the formula —O—R—O—, wherein R is a straight-chain or branched alkylene group having from 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$C_3$-$C_{12}$-Heterocyclyloxy is a radical of the formula R—O—, wherein R is a $C_3$-$C_{12}$-heterocyclyl group having from 3 to 12, in particular from 3 to 7 carbon atoms as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical having from 1 to 6, preferably from 1 to 4 carbon atoms as defined herein. Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1-methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$ alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—S(O)$_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonyl is a radical of the formula R—S(O)$_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—S(O)$_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$C_3$-$C_{12}$-Heterocyclylsulfonyl is a radical of the formula R—S(O)$_2$—, wherein R is $C_3$-$C_{12}$-heterocyclyl as defined herein.

Aminosulfonyl is NH$_2$—S(O)$_2$—.

$C_1$-$C_6$-Alkylaminosulfonyl is a radical of the formula R—NH—S(O)$_2$— wherein R is an alkyl radical having from 1 to 6, preferably from 1 to 4 carbon atoms as defined herein. Examples include methylaminosulfonyl, ethylaminosulfonyl, n-propylaminosulfonyl, iso-propylaminosulfonyl, n-butylaminosulfonyl, 2-butylaminosulfonyl, iso-butylaminosulfonyl, tert-butylaminosulfonyl.

Di-$C_1$-$C_6$-alkylaminosulfonyl is a radical of the formula RR'N—S(O)$_2$— wherein R and R' are independently of each other an alkyl radical having from 1 to 6, preferably from 1 to 4 carbon atoms as defined herein. Examples include dimethylaminosulfonyl, diethylaminosulfonyl, N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is NH$_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino, tert-butylamino.

(Halogenated $C_1$-$C_6$-alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

Di-$C_1$-$C_6$-alkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino.

Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido (methylcarbonylamino), propionamido, n-butyramido, 2-methylpropionamido (iso-propylcarbonylamino), 2,2-dimethylpropionamido and the like.

(Halogenated $C_1$-$C_6$-alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_2$-$C_6$-Alkenylamino is a radical of the formula R—NH—, wherein R is a straight-chain or branched alkenyl group having from 2 to 6, in particular 2 to 4 carbon atoms. Examples include vinylamino, allylamino (2-propen-1-ylamino), 1-propen-1-ylamino, 2-propen-2-ylamino, methallylamino (2-methylprop-2-en-1-ylamino) and the like. $C_3$-$C_5$-Alkenylamino is, in particular, allylamino, 1-methylprop-2-en-1-ylamino, 2-buten-1-ylamino, 3-buten-1-ylamino, methallylamino, 2-penten-1-ylamino, 3-penten-1-ylamino, 4-penten-1-ylamino, 1-methylbut-2-en-1-ylamino or 2-ethylprop-2-en-1-ylamino.

$C_6$-$C_{12}$-Arylamino is a radical of the formula R—NH—, wherein R is an aryl group having from 6 to 12, in particular 6 carbon atoms as defined herein. Examples include phenylamine.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, iso-propylsulfonylamino, n-butylsulfonylamino, 2-butylsulfonylamino, iso-butylsulfonylamino, tert-butylsulfonylamino. (Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —NO$_2$.

$C_3$-$C_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (heteroaryl), which generally has 5, 6 or 7 ring forming atoms. Thus, the term $C_3$-$C_{12}$-heterocyclyl is meant to denote 3- to 12-membered heterocyclic radicals $M_3$-$M_{12}$-heterocyclyl, wherein the prefix $M_n$-$M_m$ indicates in each case the possible number of ring forming atoms (ring members) in the group. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $C_3$-$C_{12}$-heterocyclyl include:

C- or N-bound 3-4-membered, saturated rings, such as 2-oxiranyl, 2-oxetanyl, 3-oxetanyl, 2-aziridinyl, 3-thiethanyl, 1-azetidinyl, 2-azetidinyl, 3-azetidinyl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as tetrahydropyrrol-1-yl (pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as piperidin-1-yl, hexahydropyrimidin-1-yl, hexahydropyrazin-1-yl (piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholin-1-yl), tetrahydro-1,2-oxazin-2-yl;

C-bound, 5-membered, partially unsaturated rings, such as
2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetra-hydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetra-hydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3- thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1, 4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as
2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as
1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihdro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as
2-furyl, 3-furyl, 5-furyl, 2-thienyl, 3-thienyl, 5-thienyl, pyrrol-2-yl, pyrrol-3-yl, pyrrol-5-yl, pyrazol-3-yl, pyrazol-4-yl, pyrazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, 1,2,3-oxadiazol-imidazol-4-yl, 4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as
pyridin-2-yl, pyridin-3-yl (3-pyridyl), pyridin-4-yl (4-pyridyl), pyridin-5-yl, pyridazin-3-yl, pyridazin-4-yl, pyridazin-6-yl, pyrimidin-2-yl, pyrimidin-4-yl, pyrimidin-5-yl, pyrazin-2-yl, pyrazin-5-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as
pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocyde, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzthienyl, benzo[b]thiazolyl, benzoxazolyl, benzthiazolyl, benzimidazolyl, imidazo[b]thiazolyl, thieno[b]pyridyl, imidazo[a]pyridyl, pyrazo[a]pyridyl and pyrrol[d]pyrimidyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, dihydrobenzofuryl, chromenyl, chromanyl, dihydropyrrol[a]imidazolyl and tetrahydro benzothiazolyl.

$C_3$-$C_{12}$-Heteroarylene is a heteroaryl diradical. Examples include pyrid-2,5-ylene and pyrid-2,4-ylene.

With respect to the compounds' capability of inhibiting glycine transporter 1, the variables $R^1$, $R^{2a}$, $R^{2b}$, $R^{3a}$, $R^{3b}$, $R^4$, $Y^1$, $R^{5a}$, $R^{5b}$, $R^6$, $R^{7a}$, $R^{7b}$, $R^{7c}$, $R^{7d}$, $R^{7e}$, $R^{7f}$, $R^{8a}$, $R^{8b}$, $R^{8c}$, $R^{8a}$, $R^{8d}$, $R^{8e}$, $R^{9a}$, $R^{9b}$, $R^{9c}$, $R^{9d}$, $R^{10}$, $R^{11a}$, $R^{11b}$, $R^{12}$, $R^{13}$, $R^{14}$, $R^{15}$, $R^{16a}$, $R^{16b}$, $R^{17}$, $R^{18}$, $R^{19}$, $R^{20a}$, $R^{20b}$, $R^{21}$, n1, n2, n3, n4 and n5 preferably have the following meanings which, when taken alone or in combination, represent particular embodiments of the pyrrolidine derivatives of the formula (I) or any other formula disclosed herein.

Such embodiments of the invention include the following embodiments E1 to E312:

E1. The compounds of formula (I) as defined herein.
E2. The compounds of embodiment 1, wherein the term "substituted" means that a radical is substituted with 1, 2 or 3 substituents which are selected from the group consisting of halogen, $C_1$-$C_4$-alkyl, halogenated-$C_1$-$C_4$-alkyl, $C_3$-$C_6$-aryl-$C_1$-$C_4$-alkyl, hydroxy-$C_1$-$C_4$-alkyl, hydroxy-(halogenated $C_1$-$C_4$-alkyl), $C_1$-$C_4$-alkoxy-$C_1$-$C_4$-alkyl, amino-$C_1$-$C_4$-alkyl, $C_3$-$C_{12}$-heterocyclyl-$C_1$-$C_4$-alkyl, $C_3$-$C_7$-cycloalkyl, $C_2$-$C_4$-alkenyl, —CN, —$CO_2$H, $C_1$-$C_4$-alkoxycarbonyl, aminocarbonyl, $C_1$-$C_4$-alkylaminocarbonyl, (di-$C_1$-$C_4$-alkylamino)carbonyl, $C_6$-$C_{12}$-arylaminocarbonyl, $C_3$-$C_{12}$-heterocyclylamino carbonyl, $C_6$-$C_{12}$-aryl, oxo (=O), OH, $C_1$-$C_4$-alkoxy, halogenated-$C_1$-$C_4$-alkoxy, $C_3$-$C_7$-cycloalkoxy, carboxy-$C_1$-$C_4$-alkoxy, $C_6$-$C_{12}$-aryl-$C_1$-$C_4$-alkoxy, $C_6$-$C_{12}$-aryloxy, $C_3$-$C_{12}$-heterocyclyl-$C_1$-$C_4$-alkoxy, SH, $C_1$-$C_4$-alkylthio, $C_1$-$C_4$-alkylsulfonyl, $C_1$-$C_4$-alkylaminosulfonyl, di-$C_1$-$C_4$-alkylaminosulfonyl, $C_3$-$C_6$-arylsulfonyl, aminosulfonyl, $C_3$-$C_6$-arylaminosulfonyl, $C_3$-$C_{12}$-heterocyclylaminosulfonyl, $NH_2$, $C_1$-$C_4$-alkylamino, di-$C_1$-$C_4$-alkylamino, $C_6$-$C_{12}$-aryl-$C_1$-$C_4$-alkylamino, $C_1$-$C_4$-alkylcarbonylamino, $C_3$-$C_6$-arylcarbonylamino, $C_3$-$C_{12}$-heterocyclylcarbonylamino, $C_1$-$C_6$-alkylsulfonylamino, $C_3$-$C_6$-arylsulfonylamino, $C_3$-$C_{12}$-heterocyclylsulfonylamino and $C_3$-$C_{12}$-heterocyclyl, wherein aryl and heterocyclyl may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.
E3. The compounds of embodiment 1 or 2, wherein $R^1$ is an optionally substituted 5-membered heterocyclic ring containing at least 1 N atom and optionally 1 or 2 further heteroatoms selected from N, O and S.

E4. The compounds of any one of embodiments 1-3, wherein $R^1$ is 5-membered heterocyclic ring containing at least 1 N atom and optionally 1 or 2 further heteroatoms selected from N, O and S, wherein the ring is optionally substituted with 1, 2, or 3 substituents independently selected from the group consisting of halogen, $C_1$-$C_4$-alkyl, halogenated $C_1$-$C_4$-alkyl, $C_3$-$C_6$-cycloalkyl, $C_1$-$C_4$-alkoxycarbonyl and $C_1$-$C_4$-alkylcarbonylamino.

E5. The compounds of any one of embodiments 1-4, wherein $R^1$ is an optionally substituted 5-membered heterocyclic ring containing 1 or 2 N and 1 O.

E6. The compounds of any one of embodiments 1-4, wherein $R^1$ is an optionally substituted 5-membered heterocyclic ring containing 1 or 2 N and 1 S.

E7. The compounds of any one of embodiments 1-4, wherein $R^1$ is an optionally substituted 5-membered heterocyclic ring containing 1, 2, or 3 N.

E8. The compounds of embodiment 7, wherein $R^1$ is an optionally substituted 5-membered heterocyclic ring containing 2 N.

E9. The compounds of embodiment 8, wherein $R^1$ is optionally substituted 1,3-diazolyl.

E10. The compounds of embodiment 9, wherein the optionally substituted 1,3-diazolyl is 1,3-diazolyl optionally substituted with halogen or $C_1$-$C_4$-alkyl.

E11. The compounds of embodiment 9, wherein the optionally substituted 1,3-diazolyl is 1-methyl-1,3-diazol-4-yl.

E12. The compounds of embodiment 7, wherein $R^1$ is an optionally substituted 5-membered heterocyclic ring containing 3 N.

E13. The compounds of embodiment 12, wherein $R^1$ is the optionally substituted 1,2,3-triazolyl.

E14. The compounds of embodiment 13, wherein the optionally substituted 1,2,3-triazolyl is 1,2,3-triazolyl optionally substituted with $C_1$-$C_4$-alkyl.

E15. The compounds of embodiment 13, wherein the optionally substituted 1,2,3-triazolyl is 1-methyl-1,2,3-triazol-4-yl.

E16. The compounds of any one of embodiments 1-15, wherein $R^{2a}$ is hydrogen, halogen or $C_1$-$C_3$-alkyl, and $R^{2b}$ is hydrogen.

E17. The compounds of any one of embodiments 1-15, wherein $R^{2a}$, $R^{2b}$ are hydrogen.

E18. The compounds of any one of embodiments 1-17, wherein $R^{3a}$ is $C_3$-$C_{12}$-cycloalkyl, hydroxy, $C_1$-$C_6$-alkoxy, $C_3$-$C_{12}$-cycloalkyl-$C_1$-$C_4$-alkoxy, $C_2$-$C_6$-alkenyloxy, $C_6$-$C_{12}$-aryl-$C_1$-$C_4$-alkoxy, optionally substituted $C_6$-$C_{12}$-aryloxy, or optionally substituted $C_3$-$C_{12}$-heterocyclyl.

E19. The compounds of any one of embodiments 1-18, wherein $R^{3a}$ is optionally substituted $C_6$-$C_{12}$-aryl, provided that $R^{3a}$ is not 3,4-di-O-substituted phenyl.

E20. The compounds of any one of embodiments 1-18, wherein $R^{3a}$ is optionally substituted $C_6$-$C_{12}$-aryl, provided that there is not more than one O-bound substituent.

E21. The compounds of any one of embodiments 1-18, wherein $R^{3a}$ is $C_6$-$C_{12}$-aryl optionally substituted with 1, 2, or 3 substituents independently selected from the group consisting of halogen, $C_1$-$C_4$-alkyl and $C_1$-$C_4$-alkoxy.

E22. The compounds of any one of embodiments 1-18, wherein $R^{3a}$ is $C_6$-$C_{12}$-aryl optionally substituted with 1, 2, or 3 substituents independently selected from the group consisting of halogen and $C_1$-$C_4$-alkyl.

E23. The compounds of any one of embodiments 1-18, wherein $R^{3a}$ is $C_6$-$C_{12}$-aryloxy optionally substituted with 1, 2, or 3 substituents independently selected from the group consisting of halogen and $C_1$-$C_4$-alkyl.

E24. The compounds of any one of embodiments 1-18, wherein $R^{3a}$ is $C_3$-$C_{12}$-heterocyclyl optionally substituted with 1, 2, or 3 substituents independently selected from the group consisting of halogen, $C_1$-$C_4$-alkyl and $C_3$-$C_6$-cycloalkyl.

E25. The compounds of any one of embodiments 1-24, wherein $R^{3b}$ is hydrogen.

E26. The compounds of any one of embodiments 1-25, wherein $Y^1$ is $>CR^6$—.

E27. The compounds of any one of embodiments 1-26, wherein $R^6$ is hydrogen, $C_1$-$C_6$-alkyl, $C_6$-$C_{12}$-aryl-$C_1$-$C_4$-alkyl, hydroxy-$C_1$-$C_6$-alkyl, or hydroxyl.

E28. The compounds of any one of embodiments 1-26, wherein $R^6$ is hydrogen, methyl, benzyl, hydroxy-methyl, or hydroxy.

E29. The compounds of any one of embodiments 1-28, wherein $Y^1$ is $>N$—.

E30. The compounds of any one of embodiments 1-28, wherein $Y^1$ is $>N$— and $R^4$ is —$(CR^{7e}R^{7f})_{n3}R^{12}$.

E31. The compounds of any one of embodiments 1-30, wherein $R^{5a}$ is hydrogen, halogen or $C_1$-$C_3$-alkyl, and $R^{5b}$ is hydrogen.

E32. The compounds of any one of embodiments 1-30, wherein $R^{5a}$, $R^{5b}$ are hydrogen.

E33. The compounds of any one of embodiments 1-30, wherein $R^{5a}$, $R^{5b}$ together with the carbon atom to which they are bound form a C=O.

E34. The compounds of any one of embodiments 1-33, wherein $R^4$ is —$(CR^{7a}R^{7b})_{n1}OR^{10}$, —$(CR^{7c}R^{7d})_{n2}NR^{11a}R^{11b}$, —$(CR^{7e}R^{7f})_{n3}R^{12}$, optionally substituted $C_6$-$C_{12}$-aryl, —$NR^{8a}(CR^{9a}R^{9b})_{n4}R^{13}$, —$NR^{8b}COR^{14}$, —$NR^{8c}COOR^{15}$, —$NR^{8d}CONR^{16a}R^{16b}$, —$O(CR^{9c}R^{9d})_{n5}R^{18}$, —$COR^{19}$, —$CONR^{20a}R^{20b}$, —$SO_2R^{21}$, or optionally substituted $C_3$-$C_{12}$-heterocyclyl.

E35. The compounds of any one of embodiments 1-34, having formula

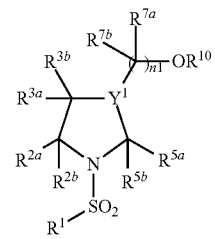

(Ia)

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and $R^{7a}$, $R^{7b}$ are independently hydrogen or $C_1$-$C_6$-alkyl;

n1 is 1, 2, 3, or 4; and $R^{10}$ is hydrogen, optionally substituted $C_6$-$C_{12}$-aryl, or optionally substituted $C_3$-$C_{12}$-heterocyclyl.

E36. The compounds of embodiment 35, wherein $R^{2a}$, $R^{2b}$ are hydrogen.

E37. The compounds of embodiment 35 or 36, wherein $R^{3a}$ is optionally substituted $C_6$-$C_{12}$-aryl.

E38. The compounds of any one of embodiments 35-37, wherein Rb is hydrogen.

E39. The compounds of any one of embodiments 35-38, wherein $Y^1$ is $>CR^6$.

E40. The compounds of any one of embodiments 35-39, wherein $R^6$ is hydrogen.

E41. The compounds of any one of embodiments 35-40, wherein $R^{7a}$, $R^{7b}$ are hydrogen.
E42. The compounds of any one of embodiments 35-41, wherein n1 is 1.
E43. The compounds of any one of embodiments 35-42, wherein $R^{5a}$, $R^{5b}$ are hydrogen.
E44. The compounds of embodiment 35, wherein
   $R^1$ is an optionally substituted 5-membered heterocyclic ring containing at least 1 N atom and optionally 1 or 2 further heteroatoms selected from N, O and S;
   $R^{2a}$, $R^{2b}$
      are hydrogen;
   $R^{3a}$ is optionally substituted $C_6$-$C_{12}$-aryl;
   $R^{3b}$ is hydrogen;
   $Y^1$ is >$CR^6$;
   $R^6$ is hydrogen;
   $R^{7a}$, $R^{7b}$
      are hydrogen;
   n1 is 1;
   $R^{10}$ is hydrogen, optionally substituted $C_6$-$C_{12}$-aryl, or optionally substituted $C_3$-$C_{12}$-heterocyclyl; and
   $R^{5a}$, $R^{5b}$
      are hydrogen.
E45. The compounds of any one of embodiments 35-44, wherein $R^1$ is an optionally substituted 5-membered heterocyclic ring containing 1, 2, or 3 N.
E46. The compounds of any one of embodiments 35-45, wherein $R^1$ is an optionally substituted 5-membered heterocyclic ring containing 2 N.
E47. The compounds of any one of embodiments 35-46, wherein $R^1$ is optionally substituted 1,3-diazolyl.
E48. The compounds of any one of embodiments 35-47, wherein $R^1$ is 1,3-diazolyl optionally substituted with halogen or $C_1$-$C_4$-alkyl.
E49. The compounds of any one of embodiments 35-48, wherein $R^{3a}$ is $C_6$-$C_{12}$-aryl optionally substituted with 1, 2, or 3 substituents independently selected from the group consisting of halogen and $C_1$-$C_4$-alkyl.
E50. The compounds of any one of embodiments 35-49, wherein $R^{10}$ is $C_6$-$C_{12}$-aryl optionally substituted with 1, 2, or 3 substituents independently selected from the group consisting of halogen, $C_1$-$C_4$-alkyl, halogenated $C_1$-$C_4$-alkyl and halogenated $C_1$-$C_4$-alkoxy.
E51. The compounds of any one of embodiments 35-49, wherein $R^{10}$ is $C_3$-$C_{12}$-heterocyclyl optionally substituted with 1, 2, or 3 substituents independently selected from the group consisting of halogenated $C_1$-$C_4$-alkyl.
E52. The compounds of embodiment 35, wherein
   $R^1$ is 1,3-diazolyl optionally substituted with halogen or $C_1$-$C_4$-alkyl;
   $R^{2a}$, $R^{2b}$
      are hydrogen;
   $R^{3a}$ is $C_6$-$C_{12}$-aryl optionally substituted with 1, 2, or 3 substituents independently selected from the group consisting of halogen and $C_1$-$C_4$-alkyl;
   $R^{3b}$ is hydrogen;
   $Y^1$ is >$CR^6$;
   $R^6$ is hydrogen;
   $R^{7a}$, $R^{7b}$
      are hydrogen;
   n1 is 1;
   $R^{10}$ is hydrogen, $C_6$-$C_{12}$-aryl optionally substituted with 1, 2, or 3 substituents independently selected from the group consisting of halogen, $C_1$-$C_4$-alkyl, halogenated $C_1$-$C_4$-alkyl and halogenated $C_1$-$C_4$-alkoxy, or $C_3$-$C_{12}$-heterocyclyl optionally substituted with 1, 2, or 3 substituents independently selected from the group consisting of halogenated $C_1$-$C_4$-alkyl; and
   $R^{5a}$, $R^{5b}$
      are hydrogen.
E53. The compounds of any one of embodiments 35-52, wherein $R^1$ is 1-methyl-1,3-diazol-4-yl.
E54. The compounds of any one of embodiments 35-53, wherein $R^{3a}$ is 4-F-phenyl.
E55. The compounds of any one of embodiments 1-34, having formula

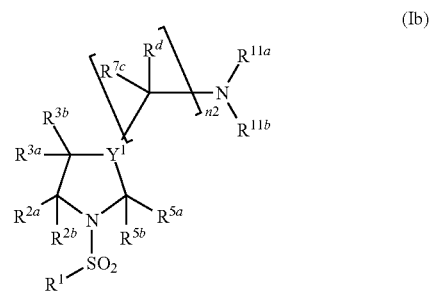

(Ib)

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and
   $R^{7e}$, $R^{7d}$
      are independently hydrogen or $C_1$-$C_6$-alkyl;
   n2 is 1, 2, 3 or 4;
   $R^{11a}$ is $C_1$-$C_8$-alkyl, (optionally substituted $C_3$-$C_{12}$-cycloalkyl)-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl; and
   $R^{11b}$
      is hydrogen or $C_1$-$C_6$-alkyl.
E56. The compounds of embodiment 55, wherein $R^{2a}$, $R^{2b}$ are hydrogen.
E57. The compounds of embodiment 55 or 56, wherein $R^{3a}$ is optionally substituted $C_6$-$C_{12}$-aryl.
E58. The compounds of any one of embodiments 55-57, wherein $R^{3b}$ is hydrogen.
E59. The compounds of any one of embodiments 55-58, wherein $Y^1$ is >$CR^6$.
E60. The compounds of any one of embodiments 55-59, wherein $R^6$ is hydrogen.
E61. The compounds of any one of embodiments 55-60, wherein $R^{7c}$, $R^{7d}$ are hydrogen.
E62. The compounds of any one of embodiments 55-61, wherein n2 is 1.
E63. The compounds of any one of embodiments 55-62, wherein $R^{11a}$ is $C_1$-$C_8$-alkyl, $C_3$-$C_{12}$-cycloalkyl-$C_1$-$C_4$-alkyl, $C_1$-$C_6$-alkoxy-$C_1$-$C_6$-alkyl, $C_6$-$C_{12}$-aryl-$C_1$-$C_4$-alkyl, or optionally substituted $C_6$-$C_{12}$-aryl.
E64. The compounds of any one of embodiments 55-63, wherein $R^{11b}$ is hydrogen.
E65. The compounds of any one of embodiments 55-64, wherein $R^{5a}$, $R^{5b}$ are hydrogen.
E66. The compounds of embodiment 55, wherein
   $R^1$ is an optionally substituted 5-membered heterocyclic ring containing at least 1 N atom and optionally 1 or 2 further heteroatoms selected from N, O and S;
   $R^{2a}$, $R^{2b}$
      are hydrogen;
   $R^{3a}$ is optionally substituted $C_6$-$C_{12}$-aryl;

$R^{3b}$ is hydrogen;
$Y^1$ is $>CR^6$;
$R^6$ is hydrogen;
$R^{7c}$, $R^{7d}$
   are hydrogen,
n2 is 1;
$R^{11a}$ is $C_1$-$C_8$-alkyl, $C_3$-$C_{12}$-cycloalkyl-$C_1$-$C_4$-alkyl, $C_1$-$C_6$-alkoxy-$C_1$-$C_6$-alkyl, $C_6$-$C_{12}$-aryl-$C_1$-$C_4$-alkyl, or optionally substituted $C_6$-$C_{12}$-aryl;
$R^{11b}$ is hydrogen; and
$R^{5a}$, $R^{5b}$
   are hydrogen.

E67. The compounds of any one of embodiments 55-66, wherein $R^1$ is an optionally substituted 5-membered heterocyclic ring containing 1, 2, or 3 N.

E68. The compounds of any one of embodiments 55-67, wherein $R^1$ is an optionally substituted 5-membered heterocyclic ring containing 2 N.

E69. The compounds of any one of embodiments 55-68, wherein $R^1$ is optionally substituted 1,3-diazolyl.

E70. The compounds of any one of embodiments 55-69, wherein $R^1$ is 1,3-diazolyl optionally substituted with halogen or $C_1$-$C_4$-alkyl.

E71. The compounds of any one of embodiments 55-70, wherein $R^{3a}$ is $C_6$-$C_{12}$-aryl optionally substituted with 1, 2, or 3 substituents independently selected from the group consisting of halogen and $C_1$-$C_4$-alkyl.

E72. The compounds of any one of embodiments 55-71, wherein $R^{11a}$ is $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, amino-$C_1$-$C_4$-alkyl, amino-carbonyl and halogenated $C_1$-$C_4$-alkoxy.

E73. The compounds of embodiment 55, wherein
$R^1$ is 1,3-diazolyl optionally substituted with halogen or $C_1$-$C_4$-alkyl;
$R^{2a}$, $R^{2b}$
   are hydrogen;
$R^{3a}$ is $C_6$-$C_{12}$-aryl optionally substituted with 1, 2, or 3 substituents independently selected from the group consisting of halogen and $C_1$-$C_4$-alkyl;
$R^{3b}$ is hydrogen;
$Y^1$ is $>CR^6$;
$R^6$ is hydrogen;
$R^{7c}$, $R^{7d}$
   are hydrogen,
n2 is 1;
$R^{11a}$ is $C_1$-$C_8$-alkyl, $C_3$-$C_{12}$-cycloalkyl-$C_1$-$C_4$-alkyl, $C_1$-$C_6$-alkoxy-$C_1$-$C_6$-alkyl, $C_6$-$C_{12}$-aryl-$C_1$-$C_4$-alkyl, or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, amino-$C_1$-$C_4$-alkyl, amino-carbonyl and halogenated $C_1$-$C_4$-alkoxy;
$R^{11b}$ is hydrogen; and
$R^{5a}$, $R^{5b}$
   are hydrogen.

E74. The compounds of any one of embodiments 55-73, wherein $R^1$ is 1-methyl-1,3-diazol-4-yl.

E75. The compounds of any one of embodiments 55-74, wherein $R^{3a}$ is 4-F-phenyl.

E76. The compounds of any one of embodiments 1-34, having formula

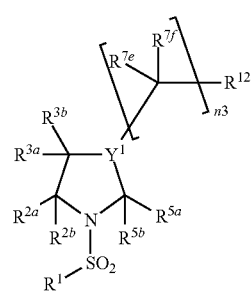

(Ic)

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and
$R^{7e}$, $R^{7f}$
   are independently hydrogen or $C_1$-$C_6$-alkyl;
n3 is 1, 2, 3, or 4; and
$R^{12}$ is optionally substituted $C_6$-$C_{12}$-aryl or optionally substituted $C_3$-$C_{12}$-heterocyclyl.

E77. The compounds of embodiment 76, wherein $R^{2a}$, $R^{2b}$ are hydrogen.

E78. The compounds of embodiment 76 or 77, wherein $R^{3a}$ is $C_3$-$C_{12}$-cycloalkyl or optionally substituted $C_6$-$C_{12}$-aryl.

E79. The compounds of any one of embodiments 76-78, wherein $R^{3b}$ is hydrogen.

E80. The compounds of any one of embodiments 76-79, wherein $Y^1$ is $>CR^6$.

E81. The compounds of any one of embodiments 76-80, wherein $R^6$ is hydrogen or hydroxy.

E82. The compounds of any one of embodiments 76-79, wherein $Y^1$ is $>N$—.

E83. The compounds of any one of embodiments 76-79, wherein $Y^1$ is $>N$— and $R^{5a}$, $R^{5b}$ together with the carbon atom to which they are bound form a C=O.

E84. The compounds of any one of embodiments 76-83, wherein $R^{7e}$, $R^{7f}$ are hydrogen.

E85. The compounds of any one of embodiments 76-84, wherein n3 is 1.

E86. The compounds of any one of embodiments 76-85, wherein $R^{5a}$, $R^{5b}$ are hydrogen or together with the carbon atom to which they are bound may form a C=O.

E87. The compounds of embodiment 76, wherein
$R^1$ is an optionally substituted 5-membered heterocyclic ring containing at least 1 N atom and optionally 1 or 2 further heteroatoms selected from N, O and S;
$R^{2a}$, $R^{2b}$
   are hydrogen;
$R^{3a}$ is $C_3$-$C_{12}$-cycloalkyl or optionally substituted $C_6$-$C_{12}$-aryl;
$R^{3b}$ is hydrogen;
$Y^1$ is $>CR^6$ or $>N$—;
$R^6$ is hydrogen or hydroxy;
$R^{7e}$, $R^{7f}$
   are hydrogen,
n3 is 1;
$R^{12}$ is optionally substituted $C_6$-$C_{12}$-aryl or optionally substituted $C_3$-$C_{12}$-heterocyclyl; and
$R^{5a}$, $R^{5b}$
   are hydrogen or together with the carbon atom to which they are bound may form a C=O.

E88. The compounds of any one of embodiments 76-87, wherein $R^1$ is an optionally substituted 5-membered heterocyclic ring containing 1, 2 or 3 N.

E89. The compounds of any one of embodiments 76-88, wherein $R^1$ is an optionally substituted 5-membered heterocyclic ring containing 2 N.
E90. The compounds of any one of embodiments 76-89, wherein $R^1$ is optionally substituted 1,3-diazolyl.
E91. The compounds of any one of embodiments 76-90, wherein $R^1$ is 1,3-diazolyl optionally substituted with halogen or $C_1$-$C_4$-alkyl.
E92. The compounds of any one of embodiments 76-91, wherein $R^{3a}$ is $C_3$-$C_{12}$-cycloalkyl or $C_6$-$C_{12}$-aryl optionally substituted with halogen.
E93. The compounds of any one of embodiments 76-92, wherein $R^{12}$ is $C_6$-$C_{12}$-aryl optionally substituted with 1, 2, or 3 substituents independently selected from the group consisting of halogen and $C_1$-$C_4$-alkyl.
E94. The compounds of any one of embodiments 76-92, wherein $R^{12}$ is $C_3$-$C_{12}$-heterocyclyl optionally substituted with 1, 2, or 3 substituents independently selected from the group consisting of $C_1$-$C_4$-alkyl and halogenated $C_1$-$C_4$-alkyl.
E95. The compounds of embodiment 76, wherein
$R^1$ is 1,3-diazolyl optionally substituted with halogen or $C_1$-$C_4$-alkyl;
$R^{2a}$, $R^{2b}$
are hydrogen;
$R^{3a}$ is $C_3$-$C_{12}$-cycloalkyl or $C_6$-$C_{12}$-aryl optionally substituted with halogen and $C_1$-$C_4$-alkyl;
$R^{3b}$ is hydrogen;
$Y^1$ is $>CR^6$ or $>N-$;
$R^6$ is hydrogen or hydroxy;
$R^{7e}$, $R^{7f}$
are hydrogen,
n3 is 1;
$R^{12}$ is $C_6$-$C_{12}$-aryl optionally substituted with 1, 2, or 3 substituents independently selected from the group consisting of halogen, or $C_3$-$C_{12}$-heterocyclyl optionally substituted with 1, 2, or 3 substituents independently selected from the group consisting of $C_1$-$C_4$-alkyl and halogenated $C_1$-$C_4$-alkyl; and
$R^{5a}$, $R^{5b}$
are hydrogen or together with the carbon atom to which they are bound may form a C=O.
E96. The compounds of any one of embodiments 76-95, wherein $R^1$ is 1-methyl-1,3-diazol-4-yl.
E97. The compounds of any one of embodiments 1-34, wherein $R^4$ is optionally substituted $C_6$-$C_{12}$-aryl.
E98. The compounds of embodiment 97, wherein $R^{2a}$, $R^{2b}$ are hydrogen.
E99. The compounds of embodiment 97 or 98, wherein $R^{3a}$ is optionally substituted $C_6$-$C_{12}$-aryl.
E100. The compounds of any one of embodiments 97-99, wherein $R^{3b}$ is hydrogen.
E101. The compounds of any one of embodiments 97-100, wherein $Y^1$ is $>CR^6$.
E102. The compounds of any one of embodiments 97-101, wherein $R^6$ is hydrogen.
E103. The compounds of any one of embodiments 97-102, wherein $R^{5a}$, $R^{5b}$ are hydrogen.
E104. The compounds of embodiment 97, wherein
$R^1$ is an optionally substituted 5-membered heterocyclic ring containing at least 1 N atom and optionally 1 or 2 further heteroatoms selected from N, O and S;
$R^{2a}$, $R^{2b}$
are hydrogen;
$R^{3a}$ is optionally substituted $C_6$-$C_{12}$-aryl;
$R^{3b}$ is hydrogen;
$R^4$ is optionally substituted $C_6$-$C_{12}$-aryl;
$Y^1$ is $>CR^6$;
$R^6$ is hydrogen; and
$R^{5a}$, $R^{5b}$
are hydrogen.
E105. The compounds of any one of embodiments 97-104, wherein $R^1$ is an optionally substituted 5-membered heterocyclic ring containing 1, 2, or 3 N.
E106. The compounds as embodiment any one of embodiments 97-105, wherein $R^1$ is an optionally substituted 5-membered heterocyclic ring containing 2 N.
E107. The compounds of any one of embodiments 97-106, wherein $R^1$ is optionally substituted 1,3-diazolyl.
E108. The compounds of any one of embodiments 97-107, wherein $R^1$ is 1,3-diazolyl optionally substituted with halogen or $C_1$-$C_4$-alkyl.
E109. The compounds of any one of embodiments 97-108, wherein $R^{3a}$ is $C_6$-$C_{12}$-aryl optionally substituted with 1, 2, or 3 substituents independently selected from the group consisting of halogen and $C_1$-$C_4$-alkyl.
E110. The compounds of any one of embodiments 97-109, wherein $R^4$ is $C_6$-$C_{12}$-aryl optionally substituted with 1, 2, or 3 substituents independently selected from the group consisting of halogen.
E111. The compounds of embodiment 97, wherein
$R^1$ is 1,3-diazolyl optionally substituted with halogen or $C_1$-$C_4$-alkyl;
$R^{2a}$, $R^{2b}$
are hydrogen;
$R^{3a}$ is $C_6$-$C_{12}$-aryl optionally substituted with halogen and $C_1$-$C_4$-alkyl;
$R^{3b}$ is hydrogen;
$R^4$ is $C_6$-$C_{12}$-aryl optionally substituted with 1, 2, or 3 substituents independently selected from the group consisting of halogen;
$Y^1$ is $>CR^6$;
$R^6$ is hydrogen; and
$R^{5a}$, $R^{5a}$
are hydrogen.
E112. The compounds of any one of embodiments 97-111, wherein $R^1$ is 1-methyl-1,3-diazol-4-yl.
E113. The compounds of any one of embodiments 97-112, wherein $R^{3a}$ is 4-F-phenyl.
E114. The compounds of any one of embodiments 1-34, having formula

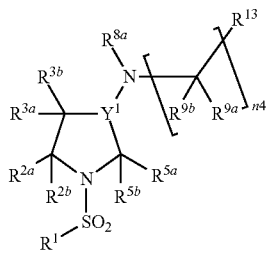

(Id)

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and
$R^{8a}$ is hydrogen, $C_1$-$C_6$-alkyl, or $C_1$-$C_6$alkylcarbonyl, or
$R^6$, $R^{8a}$
together are optionally substituted $C_1$-$C_5$-alkylene, wherein one or more —$CH_2$— of $C_1$-$C_5$-alkylene may be independently replaced by a an oxygen atom or C=O;

$R^{9a}, R^{9b}$
  are independently hydrogen, halogen, $C_1$-$C_6$-alkyl, hydroxy, or $C_1$-$C_6$-alkoxy;
n4 is 0, 1, 2, 3, or 4;
$R^{13}$ is hydrogen, $C_1$-$C_8$-alkyl, halogenated $C_1$-$C_6$-alkyl, (optionally substituted $C_3$-$C_{12}$-cycloalkyl)-$C_1$-$C_4$-alkyl, $C_1$-$C_6$-alkoxy-$C_1$-$C_6$-alkyl, optionally substituted $C_3$-$C_{12}$-cycloalkyl, $C_2$-$C_6$-alkenyl, optionally substituted $C_3$-$C_6$-cycloalkenyl, optionally substituted $C_6$-$C_{12}$-aryl, hydroxy, $C_1$-$C_6$-alkoxy, $C_1$-$C_6$-alkoxy-$C_1$-$C_4$-alkoxy, optionally substituted $C_6$-$C_{12}$-aryloxy, optionally substituted $C_3$-$C_{12}$-heterocyclyloxy, optionally substituted $C_3$-$C_{12}$-heterocyclyl, or tri-($C_1$-$C_4$-alkyl)-silyloxy.

E115. The compounds of embodiment 114, wherein $R^{2a}, R^{2b}$ are hydrogen.

E116. The compounds of embodiment 114 or 115, wherein $R^{3a}$ is $C_3$-$C_{12}$-cycloalkyl, optionally substituted $C_6$-$C_{12}$-aryl, hydroxy, $C_1$-$C_6$-alkoxy, $C_3$-$C_{12}$-cycloalkyl-$C_1$-$C_4$-alkoxy, $C_2$-$C_6$-alkenyloxy, $C_6$-$C_{12}$-aryl-$C_1$-$C_4$-alkoxy, optionally substituted $C_6$-$C_{12}$-aryloxy, or optionally substituted $C_3$-$C_{12}$-heterocyclyl.

E117. The compounds of any one of embodiments 114-116, wherein $R^{3b}$ is hydrogen or hydroxy.

E118. The compounds of any one of embodiments 114-117, wherein $Y^1$ is $>CR^6$.

E119. The compounds of any one of embodiments 114-118, wherein $R^6$ is hydrogen, $C_1$-$C_6$-alkyl, or hydroxy-$C_1$-$C_6$-alkyl.

E120. The compounds of any one of embodiments 114-119, wherein $R^{9a}, R^{9b}$ are independently hydrogen, halogen, $C_1$-$C_6$-alkyl, or $C_1$-$C_6$-alkoxy.

E121. The compounds of any one of embodiments 114-120, wherein $R^{9a}$ is hydrogen, halogen, $C_1$-$C_6$-alkyl, or $C_1$-$C_6$-alkoxy and $R^{9b}$ is hydrogen.

E122. The compounds of any one of embodiments 114-121, wherein $R^{13}$ is hydrogen, $C_1$-$C_8$-alkyl, halogenated $C_1$-$C_6$-alkyl, $C_1$-$C_6$-alkoxy-$C_1$-$C_6$-alkyl, optionally substituted $C_3$-$C_{12}$-cycloalkyl, $C_2$-$C_6$-alkenyl, optionally substituted $C_3$-$C_6$-cycloalkenyl, optionally substituted $C_6$-$C_{12}$-aryl, $C_1$-$C_6$-alkoxy, $C_1$-$C_6$-alkoxy-$C_1$-$C_4$-alkoxy, optionally substituted $C_6$-$C_{12}$-aryloxy, optionally substituted $C_3$-$C_{12}$-heterocyclyl, or tri-($C_1$-$C_4$-alkyl)-silyloxy.

E123. The compounds of any one of embodiments 114-122, wherein $R^{5a}, R^{5b}$ are hydrogen;

E124. The compounds of embodiment 114, wherein
  $R^1$ is an optionally substituted 5-membered heterocyclic ring containing at least 1 N atom and optionally 1 or 2 further heteroatoms selected from N, O and S;
  $R^{2a}, R^{2b}$
    are hydrogen;
  $R^{3a}$ is $C_3$-$C_{12}$-cycloalkyl, optionally substituted $C_6$-$C_{12}$-aryl, hydroxy, $C_1$-$C_6$-alkoxy, $C_3$-$C_{12}$-cycloalkyl-$C_1$-$C_4$-alkoxy, $C_2$-$C_6$-alkenyloxy, $C_6$-$C_{12}$-aryl-$C_1$-$C_4$-alkoxy, optionally substituted $C_6$-$C_{12}$-aryloxy, or optionally substituted $C_3$-$C_{12}$-heterocyclyl;
  $R^{3b}$ is hydrogen or hydroxy;
  $Y^1$ is $>CR^6$;
  $R^6$ is hydrogen, $C_1$-$C_6$-alkyl, or hydroxy-$C_1$-$C_6$-alkyl
  $R^{8a}$ is hydrogen, $C_1$-$C_6$-alkyl, or $C_1$-$C_6$alkylcarbonyl, or
  $R^6, R^{8a}$
    are together optionally substituted $C_1$-$C_5$-alkylene, wherein one or more —$CH_2$— of $C_1$-$C_5$-alkylene may be independently replaced by a an oxygen atom or C=O;
  $R^{9a}$ is hydrogen, halogen, $C_1$-$C_6$-alkyl, or $C_1$-$C_6$-alkoxy;
  $R^{9b}$ is hydrogen;
  n4 is 0, 1, 2, 3, or 4;
  $R^{13}$ is hydrogen, $C_1$-$C_8$-alkyl, halogenated $C_1$-$C_6$-alkyl, $C_1$-$C_6$-alkoxy-$C_1$-$C_6$-alkyl, optionally substituted $C_3$-$C_{12}$-cycloalkyl, $C_2$-$C_6$-alkenyl, optionally substituted $C_3$-$C_6$-cycloalkenyl, optionally substituted $C_6$-$C_{12}$-aryl, $C_1$-$C_6$-alkoxy, $C_1$-$C_6$-alkoxy-$C_1$-$C_4$-alkoxy, optionally substituted $C_6$-$C_{12}$-aryloxy optionally substituted $C_3$-$C_{12}$-heterocyclyl, or tri-($C_1$-$C_4$-alkyl)-silyloxy; and
  $R^{5a}, R^{5b}$
    are hydrogen.

E125. The compounds of any one of embodiments 114-124, wherein $R^1$ is an optionally substituted 5-membered heterocyclic ring containing 1, 2 or 3 N.

E126. The compounds of any one of embodiments 114-125, wherein $R^1$ is an optionally substituted 5-membered heterocyclic ring containing 2 N.

E127. The compounds of any one of embodiments 114-126, wherein $R^1$ is optionally substituted 1,3-diazolyl.

E128. The compounds of any one of embodiments 114-127, wherein $R^1$ is 1,3-diazolyl optionally substituted with halogen or $C_1$-$C_4$-alkyl.

E129. The compounds of any one of embodiments 114-125, wherein $R^1$ is an optionally substituted 5-membered heterocyclic ring containing 3 N.

E130. The compounds of any one of embodiments 114-125 or 129, wherein $R^1$ is optionally substituted 1,2,3-triazolyl.

E131. The compounds of in any one of embodiments 114-125, 129 or 130 wherein $R^1$ is 1,2,3-triazolyl optionally substituted with $C_1$-$C_4$-alkyl.

E132. The compounds of any one of embodiments 114-131, wherein $R^{3a}$ is $C_6$-$C_{12}$-aryl optionally substituted with 1, 2, or 3 substituents independently selected from the group consisting of halogen and $C_1$-$C_4$-alkyl.

E133. The compounds of any one of embodiments 114-131, wherein $R^{3a}$ is $C_6$-$C_{12}$-aryloxy optionally substituted with 1, 2, or 3 substituents independently selected from the group consisting of halogen and $C_1$-$C_4$-alkyl.

E134. The compounds of any one of embodiments 114-131, wherein $R^{3a}$ is $C_3$-$C_{12}$-heterocyclyl optionally substituted with 1, 2, or 3 substituents independently selected from the group consisting of halogen, $C_1$-$C_4$-alkyl and $C_3$-$C_6$-cycloalkyl.

E135. The compounds of any one of embodiments 114-134, wherein $R^{13}$ is $C_3$-$C_{12}$-cycloalkyl optionally substituted with 1, 2, or 3 substituents independently selected from the group consisting of halogen, $C_1$-$C_4$-alkyl, halogenated $C_1$-$C_4$-alkyl, $C_1$-$C_4$-alkoxy-$C_1$-$C_4$-alkyl and $C_6$-$C_{12}$-aryl.

E136. The compounds of any one of embodiments 114-134, wherein $R^{13}$ is $C_3$-$C_6$-cycloalkenyl optionally substituted with 1, 2, or 3 substituents independently selected from the group consisting of $C_1$-$C_4$-alkyl.

E137. The compounds of any one of embodiments 114-134, wherein $R^{13}$ is $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, hydroxy-(halogenated $C_1$-$C_4$-alkyl), CN, $C_6$-$C_{12}$-aryl, $C_1$-$C_4$-alkoxy, halogenated $C_1$-$C_4$-alkoxy, $C_6$-$C_{12}$ aryl-$C_1$-$C_4$-alkoxy, $C_6$-$C_{12}$-aryloxy, $C_1$-$C_4$-alkyl-sulfonyl, $C_1$-$C_4$-alkyl-carbonylamino and $C_3$-$C_{12}$-heterocyclyl.

E138. The compounds of any one of embodiments 114-134, wherein $R^{13}$ is $C_6$-$C_{12}$-aryloxy optionally substituted with 1, 2, or 3 substituents independently selected from the group consisting of halogen and $C_1$-$C_4$-alkyl.

E139. The compounds of any one of embodiments 114-134, wherein $R^{13}$ is $C_3$-$C_{12}$-heterocyclyl optionally substituted with 1, 2, or 3 substituents independently selected from the group consisting of halogen, $C_1$-$C_4$-alkyl, halogenated $C_1$-$C_4$-alkyl, $C_6$-$C_{12}$-aryl-$C_1$-$C_4$-alkyl, $C_3$-$C_6$-cycloalkyl, hydroxy, CN, $C_6$-$C_{12}$-aryl optionally substituted with halogen or $C_1$-$C_4$-alkyl, $C_1$-$C_4$-alkoxy, halogenated $C_1$-$C_4$-alkoxy, $C_3$-$C_6$-cycloalkoxy, $C_6$-$C_{12}$ aryl-$C_1$-$C_4$-alkoxy, $C_3$-$C_{12}$-heterocyclyl-$C_1$-$C_4$-alkoxy and $C_3$-$C_{12}$-heterocyclyl.

E140. The compounds of embodiment 114, wherein
  $R^1$ is 1,3-diazolyl optionally substituted with halogen or $C_1$-$C_4$-alkyl, or 1,2,3-triazolyl optionally substituted with $C_1$-$C_4$-alkyl;
  $R^{2a}$, $R^{2b}$
    are hydrogen;
  $R^{3a}$ is $C_3$-$C_{12}$-cycloalkyl, $C_6$-$C_{12}$-aryl optionally substituted with 1, 2, or 3 substituents independently selected from the group consisting of halogen and $C_1$-$C_4$-alkyl, or hydroxy, $C_1$-$C_6$-alkoxy, $C_3$-$C_{12}$-cycloalkyl-$C_1$-$C_4$-alkoxy, $C_2$-$C_6$-alkenyloxy, $C_6$-$C_{12}$-aryl-$C_1$-$C_4$-alkoxy, $C_6$-$C_{12}$-aryloxy optionally substituted with 1, 2, or 3 substituents independently selected from the group consisting of halogen and $C_1$-$C_4$-alkyl, or $C_3$-$C_{12}$-heterocyclyl optionally substituted with 1, 2, or 3 substituents independently selected from the group consisting of halogen, $C_1$-$C_4$-alkyl and $C_3$-$C_6$-cycloalkyl;
  $R^{3b}$ is hydrogen or hydroxy;
  $Y^1$ is >$CR^6$;
  $R^6$ is hydrogen, $C_1$-$C_6$-alkyl, or hydroxy-$C_1$-$C_6$-alkyl, or
  $R^{8a}$ is hydrogen, $C_1$-$C_6$-alkyl, or $C_1$-$C_6$-alkylcarbonyl, or
  $R^6$, $R^{8a}$
    are together optionally substituted $C_1$-$C_5$-alkylene, wherein one or more —$CH_2$— of $C_1$-$C_5$-alkylene may be independently replaced by a an oxygen atom or C=O;
  $R^{9a}$ is hydrogen, halogen, $C_1$-$C_6$-alkyl, or $C_1$-$C_6$-alkoxy;
  $R^{9b}$ is hydrogen;
  n4 is 0, 1, 2, 3, or 4;
  $R^{13}$ is hydrogen, $C_1$-$C_8$-alkyl, halogenated $C_1$-$C_6$-alkyl, $C_1$-$C_6$-alkoxy-$C_1$-$C_6$-alkyl, $C_3$-$C_{12}$-cycloalkyl optionally substituted with 1, 2, or 3 substituents independently selected from the group consisting of halogen, $C_1$-$C_4$-alkyl, halogenated $C_1$-$C_4$-alkyl, $C_1$-$C_4$-alkoxy-$C_1$-$C_4$-alkyl and $C_6$-$C_{12}$-aryl, or $C_2$-$C_6$-alkenyl, $C_3$-$C_6$-cycloalkenyl optionally substituted with 1, 2, or 3 substituents independently selected from the group consisting of $C_1$-$C_4$-alkyl, or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, hydroxy-(halogenated $C_1$-$C_4$-alkyl), CN, $C_6$-$C_{12}$-aryl, $C_1$-$C_4$-alkoxy, halogenated $C_1$-$C_4$-alkoxy, $C_6$-$C_{12}$-aryl-$C_1$-$C_4$-alkoxy, $C_6$-$C_{12}$-aryloxy, $C_1$-$C_4$-alkylsulfonyl, $C_1$-$C_4$-alkyl-carbonylamino and $C_3$-$C_{12}$-heterocyclyl, or $C_1$-$C_6$-alkoxy, $C_1$-$C_6$-alkoxy-$C_1$-$C_4$-alkoxy, $C_6$-$C_{12}$-aryloxy optionally substituted with 1, 2, or 3 substituents independently selected from the group consisting of halogen and $C_1$-$C_4$-alkyl, or $C_3$-$C_{12}$-heterocyclyl optionally substituted with 1, 2, or 3 substituents independently selected from the group consisting of halogen, $C_1$-$C_4$-alkyl, halogenated $C_1$-$C_4$-alkyl, $C_6$-$C_{12}$-aryl-$C_1$-$C_6$-alkyl, $C_3$-$C_6$-cycloalkyl, hydroxy, CN, $C_6$-$C_{12}$-aryl optionally substituted with halogen and $C_1$-$C_4$-alkyl, $C_1$-$C_4$-alkoxy, halogenated $C_1$-$C_4$-alkoxy, $C_3$-$C_6$-cycloalkoxy, $C_6$-$C_{12}$ aryl-$C_1$-$C_4$-alkoxy, $C_3$-$C_{12}$-heterocyclyl-$C_1$-$C_4$-alkoxy and $C_3$-$C_{12}$-heterocyclyl, or tri-($C_1$-$C_4$-alkyl)-silyloxy; and
  $R^{5a}$, $R^{5b}$
    are hydrogen.

E141. The compounds of any one of embodiments 114-140, wherein $R^1$ is 1-methyl-1,3-diazol-4-yl.

E142. The compounds of any one of embodiments 114-140, wherein $R^1$ is 1-methyl-1,2,3-triazol-4-yl.

E143. The compounds of any one of embodiments 114-142, wherein $R^{3a}$ is phenyl or 4-F-phenyl.

E144. The compounds of any one of embodiments 114-142, wherein $R^{3a}$ is tetrahydrofuran-2-yl or tetrahydropyran-2-yl.

E145. The compounds of any one of embodiments 114-144, wherein $R^6$ is hydrogen, methyl, or hydroxymethyl.

E146. The compounds of any one of embodiments 114-145, wherein $R^{13}$ is a group of the formula (Id1):

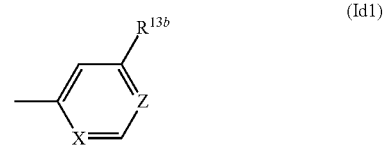

(Id1)

wherein
  X is >CH— or >N—;
  Z is >C—$R^{13c}$ or >N—;
  $R^{13b}$ is halogen, $C_1$-$C_4$-alkyl, halogenated $C_1$-$C_4$-alkyl, hydroxy-(halogenated $C_1$-$C_4$-alkyl), $C_6$-$C_{12}$-aryl-$C_1$-$C_4$-alkyl, $C_3$-$C_6$-cycloalkyl, CN, $C_6$-$C_{12}$-aryl optionally substituted with halogen or $C_1$-$C_4$-alkyl, $C_1$-$C_4$-alkoxy, halogenated $C_1$-$C_4$-alkoxy, $C_3$-$C_6$-cycloalkoxy, $C_6$-$C_{12}$ aryl-$C_1$-$C_4$-alkoxy, $C_3$-$C_{12}$-heterocyclyl-$C_1$-$C_4$-alkoxy, $C_6$-$C_{12}$-aryloxy, $C_1$-$C_4$-alkyl-sulfonyl, $C_1$-$C_4$-alkyl-carbonylamino or $C_3$-$C_{12}$-heterocyclyl; and
  $R^{13c}$ is hydrogen or halogen.

E147. The compounds of embodiment 146, wherein $R^{8a}$ is hydrogen.

E148. The compounds of embodiment 146 or 147, wherein n4 is 0.

E149. The compounds of embodiment 146 or 147, wherein n4 is 1.

E150. The compounds of embodiment 149, wherein $R^{9a}$ and $R^{9b}$ are both hydrogen.

E151. The compounds of any one of embodiments 114-150, wherein $R^6$ and $R^{8a}$ together are —C(O)OCH$_2$—.

E152. The compounds of any one of embodiments 1-34, having formula

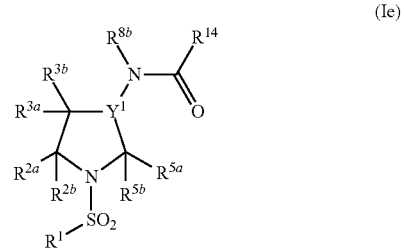

(Ie)

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and
  $R^{8b}$ is hydrogen, $C_1$-$C_6$-alkyl, or $C_1$-$C_6$-alkylcarbonyl, or $R^6$, $R^{8b}$
together are optionally substituted $C_1$-$C_5$-alkylene, wherein one or more —$CH_2$— of $C_1$-$C_5$-alkylene may be independently replaced by a an oxygen atom or C=O; and $R^{14}$ is $C_1$-$C_8$-alkyl, halogenated $C_1$-$C_6$-alkyl, (optionally substituted $C_3$-$C_{12}$-cycloalkyl)$C_1$-$C_4$-alkyl, (optionally substituted $C_6$-$C_{12}$-aryl)-$C_1$-$C_4$-alkyl, hydroxy-$C_1$-$C_6$-alkyl, $C_1$-$C_6$-alkoxy-$C_1$-$C_6$-alkyl, (optionally substituted $C_6$-$C_{12}$-aryloxy)-$C_1$-$C_4$-alkyl, $C_1$-$C_6$-alkylcarbonyl-$C_1$-$C_4$-alkyl, $C_1$-$C_6$-alkoxycarbonyl-$C_1$-$C_4$-alkyl, $C_1$-$C_6$-alkylaminocarbonyl-$C_1$-$C_4$-alkyl, optionally substituted ($C_3$-$C_{12}$-heterocyclyl)-$C_1$-$C_4$-alkyl, optionally substituted $C_3$-$C_{12}$-cycloalkyl, optionally substituted $C_6$-$C_{12}$-aryl, or optionally substituted $C_3$-$C_{12}$-heterocyclyl.

E153. The compounds of embodiment 152, wherein $R^{2a}$, $R^{2b}$ are hydrogen.

E154. The compounds of embodiment 152 or 153, wherein $R^{3a}$ is optionally substituted $C_6$-$C_{12}$-aryl or $C_3$-$C_{12}$-heterocyclyl.

E155. The compounds of any one of embodiments 152-154, wherein $R^{3b}$ is hydrogen or hydroxy.

E156. The compounds of any one of embodiments 152-155, wherein $R^{3b}$ is hydrogen.

E157. The compounds of any one of embodiments 152-156, wherein $Y^1$ is >$CR^6$.

E158. The compounds of any one of embodiments 152-157, wherein $R^6$ is hydrogen.

E159. The compounds of any one of embodiments 152-158, wherein $R^{8b}$ is hydrogen.

E160. The compounds of any one of embodiments 152-159, wherein $R^{14}$ is $C_1$-$C_8$-alkyl, halogenated $C_1$-$C_6$-alkyl, $C_3$-$C_{12}$-cycloalkyl-$C_1$-$C_4$-alkyl, hydroxy-$C_1$-$C_6$-alkyl, (optionally substituted $C_6$-$C_{12}$-aryloxy)-$C_1$-$C_4$-alkyl, $C_1$-$C_6$-alkylcarbonyl-$C_1$-$C_4$-alkyl, $C_1$-$C_6$-alkoxycarbonyl-$C_1$-$C_4$-alkyl, optionally substituted $C_3$-$C_{12}$-cycloalkyl, optionally substituted $C_6$-$C_{12}$-aryl, or optionally substituted $C_3$-$C_{12}$-heterocyclyl.

E161. The compounds of any one of embodiments 152-160, wherein $R^{5a}$, $R^{5b}$ are hydrogen.

E162. The compounds of embodiment 152, wherein
$R^1$ is an optionally substituted 5-membered heterocyclic ring containing at least 1 N atom and optionally 1 or 2 further heteroatoms selected from N, O and S;
$R^{2a}$, $R^{2b}$ are hydrogen;
$R^{3a}$ is optionally substituted $C_6$-$C_{12}$-aryl or $C_3$-$C_{12}$-heterocyclyl;
$R^{3b}$ is hydrogen;
$Y^1$ is >$CR^6$;
$R^6$ is hydrogen;
$R^{8b}$ is hydrogen;
$R^{14}$ is $C_1$-$C_8$-alkyl, halogenated $C_1$-$C_6$-alkyl, $C_3$-$C_{12}$-cycloalkyl-$C_1$-$C_4$-alkyl, hydroxy-$C_1$-$C_6$-alkyl, (optionally substituted $C_6$-$C_{12}$-aryloxy)-$C_1$-$C_4$-alkyl, $C_1$-$C_6$-alkylcarbonyl-$C_1$-$C_4$-alkyl, $C_1$-$C_6$-alkoxycarbonyl-$C_1$-$C_4$-alkyl, optionally substituted $C_3$-$C_{12}$-cycloalkyl, optionally substituted $C_6$-$C_{12}$-aryl, or optionally substituted $C_3$-$C_{12}$-heterocyclyl; and
$R^{5a}$, $R^{5b}$ are hydrogen.

E163. The compounds of any one of embodiments 152-162, wherein $R^1$ is an optionally substituted 5-membered heterocyclic ring containing 1, 2, or 3 N.

E164. The compounds of any one of embodiments 152-163, wherein $R^1$ is an optionally substituted 5-membered heterocyclic ring containing 2 N.

E165. The compounds of any one of embodiments 152-164, wherein $R^1$ is optionally substituted 1,3-diazolyl.

E166. The compounds of any one of embodiments 152-165, wherein $R^1$ is 1,3-diazolyl optionally substituted with halogen or $C_1$-$C_4$-alkyl.

E167. The compounds of any one of embodiments 152-166, wherein $R^{3a}$ is $C_6$-$C_{12}$-aryl optionally substituted with 1, 2, or 3 substituents independently selected from the group consisting of halogen, $C_1$-$C_4$-alkyl and $C_1$-$C_4$-alkoxy.

E168. The compounds of any one of embodiments 152-167, wherein $R^{14}$ is $C_6$-$C_{12}$-aryloxy-$C_1$-$C_4$-alkyl, with $C_6$-$C_{12}$-aryloxy being optionally substituted with 1, 2, or 3 substituents independently selected from the group consisting of halogen.

E169. The compounds of any one of embodiments 152-167, wherein $R^{14}$ is $C_3$-$C_{12}$-cycloalkyl optionally substituted with 1, 2, or 3 substituents independently selected from the group consisting of halogenated $C_1$-$C_4$-alkyl.

E170. The compounds of any one of embodiments 152-167, wherein $R^{14}$ is $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, CN and $C_1$-$C_4$-alkoxy.

E171. The compounds of any one of embodiments 152-167, wherein $R^{14}$ is $C_6$-$C_{12}$-aryl optionally substituted with 1, 2, or 3 substituents independently selected from the group consisting of $C_1$-$C_4$-alkyl and CN.

E172. The compounds of any one of embodiments 152-167, wherein $R^{14}$ is $C_3$-$C_{12}$-heterocyclyl optionally substituted with 1, 2, or 3 substituents independently selected from the group consisting of halogen and halogenated $C_1$-$C_4$-alkyl.

E173. The compounds of embodiment 152, wherein
$R^1$ is 1,3-diazolyl optionally substituted with halogen or $C_1$-$C_4$-alkyl;
$R^{2a}$, $R^{2b}$ are hydrogen;
$R^{3a}$ is $C_6$-$C_{12}$-aryl optionally substituted with 1, 2, or 3 substituents independently selected from the group consisting of halogen, $C_1$-$C_4$-alkyl and $C_1$-$C_4$-alkoxy, or $C_3$-$C_{12}$-heterocyclyl;
$R^{3b}$ is hydrogen;
$Y^1$ is >$CR^6$;
$R^6$ is hydrogen;
$R^{8b}$ is hydrogen;
$R^{14}$ is $C_1$-$C_8$-alkyl, halogenated $C_1$-$C_6$-alkyl, $C_3$-$C_{12}$-cycloalkyl-$C_1$-$C_4$-alkyl, hydroxy-$C_1$-$C_6$-alkyl, (halogenated $C_6$-$C_{12}$-aryloxy)-$C_1$-$C_4$-alkyl, $C_1$-$C_6$-alkylcarbonyl-$C_1$-$C_4$-alkyl, $C_1$-$C_6$-alkoxycarbonyl-$C_1$-$C_4$-alkyl, $C_3$-$C_{12}$-cycloalkyl optionally substituted with 1, 2, or 3 substituents independently selected from the group consisting of halogenated $C_1$-$C_4$-alkyl, or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, CN and $C_1$-$C_4$-alkoxy, or $C_3$-$C_{12}$-heterocyclyl optionally substituted with 1, 2, or 3 substituents independently selected from the group consisting of halogen and halogenated $C_1$-$C_4$-alkyl; and
$R^{5a}$, $R^{5b}$ are hydrogen.

E174. The compounds of any one of embodiments 152-173, wherein $R^1$ is 1-methyl-1,3-diazol-4-yl.

E175. The compounds of any one of embodiments 152-174, wherein $R^{3a}$ is phenyl, halogenated phenyl, 4-OMe-phenyl, or pyrid-2-yl.

E176. The compounds of any one of embodiments 1-34, having formula

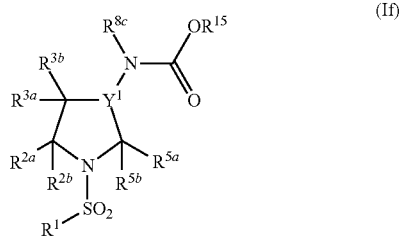

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and $R^{8c}$ is hydrogen, $C_1$-$C_6$-alkyl, or $C_1$-$C_6$-alkylcarbonyl, or $R^6$, $R^{8c}$
together are optionally substituted $C_1$-$C_5$-alkylene, wherein one or more —$CH_2$— of $C_1$-$C_5$-alkylene may be independently replaced by a an oxygen atom or C=O;

$R^{15}$ is $C_1$-$C_8$-alkyl, optionally substituted $C_6$-$C_{12}$-aryl, or optionally substituted $C_3$-$C_{12}$-heterocyclyl.

E177. The compounds of embodiment 176, wherein $R^{2a}$, $R^{2b}$ are hydrogen.

E178. The compounds of embodiment 176 or 177, wherein $R^{3a}$ is optionally substituted $C_6$-$C_{12}$-aryl.

E179. The compounds of any one of embodiments 176-178, wherein $R^{3b}$ is hydrogen.

E180. The compounds of any one of embodiments 176-179, wherein $Y^1$ is >$CR^6$.

E181. The compounds of any one of embodiments 176-180, wherein $R^6$ is hydrogen.

E182. The compounds of any one of embodiments 176-181, wherein $R^{8c}$ is hydrogen.

E183. The compounds of any one of embodiments 176-182, wherein $R^{15}$ is $C_1$-$C_6$-alkyl or $C_6$-$C_{12}$-aryl.

E184. The compounds of any one of embodiments 176-183, wherein $R^{5a}$, $R^{5b}$ are hydrogen.

E185. The compounds of embodiment 176, wherein
$R^1$ is an optionally substituted 5-membered heterocyclic ring containing at least 1 N atom and optionally 1 or 2 further heteroatoms selected from N, O and S;
$R^{2a}$, $R^{2b}$ are hydrogen;
$R^{3a}$ is optionally substituted $C_6$-$C_{12}$-aryl;
$R^{3b}$ is hydrogen;
$Y^1$ is >$CR^6$;
$R^6$ is hydrogen;
$R^{8c}$ is hydrogen;
$R^{15}$ is $C_1$-$C_6$-alkyl or $C_6$-$C_{12}$-aryl; and
$R^{5a}$, $R^{5b}$ are hydrogen.

E186. The compounds of any one of embodiments 176-185, wherein $R^1$ is an optionally substituted 5-membered heterocyclic ring containing 1, 2, or 3 N.

E187. The compounds of any one of embodiments 176-186, wherein $R^1$ is an optionally substituted 5-membered heterocyclic ring containing 2 N.

E188. The compounds of any one of embodiments 176-187, wherein $R^1$ is optionally substituted 1,3-diazolyl.

E189. The compounds of any one of embodiments 176-188, wherein $R^1$ is 1,3-diazolyl optionally substituted with halogen or $C_1$-$C_4$-alkyl.

E190. The compounds of any one of embodiments 176-189, wherein $R^{3a}$ is $C_6$-$C_{12}$-aryl optionally substituted with 1, 2, or 3 substituents independently selected from the group consisting of halogen and $C_1$-$C_4$-alkyl.

E191. The compounds of embodiment 176, wherein
$R^1$ is 1-methyl-1,3-diazol-4-yl;
$R^{2a}$, $R^{2b}$ are hydrogen;
$R^{3a}$ is $C_6$-$C_{12}$-aryl optionally substituted with 1, 2, or 3 substituents independently selected from the group consisting of halogen and $C_1$-$C_4$-alkyl;
$R^{3b}$ is hydrogen;
$Y^1$ is >$CR^6$;
$R^6$ is hydrogen;
$R^{8c}$ is hydrogen;
$R^{15}$ is $C_1$-$C_8$-alkyl or $C_6$-$C_{12}$-aryl; and
$R^{5a}$, $R^{5b}$ are hydrogen;

E192. The compounds of any one of embodiments 176-191, wherein $R^1$ is 1-methyl-1,3-diazol-4-yl.

E193. The compounds of any one of embodiments 176-192, wherein $R^{3a}$ is phenyl or 4-F-phenyl.

E194. The compounds of any one of embodiments 1-34, having formula

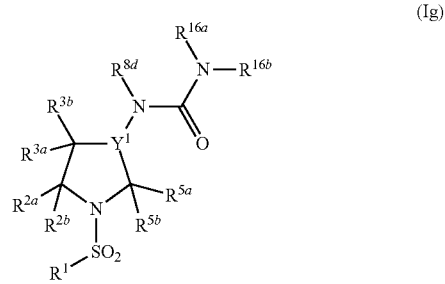

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and $R^{8d}$ is hydrogen, $C_1$-$C_6$-alkyl, or $C_1$-$C_6$-alkylcarbonyl, or $R^6$, $R^{8d}$
together are optionally substituted $C_1$-$C_5$-alkylene, wherein one or more —$CH_2$— of $C_1$-$C_5$-alkylene may be independently replaced by a an oxygen atom or C=O;

$R^{16a}$ is (optionally substituted $C_6$-$C_{12}$-aryl)-$C_1$-$C_4$-alkyl, optionally substituted ($C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl; and $R^{16b}$ is hydrogen or $C_1$-$C_6$-alkyl.

E195. The compounds of embodiment 194, wherein $R^{2a}$, $R^{2b}$ are hydrogen.

E196. The compounds of embodiment 194 or 195, wherein $R^{3a}$ is optionally substituted $C_6$-$C_{12}$-aryl.

E197. The compounds of any one of embodiments 194-196, wherein $R^{3b}$ is hydrogen.

E198. The compounds of any one of embodiments 194-197, wherein $Y^1$ is >$CR^6$.

E199. The compounds of any one of embodiments 194-198, wherein $R^6$ is hydrogen.

E200. The compounds of any one of embodiments 194-199, wherein $R^{8d}$ is hydrogen.

E201. The compounds of any one of embodiments 194-200, wherein $R^{16a}$ is (optionally substituted $C_6$-$C_{12}$-aryl)-$C_1$-$C_4$-alkyl or optionally substituted $C_6$-$C_{12}$-aryl.

E202. The compounds of any one of embodiments 194-201, wherein $R^{16b}$ is hydrogen.

E203. The compounds of any one of embodiments 194-202, wherein $R^{5a}$, $R^{5b}$ are hydrogen.

E204. The compounds of embodiment 194, wherein
$R^1$ is an optionally substituted 5-membered heterocyclic ring containing at least 1 N atom and optionally 1 or 2 further heteroatoms selected from N, O and S;
$R^{2a}$, $R^{2b}$
   are hydrogen;
$R^{3a}$ is optionally substituted $C_6$-$C_{12}$-aryl;
$R^{3b}$ is hydrogen;
$Y^1$ is >$CR^6$;
$R^6$ is hydrogen;
$R^{8d}$ is hydrogen;
$R^{16a}$ is (optionally substituted $C_6$-$C_{12}$-aryl)-$C_1$-$C_4$-alkyl or optionally substituted $C_6$-$C_{12}$-aryl;
$R^{16b}$ is hydrogen; and
$R^{5a}$, $R^{5b}$
   are hydrogen.

E205. The compounds of any one of embodiments 194-204, wherein $R^1$ is an optionally substituted 5-membered heterocyclic ring containing 1, 2, or 3 N.

E206. The compounds of any one of embodiments 194-205, wherein $R^1$ is an optionally substituted 5-membered heterocyclic ring containing 2 N.

E207. The compounds of any one of embodiments 194-206, wherein $R^1$ is optionally substituted 1,3-diazolyl.

E208. The compounds of any one of embodiments 194-207, wherein $R^1$ is 1,3-diazolyl optionally substituted with halogen or $C_1$-$C_4$-alkyl.

E209. The compounds of any one of embodiments 194-208, wherein $R^{3a}$ is $C_6$-$C_{12}$-aryl optionally substituted with 1, 2, or 3 substituents independently selected from the group consisting of halogen and $C_1$-$C_4$-alkyl.

E210. The compounds of any one of embodiments 194-209, wherein $R^{16a}$ is $C_6$-$C_{12}$-aryl-$C_1$-$C_4$-alkyl, with $C_6$-$C_{12}$-aryl being optionally substituted with 1, 2, or 3 substituents independently selected from the group consisting of halogen.

E211. The compounds of any one of embodiments 194-209, wherein $R^{16a}$ is $C_6$-$C_{12}$-aryl optionally substituted with 1, 2, or 3 substituents independently selected from the group consisting of halogen.

E212. The compounds of embodiment 194, wherein
$R^1$ is 1,3-diazolyl optionally substituted with halogen or $C_1$-$C_4$-alkyl;
$R^{2a}$, $R^{2b}$
   are hydrogen;
$R^{3a}$ is $C_6$-$C_{12}$-aryl optionally substituted with 1, 2, or 3 substituents independently selected from the group consisting of halogen and $C_1$-$C_4$-alkyl;
$R^{3b}$ is hydrogen;
$Y^1$ is >$CR^6$;
$R^6$ is hydrogen;
$R^{8d}$ is hydrogen;
$R^{16a}$ is $C_6$-$C_{12}$-aryl-$C_1$-$C_4$-alkyl or $C_6$-$C_{12}$-aryl, with $C_6$-$C_{12}$-aryl being optionally substituted with 1, 2, or 3 substituents independently selected from the group consisting of halogen;
$R^{16b}$ is hydrogen; and
$R^{5a}$, $R^{5b}$
   are hydrogen.

E213. The compounds of any one of embodiments 194-212, wherein $R^1$ is 1-methyl-1,3-diazol-4-yl.

E214. The compounds of any one of embodiments 194-213, wherein $R^{3a}$ is 4-F-phenyl.

E215. The compounds of any one of embodiments 1-34, having formula (Ih)

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and
$R^{9e}$, $R^{9d}$
   are independently hydrogen, halogen, or $C_1$-$C_6$-alkyl;
n5 is 0, 1, 2, 3, or 4; and
$R^{18}$ is hydrogen, optionally substituted $C_1$-$C_8$-alkyl, optionally substituted $C_3$-$C_{12}$-cycloalkyl, $C_1$-$C_6$-alkyl-carbonyl, $C_1$-$C_6$-alkoxycarbonyl, halogenated $C_1$-$C_6$-alkoxycarbonyl, $C_6$-$C_{12}$-aryloxycarbonyl, $C_1$-$C_6$-alkylaminocarbonyl, (halogenated $C_1$-$C_4$-alkyl)aminocarbonyl, $C_6$-$C_{12}$-arylaminocarbonyl, optionally substituted $C_6$-$C_{12}$-aryl, $C_1$-$C_6$-alkylamine, ($C_3$-$C_{12}$-cycloalkyl-$C_1$-$C_4$-alkyl)amino, (halogenated $C_1$-$C_6$-alkyl)amino, ($C_1$-$C_6$-alkoxy-$C_1$-$C_6$-alkyl)amino, ($C_6$-$C_{12}$-aryl-$C_1$-$C_4$-alkyl)amino, $C_1$-$C_6$-dialkylamine, optionally substituted $C_6$-$C_{12}$-arylamine, or optionally substituted $C_3$-$C_{12}$-heterocyclyl.

E216. The compounds of embodiment 215, wherein $R^{2a}$, $R^{2b}$ are hydrogen.

E217. The compounds of embodiment 215 or 216, wherein $R^{3a}$ is optionally substituted $C_6$-$C_{12}$-aryl or optionally substituted $C_3$-$C_{12}$-heterocyclyl.

E218. The compounds of any one of embodiments 215-217, wherein $R^{3b}$ is hydrogen.

E219. The compounds of any one of embodiments 215-218, wherein $Y^1$ is >$CR^6$.

E220. The compounds of any one of embodiments 215-219, wherein $R^6$ is hydrogen or $C_6$-$C_{12}$-aryl-$C_1$-$C_4$-alkyl.

E221. The compounds of any one of embodiments 215-220, wherein $R^6$ is hydrogen or benzyl.

E222. The compounds of any one of embodiments 215-221, wherein $R^6$ is hydrogen.

E223. The compounds of any one of embodiments 215-222, wherein n5 is 0, 1, or 2.

E224. The compounds of any one of embodiments 215-223, wherein $R^{9c}$ and $R^{9d}$ are hydrogen.

E225. The compounds of any one of embodiments 215-224, wherein $R^{18}$ is hydrogen, $C_1$-$C_8$-alkyl, $C_1$-$C_6$-alkoxycarbonyl, $C_1$-$C_6$-alkylaminocarbonyl, (halogenated $C_1$-$C_4$-alkyl)aminocarbonyl, optionally substituted $C_6$-$C_{12}$-aryl, $C_1$-$C_6$-alkylamine, (halogenated $C_1$-$C_6$-alkyl)amino, optionally substituted $C_6$-$C_{12}$-arylamine, or optionally substituted $C_3$-$C_{12}$-heterocyclyl.

E226. The compounds of any one of embodiments 215-225, wherein $R^{5a}$, $R^{5b}$ are hydrogen.

E227. The compounds of embodiment 215, wherein
  $R^1$ is an optionally substituted 5-membered heterocyclic ring containing at least 1 N atom and optionally 1 or 2 further heteroatoms selected from N, O and S;
  $R^{2a}$, $R^{2b}$
    are hydrogen;
  $R^{3a}$ is optionally substituted $C_6$-$C_{12}$-aryl or optionally substituted $C_3$-$C_{12}$-heterocyclyl;
  $R^{3b}$ is hydrogen;
  $Y^1$ is >$CR^6$;
  $R^6$ is hydrogen;
  $R^{9c}$, $R^{9d}$
    are hydrogen;
  n5 is 0, 1, or 2;
  $R^{18}$ is hydrogen, $C_1$-$C_8$-alkyl, $C_1$-$C_6$-alkoxycarbonyl, $C_1$-$C_6$-alkylaminocarbonyl, (halogenated $C_1$-$C_4$-alkyl)aminocarbonyl, optionally substituted $C_6$-$C_{12}$-aryl, $C_1$-$C_6$-alkylamine, (halogenated $C_1$-$C_6$-alkyl)amino, optionally substituted $C_6$-$C_{12}$-arylamine, or optionally substituted $C_3$-$C_{12}$-heterocyclyl; and
  $R^{5a}$, $R^{5b}$
    are hydrogen.
E228. The compounds of any one of embodiments 215-227, wherein $R^1$ is an optionally substituted 5-membered heterocyclic ring containing 1, 2, or 3 N.
E229. The compounds of any one of embodiments 215-228, wherein $R^1$ is an optionally substituted 5-membered heterocyclic ring containing 2 N.
E230. The compounds of any one of embodiments 215-229, wherein $R^1$ is optionally substituted 1,3-diazolyl.
E231. The compounds of any one of embodiments 215-230, wherein $R^1$ is 1,3-diazolyl optionally substituted with halogen or $C_1$-$C_4$-alkyl.
E232. The compounds of any one of embodiments 215-231, wherein $R^{3a}$ is $C_6$-$C_{12}$-aryl optionally substituted with 1, 2, or 3 substituents independently selected from the group consisting of halogen and $C_1$-$C_4$-alkyl, or $C_3$-$C_{12}$-heterocyclyl optionally substituted with 1, 2, or 3 substituents independently selected from the group consisting of halogen and $C_1$-$C_4$-alkyl.
E233. The compounds of any one of embodiments 215-232, wherein $R^{18}$ is $C_6$-$C_{12}$-aryl optionally substituted with 1, 2, or 3 substituents independently selected from the group consisting of halogen, $C_1$-$C_4$-alkyl and $C_1$-$C_4$-alkyl-sulfonyl.
E234. The compounds of any one of embodiments 215-232, wherein $R^{18}$ is $C_6$-$C_{12}$-arylamine optionally substituted with 1, 2, or 3 substituents independently selected from the group consisting of halogen.
E235. The compounds of any one of embodiments 215-232, wherein $R^{18}$ is $C_3$-$C_{12}$-heterocyclyl optionally substituted with 1, 2, or 3 substituents independently selected from the group consisting of halogenated $C_1$-$C_4$-alkyl.
E236. The compounds of embodiment 215, wherein
  $R^1$ is 1,3-diazolyl optionally substituted with halogen or $C_1$-$C_4$-alkyl;
  $R^{2a}$, $R^{2b}$
    are hydrogen;
  $R^{3a}$ is $C_6$-$C_{12}$-aryl optionally substituted with 1, 2, or 3 substituents independently selected from the group consisting of halogen and $C_1$-$C_4$-alkyl, or $C_3$-$C_{12}$-heterocyclyl optionally substituted with 1, 2, or 3 substituents independently selected from the group consisting of halogen and $C_1$-$C_4$-alkyl;
  $R^{3b}$ is hydrogen;
  $Y^1$ is >$CR^6$;
  $R^6$ is hydrogen;
  $R^{9c}$, $R^{9d}$
    are hydrogen;
  n5 is 0, 1, or 2;
  $R^{18}$ is hydrogen, $C_1$-$C_8$-alkyl, $C_1$-$C_6$-alkoxycarbonyl, $C_1$-$C_6$-alkylaminocarbonyl, (halogenated $C_1$-$C_4$-alkyl)aminocarbonyl, $C_6$-$C_{12}$-aryl optionally substituted with 1, 2, or 3 substituents independently selected from the group consisting of halogen, $C_1$-$C_4$-alkyl and $C_1$-$C_4$-alkyl-sulfonyl, or $C_1$-$C_6$-alkylamine, (halogenated $C_1$-$C_6$-alkyl)amino, $C_6$-$C_{12}$-arylamine optionally substituted with 1, 2, or 3 substituents independently selected from the group consisting of halogen, or $C_3$-$C_{12}$-heterocyclyl optionally substituted with 1, 2, or 3 substituents independently selected from the group consisting of halogenated $C_1$-$C_4$-alkyl; and
  $R^{5a}$, $R^{5b}$
    are hydrogen.
E237. The compounds of any one of embodiments 215-236, wherein $R^1$ is 1-methyl-1,3-diazol-4-yl.
E238. The compounds of any one of embodiments 215-237, wherein $R^{3a}$ is phenyl or 4-F-phenyl.
E239. The compounds of any one of embodiments 1-34, having formula (Ii)

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and
  $R^{19}$ is optionally substituted $C_6$-$C_{12}$-aryl or optionally substituted $C_3$-$C_{12}$-heterocyclyl.
E240. The compounds of embodiment 239, wherein $R^{2a}$, $R^{2b}$ are hydrogen.
E241. The compounds of embodiment 239 or 240, wherein $R^{3a}$ is optionally substituted $C_6$-$C_{12}$-aryl.
E242. The compounds of any one of embodiments 239-241, wherein $R^{3b}$ is hydrogen.
E243. The compounds of any one of embodiments 239-242, wherein $Y^1$ is >$CR^6$.
E244. The compounds of any one of embodiments 239-243, wherein $R^6$ is hydrogen.
E245. The compounds of any one of embodiments 239-244, wherein $R^{19}$ is optionally substituted $C_6$-$C_{12}$-aryl.
E246. The compounds of any one of embodiments 239-245, wherein $R^{5a}$, $R^{5b}$ are hydrogen.
E247. The compounds of embodiment 239, wherein
  $R^1$ is an optionally substituted 5-membered heterocyclic ring containing at least 1 N atom and optionally 1 or 2 further heteroatoms selected from N, O and S;
  $R^{2a}$, $R^{2b}$
    are hydrogen;
  $R^{3a}$ is optionally substituted $C_6$-$C_{12}$-aryl;
  $R^{3b}$ is hydrogen;
  $Y^1$ is >$CR^6$;
  $R^6$ is hydrogen;
  $R^{19}$ is optionally substituted $C_6$-$C_{12}$-aryl; and
  $R^{5a}$, $R^{5b}$
    are hydrogen.

E248. The compounds of any one of embodiments 239-247, wherein $R^1$ is an optionally substituted 5-membered heterocyclic ring containing 1, 2, or 3 N.
E249. The compounds of any one of embodiments 239-248, wherein $R^1$ is an optionally substituted 5-membered heterocyclic ring containing 2 N.
E250. The compounds of any one of embodiments 239-249, wherein $R^1$ is optionally substituted 1,3-diazolyl.
E251. The compounds of any one of embodiments 239-250, wherein $R^1$ is 1,3-diazolyl optionally substituted with halogen or $C_1$-$C_4$-alkyl.
E252. The compounds of any one of embodiments 239-251, wherein $R^{3a}$ is $C_6$-$C_{12}$-aryl optionally substituted with 1, 2, or 3 substituents independently selected from the group consisting of halogen and $C_1$-$C_4$-alkyl.
E253. The compounds of any one of embodiments 239-252, wherein $R^{19}$ is $C_6$-$C_{12}$-aryl optionally substituted with 1, 2, or 3 substituents independently selected from the group consisting of halogen, $C_1$-$C_4$-alkyl, halogenated $C_1$-$C_4$-alkyl and halogenated $C_1$-$C_4$-alkoxy.
E254. The compounds of embodiment 239, wherein
$R^1$ is 1,3-diazolyl optionally substituted with halogen or $C_1$-$C_4$-alkyl;
$R^{2a}$, $R^{2b}$
are hydrogen;
$R^{3a}$ is $C_6$-$C_{12}$-aryl optionally substituted with 1, 2, or 3 substituents independently selected from the group consisting of halogen and $C_1$-$C_4$-alkyl;
$R^{3b}$ is hydrogen;
$Y^1$ is >$CR^6$;
$R^6$ is hydrogen;
$R^{19}$ is $C_6$-$C_{12}$-aryl optionally substituted with 1, 2, or 3 substituents independently selected from the group consisting of halogen, $C_1$-$C_4$-alkyl, halogenated $C_1$-$C_4$-alkyl and halogenated $C_1$-$C_4$-alkoxy; and
$R^{5a}$, $R^{5b}$
are hydrogen.
E255. The compounds of any one of embodiments 239-254, wherein $R^1$ is 1-methyl-1,3-diazol-4-yl.
E256. The compounds of any one of embodiments 239-255, wherein $R^{3a}$ is 4-F-phenyl.
E257. The compounds of any one of embodiments 1-34, having formula

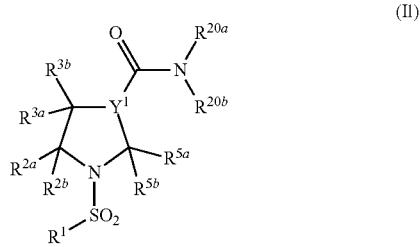

(II)

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and
$R^{20a}$ is $C_1$-$C_8$-alkyl, (optionally substituted $C_3$-$C_{12}$-cycloalkyl)-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl; and
$R^{20b}$ is hydrogen or $C_1$-$C_8$-alkyl.
E258. The compounds of embodiment 257, wherein $R^{2a}$, $R^{2b}$ are hydrogen.

E259. The compounds of embodiment 257 or 258, wherein $R^{3a}$ is optionally substituted $C_6$-$C_{12}$-aryl.
E260. The compounds of any one of embodiments 257-259, wherein $R^{3b}$ is hydrogen.
E261. The compounds of any one of embodiments 257-260, wherein $Y^1$ is >$CR^6$.
E262. The compounds of any one of embodiments 257-261, wherein $R^6$ is hydrogen.
E263. The compounds of any one of embodiments 257-262, wherein $R^{20a}$ is $C_1$-$C_8$-alkyl, $C_3$-$C_{12}$-cycloalkyl-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl.
E264. The compounds of any one of embodiments 257-263, wherein $R^{5a}$, $R^{5b}$ are hydrogen.
E265. The compounds of embodiment 257, wherein
$R^1$ is an optionally substituted 5-membered heterocyclic ring containing at least 1 N atom and optionally 1 or 2 further heteroatoms selected from N, O and S;
$R^{2a}$, $R^{2b}$
are hydrogen;
$R^{3a}$ is optionally substituted $C_6$-$C_{12}$-aryl;
$R^{3b}$ is hydrogen;
$Y^1$ is >$CR^6$;
$R^6$ is hydrogen;
$R^{20a}$ is $C_1$-$C_8$-alkyl, $C_3$-$C_{12}$-cycloalkyl-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;
$R^{20b}$ is hydrogen or $C_1$-$C_8$-alkyl; and
$R^{5a}$, $R^{5b}$
are hydrogen.
E266. The compounds of any one of embodiments 257-265, wherein $R^1$ is an optionally substituted 5-membered heterocyclic ring containing 1, 2, or 3 N.
E267. The compounds of any one of embodiments 257-266, wherein $R^1$ is an optionally substituted 5-membered heterocyclic ring containing 2 N.
E268. The compounds of any one of embodiments 257-267, wherein $R^1$ is optionally substituted 1,3-diazolyl.
E269. The compounds of any one of embodiments 257-268, wherein $R^1$ is 1,3-diazolyl optionally substituted with halogen or $C_1$-$C_4$-alkyl.
E270. The compounds of any one of embodiments 257-269, wherein $R^{3a}$ is $C_6$-$C_{12}$-aryl optionally substituted with 1, 2, or 3 substituents independently selected from the group consisting of halogen and $C_1$-$C_4$-alkyl.
E271. The compounds of any one of embodiments 257-270, wherein $R^{20a}$ is $C_6$-$C_{12}$-aryl-$C_1$-$C_4$-alkyl, with $C_6$-$C_{12}$-aryl being optionally substituted with 1, 2, or 3 substituents independently selected from the group consisting of halogen, halogenated $C_1$-$C_4$-alkyl and halogenated $C_1$-$C_4$-alkoxy.
E272. The compounds of any one of embodiments 257-270, wherein $R^{20a}$ is $C_3$-$C_{12}$-heterocyclyl$C_1$-$C_4$-alkyl, with $C_3$-$C_{12}$-heterocyclyl being optionally substituted with 1, 2, or 3 substituents independently selected from the group consisting of halogenated $C_1$-$C_4$-alkyl.
E273. The compounds of any one of embodiments 257-270, wherein $R^{20a}$ is $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, CN and halogenated $C_1$-$C_4$-alkoxy.

E274. The compounds of any one of embodiments 257-270, wherein $R^{20a}$ is $C_3$-$C_{12}$-heterocyclyl optionally substituted with 1, 2, or 3 substituents independently selected from the group consisting of halogenated $C_1$-$C_4$-alkyl.

E275. The compounds of embodiment 257, wherein
$R^1$ is 1,3-diazolyl optionally substituted with halogen or $C_1$-$C_4$-alkyl;
$R^{2a}$, $R^{2b}$
are hydrogen;
$R^{3a}$ is $C_6$-$C_{12}$-aryl optionally substituted with 1, 2, or 3 substituents independently selected from the group consisting of halogen and $C_1$-$C_4$-alkyl;
$R^{3b}$ is hydrogen;
$Y^1$ is >$CR^6$;
$R^6$ is hydrogen;
$R^{20a}$ is $C_1$-$C_8$-alkyl, $C_3$-$C_{12}$-cycloalkyl-$C_1$-$C_4$-alkyl, $C_1$-$C_6$-alkoxy-$C_1$-$C_6$-alkyl, $C_6$-$C_{12}$-aryl-$C_1$-$C_4$-alkyl and $C_6$-$C_{12}$-aryl is optionally substituted with 1, 2, or 3 substituents independently selected from the group consisting of halogen, halogenated $C_1$-$C_4$-alkyl and halogenated $C_1$-$C_4$-alkoxy, or $C_3$-$C_{12}$-heterocyclyl-$C_1$-$C_4$-alkyl and $C_3$-$C_{12}$-heterocyclyl is optionally substituted with 1, 2, or 3 substituents independently selected from the group consisting of halogenated $C_1$-$C_4$-alkyl, or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, CN and halogenated $C_1$-$C_4$-alkoxy, or $C_3$-$C_{12}$-heterocyclyl optionally substituted with 1, 2, or 3 substituents independently selected from the group consisting of halogenated $C_1$-$C_4$-alkyl;
$R^{20b}$ is hydrogen or $C_1$-$C_8$-alkyl; and
$R^{5a}$, $R^{5b}$
are hydrogen.

E276. The compounds of any one of embodiments 257-275, wherein $R^1$ is 1-methyl-1,3-diazol-4-yl.

E277. The compounds of any one of embodiments 257-276, wherein $R^{3a}$ is 4-F-phenyl.

E278. The compounds of any one of embodiments 257-277, wherein $R^{20b}$ is hydrogen or butyl.

E279. The compounds of any one of embodiments 1-34, having formula

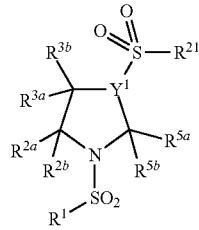

(Im)

wherein $R^1$, $R^{2a}$, $R^{2b}$, $R^{3a}$, $R^{3b}$, $Y^1$, $R^{5a}$ and $R^{5b}$ are as defined in any one of embodiments 1-34, and
$R^{21}$ is optionally substituted $C_6$-$C_{12}$-aryl, or optionally substituted $C_3$-$C_{12}$-heterocyclyl.

E280. The compounds of embodiment 279, wherein $R^{2a}$, $R^{2b}$ are hydrogen.

E281. The compounds of embodiment 279 or 280, wherein $R^{3a}$ is optionally substituted $C_6$-$C_{12}$-aryl.

E282. The compounds of any one of embodiments 279-281, wherein $R^{3b}$ is hydrogen.

E283. The compounds of any one of embodiments 279-282, wherein $Y^1$ is >$CR^6$.

E284. The compounds of any one of embodiments 279-283, wherein $R^6$ is hydrogen.

E285. The compounds of any one of embodiments 279-284, wherein $R^{21}$ is $C_6$-$C_{12}$-aryl.

E286. The compounds of any one of embodiments 279-285, wherein $R^{5a}$, $R^{5b}$ are hydrogen.

E287. The compounds of embodiment 279, wherein
$R^1$ is an optionally substituted 5-membered heterocyclic ring containing at least 1 N atom and optionally 1 or 2 further heteroatoms selected from N, O and S;
$R^{2a}$, $R^{2b}$
are hydrogen;
$R^{3a}$ is optionally substituted $C_6$-$C_{12}$-aryl;
$R^{3b}$ is hydrogen;
$Y^1$ is >$CR^6$;
$R^6$ is hydrogen;
$R^{21}$ is $C_6$-$C_{12}$-aryl; and
$R^{5a}$, $R^{5b}$
are hydrogen.

E288. The compounds of any one of embodiments 279-287, wherein $R^1$ is an optionally substituted 5-membered heterocyclic ring containing 1, 2, or 3 N.

E289. The compounds of any one of embodiments 279-288, wherein $R^1$ is an optionally substituted 5-membered heterocyclic ring containing 2 N.

E290. The compounds of any one of embodiments 279-289, wherein $R^1$ is optionally substituted 1,3-diazolyl.

E291. The compounds of any one of embodiments 279-290, wherein $R^1$ is 1,3-diazolyl optionally substituted with halogen or $C_1$-$C_4$-alkyl.

E292. The compounds of any one of embodiments 279-291, wherein $R^{3a}$ is $C_6$-$C_{12}$-aryl.

E293. The compounds of embodiment 279, wherein
$R^1$ is 1,3-diazolyl optionally substituted with halogen or $C_1$-$C_4$-alkyl;
$R^{2a}$, $R^{2b}$
are hydrogen;
$R^{3a}$ is $C_6$-$C_{12}$-aryl;
$R^{3b}$ is hydrogen;
$Y^1$ is >$CR^6$;
$R^6$ is hydrogen;
$R^{21}$ is $C_6$-$C_{12}$-aryl; and
$R^{5a}$, $R^{5b}$
are hydrogen.

E294. The compounds of any one of embodiments 279-293, wherein $R^1$ is 1-methyl-1,3-diazol-4-yl.

E295. The compounds of any one of embodiments 279-294, wherein $R^{3a}$ is phenyl.

E296. The compounds of any one of embodiments 279-295, wherein $R^{21}$ is phenyl.

E297. The compounds of any one of embodiments 1-34, wherein $R^4$ is optionally substituted $C_3$-$C_{12}$-heterocyclyl.

E298. The compounds of embodiment 297, wherein $R^{2a}$, $R^{2b}$ are hydrogen.

E299. The compounds of embodiment 297 or 298, wherein $R^{3a}$ is optionally substituted $C_6$-$C_{12}$-aryl or $C_3$-$C_{12}$-heterocyclyl.

E300. The compounds of any one of embodiments 297-299, wherein $R^{3b}$ is hydrogen.

E301. The compounds of any one of embodiments 297-300, wherein $Y^1$ is >$CR^6$.

E302. The compounds of any one of embodiments 297-301, wherein $R^6$ is hydrogen.

E303. The compounds of any one of embodiments 297-302, wherein $R^{5a}$, $R^{5b}$ are hydrogen.

E304. The compounds of embodiment 297, wherein
- $R^1$ is an optionally substituted 5-membered heterocyclic ring containing at least 1 N atom and optionally 1 or 2 further heteroatoms selected from N, O and S;
- $R^{2a}$, $R^{2b}$
  - are hydrogen;
- $R^{3a}$ is optionally substituted $C_6$-$C_{12}$-aryl or $C_3$-$C_{12}$-heterocyclyl;
- $R^{3b}$ is hydrogen;
- $R^4$ is optionally substituted $C_3$-$C_{12}$-heterocyclyl;
- $Y^1$ is $>CR^6$;
- $R^6$ is hydrogen; and
- $R^{5a}$, $R^{5b}$
  - are hydrogen.

E305. The compounds of any one of embodiments 297-304, wherein $R^1$ is an optionally substituted 5-membered heterocyclic ring containing 1, 2 or 3 N.

E306. The compounds of any one of embodiments 297-305, wherein $R^1$ is an optionally substituted 5-membered heterocyclic ring containing 2 N.

E307. The compounds of any one of embodiments 297-306, wherein $R^1$ is optionally substituted 1,3-diazolyl.

E308. The compounds of any one of embodiments 297-307, wherein $R^1$ is 1,3-diazolyl optionally substituted with halogen or $C_1$-$C_4$-alkyl.

E309. The compounds of any one of embodiments 297-308, wherein $R^{3a}$ is $C_6$-$C_{12}$-aryl optionally substituted with 1, 2, or 3 substituents independently selected from the group consisting of halogen and $C_1$-$C_4$-alkyl.

E310. The compounds of any one of embodiments 297-309, wherein $R^4$ is a $C_3$-$C_{12}$-heterocyclyl substituted with 1, 2, or 3 substituents independently selected from the group consisting of halogen, $C_1$-$C_4$-alkyl and halogenated $C_1$-$C_4$-alkyl.

E311. The compounds of embodiment 297, wherein
- $R^1$ is 1,3-diazolyl optionally substituted with halogen or $C_1$-$C_4$-alkyl;
- $R^{2a}$, $R^{2b}$
  - are hydrogen;
- $R^{3a}$ is $C_6$-$C_{12}$-aryl optionally substituted with 1, 2, or 3 substituents independently selected from the group consisting of halogen and $C_1$-$C_4$-alkyl, or $C_3$-$C_{12}$-heterocyclyl;
- $R^{3b}$ is hydrogen;
- $R^4$ is $C_3$-$C_{12}$-heterocyclyl substituted with 1, 2, or 3 substituents independently selected from the group consisting of halogen, $C_1$-$C_6$-alkyl and halogenated $C_1$-$C_4$-alkyl;
- $Y^1$ is $>CR^6$;
- $R^6$ is hydrogen; and
- $R^{5a}$, $R^{5b}$
  - are hydrogen.

E312. The compounds of any one of embodiments 297-311, wherein $R^1$ is 1-methyl-1,3-diazol-4-yl.

E313. The compounds of any one of embodiments 297-311, wherein $R^{3a}$ is phenyl, 4-F-phenyl, or pyrid-2-yl.

According to one embodiment, the present invention relates to pyrrolidine derivatives of the formula (I), wherein
$R^1$ is $C_1$-$C_8$-alkyl, (optionally substituted $C_3$-$C_{12}$-cycloalkyl)-$C_1$-$C_4$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_3$-$C_{12}$-cycloalkyl, optionally substituted $C_6$-$C_{12}$-aryl, or optionally substituted $C_3$-$C_{12}$-heterocyclyl;
$R^{2a}$, $R^{2b}$
  are independently hydrogen, halogen, or $C_1$-$C_3$-alkyl; or
$R^{2a}$, $R^{2b}$
  together with the carbon atom to which they are bound may form a C=O;
$R^{3a}$
  is $C_3$-$C_{12}$-cycloalkyl, optionally substituted $C_6$-$C_{12}$-aryl, hydroxy, $C_1$-$C_6$-alkoxy, halogenated $C_1$-$C_6$-alkoxy, $C_3$-$C_{12}$-cycloalkyl-$C_1$-$C_4$-alkoxy, $C_2$-$C_6$-alkenyloxy, $C_6$-$C_{12}$-aryl-$C_1$-$C_4$-alkoxy, $C_3$-$C_{12}$-heterocyclyl-$C_1$-$C_4$-alkoxy, optionally substituted $C_6$-$C_{12}$-aryloxy, $C_3$-$C_{12}$-heterocyclyloxy, or optionally substituted $C_3$-$C_{12}$-heterocyclyl;
$R^{3b}$ is hydrogen, $C_1$-$C_6$-alkyl, or hydroxy;
$Y^1$ is $>CR^6$— or $>N$—;
$R^6$ is hydrogen, $C_1$-$C_6$-alkyl, halogenated $C_1$-$C_6$-alkyl, (optionally substituted $C_6$-$C_{12}$-aryl)-$C_1$-$C_4$-alkyl, hydroxy-$C_1$-$C_6$-alkyl, $C_1$-$C_4$-alkoxy-$C_1$-$C_6$-alkyl, or hydroxy;
$R^4$ is —$(CR^{7a}R^{7b})_{n1}OR^{10}$, —$(CR^{7c}R^{7d})_{n2}NR^{11a}R^{11b}$, —$(CR^{7e}R^{7f})_{n3}R^{12}$, optionally substituted $C_6$-$C_{12}$-aryl, —$NR^{8a}(CR^{9a}R^{9b})_{n4}R^{13}$, —$NR^{8b}COR^{14}$, —$NR^{8c}COOR^{15}$, —$NR^{8d}CONR^{16a}R^{16b}$, —$NR^{8e}SO_2R^{17}$, —$O(CR^{9c}R^{9d})_{n5}R^{18}$, —$COR^{19}$, —$CONR^{20a}R^{20b}$, —$SO_2R^{21}$, or optionally substituted $C_3$-$C_{12}$-heterocyclyl;
$R^{7a}$, $R^{7b}$
  are independently hydrogen or $C_1$-$C_6$-alkyl;
n1 is 1, 2, 3, or 4;
$R^{10}$ is hydrogen, optionally substituted $C_6$-$C_{12}$-aryl, or optionally substituted $C_3$-$C_{12}$-heterocyclyl;
$R^{7c}$, $R^{7d}$
  are independently hydrogen or $C_1$-$C_6$-alkyl;
n2 is 1, 2, 3, or 4;
$R^{11a}$ is $C_1$-$C_8$-alkyl, (optionally substituted $C_3$-$C_{12}$-cycloalkyl)-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;
$R^{11b}$
  is hydrogen or $C_1$-$C_6$-alkyl;
$R^{7e}$, $R^{7f}$
  are independently hydrogen or $C_1$-$C_6$-alkyl;
n3 is 1, 2, 3, or 4;
$R^{12}$
  is optionally substituted $C_6$-$C_{12}$-aryl or optionally substituted $C_3$-$C_{12}$-heterocyclyl;
$R^{8a}$, $R^{8b}$, $R^{8c}$, $R^{8d}$, $R^{8e}$
  are independently hydrogen, $C_1$-$C_6$-alkyl, or $C_1$-$C_6$-alkylcarbonyl, or
$R^6$ and one of $R^{8a}$, $R^{8b}$, $R^{8c}$, $R^{8d}$, or $R^{8e}$
  together are optionally substituted $C_1$-$C_5$-alkylene, wherein one or more —$CH_2$— of $C_1$-$C_5$-alkylene may be independently replaced by a an oxygen atom or C=O;
$R^{9a}$, $R^{9b}$
  are independently hydrogen, halogen, $C_1$-$C_6$-alkyl, hydroxy, or $C_1$-$C_6$-alkoxy;
n4 is 0, 1, 2, 3, or 4;
$R^{13}$ is hydrogen, $C_1$-$C_8$-alkyl, halogenated $C_1$-$C_6$-alkyl, (optionally substituted $C_3$-$C_{12}$-cycloalkyl)-$C_1$-$C_4$-alkyl, $C_1$-$C_6$-alkoxy-$C_1$-$C_6$-alkyl, optionally substituted $C_3$-$C_{12}$-cycloalkyl, $C_2$-$C_6$-alkenyl, optionally substituted $C_3$-$C_6$-cycloalkenyl, optionally substituted $C_6$-$C_{12}$-aryl, hydroxy, $C_1$-$C_6$-alkoxy, $C_1$-$C_6$-alkoxy-$C_1$-$C_4$-alkoxy, optionally substituted $C_6$-$C_{12}$-aryloxy, optionally substituted $C_3$-$C_{12}$-heterocyclyloxy, optionally substituted $C_3$-$C_{12}$-heterocyclyl, or tri-($C_1$-$C_4$-alkyl)-silyloxy;
$R^{14}$ is $C_1$-$C_8$-alkyl, halogenated $C_1$-$C_6$-alkyl, (optionally substituted $C_3$-$C_{12}$-cycloalkyl)-$C_1$-$C_4$-alkyl, (optionally substituted $C_6$-$C_{12}$-aryl)-$C_1$-$C_4$-alkyl, hydroxy-$C_1$-$C_6$-alkyl, $C_1$-$C_6$-alkoxy-$C_1$-$C_6$-alkyl, (optionally substituted $C_6$-$C_{12}$-aryloxy)-$C_1$-$C_4$-alkyl, $C_1$-$C_6$-alkylcarbonyl-$C_1$-$C_4$-alkyl, $C_1$-$C_6$-alkoxycarbonyl-$C_1$-$C_4$-alkyl, $C_1$-$C_6$-alkylaminocarbonyl-$C_1$-$C_4$-alkyl, optionally substituted ($C_3$-$C_{12}$-heterocyclyl)-$C_1$-$C_4$-alkyl, optionally substituted $C_3$-$C_{12}$-cycloalkyl, optionally substituted $C_6$-$C_{12}$-aryl, or optionally substituted $C_3$-$C_{12}$-heterocyclyl;

$R^{15}$ is $C_1$-$C_8$-alkyl, optionally substituted $C_6$-$C_{12}$-aryl, or optionally substituted $C_3$-$C_{12}$-heterocyclyl;

$R^{16a}$ is (optionally substituted $C_6$-$C_{12}$-aryl)-$C_1$-$C_4$-alkyl, optionally substituted ($C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{16b}$ is hydrogen or $C_1$-$C_6$-alkyl;

$R^{17}$ is (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{9c}$, $R^{9d}$ are independently hydrogen, halogen, or $C_1$-$C_6$-alkyl;

n5 is 0, 1, 2, 3, or 4;

$R^{18}$ is hydrogen, $C_1$-$C_8$-alkyl, optionally substituted $C_3$-$C_{12}$-cycloalkyl, $C_1$-$C_6$alkylcarbonyl, $C_1$-$C_6$-alkoxycarbonyl, halogenated $C_1$-$C_6$-alkoxycarbonyl, $C_6$-$C_{12}$-aryloxycarbonyl, $C_1$-$C_6$-alkylaminocarbonyl, (halogenated $C_1$-$C_4$-alkyl)aminocarbonyl, $C_6$-$C_{12}$arylaminocarbonyl, optionally substituted $C_6$-$C_{12}$-aryl, $C_1$-$C_6$-alkylamine, ($C_3$-$C_{12}$-cycloalkyl-$C_1$-$C_4$-alkyl)amino, (halogenated $C_1$-$C_6$-alkyl)amino, ($C_1$-$C_6$-alkoxy-$C_1$-$C_6$-alkyl)amino, ($C_6$-$C_{12}$-aryl-$C_1$-$C_4$-alkyl)amino, $C_1$-$C_6$-dialkylamine, optionally substituted $C_6$-$C_{12}$-arylamine, or optionally substituted $C_3$-$C_{12}$-heterocyclyl;

$R^{19}$ is optionally substituted $C_6$-$C_{12}$-aryl or optionally substituted $C_3$-$C_{12}$-heterocyclyl;

$R^{20a}$ is $C_1$-$C_8$-alkyl, (optionally substituted $C_3$-$C_{12}$-cycloalkyl)-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{20b}$ is hydrogen or $C_1$-$C_8$-alkyl;

$R^{21}$ is optionally substituted $C_6$-$C_{12}$-aryl, or optionally substituted $C_3$-$C_{12}$-heterocyclyl; and $R^{5a}$, $R^{5b}$ are independently hydrogen, halogen, or $C_1$-$C_3$-alkyl, or $R^{5a}$, $R^{5b}$ together with the carbon atom to which they are bound may form a C=O, or a physiologically tolerated salt thereof.

$R^1$ is $C_1$-$C_8$-alkyl (e.g. methyl; ethyl, or n-propyl), (optionally substituted $C_3$-$C_{12}$-cycloalkyl)-$C_1$-$C_4$-alkyl (e.g. cyclopropylmethyl), (optionally substituted $C_6$-$C_{12}$-aryl)-$C_1$-$C_4$-alkyl, (optionally substituted $C_3$-$C_{12}$-heterocyclyl)-$C_1$-$C_4$-alkyl (e.g. tetrahydropyran-2-yl-methyl), optionally substituted $C_3$-$C_{12}$-cycloalkyl (e.g. cyclobutyl, or cyclohexyl), optionally substituted $C_6$-$C_{12}$-aryl (e.g. phenyl, 2-Cl-phenyl, 4-Cl-phenyl, 3-Cl-phenyl, 2,4-dichlorophenyl, 4-CF$_3$-phenyl, 2-Cl-3-CF$_3$-phenyl, 2-CN-phenyl, 2-aminocarbonyl-phenyl, or 4-OMe-phenyl), or optionally substituted $C_3$-$C_{12}$-heterocyclyl (e.g. 2,5-dimethyl-furan-3-yl, 4-methyl-thiophen-2-yl, 5-methyl-thiophen-2-yl, 5-ethyl-thiophen-2-yl, 2,5-dimethyl-thiophen-3-yl, 5-Cl-thiophen-2-yl, 2-methoxycarbonyl-thiophen-3-yl, 3-methoxy-4-methoxycarbonyl-thiophen-2-yl, 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-CF$_3$-1,2-diazol-4-yl, 1-cyclopentyl-3-Me-1,2-diazol-4-yl, 1,3,5-trimethyl-1,2-diazol-4-yl, 1-CHF$_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, 2-methylcarbonylamino-1,3-thiazol-5-yl, 3-pyridyl, 2-CF$_3$-pyrid-5-yl, 2-(morpholin-1-yl)-pyrid-5-yl, 2-OMe-pyrid-5-yl, 1-methylcarbonyl-indolin-5-yl, 1,2-benzoxazol-5-yl, 1,4-dihydroquinoxaline-2,3-dion-6-yl, 6-chloro-imidazo[2,1-b]thiazol-5-yl, 6,7-dihydro-5H-pyrrolo[1,2-a]imidazol-3-yl, 3H-1,3-benzoxazol-2-on-5-yl, 3,3-dimethylindolin-2-on-5-yl, indolin-2-on-5-yl, 1,3-dihydrobenzimidazol-2-on-5-yl, 1H-quinazoline-2,4-dion-6-yl, 6-Me-4H-1,4-benzoxazin-3-on-7-yl, 2,3-dihydrobenzofuran-5-yl, 2,3-dihydro-1,4-benzodioxin-6-yl, 1,3-benzodioxol-5-yl, isoquinoline-5-yl, 3,4-dihydro-1H-quinolin-2-on-6yl, 1-Me-indol-5yl, pyrrolidin-1-yl, 4-Me-piperidin-1-yl, morpholin-1-yl, a further example being 1-ethyl-1,3-diazol-4-yl or 1-methyl-1,2,4-triazol-3-yl).

Preferably, $R^1$ is an optionally substituted 5-membered heterocyclic ring containing at least 1 N atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-iso-propyl-3-methyl-1,2-diazol-4-yl, 1-Me-3-CF$_3$-1,2-diazol-4-yl, 1-cyclopentyl-3-Me-1,2-diazol-4-yl, 1,3,5-trimethyl-1,2-diazol-4-yl, 1-CHF$_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl).

According to one embodiment, $R^1$ is an optionally substituted 5-membered heterocyclic ring containing 1 or 2 N and 1 O (e.g. 5-methyl-1,2-oxazol-4-yl or 3,5-dimethyl-1,2-oxazol-4-yl). According to an alternative embodiment, $R^1$ is an optionally substituted 5-membered heterocyclic ring containing 1 or 2 N and 1 S (e.g. 2,4-dimethyl-1,3-thiazol-5-yl or 2-methylcarbonylamino-1,3-thiazol-5-yl). According to a further alternative embodiment, $R^1$ is an optionally substituted 5-membered heterocyclic ring containing 1, 2 or 3 N (e.g. 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-iso-propyl-3-methyl-1,2-diazol-4-yl, 1-Me-3-CF$_3$-1,2-diazol-4-yl, 1-cyclopentyl-3-Me-1,2-diazol-4-yl, 1,3,5-trimethyl-1,2-diazol-4-yl, 1-CHF$_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl or 1-Me-1,2,3-triazol-4-yl, a further example being 1-ethyl-1,3-diazol-4-yl or 1-methyl-1,2,4-triazol-3-yl).

Preferably, $R^1$ is an optionally substituted 5-membered heterocyclic ring containing 2 N which, in particular, is optionally substituted 1,3-diazolyl.

According to a further preferred embodiment, $R^1$ is an optionally substituted 5-membered heterocyclic ring containing 3 N which, in particular, is optionally substituted 1,2,3-triazolyl.

In connection with $R^1$, substituted 5-membered heterocyclic rings containing at least 1 N atom and optionally 1 or 2 further heteroatoms selected from N, O and S in particular include 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxycarbonyl and $C_1$-$C_6$-alkylcarbonylamino.

Preferably, the substituent(s) on the heterocyclic ring are independently selected from the group consisting of halogen and $C_1$-$C_6$-alkyl.

In particular, the substituent(s) on the heterocyclic ring are independently selected from the group consisting of $C_1$-$C_6$-alkyl, especially $C_1$-$C_4$-alkyl (e.g. methyl).

According to a particular embodiment, 1,3-diazolyl is substituted with halogen or $C_1$-$C_6$-alkyl as described herein. According to a specific embodiment, $R^1$ is 1-methyl-1,3-diazol-4-yl.

According to a further particular embodiment, 1,2,3-triazolyl is substituted with $C_1$-$C_6$-alkyl as described herein. According to a further specific embodiment, $R^1$ is 1-methyl-1,2,3-triazol-4-yl.

$R^{2a}$, $R^{2b}$ are independently hydrogen, halogen (e.g. F), or $C_1$-$C_3$-alkyl (e.g. methyl, ethyl, n-propyl, or iso-propyl), or $R^{2a}$, $R^{2b}$ together with the carbon atom to which they are bound may form a C=O.

According to one particular embodiment $R^{2a}$ is hydrogen, halogen (e.g. F) or $C_1$-$C_3$-alkyl (e.g. methyl or ethyl), and $R^{2b}$ is hydrogen. Preferably, $R^{2a}$, $R^{2b}$ are both hydrogen.

$R^{3a}$ is $C_3$-$C_{12}$-cycloalkyl (cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), hydroxy, $C_1$-$C_6$-alkoxy (e.g. methoxy, ethoxy, n-propoxy, iso-propoxy, or iso-butoxy) halogenated $C_1$-$C_6$-alkoxy (e.g. $OCF_3$), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), $C_3$-$C_{12}$-heterocyclyl-$C_1$-$C_4$-alkoxy (e.g. 2-(N-pyrrolidinyl)ethoxy, 2-(N-morpholinyl)ethoxy, or 2-(N-imidazolyl)ethoxy), optionally substituted $C_6$-$C_{12}$-aryloxy (e.g. phenoxy or 4-F-phenoxy), $C_3$-$C_{12}$-heterocyclyloxy (e.g. pyridin-2-yloxy), or optionally substituted $C_3$-$C_{12}$-heterocyclyl (tetrahydrofuran-2-yl, tetrahydrofuran-3-yl, tetrahydropyran-2-yl, tetrahydropyran-3-yl, 1-cyclopropyl-piperidin-4-yl, 1-cyclopropylpiperidin-3-yl, 2-pyridyl, 3-pyridyl, 3-F-pyrid-2-yl, 1,3-oxazol-4-yl, 1,3-oxazol-2-yl, 3-F-azetidin-1-yl, morpholin-1-yl, pyrrolidin-1-yl, piperidin-1-yl, 2-Me-piperidin-1yl, 3-Me-piperidin-1yl, 4-Me-piperidin-1-yl, 4-F-piperidin-1-yl, 4,4-diF-piperidin-1-yl, or azepan-1-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, 1-methyl-piperidin-2-yl, or 5-F-pyrid-2-yl). Additionally, $R^{3a}$ and one of $R^{2a}$ or $R^{2b}$ together with the carbon atoms to which they are bound may form an optionally substituted anellated $C_6$-$C_{12}$-aryl (e.g. phenyl) such as a group of the formula:

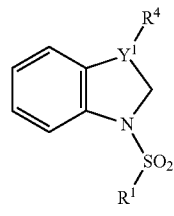

(which is shown herein for illustration purpose without being intended to limit the scope of the invention).

In particular, $R^{3a}$ is $C_3$-$C_{12}$-cycloalkyl (cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), $C_3$-$C_{12}$-heterocyclyloxy (e.g. pyridin-2-yloxy), or optionally substituted $C_3$-$C_{12}$-heterocyclyl (tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, 1,3-oxazol-2-yl, 3-F-azetidin-1-yl, morpholin-1-yl, pyrrolidin-1-yl, piperidin-1-yl, 2-Me-piperidin-1yl, 3-Me-piperidin-1yl, 4-Me-piperidin-1-yl, 4-F-piperidin-1-yl, 4,4-diF-piperidin-1yl, or azepan-1-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, 1-Me-piperidin-2-yl, or 5-F-pyrid-2-yl). In particular, $R^{3a}$ and one of $R^{2a}$ or $R^{2b}$ together with the carbon atoms to which they are bound may form an anellated $C_6$-$C_{12}$-aryl (e.g. phenyl).

Preferably, $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluorophenyl, a further example being 2-Me-phenyl, 3-Me-phenyl, or 4-Me-phenyl), or optionally substituted $C_3$-$C_{12}$-heterocyclyl (tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, 1,3-oxazol-2-yl, 3-F-azetidin-1-yl, morpholin-1-yl, pyrrolidin-1-yl, piperidin-1-yl, 2-Me-piperidin-1yl, 3-Me-piperidin-1yl, 4-Me-piperidin-1-yl, 4-F-piperidin-1-yl, 4,4-diF-piperidin-1yl, or azepan-1-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, 1-Me-piperidin-2-yl, or 5-F-pyrid-2-yl).

According to one preferred embodiment, $R^{3a}$ is optionally substituted $C_6$-$C_{12}$-aryl wherein $C_6$-$C_{12}$-aryl is phenyl, in particular phenyl optionally substituted with 1, 2, or 3 substituents independently selected from the group consisting of halogen (e.g. phenyl, 4-F-phenyl, 2-F-phenyl, 3-F-phenyl, 2-Cl-phenyl, 2-Br-phenyl, 3-Cl-phenyl, or 2,4,5-trifluorophenyl).

According to a further preferred embodiment, $R^{3a}$ is optionally substituted $C_3$-$C_{12}$-heterocyclyl wherein $C_3$-$C_{12}$-heterocyclyl is in particular tetrahydrofuranyl or tetrahydropyranyl, preferably unsubstituted tetrahydrofuranyl (e.g. tetrahydrofuran-2-yl) or unsubstituted tetrahydropyranyl (e.g. tetrahydropyran-2-yl), or wherein $C_3$-$C_{12}$-heterocyclyl is pyridyl (e.g. 5-F-pyrid-2-yl) or piperidinyl.

According to an additional aspect, $R^{3a}$ is not 3,4-di-O-substituted phenyl if $R^{3a}$ is optionally substituted $C_6$-$C_{12}$- aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl). According to a further additional aspect, there is not more than one O-bound substituent on the aryl group if $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl).

In connection with $R^{3a}$, substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy.

Preferably, the substituent(s) on $C_6$-$C_{12}$-aryl are independently selected from the group consisting of halogen.

In connection with $R^{3a}$, substituted $C_6$-$C_{12}$-aryloxy in particular includes $C_6$-$C_{12}$-aryloxy, such as phenoxy, which is substituted with 1, 2, or 3 substituents independently selected from the group consisting of halogen and $C_1$-$C_4$-alkyl.

Preferably, the substituent(s) on $C_6$-$C_{12}$-aryloxy are independently selected from the group consisting of halogen.

In connection with $R^{3a}$, substituted $C_3$-$C_{12}$-heterocyclyl in particular includes $C_3$-$C_{12}$-heterocyclyl, such as pyridyl, piperidinyl, isoxazolyl, diazolyl, tetrahydrofuranyl, tetrahydropyranyl, or morpholinyl, a further example being dioxolanyl, dioxanyl, dioxepanyl, or dioxaspiro[2.5]octanyl, which is substituted with 1, 2, or 3 substituents independently selected from the group consisting of halogen, $C_1$-$C_4$-alkyl and $C_3$-$C_6$-cycloalkyl.

Preferably, the substituent(s) on $C_3$-$C_{12}$-heterocyclyl are independently selected from the group consisting of halogen.

$R^{3b}$ is hydrogen, $C_1$-$C_6$-alkyl, or hydroxy. Additionally, $R^{3a}$ and $R^{3b}$ together may be optionally substituted $C_2$-$C_5$-alkylene (e.g. 1,2-ethylene, 1,3-propylene, 1,4-butylene, or 1,5-pentylene), preferably unsubstituted $C_2$-$C_5$-alkylene (e.g. 1,5-pentylene). Preferably, Rb is hydrogen.

In connection with $R^{3a}$ and $R^{3b}$, substituted $C_2$-$C_5$-alkylene in particular includes $C_2$-$C_5$-alkylene, such as 1,2-ethylene, 1,3-propylene, 1,4-butylene, or 1,5-pentylene, which is substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

$Y^1$ is >CR$^6$— or >N—.

Preferably, $Y^1$ is >CR$^6$—.

$R^6$ is hydrogen, $C_1$-$C_6$-alkyl (e.g. methyl, ethyl, n-propyl, iso-propyl, or iso-butyl), halogenated $C_1$-$C_6$-alkyl (e.g. CF$_3$ or CF$_2$H), (optionally substituted $C_6$-$C_{12}$-aryl)-$C_1$-$C_4$-alkyl (e.g. benzyl), hydroxy-$C_1$-$C_6$-alkyl (e.g. —CH$_2$OH or —(CH$_2$)$_2$OH), $C_1$-$C_4$-alkoxy-$C_1$-$C_6$-alkyl (e.g. methoxymethyl, 2-ethoxypropyl, or 3-ethoxypropyl), or hydroxy. Additionally, $R^6$ and $R^{3a}$ or $R^{3b}$ together may be optionally substituted $C_1$-$C_5$-alkylene (e.g. 1,3-propylene or 1,4-butylene); or $R^6$ may be $C_1$-$C_4$-alkylene (e.g. methylene or 1,2-ethylene) that is bound to a carbon atom in $R^{3a}$, and $R^{3a}$ is an optionally substituted $C_6$-$C_{12}$-aryl (e.g. phenyl) or an optionally substituted $C_3$-$C_{12}$-heterocyclyl (e.g. pyridyl or piperidinyl).

In particular, $R^6$ is hydrogen, $C_1$-$C_6$-alkyl (e.g. methyl or ethyl), $C_6$-$C_{12}$-aryl-$C_1$-$C_4$-alkyl (e.g. benzyl or phenethyl), hydroxy-$C_1$-$C_6$-alkyl (e.g. —CH$_2$OH, or —(CH$_2$)$_2$OH), or hydroxy, i.e., $R^6$ is, e.g., hydrogen, methyl, benzyl, hydroxymethyl, or hydroxy. In particular, $R^6$ and $R^{3a}$ or $R^{3b}$ together may be optionally substituted $C_1$-$C_5$-alkylene (e.g. 1,3-propylene or 1,4-butylene) such as a group of the formula:

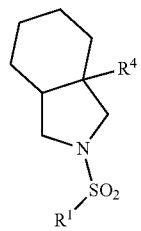

(which is shown herein for illustration purpose without being intended to limit the scope of the invention).

Alternatively, Rb may be $C_1$-$C_4$-alkylene (e.g. methylene or 1,2-ethylene) that is bound to a carbon atom in $R^{3a}$, and $R^{3a}$ is an optionally substituted $C_6$-$C_{12}$-aryl (e.g. phenyl) such as a group of the formula:

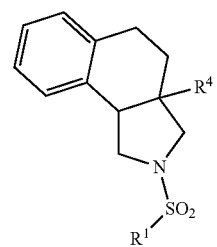

(which is shown herein for illustration purpose without being intended to limit the scope of the invention).

In connection with $R^6$ and $R^{3a}$ or $R^{3b}$, substituted $C_1$-$C_5$-alkylene in particular includes $C_1$-$C_5$-alkylene, such as methylene or 1,2-ethylene, which is substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

Preferably, $R^6$ is hydrogen. It is further preferred if $R^6$ and $R^{3a}$ or $R^{3b}$ together are $C_1$-$C_5$-alkylene (e.g. 1,3-propylene or 1,4-butylene); or if $R^6$ is $C_1$-$C_4$-alkylene (e.g. methylene or 1,2-ethylene) that is bound to a carbon atom in $R^{3a}$, and $R^{3a}$ is an optionally substituted $C_6$-$C_{12}$-aryl (e.g. phenyl). According to some embodiments, $Y^1$ is >N—. In particular, $Y^1$ is >N— if $R^4$ is —(CR$^{7e}$R$^{7f}$)$_{n3}$R$^{12}$.

$R^4$ is —(CR$^{7a}$R$^{7b}$)$_{n1}$OR$^{10}$, —(CR$^{7c}$R$^{7d}$)$_{n2}$NR$^{11a}$R$^{11b}$, —(CR$^{7e}$R$^{7f}$)$_{n3}$R$^{12}$, optionally substituted $C_6$-$C_{12}$- aryl, —NR$^{8a}$(CR$^{9a}$R$^{9b}$)$_{n4}$R$^{13}$, —NR$^{8b}$COR$^{14}$, —NR$^{8c}$COOR$^{15}$, —NR$^{8d}$CONR$^{16a}$R$^{16b}$, —NR$^{8e}$SO$_2$R$^{17}$, —O(CR$^{9c}$R$^{9d}$)$_{n5}$R$^{18}$, —COR$^{19}$, —CONR$^{20a}$R$^{20b}$, —SO$_2$R$^{21}$, or optionally substituted $C_3$-$C_{12}$-heterocyclyl (e.g. 1-propyl-1,2,3-triazol-4-yl, 4-butyl-1,2,3-triazolyl-1-yl, 4-chloroisoindolin-1-one, 7-(trifluoromethyl)-3,4-dihydro-1H-quinazolin-2-on-1-yl, a further example being 5-butyloxazolidin-2-on-3-yl, 1,4-thiazinan-1,1-dioxide-4-yl, indolinyl, indolin-2-on-1-yl, 6-CF$_3$-indolin-2-on-1-yl, isoindolinyl, or isoindolin-1-on-2-yl).

In particular, $R^4$ is —(CR$^{7a}$R$^{7b}$)$_{n1}$OR$^{10}$, —(CR$^{7c}$R$^{7d}$)$_{n2}$NR$^{11a}$R$^{11b}$, —(CR$^{7e}$R$^{7f}$)$_{n3}$R$^{12}$, optionally substituted $C_6$-$C_{12}$-aryl, —NR$^{8a}$(CR$^{9a}$R$^{9b}$)$_{n4}$R$^{13}$, —NR$^{8b}$COR$^{14}$, —NR$^{8c}$COOR$^{15}$, —NR$^{8d}$CONR$^{16a}$R$^{16b}$, —O(CR$^{9c}$R$^{9d}$)$_{n5}$R$^{18}$, —COR$^{19}$, —CONR$^{20a}$R$^{20b}$, SO$_2$R$^{21}$, or optionally substituted $C_3$-$C_{12}$-heterocyclyl (e.g. 1-propyl-1,2,3-triazol-4-yl, 4-butyl-1,2,3-triazolyl-1-yl, 4-chloroisoindolin-1-one, or 7-(trifluoromethyl)-3,4-dihydro-1H-quinazolin-2-on-1-yl, a further example being 5-butyloxazolidin-2-on-3-yl, 1,4-thiazinan-1,1-dioxide-4-yl, indolinyl, indolin-2-on-1-yl, 6-CF$_3$-indolin-2-on-1-yl, isoindolinyl, or isoindolin-1-on-2-yl).

Preferably, R$^4$ is —NR$^{8a}$(CR$^{9a}$R$^{9b}$)$_{n4}$R$^{13}$ or —O(CR$^{9c}$R$^{9d}$)$_{n5}$R$^{18}$. More preferably, R$^4$ is —NR$^{8a}$(CR$^{9a}$R$^{9b}$)$_{n4}$R$^{13}$.

In connection with R$^4$, substituted C$_6$-C$_{12}$-aryl in particular includes C$_6$-C$_{12}$-aryl, such as phenyl, which is substituted with 1, 2, or 3 substituents independently selected from the group consisting of halogen. Additional substituents may be selected from the group consisting of halogenated C$_1$-C$_4$-alkyl.

In connection with R$^4$, substituted C$_3$-C$_{12}$-heterocyclyl in particular includes C$_3$-C$_{12}$-heterocyclyl, such as pyridyl, isoxazolyl, diazolyl, 1,2,3-triazolyl, dihydroquinazolyn, or isoindolinyl, a further example being oxazolidinyl, thiazinanyl, or indolinyl, which is substituted with 1, 2, or 3 substituents independently selected from the group consisting of halogen, C$_1$-C$_6$-alkyl, halogenated C$_1$-C$_6$-alkyl and hydroxy.

In particular, R$^{5a}$, R$^{5b}$ are independently hydrogen, halogen, or C$_1$-C$_3$-alkyl (e.g. methyl, ethyl, n-propyl, or isopropyl) or R$^{5a}$, R$^{5b}$ together with the carbon atom to which they are bound may form a C═O. In particular, one of R$^{5a}$ or R$^{5b}$ and one of R$^{2a}$ or R$^{2b}$ together may be optionally substituted C$_1$-C$_5$-alkylene, preferably unsubstituted C$_1$-C$_5$-alkylene (e.g. 1,2-ethylene).

In connection with R$^{5a}$, R$^{5b}$, R$^{2a}$ and R$^{2b}$, substituted C$_1$-C$_5$-alkylene in particular includes C$_1$-C$_5$-alkylene, such as 1,2-ethylene, which is substituted with 1, 2 or 3 substituents selected from the group consisting of halogen, C$_1$-C$_4$-alkyl, C$_1$-C$_4$-haloalkyl, C$_1$-C$_4$-alkoxy and C$_1$-C$_4$-haloalkoxy.

Preferably, R$^{5a}$ is hydrogen, halogen or C$_1$-C$_3$-alkyl (e.g. methyl or ethyl), and R$^{5b}$ is hydrogen. More preferably, R$^{5a}$, R$^{5b}$ are both hydrogen.

According to a one embodiment, R$^4$ is —(CR$^{7a}$R$^{7b}$)$_{n1}$OR$^{10}$. Thus, the present invention relates to the pyrrolidine derivatives of the formula (Ia):

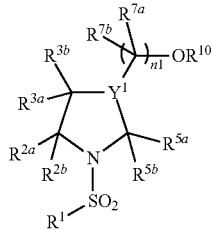

(Ia)

wherein R$^1$, R$^{2a}$, R$^{2b}$, R$^{3a}$, R$^{3b}$, Y$^1$, R$^{5a}$ and R$^{5b}$ are as defined herein, and R$^{7a}$, R$^{7b}$
are independently hydrogen or C$_1$-C$_6$-alkyl (e.g. methyl or ethyl), in particular, hydrogen;
n1 is 1, 2, 3 or 4, in particular 1; and
R$^{10}$ is hydrogen, optionally substituted C$_6$-C$_{12}$-aryl (e.g. phenyl, 3-F-phenyl, 3-Me-phenyl, 3-CF$_3$-phenyl, 2-Cl-3-CF$_3$-phenyl, or 3-OCF$_3$-phenyl, a further example being 2-F-phenyl, 4-F-phenyl, 2-Cl-phenyl, 2,3-diF-phenyl, 2,4-diF-phenyl, 2,5-diF-phenyl, 4-Cl-phenyl, 2-Cl-4-F-phenyl, 4-Cl-3-F-phenyl, 2-Me-phenyl, 4-Me-phenyl, 2-CF$_3$-phenyl, 4-CF$_3$-phenyl, 2-Cl-4-CF$_3$-phenyl, 3-OCHF$_2$-phenyl, 2-OCF$_3$-phenyl, 4-OCF$_3$-phenyl, 3-OMe-phenyl, 2-OEt-phenyl, 2-cyclopentyl-phenyl, 2-cyclohexyl-phenyl, 3-ethynyl-phenyl, 2-CN-phenyl, 4-CN-phenyl, 2-F-4-CN-phenyl, 3-dimethylamino-phenyl, 4-(morpholin-4-yl)-phenyl, 2-pyrrolidinyl-phenyl, 2-piperidin-phenyl, indan-5-yl, naphthyl, or tetralin-5-yl), or optionally substituted C$_3$-C$_{12}$-heterocyclyl (e.g. 6-CF$_3$-pyrimid-4-yl, 4-CF$_3$-pyrid-2-yl, or 2-CF$_3$-pyrid-4-yl, a further example being pyrid-2-yl, pyrid-3-yl, pyrid-4-yl, pyrazin-2-yl, pyridazin-3-yl, quinolin-6-yl, isoquinolin-5-yl, 1,2-bezoxazol-6-yl, or 2-Me-1,3-benzoxazol-5-yl).

In connection with R$^{10}$, substituted C$_6$-C$_{12}$-aryl in particular includes C$_6$-C$_{12}$-aryl, such as phenyl or naphthyl, a further example being indanyl or tetralinyl, which is substituted with 1, 2, or 3 substituents independently selected from the group consisting of halogen, C$_1$-C$_4$-alkyl, halogenated C$_1$-C$_4$-alkyl and halogenated C$_1$-C$_4$-alkoxy. Additional substituents may be selected from the group consisting of C$_3$-C$_6$-cycloalkyl, C$_1$-C$_4$-alkynyl, CN, C$_1$-C$_4$-alkoxy, di-C$_1$-C$_4$-alkyl-amino and C$_3$-C$_{12}$-heterocyclyl.

In connection with R$^{10}$, substituted C$_3$-C$_{12}$-heterocyclyl in particular includes C$_3$-C$_{12}$-heterocyclyl, such as pyridyl, pyrimidyl, or pyridazyl, a further example being pyrazyl, quinolinyl, isoquinolinyl or benzoxazolyl, which is substituted with 1, 2, or 3 substituents independently selected from the group consisting of halogenated C$_1$-C$_4$-alkyl. Additional substituents may be selected from the group consisting of C$_1$-C$_4$-alkyl.

R$^{2a}$, R$^{2b}$—in the pyrrolidine derivatives of formula (Ia)—are, in particular, hydrogen.

R$^{3a}$—in the pyrrolidine derivatives of formula (Ia)—is, in particular, C$_3$-C$_{12}$-cycloalkyl (e.g. cyclopropyl, cyclobutyl, cyclopentyl, or cyclohexyl), optionally substituted C$_6$-C$_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), C$_3$-C$_{12}$-cycloalkyl-C$_1$-C$_4$-alkoxy (e.g. cyclopropylmethoxy or cyclohexylmethoxy), C$_2$-C$_6$-alkenyloxy (e.g. allyloxy or 2-methylprop-2-en-1-oxy), C$_6$-C$_{12}$-aryl-C$_1$-C$_4$-alkoxy (e.g. benzyloxy), optionally substituted C$_6$-C$_{12}$-aryloxy (e.g. phenoxy or 4-F-phenoxy). Additionally, R$^{3a}$—in the pyrrolidine derivatives of formula (Ia)—may be, in particular, optionally substituted C$_3$-C$_{12}$-heterocyclyl (e.g. tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, 1,3-oxazol-2-yl, 3-F-azetidin-1-yl, morpholin-1-yl, pyrrolidin-1-yl, piperidin-1-yl, 2-Me-piperidin-1yl, 3-Me-piperidin-1yl, 4-Me-piperidin-1yl, 4-F-piperidin-1-yl, 4,4-diF-piperidin-1yl, or azepan-1-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, 1-Me-piperidin-2-yl, or 5-F-pyrid-2-yl). Preferably, R$^{3a}$ is optionally substituted C$_6$-C$_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl). It is further preferred if R$^{3a}$ is C$_3$-C$_{12}$-heterocyclyl (e.g. pyrid-2-yl).

R$^{3b}$—in the pyrrolidine derivatives of formula (Ia)—is, in particular, hydrogen.

Y$^1$—in the pyrrolidine derivatives of formula (Ia)—is, in particular, >CR$^6$.

R$^6$—in the pyrrolidine derivatives of formula (Ia)—is, in particular, hydrogen.

R$^{5a}$, R$^{5b}$—in the pyrrolidine derivatives of formula—(Ia) are, in particular, hydrogen.

Particular embodiments of the pyrrolidine derivatives of formula (Ia) result if:

$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-iso-propyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$
are hydrogen;

$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl);

$R^{3b}$ is hydrogen;

$Y^1$ is >$CR^6$;

$R^6$ is hydrogen;

$R^{7a}$, $R^{7b}$
are hydrogen;

n1 is 1;

$R^{10}$ is hydrogen, optionally substituted $C_6$-$C_{12}$-aryl (e.g. phenyl, 3-F-phenyl, 3-Me-phenyl, 3-$CF_3$-phenyl, 2-Cl-3-$CF_3$-phenyl, or 3-$OCF_3$-phenyl, a further example being 2-F-phenyl, 4-F-phenyl, 2-Cl-phenyl, 2,3-diF-phenyl, 2,4-diF-phenyl, 2,5-diF-phenyl, 4-Cl-phenyl, 2-Cl-4-F-phenyl, 4-Cl-3-F-phenyl, 2-Me-phenyl, 4-Me-phenyl, 2-$CF_3$-phenyl, 4-$CF_3$-phenyl, 2-Cl-4-$CF_3$-phenyl, 3-$OCHF_2$-phenyl, 2—$OCF_3$-phenyl, 4-$OCF_3$-phenyl, 3-OMe-phenyl, 2-OEt-phenyl, 2-cyclopentyl-phenyl, 2-cyclohexyl-phenyl, 3-ethynyl-phenyl, 2-CN-phenyl, 4-CN-phenyl, 2-F-4-CN-phenyl, 3-dimethylamino-phenyl, 4-(morpholin-4-yl)-phenyl, 2-pyrrolidinyl-phenyl, 2-piperidin-phenyl, indan-5-yl, naphthyl, or tetralin-5-yl), or optionally substituted $C_3$-$C_{12}$-heterocyclyl (e.g. 6-$CF_3$-pyrimid-4-yl, 4-$CF_3$-pyrid-2-yl, or 2-$CF_3$-pyrid-4-yl, a further example being pyrid-2-yl, pyrid-3-yl, pyrid-4-yl, pyrazin-2-yl, pyridazin-3-yl, quinolin-6-yl, isoquinolin-5-yl, 1,2-bezoxazol-6-yl, or 2-Me-1,3-benzoxazol-5-yl); and $R^{5a}$, $R^{5b}$
are hydrogen.

Additional particular embodiments of the pyrrolidine derivatives of formula (Ia) result if:

$R^{3a}$ is optionally substituted $C_3$-$C_{12}$-heterocyclyl (e.g. pyrid-2-yl); and $R^1$, $R^{2a}$, $R^{2b}$, $R^{3b}$, $Y^1$, $R^6$, $R^{7a}$, $R^{7b}$, n1, $R^{10}$, $R^{5a}$ and $R^{5b}$ are as defined above.

According to a particular embodiment, $R^1$—in the pyrrolidine derivatives of formula (Ia)—is an optionally substituted 5-membered heterocyclic ring containing 1 or 2 N and 1 O(e.g. 5-methyl-1,2-oxazol-4-yl or 3,5-dimethyl-1,2-oxazol-4-yl). According to an alternative particular embodiment, $R^1$ is an optionally substituted 5-membered heterocyclic ring containing 1 or 2 N and 1 S (e.g. 2,4-dimethyl-1,3-thiazol-5-yl or 2-methylcarbonylamino-1,3-thiazol-5-yl). According to a further particular alternative embodiment, $R^1$ is an optionally substituted 5-membered heterocyclic ring containing 1, 2 or 3 N (e.g. 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-iso-propyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl or 1-Me-1,2,3-triazol-4-yl, a further example being 1-ethyl-1,3-diazol-4-yl or 1-methyl-1,2,4-triazol-3-yl).

Preferably, $R^1$—in the pyrrolidine derivatives of formula (Ia)—is an optionally substituted 5-membered heterocyclic ring containing 2 N which, in particular, is optionally substituted 1,3-diazolyl.

According to a further preferred embodiment, $R^1$—in the pyrrolidine derivatives of formula (Ia)—is an optionally substituted 5-membered heterocyclic ring containing 3 N which, in particular, is optionally substituted 1,2,3-triazolyl.

In connection with $R^1$ and the pyrrolidine derivatives of formula (Ia), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives of formula (Ia), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituents on $C_6$-$C_{12}$-aryl are independently selected from the group consisting of halogen.

According to a preferred embodiment, $R^{3a}$—in the pyrrolidine derivatives of formula (Ia)—is $C_6$-$C_{12}$-aryl, in particular phenyl, optionally substituted with 1, 2, or 3 substituents independently selected from the group consisting of halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluoro-phenyl).

Further preferred embodiments of pyrrolidine derivatives of formula (Ia) result if:

$R^1$ is 1,3-diazolyl optionally substituted with halogen or $C_1$-$C_4$-alkyl (e.g. 1-methyl-1,3-diazol-4-yl);

$R^{2a}$, $R^{2b}$
are hydrogen;

$R^{3a}$ is $C_6$-$C_{12}$-aryl, in particular phenyl, optionally substituted with 1, 2, or 3 substituents independently selected from the group consisting of halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluorophenyl);

$R^{3b}$ is hydrogen;

$Y^1$ is $>CR^6$;
$R^6$ is hydrogen;
$R^{7a}$, $R^{7b}$
  are hydrogen;
n1 is 1;
$R^{10}$ is hydrogen, $C_6$-$C_{12}$-aryl (e.g. phenyl) optionally substituted with 1, 2, or 3 substituents independently selected from the group consisting of halogen, $C_1$-$C_4$-alkyl, halogenated $C_1$-$C_4$-alkyl and halogenated $C_1$-$C_4$-alkoxy, or $C_3$-$C_{12}$-heterocyclyl optionally substituted with 1, 2, or 3 substituents independently selected from the group consisting of halogenated $C_1$-$C_4$-alkyl; and
$R^{5a}$, $R^{5b}$
  are hydrogen.

Additional preferred embodiments of pyrrolidine derivatives of formula (Ia) result if:
$R^{10}$ is $C_6$-$C_{12}$-aryl (e.g. phenyl) optionally substituted with 1, 2, or 3 substituents independently selected from the group consisting of $C_3$-$C_6$-cycloalkyl, $C_1$-$C_4$-alkynyl, CN, $C_1$-$C_4$-alkoxy, di-$C_1$-$C_4$-alkyl-amino and $C_3$-$C_{12}$-heterocyclyl, or $C_3$-$C_{12}$-heterocyclyl optionally substituted with 1, 2, or 3 substituents independently selected from the group consisting of $C_1$-$C_4$-alkyl; and
$R^1$, $R^{2a}$, $R^{2b}$, $R^{3a}$, $R^{3b}$, $Y^1$, $R^6$, $R^{7a}$, $R^{7b}$, n1, $R^{5a}$ and $R^{5b}$
  are as defined above.

According to a further embodiment, $R^4$ is —$(CR^{7c}R^{7d})_{n2}$NR$^{11a}$R$^{11b}$. Thus, the present invention relates to the pyrrolidine derivatives of the formula (Ib):

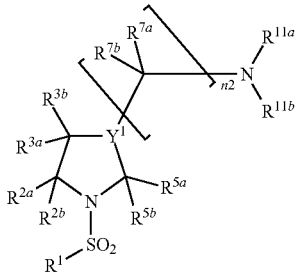

(Ib)

wherein $R^1$, $R^{2a}$, $R^{2b}$, $R^{3a}$, $R^{3b}$, $Y^1$, $R^{5a}$ and $R^{5b}$ are as defined herein, and
$R^{7c}$, $R^{7d}$
  are independently hydrogen or $C_1$-$C_6$-alkyl (e.g. methyl or ethyl), in particular, hydrogen;
n2 is 1, 2, 3, or 4, in particular, 1;
$R^{11a}$ is $C_1$-$C_8$-alkyl (e.g. methyl, ethyl, n-propyl, or n-butyl), (optionally substituted $C_3$-$C_{12}$-cycloalkyl)-$C_1$-$C_4$-alkyl (e.g. cyclopropyl-methyl), $C_1$-$C_6$-alkoxy-$C_1$-$C_6$-alkyl (e.g. 2-methoxy-ethyl, 2-ethoxy-ethyl, 2-isopropoxy-ethyl, 1-methyl-2-methoxy-ethyl, 3-methoxypropyl, 3-ethoxy-propyl, or 3-isopropoxy-propyl), (optionally substituted $C_6$-$C_{12}$-aryl)-$C_1$-$C_4$-alkyl (e.g. benzyl), (optionally substituted $C_3$-$C_{12}$-heterocyclyl)-$C_1$-$C_4$-alkyl, optionally substituted $C_6$-$C_{12}$-aryl (e.g. phenyl, 4-F-phenyl, 3-Cl-phenyl, 3,5-diCl-phenyl, 3-Cl-4-F-phenyl, 3-Me-phenyl, 3-(aminomethyl)-phenyl, 3-CF$_3$-phenyl, 4-CF$_3$-phenyl, 2-Cl-4-CF$_3$-phenyl, 3-Cl-4-CF$_3$-phenyl, 3-CF$_3$-4-F-phenyl, 3-OCF$_3$-phenyl, 3-OCF$_3$-4-F-phenyl, 3-OCF$_3$-4-Cl-phenyl, or 3-(aminocarbonyl)-phenyl), or optionally substituted $C_3$-$C_{12}$-heterocyclyl; and
$R^{11b}$ is hydrogen or (e.g. methyl, ethyl, n-propyl or n-butyl).
In particular, $R^{11a}$ is $C_1$-$C_8$-alkyl (e.g. n-propyl or n-butyl), $C_3$-$C_{12}$-cycloalkyl-$C_1$-$C_4$-alkyl (e.g. cyclopropyl-methyl), $C_1$-$C_6$-alkoxy-$C_1$-$C_6$-alkyl (e.g. 2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), $C_6$-$C_{12}$-aryl-$C_1$-$C_4$-alkyl (e.g. benzyl), or optionally substituted $C_6$-$C_{12}$-aryl (e.g. phenyl, 4-F-phenyl, 3-Cl-phenyl, 3,5-diCl-phenyl, 3-Cl-F-phenyl, 3-Me-phenyl, 3-(aminomethyl)-phenyl, 3-CF$_3$-phenyl, 4-CF$_3$-phenyl, 2-Cl-4-CF$_3$-phenyl, 3-Cl-4-CF$_3$-phenyl, 3-CF$_3$-4-F-phenyl, 3-OCF$_3$-phenyl, 3-OCF$_3$-4-F-phenyl, 3-OCF$_3$-4-Cl-phenyl, or 3-(aminocarbonyl)phenyl).

In connection with $R^{11a}$, substituted $C_6$-$C_{12}$-aryl in particular includes $C_6$-$C_{12}$-aryl, such as phenyl, substituted with 1, 2, or 3 substituents independently selected from the group consisting of halogen, $C_1$-$C_4$-alkyl, halogenated $C_1$-$C_4$-alkyl, amino-$C_1$-$C_4$-alkyl, amino-carbonyl and halogenated $C_1$-$C_4$-alkoxy.

In particular, $R^{11b}$ is hydrogen.
$R^{2a}$, $R^{2b}$—in the pyrrolidine derivatives of formula (Ib)—are, in particular, both hydrogen.
$R^{3a}$—in the pyrrolidine derivatives of formula (Ib)—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), or optionally substituted $C_6$-$C_{12}$-aryloxy (e.g. phenoxy or 4-F-phenoxy). Preferably, $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl).

$R^{3b}$—in the pyrrolidine derivatives of formula (Ib)—is, in particular, hydrogen.
$Y^1$—in the pyrrolidine derivatives of formula (Ib)—is, in particular, $>CR^6$.
$R^6$—in the pyrrolidine derivatives of formula (Ib)—is, in particular, hydrogen.
$R^{5a}$, $R^{5b}$ in the pyrrolidine derivatives of formula (Ib)—are, in particular, hydrogen.

Particular embodiments of the pyrrolidine derivatives of formula (Ib) result if:
$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-CF$_3$-1,2-diazol-4-yl, 1-cyclopentyl-3-Me-1,2-diazol-4-yl, 1,3,5-trimethyl-1,2-diazol-4-yl, 1-CHF$_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$
are hydrogen;
$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl or 2,4,5-trifluoro-phenyl, a further example being 2-Me-phenyl, 3-Me-phenyl, or 4-Me-phenyl);
$R^{3b}$ is hydrogen;
$Y^1$ is >$CR^6$;
$R^6$ is hydrogen;
$R^{7c}$, $R^{7d}$
are hydrogen;
n2 is 1;
$R^{11a}$ is $C_1$-$C_8$-alkyl (e.g. n-propyl or n-butyl), $C_3$-$C_{12}$-cycloalkyl-$C_1$-$C_4$-alkyl (e.g. cyclopropylmethyl) $C_1$-$C_6$-alkoxy-$C_1$-$C_6$-alkyl (e.g. 2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), $C_6$-$C_{12}$-aryl-$C_1$-$C_4$-alkyl (e.g. benzyl), optionally substituted $C_6$-$C_{12}$-aryl (e.g. phenyl, 4-F-phenyl, 3-Cl-phenyl, 3,5-diCl-phenyl, 3-Cl-F-phenyl, 3-Me-phenyl, 3-(aminomethyl)-phenyl, 3-$CF_3$-phenyl, 4-$CF_3$-phenyl, 2-Cl-4-$CF_3$-phenyl, 3-Cl-4-$CF_3$-phenyl, 3-$CF_3$-4-F-phenyl, 3-$OCF_3$-phenyl, 3-$OCF_3$-4-F-phenyl, 3-$OCF_3$-4-Cl-phenyl, or 3-(aminocarbonyl)-phenyl);
$R^{11b}$ is hydrogen; and
$R^{5a}$, $R^{5b}$ are
hydrogen.
Preferably, $R^1$—in the pyrrolidine derivatives of formula (Ib)—is an optionally substituted 5-membered heterocyclic ring containing 2 N which, in particular, is optionally substituted 1,3-diazolyl.
According to a further preferred embodiment, $R^1$—in the pyrrolidine derivatives of formula (Ib)—is an optionally substituted 5-membered heterocyclic ring containing 3 N which, in particular, is optionally substituted 1,2,3-triazolyl.
In connection with $R^1$ and the pyrrolidine derivatives of formula (Ib), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.
In connection with $R^{3a}$ and the pyrrolidine derivatives of formula (Ib), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituents on $C_6$-$C_{12}$-aryl are independently selected from the group consisting of halogen.
According to a preferred embodiment, $R^{3a}$—in the pyrrolidine derivatives of formula (Ib)—is $C_6$-$C_{12}$-aryl, in particular phenyl, optionally substituted with 1, 2, or 3 substituents independently selected from the group consisting of halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluoro-phenyl).
Further preferred embodiments of pyrrolidine derivatives of formula (Ib) result if:
$R^1$ is 1,3-diazolyl optionally substituted with halogen or $C_1$-$C_4$-alkyl (e.g. 1-methyl-1,3-diazol-4-yl);
$R^{2a}$, $R^{2b}$
are hydrogen;
$R^{3a}$ is $C_6$-$C_{12}$-aryl optionally substituted with 1, 2, or 3 substituents independently selected from the group consisting of halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluoro-phenyl);
$R^{3b}$ is hydrogen;
$Y^1$ is >$CR^6$;
$R^6$ is hydrogen;
$R^{7c}$, $R^{7d}$
are hydrogen;
n2 is 1;
$R^{11a}$ is $C_1$-$C_8$-alkyl (e.g. n-propyl or n-butyl), $C_3$-$C_{12}$-cycloalkyl-$C_1$-$C_4$-alkyl (e.g. cyclopropylmethyl), $C_1$-$C_6$-alkoxy-$C_1$-$C_6$-alkyl (e.g. 2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), $C_6$-$C_{12}$-aryl-$C_1$-$C_4$-alkyl (e.g. benzyl), or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, amino-$C_1$-$C_4$-alkyl, aminocarbonyl and halogenated $C_1$-$C_4$-alkoxy (e.g. phenyl, 4-F-phenyl, 3-Cl-phenyl, 3,5-diCl-phenyl, 3-Cl-F-phenyl, 3-Me-phenyl, 3-(aminomethyl)-phenyl, 3-$CF_3$-phenyl, 4-$CF_3$-phenyl, 2-Cl-4-$CF_3$-phenyl, 3-$C_{1-4}$-$CF_3$-phenyl, 3-$CF_3$-4-F-phenyl, 3-$OCF_3$-phenyl, 3-$OCF_3$-4-F-phenyl, 3-$OCF_3$-4-Cl-phenyl, or 3-(aminocarbonyl)-phenyl);
$R^{11b}$ is hydrogen; and
$R^{5a}$, $R^{5b}$
are hydrogen.
According to a further embodiment, $R^4$ is —$(CR^{7e}R^{7f})_{n3}$ $R^{12}$. Thus, the present invention relates to the pyrrolidine derivatives of the formula (Ic):

(Ic)

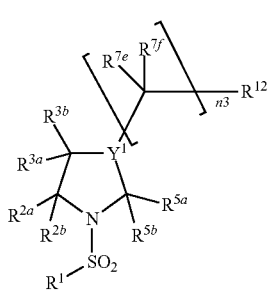

wherein $R^1$, $R^{2a}$, $R^{2b}$, $R^{3a}$, $R^{3b}$, $Y^1$, $R^{5a}$ and $R^{5b}$ are as defined herein, and
$R^{7e}$, $R^{7f}$
are independently hydrogen or $C_1$-$C_6$-alkyl (e.g. methyl or ethyl), in particular, hydrogen;
n3 is 1, 2, 3, or 4, in particular, 1; and
$R^{12}$ is optionally substituted $C_6$-$C_{12}$-aryl (e.g. phenyl, 3-Cl-phenyl, or 3-Br-phenyl, a further example being 3-$CF_3$-phenyl) or optionally substituted $C_3$-$C_{12}$-heterocyclyl (e.g. 4-$CF_3$-pyrid-2-yl or 1-propyl-1,2,3-triazol-4-yl).
In connection with $R^{12}$, substituted $C_6$-$C_{12}$-aryl in particular includes $C_6$-$C_{12}$-aryl, such as phenyl, which is substituted with 1, 2, or 3 substituents independently selected from the group consisting of halogen. Additional substituents may be selected from the group consisting of halogenated $C_1$-$C_4$-alkyl.

In connection with $R^{12}$, substituted $C_3$-$C_{12}$-heterocyclyl in particular includes $C_3$-$C_{12}$-heterocyclyl, such as pyridyl or triazolyl, which is substituted with 1, 2, or 3 substituents independently selected from the group consisting of $C_1$-$C_4$-alkyl and halogenated $C_1$-$C_4$-alkyl.

$R^{2a}$, $R^{2b}$—pyrrolidine derivatives of formula (Ic)—are, in particular, hydrogen.

$R^{3a}$—in pyrrolidine derivatives of formula (Ic)—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), or optionally substituted $C_6$-$C_{12}$-aryloxy (e.g. phenoxy or 4-F-phenoxy). Additionally, $R^{3a}$—in pyrrolidine derivatives of formula (Ic)—may be, in particular, optionally substituted $C_3$-$C_{12}$-heterocyclyl (e.g. tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, 1,3-oxazol-2-yl, 3-F-azetidin-1-yl, piperidin-1-yl, 2-Me-piperidin-1-yl, 3-Me-piperidin-1-yl, 4-Me-piperidin-1-yl, 4-F-piperidin-1-yl, 4,4-diF-piperidin-1yl, or azepan-1-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, 1-Me-piperidin-2-yl, or 5-F-pyrid-2-yl). Preferably, $R^{3a}$ is $C_3$-$C_{12}$-cycloalkyl (e.g. cyclopropyl, cyclobutyl, cyclopentyl, or cyclohexyl) or optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl). It is further preferred if $R^{3a}$ is optionally substituted $C_3$-$C_{12}$-heterocyclyl (e.g. 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, or 5,7-dioxaspiro[2.5]octan-6-yl).

$R^{3b}$—in the pyrrolidine derivatives of formula (Ic)—is, in particular, hydrogen.

$Y^1$—in the pyrrolidine derivatives of formula (Ic)—is, in particular, >$CR^6$.

$R^6$—in the pyrrolidine derivatives of formula (Ic)—is, in particular, hydrogen or hydroxy.

$R^{5a}$, $R^{5b}$—in the pyrrolidine derivatives of formula (Ic)—are, in particular, hydrogen or together with the carbon atom to which they are bound may form a C=O.

If $Y^1$—in the pyrrolidine derivatives of formula (Ic)—is >N—$R^{5a}$, $R^{5b}$ together with the carbon atom to which they are bound form, in particular, a C=O.

Particular embodiments of pyrrolidine derivatives of formula (Ic) result if:

$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-CF$_3$-1,2-diazol-4-yl, 1-cyclopentyl-3-Me-1,2-diazol-4-yl, 1,3,5-trimethyl-1,2-diazol-4-yl, 1-CHF$_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$ are hydrogen;

$R^{3a}$ is $C_3$-$C_{12}$-cycloalkyl (e.g. cyclopropyl, cyclobutyl, cyclopentyl, or cyclohexyl) or optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl);

$R^{3b}$ is hydrogen;

$Y^1$ is >$CR^6$ or >N—;

$R^6$ is hydrogen or hydroxy;

$R^{7e}$, $R^{7f}$ are hydrogen;

n3 is 1;

$R^{12}$ is optionally substituted $C_6$-$C_{12}$-aryl (e.g. phenyl, 3-Cl-phenyl, or 3-Br-phenyl, a further example being 3-CF$_3$-phenyl) or optionally substituted $C_3$-$C_{12}$-heterocyclyl (e.g. 4-CF$_3$-pyrid-2-yl or 1-propyl-1,2,3-triazol-4-yl); and $R^{5a}$, $R^{5b}$ are hydrogen or together with the carbon atom to which they are bound may form a C=O.

Further particular embodiments of pyrrolidine derivatives of formula (Ic) result if:

$R^{3a}$ is optionally substituted $C_3$-$C_{12}$-heterocyclyl (e.g. 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, or 5,7-dioxaspiro[2.5]octan-6-yl); and $R^1$, $R^{2a}$, $R^{2b}$, $R^{3b}$, $Y^1$, $R^6$, $R^{7e}$, $R^{7f}$, n3, $R^{12}$, $R^{5a}$ and $R^{5b}$ are as defined above.

Preferably, $R^1$—in the pyrrolidine derivatives of formula (Ic)—is an optionally substituted 5-membered heterocyclic ring containing 2 N which, in particular, is optionally substituted 1,3-diazolyl.

According to a further preferred embodiment, $R^1$—in the pyrrolidine derivatives of formula (Ic)—is an optionally substituted 5-membered heterocyclic ring containing 3 N which, in particular, is optionally substituted 1,2,3-triazolyl.

In connection with $R^1$ and the pyrrolidine derivatives of formula (Ic), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives of formula (Ic), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituents on $C_6$-$C_{12}$-aryl are independently selected from the group consisting of halogen.

According to a preferred embodiment, $R^{3a}$—in the pyrrolidine derivatives of formula (Ic)—is $C_3$-$C_{12}$-cycloalkyl (e.g. cyclopropyl, cyclobutyl, cyclopentyl, or cyclohexyl) or $C_6$-$C_{12}$-aryl, in particular phenyl, optionally substituted with 1, 2, or 3 substituents independently selected from the group consisting of halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluoro-phenyl).

According to an additional preferred embodiment, $R^{3a}$—in the pyrrolidine derivatives of formula (Ic) may be $C_3$-$C_{12}$-heterocyclyl (e.g. 1,3-dioxan-2-yl).

Further preferred embodiments of pyrrolidine derivatives of formula (Ic) result if:
$R^1$ is 1,3-diazolyl optionally substituted with halogen or $C_1$-$C_4$-alkyl and preferably 1-methyl-1,3-diazol-4-yl;
$R^{2a}$, $R^{2b}$
  are hydrogen;
$R^{3a}$ is $C_3$-$C_{12}$-cycloalkyl (e.g. cyclopropyl) or $C_6$-$C_{12}$-aryl optionally substituted with halogen (e.g. phenyl, 2-Br-phenyl, or 4-F-phenyl);
$R^{3b}$ is hydrogen;
$Y^1$ is >$CR^6$ or >N—;
$R^6$ is hydrogen or hydroxy;
$R^{7e}$, $R^{7f}$
  are hydrogen;
n3 is 1;
$R^{12}$ is $C_6$-$C_{12}$-aryl optionally substituted with 1, 2, or 3 substituents independently selected from the group consisting of halogen (e.g. phenyl, 3-Cl-phenyl, or 3-Br-phenyl), or $C_3$-$C_{12}$-heterocyclyl optionally substituted with 1, 2, or 3 substituents independently selected from the group consisting of $C_1$-$C_4$-alkyl and halogenated $C_1$-$C_4$-alkyl (e.g. 4-$CF_3$-pyrid-2-yl or 1-propyl-1,2,3-triazol-4-yl); and
$R^{5a}$, $R^{5b}$
  are hydrogen or together with the carbon atom to which they are bound may form a C=O.

Further preferred embodiments of pyrrolidine derivatives of formula (Ic) result if:
$R^{3a}$ is $C_3$-$C_{12}$-heterocyclyl (e.g. 1,3-dioxan-2-yl); and
$R^1$, $R^{2a}$, $R^{2b}$, $R^{3b}$, $Y^1$, $R^6$, $R^{7e}$, $R^{7f}$, n3, $R^{12}$, $R^{5a}$ and $R^{5b}$ are as defined above.

According to a further embodiment, $R^4$ is optionally substituted $C_6$-$C_{12}$-aryl (e.g. phenyl, 4-Cl-phenyl, or 2-Cl-phenyl, a further example being 3-$CF_3$-phenyl).

In connection with $R^4$ being optionally substituted $C_6$-$C_{12}$-aryl, substituted $C_6$-$C_{12}$-aryl in particular includes $C_6$-$C_{12}$-aryl, such as phenyl, which is substituted with 1, 2, or 3 substituents independently selected from the group consisting of halogen. Additional substituents may be selected from the group consisting of halogenated $C_1$-$C_4$-alkyl.

$R^{2a}$, $R^{2b}$—in the pyrrolidine derivatives wherein $R^4$ is optionally substituted $C_6$-$C_{12}$-aryl—are, in particular, hydrogen.

$R^{3a}$—in the pyrrolidine derivatives wherein $R^4$ is optionally substituted $C_6$-$C_{12}$-aryl—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), or optionally substituted $C_6$-$C_{12}$-aryloxy (e.g. phenoxy or 4-F-phenoxy). Preferably, $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl).

$R^{3b}$—in the pyrrolidine derivatives wherein $R^4$ is optionally substituted $C_6$-$C_{12}$-aryl—is, in particular, hydrogen.

$Y^1$—in the pyrrolidine derivatives wherein $R^4$ is optionally substituted $C_6$-$C_{12}$-aryl—is, in particular, >$CR^6$.

$R^6$—in the pyrrolidine derivatives wherein $R^4$ is optionally substituted $C_6$-$C_{12}$-aryl—is, in particular, hydrogen.

$R^{5a}$, $R^{5b}$—in the pyrrolidine derivatives wherein $R^4$ is optionally substituted $C_6$-$C_{12}$-aryl—are, in particular, hydrogen.

Particular embodiments of the pyrrolidine derivatives wherein $R^4$ is optionally substituted $C_6$-$C_{12}$-aryl result if:
$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);
$R^{2a}$, $R^{2b}$
  are hydrogen;
$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl);
$R^{3b}$ is hydrogen;
$R^4$ is optionally substituted $C_6$-$C_{12}$-aryl (e.g. phenyl, 4-Cl-phenyl, or 2-Cl-phenyl, a further example being 3-$CF_3$-phenyl);
$Y^1$ is >$CR^6$;
$R^6$ is hydrogen; and
$R^{5a}$, $R^{5b}$ are hydrogen.

Preferably, $R^1$—in the pyrrolidine derivatives wherein $R^4$ is optionally substituted $C_6$-$C_{12}$-aryl—is an optionally substituted 5-membered heterocyclic ring containing 2 N which, in particular, is optionally substituted 1,3-diazolyl.

According to a further preferred embodiment, $R^1$—in the pyrrolidine derivatives wherein $R^4$ is optionally substituted $C_6$-$C_{12}$-aryl—is an optionally substituted 5-membered heterocyclic ring containing 3 N which, in particular, is optionally substituted 1,2,3-triazolyl.

In connection with $R^1$ and the pyrrolidine derivatives wherein $R^4$ is optionally substituted $C_6$-$C_{12}$-aryl, substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives wherein $R^4$ is optionally substituted $C_6$-$C_{12}$-aryl, substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituents on $C_6$-$C_{12}$-aryl are independently selected from the group consisting of halogen.

According to a preferred embodiment, $R^{3a}$—in the pyrrolidine derivatives wherein $R^4$ is optionally substituted $C_6$-$C_{12}$-aryl—is $C_6$-$C_{12}$-aryl, in particular phenyl, optionally substituted with 1, 2, or 3 substituents independently selected from the group consisting of halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluoro-phenyl).

Further preferred embodiments of the pyrrolidine derivatives wherein $R^4$ is optionally substituted $C_6$-$C_{12}$-aryl result if:

$R^1$ is 1,3-diazolyl optionally substituted with halogen or $C_1$-$C_4$-alkyl and preferably 1-methyl-1,3-diazol-4-yl;

$R^{2a}$, $R^{2b}$ are hydrogen;

$R^{3a}$ is $C_6$-$C_{12}$-aryl optionally substituted with halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluoro-phenyl);

$R^{3b}$ is hydrogen;

$R^4$ is $C_6$-$C_{12}$-aryl optionally substituted with 1, 2, or 3 substituents independently selected from the group consisting of halogen (e.g. phenyl, 4-Cl-phenyl, or 2-Cl-phenyl);

$Y^1$ is $>CR^6$;

$R^6$ is hydrogen; and $R^{5a}$, $R^{5b}$ are hydrogen.

Additional preferred embodiments of the pyrrolidine derivatives wherein $R^4$ is optionally substituted $C_6$-$C_{12}$-aryl result if:

$R^4$ is $C_6$-$C_{12}$-aryl optionally substituted with 1, 2, or 3 substituents independently selected from the group consisting of halogenated $C_1$-$C_4$-alkyl (e.g. 3-$CF_3$-phenyl), and $R^1$, $R^{2a}$, $R^{2b}$, $R^{3a}$, $R^{3b}$, $Y^1$, $R^6$, $R^{5a}$ and $R^{5b}$ are as defined above.

According to a further embodiment, $R^4$ is —$NR^{8a}$($CR^{9a}R^{9b}$)$_{n4}R^{13}$. Thus, the present invention relates to the pyrrolidine derivatives of the formula (Id):

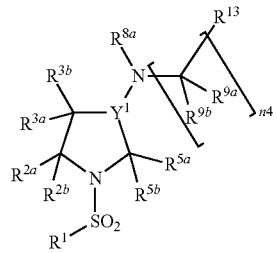

(Id)

wherein $R^1$, $R^{2a}$, $R^{2b}$, $R^{3a}$, $R^{3b}$, $Y^1$, $R^{5a}$ and $R^{5b}$ are as defined herein, and $R^{8a}$ is hydrogen, $C_1$-$C_6$-alkyl (e.g. methyl, ethyl, n-propyl, iso-propyl, pentyl, or hexyl), or $C_1$-$C_6$-alkylcarbonyl (e.g. methylcarbonyl), or $R^6$, $R^{8a}$ together are optionally substituted $C_1$-$C_5$-alkylene, wherein one or more —$CH_2$— of $C_1$-$C_5$-alkylene may be independently replaced by a an oxygen atom or C=O (e.g. —C(O)OCH$_2$—), or $R^{3a}$ and $R^{8a}$ together are optionally substituted $C_1$-$C_5$-alkylene (e.g. 1,2-ethylene or 1,3-propylene);

$R^{9a}$, $R^{9b}$ are independently hydrogen, halogen (e.g. F, Cl, or Br), $C_1$-$C_6$-alkyl (e.g. methyl, ethyl, tert-butyl, or 2,3-dimethyl-propyl), halogenated $C_1$-$C_6$-alkyl, (e.g. trifluoromethyl), hydroxy, or $C_1$-$C_6$-alkoxy (e.g. methoxy or ethoxy);

n4 is 0, 1, 2, 3, or 4; and $R^{13}$ is hydrogen, $C_1$-$C_8$-alkyl (e.g. methyl, ethyl, n-butyl, tert-butyl, pentyl, or hexyl), halogenated $C_1$-$C_6$-alkyl (e.g. —$CF_3$ or —$CF_2Me$), (optionally substituted $C_3$-$C_{12}$-cycloalkyl)-$C_1$-$C_4$-alkyl (e.g. cyclopropyl-methyl or cyclohexyl-methyl), $C_1$-$C_6$-alkoxy-$C_1$-$C_6$-alkyl (e.g. methoxymethyl), optionally substituted $C_3$-$C_{12}$-cycloalkyl (e.g. cyclopropyl, 2-propyl-cyclopropyl, 1-(methoxy-methyl)-cyclopropyl, 2-phenyl-cyclopropyl, cyclopentyl, cyclopentyl, 3,3-dimethylcyclopentyl, cyclohexyl, 3,3-dimethyl-cyclohexyl, 4,4-dimethyl-cyclohexyl, 1-methyl-cyclohexyl, 1-$CF_3$-cyclopropyl, 4-$CF_3$-cyclohexyl, 3-$CF_3$-cyclohexyl, or 4,4-diF-cyclohexyl, a further example being 1-phenyl-cyclopropyl, 1-(4-F-phenyl)-cyclopropyl, (3-Cl-phenyl)-cyclopropyl, 2-phenyl-cyclobutyl, 3-phenyl-cyclobutyl, 3-(4-F-phenyl)cyclobutyl, 3-(2-F-phenyl)-cyclobutyl, 2-Cl-cyclopentyl, 2-Me-cyclopentyl, 3-Me-cyclopentyl, 2-phenyl-cyclopentyl, 3-(2-pyridyl)-cyclopentyl, 3-Me-cyclohexyl, 3,3,5,5-tetraMe-cyclohexyl, 4-Me-cyclohexyl, 4-Et-cyclohexyl, 2-$CF_3$-cyclohexyl, 2-Me-5-isopropenyl-cyclohexyl, 2-phenyl-cyclohexyl, 3-phenyl-cyclohexyl, 4-phenyl-cyclohexyl, 2-EtO-cyclohexyl, decalin-1-yl, decalin-2-yl, norbornan-2-yl, 1,7,7-trimethyl-norbornan-2-yl, 5-iPr-2-Me-3-bicyclo[3.1.0]hexanyl, bicyclo[3.2.1]octanyl, or 3-bicyclo[1.1.1]pentanyl), $C_2$-$C_6$-alkenyl (e.g. hex-2-enyl), optionally substituted $C_3$-$C_6$-cycloalkenyl (e.g. 1,3,3-trimethylcyclohexen-2-yl), optionally substituted $C_6$-$C_{12}$-aryl (e.g. phenyl, 2-F-phenyl, 4-F-phenyl, 3-F-phenyl, 2-Cl-phenyl, 3-Cl-phenyl, 4-Cl-phenyl, 2,3-diF-phenyl, 2,4-diF-phenyl, 2,5-diF-phenyl, 3,4-diF-phenyl, 2,3,4-triF-phenyl, 2,4-diCl-phenyl, 3,4-diCl-phenyl, 3-F-4-Cl-phenyl, 3-Cl-F-phenyl, 3-Cl-5-F-phenyl, 3,4-diF-5-Cl-phenyl, 2-Me-phenyl, 3-Me-phenyl, 4-Me-phenyl, 3-iPr-phenyl, 3-tBu-phenyl, 3-Me-4-F-phenyl, 3-Me-4-

Cl-phenyl, 3-iPr-4-Cl-phenyl, 3-(1-OH-1-CF$_3$-Et)-phenyl, 3-CHF$_2$-4-F-phenyl, 2-CF$_3$-phenyl, 3-CF$_3$-phenyl, 4-CF$_3$-phenyl, 3-Cl-4-CF$_3$-phenyl, 2-F-3-CF$_3$-phenyl, 2-F-5-CF$_3$-phenyl, 3-F-5-CF$_3$-phenyl, 2-Cl-4-CF$_3$-phenyl, 2-Cl-3-CF$_3$-phenyl, 3-CF$_3$-4-F-phenyl, 3-CF$_3$-4-Cl-phenyl, 3-Me-4-CF$_3$-phenyl, 3-CF$_3$-4-Me-phenyl, 3,4-diCF$_3$-phenyl, 4-OMe-phenyl, 3-OiPr-phenyl, 3-CF$_3$-4-OMe-phenyl, 3-OCH$_2$CF$_3$-phenyl, 3-OCF$_3$-phenyl, 2-OCHF$_2$-5-Cl-phenyl, 3-OCF$_3$-4-F-phenyl, 3-OCF$_3$-4-Cl-phenyl, 3-OBn-phenyl, 3-OPh-phenyl, 3-CN-phenyl, 4-CN-phenyl, 2-F-3-CN-phenyl, 2-F-4-CN-phenyl, 3-F-4-CN-phenyl, 2-F-5-CN-phenyl, 3-F-5-CN-phenyl, 3-Cl-4-CN-phenyl, 2-Cl-5-CN-phenyl, 3-Cl-5-CN-phenyl, 3-CN-4-Cl-phenyl, 2-Me-3-CN-phenyl, 2-Me-5-CN-phenyl, 3-Me-5-CN-phenyl, 3-CF$_3$-4-CN-phenyl, 3-CN-4-OMe-phenyl, 3-CN-4-OCF$_3$-phenyl, 3-phenyl-phenyl, 3-MeSO$_2$-phenyl, 3-(piperidin-4-yl)phenyl, 2-methylcarbonylamino-5-Cl-phenyl, 3-(pyrid-2-yl)-phenyl, 3-(pyrid-3-yl)-4F-phenyl, 3-(pyrid-4-yl)-4F-phenyl, 3-(pyrimid-5-yl)-4F-phenyl, indan-5-yl, 2-chlor-indan-5-yl, or tetralin-6-yl, a further example being 2,4-diF-3-Cl-phenyl, 3-Et-4-Cl-phenyl, 3-(2-methoxyethyl)-phenyl, 3-(2-OH-ethyl)-phenyl, 3-(1-OH-1-Me-ethyl)-phenyl, 3-CHF$_2$-phenyl, 3-CF$_3$-2,4-diF-phenyl, 3-(dimethylamino-methyl)-phenyl, 3-(morpholin-4-ylmethyl)-phenyl, 3-cyclopropyl-phenyl, 3-OEt-phenyl, 3-OPr-phenyl, 3-OtBu-phenyl, 3-(cyclopropylmethoxy)-phenyl, 3-(OMe-methoxy)-phenyl, 3-(2-dimethylamino-ethoxy)phenyl, 3-CF$_3$-4-OH-phenyl, 3-OCH$_2$CHF$_2$-phenyl, 3-OCHF$_2$-phenyl, 3-OCHF$_2$-4-F-phenyl, 3-OCF$_3$-4-OMe-phenyl, 3-cyclopropoxy-phenyl, 3-methylcarbonyl-phenyl, 3-dimethylamino-phenyl, 3-(2-pyridyloxy)-phenyl, 3-(pyrimidin-2-yloxy)-phenyl, indanyl, indan-2-yl, 2-F-indanyl, 4-F-indanyl, 5-F-indanyl, 6-F-indanyl, 7-F-indanyl, 3-Me-indanyl, 4-Me-indanyl, 5-Me-indanyl, 6-Me-indanyl, 4-CF$_3$-indanyl, 5-CF$_3$-indanyl, 6-CF$_3$-indanyl, 3,3-dimethyl-indanyl, tetralin-2-yl, 7-F-tetralin-2-yl, 6-F-tetralin-2-yl, tetralinyl, 6-Ftetralinyl, 5-F-tetralinyl, or 7-F-tetralinyl), hydroxy, C$_1$-C$_6$-alkoxy (e.g. methoxy, ethoxy, or n-propyloxy), C$_1$-C$_6$-alkoxy-C$_1$-C$_4$-alkoxy (e.g. 2-methoxy-ethoxy), optionally substituted C$_6$-C$_{12}$-aryloxy (e.g. 4-F-phenoxy or 4-tertbutyl-phenoxy), optionally substituted C$_3$-C$_{12}$-heterocyclyloxy (e.g. pyridin-2-yloxy), optionally substituted C$_3$-C$_{12}$-heterocyclyl (e.g. propyl-furan-2-yl, 2-CF$_3$-furan-5-yl, 1,2-dimethyl-5-CN-pyrrol-3-yl, 2,3-diMe-thiophen-5-yl, 2-Me-thiophen-5-yl, 2-Cl-thiophen-5-yl, 3-Cl-thiophen-2-yl, 2,5-diCl-thiophen-3-yl, 2-tetrahydropyranyl-thiophen-5-yl, 1,3-thiazol-5-yl, 4-Me-1,3-thiazol-2-yl, 2-Me-1,3-thiazol-5-yl, 5-Me-1,3-thiazol-2-yl, 4-Me-1,3-thiazol-5-yl, 2-Me-1,3-thiazol-4-yl, 4-iso-propyl-1,3-thiazol-2-yl, 2,4-diMe-1,3-thiazol-5-yl, 2-phenyl-4-Me-1,3-thiazol-5-yl, 4-phenyl-1,3-thiazol-5-yl, 2-(4-Me-phenyl)-1,3-thiazol-5-yl, 4-(4-F-phenyl)-1,3-thiazol-2-yl, 2-Cl-1,3-thiazol-4-yl, 4-Cl-1,3-thiazol-5-yl, 2-Br-1,3-thiazol-5-yl, 4-Br-1,3-thiazol-5-yl, 4-Me-5-Br-1,3-thiazol-2-yl, 2,4-dichloro-1,3-thiazol-5-yl, 1,5-dimethyl-1,2,4-triazol-3-yl, pyrid-2-yl, pyrid-3-yl, pyrid-4-yl, 4-F-pyrid-2-yl, 5-F-pyrid-2-yl, 6-F-pyrid-2-yl, 4-Cl-pyrid-2-yl, 5-F-pyrid-3-yl, 2-F-pyrid-4-yl, 3,5-diCl-pyrid-4-yl, 4,5-diCl-pyrid-2-yl, 2-Cl-3F-pyrid-4-yl, 5-Me-pyrid-2-yl, 4-iPr-pyrid-2-yl, 4-Me-5-F-pyrid-2-yl, 4-CF$_3$-pyrid-2-yl, 5-CF$_3$-pyrid-2-yl, 6-CF$_3$-pyrid-2-yl, 5-CF$_3$-pyrid-3-yl, 2-CF$_3$-pyrid-4-yl, 3-F-4-CF$_3$-pyrid-2-yl, 4-CF$_3$-5-F-pyrid-2-yl, 4-CF$_3$-5-Cl-pyrid-2-yl, 3,5-diF-4-CF$_3$-pyrid-2-yl, 4-OCH$_2$CF$_3$-pyrid-2-yl, 4-OCH$_2$CF$_3$-5-F-pyrid-2-yl, 4-OCH$_2$CF$_3$-5-Cl-pyrid-2-yl, 4-OBn-5-F-pyrid-2-yl, 3-(4-F-phenyl)-pyrid-5-yl, 2-(4-F-phenyl)-pyrid-3-yl, 4-(pyrid-4-yl)-pyrid-2-yl, 4-(pyrid-3-yl)pyrid-2-yl, 5-cyclopropyl-pyraz-2-yl, 5-cyclobutyl-pyraz-2-yl, 5-pyrrolidin-pyraz-2-yl, pyridaz-3-yl, 4-CF$_3$-pyridaz-3-yl, 5-CF$_3$-pyridaz-3-yl, 5-F-pyrimid-2-yl, 6-Cl-pyrimid-4-yl, 6-Me-pyrimid-4-yl, 6-Et-pyrimid-4-yl, 6-Pr-pyrimid-4-yl, 6-iPr-pyrimid-4-yl, 4-CF$_3$-pyrimid-2-yl, 6-CF$_3$-pyrimid-4-yl, 2-Me-6-Cl-pyrimid-4-yl, 2-Me-6-CF$_3$-pyrimid-4-yl, 2-OMe-6-CF$_3$-pyrimid-4-yl, 2-OMe-pyrimid-4-yl, 6-OMe-pyrimid-4-yl, 6-OEt-pyrimid-4-yl, 6-Opr-pyrimid-4-yl, 6-OiPr-pyrimid-4-yl, 6-OiBu-pyrimid-4-yl, 6-OBu-pyrimid-4-yl, 6-OBn-pyrimid-4-yl, 6-cyclobutyloxy-pyrimid-4-yl, 6-cyclopentyloxy-pyrimid-4-yl, 6-cyclohexyloxy-pyrimid-4-yl, 6-cyclopropyl-pyrimid-4-yl, 6-phenyl-pyrimid-4-yl, 6-(2-F-phenyl)-pyrimid-4-yl, 6-(3-F-phenyl)-pyrimid-4-yl, 6-(4-F-phenyl)-pyrimid-4-yl, 6-Cl-pyrimid-4-yl, 6-(2-Me-phenyl)-pyrimid-4-yl, 6-(3-Me-phenyl)-pyrimid-4-yl, 6-(4-Me-phenyl)-pyrimid-4-yl, 6-(3-Cl-phenyl)-pyrimid-4-yl, 6-(4-Cl-phenyl)-pyrimid-4-yl, 2-(morpholin-1-yl)-pyrimid-4-yl, 6-(azetidin-3-yl-methoxy)-pyrimid-4-yl, 6-(pyrrolidin-3-ylmethoxy)-pyrimid-4-yl, 6-(pyrrolidin-2-yl-methoxy)-pyrimid-4-yl, benzofuran-5-yl, 2-Me-benzofuran-3-yl, 2-Et-benzofuran-3-yl, benzothiophen-5-yl, benzothiophen-6-yl, 5-Me-benzothiophen-2-yl, 5-F-benzothiophen-2-yl, 3-Cl-benzothiophen-2-yl, benzothiazol-2-yl, isoquinolin-6-yl, isoquinolin-7-yl, quinolin-6-yl, quinolin-7-yl, 4,5,6,7-tetrahydro-1,3-benzothiazol-2-yl, 2,3-dihydrobenzofuran-5-yl, 7H-pyrrolo[2,3-d]pyrimidin-4-yl, pyrazolo[1,5-a]pyridine-3-yl, pyrazolo[1,5-a]pyridine-7-yl, imidazo[1,2-a]pyridin-8-yl, 5-methyl-imidazo[1,2-a]pyridin-3-yl, 6-chloro-2-methyl-imidazo[1,2-a]pyridin-3-yl, 6-bromo-2-methyl-imidazo[1,2-a]pyridin-3-yl, thieno[2,3-b]pyridin-2-yl, N-benzyl-indolin-6-yl, indolinon-4-yl, chroman-6-yl, 4,4-dimethylchroman-6-yl, 4,4-dimethyl-1,3-dioxan-2-yl, 2-Me-tetrahydrofuran-3-yl, tetrahydrofuran-3-yl, tetrahydropyran-4-yl, 4-Me-tetrahydropyran-4-yl, 2,2-diMe-tetrahydropyran-4-yl, 1-iso-propyl-piperidin-4-yl, 1-ethyl-piperidin-3-yl, or 2-CF$_3$-piperazin-5-yl, a further example being iBu-pyrazol-4-yl, 1-CHF$_2$-5-Me-1,2-diazol-4-yl, 1-benzyl-5-F-1,2,4-triazol-3-yl, 2-Me-pyrid-4-yl, 2-iPr-pyrid-4-yl, 4-phenyl-pyrid-2-yl, 2-cyclopropyl-pyrid-4-yl, 2-OMe-pyrid-4-yl, 2-OEt-pyrid-4-yl, 2-cyclopropylmethoxy-pyrid-4-yl, 2-OiPr-pyrid-4-yl, 2-OCH$_2$CF$_3$-pyrid-4-yl, 2-cyclopropoxy-pyrid-4-yl, 2-cyclobutoxy-pyrid-4-yl, 4,5-diCl-pyrimidin-2yl, benzothiophen-3-yl, 2,2-diF-1,3-benzodioxol-5-yl, 5,6,7,8-tetrahydro-isoquinolin-5-yl, 5,6,7,8-tetrahydro-isoquinolin-8-yl, quinolin-8-yl, 1-Me-3,4-dihydro-2H-quinolin-4-yl, 2-Me-3,4-dihydro-1H-isoquinolin-6-yl, 5,6,7,8-tetrahydro-quinolin-5-yl, 5,6,7,8-tetrahydro-quinolin-8-yl, 5,6,7,8-tetrahydro-quinolin-6-yl, 2,3-dihydrobenzofuran-3-yl, pyrazolo[1,5-a]pyrimidin-6-yl, imidazo[1,5-a]pyrazinyl, 3-methyl-imidazo[1,5-a]pyrazinyl, 3-Me[1,2,4]triazolo[4,3-a]pyridin-6-yl, imidazo[1,2-a]pyrazin-6-yl, 2-Me-isoindolin-1-on-6-yl, 2,2-dimethyl-7-CF$_3$-chroman-4-yl, 7-CF$_3$-chroman-4-yl, 7-OCF$_3$-chroman-4-yl, isochroman-4-yl, 6,6-dimethyl-1,3-dioxan-2-yl, tetrahydropyran-3-yl, 1-phenyl-pyrrolidin-3-yl, piperidin-3yl, 1,3-dimethyl-piperidin-4-yl, 1-cyclopropyl-piperidin-4-yl, 1-(triF-methyl-carbonyl)-piperidin-3-yl, quinuclidin-2-yl, 6,7-dihydro-5H-cyclopenta[b]pyridine-7-yl, 6,7-dihydro-5H-cyclopenta[b]pyridine-5-yl, 6,7-dihydro-5H-cyclopenta[c]pyridine-7-yl, 6,7-dihydro-5H-cyclopenta[c]pyridine- 5-yl, 5,6-dihydro-4H-cyclopenta[b]thiophen-4-yl, or 1,2,3,5,6,7,8,8a-octahydroindolizin), or tri-($C_1$-$C_4$-alkyl)-silyloxy.

Further embodiments of pyrrolidine derivatives of formula (Id) result if $R^{8a}$ is hydrogen, $C_1$-$C_6$-alkyl (e.g. methyl, ethyl, n-propyl, iso-propyl, pentyl, or hexyl), or $C_1$-$C_6$-alkylcarbonyl (e.g. methylcarbonyl), or $R^6$, $R^8$
together are optionally substituted $C_1$-$C_5$-alkylene, wherein one or more —$CH_2$— of $C_1$-$C_5$-alkylene may be independently replaced by a an oxygen atom or C=O (e.g. —C(O)OCH$_2$—);

$R^{9a}$, $R^{9b}$
are independently hydrogen, halogen (e.g. F, Cl, or Br), $C_1$-$C_6$-alkyl (e.g. methyl, ethyl, tert-butyl, or 2,3-dimethyl-propyl), hydroxy, or $C_1$-$C_6$-alkoxy (e.g. methoxy or ethoxy);

and $R^1$, $R^{2a}$, $R^{2b}$, $R^{3a}$, $R^{3b}$, $Y^1$, $R^{5a}$, $R^{5b}$, n4, $R^{13}$ are as defined above.

In particular, $R^{9a}$, $R^{9b}$ are independently hydrogen, halogen, $C_1$-$C_6$-alkyl (e.g. methyl, ethyl, tertbutyl, or 2,3-dimethyl-propyl), or $C_1$-$C_6$-alkoxy (e.g. methoxy). In particular, $R^{9a}$, $R^{9b}$ may be independently halogenated $C_1$-$C_6$-alkyl (e.g. trifluoromethyl).

In particular, $R^{13}$ is hydrogen, $C_1$-$C_8$-alkyl (e.g. methyl, ethyl, n-butyl, tert-butyl, pentyl, or hexyl), halogenated $C_1$-$C_6$-alkyl (e.g. —$CF_3$ or —$CF_2$Me), $C_1$-$C_6$-alkoxy-$C_1$-$C_6$-alkyl (e.g. methoxy-methyl), optionally substituted $C_3$-$C_{12}$-cycloalkyl (e.g. cyclopropyl, 2-propyl-cyclopropyl, 1-(methoxymethyl)-cyclopropyl, 2-phenyl-cyclopropyl, cyclopentyl, cyclopentyl, 3,3-dimethylcyclopentyl, cyclohexyl, 3,3-dimethyl-cyclohexyl, 4,4-dimethyl-cyclohexyl, 1-methyl-cyclohexyl, 1-$CF_3$-cyclopropyl, 4-$CF_3$-cyclohexyl, 3-$CF_3$-cyclohexyl, or 4,4-diF-cyclohexyl, a further example being 1-phenyl-cyclopropyl, 1-(4-F-phenyl)-cyclopropyl, (3-Cl-phenyl)-cyclopropyl, 2-phenylcyclobutyl, 3-phenyl-cyclobutyl, 3-(4-F-phenyl)-cyclobutyl, 3-(2-F-phenyl)-cyclobutyl, 2-Cl-cyclopentyl, 2-Me-cyclopentyl, 3-Me-cyclopentyl, 2-phenyl-cyclopentyl, 3-(2-pyridyl)cyclopentyl, 3-Me-cyclohexyl, 3,3,5,5-tetraMe-cyclohexyl, 4-Me-cyclohexyl, 4-Et-cyclohexyl, 2-$CF_3$-cyclohexyl, 2-Me-5-isopropenyl-cyclohexyl, 2-phenyl-cyclohexyl, 3-phenyl-cyclohexyl, 4-phenyl-cyclohexyl, 2-EtO-cyclohexyl, decalin-1-yl, decalin-2-yl, norbornan-2-yl, 1,7,7-trimethyl-norbornan-2-yl, 5-iPr-2-Me-3-bicyclo[3.1.0]hexanyl, bicyclo[3.2.1]octanyl, or 3-bicyclo[1.1.1]pentanyl), $C_2$-$C_6$-alkenyl (e.g. hex-2-enyl), optionally substituted $C_3$-$C_6$-cycloalkenyl (e.g. 1,3,3-trimethylcyclohexen-2-yl), optionally substituted $C_6$-$C_{12}$-aryl (e.g. phenyl, 2-F-phenyl, 4-F-phenyl, 3-F-phenyl, 2-Cl-phenyl, 3-Cl-phenyl, 4-Cl-phenyl, 2,3-diF-phenyl, 2,4-diF-phenyl, 2,5-diF-phenyl, 3,4-diF-phenyl, 2,3,4-triF-phenyl, 2,4-diCl-phenyl, 3,4-diCl-phenyl, 3-F-4-Cl-phenyl, 3-Cl-F-phenyl, 3-Cl-5-F-phenyl, 3,4-diF-5-Cl-phenyl, 2-Me-phenyl, 3-Me-phenyl, 4-Me-phenyl, 3-iPr-phenyl, 3-tBu-phenyl, 3-Me-4-F-phenyl, 3-Me-4-Cl-phenyl, 3-iPr-4Cl-phenyl, 3-(1-OH-1-$CF_3$-Et)-phenyl, 3-$CHF_2$-4-F-phenyl, 2-$CF_3$-phenyl, 3-$CF_3$-phenyl, 4-$CF_3$-phenyl, 3-Cl-4-$CF_3$-phenyl, 2-F-3-$CF_3$-phenyl, 2-F-5-$CF_3$-phenyl, 3-F-5-$CF_3$-phenyl, 2-Cl-4-$CF_3$-phenyl, 2-Cl-3-$CF_3$-phenyl, 3-$CF_3$-4-F-phenyl, 3-$CF_3$-4-Cl-phenyl, 3-Me-4-$CF_3$-phenyl, 3-$CF_3$-4-Me-phenyl, 3,4-di$CF_3$-phenyl, 4-OMe-phenyl, 3-OiPr-phenyl, 3-$CF_3$-4-OMe-phenyl, 3-$OCH_2CF_3$-phenyl, 3-$OCF_3$-phenyl, 3-$OCHF_2$-5-Cl-phenyl, 3-$OCF_3$-4-F-phenyl, 3-$OCF_3$-4-Cl-phenyl, 3-OBn-phenyl, 3-OPh-phenyl, 3-CN-phenyl, 4-CN-phenyl, 2-F-3-CN-phenyl, 2-F-4-CN-phenyl, 3-F-4-CN-phenyl, 2-F-5-CN-phenyl, 3-F-5-CN-phenyl, 3-Cl-4-CN-phenyl, 2-Cl-5-CN-phenyl, 3-Cl-5-CN-phenyl, 3-CN-4-Cl-phenyl, 2-Me-3-CN-phenyl, 2-Me-5-CN-phenyl, 3-Me-5-CN-phenyl, 3-$CF_3$-4-CN-phenyl, 3-CN-4-OMe-phenyl, 3-CN-4-$OCF_3$-phenyl, 3-phenyl-phenyl, 3-$MeSO_2$-phenyl, 3-(piperidin-4-yl)-phenyl, 2-methylcarbonylamino-5-Cl-phenyl, 3-(pyrid-2-yl)-phenyl, 3-(pyrid-3-yl)-4F-phenyl, 3-(pyrid-4-yl)-4F-phenyl, 3-(pyrimid-5-yl)-4F-phenyl, indan-5-yl, 2-chlor-indan-5-yl, or tetralin-6-yl, a further example being 2,4-diF-3-Cl-phenyl, 3-Et-4-Cl-phenyl, 3-(2-methoxyethyl)-phenyl, 3-(2—OH-ethyl)-phenyl, 3-(1-OH-1-Me-ethyl)-phenyl, 3-$CHF_2$-phenyl, 3-$CF_3$-2,4-diF-phenyl, 3-(dimethylamino-methyl)-phenyl, 3-(morpholin-4-yl-methyl)-phenyl, 3-cyclopropyl-phenyl, 3-OEt-phenyl, 3-OPr-phenyl, 3-OtBu-phenyl, 3-(cyclopropylmethoxy)phenyl, 3-(OMe-methoxy)-phenyl, 3-(2-dimethylamino-ethoxy)-phenyl, 3-$CF_3$-4-OH-phenyl, 3-$OCH_2CHF_2$-phenyl, 3-$OCHF_2$-phenyl, 3-$OCHF_2$-4-F-phenyl, 3-$OCF_3$-4-OMe-phenyl, 3-cyclopropoxy-phenyl, 3-methylcarbonyl-phenyl, 3-dimethylamino-phenyl, 3-(2-pyridyloxy)phenyl, 3-(pyrimidin-2-yloxy)-phenyl, indanyl, indan-2-yl, 2-F-indanyl, 4-F-indanyl, 5-F-indanyl, 6-F-indanyl, 7-F-indanyl, 3-Me-indanyl, 4-Me-indanyl, 5-Me-indanyl, 6-Me-indanyl, 4-$CF_3$-indanyl, 5-$CF_3$-indanyl, 6-$CF_3$-indanyl, 3,3-dimethyl-indanyl, tetralin-2-yl, 7-F-tetralin-2-yl, 6-F-tetralin-2-yl, tetralin-6-yl, 6-F-tetralinyl, 5-F-tetralinyl, or 7-F-tetralinyl), $C_1$-$C_6$-alkoxy (e.g. methoxy, ethoxy, or n-propyloxy), $C_1$-$C_6$-alkoxy-$C_1$-$C_4$-alkoxy (e.g. 2-methoxy-ethoxy), optionally substituted $C_6$-$C_{12}$-aryloxy (e.g. 4-F-phenoxy or 4-tert-butyl-phenoxy), optionally substituted $C_3$-$C_{12}$-heterocyclyl (e.g. e.g. n-propyl-furan-2-yl, 2-$CF_3$-furan-5-yl, 1,2-dimethyl-5-CN-pyrrol-3-yl, 2,3-diMe-thiophen-5-yl, 2-Me-thiophen-5-yl, 2-Cl-thiophen-5-yl, 3-Cl-thiophen-2-yl, 2,5-diClthiophen-3-yl, 2-tetrahydropyranyl-thiophen-5-yl, 1,3-thiazol-5-yl, 4-Me-1,3-thiazol-2-yl, 2-Me-1,3-thiazol-5-yl, 5-Me-1,3-thiazol-2-yl, 4-Me-1,3-thiazol-5-yl, 2-Me-1,3-thiazol-4-yl, 4-iso-propyl-1,3-thiazol-2-yl, 2,4-diMe-1,3-thiazol-5-yl, 2-phenyl-4-Me-1,3-thiazol-5-yl, 4-phenyl-1,3-thiazol-5-yl, 2-(4-Me-phenyl)-1,3-thiazol-5-yl, 4-(4-F-phenyl)-1,3-thiazol-2-yl, 2-Cl-1,3-thiazol-4-yl, 4-Cl-1,3-thiazol-5-yl, 2-Br-1,3-thiazol-5-yl, 4-Br-1,3-thiazol-2-yl, 4-Me-5-Br-1,3-thiazol-2-yl, 2,4-dichloro-1,3-thiazol-5-yl, 1,5-dimethyl-1,2,4-triazol-3-yl, pyrid-2-yl, pyrid-3-yl, pyrid-4-yl, 4-F-pyrid-2-yl, 5-F-pyrid-2-yl, 6-F-pyrid-2-yl, 4-Cl-pyrid-2-yl, 5-F-pyrid-3-yl, 2-F-pyrid-4-yl, 3,5-diCl-pyrid-4-yl, 4,5-diCl-pyrid-2-yl, 2-Cl-3F-pyrid-4-yl, 5-Me-pyrid-2-yl, 4-iPr-pyrid-2-yl, 4-Me-5-F-pyrid-2-yl, 4-$CF_3$-pyrid-2-yl, 5-$CF_3$-pyrid-2-yl, 6-$CF_3$-pyrid-2-yl, 5-$CF_3$-pyrid-3-yl, 2-$CF_3$-pyrid-4-yl, 3-F-4-$CF_3$-pyrid-2-yl, 4-$CF_3$-5-F-pyrid-2-yl, 4-$CF_3$-5-Cl-pyrid-2-yl, 3,5-diF-4-$CF_3$-pyrid-2-yl, 4-$OCH_2CF_3$-pyrid-2-yl, 4-$OCH_2CF_3$-5-F-pyrid-2-yl, 4-$OCH_2CF_3$-5-Cl-pyrid-2-yl, 4-OBn-5-F-pyrid-2-yl, 3-(4-F-phenyl)-pyrid-5-yl, 2-(4-F-phenyl)-pyrid-3-yl, 4-(pyrid-4-yl)-pyrid-2-yl, 4-(pyrid-3-yl)-pyrid-2-yl, 5-cyclopropyl-pyraz-2-yl, 5-cyclobutyl-pyraz-2-yl, 5-pyrrolidin-pyraz-2-yl, pyridaz-3-yl, 4-$CF_3$-pyridaz-3-yl, 5-$CF_3$-pyridaz-3-yl, 5-F-pyrimid-2-yl, 6-Cl-pyrimid-4-yl, 6-Me-pyrimid-4-yl, 6-Et-pyrimid-4-yl, 6-Pr-pyrimid-4-yl, 6-iPr-pyrimid-4-yl, 4-$CF_3$-pyrimid-2-yl, 6-$CF_3$-pyrimid-4-yl, 2-Me-6-Cl-pyrimid-4-yl, 2-Me-6-$CF_3$-pyrimid-4-yl, 2-OMe-6-$CF_3$-pyrimid-4-yl, 2-OMe-pyrimid-4-yl, 6-OMe-pyrimid-4-yl, 6-OEt-pyrimid-4-yl, 6-Opr-pyrimid-4-yl, 6-OiPr-pyrimid-4-yl, 6-OiBu-pyrimid-4-yl, 6-OBu-pyrimid-4-yl, 6-OBn-pyrimid-4-yl, 6-cyclobutyloxy-pyrimid-4-yl, 6-cyclopentyloxy-pyrimid-4-yl, 6-cyclohexyloxy-pyrimid-4-yl, 6-cyclopropyl-pyrimid-4-yl, 6-phenyl-pyrimid-4-yl, 6-(2-F-phenyl)-pyrimid-4-yl, 6-(3-F-phenyl)-pyrimid-4-yl, 6-(4-F-phenyl)-pyrimid-4-yl, 6-Cl-pyrimid-4-yl, 6-(2-

Me-phenyl)-pyrimid-4-yl, 6-(3-Me-phenyl)-pyrimid-4-yl, 6-(4-Me-phenyl)-pyrimid-4-yl, 6-(3-Cl-phenyl)-pyrimid-4-yl, 6-(4-Cl-phenyl)-pyrimid-4-yl, 2-(morpholin-1-yl)-pyrimid-4-yl, 6-(azetidin-3-yl-methoxy)pyrimid-4-yl, 6-(pyrrolidin-3-yl-methoxy)-pyrimid-4-yl, 6-(pyrrolidin-2-yl-methoxy)-pyrimid-4-yl, benzofuran-5-yl, 2-Me-benzofuran-3-yl, 2-Et-benzofuran-3-yl, benzothiophen-5-yl, benzothiophen-6-yl, 5-Me-benzothiophen-2-yl, 5-F-benzothiophen-2-yl, 3-Cl-benzothiophen-2-yl, benzothiazol-2-yl, isoquinolin-6-yl, isoquinolin-7-yl, quinolin-6-yl, quinolin-7-yl, 4,5,6,7-tetrahydro-1,3-benzothiazol-2-yl, 2,3-dihydrobenzofuran-5-yl, 7H-pyrrolo[2,3-d]pyrimidin-4-yl, pyrazolo[1,5-a]pyridine-3-yl, pyrazolo[1,5-a]pyridine-7-yl, imidazo[1,2-a]pyridin-8-yl, 5-methyl-imidazo[1,2-a]pyridin-3-yl, 6-chloro-2-methyl-imidazo[1,2-a]pyridin-3-yl, 6-bromo-2-methyl-imidazo[1,2-a]pyridin-3-yl, thieno[2,3-b]pyridin-2-yl, N-benzyl-indolin-6-yl, indolinon-4-yl, chroman-6-yl, 4,4-dimethylchroman-6-yl, 4,4-dimethyl-1,3-dioxan-2-yl, 2-Me-tetrahydrofuran-3-yl, tetrahydrofuran-3-yl, tetrahydropyran-4-yl, 4-Me-tetrahydropyran-4-yl, 2,2-diMe-tetrahydropyran-4-yl, 1-isopropyl-piperidin-4-yl, 1-ethyl-piperidin-3-yl, or 2-CF$_3$-piperazin-5-yl, a further example being iBu-pyrazol-4-yl, 1-CHF$_2$-5-Me-1,2-diazol-4-yl, 1-benzyl-5-F-1,2,4-triazol-3-yl, 2-Me-pyrid-4-yl, 2-iPr-pyrid-4-yl, 4-phenyl-pyrid-2yl, 2-cyclopropyl-pyrid-4-yl, 2-OMe-pyrid-4-yl, 2-OEt-pyrid-4-yl, 2-cyclopropylmethoxy-pyrid-4-yl, 2-OiPr-pyrid-4-yl, 2-OCH$_2$CF$_3$-pyrid-4-yl, 2-cyclopropoxy-pyrid-4-yl, 2-cyclobutoxy-pyrid-4-yl, 4,5-diCl-pyrimidin-2yl, benzothiophen-3-yl, 2,2-diF-1,3-benzodioxol-5-yl, 5,6,7,8-tetrahydro-isoquinolin-5-yl, 5,6,7,8-tetrahydro-isoquinolin-8-yl, quinolin-8-yl, 1-Me-3,4-dihydro-2H-quinolin-4-yl, 2-Me-3,4-dihydro-1H-isoquinolin-6-yl, 5,6,7,8-tetrahydro-quinolin-5-yl, 5,6,7,8-tetrahydro-quinolin-8-yl, 5,6,7,8-tetrahydro-quinolin-6-yl, 2,3-dihydrobenzofuran-3-yl, pyrazolo[1,5-a]pyrimidin-6-yl, imidazo[1,5-a]pyrazinyl, 3-methyl-imidazo[1,5-a]pyrazinyl, 3-Me-[1,2,4]triazolo[4,3-a]pyridin-6-yl, imidazo[1,2-a]pyrazin-6-yl, 2-Me-isoindolin-1-on-6-yl, 2,2-dimethyl-7-CF$_3$-chroman-4-yl, 7-CF$_3$-chroman-4-yl, 7-OCF$_3$-chroman-4-yl, isochroman-4-yl, 6,6-dimethyl-1,3-dioxan-2-yl, tetrahydropyran-3-yl, 1-phenyl-pyrrolidin-3-yl, piperidin-3-yl, 1,3-dimethyl-piperidin-4-yl, 1-cyclopropyl-piperidin-4-yl, 1-(tri-Fmethyl-carbonyl)-piperidin-3-yl, quinuclidin-2-yl, 6,7-dihydro-5H-cyclopenta[b]pyridine-7-yl, 6,7-dihydro-5H-cyclopenta[b]pyridine-5-yl, 6,7-dihydro-5H-cyclopenta[c]pyridine-7-yl, 6,7-dihydro-5H-cyclopenta[c]pyridine-5-yl, 5,6-dihydro-4H-cyclopenta[b]thiophen-4-yl, or 1,2,3,5,6,7,8,8a-octahydroindolizin), or tri-(C$_1$-C$_4$-alkyl)-silyloxy.

$R^{2a}$, $R^{2b}$—in the pyrrolidine derivatives of formula (Id)—are, in particular, hydrogen.

$R^{3a}$—in the pyrrolidine derivatives of formula (Id)—is, in particular, C$_3$-C$_{12}$-cycloalkyl (e.g. cyclopropyl, cyclobutyl, cyclopentyl, or cyclohexyl), optionally substituted C$_6$-C$_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), hydroxy, C$_1$-C$_6$-alkoxy (e.g. methoxy, ethoxy, n-propoxy, iso-propoxy, or iso-butoxy), halogenated C$_1$-C$_6$-alkoxy (e.g OCF$_3$), C$_3$-C$_{12}$-cycloalkyl-C$_1$-C$_4$-alkoxy (e.g. cyclopropylmethoxy or cyclohexylmethoxy), C$_2$-C$_6$-alkenyloxy (e.g. allyloxy or 2-methylprop-2-en-1-oxy), C$_6$-C$_{12}$-aryl-C$_1$-C$_4$-alkoxy (e.g. benzyloxy), C$_3$-C$_{12}$-heterocyclyl-C$_1$-C$_4$-alkoxy (e.g. 2-(N-pyrrolidinyl)ethoxy, 2-(N-morpholinyl)ethoxy and 2-(N-imidazolyl)ethoxy), optionally substituted C$_6$-C$_{12}$-aryloxy (e.g. phenoxy or 4-F-phenoxy), C$_3$-C$_{12}$-heterocyloxy (e.g. pyridin-2-yloxy), or optionally substituted C$_3$-C$_{12}$-heterocyclyl (tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, or 1,3-oxazol-2-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, morpholin-4-yl, pyrrolidinyl, piperidyl, 4-F-piperidyl, 4,4-diF-piperidyl, 1-Me-piperid-2-yl, or 5-F-pyrid-2-yl).

In particular, $R^{3a}$ and one of $R^{2a}$ or $R^{2b}$ together with the carbon atoms to which they are bound may form an optionally substituted anellated C$_6$-C$_{12}$-aryl.

Preferably, $R^{3a}$ is C$_3$-C$_{12}$-cycloalkyl (e.g. cyclopropyl, cyclobutyl, cyclopentyl, or cyclohexyl), optionally substituted C$_6$-C$_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), hydroxy, C$_1$-C$_6$-alkoxy (e.g. methoxy, ethoxy, n-propoxy, iso-propoxy, or iso-butoxy), C$_3$-C$_{12}$-cycloalkyl-C$_1$-C$_4$-alkoxy (e.g. cyclopropylmethoxy or cyclohexylmethoxy), C$_2$-C$_6$-alkenyloxy (e.g. allyloxy or 2-methylprop-2-en-1-oxy), C$_6$-C$_{12}$-aryl-C$_1$-C$_4$-alkoxy (e.g. benzyloxy), optionally substituted C$_6$-C$_{12}$-aryloxy (e.g. phenoxy or 4-F-phenoxy) or optionally substituted C$_3$-C$_{12}$-heterocyclyl (tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, or 1,3-oxazol-2-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, morpholin-4-yl, pyrrolidinyl, piperidyl, 4-F-piperidyl, 4,4-diF-piperidyl, 1-Me-piperid-2-yl, or 5-F-pyrid-2-yl).

It is further preferred if $R^{3a}$ and one of $R^{2a}$ or $R^{2b}$ together with the carbon atoms to which they are bound form an anellated C$_6$-C$_{12}$-aryl.

$R^{3b}$—in the pyrrolidine derivatives of formula (Id)—is, in particular, hydrogen or hydroxy.

$Y^1$—in the pyrrolidine derivatives of formula (Id)—is, in particular, >CR$^6$.

$R^6$—in the pyrrolidine derivatives of formula (Id)—is, in particular, hydrogen, C$_1$-C$_6$-alkyl (e.g. methyl), or hydroxy-C$_1$-C$_6$-alkyl (e.g. —CH$_2$OH).

In particular, $R^6$ and $R^{3a}$ or $R^{3b}$ together may be optionally substituted C$_1$-C$_5$-alkylene, preferably unsubstituted C$_1$-C$_5$-alkylene (e.g. 1,3-propylene or 1,4-butylene); or $R^6$ may be C$_1$-C$_4$-alkylene (e.g. methylene or 1,2-ethylene) that is bound to a carbon atom in $R^{3a}$, and $R^{3a}$ is an optionally substituted C$_6$-C$_{12}$-aryl (e.g. phenyl).

$R^{5a}$, $R^{5b}$—in the pyrrolidine derivatives of formula (Id)—are, in particular, hydrogen.

Particular embodiments of pyrrolidine derivatives of formula (Id) result if:

$R^1$ is an optionally substituted 5-membered heterocyclic ring containing at least 1 N ring atom and optionally 1 or 2 further heteroatoms selected from N, O and S (e.g. e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me- 3-CF$_3$-1,2-diazol-4-yl, 1-cyclopentyl-3-Me-1,2-diazol-4-yl, 1,3,5-trimethyl-1,2-diazol-4-yl, 1-CHF$_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$
are hydrogen;

$R^{3a}$ is C$_3$-C$_{12}$-cycloalkyl (e.g. cyclopropyl, cyclobutyl, cyclopentyl, or cyclohexyl), optionally substituted C$_6$-C$_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), hydroxy, C$_1$-C$_6$-alkoxy (e.g. methoxy, ethoxy, n-propoxy, isopropoxy, or iso-butoxy), C$_3$-C$_{12}$-cycloalkyl-C$_1$-C$_4$-alkoxy (e.g. cyclopropylmethoxy or cyclohexylmethoxy), C$_2$-C$_6$-alkenyloxy (e.g. allyloxy or 2-methylprop-2-en-1-oxy), C$_6$-C$_{12}$-aryl-C$_1$-C$_4$-alkoxy (e.g. benzyloxy), optionally substituted C$_6$-C$_{12}$-aryloxy (e.g. phenoxy or 4-F-phenoxy) or optionally substituted C$_3$-C$_{12}$-heterocyclyl (tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, or 1,3-oxazol-2-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, morpholin-4-yl, pyrrolidinyl, piperidyl, 4-F-piperidyl, 4,4-diF-piperidyl, 1-Me-piperid-2-yl, or 5-F-pyrid-2-yl), or $R^{3a}$ and one of $R^{2a}$ or $R^{2b}$
together with the carbon atoms to which they are bound may form an anellated C$_6$-C$_{12}$-aryl;

$R^{3b}$ is hydrogen or hydroxy;
$Y^1$ is >CR$^6$;
$R^6$ is hydrogen, C$_1$-C$_6$-alkyl, or hydroxy-C$_1$-C$_6$-alkyl (e.g. —CH$_2$OH), or $R^6$ and $R^{3a}$ or $R^{3b}$
together are C$_1$-C$_5$-alkylene, or $R^6$
is C$_1$-C$_4$-alkylene (e.g. methylene or 1,2-ethylene) that is bound to a carbon atom in $R^{3a}$, and $R^{3a}$ is an optionally substituted C$_6$-C$_{12}$-aryl (e.g. phenyl);

$R^{8a}$ is hydrogen, C$_1$-C$_6$-alkyl (e.g. methyl, ethyl, n-propyl, iso-propyl, pentyl, or hexyl), or C$_1$-C$_6$-alkylcarbonyl (e.g. methylcarbonyl), or $R^6$, $R^{8a}$
are together optionally substituted C$_1$-C$_5$-alkylene, wherein one or more —CH$_2$— of C$_1$-C$_5$-alkylene may be independently replaced by a an oxygen atom or C=O e.g. —C(O)OCH$_2$—); or $R^{3a}$ and $R^{8a}$
together are optionally substituted C$_1$-C$_5$-alkylene (e.g. 1,2-ethylene or 1,3-propylene);

$R^{9a}$ is hydrogen, halogen (e.g. F), C$_1$-C$_6$-alkyl (e.g. methyl, ethyl, tert-butyl, or 2,3-dimethylpropyl), halogenated C$_1$-C$_6$-alkyl (e.g. trifluoromethyl), or C$_1$-C$_6$-alkoxy (e.g. methoxy or ethoxy);

$R^{9b}$ is hydrogen or halogen (e.g. F);
n4 is 0, 1, 2, 3, or 4;
$R^{13}$ is hydrogen, C$_1$-C$_8$-alkyl (e.g. methyl, ethyl, n-butyl, tert-butyl, pentyl, or hexyl), halogenated C$_1$-C$_6$-alkyl (e.g. —CF$_3$ or —CF$_2$Me), C$_1$-C$_6$-alkoxy-C$_1$-C$_6$-alkyl (e.g. methoxymethyl), optionally substituted C$_3$-C$_{12}$-cycloalkyl (e.g. cyclopropyl, 2-propyl-cyclopropyl, 1-(methoxy-methyl)-cyclopropyl, 2-phenyl-cyclopropyl, cyclopentyl, cyclopentyl, 3,3-dimethylcyclopentyl, cyclohexyl, 3,3-dimethyl-cyclohexyl, 4,4-dimethyl-cyclohexyl, 1-methyl-cyclohexyl, 1-CF$_3$-cyclopropyl, 4-CF$_3$-cyclohexyl, 3-CF$_3$-cyclohexyl, or 4,4-diF-cyclohexyl, a further example being 1-phenyl-cyclopropyl, 1-(4-F-phenyl)-cyclopropyl, (3-Cl-phenyl)-cyclopropyl, 2-phenyl-cyclobutyl, 3-phenyl-cyclobutyl, 3-(4-F-phenyl)cyclobutyl, 3-(2-F-phenyl)-cyclobutyl, 2-Cl-cyclopentyl, 2-Me-cyclopentyl, 3-Me-cyclopentyl, 2-phenyl-cyclopentyl, 3-(2-pyridyl)-cyclopentyl, 3-Me-cyclohexyl, 3,3,5,5-tetraMe-cyclohexyl, 4-Me-cyclohexyl, 4-Et-cyclohexyl, 2-CF$_3$-cyclohexyl, 2-Me-5-isopropenyl-cyclohexyl, 2-phenyl-cyclohexyl, 3-phenyl-cyclohexyl, 4-phenyl-cyclohexyl, 2-EtO-cyclohexyl, decalin-1-yl, decalin-2-yl, norbornan-2-yl, 1,7,7-trimethyl-norbornan-2-yl, 5-iPr-2-Me-3-bicyclo[3.1.0]hexanyl, bicyclo[3.2.1]octanyl, or 3-bicyclo[1.1.1]pentanyl), C$_2$-C$_6$-alkenyl (e.g. hex-2-enyl), optionally substituted C$_3$-C$_6$-cycloalkenyl (e.g. 1,3,3-trimethylcyclohexen-2-yl), optionally substituted C$_6$-C$_{12}$-aryl (e.g. phenyl, 2-F-phenyl, 4-F-phenyl, 3-F-phenyl, 2-Cl-phenyl, 3-Cl-phenyl, 4-Cl-phenyl, 2,3-diF-phenyl, 2,4-diF-phenyl, 2,5-diF-phenyl, 3,4-diF-phenyl, 2,3,4-triF-phenyl, 2,4-diCl-phenyl, 3,4-diCl-phenyl, 3-F-4-Cl-phenyl, 3-Cl-F-phenyl, 3-Cl-5-F-phenyl, 3,4-diF-5-Cl-phenyl, 2-Me-phenyl, 3-Me-phenyl, 4-Me-phenyl, 3-iPr-phenyl, 3-tBu-phenyl, 3-Me-4-F-phenyl, 3-Me-4-Cl-phenyl, 3-iPr-4Cl-phenyl, 3-(1-OH-1-CF$_3$-Et)-phenyl, 3-CHF$_2$-4-F-phenyl, 2-CF$_3$-phenyl, 3-CF$_3$-phenyl, 4-CF$_3$-phenyl, 3-Cl-4-CF$_3$-phenyl, 2-F-3-CF$_3$-phenyl, 2-F-5-CF$_3$-phenyl, 3-F-5-CF$_3$-phenyl, 2-Cl-4-CF$_3$-phenyl, 2-Cl-3-CF$_3$-phenyl, 3-CF$_3$-4-F-phenyl, 3-CF$_3$-4-Cl-phenyl, 3-Me-4-CF$_3$-phenyl, 3-CF$_3$-4-Me-phenyl, 3,4-diCF$_3$-phenyl, 4-OMe-phenyl, 3-OiPr-phenyl, 3-CF$_3$-4-OMe-phenyl, 3-OCH$_2$CF$_3$-phenyl, 3-OCF$_3$-phenyl, 2-O°C.HF$_2$-5-Cl-phenyl, 3-OCF$_3$-4-F-phenyl, 3-OCF$_3$-4-Cl-phenyl, 3-OBn-phenyl, 3-OPh-phenyl, 3-CN-phenyl, 4-CN-phenyl, 2-F-3-CN-phenyl, 2-F-4-CN-phenyl, 3-F-4-CN-phenyl, 2-F-5-CN-phenyl, 3-F-5-CN-phenyl, 3-Cl-4-CN-phenyl, 2-Cl-5-CN-phenyl, 3-Cl-5-CN-phenyl, 3-CN-4-Cl-phenyl, 2-Me-3-CN-phenyl, 2-Me-5-CN-phenyl, 3-Me-5-CN-phenyl, 3-CF$_3$-4-CN-phenyl, 3-CN-4-OMe-phenyl, 3-CN-4-OCF$_3$-phenyl, 3-phenyl-phenyl, 3-MeSO$_2$-phenyl, 3-(piperidin-4-yl)phenyl, 2-methylcarbonylamino—S-Cl-phenyl, 3-(pyrid-2-yl)-phenyl, 3-(pyrid-3-yl)-4F-phenyl, 3-(pyrid-4-yl)-4F-phenyl, 3-(pyrimid-5-yl)-4F-phenyl, indan-5-yl, 2-chlor-indan-5-yl, or tetralin-6-yl, a further example being 2,4-diF-3-Cl-phenyl, 3-Et-4-Cl-phenyl, 3-(2-methoxyethyl)-phenyl, 3-(2-OH-ethyl)-phenyl, 3-(1-OH-1-Me-ethyl)-phenyl, 3-CHF$_2$-phenyl, 3-CF$_3$-2,4-diF-phenyl, 3-(dimethylamino-methyl)-phenyl, 3-(morpholin-4-ylmethyl)-phenyl, 3-cyclopropyl-phenyl, 3-OEt-phenyl, 3-OPr-phenyl, 3-OtBu-phenyl, 3-(cyclopropylmethoxy)-phenyl, 3-(OMe-methoxy)-phenyl, 3-(2-dimethylamino-ethoxy)phenyl, 3-CF$_3$-4-OH-phenyl, 3-OCH$_2$CHF$_2$-phenyl, 3-OCHF$_2$-phenyl, 3-OCHF$_2$-4-F-phenyl, 3-OCF$_3$-4-OMe-phenyl, 3-cyclopropoxy-phenyl, 3-methylcarbonyl-phenyl, 3-dimethylamino-phenyl, 3-(2-pyridyloxy)-phenyl, 3-(pyrimidin-2-yloxy)-phenyl, indanyl, indan-2-yl, 2-F-indanyl, 4-F-indanyl, 5-F-indanyl, 6-F-indanyl, 7-F-indanyl, 3-Me-indanyl, 4-Me-indanyl, 5-Me-indanyl, 6-Me-indanyl, 4-CF$_3$-indanyl, 5-CF$_3$-indanyl, 6-CF$_3$-indanyl, 3,3-dimethyl-indanyl, tetralin-2-yl, 7-F-tetralin-2-yl, 6-F-tetralin-2-yl, tetralinyl, 6-Ftetralinyl, 5-F-tetralinyl, or 7-F-tetralinyl), C$_1$-C$_6$-alkoxy (e.g. methoxy, ethoxy, or n-propoxy), $C_1$-$C_6$-alkoxy-$C_1$-$C_4$-alkoxy (e.g. 2-methoxy-ethoxy), optionally substituted $C_6$-$C_{12}$-aryloxy (e.g. 4-F-phenoxy or 4-tertbutyl-phenoxy), optionally substituted $C_3$-$C_{12}$-heterocyclyl (e.g. e.g. n-propyl-furan-2-yl, 2-$CF_3$-furan-5-yl, 1,2-dimethyl-5-CN-pyrrol-3-yl, 2,3-diMe-thiophen-5-yl, 2-Me-thiophen-5-yl, 2-Cl-thiophen-5-yl, 3-Cl-thiophen-2-yl, 2,5-diCl-thiophen-3-yl, 2-tetrahydropyranyl-thiophen-5-yl, 1,3-thiazol-5-yl, 4-Me-1,3-thiazol-2-yl, 2-Me-1,3-thiazol-5-yl, 5-Me-1,3-thiazol-2-yl, 4-Me-1,3-thiazol-5-yl, 2-Me-1,3-thiazol-4-yl, 4-isopropyl-1,3-thiazol-2-yl, 2,4-diMe-1,3-thiazol-5-yl, 2-phenyl-4-Me-1,3-thiazol-5-yl, 4-phenyl-1,3-thiazol-5-yl, 2-(4-Me-phenyl)-1,3-thiazol-5-yl, 4-(4-F-phenyl)-1,3-thiazol-2-yl, 2-Cl-1,3-thiazol-4-yl, 4-Cl-1,3-thiazol-5-yl, 2-Br-1,3-thiazol-5-yl, 4-Br-1,3-thiazol-2-yl, 4-Me-5-Br-1,3-thiazol-2-yl, 2,4-dichloro-1,3-thiazol-5-yl, 1,5-dimethyl-1,2,4-triazol-3-yl, pyrid-2-yl, pyrid-3-yl, pyrid-4-yl, 4-F-pyrid-2-yl, 5-F-pyrid-2-yl, 6-F-pyrid-2-yl, 4-Cl-pyrid-2-yl, 5-F-pyrid-3-yl, 2-F-pyrid-4-yl, 3,5-diCl-pyrid-4-yl, 4,5-diCl-pyrid-2-yl, 2-Cl-3F-pyrid-4-yl, 5-Me-pyrid-2-yl, 4-iPr-pyrid-2-yl, 4-Me-5-F-pyrid-2-yl, 4-$CF_3$-pyrid-2-yl, 5-$CF_3$-pyrid-2-yl, 6-$CF_3$-pyrid-2-yl, 5-$CF_3$-pyrid-3-yl, 2-$CF_3$-pyrid-4-yl, 3-F-4-$CF_3$-pyrid-2-yl, 4-$CF_3$-5-F-pyrid-2-yl, 4-$CF_3$-5-Cl-pyrid-2-yl, 3,5-diF-4-$CF_3$-pyrid-2-yl, 4-$OCH_2CF_3$-pyrid-2-yl, 4-$OCH_2CF_3$-5-F-pyrid-2-yl, 4-$OCH_2CF_3$-5-Cl-pyrid-2-yl, 4-OBn-5-F-pyrid-2-yl, 3-(4-F-phenyl)-pyrid-5-yl, 2-(4-F-phenyl)-pyrid-3-yl, 4-(pyrid-4-yl)-pyrid-2-yl, 4-(pyrid-3-yl)-pyrid-2-yl, 5-cyclopropyl-pyraz-2-yl, 5-cyclobutyl-pyraz-2-yl, 5-pyrrolidin-pyraz-2-yl, pyridaz-3-yl, 4-$CF_3$-pyridaz-3-yl, 5-$CF_3$-pyridaz-3-yl, 5-F-pyrimid-2-yl, 6-Cl-pyrimid-4-yl, 6-Me-pyrimid-4-yl, 6-Et-pyrimid-4-yl, 6-Pr-pyrimid-4-yl, 6-iPrpyrimid-4-yl, 4-$CF_3$-pyrimid-2-yl, 6-$CF_3$-pyrimid-4-yl, 2-Me-6-Cl-pyrimid-4-yl, 2-Me-6-$CF_3$-pyrimid-4-yl, 2-OMe-6-$CF_3$-pyrimid-4-yl, 2-OMe-pyrimid-4-yl, 6-OMe-pyrimid-4-yl, 6-OEt-pyrimid-4-yl, 6-OPr-pyrimid-4-yl, 6-OiPr-pyrimid-4-yl, 6-OiBu-pyrimid-4-yl, 6-OBu-pyrimid-4-yl, 6-OBn-pyrimid-4-yl, 6-cyclobutoxy-pyrimid-4-yl, 6-cyclopentoxy-pyrimid-4-yl, 6-cyclohexyloxy-pyrimid-4-yl, 6-cyclopropyl-pyrimid-4-yl, 6-phenyl-pyrimid-4-yl, 6-(2-F-phenyl)-pyrimid-4-yl, 6-(3-F-phenyl)-pyrimid-4-yl, 6-(4-F-phenyl)pyrimid-4-yl, 6-Cl-pyrimid-4-yl, 6-(2-Me-phenyl)-pyrimid-4-yl, 6-(3-Me-phenyl)-pyrimid-4-yl, 6-(4-Me-phenyl)-pyrimid-4-yl, 6-(3-Cl-phenyl)-pyrimid-4-yl, 6-(4-Cl-phenyl)pyrimid-4-yl, 2-(morpholin-1-yl)-pyrimid-4-yl, 6-(azetidin-3-yl-methoxy)-pyrimid-4-yl, 6-(pyrrolidin-3-yl-methoxy)-pyrimid-4-yl, 6-(pyrrolidin-2-yl-methoxy)-pyrimid-4-yl, benzofuran-5-yl, 2-Me-benzofuran-3-yl, 2-Et-benzofuran-3-yl, benzothiophen-5-yl, benzothiophen-6-yl, 5-Me-benzothiophen-2-yl, 5-F-benzothiophen-2-yl, 3-Cl-benzothiophen-2-yl, benzothiazol-2-yl, isoquinolin-6-yl, isoquinolin-7-yl, quinolin-6-yl, quinolin-7-yl, 4,5,6,7-tetrahydro-1,3-benzothiazol-2-yl, 2,3-dihydrobenzofuran-5-yl, 7H-pyrrolo[2,3-d]pyrimidin-4-yl, pyrazolo[1,5-a]pyridine-3-yl, pyrazolo[1,5-a]pyridine-7-yl, imidazo[1,2-a]pyridin-8-yl, 5-methyl-imidazo[1,2-a]pyridin-3-yl, 6-chloro-2-methylimidazo[1,2-a]pyridin-3-yl, 6-bromo-2-methyl-imidazo[1,2-a]pyridin-3-yl, thieno[2,3-b]pyridin-2-yl, N-benzyl-indolin-6-yl, indolinon-4-yl, chroman-6-yl, 4,4-dimethylchroman-6-yl, 4,4-dimethyl-1,3-dioxan-2-yl, 2-Me-tetrahydrofuran-3-yl, tetrahydrofuran-3-yl, tetrahydropyran-4-yl, 4-Me-tetrahydropyran-4-yl, 2,2-diMe-tetrahydropyran-4-yl, 1-isopropyl-piperidin-4-yl, 1-ethyl-piperidin-3-yl, or 2-$CF_3$-piperazin-5-yl, a further example being iBu-pyrazol-4-yl, 1-$CHF_2$-5-Me-1,2-diazol-4-yl, 1-benzyl-5-F-1,2,4-triazol-3-yl, 2-Me-pyrid-4-yl, 2-iPr-pyrid-4-yl, 4-phenyl-pyrid-2yl, 2-cyclopropyl-pyrid-4-yl, 2-OMe-pyrid-4-yl, 2-OEt-pyrid-4-yl, 2-cyclopropylmethoxy-pyrid-4-yl, 2-OiPr-pyrid-4-yl, 2-$OCH_2CF_3$-pyrid-4-yl, 2-cyclopropoxy-pyrid-4-yl, 2-cyclobutoxy-pyrid-4-yl, 4,5-diClpyrimidin-2yl, benzothiophen-3-yl, 2,2-diF-1,3-benzodioxol-5-yl, 5,6,7,8-tetrahydroisoquinolin-5-yl, 5,6,7,8-tetrahydro-isoquinolin-8-yl, quinolin-8-yl, 1-Me-3,4-dihydro-2H-quinolin-4-yl, 2-Me-3,4-dihydro-1H-isoquinolin-6-yl, 5,6,7,8-tetrahydro-quinolin-5-yl, 5,6,7,8-tetrahydro-quinolin-8-yl, 5,6,7,8-tetrahydro-quinolin-6-yl, 2,3-dihydrobenzofuran-3-yl, pyrazolo[1,5-a]pyrimidin-6-yl, imidazo[1,5-a]pyrazinyl, 3-methyl-imidazo[1,5-a]pyrazinyl, 3-Me-[1,2,4]triazolo[4,3-a]pyridin-6-yl, imidazo[1,2-a]pyrazin-6-yl, 2-Me-isoindolin-1-on-6-yl, 2,2-dimethyl-7-$CF_3$-chroman-4-yl, 7-$CF_3$-chroman-4-yl, 7-$OCF_3$-chroman-4-yl, isochroman-4-yl, 6,6-dimethyl-1,3-dioxan-2-yl, tetrahydropyran-3-yl, 1-phenyl-pyrrolidin-3-yl, piperidin-3-yl, 1,3-dimethyl-piperidin-4-yl, 1-cyclopropyl-piperidin-4-yl, 1-(tri-F-methyl-carbonyl)-piperidin-3-yl, quinuclidin-2-yl, 6,7-dihydro-5H-cyclopenta[b]pyridine-7-yl, 6,7-dihydro-5H-cyclopenta[b]pyridine-5-yl, 6,7-dihydro-5H-cyclopenta[c]pyridine-7-yl, 6,7-dihydro-5H-cyclopenta[c]pyridine-5-yl, 5,6-dihydro-4H-cyclopenta[b]thiophen-4-yl, or 1,2,3,5,6,7,8,8a-octahydroindolizin), or tri-($C_1$-$C_4$-alkyl)silyloxy; and $R^{5a}$, $R^{5b}$ are hydrogen.

Further, particular embodiments of pyrrolidine derivatives of formula (Id) result if:

$R^{3a}$ is $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), hydroxy, $C_1$-$C_6$-alkoxy (e.g. methoxy, ethoxy, n-propoxy, isopropoxy, or iso-butoxy), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenoxy or 4-F-phenoxy) or optionally substituted $C_3$-$C_{12}$-heterocyclyl (tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, or 1,3-oxazol-2-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, morpholin-4-yl, pyrrolidinyl, piperidyl, 4-F-piperidyl, 4,4-diF-piperidyl, 1-Me-piperid-2-yl, or 5-F-pyrid-2-yl);

$R^6$ is hydrogen, $C_1$-$C_6$-alkyl, or hydroxy-$C_1$-$C_6$-alkyl (e.g. —$CH_2OH$);

$R^{8a}$ is hydrogen, $C_1$-$C_6$-alkyl (e.g. methyl, ethyl, n-propyl, iso-propyl, pentyl, or hexyl), or $C_1$-$C_6$-alkylcarbonyl (e.g. methylcarbonyl), or $R^6$, $R^{8a}$ are together optionally substituted $C_1$-$C_5$-alkylene, wherein one or more —$CH_2$— of $C_1$-$C_5$-alkylene may be independently replaced by a an oxygen atom or C=O e.g. —C(O)$OCH_2$—);

$R^{9a}$ is hydrogen, halogen (e.g. F), $C_1$-$C_6$-alkyl (e.g. methyl, ethyl, tert-butyl, or 2,3-dimethylpropyl), or $C_1$-$C_6$-alkoxy (e.g. methoxy or ethoxy);

$R^{9b}$ is hydrogen;
and $R^1$, $R^{2a}$, $R^{2b}$, $R^{3b}$, $Y^1$, n4, $R^{13}$, $R^{5a}$ and $R^{5b}$ are as defined above.

According to a particular embodiment, $R^1$—in the pyrrolidine derivatives of formula (Id)—is an optionally substituted 5-membered heterocyclic ring containing 1 or 2 N and 1 O (e.g. 5-methyl-1,2-oxazol-4-yl or 3,5-dimethyl-1,2-oxazol-4-yl). According to a further particular embodiment, $R^1$—in the pyrrolidine derivatives of formula (Id)—is an optionally substituted 5-membered heterocyclic ring containing 1 or 2 N and 1 S (e.g. 2,4-dimethyl-1,3-thiazol-5-yl, or 2-methylcarbonylamino-1,3-thiazol-5-yl). According to a further particular embodiment, $R^1$—in the pyrrolidine derivatives of formula (Id)—is an optionally substituted 5-membered heterocyclic ring containing 1, 2 or 3 N (e.g. 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, or 1-Me-1,2,3-triazol-4-yl, a further example being 1-ethyl-1,3-diazol-4-yl or 1-methyl-1,2,4-triazol-3-yl).

Preferably, $R^1$—in the pyrrolidine derivatives of formula (Id)—is an optionally substituted 5-membered heterocyclic ring containing 2 N and, in particular, $R^1$ is optionally substituted 1,3-diazolyl.

According to a further preferred embodiment, $R^1$—in the pyrrolidine derivatives of formula (Id)—is an optionally substituted 5-membered heterocyclic ring containing 3 N and, in particular, $R^1$ is optionally substituted 1,2,3-triazolyl.

In connection with $R^1$ and the pyrrolidine derivatives of formula (Id), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxycarbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl. According to a further particular embodiment, 1,2,3-triazolyl is substituted with $C_1$-$C_6$-alkyl as described herein. According to a further specific embodiment, $R^1$ is 1-methyl-1,2,3-triazol-4-yl.

In connection with $R^{3a}$ and the pyrrolidine derivatives of formula (Id), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituent(s) on $C_6$-$C_{12}$-aryl are independently selected from the group consisting of halogen.

In connection with $R^{3a}$ and the pyrrolidine derivatives of formula (Id), substituted $C_6$-$C_{12}$-aryloxy in particular includes is $C_6$-$C_{12}$-aryloxy, such as phenoxy, which is substituted with 1, 2, or 3 substituents independently selected from the group consisting of halogen and $C_1$-$C_4$-alkyl.

In connection with $R^{3a}$ and the pyrrolidine derivatives of formula (Id), substituted $C_3$-$C_{12}$-heterocyclyl in particular includes $C_3$-$C_{12}$-heterocyclyl, such as pyridyl, piperidinyl, isoxazolyl, diazolyl, tetrahydrofuranyl, tetrahydropyranyl, or morpholinyl, which is substituted with 1, 2, or 3 substituents independently selected from the group consisting of halogen, $C_1$-$C_4$-alkyl or $C_3$-$C_6$-cycloalkyl. Additionally, in connection with $R^{3a}$ and the pyrrolidine derivatives of formula (Id), substituted $C_3$-$C_{12}$-heterocyclyl in particular may include $C_3$-$C_{12}$-heterocyclyl, such as pyrrolidinyl, dioxolanyl, dioxanyl, or dioxepanyl, which is substituted with 1, 2, or 3 substituents independently selected from the group consisting of halogen, $C_1$-$C_4$-alkyl and $C_3$-$C_6$-cycloalkyl.

According to a preferred embodiment, $R^{3a}$—in the pyrrolidine derivatives of formula (Id)—is $C_3$-$C_{12}$-cycloalkyl (e.g. cyclopropyl, or cyclohexyl), $C_6$-$C_{12}$-aryl, in particular phenyl, optionally substituted with 1, 2, or 3 substituents independently selected from the group consisting of halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluoro-phenyl), or hydroxy, $C_1$-$C_6$-alkoxy (e.g. methoxy, or iso-butoxy), $C_3$-$C_{12}$-cycloalkyl-$C_1$-$C_4$-alkoxy (e.g. cyclopropylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), $C_6$-$C_{12}$-aryloxy (e.g. 4-F-phenoxy) optionally substituted with 1, 2, or 3 substituents independently selected from the group consisting of halogen, or $C_3$-$C_{12}$-heterocyclyl, in particular tetrahydrofuranyl or tetrahydropyranyl,optionally substituted with 1, 2, or 3 substituents independently selected from the group consisting of halogen and $C_3$-$C_6$-cycloalkyl (e.g. tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, or 1,3-oxazol-2-yl), or in particular piperidinyl, pyridyl, dioxolanyl, dioxanyl, or dioxepanyl, optionally substituted with 1, 2, or 3 substituents independently selected from the group consisting of halogen, $C_1$-$C_4$-alkyl and $C_3$-$C_6$-cycloalkyl (e.g. 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, piperidyl, 1-Me-piperid-2-yl, or 5-F-pyrid-2-yl).

It is further preferred if $R^{3a}$ and one of $R^{2a}$ or $R^{2b}$ together with the carbon atoms to which they are bound form an anellated $C_6$-$C_{12}$-aryl.

According to a preferred embodiment, $R^{9a}$, $R^{9b}$—in the pyrrolidine derivatives of formula (Id)—are independently hydrogen, halogen (e.g. F), $C_1$-$C_6$-alkyl (e.g. methyl, ethyl, tert-butyl, or 2,3-dimethyl-propyl), or $C_1$-$C_6$-alkoxy (e.g. methoxy). It is further preferred if $R^{9a}$, $R^{9b}$—in the pyrrolidine derivatives of formula (Id)—are independently halogenated $C_1$-$C_6$-alkyl (e.g. trifluoromethyl).

More preferably, $R^{9a}$ is hydrogen, halogen (e.g. F), $C_1$-$C_6$-alkyl (e.g. methyl, ethyl, tert-butyl, or 2,3-dimethyl-propyl), or $C_1$-$C_6$-alkoxy (e.g. methoxy) and $R^{9b}$ is hydrogen. Or, more preferably, $R^{9a}$ is halogenated $C_1$-$C_6$-alkyl (e.g. trifluoromethyl). Or, more preferably, $R^{9a}$ and $R^{9b}$ are both halogen.

In connection with $R^{13}$, substituted $C_3$-$C_{12}$-cycloalkyl in particular includes $C_3$-$C_{12}$-cycloalkyl, such as cyclopropyl, cyclopentyl, or cyclohexyl, a further example being cyclobutyl, decalinyl, norbornanyl, bicyclo[3.1.0]hexanyl, bicyclo[3.2.1]octanyl, or 3-bicyclo[1.1.1]pentanyl, which is substituted with 1, 2, or 3 substituents independently selected from the group consisting of halogen, $C_1$-$C_4$-alkyl, halogenated $C_1$-$C_4$-alkyl, $C_1$-$C_4$-alkoxy-$C_1$-$C_4$-alkyl and $C_6$-$C_{12}$-aryl. Additionally, the substituents may be independently selected from the group consisting of $C_2$-$C_4$-alkenyl, $C_1$-$C_4$-alkoxy, $C_6$-$C_{12}$-aryl which may be substituted with halogen, and $C_3$-$C_{12}$-heterocyclyl.

In connection with $R^{13}$, substituted $C_3$-$C_6$-cycloalkenyl in particular includes $C_3$-$C_6$-cycloalkenyl, such as cyclohexenyl, which is substituted with 1, 2, or 3 substituents independently selected from the group consisting of $C_1$-$C_4$-alkyl.

In connection with $R^{13}$, substituted $C_6$-$C_{12}$-aryl in particular includes $C_6$-$C_{12}$-aryl, such as phenyl, a further example being indanyl or tetralinyl, which is substituted with 1, 2, or 3 substituents independently selected from the group consisting of halogen, $C_1$-$C_4$-alkyl, halogenated $C_1$-$C_4$-alkyl, hydroxy-(halogenated $C_1$-$C_4$-alkyl), CN, $C_6$-$C_{12}$-aryl, $C_1$-$C_4$-alkoxy, halogenated $C_1$-$C_4$-alkoxy, $C_6$-$C_{12}$ aryl-$C_1$-$C_4$-alkoxy, $C_6$-$C_{12}$-aryloxy, $C_1$-$C_4$-alkyl-sulfonyl, $C_1$-$C_4$-alkyl-carbonylamino and $C_3$-$C_{12}$-heterocyclyl. Additionally, the substituents may be independently selected from the group consisting of hydroxy-$C_1$-$C_4$-alkyl, $C_1$-$C_4$-alkoxy-$C_1$-$C_4$-alkyl, di-$C_1$-$C_4$-alkyl amino-$C_1$-$C_4$-alkyl, $C_3$-$C_{12}$-heterocyclyl-$C_1$-$C_4$-alkyl, $C_3$-$C_6$-cycloalkyl, $C_1$-$C_4$-alkyl-carbonyl, hydroxy, $C_3$-$C_{12}$-cycloalkyl-$C_1$-$C_4$-alkoxy, $C_3$-$C_6$-cycloalkoxy, $C_1$-$C_4$-alkoxy-$C_1$-$C_4$-alkoxy, di-$C_1$-$C_4$-alkyl amino$C_1$-$C_4$-alkoxy, $C_3$-$C_{12}$-heterocyclyloxy and di-$C_1$-$C_4$-alkyl amino.

In connection with $R^{13}$, substituted $C_6$-$C_{12}$-aryloxy in particular includes $C_6$-$C_{12}$-aryloxy, such as phenoxy, which is substituted with 1, 2, or 3 substituents independently selected from the group consisting of halogen and $C_1$-$C_4$-alkyl.

In connection with $R^{13}$, substituted $C_3$-$C_{12}$-heterocyclyl in particular includes $C_3$-$C_{12}$-heterocyclyl, such as furanyl, pyrrolyl, thiophenyl, oxazolyl, diazolyl, thiazolyl, triazolyl, pyridyl, pyrimidyl, pyrazyl, pyridazyl, benzofuranyl, benzothiophenyl, benzothiazolyl, quinolinyl or isoquinolinyl, a further example being benzodioxolyl, dihydro-benzofuranyl, dihydro-quinolinyl, dihydroisoquinolinyl, tetrahydroquinolinyl, tetrahydro-isoquinolinyl, pyrazolo[1,5-a]pyrimidinyl, imidazo[1,5-a]pyrazinyl, triazolo[4,3-a]pyridinyl, imidazo[1,2-a]pyrazinyl, isoindolinonyl, chromanyl, chromanyl, isochromanyl, dioxanyl, tetrahydropyranyl, pyrrolidinyl, piperidinyl, quinuclidinyl, dihydrocyclopenta[b]pyridinyl, dihydrocyclopenta[c]pyridinyl, dihydrocyclopenta[b]thiophenyl, or octahydroindolizinyl, which is substituted with 1, 2, or 3 substituents independently selected from the group consisting of halogen, $C_1$-$C_4$-alkyl, halogenated $C_1$-$C_4$-alkyl, $C_6$-$C_{12}$-aryl-$C_1$-$C_4$-alkyl, $C_3$-$C_6$-cycloalkyl, hydroxy, CN, $C_6$-$C_{12}$-aryl optionally substituted with halogen and $C_1$-$C_4$-alkyl, $C_1$-$C_4$-alkoxy, halogenated $C_1$-$C_4$-alkoxy, $C_3$-$C_6$-cycloalkoxy, $C_6$-$C_{12}$ aryl-$C_1$-$C_4$-alkoxy, $C_3$-$C_{12}$-heterocyclyl-$C_1$-$C_4$-alkoxy and $C_3$-$C_{12}$-heterocyclyl. Additionally, the substituents may be independently selected from the group consisting of $C_3$-$C_6$-cycloalkyl-$C_1$-$C_4$-alkoxy and halogenated $C_1$-$C_4$-alkyl-carbonyl.

According to a preferred embodiment, $R^{13}$ is hydrogen, $C_1$-$C_8$-alkyl (e.g. methyl, ethyl, n-butyl, tert-butyl, pentyl, or hexyl), halogenated $C_1$-$C_6$-alkyl (e.g. —$CF_3$ or —$CF_2Me$), $C_1$-$C_6$-alkoxy-$C_1$-$C_6$-alkyl (e.g. methoxy-methyl), $C_3$-$C_{12}$-cycloalkyl optionally substituted with 1, 2, or 3 substituents independently selected from the group consisting of halogen, $C_1$-$C_4$-alkyl, halogenated $C_1$-$C_4$-alkyl, $C_1$-$C_4$-alkoxy-$C_1$-$C_4$-alkyl and $C_6$-$C_{12}$-aryl which may be additionally substituted with halogen, and additionally from the group consisting of $C_1$-$C_4$-alkenyl, $C_1$-$C_4$-alkoxy and $C_3$-$C_{12}$-heterocyclyl (e.g. cyclopropyl, 2-propyl-cyclopropyl, 1-(methoxy-methyl)-cyclopropyl, 2-phenylcyclopropyl, cyclopentyl, 1-methyl-cyclohexyl, 1-$CF_3$-cyclopropyl, 4-$CF_3$-cyclohexyl, or 4,4-diF-cyclohexyl, a further example being 1-phenyl-cyclopropyl, 1-(4-F-phenyl)-cyclopropyl, (3-Cl-phenyl)-cyclopropyl, 2-phenyl-cyclobutyl, 3-phenyl-cyclobutyl, 3-(4-F-phenyl)-cyclobutyl, 3-(2-F-phenyl)-cyclobutyl, 2-Cl-cyclopentyl, 2-Me-cyclopentyl, 3-Me-cyclopentyl, 2-phenylcyclopentyl, 3-(2-pyridyl)-cyclopentyl, 3-Me-cyclohexyl, 3,3,5,5-tetraMe-cyclohexyl, 4-Me-cyclohexyl, 4-Et-cyclohexyl, 2-$CF_3$-cyclohexyl, 2-Me-5-isopropenyl-cyclohexyl, 2-phenyl-cyclohexyl, 3-phenyl-cyclohexyl, 4-phenyl-cyclohexyl, 2-EtO-cyclohexyl, decalin-1-yl, decalin-2-yl, norbornan-2-yl, 1,7,7-trimethyl-norbornan-2-yl, 5-iPr-2-Me-3-bicyclo[3.1.0]hexanyl, bicycle [3.2.1] octanyl, or 3-bicyclo[1.1.1]pentanyl), or $C_2$-$C_6$-alkenyl (e.g. hex-2-enyl), $C_3$-$C_6$-cycloalkenyl optionally substituted with 1, 2, or 3 substituents independently selected from the group consisting of $C_1$-$C_4$-alkyl (e.g. 1,3,3-trimethylcyclohexen-2-yl), or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, hydroxy-(halogenated $C_1$-$C_4$-alkyl), CN, $C_6$-$C_{12}$-aryl, $C_1$-$C_4$-alkoxy, halogenated $C_1$-$C_4$-alkoxy, $C_6$-$C_{12}$ aryl-$C_1$-$C_4$-alkoxy, $C_6$-$C_{12}$-aryloxy, $C_1$-$C_4$-alkylsulfonyl, $C_1$-$C_4$-alkyl-carbonylamino and $C_3$-$C_{12}$-heterocyclyl, and additionally from the group consisting of hydroxy-$C_1$-$C_4$-alkyl, $C_1$-$C_4$-alkoxy-$C_1$-$C_4$-alkyl, di-$C_1$-$C_4$-alkyl amino-$C_1$-$C_4$-alkyl, $C_3$-$C_{12}$-heterocyclyl-$C_1$-$C_4$-alkyl, $C_3$-$C_6$-cycloalkyl, $C_1$-$C_4$-alkyl-carbonyl, hydroxy, $C_3$-$C_{12}$-cycloalkyl-$C_1$-$C_4$-alkoxy, $C_3$-$C_6$-cycloalkoxy, $C_1$-$C_4$-alkoxy-$C_1$-$C_4$-alkoxy, di-$C_1$-$C_4$-alkyl amino$C_1$-$C_4$-alkoxy, $C_3$-$C_{12}$-heterocyclyloxy and di-$C_1$-$C_4$-alkyl amine (e.g. phenyl, 2-F-phenyl, 4-F-phenyl, 3-F-phenyl, 2-Cl-phenyl, 3-Cl-phenyl, 4-Cl-phenyl, 2,3-diF-phenyl, 2,4-diF-phenyl, 2,5-diF-phenyl, 3,4-diF-phenyl, 2,3,4-triF-phenyl, 2,4-diCl-phenyl, 3,4-diCl-phenyl, 3-F-4-Cl-phenyl, 3-Cl-4-F-phenyl, 3-Cl-5-F-phenyl, 3,4-diF-5-Cl-phenyl, 2-Me-phenyl, 3-Me-phenyl, 4-Me-phenyl, 3-iPr-phenyl, 3-tBu-phenyl, 3-Me-4-F-phenyl, 3-Me-4-Cl-phenyl, 3-iPr-4Cl-phenyl, 3-(1-OH-1-$CF_3$-EB-phenyl, 3-$CHF_2$-4-F-phenyl, 2-$CF_3$-phenyl, 3-$CF_3$-phenyl, 4-$CF_3$-phenyl, 3-Cl-4-$CF_3$-phenyl, 2-F-3-$CF_3$-phenyl, 2-F-5-$CF_3$-phenyl, 3-F-5-$CF_3$-phenyl, 2-Cl-4-$CF_3$-phenyl, 2-Cl-3-$CF_3$-phenyl, 3-$CF_3$-4-F-phenyl, 3-$CF_3$-4-Cl-phenyl, 3-Me-4-$CF_3$-phenyl, 3-$CF_3$-4-Me-phenyl, 3,4-di$CF_3$-phenyl, 4-OMe-phenyl, 3-OiPr-phenyl, 3-$CF_3$-4-OMe-phenyl, 3-$OCH_2CF_3$-phenyl, 3-$OCF_3$-phenyl, 2-$OCHF_2$-5-Cl-phenyl, 3-$OCF_3$-4-F-phenyl, 3-$OCF_3$-4-Cl-phenyl, 3-OBn-phenyl, 3-OPh-phenyl, 3-CN-phenyl, 4-CN-phenyl, 2-F-3-CN-phenyl, 2-F-4-CN-phenyl, 3-F-4-CN-phenyl, 2-F-5-CN-phenyl, 3-F-5-CN-phenyl, 3-Cl-4-CN-phenyl, 2-Cl-5-CN-phenyl, 3-Cl-5-CN-phenyl, 3-CN-4-Cl-phenyl, 2-Me-3-CN-phenyl, 2-Me-5-CN-phenyl, 3-Me-5-CN-phenyl, 3-$CF_3$-4-CN-phenyl, 3-CN-4-OMe-phenyl, 3-CN-4-$OCF_3$-phenyl, 3-phenyl-phenyl, 3-$MeSO_2$-phenyl, 3-(piperidin-4-yl)phenyl, 2-methylcarbonylamino-5-Cl-phenyl, 3-(pyrid-2-yl)-phenyl, 3-(pyrid-3-yl)-4F-phenyl, 3-(pyrid-4-yl)-4F-phenyl, 3-(pyrimid-5-yl)-4F-phenyl, indan-5-yl, 2-chlor-indan-5-yl, or tetralin-6-yl, a further example being 2,4-diF-3-Cl-phenyl, 3-Et-4-Cl-phenyl, 3-(2-methoxyethyl)-phenyl, 3-(2-OH-ethyl)-phenyl, 3-(1-OH-1-Me-ethyl)-phenyl, 3-$CHF_2$-phenyl, 3-$CF_3$-2,4-diF-phenyl, 3-(dimethylamino-methyl)-phenyl, 3-(morpholin-4-yl-methyl)-phenyl, 3-cyclopropyl-phenyl, 3-OEt-phenyl, 3-OPr-phenyl, 3-OtBu-phenyl, 3-(cyclopropylmethoxy)-phenyl, 3-(OMe-methoxy)phenyl, 3-(2-dimethylamino-ethoxy)-phenyl, 3-$CF_3$-4-OH-phenyl, 3-OCH$_2$CHF$_2$-phenyl, 3-OCHF$_2$-phenyl, 3-OCHF$_2$-4-F-phenyl, 3-OCF$_3$-4-OMe-phenyl, 3-cyclopropoxy-phenyl, 3-methylcarbonyl-phenyl, 3-dimethylamino-phenyl, 3-(2-pyridyloxy)-phenyl, 3-(pyrimidin-2-yloxy)-phenyl, indanyl, indan-2-yl, 2-F-indanyl, 4-F-indanyl, 5-F-indanyl, 6-F-indanyl, 7-F-indanyl, 3-Me-indanyl, 4-Me-indanyl, 5-Me-indanyl, 6-Me-indanyl, 4-CF$_3$-indanyl, 5-CF$_3$-indanyl, 6-CF$_3$-indanyl, 3,3-dimethyl-indanyl, tetralin-2-yl, 7-F-tetralin-2-yl, 6-F-tetralin-2-yl, tetralinyl, 6-F-tetralinyl, 5-F-tetralinyl, or 7-F-tetralinyl), or C$_1$-C$_6$-alkoxy (e.g. methoxy, ethoxy, or n-propoxy), C$_1$-C$_6$-alkoxy-C$_1$-C$_4$-alkoxy (e.g. 2-methoxyethoxy), C$_6$-C$_{12}$-aryloxy optionally substituted with 1, 2, or 3 substituents independently selected from the group consisting of halogen and C$_1$-C$_4$-alkyl (e.g. 4-F-phenoxy or 4-tertbutyl-phenoxy), or C$_3$-C$_{12}$-heterocyclyl optionally substituted with 1, 2, or 3 substituents independently selected from the group consisting of halogen, C$_1$-C$_4$-alkyl, halogenated C$_1$-C$_4$-alkyl, C$_6$-C$_{12}$-aryl-C$_1$-C$_6$-alkyl, C$_3$-C$_6$-cycloalkyl, hydroxy, CN, C$_6$-C$_{12}$-aryl optionally substituted with halogen and C$_1$-C$_4$-alkyl, C$_1$-C$_4$-alkoxy, halogenated C$_1$-C$_4$-alkoxy, C$_3$-C$_6$-cycloalkoxy, C$_6$-C$_{12}$ aryl-C$_1$-C$_4$-alkoxy, C$_3$-C$_{12}$-heterocyclyl-C$_1$-C$_4$-alkoxy and C$_3$-C$_{12}$-heterocyclyl, and additionally from the group consisting of C$_3$-C$_6$-cycloalkyl-C$_1$-C$_4$-alkoxy and halogenated C$_1$-C$_4$-alkyl-carbonyl(e.g. propyl-furan-2-yl, 2-CF$_3$-furan-5-yl, 1,2-dimethyl-5-CN-pyrrol-3-yl, 2,3-diMe-thiophen-5-yl, 2-Me-thiophen-5-yl, 2-Cl-thiophen-5-yl, 3-Cl-thiophen-2-yl, 2,5-diCl-thiophen-3-yl, 2-tetrahydropyranyl-thiophen-5-yl, 1,3-thiazol-5-yl, 4-Me-1,3-thiazol-2-yl, 2-Me-1,3-thiazol-5-yl, 5-Me-1,3-thiazol-2-yl, 4-Me-1,3-thiazol-5-yl, 2-Me-1,3-thiazol-4-yl, 4-isopropyl-1,3-thiazol-2-yl, 2,4-diMe-1,3-thiazol-5-yl, 2-phenyl-4-Me-1,3-thiazol-5-yl, 4-phenyl-1,3-thiazol-5-yl, 2-(4-Me-phenyl)-1,3-thiazol-5-yl, 4-(4-F-phenyl)-1,3-thiazol-2-yl, 2-Cl-1,3-thiazol-4-yl, 4-Cl-1,3-thiazol-5-yl, 2-Br-1,3-thiazol-5-yl, 4-Br-1,3-thiazol-2-yl, 4-Me-5-Br-1,3-thiazol-2-yl, 2,4-dichloro-1,3-thiazol-5-yl, 1,5-dimethyl-1,2,4-triazol-3-yl, pyrid-2-yl, pyrid-3-yl, pyrid-4-yl, 4-F-pyrid-2-yl, 5-F-pyrid-2-yl, 6-F-pyrid-2-yl, 4-Cl-pyrid-2-yl, 5-F-pyrid-3-yl, 2-F-pyrid-4-yl, 3,5-diCl-pyrid-4-yl, 4,5-diCl-pyrid-2-yl, 2-Cl-3F-pyrid-4-yl, 5-Me-pyrid-2-yl, 4-iPr-pyrid-2-yl, 4-Me-5-F-pyrid-2-yl, 4-CF$_3$-pyrid-2-yl, 5-CF$_3$-pyrid-2-yl, 6-CF$_3$-pyrid-2-yl, 5-CF$_3$-pyrid-3-yl, 2-CF$_3$-pyrid-4-yl, 3-F-4-CF$_3$-pyrid-2-yl, 4-CF$_3$-5-F-pyrid-2-yl, 4-CF$_3$-5-Cl-pyrid-2-yl, 3,5-diF-4-CF$_3$-pyrid-2-yl, 4-OCH$_2$CF$_3$-pyrid-2-yl, 4-OCH$_2$CF$_3$-5-F-pyrid-2-yl, 4-OCH$_2$CF$_3$-5-Cl-pyrid-2-yl, 4-OBn-5-F-pyrid-2-yl, 3-(4-F-phenyl)-pyrid-5-yl, 2-(4-F-phenyl)-pyrid-3-yl, 4-(pyrid-4-yl)-pyrid-2-yl, 4-(pyrid-3-yl)-pyrid-2-yl, 5-cyclopropyl-pyraz-2-yl, 5-cyclobutyl-pyraz-2-yl, 5-pyrrolidin-pyraz-2-yl, pyridaz-3-yl, 4-CF$_3$-pyridaz-3-yl, 5-CF$_3$-pyridaz-3-yl, 5-F-pyrimid-2-yl, 6-Cl-pyrimid-4-yl, 6-Me-pyrimid-4-yl, 6-Et-pyrimid-4-yl, 6-Pr-pyrimid-4-yl, 6-iPr-pyrimid-4-yl, 4-CF$_3$-pyrimid-2-yl, 6-CF$_3$-pyrimid-4-yl, 2-Me-6-Cl-pyrimid-4-yl, 2-Me-6-CF$_3$-pyrimid-4-yl, 2-OMe-6-CF$_3$-pyrimid-4-yl, 2-OMe-pyrimid-4-yl, 6-OMe-pyrimid-4-yl, 6-OEt-pyrimid-4-yl, 6-Opr-pyrimid-4-yl, 6-OiPr-pyrimid-4-yl, 6-OiBu-pyrimid-4-yl, 6-OBu-pyrimid-4-yl, 6-OBn-pyrimid-4-yl, 6-cyclobutyloxy-pyrimid-4-yl, 6-cyclopentyloxy-pyrimid-4-yl, 6-cyclohexyloxy-pyrimid-4-yl, 6-cyclopropyl-pyrimid-4-yl, 6-phenyl-pyrimid-4-yl, 6-(2-F-phenyl)-pyrimid-4-yl, 6-(3-F-phenyl)-pyrimid-4-yl, 6-(4-F-phenyl)-pyrimid-4-yl, 6-Cl-pyrimid-4-yl, 6-(2-Me-phenyl)-pyrimid-4-yl, 6-(3-Me-phenyl)-pyrimid-4-yl, 6-(4-Me-phenyl)-pyrimid-4-yl, 6-(3-Cl-phenyl)-pyrimid-4-yl, 6-(4-Cl-phenyl)-pyrimid-4-yl, 2-(morpholin-1-yl)-pyrimid-4-yl, 6-(azetidin-3-yl-methoxy)pyrimid-4-yl, 6-(pyrrolidin-3-yl-methoxy)-pyrimid-4-yl, 6-(pyrrolidin-2-yl-methoxy)-pyrimid-4-yl, benzofuran-5-yl, 2-Me-benzofuran-3-yl, 2-Et-benzofuran-3-yl, benzothiophen-5-yl, benzothiophen-6-yl, 5-Me-benzothiophen-2-yl, 5-F-benzothiophen-2-yl, 3-Cl-benzothiophen-2-yl, benzothiazol-2-yl, isoquinolin-6-yl, isoquinolin-7-yl, quinolin-6-yl, quinolin-7-yl, 4,5,6,7-tetrahydro-1,3-benzothiazol-2-yl, 2,3-dihydrobenzofuran-5-yl, 7H-pyrrolo[2,3-d]pyrimidin-4-yl, pyrazolo[1,5-a]pyridine-3-yl, pyrazolo[1,5-a]pyridine-7-yl, imidazo[1,2-a]pyridin-8-yl, 5-methyl-imidazo[1,2-a]pyridin-3-yl, 6-chloro-2-methyl-imidazo[1,2-a]pyridin-3-yl, 6-bromo-2-methyl-imidazo[1,2-a]pyridin-3-yl, thieno[2,3-b]pyridin-2-yl, N-benzyl-indolin-6-yl, indolinon-4-yl, chroman-6-yl, 4,4-dimethylchroman-6-yl, 4,4-dimethyl-1,3-dioxan-2-yl, 2-Me-tetrahydrofuran-3-yl, tetrahydrofuran-3-yl, tetrahydropyran-4-yl, 4-Me-tetrahydropyran-4-yl, 2,2-diMe-tetrahydropyran-4-yl, 1-isopropyl-piperidin-4-yl, 1-ethyl-piperidin-3-yl, or 2-CF$_3$-piperazin-5-yl, a further example being iBu-pyrazol-4-yl, 1-CHF$_2$-5-Me-1,2-diazol-4-yl, 1-benzyl-5-F-1,2,4-triazol-3-yl, 2-Me-pyrid-4-yl, 2-iPr-pyrid-4-yl, 4-phenyl-pyrid-2yl, 2-cyclopropyl-pyrid-4-yl, 2-OMe-pyrid-4-yl, 2-OEt-pyrid-4-yl, 2-cyclopropyl-methoxy-pyrid-4-yl, 2-OiPr-pyrid-4-yl, 2-OCH$_2$CF$_3$-pyrid-4-yl, 2-cyclopropoxy-pyrid-4-yl, 2-cyclobutoxy-pyrid-4-yl, 4,5-diCl-pyrimidin-2yl, benzothiophen-3-yl, 2,2-diF-1,3-benzodioxol-5-yl, 5,6,7,8-tetrahydro-isoquinolin-5-yl, 5,6, 7,8-tetrahydro-isoquinolin-8-yl, quinolin-8-yl, 1-Me-3,4-dihydro-2H-quinolin-4-yl, 2-Me-3,4-dihydro-1H-isoquinolin-6-yl, 5,6,7,8-tetrahydro-quinolin-5-yl, 5,6,7,8-tetrahydroquinolin-8-yl, 5,6,7,8-tetrahydro-quinolin-6-yl, 2,3-dihydrobenzofuran-3-yl, pyrazolo[1,5-a]pyrimidin-6-yl, imidazo[1,5-a]pyrazinyl, 3-methylimidazo[1,5-a]pyrazinyl, 3-Me-[1,2,4]triazolo[4,3-a]pyridin-6-yl, imidazo[1,2-a]pyrazin-6-yl, 2-Me-isoindolin-1-on-6-yl, 2,2-dimethyl-7-CF$_3$-chroman-4-yl, 7-CF$_3$-chroman-4-yl, 7-OCF$_3$-chroman-4-yl, isochroman-4-yl, 6,6-dimethyl-1,3-dioxan-2-yl, tetrahydropyran-3-yl, 1-phenyl-pyrrolidin-3-yl, piperidin-3-yl, 1,3-dimethyl-piperidin-4-yl, 1-cyclopropyl-piperidin-4-yl, 1-(tri-Fmethyl-carbonyl)-piperidin-3-yl, quinuclidin-2-yl, 6,7-dihydro-5H-cyclopenta[b]pyridine-7-yl, 6,7-dihydro-5H-cyclopenta[b]pyridine-5-yl, 6,7-dihydro-5H-cyclopenta[c]pyridine-7-yl, 6,7-dihydro-5H-cyclopenta[c]pyridine-5-yl, 5,6-dihydro-4H-cyclopenta[b]thiophen-4-yl, or 1,2,3,5,6,7,8,8a-octahydroindolizin), or tri-(C$_1$-C$_4$-alkyl)-silyloxy.

Further preferred embodiments of the pyrrolidine derivatives of formula (Id) result if:

R$^1$ is 1,3-diazolyl optionally substituted with halogen or C$_1$-C$_4$-alkyl (e.g. 1-methyl-1,3-diazol-4-yl), or 1,2,3-triazolyl optionally substituted with C$_1$-C$_4$-alkyl (e.g.1-methyl-1,2,3-triazol-4-yl);

R$^{2a}$, R$^{2b}$ are hydrogen;

R$^{3a}$ is C$_3$-C$_{12}$-cycloalkyl (e.g. cyclopropyl, or cyclohexyl) C$_6$-C$_{12}$-aryl optionally substituted with 1, 2, or 3 substituents independently selected from the group consisting of halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluoro-phenyl), or hydroxy, C$_1$-C$_6$-alkoxy (e.g. methoxy, or iso-butoxy), C$_3$-C$_{12}$-cycloalkyl-C$_1$-C$_4$-alkoxy (e.g. cyclopropylmethoxy), C$_2$-C$_6$-alkenyloxy (e.g. allyloxy or 2-methylprop-2-en-1-oxy), C$_6$-C$_{12}$-aryl-C$_1$-C$_4$-alkoxy (e.g. benzyloxy), C$_6$-C$_{12}$-aryloxy (e.g. 4-F-phenoxy) optionally substituted with 1, 2, or 3 substituents independently selected from the group consisting of halogen, or C$_3$-C$_{12}$-heterocyclyl optionally substituted with 1, 2, or 3 substituents independently selected from the group consisting of halogen or C$_3$-C$_6$-cycloalkyl (e.g.

tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, or 1,3-oxazol-2-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, pyrrolidinyl, piperidinyl,1-Me-piperidin-2-yl, or 5-F-pyrid-2-yl); or $R^{3a}$ and one of $R^{2a}$ or $R^{2b}$
together with the carbon atoms to which they are bound may form an anellated $C_6$-$C_{12}$-aryl;

$R^{3b}$ is hydrogen or hydroxy;

$Y^1$ is $>CR^6$;

$R^6$ is hydrogen, $C_1$-$C_6$-alkyl (e.g. methyl), or hydroxy-$C_1$-$C_6$-alkyl (e.g. —CH$_2$OH); or $R^6$ and $R^{3a}$ or $R^{3b}$
together are $C_1$-$C_5$-alkylene; or $R^6$
is $C_1$-$C_4$-alkylene (e.g. methylene or 1,2-ethylene) that is bound to a carbon atom in $R^{3a}$, and $R^{3a}$ is an optionally substituted $C_6$-$C_{12}$-aryl (e.g. phenyl);

$R^{8a}$ is hydrogen, $C_1$-$C_6$-alkyl (e.g. methyl, ethyl, n-propyl, iso-propyl, pentyl, or hexyl), or $C_1$-$C_6$alkylcarbonyl (e.g. methylcarbonyl), or $R^6$, $R^{8a}$
are together optionally substituted $C_1$-$C_5$-alkylene, wherein one or more —CH$_2$— of $C_1$-$C_5$-alkylene may be independently replaced by a an oxygen atom or C=O e.g. —C(O)OCH$_2$—);or $R^{3a}$ and $R^{8a}$
together are optionally substituted $C_1$-$C_5$-alkylene (e.g. 1,2-ethylene or 1,3-propylene);

$R^{9a}$ is hydrogen, halogen, $C_1$-$C_6$-alkyl (e.g. methyl, ethyl, tert-butyl, or 2,3-dimethyl-propyl), halogenated $C_1$-$C_6$-alkyl (e.g. trifluoromethyl) or $C_1$-$C_6$-alkoxy (e.g. methoxy or ethoxy);

$R^{9b}$ is hydrogen or halogen;

n4 is 0, 1, 2, 3, or 4;

$R^{13}$ is hydrogen, $C_1$-$C_8$-alkyl (e.g. methyl, ethyl, n-butyl, tert-butyl, pentyl, or hexyl), halogenated $C_1$-$C_6$-alkyl (e.g. —CF$_3$ or —CF$_2$Me), $C_1$-$C_6$-alkoxy-$C_1$-$C_6$-alkyl (e.g. methoxymethyl), $C_3$-$C_{12}$-cycloalkyl optionally substituted with 1, 2, or 3 substituents independently selected from the group consisting of halogen, $C_1$-$C_4$-alkyl, halogenated $C_1$-$C_4$-alkyl, $C_1$-$C_4$-alkoxy-$C_1$-$C_4$-alkyl and $C_6$-$C_{12}$-aryl, which may be additionally substituted with halogen, and additionally from the group consisting of $C_1$-$C_4$-alkenyl, $C_1$-$C_4$-alkoxy and $C_3$-$C_{12}$-heterocyclyl (e.g. cyclopropyl, 2-propyl-cyclopropyl, 1-(methoxymethyl)-cyclopropyl, 2-phenyl-cyclopropyl, cyclopentyl, cyclopentyl, 3,3-dimethylcyclopentyl, cyclohexyl, 3,3-dimethyl-cyclohexyl, 4,4-dimethyl-cyclohexyl, 1-methyl-cyclohexyl, 1-CF$_3$-cyclopropyl, 4-CF$_3$-cyclohexyl, 3-CF$_3$-cyclohexyl, or 4,4-diF-cyclohexyl, a further example being 1-phenyl-cyclopropyl, 1-(4-F-phenyl)-cyclopropyl, (3-Cl-phenyl)-cyclopropyl, 2-phenylcyclobutyl, 3-phenyl-cyclobutyl, 3-(4-F-phenyl)-cyclobutyl, 3-(2-F-phenyl)-cyclobutyl, 2-$C_1$-cyclopentyl, 2-Me-cyclopentyl, 3-Me-cyclopentyl, 2-phenyl-cyclopentyl, 3-(2-pyridyl)cyclopentyl, 3-Me-cyclohexyl, 3,3,5,5-tetraMe-cyclohexyl, 4-Me-cyclohexyl, 4-Et-cyclohexyl, 2-CF$_3$-cyclohexyl, 2-Me-5-isopropenyl-cyclohexyl, 2-phenyl-cyclohexyl, 3-phenyl-cyclohexyl, 4-phenyl-cyclohexyl, 2-EtO-cyclohexyl, decalin-1-yl, decalin-2-yl, norbornan-2-yl, 1,7,7-trimethyl-norbornan-2-yl, 5-iPr-2-Me-3-bicyclo[3.1.0]hexanyl, bicyclo[3.2.1]octanyl, or 3-bicyclo[1.1.1]pentanyl), or $C_2$-$C_6$-alkenyl (e.g. hex-2-enyl), $C_3$-$C_6$-cycloalkenyl optionally substituted with 1, 2, or 3 substituents independently selected from the group consisting of $C_1$-$C_4$-alkyl (e.g. 1,3,3-trimethylcyclohexen-2-yl), or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, hydroxy-(halogenated $C_1$-$C_4$-alkyl), CN, $C_6$-$C_{12}$-aryl, $C_1$-$C_4$-alkoxy, halogenated $C_1$-$C_4$-alkoxy, $C_6$-$C_{12}$ aryl-$C_1$-$C_4$-alkoxy, $C_6$-$C_{12}$-aryloxy, $C_1$-$C_4$-alkyl-sulfonyl, $C_1$-$C_4$-alkyl-carbonylamino and $C_3$-$C_{12}$-heterocyclyl, and additionally from the group consisting of hydroxy-$C_1$-$C_4$-alkyl, $C_1$-$C_4$-alkoxy-$C_1$-$C_4$-alkyl, di-$C_1$-$C_4$-alkyl amino-$C_1$-$C_4$-alkyl, $C_3$-$C_{12}$-heterocyclyl-$C_1$-$C_4$-alkyl, $C_3$-$C_6$-cycloalkyl, $C_1$-$C_4$-alkyl-carbonyl, hydroxy, $C_3$-$C_{12}$-cycloalkyl-$C_1$-$C_4$-alkoxy, $C_3$-$C_6$-cycloalkoxy, $C_1$-$C_4$-alkoxy-$C_1$-$C_4$-alkoxy, di-$C_1$-$C_4$-alkyl amino-$C_1$-$C_4$-alkoxy, $C_3$-$C_{12}$-heterocyclyloxy and di-$C_1$-$C_4$-alkyl amino (e.g. phenyl, 2-F-phenyl, 4-F-phenyl, 3-F-phenyl, 2-Cl-phenyl, 3-Cl-phenyl, 4-Cl-phenyl, 2,3-diF-phenyl, 2,4-diF-phenyl, 2,5-diF-phenyl, 3,4-diF-phenyl, 2,3,4-triF-phenyl, 2,4-diCl-phenyl, 3,4-diCl-phenyl, 3-F-4-Cl-phenyl, 3-Cl-F-phenyl, 3-Cl-5-F-phenyl, 3,4-diF-5-Cl-phenyl, 2-Me-phenyl, 3-Me-phenyl, 4-Me-phenyl, 3-iPr-phenyl, 3-tBu-phenyl, 3-Me-4-F-phenyl, 3-Me-4-Cl-phenyl, 3-iPr-4Cl-phenyl, 3-(1-OH-1-CF$_3$-Et)phenyl, 3-CHF$_2$-4-F-phenyl, 2-CF$_3$-phenyl, 3-CF$_3$-phenyl, 4-CF$_3$-phenyl, 3-Cl-4-CF$_3$-phenyl, 2-F-3-CF$_3$-phenyl, 2-F-5-CF$_3$-phenyl, 3-F-5-CF$_3$-phenyl, 2-Cl-4-CF$_3$-phenyl, 2-Cl-3-CF$_3$-phenyl, 3-CF$_3$-4-F-phenyl, 3-CF$_3$-4-Cl-phenyl, 3-Me-4-CF$_3$-phenyl, 3-CF$_3$-4-Me-phenyl, 3,4-diCF$_3$-phenyl, 4-OMe-phenyl, 3-OiPr-phenyl, 3-CF$_3$-4-OMe-phenyl, 3-OCH$_2$CF$_3$-phenyl, 3-OCF$_3$-phenyl, 2-OCHF$_2$-5-Cl-phenyl, 3-OCF$_3$-4-F-phenyl, 3-OCF$_3$-4-Cl-phenyl, 3-OBn-phenyl, 3-OPh-phenyl, 3-CN-phenyl, 4-CN-phenyl, 2-F-3-CN-phenyl, 2-F-4-CN-phenyl, 3-F-4-CN-phenyl, 2-F-5-CN-phenyl, 3-F-5-CN-phenyl, 3-Cl-4-CN-phenyl, 2-Cl-5-CN-phenyl, 3-Cl-5-CN-phenyl, 3-CN-4-Cl-phenyl, 2-Me-3-CN-phenyl, 2-Me-5-CN-phenyl, 3-Me-5-CN-phenyl, 3-CF$_3$-4-CN-phenyl, 3-CN-4-OMe-phenyl, 3-CN-4-OCF$_3$-phenyl, 3-phenyl-phenyl, 3-MeSO$_2$-phenyl, 3-(piperidin-4-yl)-phenyl, 2-methylcarbonylamino-5-Cl-phenyl, 3-(pyrid-2-yl)-phenyl, 3-(pyrid-3-yl)-4F-phenyl, 3-(pyrid-4-yl)-4F-phenyl, 3-(pyrimid-5-yl)-4F-phenyl, indan-5-yl, 2-chlor-indan-5-yl, or tetralin-6-yl, a further example being 2,4-diF-3-Cl-phenyl, 3-Et-4-Cl-phenyl, 3-(2-methoxyethyl)-phenyl, 3-(2-OH-ethyl)-phenyl, 3-(1-OH-1-Me-ethyl)-phenyl, 3-CHF$_2$-phenyl, 3-CF$_3$-2,4-diF-phenyl, 3-(dimethyl-amino-methyl)-phenyl, 3-(morpholin-4-ylmethyl)-phenyl, 3-cyclopropyl-phenyl, 3-OEt-phenyl, 3-OPr-phenyl, 3-OtBu-phenyl, 3-(cyclopropylmethoxy)-phenyl, 3-(OMe-methoxy)-phenyl, 3-(2-dimethylamino-ethoxy) phenyl, 3-CF$_3$-4-OH-phenyl, 3-OCH$_2$CHF$_2$-phenyl, 3-OCHF$_2$-phenyl, 3-OCHF$_2$-4-F-phenyl, 3-OCF$_3$-4-OMe-phenyl, 3-cyclopropoxy-phenyl, 3-methylcarbonyl-phenyl, 3-dimethylamino-phenyl, 3-(2-pyridyloxy)-phenyl, 3-(pyrimidin-2-yloxy)-phenyl, indanyl, indan-2-yl, 2-F-indanyl, 4-F-indanyl, 5-F-indanyl, 6-F-indanyl, 7-F-indanyl, 3-Me-indanyl, 4-Me-indanyl, 5-Me-indanyl, 6-Me-indanyl, 4-CF$_3$-indanyl, 5-CF$_3$-indanyl, 6-CF$_3$-indanyl, 3,3-dimethyl-indanyl, tetralin-2-yl, 7-F-tetralin-2-yl, 6-F-tetralin-2-yl, tetralinyl, 6-Ftetralinyl, 5-F-tetralinyl, or 7-F-tetralinyl), or $C_1$-$C_6$-alkoxy (e.g. methoxy, ethoxy, or n-propoxy), $C_1$-$C_6$-alkoxy-$C_1$-$C_4$-alkoxy (e.g. 2-methoxy-ethoxy), $C_6$-$C_{12}$-aryloxy optionally substituted with 1, 2, or 3 substituents independently selected from the group consisting of halogen and $C_1$-$C_4$-alkyl (e.g. 4-F-phenoxy or 4-tertbutyl-phenoxy), or $C_3$-$C_{12}$-heterocyclyl optionally substituted with 1, 2, or 3 substituents independently selected from the group consisting of halogen, $C_1$-$C_4$-alkyl, halogenated $C_1$-$C_4$-alkyl, $C_6$-$C_{12}$-aryl-$C_1$-$C_6$-alkyl, $C_3$-$C_6$-cycloalkyl, hydroxy, CN, $C_6$-$C_{12}$-aryl optionally substituted with halogen and $C_1$-$C_4$-alkyl, $C_1$-$C_4$-alkoxy, halogenated $C_1$-$C_4$-alkoxy, $C_3$-$C_6$-cycloalkoxy, $C_6$-$C_{12}$ aryl-$C_1$-$C_4$-alkoxy, $C_3$-$C_{12}$-heterocyclyl-$C_1$-$C_4$-alkoxy and $C_3$-$C_{12}$-heterocyclyl and additionally from the group consisting of $C_3$-$C_6$-cycloalkyl-$C_1$-$C_4$-alkoxy and halogenated $C_1$-$C_4$-alkyl-carbonyl (e.g. n-propyl-furan-2-yl, 2-$CF_3$-furan-5-yl, 1,2-dimethyl-5-CN-pyrrol-3-yl, 2,3-diMe-thiophen-5-yl, 2-Me-thiophen-5-yl, 2-Cl-thiophen-5-yl, 3-Cl-thiophen-2-yl, 2,5-diCl-thiophen-3-yl, 2-tetrahydropyranyl-thiophen-5-yl, 1,3-thiazol-5-yl, 4-Me-1,3-thiazol-2-yl, 2-Me-1,3-thiazol-5-yl, 5-Me-1,3-thiazol-2-yl, 4-Me-1,3-thiazol-5-yl, 2-Me-1,3-thiazol-4-yl, 4-isopropyl-1,3-thiazol-2-yl, 2,4-diMe-1,3-thiazol-5-yl, 2-phenyl-4-Me-1,3-thiazol-5-yl, 4-phenyl-1,3-thiazol-5-yl, 2-(4-Me-phenyl)-1,3-thiazol-5-yl, 4-(4-F-phenyl)-1,3-thiazol-2-yl, 2-Cl-1,3-thiazol-4-yl, 4-Cl-1,3-thiazol-5-yl, 2-Br-1,3-thiazol-5-yl, 4-Br-1,3-thiazol-2-yl, 4-Me-5-Br-1,3-thiazol-2-yl, 2,4-dichloro-1,3-thiazol-5-yl, 1,5-dimethyl-1,2,4-triazol-3-yl, pyrid-2-yl, pyrid-3-yl, pyrid-4-yl, 4-F-pyrid-2-yl, 5-F-pyrid-2-yl, 6-F-pyrid-2-yl, 4-Cl-pyrid-2-yl, 5-F-pyrid-3-yl, 2-F-pyrid-4-yl, 3,5-diCl-pyrid-4-yl, 4,5-diCl-pyrid-2-yl, 2-Cl-3F-pyrid-4-yl, 5-Me-pyrid-2-yl, 4-iPr-pyrid-2-yl, 4-Me-5-F-pyrid-2-yl, 4-$CF_3$-pyrid-2-yl, 5-$CF_3$-pyrid-2-yl, 6-$CF_3$-pyrid-2-yl, 5-$CF_3$-pyrid-3-yl, 2-$CF_3$-pyrid-4-yl, 3-F-4-$CF_3$-pyrid-2-yl, 4-$CF_3$-5-F-pyrid-2-yl, 4-$CF_3$-5-Cl-pyrid-2-yl, 3,5-diF-4-$CF_3$-pyrid-2-yl, 4-$OCH_2CF_3$-pyrid-2-yl, 4-$OCH_2CF_3$-5-F-pyrid-2-yl, 4-$OCH_2CF_3$-5-Cl-pyrid-2-yl, 4-OBn-5-F-pyrid-2-yl, 3-(4-F-phenyl)-pyrid-5-yl, 2-(4-F-phenyl)-pyrid-3-yl, 4-(pyrid-4-yl)-pyrid-2-yl, 4-(pyrid-3-yl)pyrid-2-yl, 5-cyclopropyl-pyraz-2-yl, 5-cyclobutyl-pyraz-2-yl, 5-pyrrolidin-pyraz-2-yl, pyridaz-3-yl, 4-$CF_3$-pyridaz-3-yl, 5-$CF_3$-pyridaz-3-yl, 5-F-pyrimid-2-yl, 6-Cl-pyrimid-4-yl, 6-Me-pyrimid-4-yl, 6-Et-pyrimid-4-yl, 6-Pr-pyrimid-4-yl, 6-iPr-pyrimid-4-yl, 4-$CF_3$-pyrimid-2-yl, 6-$CF_3$-pyrimid-4-yl, 2-Me-6-Cl-pyrimid-4-yl, 2-Me-6-$CF_3$-pyrimid-4-yl, 2-OMe-6-$CF_3$-pyrimid-4-yl, 2-OMe-pyrimid-4-yl, 6-OMe-pyrimid-4-yl, 6-OEt-pyrimid-4-yl, 6-OPr-pyrimid-4-yl, 6-OiPr-pyrimid-4-yl, 6-OiBu-pyrimid-4-yl, 6-OBu-pyrimid-4-yl, 6-OBn-pyrimid-4-yl, 6-cyclobutyloxy-pyrimid-4-yl, 6-cyclopentyloxy-pyrimid-4-yl, 6-cyclohexyloxy-pyrimid-4-yl, 6-cyclopropyl-pyrimid-4-yl, 6-phenyl-pyrimid-4-yl, 6-(2-F-phenyl)-pyrimid-4-yl, 6-(3-F-phenyl)-pyrimid-4-yl, 6-(4-F-phenyl)-pyrimid-4-yl, 6-Cl-pyrimid-4-yl, 6-(2-Me-phenyl)-pyrimid-4-yl, 6-(3-Me-phenyl)-pyrimid-4-yl, 6-(4-Me-phenyl)-pyrimid-4-yl, 6-(3-Cl-phenyl)-pyrimid-4-yl, 6-(4-Cl-phenyl)-pyrimid-4-yl, 2-(morpholin-1-yl)-pyrimid-4-yl, 6-(azetidin-3-yl-methoxy)-pyrimid-4-yl, 6-(pyrrolidin-3-ylmethoxy)-pyrimid-4-yl, 6-(pyrrolidin-2-yl-methoxy)-pyrimid-4-yl, benzofuran-5-yl, 2-Me-benzofuran-3-yl, 2-Et-benzofuran-3-yl, benzothiophen-5-yl, benzothiophen-6-yl, 5-Me-benzothiophen-2-yl, 5-F-benzothiophen-2-yl, 3-Cl-benzothiophen-2-yl, benzothiazol-2-yl, isoquinolin-6-yl, isoquinolin-7-yl, quinolin-6-yl, quinolin-7-yl, 4,5,6,7-tetrahydro-1,3-benzothiazol-2-yl, 2,3-dihydrobenzofuran-5-yl, 7H-pyrrolo[2,3-d]pyrimidin-4-yl, pyrazolo[1,5-a]pyridine-3-yl, pyrazolo[1,5-a]pyridine-7-yl, imidazo[1,2-a]pyridin-8-yl, 5-methyl-imidazo[1,2-a]pyridin-3-yl, 6-chloro-2-methyl-imidazo[1,2-a]pyridin-3-yl, 6-bromo-2-methyl-imidazo[1,2-a]pyridin-3-yl, thieno[2,3-b]pyridin-2-yl, N-benzyl-indolin-6-yl, indolinon-4-yl, chroman-6-yl, 4,4-dimethylchroman-6-yl, 4,4-dimethyl-1,3-dioxan-2-yl, 2-Me-tetrahydrofuran-3-yl, tetrahydrofuran-3-yl, tetrahydropyran-4-yl, 4-Me-tetrahydropyran-4-yl, 2,2-diMe-tetrahydropyran-4-yl, 1-isopropyl-piperidin-4-yl, 1-ethyl-piperidin-3-yl, or 2-$CF_3$-piperazin-5-yl, a further example being iBu-pyrazol-4-yl, 1-$CHF_2$-5-Me-1,2-diazol-4-yl, 1-benzyl-5-F-1,2,4-triazol-3-yl, 2-Me-pyrid-4-yl, 2-iPr-pyrid-4-yl, 4-phenyl-pyrid-2yl, 2-cyclopropyl-pyrid-4-yl, 2-OMe-pyrid-4-yl, 2-OEt-pyrid-4-yl, 2-cyclopropylmethoxy-pyrid-4-yl, 2-OiPr-pyrid-4-yl, 2-$OCH_2CF_3$-pyrid-4-yl, 2-cyclopropoxy-pyrid-4-yl, 2-cyclobutoxy-pyrid-4-yl, 4,5-diCl-pyrimidin-2yl, benzothiophen-3-yl, 2,2-diF-1,3-benzodioxol-5-yl, 5,6,7,8-tetrahydro-isoquinolin-5-yl, 5,6,7,8-tetrahydro-isoquinolin-8-yl, quinolin-8-yl, 1-Me-3,4-dihydro-2H-quinolin-4-yl, 2-Me-3,4-dihydro-1H-isoquinolin-6-yl, 5,6,7,8-tetrahydro-quinolin-5-yl, 5,6,7,8-tetrahydro-quinolin-8-yl, 5,6,7,8-tetrahydro-quinolin-6-yl, 2,3-dihydrobenzofuran-3-yl, pyrazolo[1,5-a]pyrimidin-6-yl, imidazo[1,5-a]pyrazinyl, 3-methyl-imidazo[1,5-a]pyrazinyl, 3-Me-[1,2,4]triazolo[4,3-a]pyridin-6-yl, imidazo[1,2-a]pyrazin-6-yl, 2-Me-isoindolin-1-on-6-yl, 2,2-dimethyl-7-$CF_3$-chroman-4-yl, 7-$CF_3$-chroman-4-yl, 7-$OCF_3$-chroman-4-yl, isochroman-4-yl, 6,6-dimethyl-1,3-dioxan-2-yl, tetrahydropyran-3-yl, 1-phenyl-pyrrolidin-3-yl, piperidin-3yl, 1,3-dimethyl-piperidin-4yl, 1-cyclopropyl-piperidin-4-yl, 1-(tri-F-methyl-carbonyl)-piperidin-3-yl, quinuclidin-2-yl, 6,7-dihydro-5H-cyclopenta[b]pyridine-7-yl, 6,7-dihydro-5H-cyclopenta[b]pyridine-5-yl, 6,7-dihydro-5H-cyclopenta[c]pyridine-7-yl, 6,7-dihydro-5H-cyclopenta[c]pyridine-5-yl, 5,6-dihydro-4H-cyclopenta[b]thiophen-4-yl, or 1,2,3,5,6,7,8,8a-octahydroindolizin), or tri-($C_1$-$C_4$-alkyl)-silyloxy; and $R^{5a}$, $R^{5b}$ are hydrogen.

Further preferred embodiments of the pyrrolidine derivatives of formula (Id) result if:

$R^{3a}$ is $C_3$-$C_{12}$-cycloalkyl (e.g. cyclopropyl, or cyclohexyl) $C_6$-$C_{12}$-aryl optionally substituted with 1, 2, or 3 substituents independently selected from the group consisting of halogen (e.g. phenyl, 2-Cl-phenyl, 2-Br-phenyl, 3-Cl-phenyl, 4-Cl-phenyl, 2-F-phenyl, 3-F-phenyl, 4-F-phenyl, or 2,4,5-trifluoro-phenyl), or hydroxy, $C_1$-$C_6$-alkoxy (e.g. methoxy, or iso-butoxy), $C_3$-$C_{12}$-cycloalkyl-$C_1$-$C_4$-alkoxy (e.g. cyclopropylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), $C_6$-$C_{12}$-aryloxy (e.g. 4-F-phenoxy) optionally substituted with 1, 2, or 3 substituents independently selected from the group consisting of halogen, or $C_3$-$C_{12}$-heterocyclyl optionally substituted with 1, 2, or 3 substituents independently selected from the group consisting of halogen or $C_3$-$C_6$-cycloalkyl (e.g. tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, or 1,3-oxazol-2-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, pyrrolidinyl, piperidinyl,1-Me-piperidin-2-yl, or 5-F-pyrid-2-yl);

$R^6$ is hydrogen, $C_1$-$C_6$-alkyl (e.g. methyl), or hydroxy-$C_1$-$C_6$-alkyl (e.g. —$CH_2OH$);

$R^{8a}$ is hydrogen, $C_1$-$C_6$-alkyl (e.g. methyl, ethyl, n-propyl, iso-propyl, pentyl, or hexyl), or $C_1$-$C_6$-alkylcarbonyl (e.g. methylcarbonyl), or $R^6$, $R^{8a}$
are together optionally substituted $C_1$-$C_5$-alkylene, wherein one or more —$CH_2$— of $C_1$-$C_5$-alkylene may be independently replaced by a an oxygen atom or C=O e.g. —C(O)OCH$_2$—);

$R^{9a}$ is hydrogen, halogen, $C_1$-$C_6$-alkyl (e.g. methyl, ethyl, tert-butyl, or 2,3-dimethyl-propyl), or $C_1$-$C_6$-alkoxy (e.g. methoxy or ethoxy);

$R^{9b}$ is hydrogen, and $R^{13}$ is hydrogen, $C_1$-$C_8$-alkyl (e.g. methyl, ethyl, n-butyl, tert-butyl, pentyl, or hexyl), halogenated $C_1$-$C_6$-alkyl (e.g. —$CF_3$ or —$CF_2Me$), $C_1$-$C_6$-alkoxy-$C_1$-$C_6$-alkyl (e.g. methoxy-methyl), $C_3$-$C_{12}$-cycloalkyl optionally substituted with 1, 2, or 3 substituents independently selected from the group consisting of halogen, $C_1$-$C_4$-alkyl, halogenated $C_1$-$C_4$-alkyl, $C_1$-$C_4$-alkoxy-$C_1$-$C_4$-alkyl and $C_6$-$C_{12}$-aryl (e.g. cyclopropyl, 2-propyl-cyclopropyl, 1-(methoxy-methyl)cyclopropyl, 2-phenyl-cyclopropyl, cyclopentyl, cyclopentyl, 3,3-dimethylcyclopentyl, cyclohexyl, 3,3-dimethyl-cyclohexyl, 4,4-dimethyl-cyclohexyl, 1-methyl-cyclohexyl, 1-$CF_3$-cyclopropyl, 4-$CF_3$-cyclohexyl, 3-$CF_3$-cyclohexyl, or 4,4-diF-cyclohexyl, a further example being 1-phenyl-cyclopropyl, 2-phenyl-cyclobutyl, 3-phenyl-cyclobutyl, 2-Cl-cyclopentyl, 2-Me-cyclopentyl, 3-Me-cyclopentyl, 2-phenyl-cyclopentyl, 3-Me-cyclohexyl, 3,3,5,5-tetraMe-cyclohexyl, 4-Me-cyclohexyl, 4-Et-cyclohexyl, 2-$CF_3$-cyclohexyl, 2-phenyl-cyclohexyl, 3-phenyl-cyclohexyl, 4-phenyl-cyclohexyl, decalin-1-yl, decalin-2-yl, norbornan-2-yl, 1,7,7-trimethyl-norbornan-2-yl, 5-iPr-2-Me-3-bicyclo[3.1.0]hexanyl, bicycle[3.2.1]octanyl, or 3-bicyclo[1.1.1]pentanyl), or $C_2$-$C_6$-alkenyl (e.g. hex-2-enyl), $C_3$-$C_6$-cycloalkenyl optionally substituted with 1, 2, or 3 substituents independently selected from the group consisting of $C_1$-$C_4$-alkyl (e.g. 1,3,3-trimethylcyclohexen-2-yl), or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, hydroxy-(halogenated $C_1$-$C_4$-alkyl), CN, $C_6$-$C_{12}$-aryl, $C_1$-$C_4$-alkoxy, halogenated $C_1$-$C_4$-alkoxy, $C_6$-$C_{12}$ aryl-$C_1$-$C_4$-alkoxy, $C_6$-$C_{12}$-aryloxy, $C_1$-$C_4$-alkyl-sulfonyl, $C_1$-$C_4$-alkyl-carbonylamino and $C_3$-$C_{12}$-heterocyclyl, (e.g. phenyl, 2-F-phenyl, 4-F-phenyl, 3-F-phenyl, 2-Cl-phenyl, 3-Cl-phenyl, 4-Cl-phenyl, 2,3-diF-phenyl, 2,4-diF-phenyl, 2,5-diF-phenyl, 3,4-diF-phenyl, 2,3,4-triF-phenyl, 2,4-diCl-phenyl, 3,4-diCl-phenyl, 3-F-4-Cl-phenyl, 3-Cl-F-phenyl, 3-Cl-5-F-phenyl, 3,4-diF-5-Cl-phenyl, 2-Me-phenyl, 3-Me-phenyl, 4-Me-phenyl, 3-iPr-phenyl, 3-tBu-phenyl, 3-Me-4-F-phenyl, 3-Me-4-Cl-phenyl, 3-iPr-4Cl-phenyl, 3-(1-OH-1-$CF_3$-Et)-phenyl, 3-$CHF_2$-4-F-phenyl, 2-$CF_3$-phenyl, 3-$CF_3$-phenyl, 4-$CF_3$-phenyl, 3-Cl-4-$CF_3$-phenyl, 2-F-3-$CF_3$-phenyl, 2-F-5-$CF_3$-phenyl, 3-F-5-$CF_3$-phenyl, 2-Cl-4-$CF_3$-phenyl, 2-Cl-3-$CF_3$-phenyl, 3-$CF_3$-4-F-phenyl, 3-$CF_3$-4-Cl-phenyl, 3-Me-4-$CF_3$-phenyl, 3-$CF_3$-4-Me-phenyl, 3,4-di$CF_3$-phenyl, 4-OMe-phenyl, 3-OiPr-phenyl, 3-$CF_3$-4-OMe-phenyl, 3-$OCH_2CF_3$-phenyl, 3-$OCF_3$-phenyl, 2-$OCHF_2$-5-Cl-phenyl, 3-$OCF_3$-4-F-phenyl, 3-$OCF_3$-4-Cl-phenyl, 3-OBn-phenyl, 3-OPh-phenyl, 3-CN-phenyl, 4-CN-phenyl, 2-F-3-CN-phenyl, 2-F-4-CN-phenyl, 3-F-4-CN-phenyl, 2-F-5-CN-phenyl, 3-F-5-CN-phenyl, 3-Cl-4-CN-phenyl, 2-Cl-5-CN-phenyl, 3-Cl-5-CN-phenyl, 3-CN-4-Cl-phenyl, 2-Me-3-CN-phenyl, 2-Me-5-CN-phenyl, 3-Me-5-CN-phenyl, 3-$CF_3$-4-CN-phenyl, 3-CN-4-OMe-phenyl, 3-CN-4-$OCF_3$-phenyl, 3-phenyl-phenyl, 3-$MeSO_2$-phenyl, 3-(piperidin-4-yl)-phenyl, 2-methylcarbonylamino-5-Cl-phenyl, 3-(pyrid-2-yl)phenyl, 3-(pyrid-3-yl)-4F-phenyl, 3-(pyrid-4-yl)-4F-phenyl, 3-(pyrimid-5-yl)-4F-phenyl, indan-5-yl, 2-chlorindan-5-yl, or tetralin-6-yl, a further example being 2,4-diF-3-Cl-phenyl, 3-Et-4-Cl-phenyl, 3-$CHF_2$-phenyl, 3-$CF_3$-2,4-diF-phenyl, 3-OEt-phenyl, 3-OPr-phenyl, 3-OtBu-phenyl, 3-$OCH_2CHF_2$-phenyl, 3-$OCHF_2$-phenyl, 3-$OCHF_2$-4-F-phenyl, 3-$OCF_3$-4-OMe-phenyl, 3-(2-pyridyloxy)-phenyl, 3-(pyrimidin-2-yloxy)-phenyl, indanyl, indan-2-yl, 2-F-indanyl, 4-F-indanyl, 5-F-indanyl, 6-F-indanyl, 7-F-indanyl, 3-Me-indanyl, 4-Me-indanyl, 5-Me-indanyl, 6-Me-indanyl, 4-$CF_3$-indanyl, 5-$CF_3$-indanyl, 6-$CF_3$-indanyl, 3,3-dimethyl-indanyl, tetralin-2-yl, 7-F-tetralin-2-yl, 6-F-tetralin-2-yl, tetralinyl, 6-F-tetralinyl, 5-F-tetralinyl, or 7-F-tetralinyl), or $C_1$-$C_6$-alkoxy (e.g. methoxy, ethoxy, or n-propoxy), $C_1$-$C_6$-alkoxy-$C_1$-$C_4$-alkoxy (e.g. 2-methoxy-ethoxy), $C_6$-$C_{12}$-aryloxy optionally substituted with 1, 2, or 3 substituents independently selected from the group consisting of halogen and $C_1$-$C_4$-alkyl (e.g. 4-F-phenoxy or 4-tertbutyl-phenoxy), or $C_3$-$C_{12}$-heterocyclyl optionally substituted with 1, 2, or 3 substituents independently selected from the group consisting of halogen, $C_1$-$C_4$-alkyl, halogenated $C_1$-$C_4$-alkyl, $C_6$-$C_{12}$-aryl-$C_1$-$C_6$-alkyl, $C_3$-$C_6$-cycloalkyl, hydroxy, CN, $C_6$-$C_{12}$-aryl optionally substituted with halogen and $C_1$-$C_4$-alkyl, $C_1$-$C_4$-alkoxy, halogenated $C_1$-$C_4$-alkoxy, $C_3$-$C_6$-cycloalkoxy, $C_6$-$C_{12}$ aryl-$C_1$-$C_4$-alkoxy, $C_3$-$C_{12}$-heterocyclyl-$C_1$-$C_4$-alkoxy and $C_3$-$C_{12}$-heterocyclyl (e.g. n-propyl-furan-2-yl, 2-$CF_3$-furan-5-yl, 1,2-dimethyl-5-CN-pyrrol-3-yl, 2,3-diMe-thiophen-5-yl, 2-Me-thiophen-5-yl, 2-Cl-thiophen-5-yl, 3-Cl-thiophen-2-yl, 2,5-diCl-thiophen-3-yl, 2-tetrahydropyranyl-thiophen-5-yl, 1,3-thiazol-5-yl, 4-Me-1,3-thiazol-2-yl, 2-Me-1,3-thiazol-5-yl, 5-Me-1,3-thiazol-2-yl, 4-Me-1,3-thiazol-5-yl, 2-Me-1,3-thiazol-4-yl, 4-isopropyl-1,3-thiazol-2-yl, 2,4-diMe-1,3-thiazol-5-yl, 2-phenyl-4-Me-1,3-thiazol-5-yl, 4-phenyl-1,3-thiazol-5-yl, 2-(4-Me-phenyl)-1,3-thiazol-5-yl, 4-(4-F-phenyl)-1,3-thiazol-2-yl, 2-Cl-1,3-thiazol-4-yl, 4-Cl-1,3-thiazol-5-yl, 2-Br-1,3-thiazol-5-yl, 4-Br-1,3-thiazol-2-yl, 4-Me-5-Br-1,3-thiazol-2-yl, 2,4-dichloro-1,3-thiazol-5-yl, 1,5-dimethyl-1,2,4-triazol-3-yl, pyrid-2-yl, pyrid-3-yl, pyrid-4-yl, 4-F-pyrid-2-yl, 5-F-pyrid-2-yl, 6-F-pyrid-2-yl, 4-Cl-pyrid-2-yl, 5-F-pyrid-3-yl, 2-F-pyrid-4-yl, 3,5-diCl-pyrid-4-yl, 4,5-diCl-pyrid-2-yl, 2-Cl-3F-pyrid-4-yl, 5-Me-pyrid-2-yl, 4-iPr-pyrid-2-yl, 4-Me-5-F-pyrid-2-yl, 4-$CF_3$-pyrid-2-yl, 5-$CF_3$-pyrid-2-yl, 6-$CF_3$-pyrid-2-yl, 5-$CF_3$-pyrid-3-yl, 2-$CF_3$-pyrid-4-yl, 3-F-4-$CF_3$-pyrid-2-yl, 4-$CF_3$-5-F-pyrid-2-yl, 4-$CF_3$-5-Cl-pyrid-2-yl, 3,5-diF-4-$CF_3$-pyrid-2-yl, 4-$OCH_2CF_3$-pyrid-2-yl, 4-$OCH_2CF_3$-5-F-pyrid-2-yl, 4-$OCH_2CF_3$-5-Cl-pyrid-2-yl, 4-OBn-5-F-pyrid-2-yl, 3-(4-F-phenyl)-pyrid-5-yl, 2-(4-F-phenyl)-pyrid-3-yl, 4-(pyrid-4-yl)-pyrid-2-yl, 4-(pyrid-3-yl)-pyrid-2-yl, 5-cyclopropyl-pyraz-2-yl, 5-cyclobutyl-pyraz-2-yl, 5-pyrrolidin-pyraz-2-yl, pyridaz-3-yl, 4-$CF_3$-pyridaz-3-yl, 5-$CF_3$-pyridaz-3-yl, 5-F-pyrimid-2-yl, 6-Cl-pyrimid-4-yl, 6-Me-pyrimid-4-yl, 6-Et-pyrimid-4-yl, 6-Pr-pyrimid-4-yl, 6-iPr-pyrimid-4-yl, 4-$CF_3$-pyrimid-2-yl, 6-$CF_3$-pyrimid-4-yl, 2-Me-6-Cl-pyrimid-4-yl, 2-Me-6-$CF_3$-pyrimid-4-yl, 2-OMe-6-$CF_3$-pyrimid-4-yl, 2-OMepyrimid-4-yl, 6-OMe-pyrimid-4-yl, 6-OEt-pyrimid-4-yl, 6-OPr-pyrimid-4-yl, 6-OiPrpyrimid-4-yl, 6-OiBu-pyrimid-4-yl, 6-OBu-pyrimid-4-yl, 6-OBn-pyrimid-4-yl, 6-cyclobutyloxy-pyrimid-4-yl, 6-cyclopentyloxy-pyrimid-4-yl, 6-cyclohexyloxy-pyrimid-4-yl, 6-cyclopropyl-pyrimid-4-yl, 6-phenyl-pyrimid-4-yl, 6-(2-F-phenyl)-pyrimid-4-yl, 6-(3-F-phenyl)-pyrimid-4-yl, 6-(4-F-phenyl)-pyrimid-4-yl, 6-Cl-pyrimid-4-yl, 6-(2-Me-phenyl)pyrimid-4-yl, 6-(3-Me-phenyl)-pyrimid-4-yl, 6-(4-Me-phenyl)-pyrimid-4-yl, 6-(3-Cl-phenyl)-pyrimid-4-yl, 6-(4-Cl-phenyl)-pyrimid-4-yl, 2-(morpholin-1-yl)-pyrimid-4-yl, 6-(azetidin-3-yl-methoxy)-pyrimid-4-yl, 6-(pyrrolidin-3-yl-methoxy)-pyrimid-4-yl, 6-(pyrrolidin-2-yl-methoxy)-pyrimid-4-yl, benzofuran-5-yl, 2-Me-benzofuran-3-yl, 2-Et-benzofuran-3-yl, benzothiophen-5-yl, benzothiophen-6-yl, 5-Me-benzothiophen-2-yl, 5-F-benzothiophen-2-yl, 3-Cl-benzothiophen-2-yl, benzothiazol-2-yl, isoquinolin-6-yl, isoquinolin-7-yl, quinolin-6-yl, quinolin-7-yl, 4,5,6,7-tetrahydro-1,3-benzothiazol-2-yl, 2,3-dihydrobenzofuran-5-yl, 7H-pyrrolo[2,3-d]pyrimidin-4-yl, pyrazolo[1,5-a]pyridine-3-yl, pyrazolo[1,5-a]pyridine-7-yl, imidazo[1,2-a]pyridin-8-yl, 5-methyl-imidazo[1,2-a]pyridin-3-yl, 6-chloro-2-methyl-imidazo[1,2-a]pyridin-3-yl, 6-bromo-2-methyl-imidazo[1,2-a]pyridin-3-yl, thieno[2,3-b]pyridin-2-yl, N-benzyl-indolin-6-yl, indolinon-4-yl, chroman-6-yl, 4,4-dimethylchroman-6-yl, 4,4-dimethyl-1,3-dioxan-2-yl, 2-Me-tetrahydrofuran-3-yl, tetrahydrofuran-3-yl, tetrahydropyran-4-yl, 4-Me-tetrahydropyran-4-yl, 2,2-diMe-tetrahydropyran-4-yl, 1-isopropyl-piperidin-4-yl, 1-ethyl-piperidin-3-yl, or 2-CF$_3$-piperazin-5-yl, a further example being iBu-pyrazol-4-yl, 1-CHF$_2$-5-Me-1,2-diazol-4-yl, 1-benzyl-5-F-1,2,4-triazol-3-yl, 2-Me-pyrid-4-yl, 2-iPr-pyrid-4-yl, 4-phenyl-pyrid-2yl, 2-cyclopropyl-pyrid-4-yl, 2-OMe-pyrid-4-yl, 2-OEt-pyrid-4-yl, 2-OiPr-pyrid-4-yl, 2-OCH$_2$CF$_3$-pyrid-4-yl, 2-cyclopropoxy-pyrid-4-yl, 2-cyclobutoxy-pyrid-4-yl, 4,5-diCl-pyrimidin-2yl, benzothiophen-3-yl, 2,2-diF-1,3-benzodioxol-5-yl, 5,6,7,8-tetrahydro-isoquinolin-5-yl, 5,6,7,8-tetrahydro-isoquinolin-8-yl, quinolin-8-yl, 1-Me-3,4-dihydro-2H-quinolin-4-yl, 2-Me-3,4-dihydro-1H-isoquinolin-6-yl, 5,6,7,8-tetrahydro-quinolin-5-yl, 5,6,7,8-tetrahydro-quinolin-8-yl, 5,6,7,8-tetrahydro-quinolin-6-yl, 2,3-dihydrobenzofuran-3-yl, pyrazolo[1,5-a]pyrimidin-6-yl, imidazo[1,5-a]pyrazinyl, 3-methyl-imidazo[1,5-a]pyrazinyl, 3-Me-[1,2,4]triazolo[4,3-a]pyridin-6-yl, imidazo[1,2-a]pyrazin-6-yl, 2-Me-isoindolin-1-on-6-yl, 2,2-dimethyl-7-CF$_3$-chroman-4-yl, 7-CF$_3$-chroman-4-yl, 7-OCF$_3$-chroman-4-yl, isochroman-4-yl, 6,6-dimethyl-1,3-dioxan-2-yl, tetrahydropyran-3-yl, 1-phenyl-pyrrolidin-3-yl, piperidin-3yl, 1,3-dimethylpiperidin-4yl, 1-cyclopropyl-piperidin-4-yl, quinuclidin-2-yl, 6,7-dihydro-5H-cyclopenta[b]pyridine-7-yl, 6,7-dihydro-5H-cyclopenta[b]pyridine-5-yl, 6,7-dihydro-5H-cyclopenta[c]pyridine-7-yl, 6,7-dihydro-5H-cyclopenta[c]pyridine-5-yl, 5,6-dihydro-4H-cyclopenta[b]thiophen-4-yl, or 1,2,3,5,6,7,8,8a-octahydroindolizin), or tri-(C$_1$-C$_4$-alkyl)silyloxy, and R$^1$, R$^{2a}$, R$^{2b}$, R$^{3b}$, Y$^1$, n4, R$^{5a}$ and R$^{5b}$ are as defined above.

According to a particularly preferred embodiment of the pyrrolidine derivatives of the formula (Id), R$^{3a}$ is phenyl, 4-F-phenyl, tetrahydrofuran-2-yl or tetrahydropyran-2-yl, or additionally 4-Fpyridyl or piperidinyl.

According to a further particularly preferred embodiment of the pyrrolidine derivatives of the formula (Id), R$^{13}$ is a group of the formula (Id1):

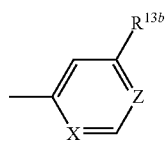

(Id1)

wherein

X is >CH— or >N—;

Z is >C—R$^{13c}$ or >N—;

R$^{13b}$ is halogen (e.g. fluoro or chloro), C$_1$-C$_4$-alkyl (e.g. methyl, ethyl, n-propyl, iso-propyl, tert-butyl), halogenated C$_1$-C$_4$-alkyl (e.g. CHF$_2$, CF$_3$), hydroxy-(halogenated C$_1$-C$_4$-alkyl) (e.g. 1-OH-1-CF$_3$-Et), C$_6$-C$_{12}$-aryl-C$_1$-C$_4$-alkyl (e.g. benzyl), C$_3$-C$_6$-cycloalkyl (e.g. cyclopropyl), CN, C$_6$-C$_{12}$-aryl optionally substituted with halogen or C$_1$-C$_4$-alkyl (e.g. phenyl, 2-F-phenyl, 4-F-phenyl, 3-F-phenyl, 3-Cl-phenyl, 4-Cl-phenyl, 2-Me-phenyl, 3-Me-phenyl, 4-Me-phenyl), C$_1$-C$_4$-alkoxy (e.g. methoxy, ethoxy, n-propoxy, iso-propoxy, a further example being n-butoxy or iso-butoxy), halogenated C$_1$-C$_4$-alkoxy (e.g.—OCHF$_2$, —OCH$_2$CF$_3$, —OCF$_3$), C$_3$-C$_6$-cycloalkoxy (e.g. cyclobutoxy, cyclopentyloxy, cyclohexyloxy, a further example being cyclopropoxy), C$_6$-C$_{12}$ aryl-C$_1$-C$_4$-alkoxy (e.g. benzyloxy), C$_3$-C$_{12}$-heterocyclyl-C$_1$-C$_4$-alkoxy (e.g. pyrrolid-3-yl-methoxy, pyrrolid-2-yl-methoxy, azetid-3-yl-methoxy), C$_6$-C$_{12}$-aryloxy (e.g. phenoxy), C$_1$-C$_4$-alkyl-sulfonyl (e.g. methylsulfonyl), C$_1$-C$_4$-alkyl-carbonylamino (e.g. 2-methylcarbonylamino) or C$_3$-C$_{12}$-heterocyclyl (e.g. piperidin-4-yl, pyrid-2-yl, pyrid-3-yl, pyrid-4-yl, pyrimid-5-yl); and R$^{13c}$ is hydrogen or halogen (e.g. fluoro, chloro).

Additional pyrrolidine derivatives of the formula (Id) result if R$^{13}$ is a group of formula (Id1) wherein R$^{13b}$ is C$_3$-C$_6$-cycloalkyl-C$_1$-C$_4$-alkoxy (e.g. cyclopropylmethoxy) and X, Z and R$^{13c}$ are as defined above.

Especially preferred among the pyrrolidine derivatives of the formula (Id) wherein R$^{13}$ is a group of the formula (Id1) are those wherein X is >CH— or >N—, and Z is >C—R$^{13c}$. According this embodiment it is particularly preferred if X is >CH—, Z is >C—R$^{13c}$ and R$^{13c}$ is hydrogen or fluoro, especially fluoro, or X is >N—, Z is >C—R$^{13c}$ and R$^{13c}$ is hydrogen or fluoro, especially fluoro.

In the pyrrolidine derivatives of the formula (Id) wherein R$^{13}$ is a group of the formula (Id1), R$^{8a}$, n4, R$^{9a}$ and R$^{9b}$ are as defined herein. Preferably, R$^{8a}$ is hydrogen, n4 is, in particular, 0 or 1, with n4=0 being particularly preferred. R$^{9a}$ and R$^{9b}$ are preferably both hydrogen if n4 is 1.

According to a further embodiment, R$^4$ is —NR$^{8b}$COR$^{14}$. Thus, the present invention relates to the pyrrolidine derivatives of the formula (Ie):

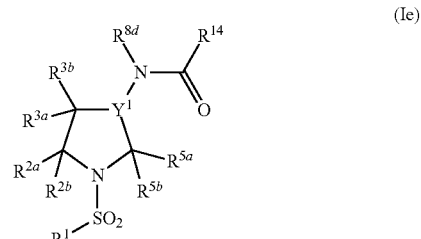

(Ie)

wherein R$^1$, R$^{2a}$, R$^{2b}$, R$^{3a}$, R$^{3b}$, Y$^1$, R$^{5a}$ and R$^{5b}$ are as defined herein, and R$^{8b}$ is hydrogen, C$_1$-C$_6$-alkyl (e.g. methyl, ethyl, iso-propyl, or n-butyl), or C$_1$-C$_6$-alkylcarbonyl (e.g. methylcarbonyl), or $R^6$, $R^{8b}$
together are optionally substituted $C_1$-$C_5$-alkylene, wherein one or more —$CH_2$— of $C_1$-$C_5$-alkylene may be independently replaced by a an oxygen atom or C=O; and $R^{14}$ is $C_1$-$C_8$-alkyl (e.g. pentyl, n-butyl, or hexyl), halogenated $C_1$-$C_6$-alkyl (e.g. 1,1-diF-butyl, 3,3-diF-butyl, 4,4,4-triF-butyl, 1,1-diF-pentyl, or 4,4-diF-pentyl), (optionally substituted $C_3$-$C_{12}$-cycloalkyl)-$C_1$-$C_4$-alkyl (e.g. cyclopropyl-methyl), (optionally substituted $C_6$-$C_{12}$-aryl) $C_1$-$C_4$-alkyl (e.g. benzyl, a further example being 4-F-benzyl, 3-F-benzyl, 3-$CF_3$-benzyl, 4-F-3-$CF_3$-benzyl, or 3-$OCF_3$-benzyl), hydroxy-$C_1$-$C_6$-alkyl (e.g. hydroxyl-methyl or 1-hydroxy-pentyl), $C_1$-$C_6$-alkoxy-$C_1$-$C_6$-alkyl (e.g. methoxy-methyl, ethoxy-methyl, or ethoxy-ethyl), (optionally substituted $C_6$-$C_{12}$-aryloxy)-$C_1$-$C_4$-alkyl (e.g. phenoxy-methyl or (4-F-phenoxy)-methyl), $C_1$-$C_6$-alkyl-carbonyl-$C_1$-$C_4$-alkyl (e.g. 2-methylcarbonyl-ethyl or 3-methylcarbonyl-propyl), $C_1$-$C_6$-alkoxycarbonyl-$C_1$-$C_4$-alkyl (e.g. 3-methoxycarbonylpropyl), $C_1$-$C_6$-alkylaminocarbonyl-$C_1$-$C_4$-alkyl (e.g. 3-methylaminocarbonyl-propyl), optionally substituted ($C_3$-$C_{12}$-heterocyclyl)-$C_1$-$C_4$-alkyl (e.g. 2-pyridyl-methyl), optionally substituted $C_3$-$C_{12}$-cycloalkyl (e.g.1-$CF_3$-cyclopropyl or 4-$CF_3$-cyclohexyl, a further example being 1-phenyl-cyclopropyl, 1-(4-F-phenyl)cyclopropyl, 1-(3-F-phenyl)cyclopropyl, 1-(3-Cl-phenyl)cyclopropyl, 1-(3-$CF_3$-phenyl)cyclopropyl, 3-hydroxymethylbycyclo[1.1.1]pentyl, 3-methoxymethyl-bycyclo[1.1.1]pentyl, 3-ethoxymethyl-bycyclo[1.1.1]pentyl, or 3-methoxycarbonyl-bycyclo[1.1.1]pentyl), optionally substituted $C_6$-$C_{12}$-aryl (e.g. phenyl, 2-F-phenyl, 3-F-phenyl, 4-F-phenyl, 2-Cl-phenyl, 3-Cl-phenyl, 4-Cl-phenyl, 2,3-diCl-phenyl, 2,4-diCl-phenyl, 3,5-diCl-phenyl, 2-Cl-F-phenyl, 2-Me-phenyl, 3-Me-phenyl, 4-Me-phenyl, 2-$CF_3$-phenyl, 3-$CF_3$-phenyl, 4-$CF_3$-phenyl, 3-Cl-4-$CF_3$-phenyl, 2-Cl-3-$CF_3$-phenyl, 2-Cl-4-$CF_3$-phenyl, 2-OMe-phenyl, 3-OMe-phenyl, 2-CN-phenyl, or 3-CN-phenyl, 4-CN-phenyl), or optionally substituted $C_3$-$C_{12}$-heterocyclyl (e.g. 3-Cl-pyridazin-6-yl, 2-Cl-pyrazin-5-yl, or 2-$CF_3$-pyrazin-5-yl).

Additional embodiments of pyrrolidine derivatives of formula (Ie) result if
$R^{3a}$ and $R^{8b}$
together are optionally substituted $C_1$-$C_5$-alkylene (e.g. 1,2-ethylene or 1,3-propylene); and
$R^1$, $R^{2a}$, $R^{2b}$, $R^{3b}$, $Y^1$, $R^6$, $R^{14}$, $R_{5a}$ and $R^{5b}$ are as defined above.

In particular, $R^{8b}$ is hydrogen. In particular, $R^{8b}$ and $R^{3a}$ together may be optionally substituted $C_1$-$C_5$-alkylene, preferably unsubstituted $C_1$-$C_5$-alkylene (e.g. 1,2-ethylene or 1,3-propylene).

In particular, $R^{14}$ is $C_1$-$C_8$-alkyl (e.g. pentyl, n-butyl, or hexyl), halogenated $C_1$-$C_6$-alkyl (e.g. 1,1-diF-butyl, 3,3-diF-butyl, 4,4,4-triF-butyl, 1,1-diF-pentyl, or 4,4-diF-pentyl), (optionally substituted $C_3$-$C_{12}$-cycloalkyl)-$C_1$-$C_4$-alkyl (e.g. cyclopropyl-methyl), hydroxy-$C_1$-$C_6$-alkyl (e.g. hydroxyl-methyl or 1-hydroxy-pentyl), (optionally substituted $C_6$-$C_{12}$-aryloxy)-$C_1$-$C_4$-alkyl (e.g. phenoxymethyl or (4-F-phenoxy)-methyl), $C_1$-$C_6$-alkylcarbonyl-$C_1$-$C_4$-alkyl (e.g. 2-methylcarbonyl-ethyl or 3-methylcarbonyl-propyl), $C_1$-$C_6$-alkoxycarbonyl-$C_1$-$C_4$-alkyl (e.g. 3-methoxycarbonyl-propyl), optionally substituted $C_3$-$C_{12}$-cycloalkyl (e.g.1-$CF_3$-cyclopropyl or 4-$CF_3$-cyclohexyl, a further example being 1-phenyl-cyclopropyl, 1-(4-F-phenyl)cyclopropyl, 1-(3-F-phenyl)cyclopropyl, 1-(3-Cl-phenyl)cyclopropyl, 1-(3-$CF_3$-phenyl)cyclopropyl, 3-hydroxymethyl-bycyclo[1.1.1]pentyl, 3-methoxymethyl-bycyclo[1.1.1]pentyl, 3-ethoxymethyl-bycyclo[1.1.1]pentyl, or 3-methoxycarbonyl-bycyclo[1.1.1]pentyl), optionally substituted $C_6$-$C_{12}$-aryl (e.g. phenyl, 2-F-phenyl, 3-F-phenyl, 4-F-phenyl, 2-Cl-phenyl, 3-Cl-phenyl, 4-Cl-phenyl, 2,3-diCl-phenyl, 2,4-diCl-phenyl, 3,5-diCl-phenyl, 2-Cl-F-phenyl, 2-Me-phenyl, 3-Me-phenyl, 4-Me-phenyl, 2-$CF_3$-phenyl, 3-$CF_3$-phenyl, 4-$CF_3$-phenyl, 3-Cl-4-$CF_3$-phenyl, 2-Cl-3-$CF_3$-phenyl, 2-Cl-4-$CF_3$-phenyl, 2-OMe-phenyl, 3-OMe-phenyl, 2-CN-phenyl, or 3-CN-phenyl, 4-CN-phenyl), or optionally substituted $C_3$-$C_{12}$-heterocyclyl (e.g. 3-Cl-pyridazin-6-yl, 2-Cl-pyrazin-5-yl, or 2-$CF_3$-pyrazin-5-yl). In particular, $R^{14}$ may be (optionally substituted $C_6$-$C_{12}$-aryl)-$C_1$-$C_4$-alkyl (e.g. benzyl, a further example being 4-F-benzyl, 3-F-benzyl, 3-$CF_3$-benzyl, 4-F-3-$CF_3$-benzyl, or 3-$OCF_3$-benzyl).

$R^{2a}$, $R^{2b}$—in pyrrolidine derivatives of formula (Ie)—are hydrogen.

$R^{3a}$—in pyrrolidine derivatives of formula (Ie)—is $C_3$-$C_{12}$-cycloalkyl (cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl), $C_3$-$C_{12}$-cycloalkyl-$C_1$-$C_4$-alkoxy (cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenyloxy or 4-F-phenyloxy), or $C_3$-$C_{12}$-heterocyclyl (e.g. pyrid-2-yl). Preferably $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl) or $C_3$-$C_{12}$-heterocyclyl (e.g. pyrid-2-yl).

$R^{3b}$—in pyrrolidine derivatives of formula (Ie)—is hydrogen or hydroxy. Preferably, $R^{3b}$ is hydrogen.

$Y^1$—in pyrrolidine derivatives of formula (Ie)—is >$CR^6$.

$R^6$—in pyrrolidine derivatives of formula (Ie)—is hydrogen. Additionally, $R^6$ and $R^{3a}$ or $R^{3b}$ together may be optionally substituted $C_1$-$C_5$-alkylene and preferably unsubstituted $C_1$-$C_5$-alkylene (e.g. 1,3-propylene or 1,4-butylene).

$R^{5a}$, $R^{5b}$—in pyrrolidine derivatives of formula (Ie)—are hydrogen.

Particular embodiments of pyrrolidine derivatives of formula (Ie) result if:

$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$
are hydrogen;

$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl) or $C_3$-$C_{12}$-heterocyclyl (e.g. pyrid-2-yl);

$R^{3b}$ is hydrogen;

$Y^1$ is >$CR^6$;
$R^6$ is hydrogen, or
$R^6$ and $R^{3a}$ or $R^{3b}$
  together are $C_1$-$C_5$-alkylene (e.g. 1,3-propylene or 1,4-butylene);
$R^{8b}$ is hydrogen, or
$R^{3a}$ and $R^{8b}$
  together are $C_1$-$C_5$-alkylene (e.g. 1,2-ethylene or 1,3-propylene);
$R^{14}$ is $C_1$-$C_8$-alkyl (e.g. pentyl, n-butyl, or hexyl), halogenated $C_1$-$C_6$-alkyl (e.g. 1,1-diF-butyl, 3,3-diF-butyl, 4,4,4-triF-butyl, 1,1-diF-pentyl, or 4,4-diF-pentyl), (optionally substituted $C_3$-$C_{12}$-cycloalkyl)-$C_1$-$C_4$-alkyl (e.g. cyclopropyl-methyl), (optionally substituted $C_6$-$C_{12}$-aryl) $C_1$-$C_4$-alkyl (e.g. benzyl, a further example being 4-F-benzyl, 3-F-benzyl, 3-$CF_3$-benzyl, 4-F-3-$CF_3$-benzyl, or 3-$OCF_3$-benzyl), hydroxy-$C_1$-$C_6$-alkyl (e.g. hydroxylmethyl or 1-hydroxy-pentyl), (optionally substituted $C_6$-$C_{12}$-aryloxy)-$C_1$-$C_4$-alkyl (e.g. phenoxy-methyl or (4-F-phenoxy)-methyl), $C_1$-$C_6$-alkylcarbonyl-$C_1$-$C_4$-alkyl (e.g. 2-methylcarbonyl-ethyl or 3-methylcarbonyl-propyl), $C_1$-$C_6$-alkoxycarbonyl-$C_1$-$C_4$-alkyl (e.g. 3-methoxycarbonylpropyl), optionally substituted $C_3$-$C_{12}$-cycloalkyl (e.g.1-$CF_3$-cyclopropyl or 4-$CF_3$-cyclohexyl, a further example being 1-phenyl-cyclopropyl, 1-(4-F-phenyl)cyclopropyl, 1-(3-F-phenyl)cyclopropyl, 1-(3-Cl-phenyl)cyclopropyl, 1-(3-$CF_3$-phenyl)cyclopropyl, 3-hydroxymethyl-bycyclo[1.1.1]pentyl, 3-methoxymethyl-bycyclo[1.1.1]pentyl, 3-ethoxymethyl-bycyclo[1.1.1]pentyl, or 3-methoxycarbonyl-bycyclo[1.1.1]pentyl), optionally substituted $C_6$-$C_{12}$-aryl (e.g. phenyl, 2-F-phenyl, 3-F-phenyl, 4-F-phenyl, 2-Cl-phenyl, 3-Cl-phenyl, 4-Cl-phenyl, 2,3-diCl-phenyl, 2,4-diCl-phenyl, 3,5-diCl-phenyl, 2-Cl-4-F-phenyl, 2-Me-phenyl, 3-Me-phenyl, 4-Me-phenyl, 2-$CF_3$-phenyl, 3-$CF_3$-phenyl, 4-$CF_3$-phenyl, 3-Cl-4-$CF_3$-phenyl, 2-Cl-3-$CF_3$-phenyl, 2-Cl-4-$CF_3$-phenyl, 2-OMe-phenyl, 3-OMe-phenyl, 2-CN-phenyl, or 3-CN-phenyl, 4-CN-phenyl), or optionally substituted $C_3$-$C_{12}$-heterocyclyl (e.g. 3-Cl-pyridazin-6-yl, 2-Cl-pyrazin-5-yl, or 2-$CF_3$-pyrazin-5-yl); and
$R^{5a}$, $R^{5b}$
  are hydrogen.
Further particular embodiments of pyrrolidine derivatives of formula (Ie) result if:
$R^6$ is hydrogen;
$R^{8b}$ is hydrogen;
$R^{14}$ is $C_1$-$C_8$-alkyl (e.g. pentyl, n-butyl, or hexyl), halogenated $C_1$-$C_6$-alkyl (e.g. 1,1-diF-butyl, 3,3-diF-butyl, 4,4,4-triF-butyl, 1,1-diF-pentyl, or 4,4-diF-pentyl), (optionally substituted $C_3$-$C_{12}$-cycloalkyl)-$C_1$-$C_4$-alkyl (e.g. cyclopropyl-methyl), hydroxy-$C_1$-$C_6$-alkyl (e.g. hydroxylmethyl or 1-hydroxy-pentyl), (optionally substituted $C_6$-$C_{12}$-aryloxy)-$C_1$-$C_4$-alkyl (e.g. phenoxy-methyl or (4-F-phenoxy)-methyl), $C_1$-$C_6$-alkylcarbonyl-$C_1$-$C_4$-alkyl (e.g. 2-methylcarbonyl-ethyl or 3-methylcarbonyl-propyl), $C_1$-$C_6$-alkoxycarbonyl-$C_1$-$C_4$-alkyl (e.g. 3-methoxycarbonyl-propyl), optionally substituted $C_3$-$C_{12}$-cycloalkyl (e.g.1-$CF_3$-cyclopropyl or 4-$CF_3$-cyclohexyl, a further example being 1-phenyl-cyclopropyl, 1-(4-F-phenyl)cyclopropyl, 1-(3-F-phenyl)cyclopropyl, 1-(3-Cl-phenyl)cyclopropyl, 1-(3-$CF_3$-phenyl)cyclopropyl, 3-hydroxymethyl-bycyclo[1.1.1]pentyl, 3-methoxymethylbycyclo[1.1.1]pentyl, 3-ethoxymethyl-bycyclo[1.1.1]pentyl, or 3-methoxycarbonylbycyclo[1.1.1]pentyl), optionally substituted $C_6$-$C_{12}$-aryl (e.g. phenyl, 2-F-phenyl, 3-F-phenyl, 4-F-phenyl, 2-Cl-phenyl, 3-Cl-phenyl, 4-Cl-phenyl, 2,3-diCl-phenyl, 2,4-diCl-phenyl, 3,5-diCl-phenyl, 2-Cl-F-phenyl, 2-Me-phenyl, 3-Me-phenyl, 4-Me-phenyl, 2-$CF_3$-phenyl, 3-$CF_3$-phenyl, 4-$CF_3$-phenyl, 3-Cl-4-$CF_3$-phenyl, 2-Cl-3-$CF_3$-phenyl, 2-Cl-4-$CF_3$-phenyl, 2-OMe-phenyl, 3-OMe-phenyl, 2-CN-phenyl, or 3-CN-phenyl, 4-CN-phenyl), or optionally substituted $C_3$-$C_{12}$-heterocyclyl (e.g. 3-Cl-pyridazin-6-yl, 2-Cl-pyrazin-5-yl, or 2-$CF_3$-pyrazin-5-yl); and
$R^1$, $R^{2a}$, $R^{2b}$, $R^{3a}$, $R^{3b}$, $Y^1$, $R^{5a}$ and $R^{5b}$ are as defined above.

Preferably, $R^1$—in the pyrrolidine derivatives of formula (Ie)—is an optionally substituted 5-membered heterocyclic ring containing 2 N which, in particular, is optionally substituted 1,3-diazolyl.

According to a further preferred embodiment, $R^1$—in the pyrrolidine derivatives of formula (Ie)—is an optionally substituted 5-membered heterocyclic ring containing 3 N which, in particular, is optionally substituted 1,2,3-triazolyl.

In connection with $R^1$ and the pyrrolidine derivatives of formula (Ie), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives of formula (Ie), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy.

According to a preferred embodiment, $R^{3a}$—in the pyrrolidine derivatives of formula (Ie)—is $C_6$-$C_{12}$-aryl, in particular phenyl, optionally substituted with 1, 2, or 3 substituents independently selected from the group consisting of halogen and $C_1$-$C_4$-alkoxy (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl) or $C_3$-$C_{12}$-heterocyclyl (e.g. 2-pyridyl).

In connection with $R^{14}$, substituted $C_6$-$C_{12}$-aryl-$C_1$-$C_4$-alkyl in particular includes $C_6$-$C_{12}$-aryl-$C_1$-$C_4$-alkyl, such as benzyl, which is substituted with 1, 2, or 3 substituents independently selected from the group consisting of halogen, halogenated $C_1$-$C_4$-alkyl and halogenated $C_1$-$C_4$-alkoxy.

In connection with $R^{14}$, substituted $C_6$-$C_{12}$-aryloxy-$C_1$-$C_4$-alkyl in particular includes $C_6$-$C_{12}$-aryloxy-$C_1$-$C_4$-alkyl, such as benzyloxy, which is substituted with 1, 2, or 3 substituents independently selected from the group consisting of halogen.

In connection with $R^{14}$, substituted $C_3$-$C_{12}$-cycloalkyl in particular includes $C_3$-$C_{12}$-cycloalkyl, such as cyclopropyl or cyclohexyl, which is substituted with 1, 2, or 3 substituents independently selected from the group consisting of halogenated $C_1$-$C_4$-alkyl.

In connection with $R^{14}$, substituted $C_6$-$C_{12}$-aryl in particular includes $C_6$-$C_{12}$-aryl, such as phenyl, which is substituted with 1, 2, or 3 substituents independently selected from the group consisting of halogen, $C_1$-$C_4$-alkyl, halogenated $C_1$-$C_4$-alkyl, CN and $C_1$-$C_4$-alkoxy. Preferably the substituents on $C_6$-$C_{12}$-aryl are independently selected from the group consisting of $C_1$-$C_4$-alkyl and CN.

In connection with $R^{14}$, substituted $C_3$-$C_{12}$-heterocyclyl in particular includes $C_3$-$C_{12}$-heterocyclyl, such as pyridazyl or pyrazyl, which is substituted with 1, 2, or 3 substituents independently selected from the group consisting of halogen and halogenated $C_1$-$C_4$-alkyl.

According to a preferred embodiment, $R^{14}$ is $C_1$-$C_8$-alkyl (e.g. pentyl, n-butyl, or hexyl), halogenated $C_1$-$C_6$-alkyl (e.g. 1,1-diF-butyl, 3,3-diF-butyl, 4,4,4-triF-butyl, 1,1-diF-pentyl, or 4,4-diF-pentyl), (optionally substituted $C_3$-$C_{12}$-cycloalkyl)-$C_1$-$C_4$-alkyl (e.g. cyclopropyl-methyl), hydroxy-C1-C6-alkyl (e.g. hydroxyl-methyl or 1-hydroxy-pentyl), (halogenated $C_6$-$C_{12}$-aryloxy)-$C_1$-$C_4$-alkyl (e.g. 4-F-phenoxy)-methyl), $C_1$-$C_6$-alkylcarbonyl-$C_1$-$C_4$-alkyl (e.g. 2-methylcarbonyl-ethyl or 3-methylcarbonyl-propyl), $C_1$-$C_6$-alkoxycarbonyl-$C_1$-$C_4$-alkyl (e.g. 3-methoxycarbonyl-propyl), $C_3$-$C_{12}$-cycloalkyl optionally substituted with 1, 2, or 3 substituents independently selected from the group consisting of halogenated $C_1$-$C_4$-alkyl (e.g.1-$CF_3$-cyclopropyl or 4-$CF_3$-cyclohexyl), $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, CN and $C_1$-$C_4$-alkoxy (e.g. phenyl, 2-F-phenyl, 3-F-phenyl, 4-F-phenyl, 2-Cl-phenyl, 3-Cl-phenyl, 4-Cl-phenyl, 2,3-diCl-phenyl, 2,4-diCl-phenyl, 3,5-diCl-phenyl, 2-Cl-F-phenyl, 2-Me-phenyl, 3-Me-phenyl, 4-Me-phenyl, 2-$CF_3$-phenyl, 3-$CF_3$-phenyl, 4-$CF_3$-phenyl, 3-Cl-4-$CF_3$-phenyl, 2-Cl-3-$CF_3$-phenyl, 2-Cl-4-$CF_3$-phenyl, 2-OMe-phenyl, 3-OMe-phenyl, 2-CN-phenyl, 3-CN-phenyl, or 4-CN-phenyl), or $C_3$-$C_{12}$-heterocyclyl optionally substituted with 1, 2, or 3 substituents independently selected from the group consisting of halogen and halogenated $C_1$-$C_4$-alkyl (e.g. 3-Cl-pyridazin-6-yl, 2-Cl-pyrazin-5-yl, or 2-$CF_3$-pyrazin-5-yl). It is further preferred if $R^{14}$ is (optionally substituted $C_6$-$C_{12}$-aryl)-$C_1$-$C_4$-alkyl (e.g. benzyl, a further example being 4-F-benzyl, 3-F-benzyl, 3-$CF_3$-benzyl, 4-F-3-$CF_3$-benzyl, or 3-$OCF_3$-benzyl).

Further preferred embodiments of the pyrrolidine derivatives of formula (Ie) result if:

$R^1$ is 1,3-diazolyl optionally substituted with halogen or $C_1$-$C_4$-alkyl (e.g. 1-methyl-1,3-diazol-4-yl);

$R^{2a}$, $R^{2b}$ are hydrogen;

$R^{3a}$ is $C_6$-$C_{12}$-aryl optionally substituted with 1, 2, or 3 substituents independently selected from the group consisting of halogen and $C_1$-$C_4$-alkoxy (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl) or $C_3$-$C_{12}$-heterocyclyl (e.g. 2-pyridyl)yl;

$R^{3b}$ is hydrogen;

$Y^1$ is >$CR^6$;

$R^6$ is hydrogen, or $R^6$ and $R^{3a}$ or $R^{3b}$
together are $C_1$-$C_5$-alkylene (e.g. 1,4-butylene);

$R^{8b}$ is hydrogen, or $R^{3a}$ and $R^{8b}$
together are $C_1$-$C_5$-alkylene (e.g. 1,2-ethylene or 1,3-propylene);

$R^{14}$ is $C_1$-$C_8$-alkyl (e.g. pentyl or n-butyl), halogenated $C_1$-$C_6$-alkyl (e.g. 1,1-diF-butyl, 3,3-diF-butyl, 4,4,4-triF-butyl, 1,1-diF-pentyl, or 4,4-diF-pentyl), (optionally substituted $C_3$-$C_{12}$-cycloalkyl)-$C_1$-$C_4$-alkyl (e.g. cyclopropyl-methyl), (optionally substituted $C_6$-$C_{12}$-aryl)-$C_1$-$C_4$-alkyl (e.g. benzyl, a further example being 4-F-benzyl, 3-F-benzyl, 3-$CF_3$-benzyl, 4-F-3-$CF_3$-benzyl, or 3-$OCF_3$-benzyl), hydroxy-$C_1$-$C_6$-alkyl (e.g. hydroxyl-methyl or 1-hydroxypentyl), (halogenated $C_6$-$C_{12}$-aryloxy)-$C_1$-$C_4$-alkyl (e.g. 4-F-phenoxy)-methyl), $C_1$-$C_6$-alkylcarbonyl-$C_1$-$C_4$-alkyl (e.g. 2-methylcarbonyl-ethyl or 3-methylcarbonyl-propyl), $C_1$-$C_6$-alkoxycarbonyl-$C_1$-$C_4$-alkyl (e.g. 3-methoxycarbonyl-propyl), $C_3$-$C_{12}$-cycloalkyl optionally substituted with 1, 2, or 3 substituents independently selected from the group consisting of halogenated $C_1$-$C_4$-alkyl (e.g.1-$CF_3$-cyclopropyl or 4-$CF_3$-cyclohexyl), $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, CN and $C_1$-$C_4$-alkoxy (e.g. phenyl, 2-F-phenyl, 3-F-phenyl, 4-F-phenyl, 2-Cl-phenyl, 3-Cl-phenyl, 4-Cl-phenyl, 2,3-diCl-phenyl, 2,4-diCl-phenyl, 3,5-diCl-phenyl, 2-Cl-F-phenyl, 2-Me-phenyl, 3-Me-phenyl, 4-Me-phenyl, 2-$CF_3$-phenyl, 3-$CF_3$-phenyl, 4-$CF_3$-phenyl, 3-Cl-4-$CF_3$-phenyl, 2-Cl-3-$CF_3$-phenyl, 2-Cl-4-$CF_3$-phenyl, 2-OMe-phenyl, 3-OMe-phenyl, 2-CN-phenyl, or 3-CN-phenyl, 4-CN-phenyl), or $C_3$-$C_{12}$-heterocyclyl optionally substituted with 1, 2, or 3 substituents independently selected from the group consisting of halogen and halogenated $C_1$-$C_4$-alkyl(e.g. 3-Cl-pyridazin-6-yl, 2-Cl-pyrazin-5-yl, or 2-$CF_3$-pyrazin-5-yl); and $R^{5a}$, $R^{5b}$
are hydrogen.

Further particular embodiments of pyrrolidine derivatives of formula (Ie) result if:

$R^6$ is hydrogen;

$R^{8b}$ is hydrogen;

$R^{14}$ is $C_1$-$C_8$-alkyl (e.g. pentyl, n-butyl, or hexyl), halogenated $C_1$-$C_6$-alkyl (e.g. 1,1-diF-butyl, 3,3-diF-butyl, 4,4,4-triF-butyl, 1,1-diF-pentyl, or 4,4-diF-pentyl), (optionally substituted $C_3$-$C_{12}$-cycloalkyl)-$C_1$-$C_4$-alkyl (e.g. cyclopropyl-methyl), hydroxy-$C_1$-$C_6$-alkyl (e.g. hydroxylmethyl or 1-hydroxy-pentyl), (optionally substituted $C_6$-$C_{12}$-aryloxy)-$C_1$-$C_4$-alkyl (e.g. phenoxy-methyl or (4-F-phenoxy)-methyl), $C_1$-$C_6$-alkylcarbonyl-$C_1$-$C_4$-alkyl (e.g. 2-methylcarbonyl-ethyl or 3-methylcarbonyl-propyl), $C_1$-$C_6$-alkoxycarbonyl-$C_1$-$C_4$-alkyl (e.g. 3-methoxycarbonyl-propyl), optionally substituted $C_3$-$C_{12}$-cycloalkyl (e.g.1-$CF_3$-cyclopropyl or 4-$CF_3$-cyclohexyl, a further example being 1-phenyl-cyclopropyl, 1-(4-F-phenyl)cyclopropyl, 1-(3-F-phenyl)cyclopropyl, 1-(3-Cl-phenyl)cyclopropyl, 1-(3-$CF_3$-phenyl)cyclopropyl, 3-hydroxymethyl-bycyclo[1.1.1]pentyl, 3-methoxymethylbycyclo[1.1.1]pentyl, 3-ethoxymethyl-bycyclo[1.1.1]pentyl, or 3-methoxycarbonylbycyclo[1.1.1]pentyl), optionally substituted $C_6$-$C_{12}$-aryl (e.g. phenyl, 2-F-phenyl, 3-F-phenyl, 4-F-phenyl, 2-Cl-phenyl, 3-Cl-phenyl, 4-Cl-phenyl, 2,3-diCl-phenyl, 2,4-diCl-phenyl, 3,5-diCl-phenyl, 2-Cl-F-phenyl, 2-Me-phenyl, 3-Me-phenyl, 4-Me-phenyl, 2-$CF_3$-phenyl, 3-$CF_3$-phenyl, 4-$CF_3$-phenyl, 3-Cl-4-$CF_3$-phenyl, 2-Cl-3-$CF_3$-phenyl, 2-Cl-4-$CF_3$-phenyl, 2-OMe-phenyl, 3-OMe-phenyl, 2-CN-phenyl, or 3-CN-phenyl, 4-CN-phenyl), or optionally substituted $C_3$-$C_{12}$-heterocyclyl (e.g. 3-Cl-pyridazin-6-yl, 2-Cl-pyrazin-5-yl, or 2-$CF_3$-pyrazin-5-yl); and $R^1$, $R^{2a}$, $R^{2b}$, $R^{3a}$, $R^{3b}$, $Y^1$, $R^{5a}$ and $R^{5b}$ are as defined above.

According to a particularly preferred embodiment, $R^{3a}$ is phenyl, or halogenated phenyl (e.g. 2-Cl-phenyl, 3-Cl-phenyl, 4-Cl-phenyl, 2-F-phenyl, 3-F-phenyl, 4-F-phenyl), 4-OMe-phenyl, or pyrid-2-yl.

According to a further embodiment, $R^4$ is —$NR^{8c}COOR^{15}$. Thus, the present invention relates to the pyrrolidine derivatives of the formula (If):

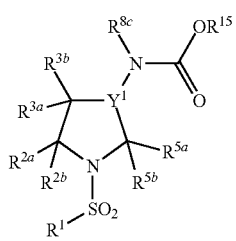

(If)

wherein $R^1$, $R^{2a}$, $R^{2b}$, $R^{3a}$, $R^{3b}$, $Y^1$, $R^{5a}$ and $R^{5b}$ are as defined herein, and $R^{8c}$ is hydrogen, $C_1$-$C_6$-alkyl (e.g. methyl, ethyl, iso-propyl, or n-butyl), or $C_1$-$C_6$-alkylcarbonyl (e.g. emthylcarbonyl), or $R^6$, $R^{8c}$
together are optionally substituted $C_1$-$C_5$-alkylene, wherein one or more —$CH_2$— of $C_1$-$C_5$-alkylene may be independently replaced by a an oxygen atom or C=O. Preferably $R^{8c}$ is hydrogen; and $R^{15}$ is $C_1$-$C_8$-alkyl (e.g. ethyl, n-propyl, n-butyl, iso-butyl, or tert-butyl), optionally substituted $C_6$-$C_{12}$-aryl (e.g. phenyl, 4-F-phenyl, 2-Cl-F-phenyl or 2-Me-phenyl), or optionally substituted $C_3$-$C_{12}$-heterocyclyl (e.g. 6-pyridazyl or 5-pyrazyl).

In particular, $R^{15}$ is $C_1$-$C_8$-alkyl (e.g. ethyl, n-propyl, n-butyl, iso-butyl, or tert-butyl), or optionally substituted $C_6$-$C_{12}$-aryl (e.g. phenyl, 4-F-phenyl, 2-Cl-F-phenyl or 2-Me-phenyl). Preferably, $R^{15}$ is $C_1$-$C_6$-alkyl (e.g. ethyl, n-propyl, n-butyl, iso-butyl, or tert-butyl) or $C_6$-$C_{12}$-aryl (e.g. phenyl).

$R^{2a}$, $R^{2b}$—in the pyrrolidine derivatives of formula (If)—are, in particular, hydrogen.

$R^{3a}$—in the pyrrolidine derivatives of formula (If)—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenyloxy or 4-F-phenyloxy), or $C_3$-$C_{12}$-heterocyclyl (e.g. pyrid-2-yl, a further example being tetrahydrofuran-2-yl or tetrahydropyran-2-yl). Preferably $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl).

$R^{3b}$—in the pyrrolidine derivatives of formula (If)—is, in particular, hydrogen.

$Y^1$—in the pyrrolidine derivatives of formula (If)—is, in particular, >$CR^6$.

$R^6$—in the pyrrolidine derivatives of formula (If)—is, in particular, hydrogen.

$R^{5a}$, $R^{5b}$—in the pyrrolidine derivatives of formula (If)—are, in particular, hydrogen.

Particular embodiments of the pyrrolidine derivatives of formula (If) result if:

$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$
are hydrogen;

$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl);

$R^{3b}$ is hydrogen;

$Y^1$ is >$CR^6$;

$R^6$ is hydrogen;

$R^{8c}$ is hydrogen;

$R^{15}$ is $C_1$-$C_8$-alkyl (e.g. ethyl, n-propyl, n-butyl, iso-butyl, or tert-bu) or $C_6$-$C_{12}$-aryl (e.g. phenyl); and $R^{5a}$, $R^{5b}$
are hydrogen.

Preferably, $R^1$—in the pyrrolidine derivatives of formula (If)—is an optionally substituted 5-membered heterocyclic ring containing 2 N which, in particular, is optionally substituted 1,3-diazolyl.

According to a further preferred embodiment, $R^1$—in the pyrrolidine derivatives of formula (If)—is an optionally substituted 5-membered heterocyclic ring containing 3 N which, in particular, is optionally substituted 1,2,3-triazolyl.

In connection with $R^1$ and the pyrrolidine derivatives of formula (If), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives of formula (If), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituent(s) on $C_6$-$C_{12}$-aryl are independently selected from the group consisting of halogen.

According to a particular embodiment, $R^{3a}$—in the pyrrolidine derivatives of formula (If)—is $C_6$-$C_{12}$-aryl, in particular phenyl, optionally substituted with 1, 2, or 3 substituents independently selected from the group consisting of halogen.

Further preferred embodiments of pyrrolidine derivatives of formula (If) result if:
$R^1$ is 1,3-diazolyl is substituted with halogen or $C_1$-$C_6$-alkyl (e.g. 1-methyl-1,3-diazol-4-yl);
$R^{2a}$, $R^{2b}$
are hydrogen;
$R^{3a}$ is $C_6$-$C_{12}$-aryl optionally substituted with 1, 2, or 3 substituents independently selected from the group consisting of halogen (e.g. phenyl, or 4-F-phenyl);
$R^{3b}$ is hydrogen;
$Y^1$ is >$CR^6$;
$R^6$ is hydrogen;
$R^{8c}$ is hydrogen;
$R^{15}$ is $C_1$-$C_8$-alkyl (e.g. ethyl, n-propyl, n-butyl, iso-butyl, or tert-butyl) or $C_6$-$C_{12}$-aryl (e.g. phenyl); and
$R^{5a}$, $R^{5b}$
are hydrogen;
According to a further embodiment, $R^4$ is —$NR^{8d}CONR^{16a}R^{16b}$. Thus, the present invention relates to the pyrrolidine derivatives of the formula (Ig):

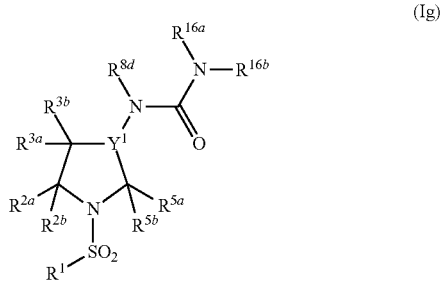

(Ig)

wherein $R^1$, $R^{2a}$, $R^{2b}$, $R^{3a}$, $R^{3b}$, $Y^1$, $R^{5a}$ and $R^{5b}$ are as defined herein, and
$R^{8d}$ is hydrogen, $C_1$-$C_6$-alkyl (e.g. methyl, ethyl, iso-propyl, or n-butyl), or $C_1$-$C_6$-alkylcarbonyl (e.g. methylcarbonyl), or
$R^6$, $R^{8d}$
together are optionally substituted $C_1$-$C_5$-alkylene, wherein one or more —$CH_2$— of $C_1$-$C_5$-alkylene may be independently replaced by a an oxygen atom or C=O;
$R^{16a}$ is (optionally substituted $C_6$-$C_{12}$-aryl)-$C_1$-$C_4$-alkyl (e.g. benzyl or (2-Cl-phenyl)-methyl), optionally substituted ($C_3$-$C_{12}$-heterocyclyl)-$C_1$-$C_4$-alkyl (e.g. 2-pyridyl-methyl), optionally substituted $C_6$-$C_{12}$-aryl (e.g. phenyl, 4-F-phenyl, 3-F-phenyl, 2-F-phenyl, 4-Cl-phenyl, or 2-Cl-phenyl, a further example being 3-Cl-phenyl), or optionally substituted $C_3$-$C_{12}$-heterocyclyl (2-pyridyl, 5-pyrazyl, or 6-pyridazyl); and
$R^{16b}$ is hydrogen or $C_1$-$C_6$-alkyl (e.g. methyl, ethyl, iso-propyl, or n-butyl).
In particular, $R^{8d}$ is hydrogen.
In particular, $R^{16a}$ is (optionally substituted $C_6$-$C_{12}$-aryl)-$C_1$-$C_4$-alkyl (e.g. benzyl or (2-Cl-phenyl)methyl) or optionally substituted $C_6$-$C_{12}$-aryl (e.g. phenyl, 4-F-phenyl, 3-F-phenyl, 2-F-phenyl, 4-Cl-phenyl, or 2-Cl-phenyl, a further example being 3-Cl-phenyl).
In particular, $R^{16b}$ is hydrogen.
$R^{2a}$, $R^{2b}$—in the pyrrolidine derivatives of formula (Ig)—are, in particular, hydrogen.
$R^{3a}$—in the pyrrolidine derivatives of formula (Ig)—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl), $C_3$-$C_{12}$-cycloalkyl-$C_1$-$C_4$-alkoxy (e.g. cyclopropylmethoxy or cyclohexyl-methoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenyloxy or 4-F-phenyloxy), or $C_3$-$C_{12}$-heterocyclyl (e.g. pyrid-2-yl). Preferably $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl).
$R^{3b}$—in the pyrrolidine derivatives of formula (Ig)—is, in particular, hydrogen.
$Y^1$—in the pyrrolidine derivatives of formula (Ig)—is, in particular, >$CR^6$.
$R^6$—in the pyrrolidine derivatives of formula (Ig)—is, in particular, hydrogen.
$R^{5a}$, $R^{5b}$—in the pyrrolidine derivatives of formula (Ig)—are, in particular, hydrogen.
Particular embodiments of the pyrrolidine derivatives of formula (If) result if:
$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);
$R^{2a}$, $R^{2b}$
are hydrogen;
$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl);
$R^{3b}$ is hydrogen;
$Y^1$ is >$CR^6$;
$R^6$ is hydrogen;
$R^{8d}$ is hydrogen;
$R^{16a}$ is (optionally substituted $C_6$-$C_{12}$-aryl)-$C_1$-$C_4$-alkyl (e.g. benzyl or (2-Cl-phenyl)-methyl) or optionally substituted $C_6$-$C_{12}$-aryl (e.g. phenyl, 4-F-phenyl, 3-F-phenyl, 2F-phenyl, 4-Cl-phenyl, or 2-Cl-phenyl, a further example being 3-Cl-phenyl);
$R^{16b}$ is hydrogen; and
$R^{5a}$, $R^{5b}$
are hydrogen.
Preferably, $R^1$—in the pyrrolidine derivatives of formula (Ig)—is an optionally substituted 5-membered heterocyclic ring containing 2 N which, in particular, is optionally substituted 1,3-diazolyl.
According to a further preferred embodiment, $R^1$—in the pyrrolidine derivatives of formula (Ig)—is an optionally substituted 5-membered heterocyclic ring containing 3 N which, in particular, is optionally substituted 1,2,3-triazolyl.

In connection with $R^1$ and the pyrrolidine derivatives of formula (Ig), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives of formula (Ig), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituent(s) on $C_6$-$C_{12}$-aryl are independently selected from the group consisting of halogen.

According to a preferred embodiment, $R^{3a}$ in the pyrrolidine derivatives of formula (Ig)—is $C_6$-$C_{12}$-aryl, in particular phenyl, optionally substituted with 1, 2, or 3 substituents independently selected from the group consisting of halogen (e.g. 4-F-phenyl).

In connection with $R^{16a}$, substituted $C_6$-$C_{12}$-aryl-$C_1$-$C_4$-alkyl in particular includes $C_6$-$C_{12}$-aryl-$C_1$-$C_4$-alkyl, such as benzyl, wherein $C_6$-$C_{12}$-aryl, such as phenyl, is substituted with 1, 2, or 3 substituents independently selected from the group consisting of halogen.

In connection with $R^{16a}$, substituted $C_6$-$C_{12}$-aryl in particular includes $C_6$-$C_{12}$-aryl, such as phenyl, which is substituted with 1, 2, or 3 substituents independently selected from the group consisting of halogen.

According to a preferred embodiment, $R^{16a}$ is $C_6$-$C_{12}$-aryl-$C_1$-$C_4$-alkyl or $C_6$-$C_{12}$-aryl, with $C_6$-$C_{12}$-aryl being optionally substituted with 1, 2, or 3 substituents independently selected from the group consisting of halogen (e.g. benzyl or (2-Cl-phenyl)-methyl and phenyl, 4-F-phenyl, 3-F-phenyl, 2F-phenyl, 4-Cl-phenyl, or 2-Cl-phenyl).

Preferred embodiments of the pyrrolidine derivatives of formula (Ig) result if:
$R^1$ is 1,3-diazolyl optionally substituted with halogen or $C_1$-$C_4$-alkyl (e.g. 1-methyl-1,3-diazol-4-yl);
$R^{2a}$, $R^{2b}$
  are hydrogen;
$R^{3a}$ is $C_6$-$C_{12}$-aryl optionally substituted with 1, 2, or 3 substituents independently selected from the group consisting of halogen (e.g. 4-F-phenyl);
$R^{3b}$ is hydrogen;
$Y^1$ is >$CR^6$;
$R^6$ is hydrogen;
$R^{8d}$ is hydrogen;
$R^{16a}$ is $C_6$-$C_{12}$-aryl-$C_1$-$C_4$-alkyl or $C_6$-$C_{12}$-aryl, with $C_6$-$C_{12}$-aryl being optionally substituted with 1, 2, or 3 substituents independently selected from the group consisting of halogen (e.g. benzyl or (2-Cl-phenyl)-methyl and phenyl, 4-F-phenyl, 3-F-phenyl, 2F-phenyl, 4-Cl-phenyl, or 2-Cl-phenyl, a further example being 3-Cl-phenyl);
$R^{16b}$ is hydrogen; and
$R^{5a}$, $R^{5b}$
  are hydrogen.

According to a further embodiment, $R^4$ is —O($CR^{9e}$$R^{9d})_{n5}R^{18}$. Thus, the present invention relates to the pyrrolidine derivatives of the formula (Ih):

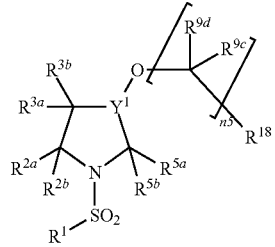

(Ih)

wherein $R^1$, $R^{2a}$, $R^{2b}$, $R^{3a}$, $R^{3b}$, $Y^1$, $R^{5a}$ and $R^{5b}$ K are as defined herein, and
$R^{9c}$, $R^{9d}$
  are independently hydrogen, halogen (e.g. F), or $C_1$-$C_6$-alkyl (e.g. methyl or ethyl);
n5 is 0, 1, 2, 3, or 4; and
$R^{18}$ is hydrogen, optionally substituted $C_1$-$C_8$-alkyl (e.g. methyl, ethyl, iso-propyl or pentyl), optionally substituted $C_3$-$C_{12}$-cycloalkyl (e.g. cyclopropyl or cyclohexyl), $C_1$-$C_6$-alkylcarbonyl (e.g. methylcarbonyl), $C_1$-$C_6$-alkoxycarbonyl (e.g. methoxycabonyl or n-butoxycarbonyl), halogenated $C_1$-$C_6$-alkoxycarbonyl (e.g. —C(O)OCF$_3$), $C_6$-$C_{12}$-aryloxycarbonyl (e.g. phenoxycarbonyl), $C_1$-$C_6$-alkylaminocarbonyl (e.g. n-propylaminocarbonyl or n-butylaminocarbonyl), (halogenated $C_1$-$C_4$-alkyl)aminocarbonyl (e.g. 2,2-diF-ethylaminocarbonyl, a further example being 2,2,2-tri F-ethylaminocarbonyl), $C_6$-$C_{12}$arylaminocarbonyl (e.g. phenylaminocarbonyl), optionally substituted $C_6$-$C_{12}$-aryl (e.g. phenyl, 3-F-phenyl, 4-F-phenyl, 4-Me-phenyl, 3-MeSO$_2$-phenyl, or 4-MeSO$_2$-phenyl, a further example being 4-F-2-CF$_3$-phenyl, 4-F-3-CF$_3$-phenyl, or 4-F-3-OCF$_3$-phenyl), $C_1$-$C_6$-alkylamine (e.g. n-propylamine), ($C_3$-$C_{12}$-cycloalkyl-$C_1$-$C_4$-alkyl)amino (e.g. cyclopropylmethylamino), (halogenated $C_1$-$C_6$-alkyl)amino (e.g. 2,2,2-triF-ethylamine, a further example being 2,2-diF-ethylamine), ($C_1$-$C_6$-alkoxy-$C_1$-$C_6$-alkyl)amino (e.g. 2-methoxyethylamine), ($C_6$-$C_{12}$-aryl-$C_1$-$C_4$-alkyl)amino (e.g. benzylamine), $C_1$-$C_6$-dialkylamine (e.g. dimethylamine), optionally substituted $C_6$-$C_{12}$-arylamine (e.g. 4-Cl-phenylamine), or optionally substituted $C_3$-$C_{12}$-heterocyclyl (e.g. 4-CF$_3$-pyrid-2-yl or 6-CF$_3$-pyrimid-4-yl, a further example being 4-Me-pyrid-2-yl).

In particular, $R^{9c}$, $R^{9d}$ are hydrogen.
In particular, n5 is 0, 1, or 2.
In particular, $R^{18}$ is hydrogen, optionally substituted $C_1$-$C_8$-alkyl (e.g. methyl, ethyl, isopropyl, or pentyl), $C_1$-$C_6$-alkoxycarbonyl (e.g. methoxycabonyl or n-butoxycarbonyl), $C_1$-$C_6$-alkylaminocarbonyl (e.g. n-propylaminocarbonyl or n-butylaminocarbonyl), (halogenated $C_1$-$C_4$-alkyl)aminocarbonyl (e.g. 2,2-diF-ethylaminocarbonyl, a further example being 2,2,2-tri F-ethylaminocarbonyl), optionally substituted $C_6$-$C_{12}$-aryl (e.g. phenyl, 3-F-phenyl, 4-F-phenyl, 4-Me-phenyl, 3-MeSO$_2$-phenyl, or 4-MeSO$_2$-phenyl, a further example being 4-F-2-CF$_3$-phenyl, 4-F-3-CF$_3$-phenyl, or 4-F-3-OCF$_3$-phenyl), $C_1$-$C_6$-alkylamine (e.g. n-propylamine), (halogenated $C_1$-$C_6$-alkyl)amino (e.g. 2,2,2-triF-ethylamine, a further example being 2,2-diF-ethylamine), optionally substituted $C_6$-$C_{12}$-arylamine (e.g. 4-Cl-phenylamine), or optionally substituted $C_3$-$C_{12}$-heterocyclyl (e.g. 4-$CF_3$-pyrid-2-yl or 6-$CF_3$-pyrimid-4-yl, a further example being 4-Me-pyrid-2-yl).

$R^{2a}$, $R^{2b}$ in pyrrolidine derivatives of formula (Ih) are, in particular, hydrogen.

$R^{3a}$—in the pyrrolidine derivatives of formula (Ih)—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenoxy or 4-F-phenoxy), or $C_3$-$C_{12}$-heterocyclyl (e.g. pyrid-2-yl). Preferably, $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), or optionally substituted $C_3$-$C_{12}$-heterocyclyl (e.g. 3-F-azetidin-1-yl, morpholin-1-yl, pyrrolidin-1-yl, piperidin-1-yl, 2-Me-piperidin-1yl, 3-Me-piperidin-1yl, 4-Me-piperidin-1yl, 4-F-piperidin-1-yl, 4,4-diF-piperidin-1yl, or azepan-1-yl).

$R^{3b}$—in the pyrrolidine derivatives of formula (Ih)—is, in particular, hydrogen.

$Y^1$—in the pyrrolidine derivatives of formula (Ih)—is, in particular, >$CR^6$.

$R^6$—in the pyrrolidine derivatives of formula (Ih)—is, in particular, hydrogen or $C_6$-$C_{12}$-aryl-$C_1$-$C_4$-alkyl (e.g. benzyl). Additionally, $R^6$ may be, in particular, $C_1$-$C_4$-alkylene (e.g. methylene or 1,2-ethylene) that is bound to a carbon atom in $R^{3a}$, and $R^{3a}$ is an optionally substituted $C_6$-$C_{12}$-aryl (e.g. phenyl) or an optionally substituted $C_3$-$C_{12}$-heterocyclyl. According to a particular embodiment, $R^6$ is hydrogen or benzyl. According to a further particular embodiment, $R^6$ may be $C_1$-$C_4$-alkylene (e.g. 1,2-ethylene) that is bound to a carbon atom in $R^{3a}$, and $R^{3a}$ is an optionally substituted $C_6$-$C_{12}$-aryl (e.g. phenyl). Preferably, $R^6$ is hydrogen. It is further preferred if $R^6$ is $C_1$-$C_4$-alkylene (e.g. 1,2-ethylene) that is bound to a carbon atom in $R^{3a}$, and $R^{3a}$ is an optionally substituted $C_6$-$C_{12}$-aryl (e.g. phenyl).

$R^{5a}$, $R^{5b}$—in the pyrrolidine derivatives of formula (Ih)—are, in particular, hydrogen.

Particular embodiments of pyrrolidine derivatives of formula (Ih) result if:
$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);
$R^{2a}$, $R^{2b}$
are hydrogen;

$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), or optionally substituted $C_3$-$C_{12}$-heterocyclyl (e.g. 3-F-azetidin-1-yl, morpholin-4-yl, pyrrolidin-1-yl, piperidin-1-yl, 2-Me-piperidin-1-yl, 3-Me-piperidin-1-yl, 4-Me-piperidin-1-yl, 4-F-piperidin-1-yl, 4,4-diF-piperidin-1yl, or azepan-1-yl);
$R^{3b}$ is hydrogen;
$Y^1$ is >$CR^6$;
$R^6$ is hydrogen;
$R^{9c}$, $R^{9d}$
are hydrogen;
n5 is 0, 1, or 2;
$R^{18}$ is hydrogen, optionally substituted $C_1$-$C_8$-alkyl (e.g. methyl, ethyl, iso-propyl, or pentyl), $C_1$-$C_6$-alkoxycarbonyl (e.g. methoxycabonyl orbutoxycarbonyl), $C_1$-$C_6$-alkylaminocarbonyl (e.g. n-propylaminocarbonyl or n-butylaminocarbonyl), (halogenated $C_1$-$C_4$-alkyl)aminocarbonyl (e.g. 2,2-diF-ethylaminocarbonyl, a further example being 2,2,2-tri F-ethylaminocarbonyl), optionally substituted $C_6$-$C_{12}$-aryl (e.g. phenyl, 3-F-phenyl, 4-F-phenyl, 4-Me-phenyl, 3-$MeSO_2$-phenyl, or 4-$MeSO_2$-phenyl, a further example being 4-F-2-$CF_3$-phenyl, 4-F-3-$CF_3$-phenyl, or 4-F-3-$OCF_3$-phenyl), $C_1$-$C_6$-alkylamine (e.g. n-propylamine), (halogenated $C_1$-$C_6$-alkyl)amino (e.g. 2,2,2-tri F-ethylamine, a further example being 2,2-diF-ethylamine), optionally substituted $C_6$-$C_{12}$-arylamine (e.g. 4-Cl-phenylamine), or optionally substituted $C_3$-$C_{12}$-heterocyclyl (e.g. 4-$CF_3$-pyrid-2-yl or 6-$CF_3$-pyrimid-4-yl, a further example being 4-Me-pyrid-2-yl); and
$R^{5a}$, $R^{5b}$
are hydrogen.

Additional particular embodiments of pyrrolidine derivatives of formula (Ih) result if:
$R^6$ is $C_1$-$C_4$-alkylene (e.g. 1,2-ethylene) that is bound to a carbon atom in $R^{3a}$, and $R^{3a}$ is an optionally substituted $C_6$-$C_{12}$-aryl (e.g. phenyl); and
$R^1$, $R^{2a}$, $R^{2b}$, $R^{3a}$, $R^{3b}$, $Y^1$, $R^{9c}$, $R^{9d}$, n5, $R^{18}$, $R^{5a}$ and $R^{5b}$ are as defined above.

Preferably, $R^1$—in the pyrrolidine derivatives of formula (Ih)—is an optionally substituted 5-membered heterocyclic ring containing 2 N which, in particular, is optionally substituted 1,3-diazolyl.

According to a further preferred embodiment, $R^1$—in the pyrrolidine derivatives of formula (Ih)—is an optionally substituted 5-membered heterocyclic ring containing 3 N which, in particular, is optionally substituted 1,2,3-triazolyl.

In connection with $R^1$ and the pyrrolidine derivatives of formula (Ih), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives of formula (Ih), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituent(s) on $C_6$-$C_{12}$-aryl are independently selected from the group consisting of halogen.

In connection with $R^{3a}$ and the pyrrolidine derivatives of formula (Ih), substituted $C_3$-$C_{12}$-heterocyclyl in particular includes $C_3$-$C_{12}$-heterocyclyl, such as azetidinyl, morpholinyl, pyrrolidinyl, piperidinyl, or azepanyl, which is substituted with 1, 2, or 3 substituents independently selected from the group consisting of halogen, $C_1$-$C_4$-alkyl and $C_1$-$C_4$-alkoxy. Preferably, the substituent(s) on $C_3$-$C_{12}$-heterocyclyl are independently selected from the group consisting of halogen and $C_1$-$C_4$-alkyl.

According to a preferred embodiment, $R^{3a}$—in the pyrrolidine derivatives of formula (Ih)—is $C_6$-$C_{12}$-aryl optionally substituted with 1, 2, or 3 substituents independently selected from the group consisting of halogen (e.g. 4-F-phenyl), or $C_3$-$C_{12}$-heterocyclyl optionally substituted with 1, 2, or 3 substituents independently selected from the group consisting of halogen and $C_1$-$C_4$-alkyl (e.g. 3-F-azetidin-1-yl, morpholin-1-yl, pyrrolidin-1-yl, piperidin-1-yl, 2-Me-piperidin-1yl, 3-Me-piperidin-1yl, 4-Me-piperidin-1yl, 4-F-piperidin-1-yl, 4,4-diF-piperidin-1yl, or azepan-1-yl).

In connection with $R^{18}$, substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkyl-sulfonyl. Additional substituents may be independently selected from the group consisting of halogenated $C_1$-$C_4$-alkyl and halogenated $C_1$-$C_4$-alkoxy.

In connection with $R^{18}$, substituted $C_6$-$C_{12}$-arylamine in particular includes $C_6$-$C_{12}$-arylamine, such as phenylamine, which is substituted with 1, 2, or 3 substituents independently selected from the group consisting of halogen.

In connection with $R^{18}$, substituted $C_3$-$C_{12}$-heterocyclyl in particular includes $C_3$-$C_{12}$-heterocyclyl, such as 2-pyridyl or 4-pyrimidyl, which is substituted with 1, 2, or 3 substituents independently selected from the group consisting of halogenated $C_1$-$C_4$-alkyl. Additional substituents may be independently selected from the group consisting of $C_1$-$C_4$-alkyl.

According to a preferred embodiment, $R^{18}$ is hydrogen, $C_1$-$C_8$-alkyl (e.g. methyl, ethyl, iso-propyl, or pentyl), $C_1$-$C_6$-alkoxycarbonyl (e.g. methoxycabonyl or n-butoxycarbonyl), $C_1$-$C_6$-alkylaminocarbonyl (e.g. n-propylaminocarbonyl or n-butylaminocarbonyl), (halogenated $C_1$-$C_4$-alkyl)aminocarbonyl (e.g. 2,2-diF-ethylaminocarbonyl, a further example being 2,2,2-tri F-ethylaminocarbonyl), $C_6$-$C_{12}$-aryl optionally substituted with 1, 2, or 3 substituents independently selected from the group consisting of halogen, $C_1$-$C_4$-alkyl and $C_1$-$C_4$-alkyl-sulfonyl, and additionally from the group consisting of halogenated $C_1$-$C_4$-alkyl and halogenated $C_1$-$C_4$-alkoxy (e.g. phenyl, 3-F-phenyl, 4-F-phenyl, 4-Me-phenyl, 3-MeSO$_2$-phenyl, or 4-MeSO$_2$-phenyl, a further example being 4-F-2-CF$_3$-phenyl, 4-F-3-CF$_3$-phenyl, or 4-F-3-OCF$_3$-phenyl), or $C_1$-$C_6$-alkylamine (e.g. n-propylamine), (halogenated $C_1$-$C_6$-alkyl)amino (e.g. 2,2,2-triF-ethylamine, a further example being 2,2-diF-ethylamine), $C_6$-$C_{12}$-arylamine optionally substituted with 1, 2, or 3 substituents independently selected from the group consisting of halogen (e.g. 4-Cl-phenylamine), or $C_3$-$C_{12}$-heterocyclyl optionally substituted with 1, 2, or 3 substituents independently selected from the group consisting of halogenated $C_1$-$C_4$-alkyl, and additionally from the group consisting of $C_1$-$C_4$-alkyl (e.g. 4-CF$_3$-pyrid-2-yl or 6-CF$_3$-pyrimid-4-yl, a further example being 4-Me-pyrid-2-yl).

Further preferred embodiments of the pyrrolidine derivatives of formula (Ih) result if:

$R^1$ is 1,3-diazolyl optionally substituted with halogen or $C_1$-$C_4$-alkyl (e.g. 1-methyl-1,3-diazol-4-yl);

$R^{2a}$, $R^{2b}$ are hydrogen;

$R^{3a}$ $C_6$-$C_{12}$-aryl optionally substituted with 1, 2, or 3 substituents independently selected from the group consisting of halogen (e.g. 4-F-phenyl), or $C_3$-$C_{12}$-heterocyclyl optionally substituted with 1, 2, or 3 substituents independently selected from the group consisting of halogen and $C_1$-$C_4$-alkyl (e.g. 3-F-azetidin-1-yl, morpholin-1-yl, pyrrolidin-1-yl, piperidin-1-yl, 2-Me-piperidin-1yl, 3-Me-piperidin-1yl, 4-Me-piperidin-1yl, 4-F-piperidin-1-yl, 4,4-diF-piperidin-1yl, or azepan-1-yl);

$R^{3b}$ is hydrogen;

$Y^1$ is >CR$^6$;

$R^6$ is hydrogen, or $R^6$ is $C_1$-$C_4$-alkylene (e.g. 1,2-ethylene) that is bound to a carbon atom in $R^{3a}$, and $R^{3a}$ is an optionally substituted $C_6$-$C_{12}$-aryl (e.g. phenyl);

$R^{9c}$, $R^{9d}$ are hydrogen;

n5 is 0, 1, or 2;

$R^{18}$ is hydrogen, $C_1$-$C_8$-alkyl (e.g. methyl, ethyl, iso-propyl, or pentyl), $C_1$-$C_6$-alkoxycarbonyl (e.g. methoxycabonyl or n-butoxycarbonyl), $C_1$-$C_6$-alkylaminocarbonyl (e.g. n-propylaminocarbonyl or n-butylaminocarbonyl), (halogenated $C_1$-$C_4$-alkyl)aminocarbonyl (e.g. 2,2-diF-ethylaminocarbonyl, a further example being 2,2,2-tri F-ethylaminocarbonyl), $C_6$-$C_{12}$-aryl optionally substituted with 1, 2, or 3 substituents independently selected from the group consisting of halogen, $C_1$-$C_4$-alkyl and $C_1$-$C_4$-alkyl-sulfonyl, and additionally from the group consisting of halogenated $C_1$-$C_4$-alkyl and halogenated $C_1$-$C_4$-alkoxy (e.g. phenyl, 3-F-phenyl, 4-F-phenyl, 4-Me-phenyl, 3-MeSO$_2$-phenyl, or 4-MeSO$_2$-phenyl, a further example being 4-F-2-CF$_3$-phenyl, 4-F-3-CF$_3$-phenyl, or 4-F-3-OCF$_3$-phenyl), or $C_1$-$C_6$-alkylamine (e.g. n-propylamine), (halogenated $C_1$-$C_6$-alkyl)amino (e.g. 2,2,2-triF-ethylamine, a further example being 2,2-diF-ethylamine), $C_6$-$C_{12}$-arylamine optionally substituted with 1, 2, or 3 substituents independently selected from the group consisting of halogen (e.g. 4-Cl-phenylamine), or $C_3$-$C_{12}$-heterocyclyl optionally substituted with 1, 2, or 3 substituents independently selected from the group consisting of halogenated $C_1$-$C_4$-alkyl, and additionally from the group consisting of $C_1$-$C_4$-alkyl (e.g. 4-CF$_3$-pyrid-2-yl or 6-CF$_3$-pyrimid-4-yl, a further example being 4-Me-pyrid-2-yl); and $R^{5a}$, $R^{5b}$ are hydrogen.

Further preferred embodiments of pyrrolidine derivatives of formula (Ih) result if:

$R^6$ is hydrogen;

$R^{18}$ is hydrogen, $C_1$-$C_8$-alkyl (e.g. methyl, ethyl, iso-propyl, or pentyl), $C_1$-$C_6$-alkoxycarbonyl (e.g. methoxycabonyl or n-butoxycarbonyl), $C_1$-$C_6$-alkylaminocarbonyl (e.g. n-propylaminocarbonyl or n-butylaminocarbonyl), (halogenated $C_1$-$C_4$-alkyl)aminocarbonyl (e.g. 2,2-diF-ethylaminocarbonyl, a further example being 2,2,2-tri F-ethylaminocarbonyl), $C_6$-$C_{12}$-aryl optionally substituted with 1, 2, or 3 substituents independently selected from the group consisting of halogen, $C_1$-$C_4$-alkyl and $C_1$-$C_4$-alkyl-sulfonyl (e.g. phenyl, 3-F-phenyl, 4-F-phenyl, 4-Me-phenyl, 3-MeSO$_2$-phenyl, or 4-MeSO$_2$-phenyl]), or $C_1$-$C_6$-alkylamine (e.g. n-propylamine), (halogenated $C_1$-$C_6$-alkyl)amino (e.g. 2,2,2-triF-ethylamine, a further example being 2,2-diF-ethylamine), $C_6$-$C_{12}$-arylamine optionally substituted with 1, 2, or 3 substituents independently selected from the group consisting of halogen (e.g. 4-Cl-phenylamine), or $C_3$-$C_{12}$-heterocyclyl optionally substituted with 1, 2, or 3 substituents independently selected from the group consisting of halogenated $C_1$-$C_4$-alkyl (e.g. 4-CF$_3$-pyrid-2-yl or 6-CF$_3$-pyrimid-4-yl); and $R^1$, $R^{2a}$, $R^{2b}$, $R^{3a}$, $R^{3b}$, $Y^1$, $R^{9c}$, $R^{9d}$, n5, $R^{5a}$ and $R^{5b}$ are as defined above.

According to a further embodiment, $R^4$ is —$COR^{19}$. Thus, the present invention relates to the pyrrolidine derivatives of the formula (II):

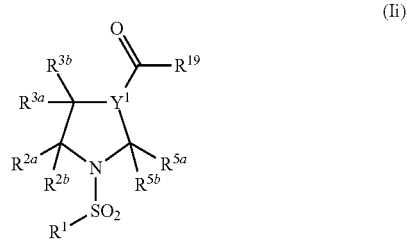

wherein $R^1$, $R^{2a}$, $R^{2b}$, $R^{3a}$, $R^{3b}$, $Y^1$, $R^{5a}$ and $R^{5b}$ are as defined herein, and $R^{19}$ is optionally substituted $C_6$-$C_{12}$-aryl (e.g. phenyl, 3-F-phenyl, 4-F-phenyl, 3-Cl-phenyl, 3,4-diF-phenyl, 3-F-4-Cl-phenyl, 3-F-5-Cl-phenyl, 3-Me-phenyl, 3-CF$_3$-phenyl, 3-OCF$_3$-phenyl, or 4-OCF$_3$-phenyl) or optionally substituted $C_3$-$C_{12}$-heterocyclyl (e.g. 2-pyridyl or 6-pyrimidyl).

In particular, $R^{19}$ is optionally substituted $C_6$-$C_{12}$-aryl (e.g. phenyl, 3-F-phenyl, 4-F-phenyl, 3-Cl-phenyl, 3,4-diF-phenyl, 3,4-diCl-phenyl, 3,5-diCl-phenyl, 3-F-4-Cl-phenyl, 3-F-5-Cl-phenyl, 3-Me-phenyl, 3-CF$_3$-phenyl, 3-OCF$_3$-phenyl, or 4-OCF$_3$-phenyl).

$R^{2a}$, $R^{2b}$—in the pyrrolidine derivatives of formula (II)—are, in particular, hydrogen.

$R^{3a}$—in the pyrrolidine derivatives of formula (II)—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenoxy or 4-F-phenoxy), or $C_3$-$C_{12}$-heterocyclyl (e.g. pyrid-2-yl). Preferably, $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl). It is further preferred if $R^{3a}$ is $C_3$-$C_{12}$-heterocyclyl (e.g. pyrid-2-yl).

$R^{3b}$—in the pyrrolidine derivatives of formula (II)—is, in particular, hydrogen.

$Y^1$—in the pyrrolidine derivatives of formula (II)—is, in particular, >$CR^6$.

$R^6$—in the pyrrolidine derivatives of formula (II)—is, in particular, hydrogen.

$R^{5a}$, $R^{5b}$—in the pyrrolidine derivatives of formula (II)—are, in particular, hydrogen.

Particular embodiments of the pyrrolidine derivatives of formula (II) result if $R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-CF$_3$-1,2-diazol-4-yl, 1-cyclopentyl-3-Me-1,2-diazol-4-yl, 1,3,5-trimethyl-1,2-diazol-4-yl, 1-CHF$_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$ are hydrogen;

$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl);

$R^{3b}$ is hydrogen;

$Y^1$ is >$CR^6$;

$R^6$ is hydrogen;

$R^{19}$ is optionally substituted $C_6$-$C_{12}$-aryl (e.g. phenyl, 3-F-phenyl, 4-F-phenyl, 3-Cl-phenyl, 3,4-diF-phenyl, 3,4-diCl-phenyl, 3,5-diCl-phenyl, 3-F-4-Cl-phenyl, 3-F-5-Cl-phenyl, 3-Me-phenyl, 3-CF$_3$-phenyl, 3-OCF$_3$-phenyl, or 4-OCF$_3$-phenyl); and $R^{5a}$, $R^{5b}$ are hydrogen.

Additional particular embodiments of the pyrrolidine derivatives of formula (Ii) result if $R^{3a}$ is $C_3$-$C_{12}$-heterocyclyl (e.g. pyrid-2-yl); and $R^1$, $R^{2a}$, $R^{2b}$, $R^{3b}$, $Y^1$, $R^6$, $R^{19}$, $R^{5a}$ and $R^{5b}$ are as defined above.

Preferably, $R^1$—in the pyrrolidine derivatives of formula (Ii)—is an optionally substituted 5-membered heterocyclic ring containing 2 N which, in particular, is optionally substituted 1,3-diazolyl.

According to a further preferred embodiment, $R^1$—in the pyrrolidine derivatives of formula (Ii)—is an optionally substituted 5-membered heterocyclic ring containing 3 N which, in particular, is optionally substituted 1,2,3-triazolyl.

In connection with $R^1$ and the pyrrolidine derivatives of formula (Ii), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives of formula (Ii), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituent(s) on $C_6$-$C_{12}$-aryl are independently selected from the group consisting of halogen.

According to a preferred embodiment, $R^{3a}$—in the pyrrolidine derivatives of formula (Ii)—is $C_6$-$C_{12}$-aryl, in particular phenyl, optionally substituted with 1, 2, or 3 substituents independently selected from the group consisting of halogen (e.g. 4-F-phenyl). According to an additional preferred embodiment, $R^{3a}$—in the pyrrolidine derivatives of formula (Ii)—is $C_3$-$C_{12}$-heterocyclyl such as pyrid-2-yl.

In connection with $R^{19}$, substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl, halogenated $C_1$-$C_4$-alkyl and halogenated $C_1$-$C_4$-alkoxy.

According to a preferred embodiment, $R^{19}$ is $C_6$-$C_{12}$-aryl optionally substituted with 1, 2, or 3 substituents independently selected from the group consisting of halogen, $C_1$-$C_4$-alkyl, halogenated $C_1$-$C_4$-alkyl and halogenated $C_1$-$C_4$-alkoxy (e.g phenyl, 3-F-phenyl, 4-F-phenyl, 3-Cl-phenyl, 3,4-diF-phenyl, 3,4-diCl-phenyl, 3,5-diCl-phenyl, 3-F-4-Cl-phenyl, 3-F-5-Cl-phenyl, 3-Me-phenyl, 3-$CF_3$-phenyl, 3-$OCF_3$-phenyl, or 4-$OCF_3$-phenyl).

Further preferred embodiments of the pyrrolidine derivatives of formula (Ii) result if:

$R^1$ is 1,3-diazolyl optionally substituted with halogen or $C_1$-$C_4$-alkyl (e.g. 1-methyl-1,3-diazol-4-yl);

$R^{2a}$, $R^{2b}$ are hydrogen;

$R^{3a}$ is $C_6$-$C_{12}$-aryl optionally substituted with 1, 2, or 3 substituents independently selected from the group consisting of halogen (e.g. 4-F-phenyl);

$R^{3b}$ is hydrogen;

$Y^1$ is >$CR^6$;

$R^6$ is hydrogen;

$R^{19}$ $C_6$-$C_{12}$-aryl optionally substituted with 1, 2, or 3 substituents independently selected from the group consisting of halogen, $C_1$-$C_4$-alkyl, halogenated $C_1$-$C_4$-alkyl and halogenated $C_1$-$C_4$-alkoxy (e.g. phenyl, 3-F-phenyl, 4-F-phenyl, 3-Cl-phenyl, 3,4-diF-phenyl, 3,4-diCl-phenyl, 3,5-diCl-phenyl, 3-F-4-Cl-phenyl, 3-F-5-Cl-phenyl, 3-Me-phenyl, 3-$CF_3$-phenyl, 3-$OCF_3$-phenyl, or 4-$OCF_3$-phenyl); and $R^{5a}$, $R^{5b}$ are hydrogen.

Additional preferred embodiments of the pyrrolidine derivatives of formula (Ii) result if $R^{3a}$ is $C_3$-$C_{12}$-heterocyclyl (e.g. pyrid-2-yl); and $R^1$, $R^{2a}$, $R^{2b}$, $R^{3b}$, $Y^1$, $R^6$, $R^{19}$, $R^{5a}$ and $R^{5b}$ are as defined above.

According to a further particular embodiment $R^4$ is —$CONR^{20a}R^{20b}$. Thus, the present invention relates to the pyrrolidine derivatives of the formula (Il):

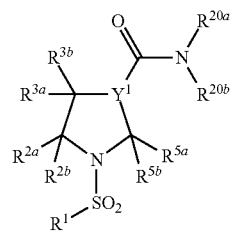

(II)

wherein $R^1$, $R^{2a}$, $R^{2b}$, $R^{3a}$, $R^{3b}$, $Y^1$, $R^{5a}$ and $R^{5b}$ are as defined herein, and $R^{20a}$ is $C_1$-$C_8$-alkyl (e.g. n-propyl, n-butyl, hexyl, pentyl, or 6-Me-heptyl), (optionally substituted $C_3$-$C_{12}$-cycloalkyl)-$C_1$-$C_4$-alkyl (e.g. cyclopropyl-methyl), $C_1$-$C_6$-alkoxy-$C_1$-$C_6$-alkyl (e.g. 2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), (optionally substituted $C_6$-$C_{12}$-aryl)-$C_1$-$C_4$-alkyl (e.g. benzyl, (4-F-phenyl)methyl, (3-Cl-phenyl)methyl, (4-Cl-phenyl)methyl, (3,4-diF-phenyl)methyl, (3-Cl-F-phenyl) methyl, (3-$CF_3$-phenyl)methyl, (2-Cl-4-$CF_3$-phenyl) methyl, (2-Cl-5-$CF_3$-phenyl)methyl, or (3-$OCF_3$-phenyl) methyl)), (optionally substituted $C_3$-$C_{12}$-heterocyclyl)-$C_1$-$C_4$-alkyl (e.g. (pyrid-2-yl)-methyl or (4-$CF_3$-Pyrid-2-yl)methyl), optionally substituted $C_6$-$C_{12}$-aryl (e.g. phenyl, 4-F-phenyl, 3-Cl-phenyl, 3,5-diCl-phenyl, 3-Cl-F-phenyl, 3-Me-phenyl, 3-$CF_3$-phenyl, 4-$CF_3$-phenyl, 2-Cl-3-$CF_3$-phenyl, 3-Cl-4-$CF_3$-phenyl, 3-$CF_3$-4-F-phenyl, 3-CN-phenyl, 3-$OCF_3$-phenyl, 3-$OCF_3$-4-F-phenyl, or 3-$OCF_3$-4-Cl-phenyl), or optionally substituted $C_3$-$C_{12}$-heterocyclyl (e.g. 4-$CF_3$-pyrid-2-yl); and $R^{20b}$ is hydrogen or $C_1$-$C_8$-alkyl (e.g. methyl, ethyl, or n-butyl).

In particular, $R^{20a}$ is $C_1$-$C_8$-alkyl (e.g. n-propyl, n-butyl, hexyl, pentyl, or 6-Me-heptyl), ($C_3$-$C_{12}$-cycloalkyl)-$C_1$-$C_4$-alkyl (e.g. cyclopropyl-methyl), $C_1$-$C_6$-alkoxy-$C_1$-$C_6$-alkyl (e.g. 2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), (optionally substituted $C_6$-$C_{12}$-aryl)-$C_1$-$C_4$-alkyl (e.g. benzyl, (4-F-phenyl)methyl, (3-Cl-phenyl)methyl, (4-Cl-phenyl)methyl, (3,4-diF-phenyl)methyl, (3-Cl-F-phenyl)methyl, (3-$CF_3$-phenyl)methyl, (2-Cl-4-$CF_3$-phenyl)methyl, (2-Cl-5-$CF_3$-phenyl)methyl, or (3-$OCF_3$-phenyl)methyl)), (optionally substituted $C_3$-$C_{12}$-heterocyclyl)-$C_1$-$C_4$-alkyl (e.g. (pyrid-2-yl)-methyl or (4-$CF_3$-pyrid-2-yl)methyl), optionally substituted $C_6$-$C_{12}$-aryl (e.g. phenyl, 4-F-phenyl, 3-Cl-phenyl, 3,5-diCl-phenyl, 3-Cl-F-phenyl, 3-Me-phenyl, 3-$CF_3$-phenyl, 4-$CF_3$-phenyl, 2-Cl-3-$CF_3$-phenyl, 3-Cl-4-$CF_3$-phenyl, 3-$CF_3$-4-F-phenyl, 3-CN-phenyl, 3-$OCF_3$-phenyl, 3-$OCF_3$-4-F-phenyl, or 3-$OCF_3$-4-Cl-phenyl), or optionally substituted $C_3$-$C_{12}$-heterocyclyl (e.g. 4-$CF_3$-pyrid-2-yl).

$R^{2a}$, $R^{2b}$—in the pyrrolidine derivatives of formula (Il)—are, in particular, hydrogen.

$R^{3a}$—in the pyrrolidine derivatives of formula (II)—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl), $C_3$-$C_{12}$-cycloalkyl-$C_1$-$C_4$-alkoxy (e.g. cyclopropylmethoxy or cyclohexyl-methoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenoxy or 4-F- phenoxy), or $C_3$-$C_{12}$-heterocyclyl (e.g. pyrid-2-yl). Preferably, $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl).

$R^{3b}$—in the pyrrolidine derivatives of formula (II)—is, in particular, hydrogen.

Additionally, $R^{3a}$ and $R^{3b}$ together may be, in particular, optionally substituted $C_2$-$C_5$-alkylene (e.g. 1,2-ethylene, 1,3-propylene, 1,4-butylene, or 1,5-pentylene).

$Y^1$—in the pyrrolidine derivatives of formula (II)—is, in particular, >$CR^6$.

$R^6$—in the pyrrolidine derivatives of formula (II)—is, in particular, hydrogen.

$R^{5a}$, $R^{5b}$—in the pyrrolidine derivatives of formula (II)—are, in particular, hydrogen.

Particular embodiments of the pyrrolidine derivatives of formula (II) result if:

$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$ are hydrogen;

$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl);

$R^{3b}$ is hydrogen;

$Y^1$ is >$CR^6$;

$R^6$ is hydrogen;

$R^{20a}$ is $C_1$-$C_8$-alkyl (e.g. n-propyl, n-butyl, hexyl, pentyl, or 6-Me-heptyl), ($C_3$-$C_{12}$-cycloalkyl)$C_1$-$C_4$-alkyl (e.g. cyclopropyl-methyl), $C_1$-$C_6$-alkoxy-$C_1$-$C_6$-alkyl (e.g. 2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), (optionally substituted $C_6$-$C_{12}$-aryl)-$C_1$-$C_4$-alkyl (e.g. benzyl, (4-F-phenyl)methyl, (3-Cl-phenyl)methyl, (4-Cl-phenyl)methyl, (3,4-diF-phenyl)methyl, (3-Cl-F-phenyl)methyl, (3-$CF_3$-phenyl)methyl, (2-Cl-4-$CF_3$-phenyl)methyl, (2-Cl-5-$CF_3$-phenyl)methyl, or (3-$OCF_3$-phenyl)methyl)), (optionally substituted $C_3$-$C_{12}$-heterocyclyl)-$C_1$-$C_4$-alkyl (e.g. (pyrid-2-yl)-methyl or (4-$CF_3$-pyrid-2-yl)methyl), optionally substituted $C_6$-$C_{12}$-aryl (e.g. phenyl, 4-F-phenyl, 3-Cl-phenyl, 3,5-diCl-phenyl, 3-Cl-F-phenyl, 3-Me-phenyl, 3-$CF_3$-phenyl, 4-$CF_3$-phenyl, 2-Cl-3-$CF_3$-phenyl, 3-Cl-4-$CF_3$-phenyl, 3-$CF_3$-4-F-phenyl, 3-CN-phenyl, 3-$OCF_3$-phenyl, 3-$OCF_3$-4-F-phenyl, or 3-$OCF_3$-4-Cl-phenyl), or optionally substituted $C_3$-$C_{12}$-heterocyclyl (e.g. 4-$CF_3$-pyrid-2-yl);

$R^{20b}$ is hydrogen or $C_1$-$C_8$-alkyl (e.g. methyl, ethyl, or n-butyl); and $R^{5a}$, $R^{5b}$ are hydrogen.

Additional particular embodiments of the pyrrolidine derivatives of formula (II) result if $R^{3a}$ and $R^{3b}$ together are optionally substituted $C_2$-$C_5$-alkylene (e.g. 1,2-ethylene, 1,3-propylene, 1,4-butylene, or 1,5-pentylene); and $R^1$, $R^{2a}$, $R^{2b}$, $Y^1$, $R^6$, $R^{20a}$, $R^{20b}$, $R^{5a}$ and $R^{5b}$ are as defined above.

Preferably, $R^1$—in the pyrrolidine derivatives of formula (II)—is an optionally substituted 5-membered heterocyclic ring containing 2 N which, in particular, is optionally substituted 1,3-diazolyl.

According to a further preferred embodiment, $R^1$—in the pyrrolidine derivatives of formula (II)—is an optionally substituted 5-membered heterocyclic ring containing 3 N which, in particular, is optionally substituted 1,2,3-triazolyl.

In connection with $R^1$ and the pyrrolidine derivatives of formula (II), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives of formula (II), substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituent(s) on $C_6$-$C_{12}$-aryl are independently selected from the group consisting of halogen.

According to a preferred embodiment, $R^{3a}$—in the pyrrolidine derivatives of formula (II)—is $C_6$-$C_{12}$-aryl, in particular phenyl, optionally substituted with 1, 2, or 3 substituents independently selected from the group consisting of halogen (e.g. 4-F-phenyl).

According to an additional preferred embodiment, $R^{3a}$ and $R^{3b}$—in the pyrrolidine derivatives of formula (II)—together may be $C_2$-$C_5$-alkylene (e.g. 1,5-pentylene).

In connection with $R^{20a}$, substituted $C_6$-$C_{12}$-aryl-$C_1$-$C_4$-alkyl in particular includes $C_6$-$C_{12}$-aryl-$C_1$-$C_4$-alkyl, such as benzyl, which is substituted with 1, 2, or 3 substituents independently selected from the group consisting of halogen, halogenated $C_1$-$C_4$-alkyl and halogenated $C_1$-$C_4$-alkoxy.

In connection with $R^{20a}$, substituted $C_3$-$C_{12}$-heterocyclyl-$C_1$-$C_4$-alkyl in particular includes $C_3$-$C_{12}$-heterocyclyl-$C_1$-$C_4$-alkyl, such as pyridyl-methyl, which is substituted with 1, 2, or 3 substituents independently selected from the group consisting of halogenated $C_1$-$C_4$-alkyl.

In connection with $R^{20a}$, substituted $C_6$-$C_{12}$-aryl in particular includes $C_6$-$C_{12}$-aryl, such as phenyl, which is substituted with 1, 2, or 3 substituents independently selected from the group consisting of halogen, $C_1$-$C_4$-alkyl, halogenated $C_1$-$C_4$-alkyl, CN and halogenated $C_1$-$C_4$-alkoxy.

In connection with $R^{20a}$, substituted $C_3$-$C_{12}$-heterocyclyl in particular includes $C_3$-$C_{12}$-heterocyclyl, such as pyridyl, which is substituted with 1, 2, or 3 substituents independently selected from the group consisting of halogenated $C_1$-$C_4$-alkyl.

According to a preferred embodiment, $R^{20a}$ is $C_1$-$C_8$-alkyl (e.g. n-propyl, n-butyl, hexyl, pentyl, or 6-Me-heptyl), $C_3$-$C_{12}$-cycloalkyl-$C_1$-$C_4$-alkyl (e.g. cyclopropyl-methyl), $C_1$-$C_6$-alkoxy-$C_1$-$C_6$-alkyl (e.g. 2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), $C_6$-$C_{12}$-aryl-$C_1$-$C_4$-alkyl wherein $C_6$-$C_{12}$-aryl is optionally substituted with 1, 2, or 3 substituents independently selected from the group consisting of halogen, halogenated $C_1$-$C_4$-alkyl and halogenated $C_1$-$C_4$-alkoxy (e.g. benzyl, (4-F-phenyl)methyl, (3-Cl-phenyl)methyl, (4-Cl-phenyl)methyl, (3,4-diF-phenyl)methyl, (3-Cl-4-F-phenyl)methyl, (3-CF$_3$-phenyl)methyl, (2-Cl-4-CF$_3$-phenyl)methyl, (2-Cl-5-CF$_3$-phenyl)methyl, or (3-OCF$_3$-phenyl)methyl)), or $C_3$-$C_{12}$-heterocyclyl-$C_1$-$C_4$-alkyl wherein $C_3$-$C_{12}$-heterocyclyl is optionally substituted with 1, 2, or 3 substituents independently selected from the group consisting of halogenated $C_1$-$C_4$-alkyl (e.g. (pyrid-2-yl)-methyl or (4-CF$_3$-pyrid-2-yl)methyl), or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, CN and halogenated $C_1$-$C_4$-alkoxy (e.g. phenyl, 4-F-phenyl, 3-Cl-phenyl, 3,5-diCl-phenyl, 3-Cl-F-phenyl, 3-Me-phenyl, 3-CF$_3$-phenyl, 4-CF$_3$-phenyl, 2-Cl-3-CF$_3$-phenyl, 3-Cl-4-CF$_3$-phenyl, 3-CF$_3$-4-F-phenyl, 3-CN-phenyl, 3-OCF$_3$-phenyl, 3-OCF$_3$-4-F-phenyl, or 3-OCF$_3$-4-Cl-phenyl), or $C_3$-$C_{12}$-heterocyclyl optionally substituted with 1, 2, or 3 substituents independently selected from the group consisting of halogenated $C_1$-$C_4$-alkyl (e.g. 4-CF$_3$-pyrid-2-yl).

Further preferred embodiments of the pyrrolidine derivatives of formula (Il) result if:
$R^1$ is 1,3-diazolyl optionally substituted with halogen or $C_1$-$C_4$-alkyl (e.g. 1-methyl-1,3-diazol-4-yl);
$R^{2a}$, $R^{2b}$ are hydrogen;
$R^{3a}$ is $C_6$-$C_{12}$-aryl optionally substituted with 1, 2, or 3 substituents independently selected from the group consisting of halogen (e.g. 4-F-phenyl);
$R^{3b}$ is hydrogen;
$Y^1$ is >CR$^6$;
$R^6$ is hydrogen;
$R^{20a}$ is $C_1$-$C_8$-alkyl (e.g. n-propyl, n-butyl, hexyl, pentyl, or 6-Me-heptyl), $C_3$-$C_{12}$-cycloalkyl-$C_1$-$C_4$-alkyl (e.g. cyclopropyl-methyl), $C_1$-$C_6$-alkoxy-$C_1$-$C_6$-alkyl (e.g. 2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), $C_6$-$C_{12}$-aryl-$C_1$-$C_4$-alkyl wherein $C_6$-$C_{12}$-aryl is optionally substituted with 1, 2, or 3 substituents independently selected from the group consisting of halogen, halogenated $C_1$-$C_4$-alkyl and halogenated $C_1$-$C_4$-alkoxy (e.g. benzyl, (4-F-phenyl)methyl, (3-Cl-phenyl)methyl, (4-Cl-phenyl)methyl, (3,4-diF-phenyl)methyl, (3-Cl-F-phenyl)methyl, (3-CF$_3$-phenyl)methyl, (2-Cl-4-CF$_3$-phenyl)methyl, (2-Cl-5-CF$_3$-phenyl)methyl, or (3-OCF$_3$-phenyl)methyl)), or $C_3$-$C_{12}$-heterocyclyl-$C_1$-$C_4$-alkyl wherein $C_3$-$C_{12}$-heterocyclyl is optionally substituted with 1, 2, or 3 substituents independently selected from the group consisting of halogenated $C_1$-$C_4$-alkyl (e.g. (pyrid-2-yl)-methyl or (4-CF$_3$-pyrid-2-yl)methyl), or $C_6$-$C_{12}$-aryl optionally substituted with 1, 2, or 3 substituents independently selected from the group consisting of halogen, $C_1$-$C_4$-alkyl, halogenated $C_1$-$C_4$-alkyl, CN and halogenated $C_1$-$C_4$-alkoxy (e.g. phenyl, 4-F-phenyl, 3-Cl-phenyl, 3,5-diCl-phenyl, 3-Cl-F-phenyl, 3-Me-phenyl, 3-CF$_3$-phenyl, 4-CF$_3$-phenyl, 2-Cl-3-CF$_3$-phenyl, 3-Cl-4-CF$_3$-phenyl, 3-CF$_3$-4-F-phenyl, 3-CN-phenyl, 3-OCF$_3$-phenyl, 3-OCF$_3$-4-F-phenyl, or 3-OCF$_3$-4-Cl-phenyl), or $C_3$-$C_{12}$-heterocyclyl optionally substituted with 1, 2, or 3 substituents independently selected from the group consisting of halogenated $C_1$-$C_4$-alkyl (e.g. 4-CF$_3$-pyrid-2-yl);
$R^{20b}$ is hydrogen or $C_1$-$C_8$-alkyl (e.g. n-butyl); and
$R^{5a}$, $R^{5b}$ are hydrogen.

Additional preferred embodiments of the pyrrolidine derivatives of formula (Il) result if
$R^{3a}$ and $R^{3b}$
together are $C_2$-$C_5$-alkylene (e.g. 1,5-pentylene); and
$R^1$, $R^{2a}$, $R^{2b}$, $Y^1$, $R^6$, $R^{20a}$, $R^{20b}$, $R^{5a}$ and $R^{5b}$ are as defined above.

According to a further embodiment, $R^4$ is —SO$_2$R$^{21}$. Thus, the present invention relates to the pyrrolidine derivatives of the formula (Im):

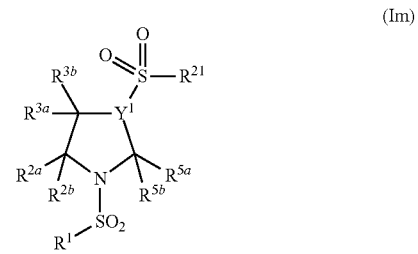

(Im)

wherein $R^1$, $R^{2a}$, $R^{2b}$, $R^{2a}$, $R^{3b}$, $Y^1$, $R^{5a}$ and $R^{5b}$ are as defined herein, and
$R^{21}$ is optionally substituted $C_6$-$C_{12}$-aryl (e.g. phenyl, 2-Cl-phenyl, or 4-Me-phenyl), or optionally substituted $C_3$-$C_{12}$-heterocyclyl (e.g. 2-pyridyl).

In particular, $R^{21}$ is $C_6$-$C_{12}$-aryl (e.g. phenyl).

$R^{2a}$, $R^{2b}$—in the pyrrolidine derivatives of formula (Im)—are, in particular, hydrogen.

$R^{3a}$—in the pyrrolidine derivatives of formula (Im)—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenoxy or 4-F-phenoxy), or $C_3$-$C_{12}$-heterocyclyl (e.g. pyrid-2-yl). Preferably, $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl).

$R^{3b}$—in the pyrrolidine derivatives of formula (Im)—is, in particular, hydrogen.

$Y^1$—in the pyrrolidine derivatives of formula (Im)—is, in particular, >CR$^6$.

$R^6$—in the pyrrolidine derivatives of formula (Im)—is, in particular, hydrogen.

$R^{5a}$, $R^{5b}$—in the pyrrolidine derivatives of formula (Im)—are, in particular, hydrogen.

Particular embodiments of the pyrrolidine derivatives of formula (Im) result if:

$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$ are hydrogen;

$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl);

$R^{ab}$ is hydrogen;

$Y^1$ is >$CR^6$;

$R^6$ is hydrogen;

$R^{5a}$, $R^{5b}$ are hydrogen; and $R^{21}$ is $C_6$-$C_{12}$-aryl (e.g. phenyl).

Preferably, $R^1$—in the pyrrolidine derivatives of formula (Im)—is an optionally substituted 5-membered heterocyclic ring containing 2 N which, in particular, is optionally substituted 1,3-diazolyl.

According to a further preferred embodiment, $R^1$—in the pyrrolidine derivatives of formula (Im)—is an optionally substituted 5-membered heterocyclic ring containing 3 N which, in particular, is optionally substituted 1,2,3-triazolyl.

In connection with $R^1$ and the pyrrolidine derivatives of formula (Im), substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

According to a preferred embodiment, $R^{3a}$—in the pyrrolidine derivatives of formula (Im)—is $C_6$-$C_{12}$-aryl (e.g. phenyl).

Further preferred embodiments of the pyrrolidine derivatives of formula (Im) result if:

$R^1$ is 1,3-diazolyl optionally substituted with halogen or $C_1$-$C_4$-alkyl (e.g. 1-methyl-1,3-diazol-4-yl);

$R^{2a}$, $R^{2b}$ are hydrogen;

$R^{3a}$ is $C_6$-$C_{12}$-aryl (e.g. phenyl);

$R^{3b}$ is hydrogen;

$Y^1$ is >$CR^6$;

$R^6$ is hydrogen;

$R^{21}$ is $C_6$-$C_{12}$-aryl (e.g. phenyl); and $R^{5a}$, $R^{5b}$ are hydrogen.

According to a further embodiment $R^4$ is optionally substituted $C_3$-$C_{12}$-heterocyclyl (e.g. 4-chloroisoindolin-1-one; 7-(trifluoromethyl)-3,4-dihydro-1H-quinazolin-2-on-1-yl, 4-butyl-1,2,3-triazol-1-yl, 1-propyl-1,2,3-triazol-4-yl, 5-(4-$CF_3$-phenyl)-4,5-dihydroisooxazol-3-yl, 5-(4-$CF_3$-phenyl)-oxazol-2-yl, or 5-(3-Cl-phenyl)-imidazol-2-yl, a further example being 5-butyloxazolidin-2-on-3-yl, 1,4-thiazinan-1,1-dioxide-4-yl, indolinyl, indolin-2-on-1-yl, 6-$CF_3$-indolin-2-on-1-yl, isoindolinyl, or isoindolin-1-on-2-yl).

$R^{3a}$—in the pyrrolidine derivatives wherein $R^4$ is optionally substituted $C_3$-$C_{12}$-heterocyclyl—is, in particular, $C_3$-$C_{12}$-cycloalkyl (e.g. cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl), $C_3$-$C_{12}$-cycloalkyl-$C_1$-$C_4$-alkoxy (e.g. cyclopropylmethoxy or cyclohexylmethoxy), $C_2$-$C_6$-alkenyloxy (e.g. allyloxy or 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenoxy or 4-F-phenoxy), or $C_3$-$C_{12}$-heterocyclyl (e.g. pyrid-2-yl). Preferably, $R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl) or $C_3$-$C_{12}$-heterocyclyl (e.g. pyrid-2-yl).

$R^{3b}$—in the pyrrolidine derivatives wherein $R^4$ is optionally substituted $C_3$-$C_{12}$-heterocyclyl—is, in particular, hydrogen.

$Y^1$—in the pyrrolidine derivatives wherein $R^4$ is optionally substituted $C_3$-$C_{12}$-heterocyclyl—is, in particular, >$CR^6$.

$R^6$—in the pyrrolidine derivatives wherein $R^4$ is optionally substituted $C_3$-$C_{12}$-heterocyclyl—is, in particular, hydrogen.

$R^{5a}$, $R^{5b}$—in the pyrrolidine derivatives wherein $R^4$ is optionally substituted $C_3$-$C_{12}$-heterocyclyl—are, in particular, hydrogen.

Particular embodiments of the pyrrolidine derivatives of the invention result if:

$R^1$ is an optionally substituted 5-membered heterocyclic ring containing at least 1 N ring atom and optionally 1 or 2 further heteroatoms selected from N, O and S (e.g. 1-methyl-2-methoxycarbonyl-pyrrol-5-yl, 1-methyl-pyrrol-3-yl, 5-methyl-1,2-oxazol-4-yl, 3,5-dimethyl-1,2-oxazol-4-yl, 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-5-yl, 1,3-dimethyl-5-Cl-1,2-diazol-4-yl, 1-isopropyl-3-methyl-1,2-diazol-4-yl, 1-Me-3-$CF_3$-1,2-diazol-4-yl, 1-cyclopentyl-3-Me-1,2-diazol-4-yl, 1,3,5-trimethyl-1,2-diazol-4-yl, 1-$CHF_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 2,4-dimethyl-1,3-thiazol-5-yl, or 2-methylcarbonylamino-1,3-thiazol-5-yl, a further example being 1-ethyl-1,3-diazol-4-yl or 1-methyl-1,2,4-triazol-3-yl);

$R^{2a}$, $R^{2b}$
are hydrogen;
$R^{3a}$ is optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl) or $C_3$-$C_{12}$-heterocyclyl (e.g. pyrid-2-yl);
$R^{3b}$ is hydrogen;
$R^4$ is optionally substituted $C_3$-$C_{12}$-heterocyclyl (e.g. 4-chloroisoindolin-1-one; 7-(trifluoromethyl)-3,4-dihydro-1H-quinazolin-2-on-1-yl, 4-butyl-1,2,3-triazol-1-yl, 1-propyl-1,2,3-triazol-4-yl, 5-(4-$CF_3$-phenyl)-4,5-dihydroisooxazol-3-yl, 5-(4-$CF_3$-phenyl)-oxazol-2-yl, or 5-(3-Cl-phenyl)-imidazol-2-yl, a further example being 5-butyl-oxazolidin-2-on-3-yl, 1,4-thiazinane-1,1-dioxide, indolinyl, indolin-2-on-1-yl, 6-$CF_3$-indolin-2-on-1-yl, isoindolinyl, or isoindolin-1-on-2-yl);
$Y^1$ is >$CR^6$;
$R^6$ is hydrogen; and
$R^{5a}$, $R^{5b}$
are hydrogen.

Preferably, $R^1$—in the pyrrolidine derivatives wherein $R^4$ is optionally substituted $C_3$-$C_{12}$-heterocyclyl—is an optionally substituted 5-membered heterocyclic ring containing 2 N which, in particular, is optionally substituted 1,3-diazolyl.

According to a further preferred embodiment, $R^1$—in the pyrrolidine derivatives wherein $R^4$ is optionally substituted $C_3$-$C_{12}$-heterocyclyl—is an optionally substituted 5-membered heterocyclic ring containing 3 N which, in particular, is optionally substituted 1,2,3-triazolyl.

In connection with $R^1$ and the pyrrolidine derivatives wherein $R^4$ is optionally substituted $C_3$-$C_{12}$-heterocyclyl, substituted 5-membered heterocyclic ring containing at least 1 N ring atom and optionally 1 or 2 further heteroatoms selected from N, O and S in particular includes 5-membered heterocyclic rings, such as pyrrolyl, isoxazolyl, pyrazolyl, imidazolyl, thiazolyl and triazolyl, which are substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxy-carbonyl and $C_1$-$C_6$-alkyl-carbonylamino. Preferably, the substituent(s) on the heterocyclic ring are independently selected from the group consisting of halogen and $C_1$-$C_6$-alkyl. In particular, the substituent(s) on the heterocyclic ring are independently selected from the group consisting of $C_1$-$C_6$-alkyl, especially $C_1$-$C_4$-alkyl (e.g. methyl). According to a particular embodiment, 1,3-diazolyl is substituted with halogen or $C_1$-$C_6$-alkyl as described herein. According to a specific embodiment, $R^1$ is 1-methyl-1,3-diazol-4-yl.

In connection with $R^{3a}$ and the pyrrolidine derivatives wherein $R^4$ is optionally substituted $C_3$-$C_{12}$-heterocyclyl, substituted $C_6$-$C_{12}$-aryl in particular includes $C_6$-$C_{12}$-aryl, such as phenyl or naphthyl, which is substituted with 1, 2, or 3 substituents independently selected from the group consisting of halogen, $C_1$-$C_4$-alkyl and $C_1$-$C_4$-alkoxy. Preferably, the substituent(s) on $C_6$-$C_{12}$-aryl are independently selected from the group consisting of halogen.

In connection with $R^{3a}$ and the pyrrolidine derivatives wherein $R^4$ is optionally substituted $C_3$-$C_{12}$-heterocyclyl, substituted $C_3$-$C_{12}$-heterocyclyl in particular includes $C_3$-$C_{12}$-heterocyclyl, such as pyridyl, which is substituted with 1, 2, or 3 substituents independently selected from the group consisting of halogen, $C_1$-$C_4$-alkyl and halogenated $C_1$-$C_4$-alkyl.

According to a preferred embodiment, $R^{3a}$—in the pyrrolidine derivatives wherein $R^4$ is optionally substituted $C_3$-$C_{12}$-heterocyclyl—is $C_6$-$C_{12}$-aryl, in particular phenyl, optionally substituted with 1, 2, or 3 substituents independently selected from the group consisting of halogen (e.g. phenyl, 4-F-phenyl), or $C_3$-$C_{12}$-heterocyclyl (e.g. pyrid-2-yl).

In connection with $R^4$, substituted $C_3$-$C_{12}$-heterocyclyl in particular includes $C_3$-$C_{12}$-heterocyclyl, such as triazolyl or isoindolinonyl, and additionally such as oxazodinonyl, isoindolinyl, indolinyl, indolinoyl, or thiazinanyl-1,1-dioxide, which is substituted with 1, 2, or 3 substituents independently selected from the group consisting of halogen, $C_1$-$C_4$-alkyl and halogenated $C_1$-$C_4$-alkyl.

According to a preferred embodiment, $R^4$—in the pyrrolidine derivatives wherein $R^4$ is optionally substituted $C_3$-$C_{12}$-heterocyclyl—is $C_3$-$C_{12}$-heterocyclyl substituted with 1, 2, or 3 substituents independently selected from the group consisting of halogen, $C_1$-$C_6$-alkyl and halogenated $C_1$-$C_4$-alkyl (e.g. 4-chloroisoindolin-1-onyl, 7-(trifluoromethyl)-3,4-dihydro-1H-quinazolin-2-on-1-yl, 4-butyl-1,2,3-triazol-1-yl, or 1-propyl-1,2,3-triazol-4-yl, a further example being 5-butyl-oxazolidin-2-on-3-yl, 1,4-thiazinane-1,1-dioxide, indolinyl, indolin-2-on-1-yl, 6-$CF_3$-indolin-2-on-1-yl, isoindolinyl, or isoindolin-1-on-2-yl).

Further preferred embodiments of the pyrrolidine derivatives wherein $R^4$ is optionally substituted $C_3$-$C_{12}$-heterocyclyl result if:
$R^1$ is 1,3-diazolyl optionally substituted with halogen or $C_1$-$C_4$-alkyl (e.g. 1-methyl-1,3-diazol-4-yl);
$R^{2a}$, $R^{2b}$
are hydrogen;
$R^{3a}$ is $C_6$-$C_{12}$-aryl optionally substituted with 1, 2, or 3 substituents independently selected from the group consisting of halogen, or $C_3$-$C_{12}$-heterocyclyl (e.g. pyrid-2-yl);
$R^{3b}$ is hydrogen;
$R^4$ is $C_3$-$C_{12}$-heterocyclyl substituted with 1, 2, or 3 substituents independently selected from the group consisting of halogen, $C_1$-$C_6$-alkyl and halogenated $C_1$-$C_4$-alkyl (e.g. 4-chloroisoindolin-1-one; 7-(trifluoromethyl)-3,4-dihydro-1H-quinazolin-2-on-1-yl, 4-butyl-1,2,3-triazol-1-yl, 1-propyl-1,2,3-triazol-4-yl, 5-(4-$CF_3$-phenyl)-4,5-dihydroisooxazol-3-yl, 5-(4-$CF_3$-phenyl)-oxazol-2-yl, or 5-(3-Cl-phenyl)-imidazol-2-yl, a further example being 5-butyl-oxazolidin-2-on-3-yl, 1,4-thiazinane-1,1-dioxide, indolinyl, indolin-2-on-1-yl, 6-$CF_3$-indolin-2-on-1-yl, isoindolinyl, or isoindolin-1-on-2-yl);
$Y^1$ is >$CR^6$;
$R^6$ is hydrogen; and
$R^{5a}$, $R^{5b}$
are hydrogen.

Particular embodiments of pyrrolidine derivatives of the invention result if
$R^1$ is optionally substituted 5-membered heterocyclic ring containing at least 1 N ring atom and optionally 1 or 2 further heteroatoms selected from N, O and S (e.g. 1-methyl-1,3-diazol-4-yl or 1-methyl-1,2,3-triazol-4-yl);
$R^{2a}$, $R^{2b}$
are hydrogen;
$R^{3a}$ is $C_3$-$C_{12}$-cycloalkyl (cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl), hydroxy, $C_1$-$C_6$-alkoxy (e.g. methoxy, ethoxy, n-propyloxy, iso-propyxy, or iso-butoxy), $C_3$-$C_{12}$-cycloalkyl-$C_1$-$C_4$-alkoxy (cyclopropylmethoxy, cyclohexylmethoxy), $C_2$-$C_6$-alkenyloxy (e.g. allyloxy, 2-methylprop-2-en-1-oxy), $C_6$-$C_{12}$-aryl-$C_1$-$C_4$-alkoxy (e.g. benzyloxy), optionally substituted $C_6$-$C_{12}$-aryloxy (e.g. phenoxy, 4-F-phenoxy), or optionally substituted $C_3$-$C_{12}$-heterocyclyl (tetrahydrofuran-2-yl, tetrahydrofuran-3-yl, tetrahydropyran-2-yl, tetrahydropyran-3-yl, 1-cyclopropyl-piperidin-4-yl, 1-cyclopropyl-piperidin-3-yl, 2-pyridyl, 3-pyridyl, 3-F-pyrid-2-yl, 1,3-oxazol-4-yl, 1,3-oxazol-2-yl, 3-F-azetidin-1-yl, morpholin-4-yl, pyrrolidin-1-yl, piperidin-1-yl, 2-Me-piperidin-1yl, 3-Me-piperidin-1yl, 4-Me-piperidin-1yl, 4-F-piperidin-1-yl, 4,4-diF-piperidin-1yl, or azepan-1-yl, a further example being 1,3-dioxan-2-yl, 5,5-dimethyl-1,3-dioxan-2-yl, 4,6-dimethyl-1,3-dioxan-2-yl, 1,3-dioxepan-2-yl, 1,3-dioxolan-2-yl, 5,7-dioxaspiro[2.5]octan-6-yl, morpholin-3-yl, 1-Me-piperidin-2-yl, or 5-F-pyrid-2-yl); or $R^{3a}$ and one of $R^{2a}$ or $R^{2b}$
together with the carbon atoms to which they are bound may form an anellated $C_6$-$C_{12}$-aryl (e.g. phenyl);
$R^{3b}$ is hydrogen or hydroxy, or
$R^{3a}$ and $R^{3b}$
together are $C_2$-$C_5$-alkylene (e.g. 1,5-pentylene);
$Y^1$ is >$CR^6$— or >N—;
$R^6$ is hydrogen, $C_1$-$C_6$-alkyl (e.g. methyl or ethyl), $C_6$-$C_{12}$-aryl-$C_1$-$C_4$-alkyl (e.g. benzyl or phenethyl), hydroxy-$C_1$-$C_6$-alkyl (e.g. —$CH_2OH$, or —$(CH_2)_2OH$), or hydroxy, or
$R^6$ and $R^{3a}$ or $R^{3b}$
together are $C_1$-$C_5$-alkylene (e.g. 1,4-butylene), or
$R^6$
is $C_1$-$C_4$-alkylene (e.g. methylene or 1,2-ethylene) that is bound to a carbon atom in $R^{3a}$, and $R^{3a}$ is an optionally substituted $C_6$-$C_{12}$-aryl (e.g. phenyl);
$R^4$ is —$(CR^{7a}R^{7b})_{n1}OR^{10}$, —$(CR^{7c}R^{7d})_{n2}NR^{11a}R^{11b}$, —$(CR^{7e}R^{7f})_{n3}R^{12}$, optionally substituted $C_6$-$C_{12}$-aryl, —$NR^{8a}(CR^{9a}R^{9b})_{n4}R^{13}$, —$NR^{8b}COR^{14}$, —$NR^{8c}COOR^{15}$, —$NR^{8d}CONR^{16a}R^{16b}$, —$O(CR^{9c}R^{9d})_{n5}R^{18}$, —$COR^{19}$, —$CONR^{20a}R^{20b}$, —$SO_2R^{21}$, or optionally substituted $C_3$-$C_{12}$-heterocyclyl (e.g. 1-propyl-1,2,3-triazol-4-yl, 4-butyl-1,2,3-triazolyl-1-yl, 4-chloroisoindolin-1-one, or 7-(trifluoromethyl)-3,4-dihydro-1H-quinazolin-2-on-1-yl, a further example being 5-butyl-oxazolidin-2-on-3-yl, 1,4-thiazinane-1,1-dioxide, indolinyl, indolin-2-on-1-yl, 6-$CF_3$-indolin-2-on-1-yl, isoindolinyl, or isoindolin-1-on-2-yl);
$R^{7a}$, $R^{7b}$
are hydrogen, or
n1 is 1;
$R^{10}$ is hydrogen, optionally substituted $C_6$-$C_{12}$-aryl (e.g. phenyl, 3-F-phenyl, 3-Me-phenyl, 3-$CF_3$-phenyl, 2-Cl-3-$CF_3$-phenyl, or 3-$OCF_3$-phenyl, a further example being 2-F-phenyl, 4-F-phenyl, 2-Cl-phenyl, 2,3-diF-phenyl, 2,4-diF-phenyl, 2,5-diF-phenyl, 4-Cl-phenyl, 2-Cl-4-F-phenyl, 4-Cl-3-F-phenyl, 2-Me-phenyl, 4-Me-phenyl, 2-$CF_3$-phenyl, 4-$CF_3$-phenyl, 2-Cl-4-$CF_3$-phenyl, 3-$OCHF_2$-phenyl, 2-$OCF_3$-phenyl, 4-$OCF_3$-phenyl, 3-OMe-phenyl, 2-OEt-phenyl, 2-cyclopentyl-phenyl, 2-cyclohexyl-phenyl, 3-ethynyl-phenyl, 2-CN-phenyl, 4-CN-phenyl, 2-F-4-CN-phenyl, 3-dimethylamino-phenyl, 4-(morpholin-4-yl)-phenyl, 2-pirrolidinyl-phenyl, 2-piperidin-phenyl, indan-5-yl, naphthyl, or tetralin-5-yl), or optionally substituted $C_3$-$C_{12}$-heterocyclyl (e.g. 6-$CF_3$-pyrimid-4-yl, 4-$CF_3$-pyrid-2-yl, or 2-$CF_3$-pyrid-4-yl, a further example being pyrid-2-yl, pyrid-3-yl, pyrid-4-yl, pyrazin-2-yl, pyridazin-3-yl, quinolin-6-yl, isoquinolin-5-yl, 1,2-bezoxazol-6-yl, or 2-Me-1,3-benzoxazol-5-yl);

$R^{7c}$, $R^{7d}$
are hydrogen, or
n2 is 1;
$R^{11a}$ is $C_1$-$C_8$-alkyl (e.g. methyl, ethyl, n-propyl, n-butyl, or n-heptyl), $C_3$-$C_{12}$-cycloalkyl-$C_1$-$C_4$-alkyl (e.g. cyclopropyl-methyl) $C_1$-$C_6$-alkoxy-$C_1$-$C_6$-alkyl (2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), $C_6$-$C_{12}$-aryl-$C_1$-$C_4$-alkyl (e.g. benzyl), optionally substituted $C_6$-$C_{12}$-aryl (e.g. phenyl, 4-F-phenyl, 3-Cl-phenyl, 3,5-diCl-phenyl, 3-Cl-F-phenyl, 3-Me-phenyl, 3-(aminomethyl)-phenyl, 3-$CF_3$-phenyl, 4-$CF_3$-phenyl, 2-Cl-4-$CF_3$-phenyl, 3-Cl-4-$CF_3$-phenyl, 3-$CF_3$-4-F-phenyl, 3-$OCF_3$-phenyl, 3-$OCF_3$-4-F-phenyl, 3-$OCF_3$-4-Cl-phenyl, or 3-(aminocarbonyl)-phenyl);
$R^{11b}$ is hydrogen;
$R^{7e}$, $R^{7f}$
are hydrogen, or
n3 is 1;
$R^{12}$ is optionally substituted $C_6$-$C_{12}$-aryl (e.g. phenyl, 3-Cl-phenyl, or 3-Br-phenyl, a further example being 3-$CF_3$-phenyl) or optionally substituted $C_3$-$C_{12}$-heterocyclyl (e.g. 4-$CF_3$-pyrid-2-yl or 1-propyl-1,2,3-triazol-4-yl);
$R^{8a}$, $R^{8b}$, $R^{8c}$, $R^{8d}$, $R^{8e}$
are independently hydrogen or $C_1$-$C_6$-alkyl (e.g. pentyl or hexyl), or
$R^6$ and one of $R^{8a}$, $R^{8b}$, $R^{8c}$, $R^{8d}$, or $R^{8e}$
together are optionally substituted $C_1$-$C_5$-alkylene, wherein one or more —$CH_2$— of $C_1$-$C_5$-alkylene may be independently replaced by a an oxygen atom or C=O, or
$R^{3a}$ and one of $R^{8a}$ or $R^{8b}$
together are $C_1$-$C_5$-alkylene (e.g. 1,3-propylene);
$R^{9a}$, $R^{9b}$
are independently hydrogen, halogen, $C_1$-$C_6$-alkyl (e.g. methyl, ethyl, tert-butyl, 2,3-dimethyl-propyl), halogenated $C_1$-$C_6$-alkyl (e.g. trifluoro methyl), or $C_1$-$C_6$-alkoxy (e.g. methoxy or ethoxy);
n4 is 0, 1, 2, 3, or 4;
$R^{13}$ is hydrogen, $C_1$-$C_8$-alkyl (e.g. methyl, ethyl, n-butyl, tert-butyl, pentyl, or hexyl), halogenated $C_1$-$C_6$-alkyl (e.g. —$CF_3$ or —$CF_2Me$), $C_1$-$C_6$-alkoxy-$C_1$-$C_6$-alkyl (e.g. methoxy-methyl), optionally substituted $C_3$-$C_{12}$-cycloalkyl (e.g. cyclopropyl, 2-propyl-cyclopropyl, 1-(methoxy-methyl)-cyclopropyl, 2-phenyl-cyclopropyl, cyclopentyl, 1-methyl-cyclohexyl, 1-$CF_3$-cyclopropyl, 4-$CF_3$-cyclohexyl, or 4,4-diF-cyclohexyl, a further example being 1-phenylcyclopropyl, 1-(4-F-phenyl)-cyclopropyl, (3-Cl-phenyl)-cyclopropyl, 2-phenyl-cyclobutyl, 3-phenyl-cyclobutyl, 3-(4-F-phenyl)-cyclobutyl, 3-(2-F-phenyl)-cyclobutyl, 2-Cl-cyclopentyl, 2-Me-cyclopentyl, 3-Me-cyclopentyl, 2-phenyl-cyclopentyl, 3-(2-pyridyl)-cyclopentyl, 3-Me-cyclohexyl, 3,3,5,5-tetraMe-cyclohexyl, 4-Me-cyclohexyl, 4-Et-cyclohexyl, 2-$CF_3$-cyclohexyl, 2-Me-5-isopropenyl-cyclohexyl, 2-phenyl-cyclohexyl, 3-phenyl-cyclohexyl, 4-phenyl-cyclohexyl, 2-EtO-cyclohexyl, decalin-1-yl, decalin-2-yl, norbornan-2-yl, 1,7,7-trimethyl-norbornan-2-yl, 5-iPr-2-Me-3-bicyclo[3.1.0]hexanyl, bicyclo[3.2.1]octanyl, or 3-bicyclo[1.1.1]pentanyl), $C_2$-$C_6$-alkenyl (e.g. hex-2-enyl), optionally substituted $C_3$-$C_6$-cycloalkenyl (e.g. 1,3,3-trimethylcyclohexen-2-yl), optionally substituted $C_6$-$C_{12}$-aryl (e.g. phenyl, 2-F-phenyl, 4-F-phenyl, 3-F-phenyl, 2-Cl-phenyl, 3-Cl-phenyl, 4-Cl-phenyl, 2,3-diF-phenyl, 2,4-diF-phenyl, 2,5-diF-phenyl, 3,4-diF-phenyl, 2,3,4-triF-phenyl, 2,4-diCl-phenyl, 3,4-diCl-phenyl, 3-F-4-Cl-phenyl, 3-Cl-F-phenyl, 3-Cl-5-F-phenyl, 3,4-diF-5-Clphenyl, 2-Me-phenyl, 3-Me-phenyl, 4-Me-phenyl, 3-iPr-phenyl, 3-tBu-phenyl, 3-Me-4-F-phenyl, 3-Me-4-Cl-phenyl, 3-iPr-4Cl-phenyl, 3-(1-OH-1-CF$_3$-Et)-phenyl, 3-CHF$_2$-4-F-phenyl, 2-CF$_3$-phenyl, 3-CF$_3$-phenyl, 4-CF$_3$-phenyl, 3-Cl-4-CF$_3$-phenyl, 2-F-3-CF$_3$-phenyl, 2-F-5-CF$_3$-phenyl, 3-F-5-CF$_3$-phenyl, 2-Cl-4-CF$_3$-phenyl, 2-Cl-3-CF$_3$-phenyl, 3-CF$_3$-4-F-phenyl, 3-CF$_3$-4-Cl-phenyl, 3-Me-4-CF$_3$-phenyl, 3-CF$_3$-4-Me-phenyl, 3,4-diCF$_3$-phenyl, 4-OMe-phenyl, 3-OiPr-phenyl, 3-CF$_3$-4-OMe-phenyl, 3-OCH$_2$CF$_3$-phenyl, 3-OCF$_3$-phenyl, 2-OCHF$_2$-5-Cl-phenyl, 3-OCF$_3$-4-F-phenyl, 3-OCF$_3$-4-Cl-phenyl, 3-OBn-phenyl, 3-OPh-phenyl, 3-CN-phenyl, 4-CN-phenyl, 2-F-3-CN-phenyl, 2-F-4-CN-phenyl, 3-F-4-CN-phenyl, 2-F-5-CN-phenyl, 3-F-5-CN-phenyl, 3-Cl-4-CN-phenyl, 2-Cl-5-CN-phenyl, 3-Cl-5-CN-phenyl, 3-CN-4-Cl-phenyl, 2-Me-3-CN-phenyl, 2-Me-5-CN-phenyl, 3-Me-5-CN-phenyl, 3-CF$_3$-4-CN-phenyl, 3-CN-4-OMe-phenyl, 3-CN-4-OCF$_3$-phenyl, 3-phenyl-phenyl, 3-MeSO$_2$-phenyl, 3-(piperidin-4-yl)-phenyl, 2-methylcarbonylamino-5-Cl-phenyl, 3-(pyrid-2-yl)-phenyl, 3-(pyrid-3-yl)-4F-phenyl, 3-(pyrid-4-yl)-4F-phenyl, 3-(pyrimid-5-yl)-4F-phenyl, indan-5-yl, or tetralin-6-yl, a further example being 2,4-diF-3-Cl-phenyl, 3-Et-4-Cl-phenyl, 3-(2-methoxyethyl)-phenyl, 3-(2-OH-ethyl)-phenyl, 3-(1-OH-1-Me-ethyl)-phenyl, 3-CHF$_2$-phenyl, 3-CF$_3$-2,4-diF-phenyl, 3-(dimethylamino-methyl)-phenyl, 3-(morpholin-4-ylmethyl)-phenyl, 3-cyclopropyl-phenyl, 3-OEt-phenyl, 3-PPr-phenyl, 3-OtBu-phenyl, 3-(cyclopropylmethoxy)-phenyl, 3-(OMe-methoxy)-phenyl, 3-(2-dimethylamino-ethoxy)-phenyl, 3-CF$_3$-4-OH-phenyl, 3-OCH$_2$CHF$_2$-phenyl, 3-OCHF$_2$-phenyl, 3-OCHF$_2$-4-F-phenyl, 3-OCF$_3$-4-OMe-phenyl, 3-cyclopropoxy-phenyl, 3-methylcarbonyl-phenyl, 3-dimethylamino-phenyl, 3-(2-pyridyloxy)-phenyl, 3-(pyrimidin-2-yloxy)-phenyl, indanyl, indan-2-yl, 2-F-indanyl, 4-F-indanyl, 5-F-indanyl, 6-F-indanyl, 7-F-indanyl, 3-Me-indanyl, 4-Me-indanyl, 5-Me-indanyl, 6-Me-indanyl, 4-CF$_3$-indanyl, 5-CF$_3$-indanyl, 6-CF$_3$-indanyl, 3,3-dimethyl-indanyl, tetralin-2-yl, 7-F-tetralin-2-yl, 6-F-tetralin-2-yl, tetralinyl, 6-F-tetralinyl, 5-F-tetralinyl, or 7-F-tetralinyl), C$_1$-C$_6$-alkoxy (e.g. methoxy, ethoxy, or n-propoxy), C$_1$-C$_6$-alkoxy-C$_1$-C$_4$-alkoxy (e.g. 2-methoxy-ethoxy), optionally substituted C$_6$-C$_{12}$-aryloxy (e.g. 4-F-phenoxy or 4-tertbutyl-phenoxy), optionally substituted C$_3$-C$_{12}$-heterocyclyl (e.g. propyl-furan-2-yl, 2-CF$_3$-furan-2-yl, 1,2-dimethyl-5-CN-pyrrol-3-yl, 2,3-diMe-thiophen-5-yl, 2-Me-thiophen-5-yl, 2-Cl-thiophen-5-yl, 3-Cl-thiophen-2-yl, 2,5-diCl-thiophen-3-yl, 2-tetrahydropyranyl-thiophen-5-yl, 1,3-thiazol-5-yl, 4-Me-1,3-thiazol-2-yl, 2-Me-1,3-thiazol-5-yl, 5-Me-1,3-thiazol-2-yl, 4-Me-1,3-thiazol-5-yl, 2-Me-1,3-thiazol-4-yl, 4-isopropyl-1,3-thiazol-2-yl, 2,4-diMe-1,3-thiazol-5-yl, 2-phenyl-4-Me-1,3-thiazol-5-yl, 4-phenyl-1,3-thiazol-5-yl, 2-(4-Me-phenyl)-1,3-thiazol-5-yl, 4-(4-F-phenyl)-1,3-thiazol-2-yl, 2-Cl-1,3-thiazol-4-yl, 4-Cl-1,3-thiazol-5-yl, 2-Br-1,3-thiazol-5-yl, 4-Br-1,3-thiazol-2-yl, 4-Me-5-Br-1,3-thiazol-2-yl, 2,4-dichloro-1,3-thiazol-5-yl, 1,5-dimethyl-1,2,4-triazol-3-yl, pyrid-2-yl, pyrid-3-yl, pyrid-4-yl, 4-F-pyrid-2-yl, 5-F-pyrid-2-yl, 6-F-pyrid-2-yl, 4-Cl-pyrid-2-yl, 5-F-pyrid-3-yl, 2-F-pyrid-4-yl, 3,5-diCl-pyrid-4-yl, 4,5-diCl-pyrid-2-yl, 2-Cl-3F-pyrid-4-yl, 5-Me-pyrid-2-yl, 4-iPr-pyrid-2-yl, 4-Me-5-F-pyrid-2-yl, 4-CF$_3$-pyrid-2-yl, 5-CF$_3$-pyrid-2-yl, 6-CF$_3$-pyrid-2-yl, 5-CF$_3$-pyrid-3-yl, 2-CF$_3$-pyrid-4-yl, 3-F-4-CF$_3$-pyrid-2-yl, 4-CF$_3$-5-F-pyrid-2-yl, 4-CF$_3$-5-Cl-pyrid-2-yl, 3,5-diF-4-CF$_3$-pyrid-2-yl, 4-OCH$_2$CF$_3$-pyrid-2-yl, 4-OCH$_2$CF$_3$-5-F-pyrid-2-yl, 4-OCH$_2$CF$_3$-5-Cl-pyrid-2-yl, 4-OBn-5-F-pyrid-2-yl, 3-(4-F-phenyl)-pyrid-5-yl, 2-(4-F-phenyl)-pyrid-3-yl, 4-(pyrid-4-yl)-pyrid-2-yl, 4-(pyrid-3-yl)-pyrid-2-yl, 5-cyclopropyl-pyraz-2-yl, 5-cyclobutyl-pyraz-2-yl, 5-pyrrolidin-pyraz-2-yl, pyridaz-3-yl, 4-CF$_3$-pyridaz-3-yl, 5-CF$_3$-pyridaz-3-yl, 5-F-pyrimid-2-yl, 6-Cl-pyrimid-4-yl, 6-Me-pyrimid-4-yl, 6-Et-pyrimid-4-yl, 6-Pr-pyrimid-4-yl, 6-iPr-pyrimid-4-yl, 4-CF$_3$-pyrimid-2-yl, 6-CF$_3$-pyrimid-4-yl, 2-Me-6-Cl-pyrimid-4-yl, 2-Me-6-CF$_3$-pyrimid-4-yl, 2-OMe-6-CF$_3$-pyrimid-4-yl, 2-OMe-pyrimid-4-yl, 6-OMe-pyrimid-4-yl, 6-OEt-pyrimid-4-yl, 6-OPr-pyrimid-4-yl, 6-OiPr-pyrimid-4-yl, 6-OiBu-pyrimid-4-yl, 6-OBu-pyrimid-4-yl, 6-OBn-pyrimid-4-yl, 6-cyclobutyloxy-pyrimid-4-yl, 6-cyclopentyloxy-pyrimid-4-yl, 6-cyclohexyloxy-pyrimid-4-yl, 6-cyclopropyl-pyrimid-4-yl, 6-phenyl-pyrimid-4-yl, 6-(2-F-phenyl)-pyrimid-4-yl, 6-(3-F-phenyl)-pyrimid-4-yl, 6-(4-F-phenyl)-pyrimid-4-yl, 6-Cl-pyrimid-4-yl, 6-(2-Me-phenyl)-pyrimid-4-yl, 6-(3-Me-phenyl)-pyrimid-4-yl, 6-(4-Me-phenyl)-pyrimid-4-yl, 6-(3-Cl-phenyl)-pyrimid-4-yl, 6-(4-Cl-phenyl)-pyrimid-4-yl, 2-(morpholin-1-yl)-pyrimid-4-yl, 6-(azetidin-3-yl-methoxy)-pyrimid-4-yl, 6-(pyrrolidin-3-yl-methoxy)-pyrimid-4-yl, 6-(pyrrolidin-2-yl-methoxy)-pyrimid-4-yl, benzofuran-5-yl, 2-Me-benzofuran-3-yl, 2-Et-benzofuran-3-yl, benzothiophen-5-yl, benzothiophen-6-yl, 5-Me-benzothiophen-2-yl, 5-F-benzothiophen-2-yl, 3-Cl-benzothiophen-2-yl, benzothiazol-2-yl, isoquinolin-6-yl, isoquinolin-7-yl, quinolin-6-yl, quinolin-7-yl, 4,5,6,7-tetrahydro-1,3-benzothiazol-2-yl, 2,3-dihydrobenzofuran-5-yl, 7H-pyrrolo[2,3-d]pyrimidin-4-yl, pyrazolo[1,5-a]pyridine-3-yl, pyrazolo[1,5-a]pyridine-7-yl, imidazo[1,2-a]pyridin-8-yl, 5-methyl-imidazo[1,2-a]pyridin-3-yl, 6-chloro-2-methyl-imidazo[1,2-a]pyridin-3-yl, 6-bromo-2-methyl-imidazo[1,2-a]pyridin-3-yl, thieno[2,3-b]pyridin-2-yl, N-benzyl-indolin-6-yl, indolinon-4-yl, chroman-6-yl, 4,4-dimethylchroman-6-yl, 4,4-dimethyl-1,3-dioxan-2-yl, tetrahydrofuran-3-yl, tetrahydropyran-4-yl, 4-Me-tetrahydropyran-4-yl, 2,2-diMe-tetrahydropyran-4-yl, 1-isopropyl-piperidin-4-yl, or 2-CF$_3$-piperazin-5-yl, a further example being iBu-pyrazol-4-yl, 1-CHF$_2$-5-Me-1,2-diazol-4-yl, 1-benzyl-5-F-1,2,4-triazol-3-yl, 2-Me-pyrid-4-yl, 2-iPr-pyrid-4-yl, 4-phenyl-pyrid-2yl, 2-cyclopropyl-pyrid-4-yl, 2-OMe-pyrid-4-yl, 2-OEt-pyrid-4-yl, 2-cyclopropylmethoxy-pyrid-4-yl, 2-OiPr-pyrid-4-yl, 2-OCH$_2$CF$_3$-pyrid-4-yl, 2-cyclopropoxy-pyrid-4-yl, 2-cyclobutoxy-pyrid-4-yl, 4,5-diCl-pyrimidin-2yl, benzothiophen-3-yl, 2,2-diF-1,3-benzodioxol-5-yl, 5,6,7,8-tetrahydro-isoquinolin-5-yl, 5,6,7,8-tetrahydro-isoquinolin-8-yl, quinolin-8-yl, 1-Me-3,4-dihydro-2H-quinolin-4-yl, 2-Me-3,4-dihydro-1H-isoquinolin-6-yl, 5,6,7,8-tetrahydro-quinolin-5-yl, 5,6,7,8-tetrahydro-quinolin-8-yl, 5,6,7,8-tetrahydro-quinolin-6-yl, 2,3-dihydrobenzofuran-3-yl, pyrazolo[1,5-a]pyrimidin-6-yl, imidazo[1,5-a]pyrazinyl, 3-methyl-imidazo[1,5-a]pyrazinyl, 3-Me-[1,2,4]triazolo[4,3-a]pyridin-6-yl, imidazo[1,2-a]pyrazin-6-yl, 2-Me-isoindolin-1-on-6-yl, 2,2-dimethyl-7-CF$_3$-chroman-4-yl, 7-CF$_3$-chroman-4-yl, 7-OCF$_3$-chroman-4-yl, isochroman-4-yl, 6,6-dimethyl-1,3-dioxan-2-yl, tetrahydropyran-3-yl, 1-phenyl-pyrrolidin-3-yl, piperidin-3-yl, 1,3-dimethyl-piperidin-4-yl, 1-cyclopropyl-piperidin-4-yl, 1-(tri-F-methyl-carbonyl)-piperidin-3-yl, quinuclidin-2-yl, 6,7-dihydro-5H-cyclopenta[b]pyridine-7-yl, 6,7-dihydro-5H-cyclopenta[b]pyridine-5-yl, 6,7-dihydro-5H-cyclopenta[c]pyridine-7-yl, 6,7-dihydro-5H-cyclopenta[c]pyridine-5-yl, 5,6-dihydro-4H-cyclopenta[b]thiophen-4-yl, or 1,2,3,5,6,7,8,8a-octahydroindolizin), or tri-(C$_1$-C$_4$-alkyl)-silyloxy;

$R^{14}$ is $C_1$-$C_8$-alkyl (e.g. pentyl, n-butyl, or hexyl), halogenated $C_1$-$C_6$-alkyl (e.g. 1,1-diF-butyl, 3,3-diF-butyl, 4,4,4-triF-butyl, 1,1-diF-pentyl, or 4,4-diF-pentyl), (optionally substituted $C_3$-$C_{12}$-cycloalkyl)-$C_1$-$C_4$-alkyl (e.g. cyclopropyl-methyl), (optionally substituted $C_6$-$C_{12}$-aryl)-$C_1$-$C_4$-alkyl (e.g. benzyl, a further example being 4-F-benzyl, 3-F-benzyl, 3-$CF_3$-benzyl, 4-F-3-$CF_3$-benzyl, or 3-$OCF_3$-benzyl), hydroxy-$C_1$-$C_6$-alkyl (e.g. hydroxylmethyl or 1-hydroxy-pentyl), (optionally substituted $C_6$-$C_{12}$-aryloxy)-$C_1$-$C_4$-alkyl (e.g. phenoxy-methyl or (4-F-phenoxy)-methyl), $C_1$-$C_6$-alkylcarbonyl-$C_1$-$C_4$-alkyl (e.g. 2-methylcarbonyl-ethyl or 3-methylcarbonyl-propyl), $C_1$-$C_6$-alkoxycarbonyl-$C_1$-$C_4$-alkyl (e.g. 3-methoxycarbonyl-propyl), optionally substituted $C_3$-$C_{12}$-cycloalkyl (e.g. 1-$CF_3$-cyclopropyl or 4-$CF_3$-cyclohexyl, a further example being 1-phenyl-cyclopropyl, 1-(4-F-phenyl)cyclopropyl, 1-(3-F-phenyl)cyclopropyl, 1-(3-Cl-phenyl)cyclopropyl, 1-(3-$CF_3$-phenyl)cyclopropyl, 3-hydroxymethyl-bycyclo[1.1.1]pentyl, 3-methoxymethyl-bycyclo[1.1.1]pentyl, 3-ethoxymethyl-bycyclo[1.1.1]pentyl, or 3-methoxycarbonyl-bycyclo[1.1.1]pentyl), optionally substituted $C_6$-$C_{12}$-aryl (e.g. phenyl, 2-F-phenyl, 3-F-phenyl, 4-F-phenyl, 2-Cl-phenyl, 3-Cl-phenyl, 4-Cl-phenyl, 2,3-diCl-phenyl, 2,4-diCl-phenyl, 3,5-diCl-phenyl, 2-Cl-4-F-phenyl, 2-Me-phenyl, 3-Me-phenyl, 4-Me-phenyl, 2-$CF_3$-phenyl, 3-$CF_3$-phenyl, 4-$CF_3$-phenyl, 3-Cl-4-$CF_3$-phenyl, 2-Cl-3-$CF_3$-phenyl, 2-Cl-4-$CF_3$-phenyl, 2-OMe-phenyl, 3-OMe-phenyl, 2-CN-phenyl, or 3-CN-phenyl, 4-CN-phenyl), or optionally substituted $C_3$-$C_{12}$-heterocyclyl (e.g. 3-Cl-pyridazin-6-yl, 2-Cl-pyrazin-5-yl, or 2-$CF_3$-pyrazin-5-yl);

$R^{15}$ is $C_1$-$C_6$-alkyl (e.g. ethyl, n-propyl, n-butyl, iso-butyl, or tert-bu) or $C_6$-$C_{12}$-aryl (e.g. phenyl);

$R^{16a}$ is (optionally substituted $C_6$-$C_{12}$-aryl)-$C_1$-$C_4$-alkyl (e.g. benzyl or (2-Cl-phenyl)-methyl) or optionally substituted $C_6$-$C_{12}$-aryl (e.g. phenyl, 4-F-phenyl, 3-F-phenyl, 2F-phenyl, 4-Cl-phenyl, or 2-Cl-phenyl, a further example being 3-Cl-phenyl);

$R^{16b}$ is hydrogen;

$R^{9c}$, $R^{9d}$
are hydrogen;

n5 is 0, 1, or 2;

$R^{18}$ is hydrogen, optionally substituted $C_1$-$C_8$-alkyl (e.g. methyl, ethyl, iso-propyl, or pentyl), $C_1$-$C_6$-alkoxycarbonyl (e.g. methoxycabonyl or n-butoxycarbonyl), $C_1$-$C_6$-alkylaminocarbonyl (e.g. n-propylaminocarbonyl or n-butylaminocarbonyl), (halogenated $C_1$-$C_4$-alkyl)aminocarbonyl (e.g. 2,2-diF-ethylaminocarbonyl, a further example being 2,2,2-tri F-ethylaminocarbonyl), optionally substituted $C_6$-$C_{12}$-aryl (e.g. phenyl, 3-F-phenyl, 4-F-phenyl, 4-Me-phenyl, 3-$MeSO_2$-phenyl, or 4-$MeSO_2$-phenyl, a further example being 4-F-2-$CF_3$-phenyl, 4-F-3-$CF_3$-phenyl, or 4-F-3-$OCF_3$-phenyl), $C_1$-$C_6$-alkylamine (e.g. propylamine), (halogenated $C_1$-$C_6$-alkyl)amino (e.g. 2,2,2-triF-ethylamine, a further example being 2,2-diF-ethylamine), optionally substituted $C_6$-$C_{12}$-arylamine (e.g. 4-Cl-phenylamine), or optionally substituted $C_3$-$C_{12}$-heterocyclyl (e.g. 4-$CF_3$-pyrid-2-yl or 6-$CF_3$-pyrimid-4-yl, a further example being 4-Me-pyrid-2-yl);

$R^{19}$ is optionally substituted $C_6$-$C_{12}$-aryl (e.g. phenyl, 3-F-phenyl, 4-F-phenyl, 3-Cl-phenyl, 3,4-diF-phenyl, 3,4-diCl-phenyl, 3,5-diCl-phenyl, 3-F-4-Cl-phenyl, 3-F-5-Cl-phenyl, 3-Me-phenyl, 3-$CF_3$-phenyl, 3-$OCF_3$-phenyl, or 4-$OCF_3$-phenyl);

$R^{20a}$ is $C_1$-$C_8$-alkyl (e.g. n-propyl, n-butyl, hexyl, pentyl, or 6-Me-heptyl), ($C_3$-$C_{12}$-cycloalkyl)-$C_1$-$C_4$-alkyl (e.g. cyclopropyl-methyl), $C_1$-$C_6$-alkoxy-$C_1$-$C_6$-alkyl (e.g. 2-methoxy-ethyl, 2-ethoxy-ethyl, 2-isopropoxy-ethyl, 1-methyl-2-methoxy-ethyl, 3-methoxy-propyl, 3-ethoxy-propyl, or 3-isopropoxy-propyl), (optionally substituted $C_6$-$C_{12}$-aryl)-$C_1$-$C_4$-alkyl (e.g. benzyl, (4-F-phenyl)methyl, (3-Cl-phenyl)methyl, (4-Cl-phenyl)methyl, (3,4-diF-phenyl)methyl, (3-Cl-F-phenyl)methyl, (3-$CF_3$-phenyl)methyl, (2-Cl-4-$CF_3$-phenyl)methyl, (2-Cl-5-$CF_3$-phenyl)methyl, or (3-$OCF_3$-phenyl)methyl)), (optionally substituted $C_3$-$C_{12}$-heterocyclyl)-$C_1$-$C_4$-alkyl (e.g. (pyrid-2-yl)-methyl or (4-$CF_3$-pyrid-2-yl)methyl), optionally substituted $C_6$-$C_{12}$-aryl (e.g. phenyl, 4-F-phenyl, 3-Cl-phenyl, 3,5-diCl-phenyl, 3-Cl-F-phenyl, 3-Me-phenyl, 3-$CF_3$-phenyl, 4-$CF_3$-phenyl, 2-Cl-3-$CF_3$-phenyl, 3-Cl-4-$CF_3$-phenyl, 3-$CF_3$-4-F-phenyl, 3-CN-phenyl, 3-$OCF_3$-phenyl, 3-$OCF_3$-4-F-phenyl, or 3-$OCF_3$-4-Cl-phenyl), or optionally substituted $C_3$-$C_{12}$-heterocyclyl (e.g. 4-$CF_3$-pyrid-2-yl).

$R^{20b}$ is hydrogen or $C_1$-$C_8$-alkyl (e.g. methyl, ethyl, or n-butyl);

$R^{21}$ is $C_6$-$C_{12}$-aryl (e.g. phenyl); and $R^{5a}$, $R^{5b}$
are hydrogen; or $R^{5a}$, $R^{5b}$
together with the carbon atom to which they are bound may form a C=O, or.

one of $R^{2a}$ or $R^{2b}$ and one of $R^{5a}$ or $R^{5b}$
together are $C_1$-$C_5$-alkylene (e.g. 1,2-ethylene).

Further particular embodiments of pyrrolidine derivatives of the invention result if $R^1$ is optionally substituted 5-membered heterocyclic ring containing at least 1 N ring atom and optionally 1 or 2 further heteroatoms selected from N, O and S (e.g. 1-methyl-1,3-diazol-4-yl or 1-methyl-1,2,3-triazol-4-yl);

$R^{2a}$, $R^{2b}$
are hydrogen;

$R^{3a}$ is $C_3$-$C_{12}$-cycloalkyl (cyclopropyl, cyclobutyl, cyclopentyl, or cyclohexyl), optionally substituted $C_6$-$C_{12}$-aryl (e.g. phenyl, 2-Cl-phenyl, 2-Br-phenyl, 3-Cl-phenyl, 4-Cl-phenyl, 2-F-phenyl, 3-F-phenyl, 4-F-phenyl, 4-OMe-phenyl, or 2,4,5-trifluoro-phenyl, a further example being 2-Me-phenyl, 3-Me-phenyl, or 4-Me-phenyl)hydroxy, $C_1$-$C_6$-alkoxy (e.g. methoxy, ethoxy, n-propyloxy, iso-propyxy, or iso-butoxy) $C_3$-$C_{12}$-cycloalkyl-$C_1$-$C_4$-alkoxy (cyclopropylmethoxy, cyclohexylmethoxy), $C_2$-$C_6$-alkenyloxy (e.g. allyloxy, 2-methylprop-2-en-1-oxy), $C_6$-$C_{12}$-aryl-$C_1$-$C_4$-alkoxy (e.g. benzyloxy), or optionally substituted $C_6$-$C_{12}$-aryloxy (e.g. phenoxy, 4-F-phenoxy);

$R^{3b}$ is hydrogen or hydroxy;

$Y^1$ is >$CR^6$— or >N—;

$R^6$ is hydrogen, $C_1$-$C_6$-alkyl (e.g. methyl or ethyl), $C_6$-$C_{12}$-aryl-$C_1$-$C_4$-alkyl (e.g. benzyl or phenethyl), hydroxy-$C_1$-$C_6$-alkyl (e.g. —$CH_2OH$, or —$(CH_2)_2OH$), or hydroxy;

$R^4$ is —$(CR^{7a}R^{7b})_{n1}OR^{10}$, —$(CR^{7c}R^{7d})_{n2}NR^{11a}R^{11b}$, —$(CR^{7e}R^{7f})_{n3}R^{12}$, optionally substituted $C_6$-$C_{12}$-aryl, —$NR^{8a}(CR^{9a}R^{9b})_{n4}R^{13}$, —$NR^{8b}COR^{14}$, —$NR^{8c}COOR^{15}$, —$NR^{8d}CONR^{16a}R^{16b}$, —$O(CR^{9c}R^{9d})_{n5}R^{18}$, —$COR^{19}$, —$CONR^{20a}R^{20b}$, —$SO_2R^{21}$, or optionally substituted $C_3$-$C_{12}$ heterocyclyl (e.g. 1-propyl-1,2,3-triazol-4-yl, 4-butyl-1,2,3-triazolyl-1-yl, 4-chloroisoindolin-1-one, or 7-(trifluoromethyl)-3,4-dihydro-1H-quinazolin-2-on-1-yl, a further example being 5-butyl-oxazolidin-2-on-3-yl, 1,4-thiazinane-1,1-dioxide, indolinyl, indolin-2-on-1-yl, 6-$CF_3$-indolin-2-on-1-yl, isoindolinyl, or isoindolin-1-on-2-yl);

$R^{7a}$, $R^{7b}$
are hydrogen, or n1 is 1;

$R^{10}$ is hydrogen, optionally substituted $C_6$-$C_{12}$-aryl (e.g. phenyl, 3-F-phenyl, 3-Me-phenyl, 3-CF$_3$-phenyl, 2-Cl-3-CF$_3$-phenyl, or 3-OCF$_3$-phenyl, a further example being 2-F-phenyl, 4-F-phenyl, 2-Cl-phenyl, 2,3-diF-phenyl, 2,4-diF-phenyl, 2,5-diF-phenyl, 4-Cl-phenyl, 2-Cl-4-F-phenyl, 4-Cl-3-F-phenyl, 2-Me-phenyl, 4-Me-phenyl, 2-CF$_3$-phenyl, 4-CF$_3$-phenyl, 2-Cl-4-CF$_3$-phenyl, 3-OCHF$_2$-phenyl, 2-OCF$_3$-phenyl, 4-OCF$_3$-phenyl, 3-OMe-phenyl, 2-OEt-phenyl, 2-cyclopentyl-phenyl, 2-cyclohexyl-phenyl, 3-ethynyl-phenyl, 2-CN-phenyl, 4-CN-phenyl, 2-F-4-CN-phenyl, 3-dimethylamino-phenyl, 4-(morpholin-4-yl)-phenyl, 2-pirrolidinyl-phenyl, 2-piperidin-phenyl, indan-5-yl, naphthyl, or tetralin-5-yl), or optionally substituted $C_3$-$C_{12}$-heterocyclyl (e.g. 6-CF$_3$-pyrimid-4-yl, 4-CF$_3$-pyrid-2-yl, or 2-CF$_3$-pyrid-4-yl, a further example being pyrid-2-yl, pyrid-3-yl, pyrid-4-yl, pyrazin-2-yl, pyridazin-3-yl, quinolin-6-yl, isoquinolin-5-yl, 1,2-bezoxazol-6-yl, or 2-Me-1,3-benzoxazol-5-y);

$R^{7c}$, $R^{7d}$ are hydrogen, or n2 is 1;

$R_{11a}$ is $C_1$-$C_8$-alkyl (e.g. methyl, ethyl, n-propyl, n-butyl, or n-heptyl), $C_3$-$C_{12}$-cycloalkyl-$C_1$-$C_4$-alkyl (e.g. cyclopropyl-methyl) $C_1$-$C_6$-alkoxy-$C_1$-$C_6$-alkyl (2-methoxy-ethyl, 2-ethoxy-ethyl, 2-isopropyloxy-ethyl, 1-methyl-2-methoxy-ethyl, 3-methoxy-propyl, 3-ethoxy-propyl, or 3-isopropyloxy-propyl), $C_6$-$C_{12}$-aryl-$C_1$-$C_4$-alkyl (e.g. benzyl), optionally substituted $C_6$-$C_{12}$-aryl (e.g. phenyl, 4-F-phenyl, 3-Cl-phenyl, 3,5-diCl-phenyl, 3-Cl-F-phenyl, 3-Me-phenyl, 3-(aminomethyl)-phenyl, 3-CF$_3$-phenyl, 4-CF$_3$-phenyl, 2-Cl-4-CF$_3$-phenyl, 3-Cl-4-CF$_3$-phenyl, 3-CF$_3$-4-F-phenyl, 3-OCF$_3$-phenyl, 3-OCF$_3$-4-F-phenyl, 3-OCF$_3$-4-Cl-phenyl, or 3-(aminocarbonyl)-phenyl);

$R^{11b}$ is hydrogen;

$R^{7e}$, $R^{7f}$ are hydrogen, or n3 is 1;

$R^{12}$ is optionally substituted $C_6$-$C_{12}$-aryl (e.g. phenyl, 3-Cl-phenyl, or 3-Br-phenyl, a further example being 3-CF$_3$-phenyl) or optionally substituted $C_3$-$C_{12}$-heterocyclyl (e.g. 4-CF$_3$-pyrid-2-yl or 1-propyl-1,2,3-triazol-4-yl);

$R^{8a}$, $R^{8b}$, $R^{8c}$, $R^{8d}$, $R^{8e}$ are independently hydrogen or $C_1$-$C_6$-alkyl (e.g. pentyl or hexyl);

$R^6$ and one of $R^{8a}$, $R^{8b}$, $R^{8c}$, $R^{8d}$, or $R^{8e}$ together are optionally substituted $C_1$-$C_5$-alkylene, wherein one or more —CH$_2$— of $C_1$-$C_5$-alkylene may be independently replaced by a an oxygen atom or C=O;

$R^{9a}$, $R^{9b}$ are independently hydrogen, halogen, $C_1$-$C_6$-alkyl (e.g. methyl, ethyl, tert-butyl, 2,3-dimethyl-propyl), or $C_1$-$C_6$-alkoxy (e.g. methoxy or ethoxy);

n4 is 0, 1, 2, 3, or 4;

$R^{13}$ is hydrogen, $C_1$-$C_8$-alkyl (e.g. methyl, ethyl, n-butyl, tert-butyl, pentyl, or hexyl), halogenated $C_1$-$C_6$-alkyl (e.g. —CF$_3$ or —CF$_2$Me), $C_1$-$C_6$-alkoxy-$C_1$-$C_6$-alkyl (e.g. methoxy-methyl), optionally substituted $C_3$-$C_{12}$-cycloalkyl (e.g. cyclopropyl, 2-propyl-cyclopropyl, 1-(methoxymethyl)-cyclopropyl, 2-phenyl-cyclopropyl, cyclopentyl, 1-methyl-cyclohexyl, 1-CF$_3$-cyclopropyl, 4-CF$_3$-cyclohexyl, or 4,4-diF-cyclohexyl, a further example being 1-phenyl-cyclopropyl, 1-(4-F-phenyl)-cyclopropyl, (3-Cl-phenyl)-cyclopropyl, 2-phenyl-cyclobutyl, 3-phenyl-cyclobutyl, 3-(4-F-phenyl)-cyclobutyl, 3-(2-F-phenyl)-cyclobutyl, 2-Cl-cyclopentyl, 2-Me-cyclopentyl, 3-Me-cyclopentyl, 2-phenyl-cyclopentyl, 3-(2-pyridyl)-cyclopentyl, 3-Me-cyclohexyl, 3,3,5,5-tetraMe-cyclohexyl, 4-Me-cyclohexyl, 4-Et-cyclohexyl, 2-CF$_3$-cyclohexyl, 2-Me-5-isopropenyl-cyclohexyl, 2-phenyl-cyclohexyl, 3-phenyl-cyclohexyl, 4-phenyl-cyclohexyl, 2-EtO-cyclohexyl, decalin-1-yl, decalin-2-yl, norbornan-2-yl, 1,7,7-trimethyl-norbornan-2-yl, 5-iPr-2-Me-3-bicyclo[3.1.0]hexanyl, bicyclo[3.2.1]octanyl, or 3-bicyclo[1.1.1]pentanyl), $C_2$-$C_6$-alkenyl (e.g. hex-2-enyl), optionally substituted $C_3$-$C_6$-cycloalkenyl (e.g. 1,3,3-trimethylcyclohexen-2-yl), optionally substituted $C_6$-$C_{12}$-aryl (e.g. phenyl, 2-F-phenyl, 4-F-phenyl, 3-F-phenyl, 2-Cl-phenyl, 3-Cl-phenyl, 4-Cl-phenyl, 2,3-diF-phenyl, 2,4-diF-phenyl, 2,5-diF-phenyl, 3,4-diF-phenyl, 2,3,4-triF-phenyl, 2,4-diCl-phenyl, 3,4-diCl-phenyl, 3-F-4-Cl-phenyl, 3-Cl-F-phenyl, 3-Cl-5-F-phenyl, 3,4-diF-5-Cl-phenyl, 2-Me-phenyl, 3-Me-phenyl, 4-Me-phenyl, 3-iPr-phenyl, 3-tBu-phenyl, 3-Me-4-F-phenyl, 3-Me-4-Cl-phenyl, 3-iPr-4Cl-phenyl, 3-(1-OH-1-CF$_3$-EB-phenyl, 3-CHF$_2$-4-F-phenyl, 2-CF$_3$-phenyl, 3-CF$_3$-phenyl, 4-CF$_3$-phenyl, 3-Cl-4-CF$_3$-phenyl, 2-F-3-CF$_3$-phenyl, 2-F-5-CF$_3$-phenyl, 3-F-5-CF$_3$-phenyl, 2-Cl-4-CF$_3$-phenyl, 2-Cl-3-CF$_3$-phenyl, 3-CF$_3$-4-F-phenyl, 3-CF$_3$-4-Cl-phenyl, 3-Me-4-CF$_3$-phenyl, 3-CF$_3$-4-Me-phenyl, 3,4-diCF$_3$-phenyl, 4-OMe-phenyl, 3-OiPr-phenyl, 3-CF$_3$-4-OMe-phenyl, 3-OCH$_2$CF$_3$-phenyl, 3-OCF$_3$-phenyl, 2-OCHF$_2$-5-Cl-phenyl, 3-OCF$_3$-4-F-phenyl, 3-OCF$_3$-4-Cl-phenyl, 3-OBn-phenyl, 3-OPh-phenyl, 3-CN-phenyl, 4-CN-phenyl, 2-F-3-CN-phenyl, 2-F-4-CN-phenyl, 3-F-4-CN-phenyl, 2-F-5-CN-phenyl, 3-F-5-CN-phenyl, 3-Cl-4-CN-phenyl, 2-Cl-5-CN-phenyl, 3-Cl-5-CN-phenyl, 3-CN-4-Cl-phenyl, 2-Me-3-CN-phenyl, 2-Me-5-CN-phenyl, 3-Me-5-CN-phenyl, 3-CF$_3$-4-CN-phenyl, 3-CN-4-OMe-phenyl, 3-CN-4-OCF$_3$-phenyl, 3-phenyl-phenyl, 3-MeSO$_2$-phenyl, 3-(piperidin-4-yl)-phenyl, 2-methylcarbonylamino-5-Cl-phenyl, 3-(pyrid-2-yl)-phenyl, 3-(pyrid-3-yl)-4F-phenyl, 3-(pyrid-4-yl)-4F-phenyl, 3-(pyrimid-5-yl)-4F-phenyl, indan-5-yl, or tetralin-6-yl, a further example being 2,4-diF-3-Cl-phenyl, 3-Et-4-Cl-phenyl, 3-(2-methoxyethyl)-phenyl, 3-(2-OH-ethyl)-phenyl, 3-(1-OH-1-Me-ethyl)-phenyl, 3-CHF$_2$-phenyl, 3-CF$_3$-2,4-diF-phenyl, 3-(dimethylamino-methyl)-phenyl, 3-(morpholin-4-ylmethyl)-phenyl, 3-cyclopropyl-phenyl, 3-OEt-phenyl, 3-OPr-phenyl, 3-OtBu-phenyl, 3-(cyclopropylmethoxy)-phenyl, 3-(OMe-methoxy)-phenyl, 3-(2-dimethylamino-ethoxy)-phenyl, 3-CF$_3$-4-OH-phenyl, 3-OCH$_2$CHF$_2$-phenyl, 3-OCHF$_2$-phenyl, 3-OCHF$_2$-4-F-phenyl, 3-OCF$_3$-4-OMe-phenyl, 3-cyclopropoxy-phenyl, 3-methylcarbonyl-phenyl, 3-dimethylamino-phenyl, 3-(2-pyridyloxy)-phenyl, 3-(pyrimidin-2-yloxy)-phenyl, indanyl, indan-2-yl, 2-F-indanyl, 4-F-indanyl, 5-F-indanyl, 6-F-indanyl, 7-F-indanyl, 3-Me-indanyl, 4-Me-indanyl, 5-Me-indanyl, 6-Me-indanyl, 4-CF$_3$-indanyl, 5-CF$_3$-indanyl, 6-CF$_3$-indanyl, 3,3-dimethyl-indanyl, tetralin-2-yl, 7-F-tetralin-2-yl, 6-F-tetralin-2-yl, tetralinyl, 6-F-tetralinyl, 5-F-tetralinyl, or 7-F-tetralinyl), $C_1$-$C_6$-alkoxy (e.g. methoxy, ethoxy, or n-propoxy), $C_1$-$C_6$-alkoxy-$C_1$-$C_4$-alkoxy (e.g. 2-methoxy-ethoxy), optionally substituted $C_6$-$C_{12}$-aryloxy (e.g. 4-F-phenoxy or 4-tertbutyl-phenoxy), optionally substituted $C_3$-$C_{12}$-heterocyclyl (e.g. propyl-furan-2-yl, 2-CF$_3$-furan-5-yl, 1,2-dimethyl-5-CN-pyrrol-3-yl, 2,3-diMe-thiophen-5-yl, 2-Me-thiophen-5-yl, 2-Cl-thiophen-5-yl, 3-Cl-thiophen-2-yl, 2,5-diCl-thiophen-3-yl, 2-tetrahydropyranyl-thiophen-5-yl, 1,3-thiazol-5-yl, 4-Me-1,3-thiazol-2-yl, 2-Me-1,3-thiazol-5-yl, 5-Me-1,3-thiazol-2-yl, 4-Me-1,3-thiazol-5-yl, 2-Me-1,3-thiazol-4- yl, 4-isopropyl-1,3-thiazol-2-yl, 2,4-diMe-1,3-thiazol-5-yl, 2-phenyl-4-Me-1,3-thiazol-5-yl, 4-phenyl-1,3-thiazol-5-yl, 2-(4-Me-phenyl)-1,3-thiazol-5-yl, 4-(4-F-phenyl)-1,3-thiazol-2-yl, 2-Cl-1,3-thiazol-4-yl, 4-Cl-1,3-thiazol-2-yl, 2-Br-1,3-thiazol-5-yl, 4-Br-1,3-thiazol-2-yl, 4-Me-5-Br-1,3-thiazol-2-yl, 2,4-dichloro-1,3-thiazol-5-yl, 1,5-dimethyl-1,2,4-triazol-3-yl, pyrid-2-yl, pyrid-3-yl, pyrid-4-yl, 4-F-pyrid-2-yl, 5-F-pyrid-2-yl, 6-F-pyrid-2-yl, 4-Cl-pyrid-2-yl, 5-F-pyrid-3-yl, 2-F-pyrid-4-yl, 3,5-diCl-pyrid-4-yl, 4,5-diCl-pyrid-2-yl, 2-Cl-3F-pyrid-4-yl, 5-Me-pyrid-2-yl, 4-iPr-pyrid-2-yl, 4-Me-5-F-pyrid-2-yl, 4-CF$_3$-pyrid-2-yl, 5-CF$_3$-pyrid-2-yl, 6-CF$_3$-pyrid-2-yl, 5-CF$_3$-pyrid-3-yl, 2-CF$_3$-pyrid-4-yl, 3-F-4-CF$_3$-pyrid-2-yl, 4-CF$_3$-5-F-pyrid-2-yl, 4-CF$_3$-5-Cl-pyrid-2-yl, 3,5-diF-4-CF$_3$-pyrid-2-yl, 4-OCH$_2$CF$_3$-pyrid-2-yl, 4-OCH$_2$CF$_3$-5-F-pyrid-2-yl, 4-OCH$_2$CF$_3$-5-Cl-pyrid-2-yl, 4-OBn-5-F-pyrid-2-yl, 3-(4-F-phenyl)-pyrid-5-yl, 2-(4-F-phenyl)-pyrid-3-yl, 4-(pyrid-4-yl)-pyrid-2-yl, 4-(pyrid-3-yl)-pyrid-2-yl, 5-cyclopropyl-pyraz-2-yl, 5-cyclobutyl-pyraz-2-yl, 5-pyrrolidin-pyraz-2-yl, pyridaz-3-yl, 4-CF$_3$-pyridaz-3-yl, 5-CF$_3$-pyridaz-3-yl, 5-F-pyrimid-2-yl, 6-Cl-pyrimid-4-yl, 6-Me-pyrimid-4-yl, 6-Et-pyrimid-4-yl, 6-Pr-pyrimid-4-yl, 6-iPr-pyrimid-4-yl, 4-CF$_3$-pyrimid-2-yl, 6-CF$_3$-pyrimid-4-yl, 2-Me-6-Cl-pyrimid-4-yl, 2-Me-6-CF$_3$-pyrimid-4-yl, 2-OMe-6-CF$_3$-pyrimid-4-yl, 2-OMe-pyrimid-4-yl, 6-OMe-pyrimid-4-yl, 6-OEt-pyrimid-4-yl, 6-OPr-pyrimid-4-yl, 6-OiPr-pyrimid-4-yl, 6-OiBu-pyrimid-4-yl, 6-OBu-pyrimid-4-yl, 6-OBn-pyrimid-4-yl, 6-cyclobutyloxy-pyrimid-4-yl, 6-cyclopentyloxy-pyrimid-4-yl, 6-cyclohexyloxy-pyrimid-4-yl, 6-cyclopropyl-pyrimid-4-yl, 6-phenyl-pyrimid-4-yl, 6-(2-F-phenyl)-pyrimid-4-yl, 6-(3-F-phenyl)-pyrimid-4-yl, 6-(4-F-phenyl)-pyrimid-4-yl, 6-Cl-pyrimid-4-yl, 6-(2-Me-phenyl)pyrimid-4-yl, 6-(3-Me-phenyl)-pyrimid-4-yl, 6-(4-Me-phenyl)-pyrimid-4-yl, 6-(3-Cl-phenyl)-pyrimid-4-yl, 6-(4-Cl-phenyl)-pyrimid-4-yl, 2-(morpholin-1-yl)-pyrimid-4-yl, 6-(azetidin-3-yl-methoxy)-pyrimid-4-yl, 6-(pyrrolidin-3-yl-methoxy)-pyrimid-4-yl, 6-(pyrrolidin-2-yl-methoxy)-pyrimid-4-yl, benzofuran-5-yl, 2-Me-benzofuran-3-yl, 2-Et-benzofuran-3-yl, benzothiophen-5-yl, benzothiophen-6-yl, 5-Me-benzothiophen-2-yl, 5-F-benzothiophen-2-yl, 3-Cl-benzothiophen-2-yl, benzothiazol-2-yl, isoquinolin-6-yl, isoquinolin-7-yl, quinolin-6-yl, quinolin-7-yl, 4,5,6,7-tetrahydro-1,3-benzothiazol-2-yl, 2,3-dihydrobenzofuran-5-yl, 7H-pyrrolo[2,3-d]pyrimidin-4-yl, pyrazolo[1,5-a]pyridine-3-yl, pyrazolo[1,5-a]pyridine-7-yl, imidazo[1,2-a]pyridin-8-yl, 5-methyl-imidazo[1,2-a]pyridin-3-yl, 6-chloro-2-methyl-imidazo[1,2-a]pyridin-3-yl, 6-bromo-2-methyl-imidazo[1,2-a]pyridin-3-yl, thieno[2,3-b]pyridin-2-yl, N-benzyl-indolin-6-yl, indolinon-4-yl, chroman-6-yl, 4,4-dimethylchroman-6-yl, 4,4-dimethyl-1,3-dioxan-2-yl, tetrahydrofuran-3-yl, tetrahydropyran-4-yl, 4-Me-tetrahydropyran-4-yl, 2,2-diMe-tetrahydropyran-4-yl, 1-isopropyl-piperidin-4-yl, or 2-CF$_3$-piperazin-5-yl, a further example being iBu-pyrazol-4-yl, 1-CHF$_2$-5-Me-1,2-diazol-4-yl, 1-benzyl-5-F-1,2,4-triazol-3-yl, 2-Me-pyrid-4-yl, 2-iPr-pyrid-4-yl, 4-phenyl-pyrid-2yl, 2-cyclopropyl-pyrid-4-yl, 2-OMe-pyrid-4-yl, 2-OEt-pyrid-4-yl, 2-cyclopropylmethoxy-pyrid-4yl, 2-OiPr-pyrid-4-yl, 2-OCH$_2$CF$_3$-pyrid-4-yl, 2-cyclopropoxy-pyrid-4-yl, 2-cyclobutoxy-pyrid-4-yl, 4,5-diCl-pyrimidin-2yl, benzothiophen-3-yl, 2,2-diF-1,3-benzodioxol-5-yl, 5,6,7,8-tetrahydro-isoquinolin-5-yl, 5,6,7,8-tetrahydro-isoquinolin-8-yl, quinolin-8-yl, 1-Me-3,4-dihydro-2H-quinolin-6-yl, 2-Me-3,4-dihydro-1H-isoquinolin-6-yl, 5,6,7,8-tetrahydro-quinolin-5-yl, 5,6,7,8-tetrahydro-quinolin-8-yl, 5,6,7,8-tetrahydro-quinolin-6-yl, 2,3-dihydrobenzofuran-3-yl, pyrazolo[1,5-a]pyrimidin-6-yl, imidazo[1,5-a]pyrazinyl, 3-methylimidazo[1,5-a]pyrazinyl, 3-Me-[1,2,4]triazolo[4,3-a]pyridin-6-yl, imidazo[1,2-a]pyrazin-6-yl, 2-Me-isoindolin-1-on-6-yl, 2,2-dimethyl-7-CF$_3$-chroman-4-yl, 7-CF$_3$-chroman-4-yl, 7-OCF$_3$-chroman-4-yl, isochroman-4-yl, 6,6-dimethyl-1,3-dioxan-2-yl, tetrahydropyran-3-yl, 1-phenyl-pyrrolidin-3-yl, piperidin-3-yl, 1,3-dimethyl-piperidin-4-yl, 1-cyclopropyl-piperidin-4-yl, 1-(tri-F-methyl-carbonyl)-piperidin-3-yl, quinuclidin-2-yl, 6,7-dihydro-5H-cyclopenta[b]pyridine-7-yl, 6,7-dihydro-5H-cyclopenta[b]pyridine-5-yl, 6,7-dihydro-5H-cyclopenta[c]pyridine-7-yl, 6,7-dihydro-5H-cyclopenta[c]pyridine-5-yl, 5,6-dihydro-4H-cyclopenta[b]thiophen-4-yl, or 1,2,3,5,6,7,8,8a-octahydroindolizin), or tri-(C$_1$-C$_4$-alkyl)-silyloxy;

$R^{14}$ is C$_1$-C$_8$-alkyl (e.g. pentyl, n-butyl, or hexyl), halogenated C$_1$-C$_6$-alkyl (e.g. 1,1-diF-butyl, 3,3-diF-butyl, 4,4,4-triF-butyl, 1,1-diF-pentyl, or 4,4-diF-pentyl), (optionally substituted C$_3$-C$_{12}$-cycloalkyl)-C$_1$-C$_4$-alkyl (e.g. cyclopropyl-methyl), hydroxy-C$_1$-C$_6$-alkyl (e.g. hydroxyl-methyl or 1-hydroxy-pentyl), (optionally substituted C$_6$-C$_{12}$-aryloxy)-C$_1$-C$_4$-alkyl (e.g. phenoxy-methyl or (4-F-phenoxy)-methyl), C$_1$-C$_6$-alkylcarbonyl-C$_1$-C$_4$-alkyl (e.g. 2-methylcarbonyl-ethyl or 3-methylcarbonyl-propyl), C$_1$-C$_6$-alkoxycarbonyl-C$_1$-C$_4$-alkyl (e.g. 3-methoxycarbonyl-propyl), optionally substituted C$_3$-C$_{12}$-cycloalkyl (e.g. 1-CF$_3$-cyclopropyl or 4-CF$_3$-cyclohexyl, a further example being 1-phenyl-cyclopropyl, 1-(4-F-phenyl)cyclopropyl, 1-(3-F-phenyl)cyclopropyl, 1-(3-Cl-phenyl)cyclopropyl, 1-(3-CF$_3$-phenyl)cyclopropyl, 3-hydroxymethyl-bycyclo[1.1.1]pentyl, 3-methoxymethyl-bycyclo[1.1.1]pentyl, 3-ethoxymethyl-bycyclo[1.1.1]pentyl, or 3-methoxycarbonyl-bycyclo[1.1.1]pentyl), optionally substituted C$_6$-C$_{12}$-aryl (e.g. phenyl, 2-F-phenyl, 3-F-phenyl, 4-F-phenyl, 2-Cl-phenyl, 3-Cl-phenyl, 4-Cl-phenyl, 2,3-diCl-phenyl, 2,4-diCl-phenyl, 3,5-diCl-phenyl, 2-Cl-F-phenyl, 2-Me-phenyl, 3-Me-phenyl, 4-Me-phenyl, 2-CF$_3$-phenyl, 3-CF$_3$-phenyl, 4-CF$_3$-phenyl, 3-Cl-4-CF$_3$-phenyl, 2-Cl-3-CF$_3$-phenyl, 2-Cl-4-CF$_3$-phenyl, 2-OMe-phenyl, 3-OMe-phenyl, 2-CN-phenyl, or 3-CN-phenyl, 4-CN-phenyl), or optionally substituted C$_3$-C$_{12}$-heterocyclyl (e.g. 3-Cl-pyridazin-6-yl, 2-Cl-pyrazin-5-yl, or 2-CF$_3$-pyrazin-5-yl);

$R^{15}$ is C$_1$-C$_6$-alkyl (e.g. ethyl, n-propyl, n-butyl, iso-butyl, or tert-bu) or C$_6$-C$_{12}$-aryl (e.g. phenyl);

$R^{16a}$ is (optionally substituted C$_6$-C$_{12}$-aryl)-C$_1$-C$_4$-alkyl (e.g. benzyl or (2-Cl-phenyl)-methyl) or optionally substituted C$_6$-C$_{12}$-aryl (e.g. phenyl, 4-F-phenyl, 3-F-phenyl, 2F-phenyl, 4-Cl-phenyl, or 2-Cl-phenyl, a further example being 3-Cl-phenyl);

$R^{16b}$ is hydrogen;

$R^{9c}$, $R^{9d}$ are hydrogen;

n5 is 0, 1, or 2;

$R^{18}$ is hydrogen, optionally substituted C$_1$-C$_8$-alkyl (e.g. methyl, ethyl, iso-propyl, or pentyl), C$_1$-C$_6$-alkoxycarbonyl (e.g. methoxycabonyl or n-butoxycarbonyl), C$_1$-C$_6$-alkylaminocarbonyl (e.g. n-propylaminocarbonyl or n-butylaminocarbonyl), (halogenated C$_1$-C$_4$-alkyl)aminocarbonyl (e.g. 2,2-diF-ethylaminocarbonyl, a further example being 2,2,2-tri F-ethylaminocarbonyl), optionally substituted C$_6$-C$_{12}$-aryl (e.g. phenyl, 3-F-phenyl, 4-F-phenyl, 4-Me-phenyl, 3-MeSO$_2$-phenyl, or 4-MeSO$_2$-phenyl, a further example being 4-F-2-CF$_3$-phenyl, 4-F-3-CF$_3$-phenyl, or 4-F-3-OCF$_3$-phenyl), C$_1$-C$_6$-alkylamine (e.g. propylamine), (halogenated C$_1$-C$_6$-alkyl)amino (e.g. 2,2,2-triF-ethylamine, a further example being 2,2-diFethylamine), optionally substituted C$_6$-C$_{12}$-arylamine (e.g. 4-Cl-phenylamine), or optionally substituted C$_3$-C$_{12}$-heterocyclyl (e.g. 4-CF$_3$-pyrid-2-yl or 6-CF$_3$-pyrimid-4-yl, a further example being 4-Me-pyrid-2-yl);

R$^{19}$ is optionally substituted C$_6$-C$_{12}$-aryl (e.g. phenyl, 3-F-phenyl, 4-F-phenyl, 3-Cl-phenyl, 3,4-diF-phenyl, 3,4-diCl-phenyl, 3,5-diCl-phenyl, 3-F-4-Cl-phenyl, 3-F-5-Cl-phenyl, 3-Me-phenyl, 3-CF$_3$-phenyl, 3-OCF$_3$-phenyl, or 4-OCF$_3$-phenyl);

R$^{20a}$ is C$_1$-C$_8$-alkyl (e.g. n-propyl, n-butyl, hexyl, pentyl, or 6-Me-heptyl), (C$_3$-C$_{12}$-cycloalkyl)-C$_1$-C$_4$-alkyl (e.g. cyclopropyl-methyl), C$_1$-C$_6$-alkoxy-C$_1$-C$_6$-alkyl (e.g. 2-methoxy-ethyl, 2-ethoxy-ethyl, 2-isopropoxy-ethyl, 1-methyl-2-methoxy-ethyl, 3-methoxy-propyl, 3-ethoxy-propyl, or 3-isopropoxy-propyl), (optionally substituted C$_6$-C$_{12}$-aryl)-C$_1$-C$_4$-alkyl (e.g. benzyl, (4-F-phenyl)methyl, (3-Cl-phenyl)methyl, (4-Cl-phenyl)methyl, (3,4-diF-phenyl)methyl, (3-Cl-F-phenyl)methyl, (3-CF$_3$-phenyl)methyl, (2-Cl-4-CF$_3$-phenyl)methyl, (2-Cl-5-CF$_3$-phenyl)methyl, or (3-OCF$_3$-phenyl)methyl)), (optionally substituted C$_3$-C$_{12}$-heterocyclyl)-C$_1$-C$_4$-alkyl (e.g. (pyrid-2-yl)-methyl or (4-CF$_3$-pyrid-2-yl)methyl), optionally substituted C$_6$-C$_{12}$-aryl (e.g. phenyl, 4-F-phenyl, 3-Cl-phenyl, 3,5-diCl-phenyl, 3-Cl-F-phenyl, 3-Me-phenyl, 3-CF$_3$-phenyl, 4-CF$_3$-phenyl, 2-Cl-3-CF$_3$-phenyl, 3-Cl-4-CF$_3$-phenyl, 3-CF$_3$-4-F-phenyl, 3-CN-phenyl, 3-OCF$_3$-phenyl, 3-OCF$_3$-4-F-phenyl, or 3-OCF$_3$-4-Cl-phenyl), or optionally substituted C$_3$-C$_{12}$-heterocyclyl (e.g. 4-CF$_3$-pyrid-2-yl).

R$^{20b}$ is hydrogen or C$_1$-C$_8$-alkyl (e.g. methyl, ethyl, or n-butyl);

R$^{21}$ is C$_6$-C$_{12}$-aryl (e.g. phenyl); and

R$^{5a}$, R$^{5b}$
are hydrogen; or

R$^{5a}$, R$^{5b}$
together with the carbon atom to which they are bound may form a C=O.

Further particular compounds of the present invention are the individual pyrrolidine derivatives of the formula (Id2) as listed in the following tables 1 to 8 and physiologically tolerated salts thereof:

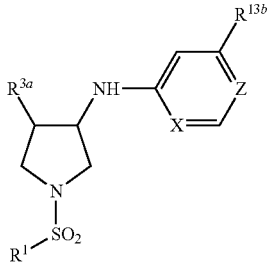

Table 1 Compounds of the formula (Id2) wherein X is =CH—, Z is =CR$^{13c}$—, R$^{13c}$ is H and the combination of R$^1$, R$^{3a}$ and R$^{13b}$ for a compound in each case corresponds to one line of Table A (A-1 to A-344).

Table 2 Compounds of the formula (Id2) wherein X is =CH—, Z is =CR$^{13c}$—, R$^{13c}$ is F and the combination of R$^1$, R$^{3a}$ and R$^{13b}$ for a compound in each case corresponds to one line of Table A (A-1 to A-344).

Table 3 Compounds of the formula (Id2) wherein X is =CH—, Z is =CR$^{13c}$—, R$^{13c}$ is Cl and the combination of R$^1$, R$^{3a}$ and R$^{13b}$ for a compound in each case corresponds to one line of Table A (A-1 to A-344).

Table 4 Compounds of the formula (Id2) wherein X is =N—, Z is =CR$^{13c}$, R$^{13c}$ is H and the combination of R$^1$, R$^{3a}$ and R$^{13b}$ for a compound in each case corresponds to one line of Table A (A-1 to A-344).

Table 5 Compounds of the formula (Id2) wherein X is =N—, Z is =CR$^{13c}$, R$^{13c}$ is F and the combination of R$^1$, R$^{3a}$ and R$^{13b}$ for a compound in each case corresponds to one line of Table A (A-1 to A-344).

Table 6 Compounds of the formula (Id2) wherein X is =N—, Z is =CR$^{13c}$—, R$^{13c}$ is Cl and the combination of R$^1$, R$^{3a}$ and R$^{13b}$ for a compound in each case corresponds to one line of Table A (A-1 to A-344).

Table 7 Compounds of the formula (Id2) wherein X is =N—, Z is =N— and the combination of R$^1$, R$^{3a}$ and R$^{13b}$ for a compound in each case corresponds to one line of Table A (A-1 to A-344).

| | R$^1$ | R$^{3a}$ | R$^{13b}$ |
|---|---|---|---|
| A-1. | 1-methyl-1,3-diazol-4-yl | Ph | H |
| A-2. | 1-methyl-1,3-diazol-4-yl | 4-F—Ph | H |
| A-3. | 1-methyl-1,3-diazol-4-yl | 2-THP | H |
| A-4. | 1-methyl-1,3-diazol-4-yl | 2-THF | H |
| A-5. | 1-methyl-1,2,3-triazol-4-yl | Ph | H |
| A-6. | 1-methyl-1,2,3-triazol-4-yl | 4-F—Ph | H |
| A-7. | 1-methyl-1,2,3-triazol-4-yl | 2-THP | H |
| A-8. | 1-methyl-1,2,3-triazol-4-yl | 2-THF | H |
| A-9. | 1-methyl-1,3-diazol-4-yl | Ph | F |
| A-10. | 1-methyl-1,3-diazol-4-yl | 4-F—Ph | F |
| A-11. | 1-methyl-1,3-diazol-4-yl | 2-THP | F |
| A-12. | 1-methyl-1,3-diazol-4-yl | 2-THF | F |
| A-13. | 1-methyl-1,2,3-triazol-4-yl | Ph | F |
| A-14. | 1-methyl-1,2,3-triazol-4-yl | 4-F—Ph | F |
| A-15. | 1-methyl-1,2,3-triazol-4-yl | 2-THP | F |
| A-16. | 1-methyl-1,2,3-triazol-4-yl | 2-THF | F |
| A-17. | 1-methyl-1,3-diazol-4-yl | Ph | Cl |
| A-18. | 1-methyl-1,3-diazol-4-yl | 4-F—Ph | Cl |
| A-19. | 1-methyl-1,3-diazol-4-yl | 2-THP | Cl |
| A-20. | 1-methyl-1,3-diazol-4-yl | 2-THF | Cl |
| A-21. | 1-methyl-1,2,3-triazol-4-yl | Ph | Cl |
| A-22. | 1-methyl-1,2,3-triazol-4-yl | 4-F—Ph | Cl |
| A-23. | 1-methyl-1,2,3-triazol-4-yl | 2-THP | Cl |
| A-24. | 1-methyl-1,2,3-triazol-4-yl | 2-THF | Cl |
| A-25. | 1-methyl-1,3-diazol-4-yl | Ph | —CH$_3$ |
| A-26. | 1-methyl-1,3-diazol-4-yl | 4-F—Ph | —CH$_3$ |
| A-27. | 1-methyl-1,3-diazol-4-yl | 2-THP | —CH$_3$ |
| A-28. | 1-methyl-1,3-diazol-4-yl | 2-THF | —CH$_3$ |
| A-29. | 1-methyl-1,2,3-triazol-4-yl | Ph | —CH$_3$ |
| A-30. | 1-methyl-1,2,3-triazol-4-yl | 4-F—Ph | —CH$_3$ |
| A-31. | 1-methyl-1,2,3-triazol-4-yl | 2-THP | —CH$_3$ |
| A-32. | 1-methyl-1,2,3-triazol-4-yl | 2-THF | —CH$_3$ |
| A-33. | 1-methyl-1,3-diazol-4-yl | Ph | —CH$_2$CH$_3$ |
| A-34. | 1-methyl-1,3-diazol-4-yl | 4-F—Ph | —CH$_2$CH$_3$ |
| A-35. | 1-methyl-1,3-diazol-4-yl | 2-THP | —CH$_2$CH$_3$ |
| A-36. | 1-methyl-1,3-diazol-4-yl | 2-THF | —CH$_2$CH$_3$ |
| A-37. | 1-methyl-1,2,3-triazol-4-yl | Ph | —CH$_2$CH$_3$ |
| A-38. | 1-methyl-1,2,3-triazol-4-yl | 4-F—Ph | —CH$_2$CH$_3$ |
| A-39. | 1-methyl-1,2,3-triazol-4-yl | 2-THP | —CH$_2$CH$_3$ |
| A-40. | 1-methyl-1,2,3-triazol-4-yl | 2-THF | —CH$_2$CH$_3$ |
| A-41. | 1-methyl-1,3-diazol-4-yl | Ph | —CH$_2$CH$_2$CH$_3$ |
| A-42. | 1-methyl-1,3-diazol-4-yl | 4-F—Ph | —CH$_2$CH$_2$CH$_3$ |
| A-43. | 1-methyl-1,3-diazol-4-yl | 2-THP | —CH$_2$CH$_2$CH$_3$ |
| A-44. | 1-methyl-1,3-diazol-4-yl | 2-THF | —CH$_2$CH$_2$CH$_3$ |
| A-45. | 1-methyl-1,2,3-triazol-4-yl | Ph | —CH$_2$CH$_2$CH$_3$ |
| A-46. | 1-methyl-1,2,3-triazol-4-yl | 4-F—Ph | —CH$_2$CH$_2$CH$_3$ |
| A-47. | 1-methyl-1,2,3-triazol-4-yl | 2-THP | —CH$_2$CH$_2$CH$_3$ |
| A-48. | 1-methyl-1,2,3-triazol-4-yl | 2-THF | —CH$_2$CH$_2$CH$_3$ |
| A-49. | 1-methyl-1,3-diazol-4-yl | Ph | —CH(CH$_3$)$_2$ |
| A-50. | 1-methyl-1,3-diazol-4-yl | 4-F—Ph | —CH(CH$_3$)$_2$ |
| A-51. | 1-methyl-1,3-diazol-4-yl | 2-THP | —CH(CH$_3$)$_2$ |
| A-52. | 1-methyl-1,3-diazol-4-yl | 2-THF | —CH(CH$_3$)$_2$ |
| A-53. | 1-methyl-1,2,3-triazol-4-yl | Ph | —CH(CH$_3$)$_2$ |
| A-54. | 1-methyl-1,2,3-triazol-4-yl | 4-F—Ph | —CH(CH$_3$)$_2$ |
| A-55. | 1-methyl-1,2,3-triazol-4-yl | 2-THP | —CH(CH$_3$)$_2$ |
| A-56. | 1-methyl-1,2,3-triazol-4-yl | 2-THF | —CH(CH$_3$)$_2$ |
| A-57. | 1-methyl-1,3-diazol-4-yl | Ph | —C(CH$_3$)$_3$ |
| A-58. | 1-methyl-1,3-diazol-4-yl | 4-F—Ph | —C(CH$_3$)$_3$ |

| | R¹ | R³ᵃ | R¹³ᵇ |
|---|---|---|---|
| A-59. | 1-methyl-1,3-diazol-4-yl | 2-THP | —C(CH₃)₃ |
| A-60. | 1-methyl-1,3-diazol-4-yl | 2-THF | —C(CH₃)₃ |
| A-61. | 1-methyl-1,2,3-triazol-4-yl | Ph | —C(CH₃)₃ |
| A-62. | 1-methyl-1,2,3-triazol-4-yl | 4-F—Ph | —C(CH₃)₃ |
| A-63. | 1-methyl-1,2,3-triazol-4-yl | 2-THP | —C(CH₃)₃ |
| A-64. | 1-methyl-1,2,3-triazol-4-yl | 2-THF | —C(CH₃)₃ |
| A-65. | 1-methyl-1,3-diazol-4-yl | Ph | —CF₃ |
| A-66. | 1-methyl-1,3-diazol-4-yl | 4-F—Ph | —CF₃ |
| A-67. | 1-methyl-1,3-diazol-4-yl | 2-THP | —CF₃ |
| A-68. | 1-methyl-1,3-diazol-4-yl | 2-THF | —CF₃ |
| A-69. | 1-methyl-1,2,3-triazol-4-yl | Ph | —CF₃ |
| A-70. | 1-methyl-1,2,3-triazol-4-yl | 4-F—Ph | —CF₃ |
| A-71. | 1-methyl-1,2,3-triazol-4-yl | 2-THP | —CF₃ |
| A-72. | 1-methyl-1,2,3-triazol-4-yl | 2-THF | —CF₃ |
| A-73. | 1-methyl-1,3-diazol-4-yl | Ph | —CHF₂ |
| A-74. | 1-methyl-1,3-diazol-4-yl | 4-F—Ph | —CHF₂ |
| A-75. | 1-methyl-1,3-diazol-4-yl | 2-THP | —CHF₂ |
| A-76. | 1-methyl-1,3-diazol-4-yl | 2-THF | —CHF₂ |
| A-77. | 1-methyl-1,2,3-triazol-4-yl | Ph | —CHF₂ |
| A-78. | 1-methyl-1,2,3-triazol-4-yl | 4-F—Ph | —CHF₂ |
| A-79. | 1-methyl-1,2,3-triazol-4-yl | 2-THP | —CHF₂ |
| A-80. | 1-methyl-1,2,3-triazol-4-yl | 2-THF | —CHF₂ |
| A-81. | 1-methyl-1,3-diazol-4-yl | Ph | —CH(OH)(CF₃)CH₃ |
| A-82. | 1-methyl-1,3-diazol-4-yl | 4-F—Ph | —CH(OH)(CF₃)CH₃ |
| A-83. | 1-methyl-1,3-diazol-4-yl | 2-THP | —CH(OH)(CF₃)CH₃ |
| A-84. | 1-methyl-1,3-diazol-4-yl | 2-THF | —CH(OH)(CF₃)CH₃ |
| A-85. | 1-methyl-1,2,3-triazol-4-yl | Ph | —CH(OH)(CF₃)CH₃ |
| A-86. | 1-methyl-1,2,3-triazol-4-yl | 4-F—Ph | —CH(OH)(CF₃)CH₃ |
| A-87. | 1-methyl-1,2,3-triazol-4-yl | 2-THP | —CH(OH)(CF₃)CH₃ |
| A-88. | 1-methyl-1,2,3-triazol-4-yl | 2-THF | —CH(OH)(CF₃)CH₃ |
| A-89. | 1-methyl-1,3-diazol-4-yl | Ph | cyclopropyl |
| A-90. | 1-methyl-1,3-diazol-4-yl | 4-F—Ph | cyclopropyl |
| A-91. | 1-methyl-1,3-diazol-4-yl | 2-THP | cyclopropyl |
| A-92. | 1-methyl-1,3-diazol-4-yl | 2-THF | cyclopropyl |
| A-93. | 1-methyl-1,2,3-triazol-4-yl | Ph | cyclopropyl |
| A-94. | 1-methyl-1,2,3-triazol-4-yl | 4-F—Ph | cyclopropyl |
| A-95. | 1-methyl-1,2,3-triazol-4-yl | 2-THP | cyclopropyl |
| A-96. | 1-methyl-1,2,3-triazol-4-yl | 2-THF | cyclopropyl |
| A-97. | 1-methyl-1,3-diazol-4-yl | Ph | phenyl |
| A-98. | 1-methyl-1,3-diazol-4-yl | 4-F—Ph | phenyl |
| A-99. | 1-methyl-1,3-diazol-4-yl | 2-THP | phenyl |
| A-100. | 1-methyl-1,3-diazol-4-yl | 2-THF | phenyl |
| A-101. | 1-methyl-1,2,3-triazol-4-yl | Ph | phenyl |
| A-102. | 1-methyl-1,2,3-triazol-4-yl | 4-F—Ph | phenyl |
| A-103. | 1-methyl-1,2,3-triazol-4-yl | 2-THP | phenyl |
| A-104. | 1-methyl-1,2,3-triazol-4-yl | 2-THF | phenyl |
| A-105. | 1-methyl-1,3-diazol-4-yl | Ph | 4-Cl-phenyl |
| A-106. | 1-methyl-1,3-diazol-4-yl | 4-F—Ph | 4-Cl-phenyl |
| A-107. | 1-methyl-1,3-diazol-4-yl | 2-THP | 4-Cl-phenyl |
| A-108. | 1-methyl-1,3-diazol-4-yl | 2-THF | 4-Cl-phenyl |
| A-109. | 1-methyl-1,2,3-triazol-4-yl | Ph | 4-Cl-phenyl |
| A-110. | 1-methyl-1,2,3-triazol-4-yl | 4-F—Ph | 4-Cl-phenyl |
| A-111. | 1-methyl-1,2,3-triazol-4-yl | 2-THP | 4-Cl-phenyl |
| A-112. | 1-methyl-1,2,3-triazol-4-yl | 2-THF | 4-Cl-phenyl |
| A-113. | 1-methyl-1,3-diazol-4-yl | Ph | 3-Cl-phenyl |
| A-114. | 1-methyl-1,3-diazol-4-y1 | 4-F—Ph | 3-Cl-phenyl |
| A-115. | 1-methyl-1,3-diazol-4-yl | 2-THP | 3-Cl-phenyl |
| A-116. | 1-methyl-1,3-diazol-4-yl | 2-THF | 3-Cl-phenyl |
| A-117. | 1-methyl-1,2,3-triazol-4-yl | Ph | 3-Cl-phenyl |
| A-118. | 1-methyl-1,2,3-triazol-4-yl | 4-F—Ph | 3-Cl-phenyl |
| A-119. | 1-methyl-1,2,3-triazol-4-yl | 2-THP | 3-Cl-phenyl |
| A-120. | 1-methyl-1,2,3-triazol-4-yl | 2-THF | 3-Cl-phenyl |
| A-121. | 1-methyl-1,3-diazol-4-yl | Ph | 4-F-phenyl |
| A-122. | 1-methyl-1,3-diazol-4-yl | 4-F—Ph | 4-F-phenyl |
| A-123. | 1-methyl-1,3-diazol-4-yl | 2-THP | 4-F-phenyl |
| A-124. | 1-methyl-1,3-diazol-4-yl | 2-THF | 4-F-phenyl |
| A-125. | 1-methyl-1,2,3-triazol-4-yl | Ph | 4-F-phenyl |
| A-126. | 1-methyl-1,2,3-triazol-4-yl | 4-F—Ph | 4-F-phenyl |
| A-127. | 1-methyl-1,2,3-triazol-4-yl | 2-THP | 4-F-phenyl |
| A-128. | 1-methyl-1,2,3-triazol-4-yl | 2-THF | 4-F-phenyl |
| A-129. | 1-methyl-1,3-diazol-4-yl | Ph | 3-F-phenyl |
| A-130. | 1-methyl-1,3-diazol-4-yl | 4-F—Ph | 3-F-phenyl |
| A-131. | 1-methyl-1,3-diazol-4-yl | 2-THP | 3-F-phenyl |
| A-132. | 1-methyl-1,3-diazol-4-yl | 2-THF | 3-F-phenyl |
| A-133. | 1-methyl-1,2,3-triazol-4-yl | Ph | 3-F-phenyl |
| A-134. | 1-methyl-1,2,3-triazol-4-yl | 4-F—Ph | 3-F-phenyl |
| A-135. | 1-methyl-1,2,3-triazol-4-yl | 2-THP | 3-F-phenyl |
| A-136. | 1-methyl-1,2,3-triazol-4-yl | 2-THF | 3-F-phenyl |
| A-137. | 1-methyl-1,3-diazol-4-yl | Ph | 2-F-phenyl |
| A-138. | 1-methyl-1,3-diazol-4-yl | 4-F—Ph | 2-F-phenyl |
| A-139. | 1-methyl-1,3-diazol-4-yl | 2-THP | 2-F-phenyl |
| A-140. | 1-methyl-1,3-diazol-4-yl | 2-THF | 2-F-phenyl |
| A-141. | 1-methyl-1,2,3-triazol-4-yl | Ph | 2-F-phenyl |
| A-142. | 1-methyl-1,2,3-triazol-4-yl | 4-F—Ph | 2-F-phenyl |
| A-143. | 1-methyl-1,2,3-triazol-4-yl | 2-THP | 2-F-phenyl |
| A-144. | 1-methyl-1,2,3-triazol-4-yl | 2-THF | 2-F-phenyl |
| A-145. | 1-methyl-1,3-diazol-4-yl | Ph | 2-Me-phenyl |
| A-146. | 1-methyl-1,3-diazol-4-yl | 4-F—Ph | 2-Me-phenyl |
| A-147. | 1-methyl-1,3-diazol-4-yl | 2-THP | 2-Me-phenyl |
| A-148. | 1-methyl-1,3-diazol-4-yl | 2-THF | 2-Me-phenyl |
| A-149. | 1-methyl-1,2,3-triazol-4-yl | Ph | 2-Me-phenyl |
| A-150. | 1-methyl-1,2,3-triazol-4-yl | 4-F—Ph | 2-Me-phenyl |
| A-151. | 1-methyl-1,2,3-triazol-4-yl | 2-THP | 2-Me-phenyl |
| A-152. | 1-methyl-1,2,3-triazol-4-yl | 2-THF | 2-Me-phenyl |
| A-153. | 1-methyl-1,3-diazol-4-yl | Ph | 3-Me-phenyl |
| A-154. | 1-methyl-1,3-diazol-4-yl | 4-F—Ph | 3-Me-phenyl |
| A-155. | 1-methyl-1,3-diazol-4-yl | 2-THP | 3-Me-phenyl |
| A-156. | 1-methyl-1,3-diazol-4-yl | 2-THF | 3-Me-phenyl |
| A-157. | 1-methyl-1,2,3-triazol-4-yl | Ph | 3-Me-phenyl |
| A-158. | 1-methyl-1,2,3-triazol-4-yl | 4-F—Ph | 3-Me-phenyl |
| A-159. | 1-methyl-1,2,3-triazol-4-yl | 2-THP | 3-Me-phenyl |
| A-160. | 1-methyl-1,2,3-triazol-4-yl | 2-THF | 3-Me-phenyl |
| A-161. | 1-methyl-1,3-diazol-4-yl | Ph | 4-Me-phenyl |
| A-162. | 1-methyl-1,3-diazol-4-yl | 4-F—Ph | 4-Me-phenyl |
| A-163. | 1-methyl-1,3-diazol-4-yl | 2-THP | 4-Me-phenyl |
| A-164. | 1-methyl-1,3-diazol-4-yl | 2-THF | 4-Me-phenyl |
| A-165. | 1-methyl-1,2,3-triazol-4-yl | Ph | 4-Me-phenyl |
| A-166. | 1-methyl-1,2,3-triazol-4-yl | 4-F—Ph | 4-Me-phenyl |
| A-167. | 1-methyl-1,2,3-triazol-4-yl | 2-THP | 4-Me-phenyl |
| A-168. | 1-methyl-1,2,3-triazol-4-yl | 2-THF | 4-Me-phenyl |
| A-169. | 1-methyl-1,3-diazol-4-yl | Ph | —CN |
| A-170. | 1-methyl-1,3-diazol-4-yl | 4-F—Ph | —CN |
| A-171. | 1-methyl-1,3-diazol-4-yl | 2-THP | —CN |
| A-172. | 1-methyl-1,3-diazol-4-yl | 2-THF | —CN |
| A-173. | 1-methyl-1,2,3-triazol-4-yl | Ph | —CN |
| A-174. | 1-methyl-1,2,3-triazol-4-yl | 4-F—Ph | —CN |
| A-175. | 1-methyl-1,2,3-triazol-4-yl | 2-THP | —CN |
| A-176. | 1-methyl-1,2,3-triazol-4-yl | 2-THF | —CN |
| A-177. | 1-methyl-1,3-diazol-4-yl | Ph | —OCH₃ |
| A-178. | 1-methyl-1,3-diazol-4-yl | 4-F—Ph | —OCH₃ |
| A-179. | 1-methyl-1,3-diazol-4-yl | 2-THP | —OCH₃ |
| A-180. | 1-methyl-1,3-diazol-4-yl | 2-THF | —OCH₃ |
| A-181. | 1-methyl-1,2,3-triazol-4-yl | Ph | —OCH₃ |
| A-182. | 1-methyl-1,2,3-triazol-4-yl | 4-F—Ph | —OCH₃ |
| A-183. | 1-methyl-1,2,3-triazol-4-yl | 2-THP | —OCH₃ |
| A-184. | 1-methyl-1,2,3-triazol-4-yl | 2-THF | —OCH₃ |
| A-185. | 1-methyl-1,3-diazol-4-yl | Ph | —OCH₂CH₃ |
| A-186. | 1-methyl-1,3-diazol-4-yl | 4-F—Ph | —OCH₂CH₃ |
| A-187. | 1-methyl-1,3-diazol-4-yl | 2-THP | —OCH₂CH₃ |
| A-188. | 1-methyl-1,3-diazol-4-yl | 2-THF | —OCH₂CH₃ |
| A-189. | 1-methyl-1,2,3-triazol-4-yl | Ph | —OCH₂CH₃ |
| A-190. | 1-methyl-1,2,3-triazol-4-yl | 4-F—Ph | —OCH₂CH₃ |
| A-191. | 1-methyl-1,2,3-triazol-4-yl | 2-THP | —OCH₂CH₃ |
| A-192. | 1-methyl-1,2,3-triazol-4-yl | 2-THF | —OCH₂CH₃ |
| A-193. | 1-methyl-1,3-diazol-4-yl | Ph | —O(CH₂)₂CH₃ |
| A-194. | 1-methyl-1,3-diazol-4-yl | 4-F—Ph | —O(CH₂)₂CH₃ |
| A-195. | 1-methyl-1,3-diazol-4-yl | 2-THP | —O(CH₂)₂CH₃ |
| A-196. | 1-methyl-1,3-diazol-4-yl | 2-THF | —O(CH₂)₂CH₃ |
| A-197. | 1-methyl-1,2,3-triazol-4-yl | Ph | —O(CH₂)₂CH₃ |
| A-198. | 1-methyl-1,2,3-triazol-4-yl | 4-F—Ph | —O(CH₂)₂CH₃ |
| A-199. | 1-methyl-1,2,3-triazol-4-yl | 2-THP | —O(CH₂)₂CH₃ |
| A-200. | 1-methyl-1,2,3-triazol-4-yl | 2-THF | —O(CH₂)₂CH₃ |
| A-201. | 1-methyl-1,3-diazol-4-yl | Ph | —O(CH₂)₃CH₃ |
| A-202. | 1-methyl-1,3-diazol-4-yl | 4-F—Ph | —O(CH₂)₃CH₃ |
| A-203. | 1-methyl-1,3-diazol-4-yl | 2-THP | —O(CH₂)₃CH₃ |
| A-204. | 1-methyl-1,3-diazol-4-yl | 2-THF | —O(CH₂)₃CH₃ |
| A-205. | 1-methyl-1,2,3-triazol-4-yl | Ph | —O(CH₂)₃CH₃ |
| A-206. | 1-methyl-1,2,3-triazol-4-yl | 4-F—Ph | —O(CH₂)₃CH₃ |
| A-207. | 1-methyl-1,2,3-triazol-4-yl | 2-THP | —O(CH₂)₃CH₃ |
| A-208. | 1-methyl-1,2,3-triazol-4-yl | 2-THF | —O(CH₂)₃CH₃ |
| A-209. | 1-methyl-1,3-diazol-4-yl | Ph | —OCH(CH₃)₂ |
| A-210. | 1-methyl-1,3-diazol-4-yl | 4-F—Ph | —OCH(CH₃)₂ |
| A-211. | 1-methyl-1,3-diazol-4-yl | 2-THP | —OCH(CH₃)₂ |
| A-212. | 1-methyl-1,3-diazol-4-yl | 2-THF | —OCH(CH₃)₂ |

-continued

| | R¹ | R³ᵃ | R¹³ᵇ |
|---|---|---|---|
| A-213. | 1-methyl-1,2,3-triazol-4-yl | Ph | —OCH(CH₃)₂ |
| A-214. | 1-methyl-1,2,3-triazol-4-yl | 4-F—Ph | —OCH(CH₃)₂ |
| A-215. | 1-methyl-1,2,3-triazol-4-yl | 2-THP | —OCH(CH₃)₂ |
| A-216. | 1-methyl-1,2,3-triazol-4-yl | 2-THF | —OCH(CH₃)₂ |
| A-217. | 1-methyl-1,3-diazol-4-yl | Ph | —OCH₂(CH₃)₂ |
| A-218. | 1-methyl-1,3-diazol-4-yl | 4-F—Ph | —OCH₂(CH₃)₂ |
| A-219. | 1-methyl-1,3-diazol-4-yl | 2-THP | —OCH₂(CH₃)₂ |
| A-220. | 1-methyl-1,3-diazol-4-yl | 2-THF | —OCH₂(CH₃)₂ |
| A-221. | 1-methyl-1,2,3-triazol-4-yl | Ph | —OCH₂(CH₃)₂ |
| A-222. | 1-methyl-1,2,3-triazol-4-yl | 4-F—Ph | —OCH₂(CH₃)₂ |
| A-223. | 1-methyl-1,2,3-triazol-4-yl | 2-THP | —OCH₂(CH₃)₂ |
| A-224. | 1-methyl-1,2,3-triazol-4-yl | 2-THF | —OCH₂(CH₃)₂ |
| A-225. | 1-methyl-1,3-diazol-4-yl | Ph | —OCH₂(pyrrolyd-3yl) |
| A-226. | 1-methyl-1,3-diazol-4-yl | 4-F—Ph | —OCH₂(pyrrolyd-3yl) |
| A-227. | 1-methyl-1,3-diazol-4-yl | 2-THP | —OCH₂(pyrrolyd-3yl) |
| A-228. | 1-methyl-1,3-diazol-4-yl | 2-THF | —OCH₂(pyrrolyd-3yl) |
| A-229. | 1-methyl-1,2,3-triazol-4-yl | Ph | —OCH₂(pyrrolyd-3yl) |
| A-230. | 1-methyl-1,2,3-triazol-4-yl | 4-F—Ph | —OCH₂(pyrrolyd-3yl) |
| A-231. | 1-methyl-1,2,3-triazol-4-yl | 2-THP | —OCH₂(pyrrolyd-3yl) |
| A-232. | 1-methyl-1,2,3-triazol-4-yl | 2-THF | —OCH₂(pyrrolyd-3yl) |
| A-233. | 1-methyl-1,3-diazol-4-yl | Ph | —OCH₂(pyrrolyd-2yl) |
| A-234. | 1-methyl-1,3-diazol-4-yl | 4-F—Ph | —OCH₂(pyrrolyd-2yl) |
| A-235. | 1-methyl-1,3-diazol-4-yl | 2-THP | —OCH₂(pyrrolyd-2yl) |
| A-236. | 1-methyl-1,3-diazol-4-yl | 2-THF | —OCH₂(pyrrolyd-2yl) |
| A-237. | 1-methyl-1,2,3-triazol-4-yl | Ph | —OCH₂(pyrrolyd-2yl) |
| A-238. | 1-methyl-1,2,3-triazol-4-yl | 4-F—Ph | —OCH₂(pyrrolyd-2yl) |
| A-239. | 1-methyl-1,2,3-triazol-4-yl | 2-THP | —OCH₂(pyrrolyd-2yl) |
| A-240. | 1-methyl-1,2,3-triazol-4-yl | 2-THF | —OCH₂(pyrrolyd-2yl) |
| A-241. | 1-methyl-1,3-diazol-4-yl | Ph | —OCH₂(azetid-3yl) |
| A-242. | 1-methyl-1,3-diazol-4-yl | 4-F—Ph | —OCH₂(azetid-3yl) |
| A-243. | 1-methyl-1,3-diazol-4-yl | 2-THP | —OCH₂(azetid-3yl) |
| A-244. | 1-methyl-1,3-diazol-4-yl | 2-THF | —OCH₂(azetid-3yl) |
| A-245. | 1-methyl-1,2,3-triazol-4-yl | Ph | —OCH₂(azetid-3yl) |
| A-246. | 1-methyl-1,2,3-triazol-4-yl | 4-F—Ph | —OCH₂(azetid-3yl) |
| A-247. | 1-methyl-1,2,3-triazol-4-yl | 2-THP | —OCH₂(azetid-3yl) |
| A-248. | 1-methyl-1,2,3-triazol-4-yl | 2-THF | —OCH₂(azetid-3yl) |
| A-249. | 1-methyl-1,3-diazol-4-yl | Ph | —OCF₃ |
| A-250. | 1-methyl-1,3-diazol-4-yl | 4-F—Ph | —OCF₃ |
| A-251. | 1-methyl-1,3-diazol-4-yl | 2-THP | —OCF₃ |
| A-252. | 1-methyl-1,3-diazol-4-yl | 2-THF | —OCF₃ |
| A-253. | 1-methyl-1,2,3-triazol-4-yl | Ph | —OCF₃ |
| A-254. | 1-methyl-1,2,3-triazol-4-yl | 4-F—Ph | —OCF₃ |
| A-255. | 1-methyl-1,2,3-triazol-4-yl | 2-THP | —OCF₃ |
| A-256. | 1-methyl-1,2,3-triazol-4-yl | 2-THF | —OCF₃ |
| A-257. | 1-methyl-1,3-diazol-4-yl | Ph | —OCH₂CF₃ |
| A-258. | 1-methyl-1,3-diazol-4-yl | 4-F—Ph | —OCH₂CF₃ |
| A-259. | 1-methyl-1,3-diazol-4-yl | 2-THP | —OCH₂CF₃ |
| A-260. | 1-methyl-1,3-diazol-4-yl | 2-THF | —OCH₂CF₃ |
| A-261. | 1-methyl-1,2,3-triazol-4-yl | Ph | —OCH₂CF₃ |
| A-262. | 1-methyl-1,2,3-triazol-4-yl | 4-F—Ph | —OCH₂CF₃ |
| A-263. | 1-methyl-1,2,3-triazol-4-yl | 2-THP | —OCH₂CF₃ |
| A-264. | 1-methyl-1,2,3-triazol-4-yl | 2-THF | —OCH₂CF₃ |
| A-265. | 1-methyl-1,3-diazol-4-yl | Ph | —O-cyclobutyl |
| A-266. | 1-methyl-1,3-diazol-4-yl | 4-F—Ph | —O-cyclobutyl |
| A-267. | 1-methyl-1,3-diazol-4-yl | 2-THP | —O-cyclobutyl |
| A-268. | 1-methyl-1,3-diazol-4-yl | 2-THF | —O-cyclobutyl |
| A-269. | 1-methyl-1,2,3-triazol-4-yl | Ph | —O-cyclobutyl |
| A-270. | 1-methyl-1,2,3-triazol-4-yl | 4-F—Ph | —O-cyclobutyl |
| A-271. | 1-methyl-1,2,3-triazol-4-yl | 2-THP | —O-cyclobutyl |
| A-272. | 1-methyl-1,2,3-triazol-4-yl | 2-THF | —O-cyclobutyl |
| A-273. | 1-methyl-1,3-diazol-4-yl | Ph | —O-cyclopentyl |
| A-274. | 1-methyl-1,3-diazol-4-yl | 4-F—Ph | —O-cyclopentyl |
| A-275. | 1-methyl-1,3-diazol-4-yl | 2-THP | —O-cyclopentyl |
| A-276. | 1-methyl-1,3-diazol-4-yl | 2-THF | —O-cyclopentyl |
| A-277. | 1-methyl-1,2,3-triazol-4-yl | Ph | —O-cyclopentyl |
| A-278. | 1-methyl-1,2,3-triazol-4-yl | 4-F—Ph | —O-cyclopentyl |
| A-279. | 1-methyl-1,2,3-triazol-4-yl | 2-THP | —O-cyclopentyl |
| A-280. | 1-methyl-1,2,3-triazol-4-yl | 2-THF | —O-cyclopentyl |
| A-281. | 1-methyl-1,3-diazol-4-yl | Ph | —O-cyclohexyl |
| A-282. | 1-methyl-1,3-diazol-4-yl | 4-F—Ph | —O-cyclohexyl |
| A-283. | 1-methyl-1,3-diazol-4-yl | 2-THP | —O-cyclohexyl |
| A-284. | 1-methyl-1,3-diazol-4-yl | 2-THF | —O-cyclohexyl |
| A-285. | 1-methyl-1,2,3-triazol-4-yl | Ph | —O-cyclohexyl |
| A-286. | 1-methyl-1,2,3-triazol-4-yl | 4-F—Ph | —O-cyclohexyl |
| A-287. | 1-methyl-1,2,3-triazol-4-yl | 2-THP | —O-cyclohexyl |
| A-288. | 1-methyl-1,2,3-triazol-4-yl | 2-THF | —O-cyclohexyl |
| A-289. | 1-methyl-1,3-diazol-4-yl | Ph | —OCH₂Ph |
| A-290. | 1-methyl-1,3-diazol-4-yl | 4-F—Ph | —OCH₂Ph |
| A-291. | 1-methyl-1,3-diazol-4-yl | 2-THP | —OCH₂Ph |
| A-292. | 1-methyl-1,3-diazol-4-yl | 2-THF | —OCH₂Ph |
| A-293. | 1-methyl-1,2,3-triazol-4-yl | Ph | —OCH₂Ph |
| A-294. | 1-methyl-1,2,3-triazol-4-yl | 4-F—Ph | —OCH₂Ph |
| A-295. | 1-methyl-1,2,3-triazol-4-yl | 2-THP | —OCH₂Ph |
| A-296. | 1-methyl-1,2,3-triazol-4-yl | 2-THF | —OCH₂Ph |
| A-297. | 1-methyl-1,3-diazol-4-yl | Ph | —SO₂Me |
| A-298. | 1-methyl-1,3-diazol-4-yl | 4-F—Ph | —SO₂Me |
| A-299. | 1-methyl-1,3-diazol-4-yl | 2-THP | —SO₂Me |
| A-300. | 1-methyl-1,3-diazol-4-yl | 2-THF | —SO₂Me |
| A-301. | 1-methyl-1,2,3-triazol-4-yl | Ph | —SO₂Me |
| A-302. | 1-methyl-1,2,3-triazol-4-yl | 4-F—Ph | —SO₂Me |
| A-303. | 1-methyl-1,2,3-triazol-4-yl | 2-THP | —SO₂Me |
| A-304. | 1-methyl-1,2,3-triazol-4-yl | 2-THF | —SO₂Me |
| A-305. | 1-methyl-1,3-diazol-4-yl | Ph | 2-pyridyl |
| A-306. | 1-methyl-1,3-diazol-4-yl | 4-F—Ph | 2-pyridyl |
| A-307. | 1-methyl-1,3-diazol-4-yl | 2-THP | 2-pyridyl |
| A-308. | 1-methyl-1,3-diazol-4-yl | 2-THF | 2-pyridyl |
| A-309. | 1-methyl-1,2,3-triazol-4-yl | Ph | 2-pyridyl |
| A-310. | 1-methyl-1,2,3-triazol-4-yl | 4-F—Ph | 2-pyridyl |
| A-311. | 1-methyl-1,2,3-triazol-4-yl | 2-THP | 2-pyridyl |
| A-312. | 1-methyl-1,2,3-triazol-4-yl | 2-THF | 2-pyridyl |
| A-313. | 1-methyl-1,3-diazol-4-yl | Ph | 3-pyridyl |
| A-314. | 1-methyl-1,3-diazol-4-yl | 4-F—Ph | 3-pyridyl |
| A-315. | 1-methyl-1,3-diazol-4-yl | 2-THP | 3-pyridyl |
| A-316. | 1-methyl-1,3-diazol-4-yl | 2-THF | 3-pyridyl |
| A-317. | 1-methyl-1,2,3-triazol-4-yl | Ph | 3-pyridyl |
| A-318. | 1-methyl-1,2,3-triazol-4-yl | 4-F—Ph | 3-pyridyl |
| A-319. | 1-methyl-1,2,3-triazol-4-yl | 2-THP | 3-pyridyl |
| A-320. | 1-methyl-1,2,3-triazol-4-yl | 2-THF | 3-pyridyl |
| A-321. | 1-methyl-1,3-diazol-4-yl | Ph | 4-pyridyl |
| A-322. | 1-methyl-1,3-diazol-4-yl | 4-F—Ph | 4-pyridyl |
| A-323. | 1-methyl-1,3-diazol-4-yl | 2-THP | 4-pyridyl |
| A-324. | 1-methyl-1,3-diazol-4-yl | 2-THF | 4-pyridyl |
| A-325. | 1-methyl-1,2,3-triazol-4-yl | Ph | 4-pyridyl |
| A-326. | 1-methyl-1,2,3-triazol-4-yl | 4-F—Ph | 4-pyridyl |
| A-327. | 1-methyl-1,2,3-triazol-4-yl | 2-THP | 4-pyridyl |
| A-328. | 1-methyl-1,2,3-triazol-4-yl | 2-THF | 4-pyridyl |
| A-329. | 1-methyl-1,3-diazol-4-yl | Ph | 5-pyrimidyl |
| A-330. | 1-methyl-1,3-diazol-4-yl | 4-F—Ph | 5-pyrimidyl |
| A-331. | 1-methyl-1,3-diazol-4-yl | 2-THP | 5-pyrimidyl |
| A-332. | 1-methyl-1,3-diazol-4-y1 | 2-THF | 5-pyrimidyl |
| A-333. | 1-methyl-1,2,3-triazol-4-yl | Ph | 5-pyrimidyl |
| A-334. | 1-methyl-1,2,3-triazol-4-yl | 4-F—Ph | 5-pyrimidyl |
| A-335. | 1-methyl-1,2,3-triazol-4-yl | 2-THP | 5-pyrimidyl |
| A-336. | 1-methyl-1,2,3-triazol-4-yl | 2-THF | 5-pyrimidyl |
| A-337. | 1-methyl-1,3-diazol-4-yl | Ph | 4-piperidyl |
| A-338. | 1-methyl-1,3-diazol-4-yl | 4-F—Ph | 4-piperidyl |
| A-339. | 1-methyl-1,3-diazol-4-yl | 2-THP | 4-piperidyl |
| A-340. | 1-methyl-1,3-diazol-4-yl | 2-THF | 4-piperidyl |
| A-341. | 1-methyl-1,2,3-triazol-4-yl | Ph | 4-piperidyl |
| A-342. | 1-methyl-1,2,3-triazol-4-yl | 4-F—Ph | 4-piperidyl |
| A-343. | 1-methyl-1,2,3-triazol-4-yl | 2-THP | 4-piperidyl |
| A-344. | 1-methyl-1,2,3-triazol-4-yl | 2-THF | 4-piperidyl |

Further particular compounds of the present invention are the pyrrolidine derivatives disclosed in preparation examples and physiologically tolerated salts thereof. These include for each preparation example the exemplified compound as well as the corresponding free base and any other physiologically tolerated salts of the free base (if the exemplified compound is a salt), or any physiologically tolerated salt of the free base (if the exemplified compound is a free base). These further include enantiomers, diastereomers, tautomers and any other isomeric forms of said compounds, be they explicitly or implicitly disclosed.

It is noted that the following compounds of formula (II)
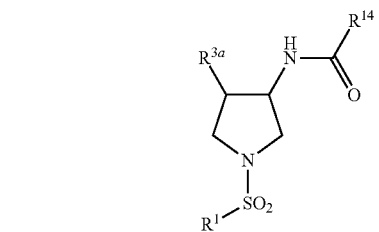
wherein $R^1$, $R^{3a}$ and $R^{14}$ are as defined in the following table -continued

| R$^1$ | R$^{3a}$ | R$^{14}$ |
| --- | --- | --- |
| 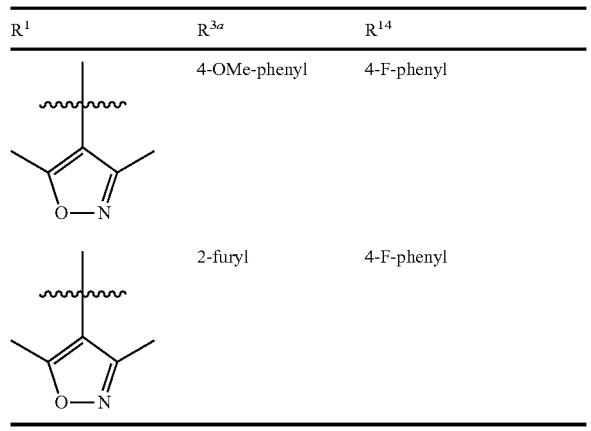 | 4-OMe-phenyl | 4-F-phenyl |
| | 2-furyl | 4-F-phenyl | are described in Baumann Marcus, et al., ACS Comb. Sci. 2011, 13, 405-413 and therefore the present invention does not encompass these compounds and physiologically tolerated salts thereof per se. However, the present invention does encompass pharmaceutical compositions comprising such pyrrolidine derivatives, and the use of such pyrrolidine derivatives for therapeutic purposes, as described herein.

The compounds of the formula (I) can be prepared by analogy to methods which are well known in the art. Suitable methods for the preparation of compounds of formula (I) are outlined in the following schemes.

The process depicted in scheme 1 is useful for obtaining pyrrolidine derivatives, wherein $Y^1$ is >CH— and $R^4$ is —N(CR$^{9a}$R$^{9b}$)$_{n4}$R$^{13}$, —NHCOR$^{14}$ or —NHCONHR$^{16a}$.

Scheme 1.

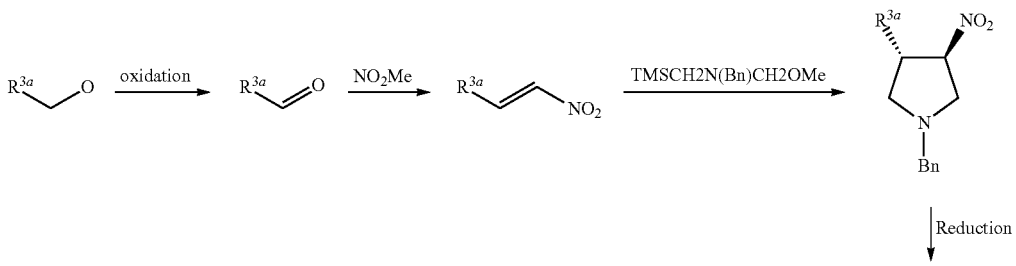

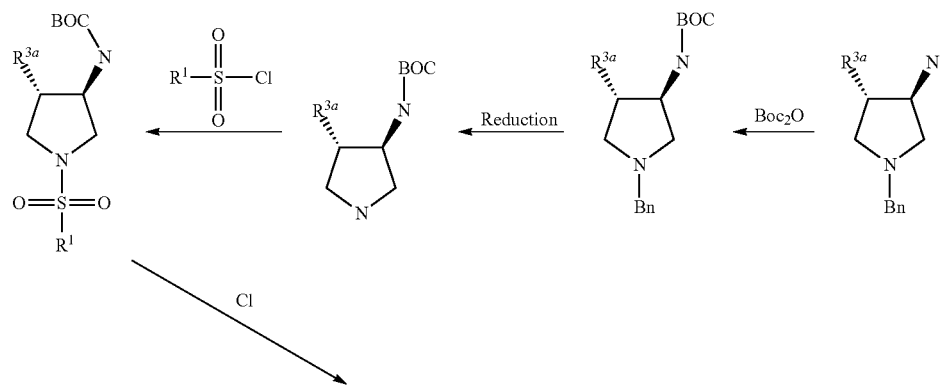

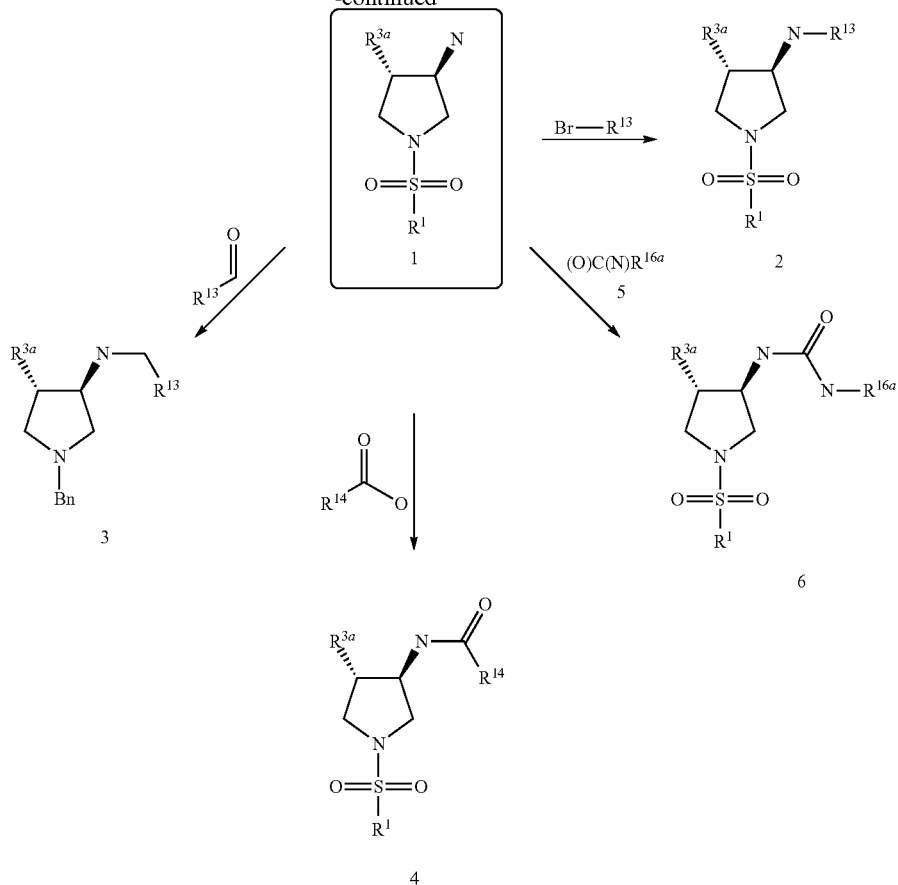

In scheme 1, the variables $R^1$, $R^{3a}$, $R^{13}$, $R^{14}$, $R^{16a}$ are as defined herein.

As shown in the above scheme 1, the intermediate of general formula 1 can be alkylated to give compounds of formula 2. Alternatively, 1 can be transformed to compounds 3 via reductive amination or can yield amides of formula 4 by coupling reaction with the corresponding acid. Reaction with isocyanates of formula 5 affords compounds of formula 6.

The process depicted in scheme 2 is useful for obtaining pyrrolidine derivatives, wherein $Y^1$ is >CH— and $R^4$ is —$(CR^{7c}R^{7d})_{n2}NR^{11a}R^{11b}$ or —$CONR^{20a}R^{20b}$.

Scheme 2.

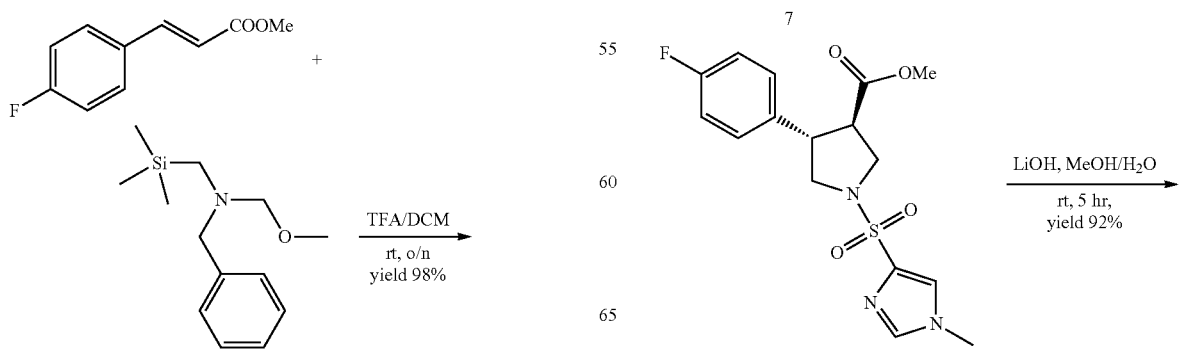

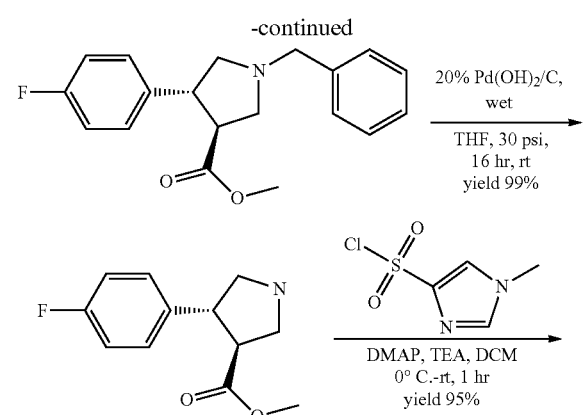

Scheme 3.

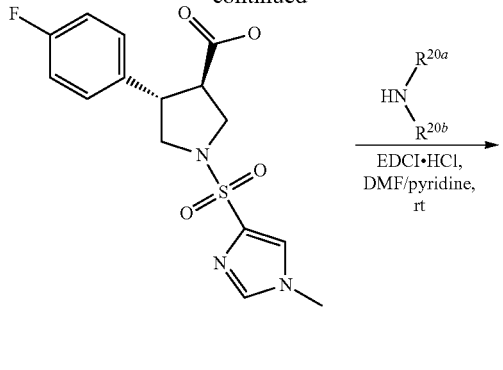

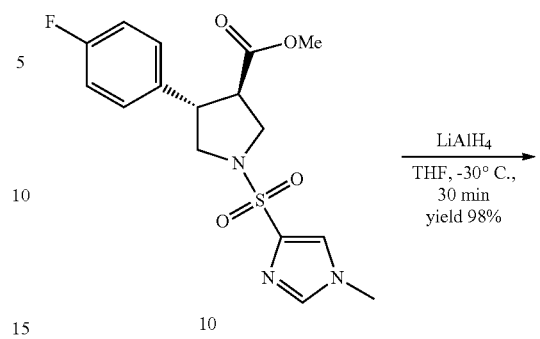

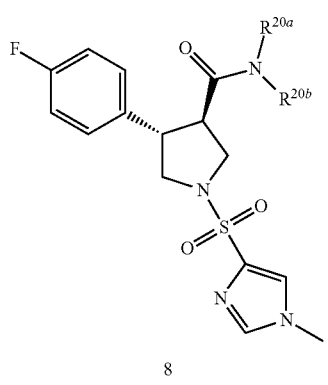

8
$R^{20b} = H$
$R^{20a} = Ar$

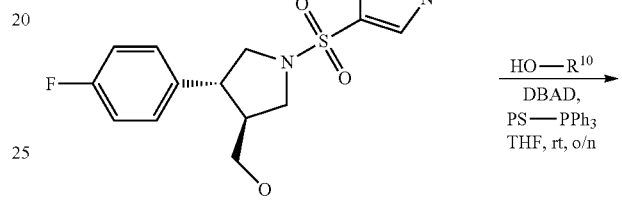

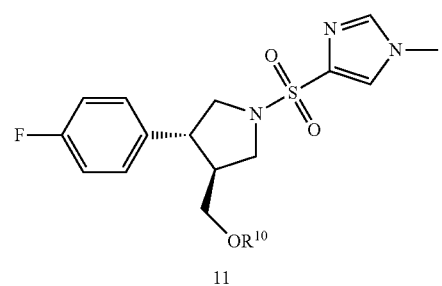

11
$R^{10} = Ar$

As shown in the above scheme 3, reduction with LiAlH$_4$ of intermediate 10 affords the corresponding alcohol which then can be transformed in the alkoxy derivatives of formula 11 via Mitsunobu coupling.

The process depicted in scheme 4 is useful for obtaining pyrrolidine derivatives, wherein $Y^1$ is >CH— and $R^4$ is —COR$^{19}$.

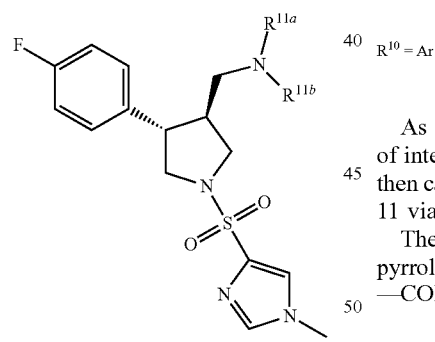

9
$R^{11b} = H$
$R^{11a} = Ar$

As shown in the above scheme 2, cycloaddition followed by benzyl deprotection afford pyrrolidine 7. Sulfonylation, methylester hydrolysis and coupling with amines yield compounds of formula 8. Reduction of compounds of formula 8 affords the corresponding amines 9.

The process depicted in scheme 3 is useful for obtaining pyrrolidine derivatives, wherein $Y^1$ is >CH— and $R^4$ is —(CR$^{7a}$R$^{7b}$)$_{n1}$NR$^{10}$.

Scheme 4.

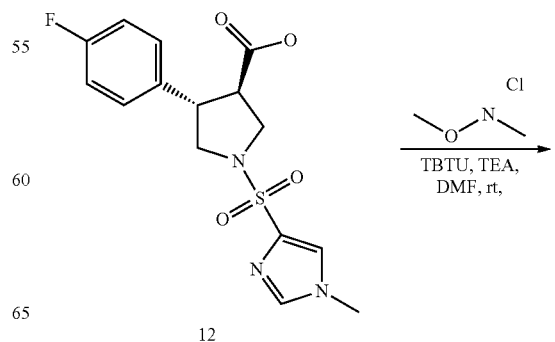

12

157
-continued

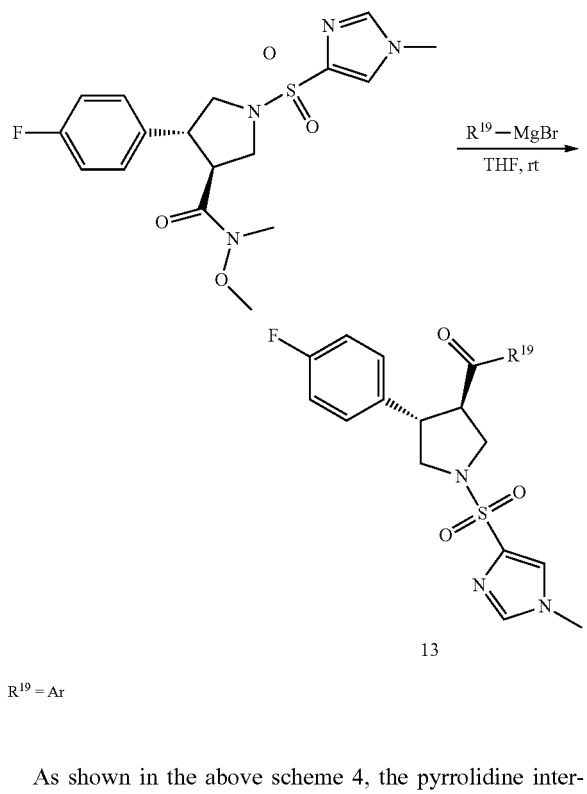

$R^{19} = Ar$

As shown in the above scheme 4, the pyrrolidine intermediate 12 can be converted in the corresponding Weinreb amide. Treatment of the Weinreb amide with Grignard reagents affords the ketones of formula 13.

The process depicted in scheme 5 is useful for obtaining pyrrolidine derivatives, wherein $Y^1$ is >CH— and $R^4$ is —O(CR$^{9c}$R$^{9d}$)$_{n5}$R$^{18}$.

Scheme 5.

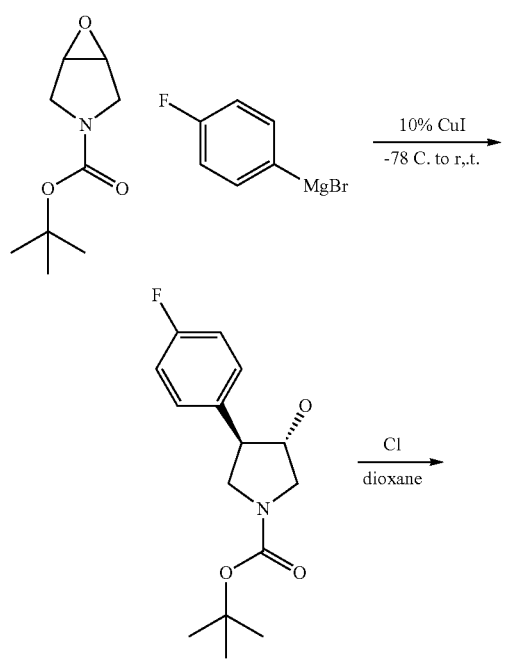

158
-continued

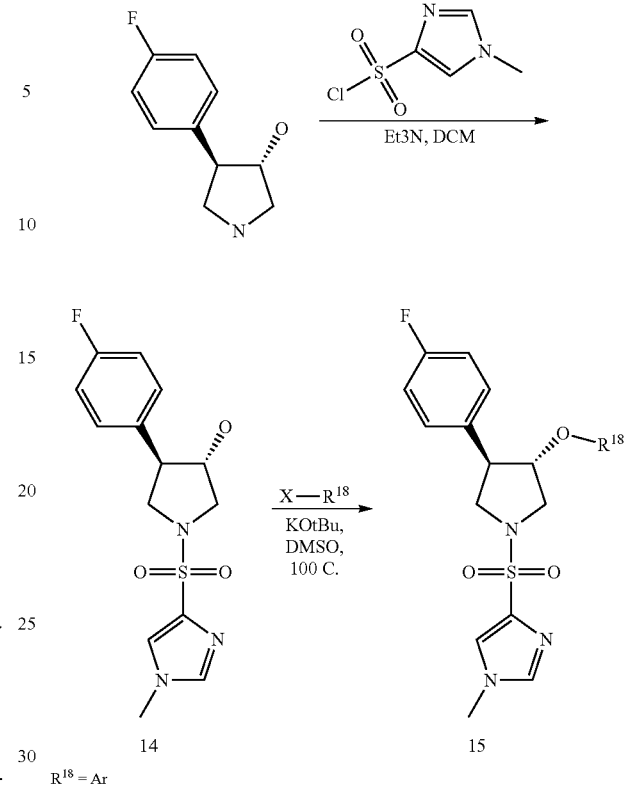

$R^{18} = Ar$

As shown in the above scheme 5, alkylation of alcohol 14 affords the compounds of formula 15.

The process depicted in scheme 6 is useful for obtaining pyrrolidine derivatives, wherein $Y^1$ is >CH—, $R^4$ is —N(CR$^{9a}$R$^{9b}$)$_{n4}$R$^{13}$ and R$^{3a}$ or R$^{3b}$ is $C_3$-$C_{12}$-heterocyclyl.

Scheme 6

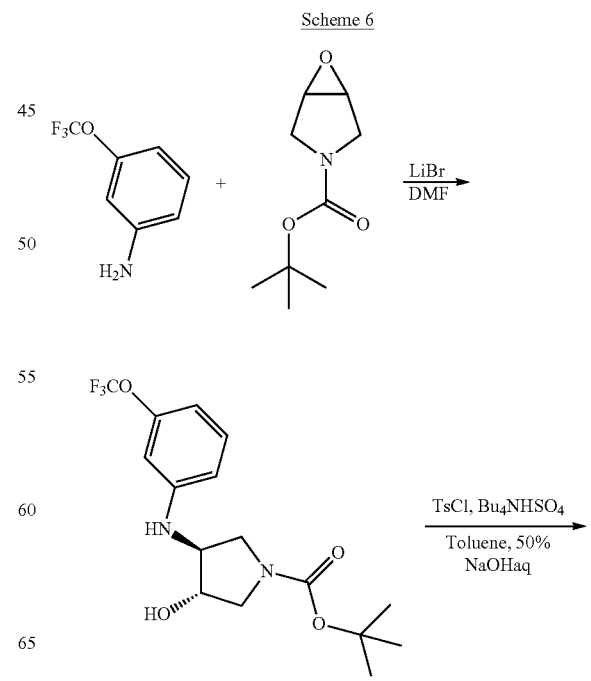

159
-continued
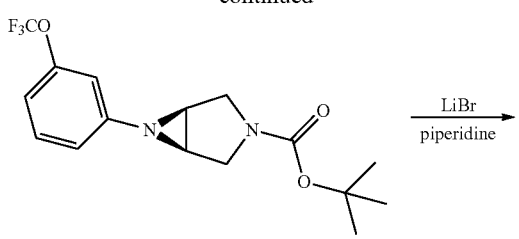
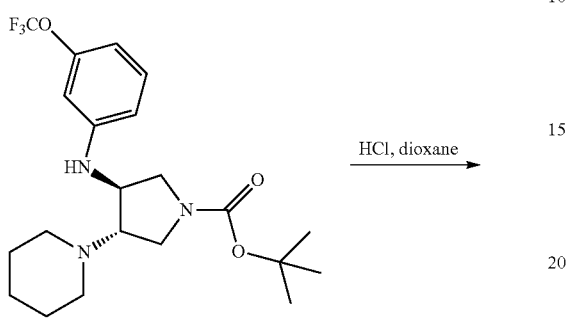
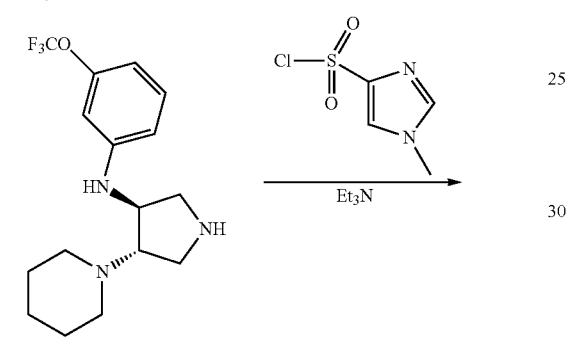
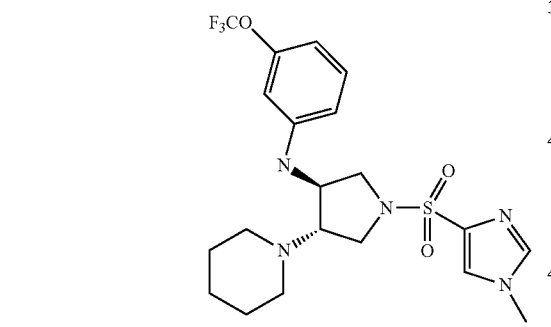
The process depicted in scheme 7 is useful for obtaining pyrrolidine derivatives, wherein $Y^1$ is >CH—, and $R^{3a}$ or $R^{3b}$ is optionally substituted $C_3$-$C_{12}$-heterocyclyl.
Scheme 7
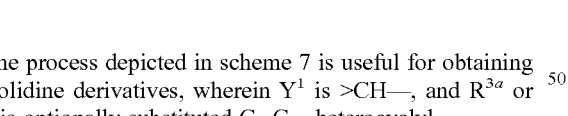
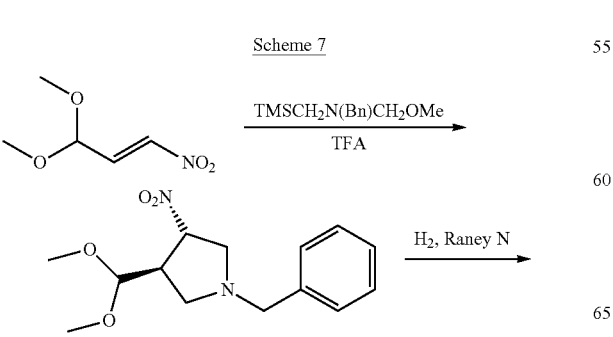
160
-continued

-continued

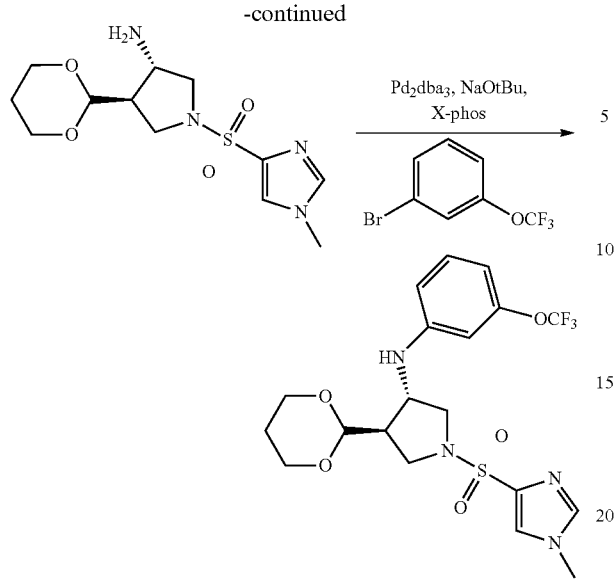
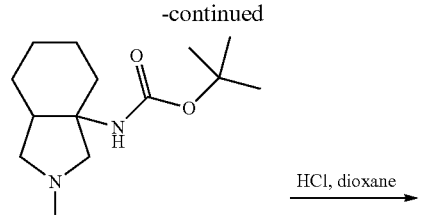

The process depicted in scheme 8 is useful for obtaining pyrrolidine derivatives, wherein $Y^1$ is $>CR^6—$ and $R^6$ and $R^{3a}$ or $R^{3b}$ together are optionally substituted $C_1$-$C_5$-alkylene.

Scheme 8

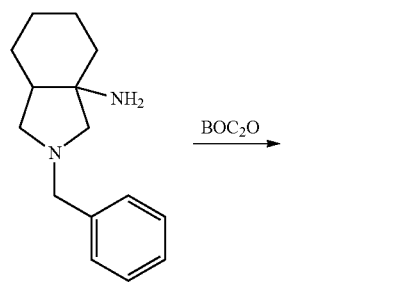

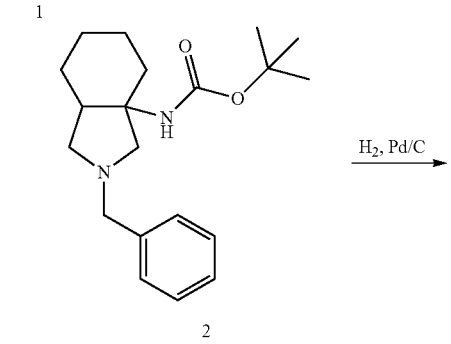

-continued

The processes depicted in schemes 9 and 10 are useful for obtaining pyrrolidine derivatives, wherein $Y^1$ is $>CR^6—$ and $R^6$ is $C_1$-$C_4$-alkylene that is bound to a carbon atom in $R^{3a}$, and $R^{3a}$ is an optionally substituted $C_6$-$C_{12}$-aryl or an optionally substituted $C_3$-$C_{12}$-heterocyclyl.

Scheme 9

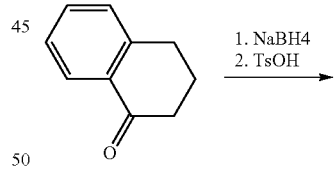

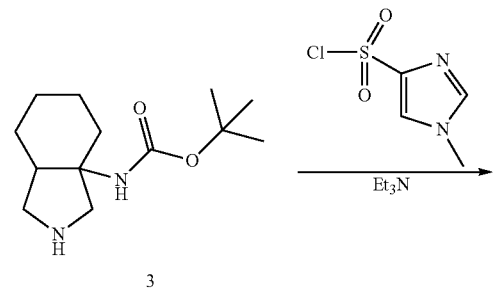

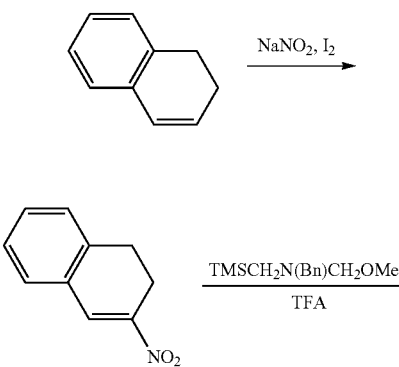

163
-continued
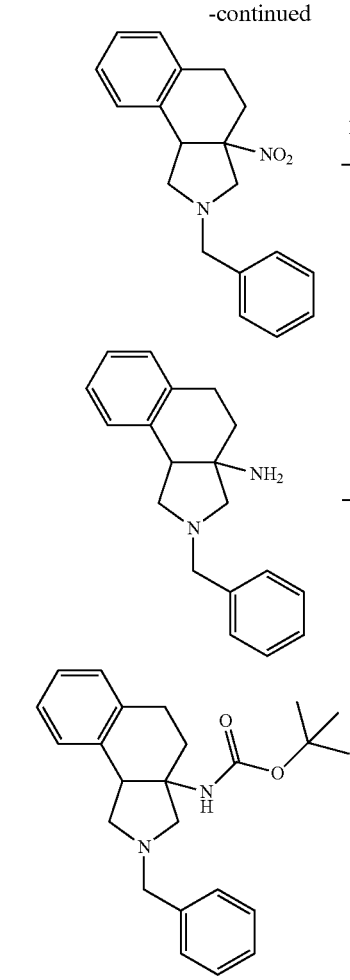
164
-continued
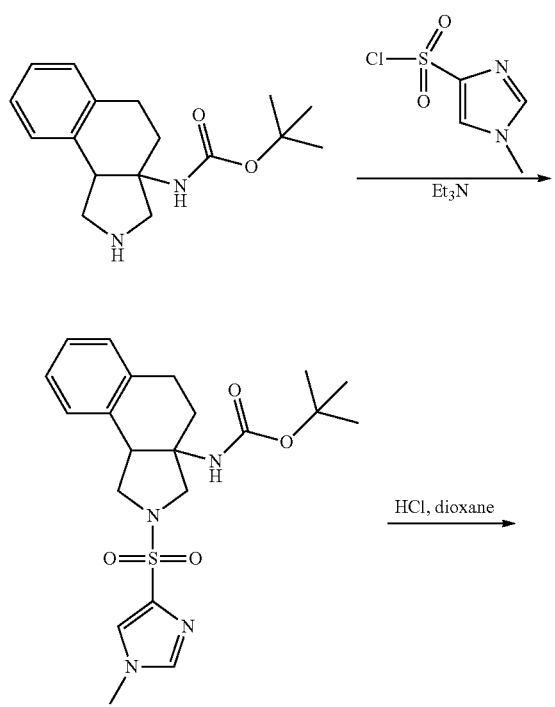
Scheme 10
The process depicted in scheme 11 is useful for obtaining pyrrolidine derivatives, wherein $Y^1$ is >CH—, $R^4$ is —$COR^{19}$ and $R^{3a}$ and $R^{3b}$ together are optionally substituted $C_2$-$C_5$-alkylene.
Scheme 11
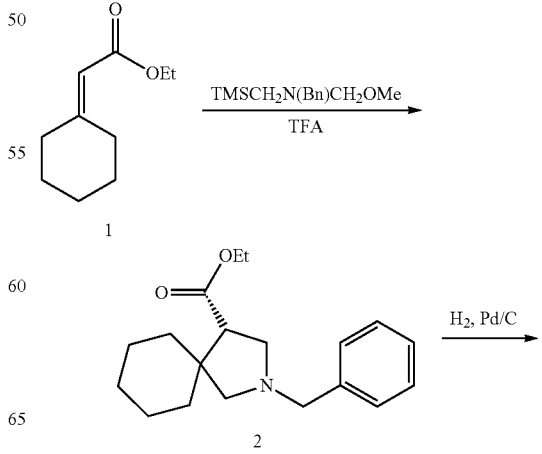

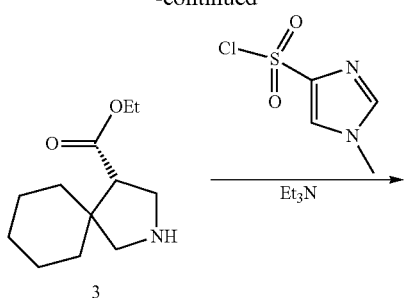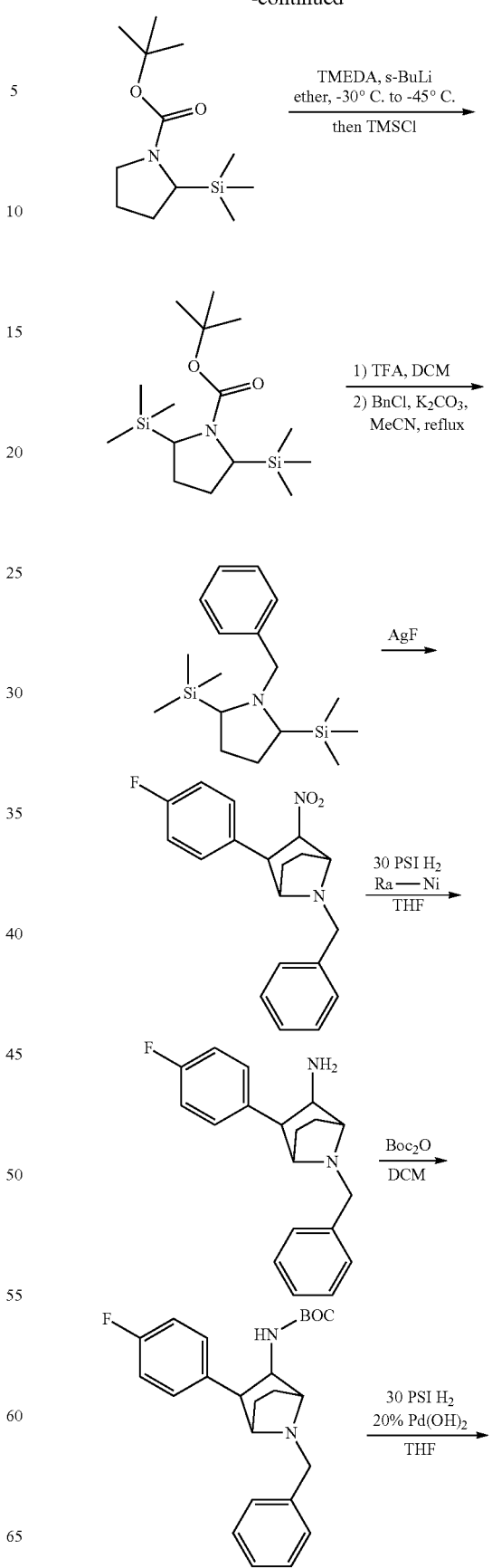
The process depicted in scheme 12 is useful for obtaining pyrrolidine derivatives, wherein $Y^1$ is >CH—, $R^4$ is —N(CR$^{9a}$R$^{9b}$)$_4$R$^{13}$ and one of R$^{2a}$ or R$^{2b}$ and one of R$^{5a}$ or R$^{5b}$ together are optionally substituted C$_1$-C$_5$-alkylene.
Scheme 12
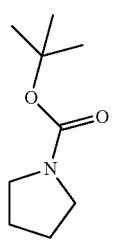

167
-continued
168
Scheme 13
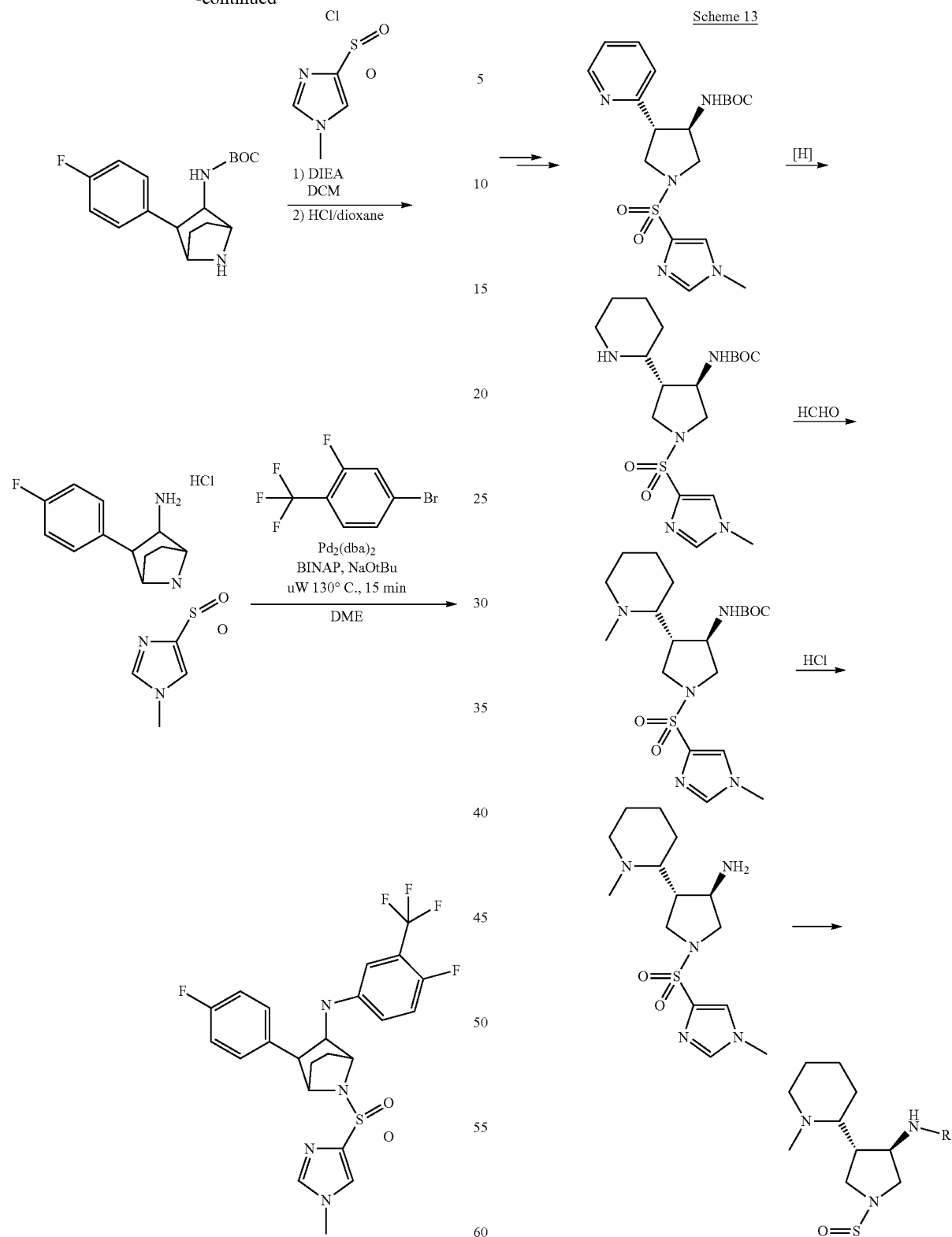
The process depicted in scheme 13 is useful for obtaining pyrrolidine derivatives, wherein $Y^1$ is >CH—, $R^4$ is —N(CR$^{9a}$R$^{9b}$)$_{n4}$R$^{13}$ and R$^{3a}$ or R$^{3b}$ is optionally substituted $C_3$-$C_{12}$-heterocyclyl.
The process depicted in scheme 14 is useful for obtaining pyrrolidine derivatives, wherein $Y^1$ is >CH— and R$^{3a}$ and one of R²ᵃ or R²ᵇ together with the carbon atoms to which they are bound form an anellated $C_6$-$C_{12}$-aryl.

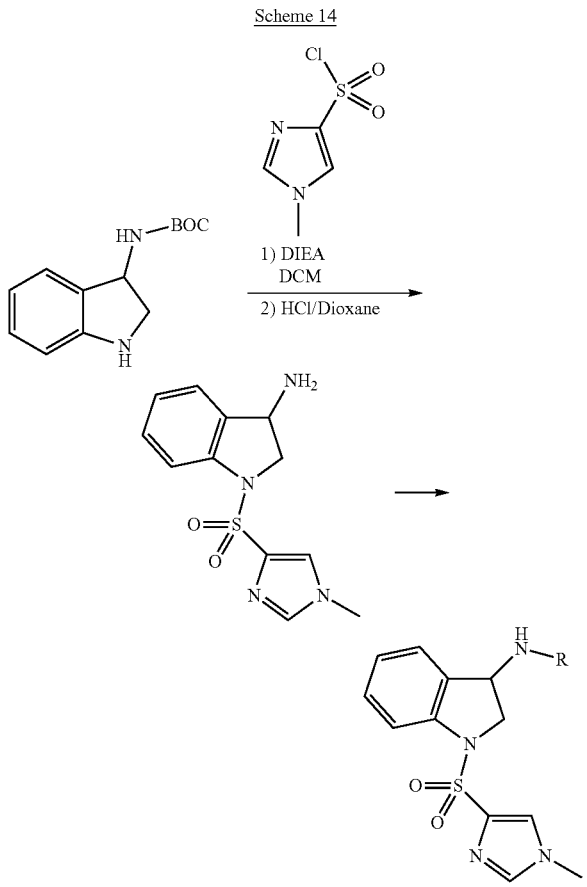

Scheme 14

Schemes 1 to 14 refer also to the preparation of the enantiomers, diastereomers, tautomers and any other isomeric forms of said compounds, be they explicitly or implicitly disclosed.

The acid addition salts of the pyrrolidine derivatives of formula (I) are prepared in a customary manner by mixing the free base with a corresponding acid, optionally in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of the formula (I) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by methodology known in the art. For instance, human GlyT1c expressing recombinant hGlyT1c_5_CHO cells can be used for measuring glycine uptake and its inhibition ($IC_{50}$) by a compound of formula (I).

Amongst the compounds of the formula (I) those are preferred which achieve effective inhibition at low concentrations. In particular, compounds of the formula (I) are preferred which inhibit glycine transporter 1 (GlyT1) at a level of $IC_{50}$<1 µMol, more preferably at a level of $IC_{50}$<0.5 µMol, particularly preferably at a level of $IC_{50}$<0.2 µMol and most preferably at a level of $IC_{50}$<0.1 µMol.

The compounds of formula (I) display good to moderate metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in therapeutic treatment. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

Amongst the compounds of the formula (I) those are particularly preferred which display good to moderate metabolic stability towards human liver microsomes. In particular, compounds of the formula (I) are preferred which display a microsomal clearance at a level of mCl<1000 µl/min/mg (mClint,u<500 L/h/kg), more preferably at a level of mCl<500 µl/min/mg (mClint,u<100 L/h/kg), particularly preferably at a level of mCl<100 µl/min/mg (mClint,u<50 L/h/kg) and most preferably at a level of mCl<50 µl/min/mg (mClint,u<5 L/h/kg).

Further, compounds of formula (I) exhibit favorable efflux properties which may lead to enhanced oral bioavailability and/or increased brain availability. According to a particular embodiment, compounds of the invention combine high affinity and high metabolic stability with favorable efflux properties.

The efflux properties of a compound can be measured in well-known assays (e.g. Caco-2, MDCK assay).

The compounds of the formula (I) according to the present invention are thus useful as pharmaceuticals.

The present invention therefore also relates to pharmaceutical compositions which comprise an inert carrier and a compound of the formula (I).

The present invention also relates to the use of the compounds of the formula (I) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Glycine transport inhibitors and in particular inhibitors of the glycine transporter GlyT1 are thus known to be useful in treating a variety of neurologic and psychiatric disorders. Further, glycine A receptors play a role in a variety of diseases in humans or other species. Increasing extracellular glycine concentrations by inhibiting glycine transport may enhance the activity of glycine A receptors. Glycine transport inhibitors and in particular inhibitors of the glycine transporter GlyT1 are thus useful in treating a variety of neurologic and psychiatric disorders.

The present invention thus further relates to the use of the compounds of the formula (I) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

According to a further particular embodiment, the disorder is pain, in particular chronic pain and especially neuropathic pain.

Pain can be classified as acute and chronic pain. Acute pain and chronic pain differ in their etiology, pathophysiology, diagnosis and treatment.

Acute pain, which occurs following tissue injury, is self-limiting, serves as an alert to ongoing tissue damage and following tissue repair it will usually subside. There are minimal psychological symptoms associated with acute pain apart from mild anxiety. Acute pain is nociceptive in nature and occurs following chemical, mechanical and thermal stimulation of A-delta and C-polymodal pain receptors.

Chronic pain, on the other hand, serves no protective biological function. Rather than being the symptom of tissue damage it is a disease in its own right. Chronic pain is unrelenting and not self-limiting and can persist for years, perhaps decades after the initial injury. Chronic pain can be refractory to multiple treatment regimes. Psychological symptoms associated with chronic pain include chronic anxiety, fear, depression, sleeplessness and impairment of social interaction. Chronic non-malignant pain is predominantly neuropathic in nature and involves damage to either the peripheral or central nervous systems.

Acute pain and chronic pain are caused by different neuro-physiological processes and therefore tend to respond to different types of treatments. Acute pain can be somatic or visceral in nature. Somatic pain tends to be a well localised, constant pain and is described as sharp, aching, throbbing or gnawing. Visceral pain, on the other hand, tends to be vague in distribution, paroxysmal in nature and is usually described as deep, aching, squeezing or colicky in nature. Examples of acute pain include post-operative pain, pain associated with trauma and the pain of arthritis. Acute pain usually responds to treatment with opioids or non-steroidal anti-inflammatory drugs.

Chronic pain, in contrast to acute pain, is described as burning, electric, tingling and shooting in nature. It can be continuous or paroxysmal in presentation. The hallmarks of chronic pain are chronic allodynia and hyperalgesia. Allodynia is pain resulting from a stimulus that normally does not ellicit a painful response, such as a light touch. Hyperalgesia is an increased sensitivity to normally painful stimuli. Primary hyperalgesia occurs immediately within the area of the injury. Secondary hyperalgesia occurs in the undamaged area surrounding the injury. Examples of chronic pain include complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

Although opioids are cheap and effective, serious and potentially life-threatening side effects occur with their use, most notably respiratory depression and muscle rigidity. In addition the doses of opioids which can be administered are limited by nausea, emesis, constipation, pruritis and urinary retention, often resulting in patients electing to receive sub-optimal pain control rather than suffer these distressing side-effects. Furthermore, these side-effects often result in patients requiring extended hospitalisation. Opioids are highly addictive and are scheduled drugs in many territories.

The compounds of formula (I) are particularly useful in the treatment of schizophrenia, bipolar disorder, depression including unipolar depression, seasonal depression and postpartum depression, premenstrual syndrome (PMS) and premenstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impartment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of the formula (I) include in particular a cognitive disorder such as dementia, cognitive impairment, attention deficit hyperactivity disorder.

Particular psychiatric disorders that can be treated with the compounds of the formula (I) include in particular an anxiety disorder, a mood disorder such as depression or a bipolar disorder, schizophrenia, a psychotic disorder.

Within the context of the treatment, the use according to the invention of the compounds of the formula (I) involves a method. In this method, an effective quantity of one or more compounds or the formula (I), as a rule formulated in accordance with pharmaceutical and veterinary practice, is administered to the individual to be treated, preferably a mammal, in particular a human being. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECVEditio-Cantor-Verlag, 1996.

The compounds of formula (I) may also be suitable for combination with other therapeutic agents.

Thus, the present invention also provides:

i) a combination comprising a compound of formula (I) with one or more further therapeutic agents;

ii) a pharmaceutical composition comprising a combination product as defined in i) above and at least one carrier, diluent or excipient;

iii) the use of a combination as defined in i) above in the manufacture of a medicament for treating or preventing a disorder, disease or condition as defined herein;

iv) a combination as defined in i) above for use in treating or preventing a disorder, disease or condition as defined herein;

v) a kit-of-parts for use in the treatment of a disorder, disease or condition as defined herein, comprising a first dosage form comprising a compound of formula (I) and one or more further dosage forms each comprising one or more further therapeutic agents for simultaneous therapeutic administration, vi) a combination as defined in i) above for use in therapy;

vii) a method of treatment or prevention of a disorder, disease or condition as defined herein comprising administering an effective amount of a combination as defined in i) above;

viii) a combination as defined in i) above for treating or preventing a disorder, disease or condition as defined herein.

The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) and at least one further therapeutic agent are within the scope of the current invention. In one embodiment of adjunctive therapeutic administration as described herein, a patient is typically stabilized on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect, the invention provides a method of treatment of a psychotic disorder by adjunctive therapeutic administration of compounds of formula (I) to a patient receiving therapeutic administration of at least one antipsychotic agent. In a further aspect, the invention provides the use of compounds of formula (I) in the manufacture of a medicament for adjunctive therapeutic administration for the treatment of a psychotic disorder in a patient receiving therapeutic administration of at least one antipsychotic agent. The invention further provides compounds of formula (I) for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I). In a further aspect, the invention provides the use of at least one antipsychotic agent in the manufacture of a medicament for adjunctive therapeutic administration for the treatment of a psychotic disorder in a patient receiving therapeutic administration of compounds of formula (I). The invention further provides at least one antipsychotic agent for adjunctive therapeutic administration for the treatment of a psychotic disorder in a patient receiving therapeutic administration of compounds of formula (I).

In a further aspect, the invention provides a method of treatment of a psychotic disorder by simultaneous therapeutic administration of compounds of formula (I) in combination with at least one antipsychotic agent. The invention further provides the use of a combination of compounds of formula (I) and at least one antipsychotic agent in the manufacture of a medicament for simultaneous therapeutic administration in the treatment of a psychotic disorder. The invention further provides a combination of compounds of formula (I) and at least one antipsychotic agent for simultaneous therapeutic administration in the treatment of a psychotic disorder. The invention further provides the use of compounds of formula (I) in the manufacture of a medicament for simultaneous therapeutic administration with at least one antipsychotic agent in the treatment of a psychotic disorder. The invention further provides compounds of formula (I) for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) in the treatment of a psychotic disorder. The invention further provides at least one antipsychotic agent for simultaneous therapeutic administration with compounds of formula (I) in the treatment of a psychotic disorder.

In further aspects, the invention provides a method of treatment of a psychotic disorder by simultaneous therapeutic administration of a pharmaceutical composition comprising compounds of formula (I) and at least one mood stabilising or antimanic agent, a pharmaceutical composition comprising compounds of formula (I) and at least one mood stabilising or antimanic agent, the use of a pharmaceutical composition comprising compounds of formula (I) and at least one mood stabilising or antimanic agent in the manufacture of a medicament for the treatment of a psychotic disorder, and a pharmaceutical composition comprising compounds of formula (I) and at least one mood stabilising or antimanic agent for use in the treatment of a psychotic disorder.

Antipsychotic agents include both typical and atypical antipsychotic drugs. Examples of antipsychotic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs are as follows: clozapine (available under the tradename CLOZARIL®, from Mylan, Zenith Goldline, UDL, Novartis); olanzapine (available under the tradename ZYPREX®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from OrthoMcNeil); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); thiothixene (available under the tradename NAVANE®, from Pfizer); trifluoperazine (10-[3-(4-methyl-1-piperazinyl)propyl]-2-(trifluoromethyl)phenothiazine dihydrochloride, available under the tradename STELAZINE®, from Smith Klein Beckman); perphenazine (available under the tradename TRILAFON®; from Schering); thioridazine (available under the tradename MELLARIL®; from Novartis, Roxane, HiTech, Teva, and Alpharma); molindone (available under the tradename MOBAN®, from Endo); and loxapine (available under the tradename LOXITANE(D; from Watson). Furthermore, benperidol (Glianimon®), perazine (Taxilan®) or melperone (Eunerpan®) may be used. Other antipsychotic drugs include promazine (available under the tradename SPARINE®), triflurpromazine (available under the tradename VESPRI N®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

In a further aspect, the invention provides a method of treatment of a neurodegenerative disorder such as Alzheimer Disease by adjunctive therapeutic administration of compounds of formula (I) to a patient receiving therapeutic administration of at least one agent suitable for the treatment of a neurodegenerative disorder such as Alzheimer Disease. In a further aspect, the invention provides the use of compounds of formula (I) in the manufacture of a medicament for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease. The invention further provides compounds of formula (I) for use for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease.

In a further aspect, the invention provides a method of treatment of a neurodegenerative disorder such as Alzheimer Disease by adjunctive therapeutic administration of at least one agent suitable for the treatment of a neurodegenerative disorder such as Alzheimer Disease to a patient receiving therapeutic administration of compounds of formula (I). In a further aspect, the invention provides the use of at least one agent suitable for the treatment of a neurodegenerative disorder such as Alzheimer Disease in the manufacture of a medicament for adjunctive therapeutic administration for the treatment of a neurodegenerative disorder such as Alzheimer Disease in a patient receiving therapeutic administration of compounds of formula (I). The invention further provides at least one agent suitable for the treatment of a neurodegenerative disorder such as Alzheimer Disease for adjunctive therapeutic administration for the treatment of a neurodegenerative disorder such as Alzheimer Disease in a patient receiving therapeutic administration of compounds of formula (I).

In a further aspect, the invention provides a method of treatment of a neurodegenerative disorder such as Alzheimer Disease by simultaneous therapeutic administration of compounds of formula (I) in combination with at least one agent suitable for the treatment of a neurodegenerative disorder such as Alzheimer Disease. The invention further provides the use of a combination of compounds of formula (I) and at least one agent suitable for the treatment of a neurodegenerative disorder such as Alzheimer Disease in the manufacture of a medicament for simultaneous therapeutic administration in the treatment of a neurodegenerative disorder such as Alzheimer Disease. The invention further provides a combination of compounds of formula (I) and at least one agent suitable for the treatment of a neurodegenerative disorder such as Alzheimer Disease for simultaneous therapeutic administration in the treatment of a neurodegenerative disorder such as Alzheimer Disease.

The invention further provides the use of compounds of formula (I) in the manufacture of a medicament for simultaneous therapeutic administration with at least one agent suitable for the treatment of a neurodegenerative disorder such as Alzheimer Disease in the treatment of a neurodegenerative disorder such as Alzheimer Disease. The invention further provides compounds of formula (I) for use for simultaneous therapeutic administration with at least one agent suitable for the treatment of a neurodegenerative disorder such as Alzheimer Disease in the treatment of a neurodegenerative disorder such as Alzheimer Disease. The invention further provides the use of at least one agent suitable for the treatment of a neurodegenerative disorder such as Alzheimer Disease in the manufacture of a medicament for simultaneous therapeutic administration with compounds of formula (I) in the treatment of a neurodegenerative disorder such as Alzheimer Disease. The invention further provides at least one agent suitable for the treatment of a neurodegenerative disorder such as Alzheimer Disease for simultaneous therapeutic administration with compounds of formula (I) in the treatment of a neurodegenerative disorder such as Alzheimer Disease.

Examples of agents suitable for the treatment of a neurodegenerative disorder such as Alzheimer Disease that are useful in the present invention include, but are not limited to: cholinesterase inhibitors, agents targeting nicotinic or muscarinic acetylcholine receptors, NMDA receptors, amyloid formation, mitochondrial dysfunctions, disease associated calpain activity, neuroinflamation, tumor necrosis factor receptors, NF-kappaB, peroxisome proliferator activator receptor gamma, Apolipoprotein E variant 4 (ApoE4), disease-associated increase of the HPA axis, epileptic discharges, vascular dysfunction, vascular risk factors, and oxidative stress.

Suitable cholinesterase inhibitors which may be used in combination with the compounds of the inventions include for example tacrine, donepezil, galantamine and rivastigmine.

Suitable NMDA receptors targeting agents which may be used in combination with the compounds of the inventions include for example memantine.

Suitable agents affecting increased HPA axis activity which may be used in combination with the compounds of the inventions include for example CRF1 antagonists or V1b antagonists.

In a further aspect therefore, the invention provides a method of treatment of pain by adjunctive therapeutic administration of compounds of formula (I) to a patient receiving therapeutic administration of at least one agent suitable for the treatment of pain. In a further aspect, the invention provides the use of compounds of formula (I) in the manufacture of a medicament for adjunctive therapeutic administration for the treatment of pain in a patient receiving therapeutic administration of at least one agent suitable for the treatment of pain. The invention further provides compounds of formula (I) for use for adjunctive therapeutic administration for the treatment of pain in a patient receiving therapeutic administration of at least one agent suitable for the treatment of pain.

In a further aspect, the invention provides a method of treatment of pain by adjunctive therapeutic administration of at least one agent suitable for the treatment of pain to a patient receiving therapeutic administration of compounds of formula (I). In a further aspect, the invention provides the use of at least one agent suitable for the treatment of pain in the manufacture of a medicament for adjunctive therapeutic administration for the treatment of pain in a patient receiving therapeutic administration of compounds of formula (I). The invention further provides at least one agent suitable for the treatment of pain for adjunctive therapeutic administration for the treatment of pain in a patient receiving therapeutic administration of compounds of formula (I).

In a further aspect, the invention provides a method of treatment of pain by simultaneous therapeutic administration of compounds of formula (I) in combination with at least one agent suitable for the treatment of pain. The invention further provides the use of a combination of compounds of formula (I) and at least one agent suitable for the treatment of pain in the manufacture of a medicament for simultaneous therapeutic administration in the treatment of pain. The invention further provides a combination of compounds of formula (I) and at least one agent suitable for the treatment of pain for simultaneous therapeutic administration in the treatment of pain. The invention further provides the use of compounds of formula (I) in the manufacture of a medicament for simultaneous therapeutic administration with at least one agent suitable for the treatment of pain in the treatment of pain. The invention further provides compounds of formula (I) for use for simultaneous therapeutic administration with at least one agent suitable for the treatment of pain in the treatment of pain. The invention further provides the use of at least one agent suitable for the treatment of pain in the manufacture of a medicament for simultaneous therapeutic administration with compounds of formula (I) in the treatment of pain. The invention further provides at least one agent suitable for the treatment of pain for simultaneous therapeutic administration with compounds of formula (I) in the treatment of pain.

Examples of agents suitable for the treatment of pain that are useful in the present invention include, but are not limited to: NSAIDs (Nonsteroidal Antiinflammatory Drugs), anticonvulsant drugs such as carbamazepine and gabapentin, sodium channel blockers, antidepressant drugs, cannabinoids and local anaesthetics.

Suitable agents used in combination with the compounds of the inventions include for example celecoxib, etoricoxib, lumiracoxib, paracetamol, tramadol, methadone, venlafaxine, imipramine, duloxetine, bupropion, gabapentin, pregabalin, lamotrigine, fentanyl, parecoxib, nefopam, remifentanil, pethidine, diclofenac, rofecoxib, nalbuphine, sufentanil, pethidine, diamorphine and butorphanol.

It will be appreciated by those skilled in the art that the compounds according to the invention may advantageously be used in conjunction with one or more other therapeutic agents, for instance, antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1B antagonists, 5HT1D antagonists, D1 agonists, M1 agonists and/or anticonvulsant agents, as well as cognitive enhancers.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Suitable anticonvulsant agents which may be used in combination of the compounds of the invention include for example divalproex, carbamazepine and diazepam.

The following examples serve to explain the invention without limiting it.

The compounds were characterized by mass spectrometry, generally recorded via HPLC-MS in a fast gradient on C18-material (electrospray-ionisation (ESI) mode).

PREPARATION EXAMPLES

Abbreviations: APCI for atmospheric pressure chemical ionization; AcOH for acetic acid; Boc for tert-butoxy carbonyl; Bu for butyl; DCI for desorption chemical ionization; DCM for dichloromethane; dimethylsulfoxide for dimethyl sulfoxide; eq for equivalent(s); ESI for electrospray ionization; EtOAc for ethyl acetate; HATU for [o-(azabenzotriazol-1-yl)-1,1,3,3-tetramethyluronium hexafluorophosphate]; HCl for hydrochloric acid; HPLC for high performance liquid chromatography; id for internal diameter; LC/MS for liquid chromatography/mass spectrometry; MeOH for methanol; $MgSO_4$ for magnesium sulfate; MP for macroporous resin; NaOAc for sodium acetate; PS for polymer supported; psi for pounds per square inch; SFC for supercritical fluid chromatography; SPE for solid phase extraction, and tBu for tert-butyl.

Definitions: Similarly indicates that that reactants may be substituted for other the reactants described, the temperature may vary by 50° C., the equivilents may differ by upto 2 fold, or any combination thereof.

Preparative HPLC Procedure: Samples were purified by preparative HPLC on a PheNomenex® Luna® C8(2) 5 µm 100 Å AXIA™ column (30 mm×75 mm) A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). Samples were injected in 1.5 mL dimethyl sulfoxide:methanol (1:1). With specified samples, ammonium acetate was used instead of trifluoroacetic acid. A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol:10 mM $NH_4OH$(aqueous) at a flow rate of 0.8 mL/minute. Loop-injection mass spectra were acquired

181 using a Finnigan LCQ running LCQ Navigator 1.2 software and a Gilson 215 liquid handler for fraction injection controlled by an Abbott developed Visual Basic application.

For chiral compounds the absolute configuration is indicated in their chemical names. A chemical name with "trans" or no stereochemistry information does not refer to a chiral compound (even if the corresponding formula depicts a chiral compound).

Example 1

2-chloro-N-{trans-1-[(1-methyl-1H-imidazol-4-yl) sulfonyl]-4-phenylpyrrolidin-3-yl}-3-(trifluoromethyl)benzamide Example 1A To a solution of trans-tert-butyl 3-amino-4-phenylpyrrolidine-1-carboxylate (0.305 g, 1.163 mmol) and 2-chloro-3-(trifluoromethyl)benzoic acid (0.261 g, 1.163 mmol) in dichloromethane (4.65 ml) was added triethylamine (0.486 ml, 3.49 mmol) and HATU (0.663 g, 1.744 mmol) and the mixture was stirred at room temperature for 2 hours. The reaction mixture was partitioned with water, the organic fraction was collected, and the aqueous fraction was washed with dichloromethane. The organic fractions were combined, dried over sodium sulfate and concentrated. The crude product was purified by silica gel chromatography (Analogix IntelliFlash 280, SF15-12) eluting with 30% ethyl acetate/hexanes to afford the title compound. MS (ESI) m/z 469.3 [M+H]$^+$ Example 1B 2-chloro-N-(trans-4-phenylpyrrolidin-3-yl)-3-(trifluoromethyl)benzamide hydrochloride To a solution of Example 1A (0.32 g, 0.682 mmol) in dioxane (0.682 ml) was added HCl in dioxane (4M, 1.706 ml, 6.82 mmol) and the mixture was stirred at room temperature for 2 hours. The solvent was evaporated and the solid was triturated twice with dichloromethane and the solvent was evaporated to afford the title compound. MS (ESI) m/z 369.2 [M+H]$^+$ Example 1C 2-chloro-N-(trans-1-(1-methyl-1H-imidazol-4-ylsulfonyl)-4-phenylpyrrolidin-3-yl)-3-(trifluoromethyl) benzamide To a solution of Example 1B (0.075 g, 0.185 mmol) in dichloromethane (0.740 ml) was added triethylamine (0.077 ml, 0.555 mmol) and 1-methyl-1H-imidazole-4-sulfonyl chloride (0.033 g, 0.185 mmol). The mixture was stirred at room temperature for 1 hour. The solvent was evaporated. The crude product was purified by HPLC to afford the title compound. MS (ESI) m/z 513.1 [M+H]+

Example 2

2-chloro-N-{trans-4-(4-methoxyphenyl)-1-[(1-methyl-1H-imidazol-4-yl)sulfonyl]pyrrolidin-3-yl}-3-(trifluoromethyl)benzamide Example 2A trans-1-benzyl-3-(4-methoxyphenyl)-4-nitropyrrolidine To a solution of (E)-1-methoxy-4-(2-nitrovinyl)benzene (5.09 g, 28 4 mmol) and N(methoxymethyl)-N-(trimethyl-

182 silylmethyl)benzylamine (8.07 g, 34.0 mmol) in 75 mL of dichloromethane at 0° C. under nitrogen was added trifluoroacetic acid (388 mg, 3.4 mmol) in one portion. The reaction was allowed to warm to ambient temperature and stirred for 16 hours. The reaction was then partitioned between dichloromethane and saturated sodium bicarbonate solution. The organic fraction was collected. The aqueous portion was washed with additional dichloromethane and the combined organic fractions were washed with water, brine and dried over sodium sulfate. The mixture was filtered, concentrated and purified on a silica gel flash column (7:3 hexane:ethyl acetate) to afford the title compound. MS (DCI) m/z 313.1 (M+H)$^+$.

Example 2B trans-1-benzyl-4-(4-methoxyphenyl)pyrrolidin-3-amine

Example 2A (4.85 mg, 15.5 mmol) and tetrahydrofuran (100 mL) were added to a Raney nickel water slurry (Grace 2800, 5.00 g) in a stainless steel reactor. The vessel was pressurized with 30 psi of hydrogen and shaken at room temperature for 16 hours. The mixture was filtered through a nylon membrane concentrated and purified on a silica gel flash column (95:5 dichloromethane: 2N ammonia in methanol) to afford the title compound as colorless oil. MS (DCI) m/z 283.1 (M+H)$^+$.

Example 2C tert-Butyl trans-1-benzyl-4-(4-methoxyphenyl)pyrrolidin-3-ylcarbamate To a solution of 2.5 g (8.86 mmol) of Example 2B in tetrahydrofuran (20 ml) was added saturated sodium bicarbonate solution (20 ml) followed by di-tert-butyl dicarbonate (1.0 M solution in tetrahyrofuran, 10 ml, 10.0 mmol) at room temperature under nitrogen. The reaction was stirred for 1 hour and then partitioned between ethyl acetate and water. The organic fraction was collected. The aqueous portion was washed several additional times with ethyl acetate and the combined organic extracts were washed with brine and dried over sodium sulfate. The mixture was filtered, concentrated and purified on a silica gel flash column (3:2 ethyl acetate hexane) to afford the title compound. MS (DCI) m/z 383.2 (M+H)$^+$.

Example 2D tert-butyl (3S,4R)-4-(4-methoxyphenyl)pyrrolidin-3-ylcarbamate

Example 2C (2.65 mg, 6.93 mmol) and 2,2,2-trifluoroethanol or tetrahydrofuran (40 mL) were added to 20% Pd(OH)$_2$/C (50% water, 0.530 g) in a stainless steel reactor. The vessel was pressurized with 30 psi of hydrogen and shaken at 50° C. for 30 minutes. The mixture was filtered through a nylon membrane, and the product was purified on a silica gel column (95:5 dichloromethane:2N ammonia in methanol) to afford the title compound. MS (DCI) m/z 293.1 (M+H)$^+$.

Example 2E tert-butyl (trans-4-(4-methoxyphenyl)-1-((1-methyl-1H-imidazol-4-yl)sulfonyl)pyrrolidin-3-yl)carbamate To a solution of the product from Example 2D (154 mg, 0.53 mmol), and triethylamine (152 mg, 1.5 mmol) in dichloromethane (8 ml) was added 1-methyl-1H-imidazole-4-sulfonyl chloride (108 mg, 0.60 mmol) in one portion at room temperature. 4-(dimethylamino)-pyridine (4 mg, 0.03 mmol) was added and the reaction stirred for two hours at room temperature. The reaction was concentrated and purified on a silica gel flash column (97:3 dichloromethane: 2N ammonia in methanol) to afford the title compound. MS (DCI) m/z 425.1 (M+H)$^+$.

Example 2F trans-4-(4-methoxyphenyl)-1-((1-methyl-1H-imidazol-4-yl)sulfonyl)pyrrolidin-3-amine The product from Example 2E (195 mg, 0.46 mmol) was stirred with 1,4-dioxane (4 ml) and hydrogen chloride in 1,4-dioxane (4M, 4 ml, 16.0 mmol) at room temperature under nitrogen overnight. The reaction was concentrated and concentrated to afford the title compound as the hydrochloride salt. MS (DCI) m/z 325.0 (M+H)$^+$.

Example 2G 2-chloro-N-{trans-1-[(1-methyl-1H-imidazol-4-yl)sulfonyl]-4-phenylpyrrolidin-3-yl}-3-(trifluoromethyl)benzamide A mixture of Example 2F, 2-chloro-3-(trifluoromethyl)benzoic acid (101 mg, 0.45 mmol), and N-(3-Dimethylaminopropyl)-N-ethylcarbodiimide hydrochloride (86 mg, 0.45 mmol) was stirred in a 1:1 solution of pyridine and N,N-dimethylformamide (5 ml) at room temperature under nitrogen for 16 hours. The reaction was concentrated and the residue was partitioned between ethyl acetate and water. The organic fraction was collected and the aqueous portion was washed with additional ethyl acetate. The combined organic fractions were washed with water, brine and dried over sodium sulfate. The mixture was filtered, concentrated and purified on a silica gel flash column (95:5 dichloromethane 2N ammonia in methanol) to afford the title compound. MS (ESI) m/z 543.2 (M+H)$^+$.

Example 3

2-chloro-N-{trans-4-(4-fluorophenyl)-1-[(1-methyl-1H-imidazol-4-yl)sulfonyl]pyrrolidin-3-yl}-3-(trifluoromethyl)benzamide Example 3A trans-4-(4-fluorophenyl)-1-(1-methyl-1H-imidazol-4-ylsulfonyl)pyrrolidin-3-amine The title compound was prepared as an HCl salt similarly to the procedures described in Example 2A-2F substituting (E)-1-fluoro-4-(2-nitrovinyl)benzene for (E)-1-methoxy-4-(2-nitrovinyl)benzene.

Example 3B 2-chloro-N-{trans-4-(4-fluorophenyl)-1-[(1-methyl-1H-imidazol-4-yl)sulfonyl]pyrrolidin-3-yl}-3-(trifluoromethyl)benzamide The title compound was prepared similarly to the procedure described in Example 2G substituting Example 3A for Example 2F. MS (ESI) m/z 531 (M+H)$^+$.

Example 4

2-chloro-N-[trans-1-(methylsulfonyl)-4-(2,4,5-trifluorophenyl)pyrrolidin-3-yl]-3-(trifluoromethyl)benzamide Example 4A (E)-1,2,4-trifluoro-5-(2-nitrovinyl)benzene A stirred solution containing 2,4,5-trifluorobenzaldehyde (16.2 g, 80.1 mmol), ammonium acetate (17.3 g, 225 mmol), nitromethane (12.2 mL, 225 mmol), and acetic acid (75 mL) was heated to 100° C. for 3 hours. The mixture was cooled to room temperature and partitioned between water and dichloromethane. The organic fraction was collected and the aqueous fraction was washed with dichloromethane. The organic fractions were combined and washed with sodium bicarbonate (aq.), brine, and water. The organic fraction was dried with sodium sulfate and purified via flash chromatography (0-100% EtOAc/hexanes) to provide the title compound.

Example 4B trans-1-benzyl-4-(2,4,5-trifluorophenyl)pyrrolidin-3-amine

The title compound was prepared similarly to the conditions described in Examples 2A-2B substituting Example 4A for (E)-1-methoxy-4-(2-nitrovinyl)benzene.

Example 4C

N-(trans-1-benzyl-4-(2,4,5-trifluorophenyl)pyrrolidin-3-yl)-2-chloro-3-(trifluoromethyl)benzamide To a stirred solution of Example 4B (3.3 g, 10.7 mmol) in a 1:1 dimethylformamide:pyridine solution (20 mL) was added 2-chloro-3-(trifluoromethyl)benzoic acid (2.9 g, 12.9 mmol) and N-(3-Dimethylaminopropyl)-N'-ethylcarbodiimide hydrochloride (2.85 g, 15 mmol). The reaction was stirred at room temperature for 18 hours. The reaction mixture was concentrate. The reaction mixture was partitioned between, EtOAc (100 mL) and 1 M HCl (200 mL). The organic layer was collected. The aqueous fraction was washed with EtOAc (100 mL). The organis fractions were combined. Purification via flash chromatography (0-100% EtOAc/hexanes) provided the title compound.

2-chloro-3-(trifluoromethyl)-N-(trans-4-(2,4,5-trifluorophenyl)pyrrolidin-3-yl)benzamide To a stirred solution of Example 4C (3.4 g, 6.63 mmol) in dichloroethane was added 1-chloroethyl carbonochloridate (1.0 g, 7.29 mmol). The reaction mixture was stirred at 80° C. for 2 hours. Some precipitate was collected via filtration to provide the title compound. The filtrate was concentrated and purified via flash chromatography (0-30% methanol/DCM) to provide the title compound.

Example 4E 2-chloro-N-[(trans-1-(methylsulfonyl)-4-(2,4,5-trifluorophenyl)pyrrolidin-3-yl]-3-(trifluoromethyl)benzamide To a stirred solution of Example 4D (50 mg, 0.18 mmol) in pyridine (2 mL) was added methanesulfonyl chloride (16 mg, 0.14 mmol). The reaction mixture stirred at 60° C. for 18 hours. The reaction mixture was then concentrated and purified via HPLC. MS (ESI) m/z 501 (M+H)$^+$.

Example 13

2-chloro-N-{trans-4-(4-chlorophenyl)-1-[(1-methyl-1H-imidazol-4-yl)sulfonyl]pyrrolidin-3-yl}-3-(trifluoromethyl)benzamide The title compound was prepared similarly to the procedures described in Example 2 substituting (E)-1-chloro-4-(2-nitrovinyl)benzene for (E)-1-methoxy-4-(2-nitrovinyl)benzene. MS (DCI) m/z 547.0 (M+H)$^+$ Example 14

2-chloro-N-{trans-1-[(1-methyl-1H-imidazol-4-yl)sulfonyl]-4-phenylpyrrolidin-3-yl}benzamide Example 14A trans-1-(1-methyl-1H-imidazol-4-ylsulfonyl)-4-phenylpyrrolidin-3-amine The title compound was prepared as an HCl salt similarly to the conditions described in Example 2A-2F substituting (E)-(2-nitrovinyl)benzene for (E)-1-methoxy-4-(2-nitrovinyl)benzene.

Example 14B 2-chloro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 2-chloro-benzoic acid for 2-chloro-3-(trifluoromethyl)benzoic acid. MS (ESI) m/z 445 (M+H)$^+$.

Example 15

3-chloro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 3-chloro-benzoic acid for 2-chloro-3-(trifluoromethyl)benzoic acid. MS (ESI) m/z 445 (M+H)$^+$.

Example 16

4-chloro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 4-chloro-benzoic acid for 2-chloro-3-(trifluoromethyl)benzoic acid. MS (ESI) m/z 445 (M+H)$^+$.

Example 17

2-fluoro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 2-fluoro-benzoic acid for 2-chloro-3-(trifluoromethyl)benzoic acid. MS (ESI) m/z 429 (M+H)$^+$.

Example 18

3-fluoro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 3-fluoro-benzoic acid for 2-chloro-3-(trifluoromethyl)benzoic acid. MS (ESI) m/z 429 (M+H)$^+$.

Example 19

4-fluoro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 4-fluoro-benzoic acid for 2-chloro-3-(trifluoromethyl)benzoic acid. MS (ESI) m/z 429 (M+H)$^+$.

Example 20

2-methoxy-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 2-methoxy-benzoic acid for 2-chloro-3-(trifluoromethyl)benzoic acid. MS (ESI) m/z 441 (M+H)$^+$.

Example 21

3-methoxy-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 3-methoxy-benzoic acid for 2-chloro-3-(trifluoromethyl)benzoic acid. MS (ESI) m/z 441 (M+H)$^+$.

Example 22

2-methyl-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 2-methyl-benzoic acid for 2-chloro-3-(trifluoromethyl)benzoic acid. MS (ESI) m/z 425 (M+H)$^+$.

Example 23

3-methyl-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 3-methyl-benzoic acid for 2-chloro-3-(trifluoromethyl)benzoic acid. MS (ESI) m/z 425 (M+H)$^+$.

Example 24

4-methyl-N-{trans-1-[(1-methyl-1H-imidazol-4-yl) sulfonyl]-4-phenylpyrrolidin-3-yl}benzamide The title compound was prepared similarly to the conditions described in Example 4C substituting Example 14A for Example 4B and substituting 4-methyl-benzoic acid for 2-chloro-3-(trifluoromethyl)benzoic acid. MS (ESI) m/z 425 (M+H)$^+$.

Example 25

N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting benzoic acid for 2-chloro-3-(trifluoromethyl)benzoic acid. MS (ESI) m/z 411 (M+H)$^+$.

Example 26

2,4-dichloro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 2,4-dichlorobenzoic acid for 2-chloro-3-(trifluoromethyl)benzoic acid. MS (ESI) m/z 479 (M+H)$^+$.

Example 27

2-chloro-4-fluoro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 2-chloro-4-fluorobenzoic acid for 2-chloro-3-(trifluoromethyl)benzoic acid. MS (ESI) m/z 463 (M+H)$^+$.

Example 29 trans-1-[(1-methyl-1H-imidazol-4-yl)sulfonyl]-N,4-diphenylpyrrolidin-3-amine

Under nitrogen, a pressure vial was charged with Example 14A (50 mg, 0.15 mmol), bromobenzene (23 mg, 0.15 mmol), 2'-(di-tert-butylphosphino)-N,N-dimethylbiphenyl-2-amine (5.0 mg, 0.02 mmol), tris(dibenzylidene-acetone) dipalladium(0) (6.7 mg, 7.3 μmol), sodium tert-butoxide (18 mg, 0.19 mmol), and toluene (1 mL). The reaction mixture was stirred at 80° C. for 3 hours. Then, the reaction mixture was concentrated. Purification via HPLC provided the title compound. MS (ESI) m/z 383 (M+H)$^+$.

Example 30

3,5-dichloro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 3,5-dichlorobenzoic acid for 2-chloro-3-(trifluoromethyl)benzoic acid. MS (ESI) m/z 479 (M+H)$^+$.

Example 31

2,3-dichloro-N-{trans-1-[(1-methyl-1H-imidazol-4-yl)sulfonyl]-4-phenylpyrrolidin-3-yl}benzamide The title compound was prepared similarly to the conditions described in Example 4C substituting Example 14A for Example 4B and substituting 2,3-dichlorobenzoic acid for 2-chloro-3-(trifluoromethyl)benzoic acid. MS (ESI) m/z 479 (M+H)$^+$.

Example 32

2-cyano-N-{trans-1-[(1-methyl-1H-imidazol-4-yl) sulfonyl]-4-phenylpyrrolidin-3-yl}benzamide The title compound was prepared similarly to the conditions described in Example 4C substituting Example 14A for Example 4B and substituting 2-cyanobenzoic acid for 2-chloro-3-(trifluoromethyl)benzoic acid. MS (ESI) m/z 436 (M+H)$^+$.

Example 33

3-cyano-N-{trans-1-[(1-methyl-1H-imidazol-4-yl) sulfonyl]-4-phenylpyrrolidin-3-yl}benzamide The title compound was prepared similarly to the conditions described in Example 4C substituting Example 14A for Example 4B and substituting 3-cyanobenzoic acid for 2-chloro-3-(trifluoromethyl)benzoic acid. MS (ESI) m/z 436 (M+H)$^+$.

Example 34

4-cyano-N-{trans-1-[(1-methyl-1H-imidazol-4-yl) sulfonyl]-4-phenylpyrrolidin-3-yl}benzamide The title compound was prepared similarly to the conditions described in Example 4C substituting Example 14A for Example 4B and substituting 4-cyanobenzoic acid for 2-chloro-3-(trifluoromethyl)benzoic acid. MS (ESI) m/z 436 (M+H)$^+$.

Example 35

N-{trans-1-[(1-methyl-1H-imidazol-4-yl)sulfonyl]-4-phenylpyrrolidin-3-yl}-2-(trifluoromethyl)benzamide The title compound was prepared similarly to the conditions described in Example 4C substituting Example 14A for Example 4B and substituting 2-(trifluoromethyl)benzoic acid for 2-chloro-3-(trifluoromethyl)benzoic acid. MS (ESI) m/z 479 (M+H)$^+$.

Example 36

N-{trans-1-[(1-methyl-1H-imidazol-4-yl)sulfonyl]-4-phenylpyrrolidin-3-yl}-3-(trifluoromethyl)benzamide The title compound was prepared similarly to the conditions described in Example 4C substituting Example 14A for Example 4B and substituting 3-(trifluoromethyl)benzoic acid for 2-chloro-3-(trifluoromethyl)benzoic acid. MS (ESI) m/z 479 (M+H)+.

Example 37

N-{trans-1-[(1-methyl-1H-imidazol-4-yl)sulfonyl]-4-phenylpyrrolidin-3-yl}-4-(trifluoromethyl)benzamide The title compound was prepared similarly to the conditions described in Example 4C substituting Example 14A for Example 4B and substituting 4-(trifluoromethyl)benzoic acid for 2-chloro-3-(trifluoromethyl)benzoic acid. MS (ESI) m/z 479 (M+H)+.

Example 38

2-chloro-N-[trans-1-{[1-methyl-3-(trifluoromethyl)-1H-pyrazol-4-yl]sulfonyl}-4-phenylpyrrolidin-3-yl]-3-(trifluoromethyl)benzamide Example 38A (trans)-1-benzyl-4-phenylpyrrolidin-3-amine 2-chloro-N-(trans-4-phenylpyrrolidin-3-yl)-3-(trifluoromethyl)benzamide The title compound was prepared similarly to the procedures described in Examples 2A-2B substituting (E)-1-fluoro-4-(2-nitrovinyl)benzene for (E)-1-methoxy-4-(2-nitrovinyl)benzene.

Example 38B 2-chloro-N-(trans-4-phenylpyrrolidin-3-yl)-3-(trifluoromethyl)benzamide The title compound was prepared similarly to Example 4C-4D substituting Example 38A for Example 4B.

Example 38C 2-chloro-N-[trans-1-{[1-methyl-3-(trifluoromethyl)-1H-pyrazol-4-yl]sulfonyl}-4-phenylpyrrolidin-3-yl]-3-(trifluoromethyl)benzamide The title compound was prepared similarly to the procedure described in Example 4E substituting Example 38B for Example 4D and substituting 1-methyl-3-(trifluoromethyl)-1H-pyrazole-4-sulfonyl chloride for methanesulfonyl chloride. MS (ESI) m/z 581 (M+H)+.

Example 39

2-chloro-N-[trans-1-{[1-(difluoromethyl)-3,5-dimethyl-1H-pyrazol-4-yl]sulfonyl}-4-phenylpyrrolidin-3-yl]-3-(trifluoromethyl)benzamide The title compound was prepared similarly to the conditions described in Example 4E substituting Example 38B for tert-butyl 3-amino-4-phenylpyrrolidine-1-carboxylate and substituting 1-(difluoromethyl)-3,5-dimethyl-1H-pyrazole-4-sulfonyl chloride for methanesulfonyl chloride. MS (ESI) m/z 577 (M+H)+.

Example 40

2-chloro-N-{trans-1-[(5-chloro-1,3-dimethyl-1H-pyrazol-4-yl)sulfonyl]-4-phenylpyrrolidin-3-yl}-3-(trifluoromethyl)benzamide The title compound was prepared similarly to the conditions described in Example 4E substituting Example 38B for tert-butyl 3-amino-4-phenylpyrrolidine-1-carboxylate and substituting 5-chloro-1,3-dimethyl-1H-pyrazole-4-sulfonyl chloride for methanesulfonyl chloride. MS (ESI) m/z 561 (M+H)+.

Example 41

2-chloro-N-{trans-1-[(1,5-dimethyl-1H-pyrazol-4-yl)sulfonyl]-4-phenylpyrrolidin-3-yl}-3-(trifluoromethyl)benzamide The title compound was prepared similarly to the conditions described in Example 4E substituting Example 38B for tert-butyl 3-amino-4-phenylpyrrolidine-1-carboxylate and substituting 1,5-dimethyl-1H-pyrazole-4-sulfonyl chloride for methanesulfonyl chloride. MS (ESI) m/z 527 (M+H)+.

Example 42

2-chloro-N-{trans-1-[(1,3-dimethyl-1H-pyrazol-4-yl)sulfonyl]-4-phenylpyrrolidin-3-yl}-3-(trifluoromethyl)benzamide The title compound was prepared similarly to the conditions described in Example 4E substituting Example 38B for tert-butyl 3-amino-4-phenylpyrrolidine-1-carboxylate and substituting 1,3-dimethyl-1H-pyrazole-4-sulfonyl chloride for methanesulfonyl chloride. MS (ESI) m/z 527 (M+H)+.

Example 43

2-chloro-N-{trans-1-[(1-methyl-1H-pyrazol-4-yl)sulfonyl]-4-phenylpyrrolidin-3-yl}-3-(trifluoromethyl)benzamide The title compound was prepared similarly to the conditions described in Example 4E substituting Example 38B for tert-butyl 3-amino-4-phenylpyrrolidine-1-carboxylate and substituting 1-methyl-1H-pyrazole-4-sulfonyl chloride for methanesulfonyl chloride. MS (ESI) m/z 513 (M+H)+.

Example 44

2-chloro-N-{trans-1-[(6-methoxypyridin-3-yl)sulfonyl]-4-phenylpyrrolidin-3-yl}-3-(trifluoromethyl)benzamide The title compound was prepared similarly to the conditions described in Example 4E substituting Example 38B for tert-butyl 3-amino-4-phenylpyrrolidine-1-carboxylate and substituting 6-methoxypyridine-3-sulfonyl chloride for methanesulfonyl chloride. MS (ESI) m/z 540 (M+H)+.

Example 45

2-chloro-N-{trans-4-phenyl-1-(pyridin-3-ylsulfonyl)pyrrolidin-3-yl}-3-(trifluoromethyl)benzamide The title compound was prepared similarly to the conditions described in Example 4E substituting Example 38B for tert-butyl 3-amino-4-phenylpyrrolidine-1-carboxylate and substituting pyridine-3-sulfonyl chloride for methanesulfonyl chloride. MS (ESI) m/z 510 (M+H)+.

Example 46

2-chloro-N-[trans-4-phenyl-1-(1H-pyrazol-4-ylsulfonyl)pyrrolidin-3-yl]-3-(trifluoromethyl)benzamide The title compound was prepared similarly to the conditions described in Example 4E substituting Example 38B for tert-butyl 3-amino-4-phenylpyrrolidine-1-carboxylate and substituting 1H-pyrazole-4-sulfonyl chloride for methanesulfonyl chloride. MS (ESI) m/z 499 (M+H)+.

Example 47

2-chloro-N-{trans-1-[(1-methyl-1H-pyrazol-5-yl)sulfonyl]-4-phenylpyrrolidin-3-yl}-3-(trifluoromethyl)benzamide The title compound was prepared similarly to the conditions described in Example 4E substituting Example 38B for tert-butyl 3-amino-4-phenylpyrrolidine-1-carboxylate and substituting 1-methyl-1H-pyrazole-5-sulfonyl chloride for methanesulfonyl chloride. MS (ESI) m/z 513 (M+H)+.

Example 48

2-chloro-N-{trans-1-[(5-chloro-1-methyl-1H-imidazol-4-yl)sulfonyl]-4-phenylpyrrolidin-3-yl}-3-(trifluoromethyl)benzamide The title compound was prepared similarly to the conditions described in Example 4E substituting Example 38B for tert-butyl 3-amino-4-phenylpyrrolidine-1-carboxylate and substituting 5-chloro-1-methyl-1H-imidazole-4-sulfonyl chloride for methanesulfonyl chloride. MS (ESI) m/z 547 (M+H)+.

Example 49

2-chloro-N-{trans-1-[(1-methyl-1H-pyrazol-3-yl)sulfonyl]-4-phenylpyrrolidin-3-yl}-3-(trifluoromethyl)benzamide The title compound was prepared similarly to the conditions described in Example 4E substituting Example 38B for tert-butyl 3-amino-4-phenylpyrrolidine-1-carboxylate and substituting 1-methyl-1H-pyrazole-3-sulfonyl chloride for methanesulfonyl chloride. MS (ESI) m/z 513 (M+H)+.

Example 50 trans-N-(4-methoxyphenyl)-1-[(1-methyl-1H-imidazol-4-yl)sulfonyl]-4-phenylpyrrolidin-3-amine The title compound was prepared similarly to the conditions described in Example 29 substituting 1-bromo-4-methoxybenzene for bromobenzene. MS (ESI) m/z 413 (M+H)+.

Example 51

3-({trans-1-[(1-methyl-1H-imidazol-4-yl)sulfonyl]-4-phenylpyrrolidin-3-yl}amino)benzonitrile The title compound was prepared similarly to the conditions described in Example 29 substituting 3-bromobenzenenitrile for bromobenzene. MS (ESI) m/z 408 (M+H)+.

Example 52

4-({trans-1-[(1-methyl-1H-imidazol-4-yl)sulfonyl]-4-phenylpyrrolidin-3-yl}amino)benzonitrile The title compound was prepared similarly to the conditions described in Example 29 substituting 4-bromobenzenenitrile for bromobenzene. MS (ESI) m/z 408 (M+H)+.

Example 53

3-fluoro-4-({trans-1-[(1-methyl-1H-imidazol-4-yl)sulfonyl]-4-phenylpyrrolidin-3-yl}amino)benzonitrile The title compound was prepared similarly to the conditions described in Example 29 substituting 4-bromo-3-fluorobenzonitrile for bromobenzene. MS (ESI) m/z 426 (M+H)+.

Example 54

2-chloro-N-{trans-4-(2-fluorophenyl)-1-[(1-methyl-1H-imidazol-4-yl)sulfonyl]pyrrolidin-3-yl}-3-(trifluoromethyl)benzamide The title compound was prepared similarly to the procedures described in Example 2 substituting (E)-1-fluoro-2-(2-nitrovinyl)benzene for (E)-1-methoxy-4-(2-nitrovinyl)benzene in Example 2A. MS (DCI) m/z 530.9 (M+H)+

Example 55

2-chloro-N-{trans-4-(3-fluorophenyl)-1-[(1-methyl-1-imidazol-4-yl)sulfonyl]pyrrolidin-3-yl}-3-(trifluoromethyl)benzamide The title compound was prepared similarly to the procedures as described in Example 2 substituting (E)-1-fluoro-3-(2-nitrovinyl)benzene for (E)-1-methoxy-4-(2-nitrovinyl)benzene in Example 2A. MS (DCI) m/z 531.2 (M+H)+

Example 56

2-chloro-N-{trans-4-(3-chlorophenyl)-1-[(1-methyl-1H-imidazol-4-yl)sulfonyl]pyrrolidin-3-yl}-3-(trifluoromethyl)benzamide The title compound was prepared similarly to procedures described in Example 2 substituting (E)-1-chloro-3-(2-nitrovinyl)benzene for (E)-1-methoxy-4-(2-nitrovinyl)benzene in Example 2A. MS (DCI) m/z 547.5 (M+H)+

Example 57 trans-1-[(1-methyl-1H-imidazol-4-yl)sulfonyl]-N-(2-methylphenyl)-4-phenylpyrrolidin-3-amine Under nitrogen, a pressure vial was charged with Example 14A as a hydrochloric salt (100 mg, 0.30 mmol), 1-bromo- 2-methylbenzene (55 mg, 0.32 mmol), 2'-(di-tert-butylphosphino)-N,N-dimethylbiphenyl-2-amine (10 mg, 0.03 mmol), tris(dibenzylidene-acetone)dipalladium(0) (13 mg, 0.02 mmol), sodium tert-butoxide (70 mg, 0.729 mmol), and toluene (2 mL). The reaction mixture was stirred at 80° C. for 6 hours. Then, the reaction mixture was concentrated. Purification via HPLC provided the title compound. MS (ESI) m/z 397 (M+H)$^+$.

Example 58 trans-1-[(1-methyl-1H-imidazol-4-yl)sulfonyl]-N-(3-methylphenyl)-4-phenylpyrrolidin-3-amine The title compound was prepared similarly to the conditions described in Example 57 substituting 1-bromo-3-methylbenzene for 1-bromo-2-methylbenzene. MS (ESI) m/z 397 (M+H)$^+$.

Example 59 trans-1-[(1-methyl-1H-imidazol-4-yl)sulfonyl]-N-(4-methylphenyl)-4-phenylpyrrolidin-3-amine The title compound was prepared similarly to the conditions described in Example 57 substituting 1-bromo-4-methylbenzene for 1-bromo-2-methylbenzene. MS (ESI) m/z 397 (M+H)$^+$.

Example 60

2-chloro-N-{trans-1-[(1-methyl-1H-imidazol-4-yl)sulfonyl]-4-phenylpyrrolidin-3-yl}-4-(trifluoromethyl)benzamide The title compound was prepared similarly to the conditions described in Example 4C substituting Example 14A for Example 4B and substituting 2-chloro-4-(trifluoromethyl)benzoic acid for 2-chloro-3-(trifluoromethyl)benzoic acid. MS (ESI) m/z 513 (M+H)$^+$.

Example 61

3-chloro-N-{trans-1-[(1-methyl-1H-imidazol-4-yl)sulfonyl]-4-phenylpyrrolidin-3-yl}-4-(trifluoromethyl)benzamide The title compound was prepared similarly to the conditions described in Example 4C substituting Example 14A for Example 4B and substituting 3-chloro-4-(trifluoromethyl)benzoic acid for 2-chloro-3-(trifluoromethyl)benzoic acid. MS (ESI) m/z 513 (M+H)$^+$.

Example 62

2-chloro-N-{trans-4-(4-fluorophenyl)-1-[(1-methyl-1H-imidazol-4-yl)sulfonyl]pyrrolidin-3-yl}-4-(trifluoromethyl)benzamide The title compound was prepared similarly to the conditions described in Example 4C substituting Example 3A for Example 4B and substituting 2-chloro-4-(trifluoromethyl)benzoic acid for 2-chloro-3-(trifluoromethyl)benzoic acid. MS (ESI) m/z 531 (M+H)$^+$.

Example 63

3-chloro-N-{trans-4-(4-fluorophenyl)-1-[(1-methyl-1H-imidazol-4-yl)sulfonyl]pyrrolidin-3-yl}-4-(trifluoromethyl)benzamide The title compound was prepared similarly to the conditions described in Example 4C substituting Example 3A for Example 4B and substituting 3-chloro-4-(trifluoromethyl)benzoic acid for 2-chloro-3-(trifluoromethyl)benzoic acid. MS (ESI) m/z 531 (M+H)$^+$.

Example 64

N-{trans-4-(4-fluorophenyl)-1-[(1-methyl-1H-imidazol-4-yl)sulfonyl]pyrrolidin-3-yl}-4-(trifluoromethyl)benzamide The title compound was prepared similarly to the conditions described in Example 4C substituting Example 3A for Example 4B and substituting 4-(trifluoromethyl)benzoic acid for 2-chloro-3-(trifluoromethyl)benzoic acid. MS (ESI) m/z 497 (M+H)$^+$.

Example 65

3,5-dichloro-N-{trans-4-(4-fluorophenyl)-1-[(1-methyl-1H-imidazol-4-yl)sulfonyl]pyrrolidin-3-yl}benzamide The title compound was prepared similarly to the conditions described in Example 4C substituting Example 3A for Example 4B and substituting 3,5-dichlorobenzoic acid for 2-chloro-3-(trifluoromethyl)benzoic acid. MS (ESI) m/z 497 (M+H)$^+$.

Example 66 trans-1-[(1-methyl-1H-imidazol-4-yl)sulfonyl]-4-phenyl-N-[2-(trifluoromethyl)phenyl]pyrrolidin-3-amine The title compound was prepared similarly to the conditions described in Example 57 substituting 1-bromo-2-(trifluoromethyl)benzene for 1-bromo-2-methylbenzene. MS (ESI) m/z 451 (M+H)$^+$.

Example 67 trans-1-[(1-methyl-1H-imidazol-4-yl)sulfonyl]-4-phenyl-N-[3-(trifluoromethyl)phenyl]pyrrolidin-3-amine The title compound was prepared similarly to the conditions described in Example 57 substituting 1-bromo-3-(trifluoromethyl)benzene for 1-bromo-2-methylbenzene. MS (ESI) m/z 451 (M+H)$^+$.

Example 68 trans-1-[(1-methyl-1H-imidazol-4-yl)sulfonyl]-4-phenyl-N-[4-(trifluoromethyl)phenyl]pyrrolidin-3-amine The title compound was prepared similarly to the conditions described in Example 57 substituting 1-bromo-4-(trifluoromethyl)benzene for 1-bromo-2-methylbenzene. MS (ESI) m/z 451 (M+H)$^+$.

Example 69 trans-N-(2-fluorophenyl)-1-[(1-methyl-1H-imidazol-4-yl)sulfonyl]-4-phenylpyrrolidin-3-amine The title compound was prepared similarly to the conditions described in Example 57 substituting 1-bromo-2-fluorobenzene for 1-bromo-2-methylbenzene. MS (ESI) m/z 401 (M+H)$^+$.

Example 70 trans-N-(3-fluorophenyl)-1-[(1-methyl-1H-imidazol-4-yl)sulfonyl]-4-phenylpyrrolidin-3-amine The title compound was prepared similarly to the conditions described in Example 57 substituting 1-bromo-3-fluorobenzene for 1-bromo-2-methylbenzene. MS (APCI) m/z 401 (M+H)$^+$.

Example 71 trans-N-(4-fluorophenyl)-1-[(1-methyl-1H-imidazol-4-yl)sulfonyl]-4-phenylpyrrolidin-3-amine The title compound was prepared similarly to the conditions described in Example 57 substituting 1-bromo-4-fluorobenzene for 1-bromo-2-methylbenzene. MS (ESI) m/z 401 (M+H)$^+$.

Example 72

3-({trans-4-(4-fluorophenyl)-1-[(1-methyl-1H-imidazol-4-yl)sulfonyl]pyrrolidin-3-yl}amino)benzonitrile The title compound was prepared similarly to the conditions described in Example 57 substituting Example 3A for Example 14A and substituting 3-bromo-benzenonitrile for 1-bromo-2-methylbenzene. MS (ESI) m/z 426 (M+H)$^+$.

Example 73 trans-N-(2-chlorophenyl)-1-[(1-methyl-1H-imidazol-4-yl)sulfonyl]-4-phenylpyrrolidin-3-amine The title compound was prepared similarly to the conditions described in Example 57 substituting 1-bromo-2-chlorobenzene for 1-bromo-2-methylbenzene. MS (APCI) m/z 418 (M+H)$^+$.

Example 74 trans-N-(3-chlorophenyl)-1-[(1-methyl-1H-imidazol-4-yl)sulfonyl]-4-phenylpyrrolidin-3-amine The title compound was prepared similarly to the conditions described in Example 57 substituting 1-bromo-3-chlorobenzene for 1-bromo-2-methylbenzene. MS (ESI) m/z 417 (M+H)$^+$.

Example 75 trans-N-(4-chlorophenyl)-1-[(1-methyl-1H-imidazol-4-yl)sulfonyl]-4-phenylpyrrolidin-3-amine The title compound was prepared similarly to the conditions described in Example 57 substituting 1-bromo-4-chlorobenzene for 1-bromo-2-methylbenzene. MS (ESI) m/z 417 (M+H)$^+$.

Example 76

4-fluoro-3-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 3-bromo-4-fluorobenzonitrile for 1-bromo-2-methylbenzene. MS (APCI) m/z 426 (M+H)$^+$.

Example 77

2-fluoro-3-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 3-bromo-2-fluorobenzonitrile for 1-bromo-2-methylbenzene. MS (ESI) m/z 426 (M+H)$^+$.

Example 78

3-fluoro-5-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 3-bromo-5-fluorobenzonitrile for 1-bromo-2-methylbenzene. MS (ESI) m/z 426 (M+H)$^+$.

Example 79

2-chloro-5-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 5-bromo-2-chlorobenzonitrile for 1-bromo-2-methylbenzene. MS (ESI) m/z 442 (M+H)$^+$.

Example 80

3-chloro-5-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 3-bromo-5-chlorobenzonitrile for 1-bromo-2-methylbenzene. MS (ESI) m/z 442 (M+H)+.

Example 81

4-chloro-3-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 3-bromo-4-chlorobenzonitrile for 1-bromo-2-methylbenzene. MS (ESI) m/z 442 (M+H)+.

Example 82

4-methyl-3-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 3-bromo-4-methylbenzonitrile for 1-bromo-2-methylbenzene. MS (ESI) m/z 422 (M+H)+.

Example 83

2-methyl-3-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 3-bromo-2-methylbenzonitrile for 1-bromo-2-methylbenzene. MS (ESI) m/z 422 (M+H)+.

Example 84 trans-4-(4-fluorophenyl)-1-[(1-methyl-1H-imidazol-4-yl)sulfonyl]-N-(2-methylphenyl)pyrrolidin-3-amine The title compound was prepared similarly to the conditions described in Example 57 substituting Example 3A for Example 14A. MS (ESI) m/z 415 (M+H)+.

Example 85 trans-4-(4-fluorophenyl)-1-[(1-methyl-1H-imidazol-4-yl)sulfonyl]-N-(3-methylphenyl)pyrrolidin-3-amine The title compound was prepared similarly to the conditions described in Example 57 substituting Example 3A for Example 14A and substituting 1-bromo-3-methylbenzene for 1-bromo-2-methylbenzene. MS (ESI) m/z 415 (M+H)+.

Example 86 trans-4-(4-fluorophenyl)-1-[(1-methyl-1H-imidazol-4-yl)sulfonyl]-N-(4-methylphenyl)pyrrolidin-3-amine The title compound was prepared similarly to the conditions described in Example 57 substituting Example 3A for Example 14A and substituting 1-bromo-4-methylbenzene for 1-bromo-2-methylbenzene. MS (ESI) m/z 415 (M+H)+.

Example 87 trans-4-(4-fluorophenyl)-1-[(1-methyl-1H-imidazol-4-yl)sulfonyl]-N-[2-(trifluoromethyl)phenyl]pyrrolidin-3-amine The title compound was prepared similarly to the conditions described in Example 57 substituting Example 3A for Example 14A and substituting 1-bromo-2-(trifluoromethyl)benzene for 1-bromo-2-methylbenzene. MS (ESI) m/z 469 (M+H)+.

Example 88 trans-4-(4-fluorophenyl)-1-[(1-methyl-1H-imidazol-4-yl)sulfonyl]-N-[3-(trifluoromethyl)phenyl]pyrrolidin-3-amine The title compound was prepared similarly to the conditions described in Example 57 substituting Example 3A for Example 14A and substituting 1-bromo-3-(trifluoromethyl)benzene for 1-bromo-2-methylbenzene. MS (ESI) m/z 469 (M+H)+.

Example 89 trans-4-(4-fluorophenyl)-1-[(1-methyl-1H-imidazol-4-yl)sulfonyl]-N-[4-(trifluoromethyl)phenyl]pyrrolidin-3-amine The title compound was prepared similarly to the conditions described in Example 57 substituting Example 3A for Example 14A and substituting 1-bromo-4-(trifluoromethyl)benzene for 1-bromo-2-methylbenzene. MS (ESI) m/z 469 (M+H)+.

Example 90 trans-N-(2-fluorophenyl)-4-(4-fluorophenyl)-1-[(1-methyl-1H-imidazol-4-yl)sulfonyl]pyrrolidin-3-amine The title compound was prepared similarly to the conditions described in Example 57 substituting Example 3A for Example 14A and substituting 1-bromo-2-fluorobenzene for 1-bromo-2-methylbenzene. MS (ESI) m/z 419 (M+H)+.

Example 91 trans-N-(3-fluorophenyl)-4-(4-fluorophenyl)-1-[(1-methyl-1H-imidazol-4-yl)sulfonyl]pyrrolidin-3-amine The title compound was prepared similarly to the conditions described in Example 57 substituting Example 3A for Example 14A and substituting 1-bromo-3-fluorobenzene for 1-bromo-2-methylbenzene. MS (ESI) m/z 419 (M+H)+.

Example 92 trans-N,4-bis(4-fluorophenyl)-1-[(1-methyl-1H-imidazol-4-yl)sulfonyl]pyrrolidin-3-amine The title compound was prepared similarly to the conditions described in Example 57 substituting Example 3A for Example 14A and substituting 1-bromo-4-fluorobenzene for 1-bromo-2-methylbenzene. MS (ESI) m/z 419 (M+H)+.

Example 93 trans-N-(2-chlorophenyl)-4-(4-fluorophenyl)-1-[(1-methyl-1H-imidazol-4-yl)sulfonyl]pyrrolidin-3-amine The title compound was prepared similarly to the conditions described in Example 57 substituting Example 3A for Example 14A and substituting 1-bromo-2-chloroobenzene for 1-bromo-2-methylbenzene. MS (ESI) m/z 435 (M+H)+.

Example 94 trans-N-(3-chlorophenyl)-4-(4-fluorophenyl)-1-[(1-methyl-1H-imidazol-4-yl)sulfonyl]pyrrolidin-3-amine The title compound was prepared similarly to the conditions described in Example 57 substituting Example 3A for Example 14A and substituting 1-bromo-3-chlorobenzene for 1-bromo-2-methylbenzene. MS (ESI) m/z 435 (M+H)+.

Example 95 trans-N-(4-chlorophenyl)-4-(4-fluorophenyl)-1-[(1-methyl-1H-imidazol-4-yl)sulfonyl]pyrrolidin-3-amine The title compound was prepared similarly to the conditions described in Example 57 substituting Example 3A for Example 14A and substituting 1-bromo-4-chlorobenzene for 1-bromo-2-methylbenzene. MS (ESI) m/z 435 (M+H)+.

Example 100

2-methoxy-5-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 5-bromo-2-methoxybenzonitrile for 1-bromo-2-methylbenzene. MS (ESI) m/z 438 (M+H)+.

Example 101

3-methyl-5-({trans-1-[(1-methyl-1H-imidazol-4-yl)sulfonyl]-4-phenylpyrrolidin-3-yl}amino)benzonitrile The title compound was prepared similarly to the conditions described in Example 57 substituting 3-bromo-5-methylbenzonitrile for 1-bromo-2-methylbenzene. MS (ESI) m/z 422 (M+H)+.

Example 102

5-({trans-1-[(1-methyl-1H-imidazol-4-yl)sulfonyl]-4-phenylpyrrolidin-3-yl}amino)-2-(trifluoromethoxy)benzonitrile The title compound was prepared similarly to the conditions described in Example 57 substituting 5-bromo-2-(trifluoromethoxy)benzonitrile for 1-bromo-2-methylbenzene. MS (ESI) m/z 476 (M–$CH_3$)+.

Example 115

2-chloro-N-{trans-4-(2-chlorophenyl)-1-[(1-methyl-1H-imidazol-4-yl)sulfonyl]pyrrolidin-3-yl}-3-(trifluoromethyl)benzamide The title compound was prepared similarly to the procedures described in Example 2 substituting (E)-1-chloro-2-(2-nitrovinyl)benzene for (E)-1-methoxy-4-(2-nitrovinyl)benzene in Example 2A. MS (DCI) m/z 547.2 (M+H)+.

Example 122

N-[trans-1-(ethylsulfonyl)-4-phenylpyrrolidin-3-yl]-4-(trifluoromethyl)benzamide

Example 122A trans-1-(ethylsulfonyl)-4-phenylpyrrolidin-3-amine

The title compound was prepared as an HCl salt similarly to Example 2A-2F substituting (E)-(2-nitrovinyl)benzene for (E)-1-methoxy-4-(2-nitrovinyl)benzene and substituting ethanesulfonyl chloride for 1-methyl-1H-imidazole-4-sulfonyl chloride.

Example 122B

N-[trans-1-(ethylsulfonyl)-4-phenylpyrrolidin-3-yl]-4-(trifluoromethyl)benzamide The title compound was prepared similarly to Example 4C substituting Example 122A for Example 4B and substituting 4-(trifluoromethyl)benzoic acid for 2-chloro-3-(trifluoromethyl)benzoic acid. MS (ESI) m/z 427 (M+H)+.

Example 123

3,5-dichloro-N-[trans-1-(ethylsulfonyl)-4-phenylpyrrolidin-3-yl]benzamide

The title compound was prepared similarly to Example 4C substituting Example 122A for Example 4B and substituting 3,5-dichlorobenzoic acid for 2-chloro-3-(trifluoromethyl)benzoic acid. MS (ESI) m/z 427 (M+H)+.

Example 124

2-chloro-N-[trans-1-(ethylsulfonyl)-4-phenylpyrrolidin-3-yl]-3-(trifluoromethyl)benzamide The title compound was prepared similarly to Example 4C substituting Example 122A for Example 4B. MS (ESI) m/z 461 (M+H)+.

Example 125

N-[trans-4-phenyl-1-(propylsulfonyl)pyrrolidin-3-yl]-4-(trifluoromethyl)benzamide

Example 125A

The title compound was prepared as an HCl salt similarly to the procedures described for Examples 2A-2F substituting (E)-(2-nitrovinyl)benzene for (E)-1-methoxy-4-(2-nitrovinyl)benzene and substituting propanesulfonyl chloride for 1-methyl-1H-imidazole-4-sulfonyl chloride.

Example 125B

N-[trans-4-phenyl-1-(propylsulfonyl)pyrrolidin-3-yl]-4-(trifluoromethyl)benzamide The title compound was prepared similarly to the procedure described in Example 4C substituting Example 125A for Example 4B and substituting 4-(trifluoromethyl)benzoic acid for 2-chloro-3-(trifluoromethyl)benzoic acid. MS (ESI) m/z 441 (M+H)$^+$.

Example 126

3,5-dichloro-N-[trans-4-phenyl-1-(propylsulfonyl)pyrrolidin-3-yl]benzamide

The title compound was prepared similarly to Example 4C substituting Example 125A for Example 4B and substituting 3,5-dichlorobenzoic acid for 2-chloro-3-(trifluoromethyl)benzoic acid. MS (ESI) m/z 441 (M+H)$^+$.

Example 127

2-chloro-N-[trans-4-phenyl-1-(propylsulfonyl)pyrrolidin-3-yl]-3-(trifluoromethyl)benzamide The title compound was prepared similarly to Example 4C substituting Example 125A for Example 4B. MS (ESI) m/z 475 (M+H)$^+$.

Example 128

N-{trans-1-[(cyclopropylmethyl)sulfonyl]-4-phenylpyrrolidin-3-yl}-4-(trifluoromethyl)benzamide

Example 128A trans-1-(cyclopropylmethylsulfonyl)-4-phenylpyrrolidin-3-amine

The title compound was prepared as an HCl salt similarly to the procedure described in Example 2A-2F substituting (E)-(2-nitrovinyl)benzene for (E)-1-methoxy-4-(2-nitrovinyl)benzene and substituting cyclopropylmethanesulfonyl chloride for 1-methyl-1H-imidazole-4-sulfonyl chloride.

Example 128B

N-{trans-1-[(cyclopropylmethyl)sulfonyl]-4-phenylpyrrolidin-3-yl}-4-(trifluoromethyl)benzamide The title compound was prepared similarly to Example 4C substituting Example 128A for Example 4B and substituting 4-(trifluoromethyl)benzoic acid for 2-chloro-3-(trifluoromethyl)benzoic acid. MS (ESI) m/z 453 (M+H)$^+$.

Example 129

3,5-dichloro-N-{trans-1-[(cyclopropylmethyl)sulfonyl]-4-phenylpyrrolidin-3-yl}benzamide The title compound was prepared similarly to Example 4C substituting Example 128A for Example 4B and substituting 3,5-dichlorobenzoic acid for 2-chloro-3-(trifluoromethyl)benzoic acid. MS (ESI) m/z 453 (M+H)$^+$.

Example 130

2-chloro-N-{trans-1-[(cyclopropylmethyl)sulfonyl]-4-phenylpyrrolidin-3-yl}-3-(trifluoromethyl)benzamide The title compound was prepared similarly to Example 4C substituting Example 128A for Example 4B. MS (ESI) m/z 487 (M+H)$^+$.

Example 131

3-{[trans-1-(ethylsulfonyl)-4-phenylpyrrolidin-3-yl]amino}benzonitrile

The title compound was prepared similarly to the procedure described in Example 57 substituting Example 122A for Example 14A and substituting 3-bromo-benzonitrile for 1-bromo-2-methylbenzene. MS (ESI) m/z 356 (M+H)$^+$.

Example 132

3-{[trans-4-phenyl-1-(propylsulfonyl)pyrrolidin-3-yl]amino}benzonitrile

The title compound was prepared similarly to the procedure described in Example 57 substituting Example 125A for Example 14A and substituting 3-bromo-benzonitrile for 1-bromo-2-methylbenzene. MS (ESI) m/z 370 (M+H)$^+$.

Example 133

3-({trans-1-[(cyclopropylmethyl)sulfonyl]-4-phenylpyrrolidin-3-yl}amino)benzonitrile The title compound was prepared similarly to the procedure described in Example 57 substituting Example 128A for Example 14A and substituting 3-bromo-benzonitrile for 1-bromo-2-methylbenzene. MS (ESI) m/z 382 (M+H)$^+$.

Example 134

N-{trans-1-[(4-methoxyphenyl)sulfonyl]-4-phenylpyrrolidin-3-yl}-4-(trifluoromethyl)benzamide

Example 134A trans-1-(4-methoxyphenylsulfonyl)-4-phenylpyrrolidin-3-amine

The title compound was prepared as an HCl salt similarly to Example 2A-2F substituting (E)-(2-nitrovinyl)benzene for (E)-1-methoxy-4-(2-nitrovinyl)benzene and substituting 4-methoxybenzene-1-sulfonyl chloride for 1-methyl-1H-imidazole-4-sulfonyl chloride.

Example 134B

N-{trans-1-[(4-methoxyphenyl)sulfonyl]-4-phenylpyrrolidin-3-yl}-4-(trifluoromethyl)benzamide The title compound was prepared similarly to the procedure described in Example 4C substituting Example 134A for Example 4B and substituting 4-(trifluoromethyl)benzoic acid for 2-chloro-3-(trifluoromethyl)benzoic acid. MS (ESI) m/z 505 (M+H)$^+$.

Example 135

3,5-dichloro-N-{trans-1-[(4-methoxyphenyl)sulfonyl]-4-phenylpyrrolidin-3-yl}benzamide The title compound was prepared similarly to the procedure described in Example 4C substituting Example 134A for Example 4B and substituting 3,5-dichlorobenzoic acid for 2-chloro-3-(trifluoromethyl)benzoic acid. MS (ESI) m/z 505 (M+H)$^+$.

Example 136

2-chloro-N-{trans-1-[(4-methoxyphenyl)sulfonyl]-4-phenylpyrrolidin-3-yl}-3-(trifluoromethyl)benzamide The title compound was prepared similarly to the procedure described in Example 4C substituting Example 134A for Example 4B. MS (ESI) m/z 539 (M+H)$^+$.

Example 137

3-({trans-1-[(4-methoxyphenyl)sulfonyl]-4-phenylpyrrolidin-3-yl}amino)benzonitrile The title compound was prepared similarly to the procedure described in Example 57 substituting Example 134A for Example 14A and substituting 3-bromo-benzonitrile for 1-bromo-2-methylbenzene. MS (ESI) m/z 434 (M+H)$^+$.

Example 142

3,5-dichloro-N-[trans-4-phenyl-1-{[4-(trifluoromethyl)phenyl]sulfonyl}pyrrolidin-3-yl]benzamide

Example 142A trans-4-phenyl-1-(4-(trifluoromethyl)phenylsulfonyl)pyrrolidin-3-amine The title compound was prepared as an HCl salt similarly to Example 2A-2F substituting (E)-(2-nitrovinyl)benzene for (E)-1-methoxy-4-(2-nitrovinyl)benzene and substituting 4-(trifluoromethyl)benzene-1-sulfonyl chloride for 1-methyl-1H-imidazole-4-sulfonyl chloride.

Example 142B 3,5-dichloro-N-[trans-4-phenyl-1-{[4-(trifluoromethyl)phenyl]sulfonyl}pyrrolidin-3-yl]benzamide The title compound was prepared similarly to the procedure described in Example 4C substituting Example 142A for Example 4B and substituting 3,5-dichlorobenzoic acid for 2-chloro-3-(trifluoromethyl)benzoic acid. MS (ESI) m/z 543 (M+H)$^+$.

Example 143

2-chloro-N-[trans-4-phenyl-1-{[4-(trifluoromethyl)phenyl]sulfonyl}pyrrolidin-3-yl]-3-(trifluoromethyl)benzamide The title compound was prepared similarly to the procedure described in Example 4C substituting Example 142A for Example 4B. MS (ESI) m/z 577 (M+H)$^+$.

Example 144

3-{[trans-4-phenyl-1-{[4-(trifluoromethyl)phenyl]sulfonyl}pyrrolidin-3-yl]amino}benzonitrile The title compound was prepared similarly to the procedure described in Example 57 substituting Example 142A for Example 14A and substituting 3-bromo-benzonitrile for 1-bromo-2-methylbenzene. MS (ESI) m/z 472 (M+H)$^+$.

Example 145

4-{[trans-3-benzyl-4-phenylpyrrolidin-1-yl]sulfonyl}-1-methyl-1H-imidazole

Example 145A (1-benzyl-4-phenylpyrrolidin-3-yl)(phenyl)methanone

A solution of N-benzyl-1-methoxy-N-((trimethylsilyl)methyl)methanamine (5.9 g, 0.025 mole) in dichloromethane (30 mL) was stirred under nitrogen, in an ice/methanol bath. Chalcone (4.16 g, 0.02 mole) was added dropwise and the mixture was stirred in the cold bath overnight. The reaction mixture was washed with aqueous sodium bicarbonate, brine, and dried over sodium sulfate. The solvent was evaporated to provide the title compound. MS (ESI) m/z 342 [M+H]$^+$.

Example 145B 3-benzyl-4-phenylpyrrolidine hydrochloride

Example 145A (8.5 g, 0.025 mole) was hydrogenated with 10% Pd/C (0.25 g) in methanol (200 mL). The reaction mixture was filtered, dissolved in methanol (100 mL) and passed through Amberlite resin. The filtrate was concentrated, redissolved in toluene and concentrated. This procedure was repeated several times until the residue was dry. MS (ESI) m/z 338 [M+H]$^+$.

Example 145C 4-(trans-3-benzyl-4-phenylpyrrolidin-1-ylsulfonyl)-1-methyl-1H-imidazole To a solution of Example 145B (0.0767 g, 0.280 mmol) in dichloromethane (1.121 ml) was added triethylamine (0.156 ml, 1.121 mmol) and 1-methyl-1H-imidazole-4-sulfonyl chloride (0.051 g, 0.280 mmol), The mixture was stirred at room temperature for 15 minutes. The solvent was evaporated. The crude material was purified by HPLC to afford the title compound. MS (ESI) m/z 382.2 [M+H]⁺.

Example 148 trans-N-benzyl-4-(4-fluorophenyl)-1-[(1-methyl-1H-imidazol-4-yl)sulfonyl]pyrrolidin-3-amine To a stirred solution of Example 3A (100 mg, 0.28 mmol) in a buffer 4 pH solution (5 mL, made from 48 g AcOH and 30.5 g NaOAc in 1 L methanol) was added benzaldehyde (24 mg, 0.22 mmol) and MgSO₄ (334 mg, 2.77 mmol). The reaction was allowed to stir for 1 hour at room temperature before MgSO₄ was removed via filtration. To the filtrate was added MPcyanoborohydride (2.19 mmol/g, 380 mg, 0.83 mmol) and the reaction was allowed to stir for 24 hours. The resin was removed via filtration and purification via HPLC provided the title compound. MS (ESI) m/z 415 (M+H)⁺.

Example 149 trans-N-[2-chloro-3-(trifluoromethyl)benzyl]-4-(4-fluorophenyl)-1-[(1-methyl-1H-imidazol-4-yl)sulfonyl]pyrrolidin-3-amine The title compound was prepared similarly to the procedure described in Example 148 substituting 2-chloro-3-(trifluoromethyl)benzaldehyde for benzaldehyde. MS (ESI) m/z 517 (M+H)⁺.

Example 150 trans-N-[2-chloro-4-(trifluoromethyl)benzyl]-4-(4-fluorophenyl)-1-[(1-methyl-1H-imidazol-4-yl)sulfonyl]pyrrolidin-3-amine The title compound was prepared similarly to the procedure described in Example 148 substituting 2-chloro-4-(trifluoromethyl)benzaldehyde for benzaldehyde. MS (ESI) m/z 517 (M+H)⁺.

Example 151 trans-N-[3-chloro-4-(trifluoromethyl)benzyl]-4-(4-fluorophenyl)-1-[(1-methyl-1H-imidazol-4-yl)sulfonyl]pyrrolidin-3-amine The title compound was prepared similarly to the procedure described in Example 148 substituting 3-chloro-4-(trifluoromethyl)benzaldehyde for benzaldehyde. MS (ESI) m/z 517 (M+H)⁺.

Example 152

3-[({trans-4-(4-fluorophenyl)-1-[(1-methyl-1H-imidazol-4-yl)sulfonyl]pyrrolidin-3-yl}amino)methyl]benzonitrile The title compound was prepared similarly to the procedure described in Example 148 substituting 3-cyanobenzaldehyde for benzaldehyde. MS (ESI) m/z 440 (M+H)⁺.

Example 153 trans-4-(4-fluorophenyl)-N-(2-methylbenzyl)-1-[(1-methyl-1H-imidazol-4-yl)sulfonyl]pyrrolidin-3-amine The title compound was prepared similarly to the procedure described in Example 148 substituting 2-methylbenzaldehyde for benzaldehyde. MS (ESI) m/z 429 (M+H)⁺.

Example 154 trans-4-(4-fluorophenyl)-N-(3-methylbenzyl)-1-[(1-methyl-1H-imidazol-4-yl)sulfonyl]pyrrolidin-3-amine The title compound was prepared similarly to the procedure described in Example 148 substituting 3-methylbenzaldehyde for benzaldehyde. MS (ESI) m/z 429 (M+H)⁺.

Example 155 trans-4-(4-fluorophenyl)-N-(4-methylbenzyl)-1-[(1-methyl-1H-imidazol-4-yl)sulfonyl]pyrrolidin-3-amine The title compound was prepared similarly to the procedure described in Example 148 substituting 4-methylbenzaldehyde for benzaldehyde. MS (ESI) m/z 429 (M+H)⁺.

Example 156 trans-N-(4-fluorobenzyl)-4-(4-fluorophenyl)-1-[(1-methyl-1H-imidazol-4-yl)sulfonyl]pyrrolidin-3-amine The title compound was prepared similarly to the procedure described in Example 148 substituting 4-fluorobenzaldehyde for benzaldehyde. MS (ESI) m/z 433 (M+H)⁺.

Example 157

(cis)-N-benzyl-1-[(1-methyl-1H-imidazol-4-yl)sulfonyl]-4-phenylpyrrolidin-3-amine Example 157A 1-benzyl-3-(benzylamino)-4-chloro-1H-pyrrole-2,5-dione To a stirred solution of 3,4-dichlorofuran-2,5-dione (5 g, 30 mmol) in acetic acid (17 mL) was added benzylamine (3.2 g, 30 mmol) and the reaction was stirred at room temperature for 1 hour. More benzylamine (3.2 g, 30 mmol) was added and the reaction was heated to 100° C. for 2 hours. The reaction mixture was concentrated. The mixture was neutralized with aqueous sodium hydroxide and partitioned with ethyl acetate. The organic fraction was collected and concentrated. Purification via flash chromatography (0-60% EtOAc/hexanes) provided the title compound.

Example 157B 1-benzyl-3-(benzylamino)-4-chloro-1H-pyrrole-2,5-dione

To a solution of Example 157A (5.5 g, 16.8 mmol) in 1,2-dimethoxyethane (60 mL) was added phenylboronic acid (2.46 g, 20.2 mmol), dicyclohexyl(2',6'-dimethoxybiphenyl-2-yl)phosphine (691 mg, 1.68 mmol), palldium(II) acetate (189 mg, 0.848 mmol), and potassium carbonate (2 M, 16.8 mL, 33.7 mmol). The reaction mixture was refluxed for 2 hours. The reaction was partitioned between water and EtOAc. The organic layer was collected and concentrated. Purification via flash chromatography (0-80% EtOAc/hexanes) provided the title compound.

Example 157C tert-butylbenzyl(1-benzyl-2,5-dioxo-4-phenyl-2,5-dihydro-1H-pyrrol-3-yl)carbamate To a stirred solution of Example 157B (4.13 g, 11.2 mmol) and triethylamine (113 mg, 1.12 mmol) in dichloromethane (50 mL) at 0° C. was added di-tert-butyl dicarbonate (1 M in tetrahydrofuran, 12.3 mL, 12.3 mmol) and N,N-dimethylpyridin-4-amine (137 mg, 1.12 mmol). The reaction was allowed to warm to room temperature after 1 hour and stirred at room temperature for 24 hours. More di-tert-butyl dicarbonate (1 M in tetrahydrofuran, 3 mL, 3 mmol) was added and the reaction mixture stirred for 2 more hours. The reaction mixture was then concentrated. Purification via flash chromatography (0-10% methanol/DCM) provided the title compound.

Example 157D tert-butylbenzyl(cis-1-benzyl-2,5-dioxo-4-phenylpyrrolidin-3-yl)carbamate To a solution of Example 157C (25 mg, 0.053 mmol) in trifluoroethane (4 ml) in a 50 ml pressure bottle was added 20% Pd(OH)$_2$/C, wet (6.25 mg, 0.045 mmol). The reaction mixture stirred for 16 hours at 30 psi hydrogen and 50° C. The mixture was filtered through a nylon membrane and the filtrate was concentrated to provide the title compound.

Example 157E tert-butylbenzyl((cis)-1-benzyl-4-phenylpyrrolidin-3-yl)carbamate

To a solution of Example 157D (2.5 g, 5 3 mmol) in tetrahydrofuran (50 mL) was added borane (1 M in tetrahydrofuran, 21.3 mL, 21.3 mmol). The reaction mixture was heated to 70° C. for 18 hours. The reaction was cooled to 50° C. and methanol (20 mL) was added slowly. The reaction mixture stirred for 1 hour. The reaction mixture was concentrated. Purification via flash chromatography (0-100% EtOAc/hexanes) provided the title compound.

Example 157F tert-butylbenzyl((cis)-4-phenylpyrrolidin-3-yl)carbamate

To a pressure vial was added Example 157E (801 mg, 1.810 mmol), tetrahydrofuran (20 ml) and Pd(OH)$_2$/C (20%, wet, 160 mg, 1.141 mmol) and the reaction mixture was stirred for 16 hours at 30 psi of hydrogen at 50° C. The mixture was filtered through a nylon membrane and the filtrate was concentrated to provide the title compound.

Example 157G (cis)-N-benzyl-1-(1-methyl-1H-imidazol-4-ylsulfonyl)-4-phenylpyrrolidin-3-amine The title compound was prepared similarly to the procedures described in Example 2E-2F substituting Example 157F for Example 2D. MS (ESI) m/z 397 (M+H)$^+$.

Example 158 trans-N-(3,4-difluorophenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 4-bromo-1,2-difluorobenzene for 1-bromo-2-methylbenzene. MS (ESI) m/z 437 (M+H)$^+$.

Example 159 trans-4-(4-fluorophenyl)-N-[4-fluoro-3-(trifluoromethyl)phenyl]-1-[(1-methyl-1H-imidazol-4-yl)sulfonyl]pyrrolidin-3-amine The title compound was prepared similarly to the procedure described in Example 57 substituting Example 3A for Example 14A and substituting 4-bromo-1-fluoro-2-(trifluoromethyl)benzene for 1-bromo-2-methylbenzene. MS (ESI) m/z 437 (M+H)$^+$.

Example 160 trans-N-(3-chloro-4-fluorophenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 4-bromo-2-chloro-1-fluorobenzene for 1-bromo-2-methylbenzene. MS (ESI) m/z 453 (M+H)$^+$.

Example 161 trans-N-(3,4-dichlorophenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 4-bromo-1,2-dichlorobenzene for 1-bromo-2-methylbenzene. MS (ESI) m/z 469 (M+H)$^+$.

Example 162 trans-N-(4-chloro-3-fluorophenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 4-bromo-1-chloro-2-fluorobenzene for 1-bromo-2-methylbenzene. MS (ESI) m/z 453 (M+H)⁺.

Example 163 trans-N-(2,3-difluorophenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 1-bromo-2,3-difluorobenzene for 1-bromo-2-methylbenzene. MS (ESI) m/z 437 (M+H)⁺.

Example 164 trans-N-(2,5-difluorophenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 1-bromo-2,5-difluorobenzene for 1-bromo-2-methylbenzene. MS (ESI) m/z 437 (M+H)⁺.

Example 165 trans-N-(2,4-difluorophenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 1-bromo-2,4-difluorobenzene for 1-bromo-2-methylbenzene. MS (ESI) m/z 437 (M+H)⁺.

Example 166 trans-4-(4-fluorophenyl)-1-[(1-methyl-1H-imidazol-4-yl)sulfonyl]-N-(2,3,4-trifluorophenyl)pyrrolidin-3-amine The title compound was prepared similarly to the procedure described in Example 57 substituting Example 3A for Example 14A and substituting 1-bromo-2,3,4-trifluorobenzene for 1-bromo-2-methylbenzene. MS (ESI) m/z 455 (M+H)⁺.

Example 167 trans-4-(4-fluorophenyl)-N-[2-fluoro-3-(trifluoromethyl)phenyl]-1-[(1-methyl-1H-imidazol-4-yl)sulfonyl]pyrrolidin-3-amine The title compound was prepared similarly to the procedure described in Example 57 substituting Example 3A for Example 14A and substituting 1-bromo-2-fluoro-3-(trifluoromethyl)benzene for 1-bromo-2-methylbenzene. MS (ESI) m/z 487 (M+H)⁺.

Example 168 trans-4-(4-fluorophenyl)-N-[3-fluoro-5-(trifluoromethyl)phenyl]-1-[(1-methyl-1H-imidazol-4-yl)sulfonyl]pyrrolidin-3-amine The title compound was prepared similarly to the procedure described in Example 57 substituting Example 3A for Example 14A and substituting 1-bromo-3-fluoro-5-(trifluoromethyl)benzene for 1-bromo-2-methylbenzene. MS (ESI) m/z 487 (M+H)⁺.

Example 169 trans-4-(4-fluorophenyl)-N-[2-fluoro-5-(trifluoromethyl)phenyl]-1-[(1-methyl-1H-imidazol-4-yl)sulfonyl]pyrrolidin-3-amine The title compound was prepared similarly to the procedure described in Example 57 substituting Example 3A for Example 14A and substituting 1-bromo-2-fluoro-5-(trifluoromethyl)benzene for 1-bromo-2-methylbenzene. MS (ESI) m/z 487 (M+H)⁺.

Example 170 trans-4-(4-fluorophenyl)-1-[(1-methyl-1H-imidazol-4-yl)sulfonyl]-N-[3-(propan-2-yl)phenyl]pyrrolidin-3-amine The title compound was prepared similarly to the procedure described in Example 57 substituting Example 3A for Example 14A and substituting 1-bromo-3-isopropylbenzene for 1-bromo-2-methylbenzene. MS (ESI) m/z 443 (M+H)⁺.

Example 171 trans-N-(3-tert-butylphenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 1-bromo-3-tert-butylbenzene for 1-bromo-2-methylbenzene. MS (ESI) m/z 457 (M+H)⁺.

Example 172 trans-N-[4-chloro-3-(trifluoromethyl)phenyl]-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 4-bromo-1-chloro-2-(trifluoromethyl)benzene for 1-bromo-2-methylbenzene. MS (ESI) m/z 503 (M+H)⁺.

Example 173 trans-N-[3-chloro-4-(trifluoromethyl)phenyl]-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 4-bromo-2-chloro-1-(trifluoromethyl)benzene for 1-bromo-2-methylbenzene. MS (ESI) m/z 503 (M+H)⁺.

Example 174 trans-N-(3-chloro-5-fluorophenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 1-bromo-3-chloro-5-fluorobenzene for 1-bromo-2-methylbenzene. MS (ESI) m/z 453 (M+H)⁺.

Example 175 trans-N-(3-chloro-4,5-difluorophenyl)-4-(4-fluorophenyl)-1-[(1-methyl-1H-imidazol-4-yl)sulfonyl]pyrrolidin-3-amine The title compound was prepared similarly to the procedure described in Example 57 substituting Example 3A for Example 14A and substituting 1-bromo-3-chloro-4,5-difluorobenzene for 1-bromo-2-methylbenzene. MS (ESI) m/z 471 (M+H)⁺.

Example 176 trans-4-(4-fluorophenyl)-1-[(1-methyl-1H-imidazol-4-yl)sulfonyl]-N-[3-(trifluoromethoxy)phenyl]pyrrolidin-3-amine The title compound was prepared similarly to the procedure described in Example 57 substituting Example 3A for Example 14A and substituting 1-bromo-3-(tirfluoromethoxy)benzene for 1-bromo-2-methylbenzene. MS (ESI) m/z 485 (M+H)⁺.

Example 177

N-{trans-4-(4-fluorophenyl)-1-[(1-methyl-1H-imidazol-4-yl)sulfonyl]pyrrolidin-3-yl}pyridin-4-amine The title compound was prepared similarly to the procedure described in Example 57 substituting Example 3A for Example 14A and substituting 4-bromopyridine hydrochloride for 1-bromo-2-methylbenzene. MS (ESI) m/z 402 (M+H)⁺.

Example 178

N-{trans-4-(4-fluorophenyl)-1-[(1-methyl-1H-imidazol-4-yl)sulfonyl]pyrrolidin-3-yl}pyridin-2-amine The title compound was prepared similarly to the procedure described in Example 57 substituting Example 3A for Example 14A and substituting 2-bromopyridine for 1-bromo-2-methylbenzene. MS (ESI) m/z 402 (M+H)⁺.

Example 179

N-{trans-4-(4-fluorophenyl)-1-[(1-methyl-1H-imidazol-4-yl)sulfonyl]pyrrolidin-3-yl}pyridin-3-amine The title compound was prepared similarly to the procedure described in Example 57 substituting Example 3A for Example 14A and substituting 3-bromopyridine for 1-bromo-2-methylbenzene. MS (ESI) m/z 402 (M+H)⁺.

Example 180

N-{trans-4-(4-fluorophenyl)-1-[(1-methyl-1H-imidazol-4-yl)sulfonyl]pyrrolidin-3-yl}-6-(trifluoromethyl)pyridin-2-amine The title compound was prepared similarly to the procedure described in Example 57 substituting Example 3A for Example 14A and substituting 2-bromo-6-(trifluoromethyl)pyridine for 1-bromo-2-methylbenzene. MS (ESI) m/z 470 (M+H)⁺.

Example 181

N-{trans-4-(4-fluorophenyl)-1-[(1-methyl-1H-imidazol-4-yl)sulfonyl]pyrrolidin-3-yl}-5-(trifluoromethyl)pyridin-3-amine The title compound was prepared similarly to the procedure described in Example 57 substituting Example 3A for Example 14A and substituting 3-bromo-5-(trifluoromethyl)pyridine for 1-bromo-2-methylbenzene. MS (ESI) m/z 470 (M+H)⁺.

Example 182

4-{[3-(3-chlorobenzyl)-4-(4-fluorophenyl)pyrrolidin-1-yl]sulfonyl}-1-methyl-1H-imidazole Example 182A 2-(3-chlorobenzyl)-3-(4-fluorophenyl)-4-nitrobutanal To a solution of (E)-1-fluoro-4-(2-nitrovinyl)benzene (1 g, 6.0 mmol) in dichloromethane (10 mL) was added 3-(3-chlorophenyl)propanal (1 g, 5.9 mmol), triethylamine (50 mL), and Lproline (50 mg, 0.43 mmol). The mixture was allowed to stir for 16 hours and the crude material was purified by silica gel column chromatography e(25% ethyl acetate/hexanes) to provide the title compound (4:1 mixture of 2 diastereomers).

Example 182B 3-(3-chlorobenzyl)-4-(4-fluorophenyl)pyrrolidine

To a solution of Example 182A (0.92 g, 2.7 mmol) in methanol (5 mL) was added 50% acetic acid (aq) (5 mL) followed by zinc (6×200 mg, 19 mmol) and sodium cyanoborohydride (120 mg, 1.9 mmol). The mixture was allowed to stir for 30 minutes. Sodium hydroxide (1 M) was added to adjust the pH value to 8. Ethyl acetate was added and the solution partitioned. The organic fraction was collected and concentrated to provide the crude title compound.

Example 182C

4-{[3-(3-chlorobenzyl)-4-(4-fluorophenyl)pyrrolidin-1-yl]sulfonyl}-1-methyl-1H-imidazole To a solution of Example 182B (289 mg, 1.0 mmol) in dichloromethane (5 mL) was added triethylamine (130 mg, 1.3 mmol), and 1-methyl-1H-imidazole-4-sulfonyl chloride (180 mg, 1.0 mmol). The mixture was allowed to stir for 20 minutes and purified by silica gel column chromatography (100% ethyl acetate). The product was recrystallized in ethyl acetate to provide the title compound. MS (ESI) m/z 434/436 (3:1) (M+H)⁺.

Example 183

2-chloro-N-{(cis)-1-[(1-methyl-1H-imidazol-4-yl)sulfonyl]-4-phenylpyrrolidin-3-yl}-3-(trifluoromethyl)benzamide Example 183A A 20 mL pressure vial was charged with Example 157 (891.1 mg, 2.247 mmol), ethanol (6 mL) and dihydroxypalladium (60.2 mg, 0.429 mmol). The mixture was stirred under 60 psi of hydrogen at 50° C. for 1.5 hours. Another 60 mg of catalyst was added, and the hydrogenation was continued for 2 hours more. The mixture was filtered through a polypropylene membrane and concentrated to provide the title compound.

Example 183B 2-chloro-N-{(cis)-1-[(1-methyl-1H-imidazol-4-yl) sulfonyl]-4-phenylpyrrolidin-3-yl}-3-(trifluoromethyl)benzamide The title compound was prepared similarly to the procedure described in Example 4C substituting Example 183A for Example 4B. MS (ESI) m/z 513 (M+H)$^+$.

Example 184

(cis)-1-[(1-methyl-1H-imidazol-4-yl)sulfonyl]-N,4-diphenylpyrrolidin-3-amine

The title compound was prepared similarly to the procedure described in Example 57 substituting Example 183A for Example 14A and substituting bromobenzene for 1-bromo-2-methylbenzene. MS (ESI) m/z 383 (M+H)$^+$.

Example 185 trans-4-(3-fluorophenyl)-1-[(1-methyl-1H-imidazol-4-yl)sulfonyl]-N-phenylpyrrolidin-3-amine Example 185A (E)-1-fluoro-3-(2-nitrovinyl)benzene A stirred solution containing 3-fluorobenzaldehyde (9.95 g, 80.1 mmol), ammonium acetate (17.3 g, 225 mmol), nitromethane (12.2 mL, 225 mmol), and acetic acid (75 mL) was heated to 100° C. for 3 hours. The mixture was cooled to room temperature and partitioned between water and dichloromethane. The organic fraction was collected and the aqueous fraction was washed with dichloromethane. The organic fractions were combined and washed with sodium bicarbonate (aq.), brine, and water. The organic fraction was dried with sodium sulfate and purification via flash chromatography (10% EtOAc/hexanes) provided the title compound.

Example 185B trans-4-(3-fluorophenyl)-1-(1-methyl-1H-imidazol-4-ylsulfonyl)pyrrolidin-3-amine The title compound was prepared as the HCl salt similarly to the procedures described in Example 2A-2F substituting Example 185A for (E)-1-methoxy-4-(2-nitrovinyl)benzene.

Example 185C trans-4-(3-fluorophenyl)-1-[(1-methyl-1H-imidazol-4-yl)sulfonyl]-N-phenylpyrrolidin-3-amine The title compound was prepared similarly to the procedure described in Example 57 substituting Example 185B for Example 14A and substituting bromobenzene for 1-bromo-2-methylbenzene. MS (ESI) m/z 401 (M+H)$^+$.

Example 186 trans-N,4-bis(3-fluorophenyl)-1-[(1-methyl-1H-imidazol-4-yl)sulfonyl]pyrrolidin-3-amine The title compound was prepared similarly to the procedure described in Example 57 substituting Example 185B for Example 14A and substituting 1-bromo-3-fluorobenzene for 1-bromo-2-methylbenzene. MS (ESI) m/z 419 (M+H)$^+$.

Example 187 trans-4-(3-fluorophenyl)-N-(4-fluorophenyl)-1-[(1-methyl-1H-imidazol-4-yl)sulfonyl]pyrrolidin-3-amine The title compound was prepared similarly to the procedure described in Example 57 substituting Example 185B for Example 14A and substituting 1-bromo-4-fluorobenzene for 1-bromo-2-methylbenzene. MS (ESI) m/z 419 (M+H)$^+$.

Example 188 trans-N-(3-chlorophenyl)-4-(3-fluorophenyl)-1-[(1-methyl-1H-imidazol-4-yl)sulfonyl]pyrrolidin-3-amine The title compound was prepared similarly to the procedure described in Example 57 substituting Example 185B for Example 14A and substituting 1-bromo-3-chlorobenzene for 1-bromo-2-methylbenzene. MS (ESI) m/z 435 (M+H)$^+$.

Example 189 trans-4-(3-fluorophenyl)-1-[(1-methyl-1H-imidazol-4-yl)sulfonyl]-N-[3-(trifluoromethyl)phenyl]pyrrolidin-3-amine The title compound was prepared similarly to the procedure described in Example 57 substituting Example 185B for Example 14A and substituting 1-bromo-3-(trifluoromethane)benzene for 1-bromo-2-methylbenzene. MS (ESI) m/z 469 (M+H)$^+$.

Example 190 trans-4-(3-fluorophenyl)-1-[(1-methyl-1H-imidazol-4-yl)sulfonyl]-N-[4-(trifluoromethyl)phenyl]pyrrolidin-3-amine The title compound was prepared similarly to the procedure described in Example 57 substituting Example 185B for Example 14A and substituting 1-bromo-4-(trifluoromethane)benzene for 1-bromo-2-methylbenzene. MS (ESI) m/z 469 (M+H)$^+$.

Example 191

N-{trans-4-(3-fluorophenyl)-1-[(1-methyl-1H-imidazol-4-yl)sulfonyl]pyrrolidin-3-yl}pyridin-4-amine The title compound was prepared similarly to the procedure described in Example 57 substituting Example 185B for Example 14A and substituting 4-bromopyridine hydrochloride for 1-bromo-2-methylbenzene. MS (ESI) m/z 402 (M+H)⁺.

Example 192 trans-N-(3,4-dichlorophenyl)-4-(3-fluorophenyl)-1-[(1-methyl-1H-imidazol-4-yl)sulfonyl]pyrrolidin-3-amine The title compound was prepared similarly to the procedure described in Example 57 substituting Example 185B for Example 14A and substituting 1-bromo-3,4-dichlorobenzene for 1-bromo-2-methylbenzene. MS (ESI) m/z 469 (M+H)⁺.

Example 193 trans-N-(4-chloro-3-fluorophenyl)-4-(3-fluorophenyl)-1-[(1-methyl-1H-imidazol-4-yl)sulfonyl]pyrrolidin-3-amine The title compound was prepared similarly to the procedure described in Example 57 substituting Example 185B for Example 14A and substituting 1-bromo-4-chloro-3-fluorobenzene for 1-bromo-2-methylbenzene. MS (ESI) m/z 453 (M+H)⁺.

Example 194 trans-N-(3-chloro-4-fluorophenyl)-4-(3-fluorophenyl)-1-[(1-methyl-1H-imidazol-4-yl)sulfonyl]pyrrolidin-3-amine The title compound was prepared similarly to the procedure described in Example 57 substituting Example 185B for Example 14A and substituting 1-bromo-3-chloro-4-fluorobenzene for 1-bromo-2-methylbenzene. MS (ESI) m/z 453 (M+H)⁺.

Example 195

N-{trans-4-(3-fluorophenyl)-1-[(1-methyl-1H-imidazol-4-yl)sulfonyl]pyrrolidin-3-yl}-6-(trifluoromethyl)pyridin-2-amine The title compound was prepared similarly to the procedure described in Example 57 substituting Example 185B for Example 14A and substituting 2-bromo-6-(trifluoromethyl)pyridine for 1-bromo-2-methylbenzene. MS (ESI) m/z 470 (M+H)⁺.

Example 196

N-{trans-4-(3-fluorophenyl)-1-[(1-methyl-1H-imidazol-4-yl)sulfonyl]pyrrolidin-3-yl}-5-(trifluoromethyl)pyridin-3-amine The title compound was prepared similarly to the procedure described in Example 57 substituting Example 185B for Example 14A and substituting 3-bromo-5-(trifluoromethyl)pyridine for 1-bromo-2-methylbenzene. MS (ESI) m/z 470 (M+H)⁺.

Example 197 trans-N-(3,4-difluorophenyl)-4-(3-fluorophenyl)-1-[(1-methyl-1H-imidazol-4-yl)sulfonyl]pyrrolidin-3-amine The title compound was prepared similarly to the procedure described in Example 57 substituting Example 185B for Example 14A and substituting 1-bromo-3,4-difluorobenzene for 1-bromo-2-methylbenzene. MS (ESI) m/z 437 (M+H)⁺.

Example 198 trans-4-(2-fluorophenyl)-1-[(1-methyl-1H-imidazol-4-yl)sulfonyl]-N-phenylpyrrolidin-3-amine Example 198A trans-4-(2-fluorophenyl)-1-(1-methyl-1H-imidazol-4-ylsulfonyl)pyrrolidin-3-amine The title compound was prepared similarly to the procedures described in Example 2A-2F substituting (E)-1-fluoro-2-(2-nitrovinyl)benzene for (E)-(2-nitrovinyl)benzene.

Example 198B trans-4-(2-fluorophenyl)-1-[(1-methyl-1H-imidazol-4-yl)sulfonyl]-N-phenylpyrrolidin-3-amine The title compound was prepared similarly to the procedure described in Example 57 substituting Example 198A for Example 14A and substituting bromobenzene for 1-bromo-2-methylbenzene. MS (ESI) m/z 401 (M+H)⁺.

Example 199 trans-4-(2-fluorophenyl)-N-(3-fluorophenyl)-1-[(1-methyl-1H-imidazol-4-yl)sulfonyl]pyrrolidin-3-amine The title compound was prepared similarly to the procedure described in Example 57 substituting Example 198A for Example 14A and substituting 1-bromo-3-fluorobenzene for 1-bromo-2-methylbenzene. MS (ESI) m/z 419 (M+H)⁺.

Example 200 trans-4-(2-fluorophenyl)-N-(4-fluorophenyl)-1-[(1-methyl-1H-imidazol-4-yl)sulfonyl]pyrrolidin-3-amine The title compound was prepared similarly to the procedure described in Example 57 substituting Example 198A

Example 201 trans-N-(3-chlorophenyl)-4-(2-fluorophenyl)-1-[(1-methyl-1H-imidazol-4-yl)sulfonyl]pyrrolidin-3-amine The title compound was prepared similarly to the procedure described in Example 57 substituting Example 198A for Example 14A and substituting 1-bromo-3-chlorobenzene for 1-bromo-2-methylbenzene. MS (ESI) m/z 435 (M+H)$^+$.

Example 202 trans-N-(4-chlorophenyl)-4-(2-fluorophenyl)-1-[(1-methyl-1H-imidazol-4-yl)sulfonyl]pyrrolidin-3-amine The title compound was prepared similarly to the procedure described in Example 57 substituting Example 198A for Example 14A and substituting 1-bromo-4-chlorobenzene for 1-bromo-2-methylbenzene. MS (ESI) m/z 435 (M+H)$^+$.

Example 203

N-{trans-4-(2-fluorophenyl)-1-[(1-methyl-1H-imidazol-4-yl)sulfonyl]pyrrolidin-3-yl}-6-(trifluoromethyl)pyridin-2-amine The title compound was prepared similarly to the procedure described in Example 57 substituting Example 198A for Example 14A and substituting 2-bromo-6-(trifluoromethyl)pyridine for 1-bromo-2-methylbenzene. MS (ESI) m/z 470 (M+H)$^+$.

Example 204

N-{trans-4-(2-fluorophenyl)-1-[(1-methyl-1H-imidazol-4-yl)sulfonyl]pyrrolidin-3-yl}-2-(trifluoromethyl)pyridin-4-amine The title compound was prepared similarly to the procedure described in Example 57 substituting Example 198A for Example 14A and substituting 4-bromo-2-(trifluoromethyl)pyridine for 1-bromo-2-methylbenzene. MS (ESI) m/z 470 (M+H)$^+$.

Example 205

4-{[3-(2-bromobenzyl)-4-(2-bromophenyl)pyrrolidin-1-yl]sulfonyl}-1-methyl-1H-imidazole

Example 205A 2-(2-bromobenzyl)-3-(2-bromophenyl)-4-nitrobutanal

The title compound was prepared using the conditions described in Example 182A substituting (E)-1-bromo-2-(2-nitrovinyl)benzene for (E)-1-fluoro-4-(2-nitrovinyl)benzene and 3-(2-bromophenyl)propanal for 3-(3-chlorophenyl)propanal.

Example 205B 3-(2-bromobenzyl)-4-(2-bromophenyl)pyrrolidine

The title compound was prepared using the conditions described in Example 182B substituting Example 205A for Example 182A.

Example 205C

4-{[3-(2-bromobenzyl)-4-(2-bromophenyl)pyrrolidin-1-yl]sulfonyl}-1-methyl-1H-imidazole The title compound was prepared using the conditions described in Example 182C substituting Example 205B for Example 182B. MS (ESI) m/z 537/539/541(1:2:1) (M+H)$^+$.

Example 206

{Trans-4-(4-fluorophenyl)-1-[(1-methyl-1H-imidazol-4-yl)sulfonyl]pyrrolidin-3-yl}methanol To a solution of Example 242C (620 mg, 1.69 mmol) in 6 mL of tetrahydrofuran at −30° C. was added lithium aluminum hydride (2N in tetrahydrofuran, 0.93 mL, 1.86 mmol). The reaction mixture stirred at −30° C. for 30 min. The reaction mixture was quenched with a saturated sodium bicarbonate solution, and the solution was partitioned with EtOAc. The organic fraction was collected, washed with water dried over sodium sulfate, and concentrated to give the title compound. MS (ESI) m/z 340.0 (M+H)$^+$.

Example 207

N-{trans-1-[(1-methyl-1H-imidazol-4-yl)sulfonyl]-4-phenylpyrrolidin-3-yl}pyridin-2-amine The title compound was prepared similarly to the procedure described in Example 57 substituting 2-bromopyridine for 1-bromo-2-methylbenzene. MS (ESI) m/z 384 (M+H)$^+$.

Example 208

N-{trans-1-[(1-methyl-1H-imidazol-4-yl)sulfonyl]-4-phenylpyrrolidin-3-yl}pyridin-3-amine The title compound was prepared similarly to the procedure described in Example 57 substituting 3-bromopyridine for 1-bromo-2-methylbenzene. MS (ESI) m/z 384 (M+H)$^+$.

Example 209

N-{trans-1-[(1-methyl-1H-imidazol-4-yl)sulfonyl]-4-phenylpyrrolidin-3-yl}pyridin-4-amine The title compound was prepared similarly to the procedure described in Example 57 substituting 4-bromopyridine for 1-bromo-2-methylbenzene. MS (ESI) m/z 384 (M+H)$^+$.

(continued) for Example 14A and substituting 1-bromo-4-fluorobenzene for 1-bromo-2-methylbenzene. MS (ESI) m/z 419 (M+H)$^+$.

Example 210

N-{trans-1-[(1-methyl-1H-imidazol-4-yl)sulfonyl]-4-phenylpyrrolidin-3-yl}-6-(trifluoromethyl)pyridin-2-amine The title compound was prepared similarly to the procedure described in Example 57 substituting 2-bromo-6-(trifluoromethyl)pyridine for 1-bromo-2-methylbenzene. MS (ESI) m/z 452 (M+H)$^+$.

Example 211

N-{trans-1-[(1-methyl-1H-imidazol-4-yl)sulfonyl]-4-phenylpyrrolidin-3-yl}-2-(trifluoromethyl)pyridin-4-amine The title compound was prepared similarly to the procedure described in Example 57 substituting 4-bromo-2-(trifluoromethyl)pyridine for 1-bromo-2-methylbenzene. MS (ESI) m/z 452 (M+H)$^+$.

Example 212

N-{trans-1-[(1-methyl-1H-imidazol-4-yl)sulfonyl]-4-phenylpyrrolidin-3-yl}-4-(trifluoromethyl)pyridin-2-amine The title compound was prepared similarly to the procedure described in Example 57 substituting 2-bromo-4-(trifluoromethyl)pyridine for 1-bromo-2-methylbenzene. MS (ESI) m/z 452 (M+H)$^+$.

Example 213

N-{trans-1-[(1-methyl-1H-imidazol-4-yl)sulfonyl]-4-phenylpyrrolidin-3-yl}-5-(trifluoromethyl)pyridin-3-amine The title compound was prepared similarly to the procedure described in Example 57 substituting 3-bromo-5-(trifluoromethyl)pyridine for 1-bromo-2-methylbenzene. MS (ESI) m/z 452 (M+H)$^+$.

Example 214 trans-N-[4-fluoro-3-(trifluoromethyl)phenyl]-1-[(1-methyl-1H-imidazol-4-yl)sulfonyl]-4-phenylpyrrolidin-3-amine The title compound was prepared similarly to the procedure described in Example 57 substituting 4-bromo-1-fluoro-2-(trifluoromethyl)benzene for 1-bromo-2-methylbenzene. MS (ESI) m/z 469 (M+H)$^+$.

Example 215 trans-N-(3-chloro-4-fluorophenyl)-1-[(1-methyl-1H-imidazol-4-yl)sulfonyl]-4-phenylpyrrolidin-3-amine The title compound was prepared similarly to the procedure described in Example 57 substituting 4-bromo-2-chloro-1-fluorobenzene for 1-bromo-2-methylbenzene. MS (ESI) m/z 435 (M+H)$^+$.

Example 216 trans-N-(3,4-difluorophenyl)-1-[(1-methyl-1H-imidazol-4-yl)sulfonyl]-4-phenylpyrrolidin-3-amine The title compound was prepared similarly to the procedure described in Example 57 substituting 4-bromo-1,2-difluorobenzene for 1-bromo-2-methylbenzene. MS (ESI) m/z 419 (M+H)$^+$.

Example 217 trans-N-[4-chloro-3-(trifluoromethyl)phenyl]-1-[(1-methyl-1H-imidazol-4-yl)sulfonyl]-4-phenylpyrrolidin-3-amine The title compound was prepared similarly to the procedure described in Example 57 substituting 4-bromo-1-chloro-2-(trifluoromethyl)benzene for 1-bromo-2-methylbenzene. MS (ESI) m/z 485 (M+H)$^+$.

Example 218 trans-N-(3,4-dichlorophenyl)-1-[(1-methyl-1H-imidazol-4-yl)sulfonyl]-4-phenylpyrrolidin-3-amine The title compound was prepared similarly to the procedure described in Example 57 substituting 4-bromo-1,2-dichlorobenzene for 1-bromo-2-methylbenzene. MS (ESI) m/z 451 (M+H)$^+$.

Example 219 trans-N-(3-chloro-4,5-difluorophenyl)-1-[(1-methyl-1H-imidazol-4-yl)sulfonyl]-4-phenylpyrrolidin-3-amine The title compound was prepared similarly to the procedure described in Example 57 substituting 5-bromo-1-chloro-2,3-difluorobenzene for 1-bromo-2-methylbenzene. MS (ESI) m/z 453 (M+H)$^+$.

Example 220 trans-1-[(1-methyl-1H-imidazol-4-yl)sulfonyl]-4-phenyl-N-[3-(propan-2-yl)phenyl]pyrrolidin-3-amine The title compound was prepared similarly to the procedure described in Example 57 substituting 1-bromo-3-isopropylbenzene for 1-bromo-2-methylbenzene. MS (ESI) m/z 425 (M+H)$^+$.

Example 221 trans-N-(3-tert-butylphenyl)-1-[(1-methyl-1H-imidazol-4-yl)sulfonyl]-4-phenylpyrrolidin-3-amine The title compound was prepared similarly to the procedure described in Example 57 substituting 1-bromo-3-tert-butyl-benzene for 1-bromo-2-methylbenzene. MS (ESI) m/z 439 (M+H)$^+$.

Example 222 trans-N-[2-fluoro-3-(trifluoromethyl)phenyl]-1-[(1-methyl-1H-imidazol-4-yl)sulfonyl]-4-phenylpyrrolidin-3-amine The title compound was prepared similarly to the procedure described in Example 57 substituting 1-bromo-2- fluoro-3-(trifluoromethyl)benzene for 1-bromo-2-methylbenzene. MS (ESI) m/z 469 (M+H)⁺.

Example 223 trans-N-[3-fluoro-5-(trifluoromethyl)phenyl]-1-[(1-methyl-1H-imidazol-4-yl)sulfonyl]-4-phenylpyrrolidin-3-amine The title compound was prepared similarly to the procedure described in Example 57 substituting 1-bromo-3-fluoro-5-(trifluoromethyl)benzene for 1-bromo-2-methylbenzene. MS (ESI) m/z 469 (M+H)⁺.

Example 224 trans-N-[2-fluoro-5-(trifluoromethyl)phenyl]-1-[(1-methyl-1H-imidazol-4-yl)sulfonyl]-4-phenylpyrrolidin-3-amine The title compound was prepared similarly to the procedure described in Example 57 substituting 1-bromo-2-fluoro-5-(trifluoromethyl)benzene for 1-bromo-2-methylbenzene. MS (ESI) m/z 469 (M+H)⁺.

Example 225 trans-N-(3-chloro-5-fluorophenyl)-1-[(1-methyl-1H-imidazol-4-yl)sulfonyl]-4-phenylpyrrolidin-3-amine The title compound was prepared similarly to the procedure described in Example 57 substituting 1-bromo-3-chloro-5-fluorobenzene for 1-bromo-2-methylbenzene. MS (ESI) m/z 435 (M+H)⁺.

Example 226 trans-1-[(1-methyl-1H-imidazol-4-yl)sulfonyl]-4-phenyl-N-[3-(trifluoromethoxy)phenyl]pyrrolidin-3-amine The title compound was prepared similarly to the procedure described in Example 57 substituting 1-bromo-3-(trifluoromethoxy)benzene for 1-bromo-2-methylbenzene. MS (ESI) m/z 467 (M+H)⁺.

Example 227

N-{trans-1-[(1-methyl-1H-imidazol-4-yl)sulfonyl]-4-phenylpyrrolidin-3-yl}-4-(trifluoromethyl)pyrimidin-2-amine The title compound was prepared similarly to the procedure described in Example 57 substituting 2-bromo-4-(trifluoromethyl)pyrimidine for 1-bromo-2-methylbenzene. MS (ESI) m/z 453 (M+H)⁺.

Example 228

N-{trans-1-[(1-methyl-1H-imidazol-4-yl)sulfonyl]-4-phenylpyrrolidin-3-yl}quinolin-7-amine The title compound was prepared similarly to the procedure described in Example 57 substituting 7-bromoquinoline for 1-bromo-2-methylbenzene. MS (ESI) m/z 434 (M+H)⁺.

Example 229

N-{trans-1-[(1-methyl-1H-imidazol-4-yl)sulfonyl]-4-phenylpyrrolidin-3-yl}quinolin-6-amine The title compound was prepared similarly to the procedure described in Example 57 substituting 6-bromoquinoline for 1-bromo-2-methylbenzene. MS (ESI) m/z 434 (M+H)⁺.

Example 230

N-{trans-1-[(1-methyl-1H-imidazol-4-yl)sulfonyl]-4-phenylpyrrolidin-3-yl}isoquinolin-6-amine The title compound was prepared similarly to the procedure described in Example 57 substituting 6-bromoisoquinoline for 1-bromo-2-methylbenzene. MS (ESI) m/z 434 (M+H)⁺.

Example 231 trans-N-(2,3-difluorophenyl)-1-[(1-methyl-1H-imidazol-4-yl)sulfonyl]-4-phenylpyrrolidin-3-amine The title compound was prepared similarly to the procedure described in Example 57 substituting 1-bromo-2,3-difluorobenzene for 1-bromo-2-methylbenzene. MS (ESI) m/z 419 (M+H)⁺.

Example 232 trans-N-(2,5-difluorophenyl)-1-[(1-methyl-1H-imidazol-4-yl)sulfonyl]-4-phenylpyrrolidin-3-amine The title compound was prepared similarly to the procedure described in Example 57 substituting 1-bromo-2,5-difluorobenzene for 1-bromo-2-methylbenzene. MS (ESI) m/z 419 (M+H)⁺.

Example 233 trans-N-(2,4-difluorophenyl)-1-[(1-methyl-1H-imidazol-4-yl)sulfonyl]-4-phenylpyrrolidin-3-amine The title compound was prepared similarly to the procedure described in Example 57 substituting 1-bromo-2,4-difluorobenzene for 1-bromo-2-methylbenzene. MS (ESI) m/z 419 (M+H)⁺.

Example 234 trans-1-[(1-methyl-1H-imidazol-4-yl)sulfonyl]-4-phenyl-N-(2,3,4-trifluorophenyl)pyrrolidin-3-amine The title compound was prepared similarly to the procedure described in Example 57 substituting 1-bromo-2,3,4-trifluorobenzene for 1-bromo-2-methylbenzene. MS (ESI) m/z 437 (M+H)⁺.

Example 235

6-fluoro-N-{trans-1-[(1-methyl-1H-imidazol-4-yl)sulfonyl]-4-phenylpyrrolidin-3-yl}pyridin-2-amine The title compound was prepared similarly to the procedure described in Example 57 substituting 2-bromo-6-fluoropyridine for 1-bromo-2-methylbenzene. MS (ESI) m/z 402 (M+H)⁺.

Example 236

2-fluoro-N-{trans-1-[(1-methyl-1H-imidazol-4-yl)
sulfonyl]-4-phenylpyrrolidin-3-yl}pyridin-4-amine The title compound was prepared similarly to the procedure described in Example 57 substituting 4-bromo-2-fluoropyridine for 1-bromo-2-methylbenzene. MS (ESI) m/z 402 (M+H)$^+$.

Example 237

5-fluoro-N-{trans-1-[(1-methyl-1H-imidazol-4-yl)
sulfonyl]-4-phenylpyrrolidin-3-yl}pyridin-3-amine The title compound was prepared similarly to the procedure described in Example 57 substituting 3-bromo-5-fluoropyridine for 1-bromo-2-methylbenzene. MS (ESI) m/z 402 (M+H)$^+$.

Example 238

6-fluoro-N-{trans-4-(4-fluorophenyl)-1-[(1-methyl-
1-imidazol-4-yl)sulfonyl]pyrrolidin-3-yl}pyridin-2-
amine The title compound was prepared similarly to the procedure described in Example 57 substituting Example 3A for Example 14A and substituting 2-bromo-6-fluoropyridine for 1-bromo-2-methylbenzene. MS (ESI) m/z 420 (M+H)$^+$.

Example 239

2-fluoro-N-{trans-4-(4-fluorophenyl)-1-[(1-methyl-
1H-imidazol-4-yl)sulfonyl]pyrrolidin-3-yl}pyridin-
4-amine The title compound was prepared similarly to the procedure described in Example 57 substituting Example 3A for Example 14A and substituting 4-bromo-2-fluoropyridine for 1-bromo-2-methylbenzene. MS (ESI) m/z 420 (M+H)$^+$.

Example 240

N-{trans-1-[(1-methyl-1H-imidazol-4-yl)sulfonyl]-
4-phenylpyrrolidin-3-yl}-6-(trifluoromethyl)pyrimi-
din-4-amine The title compound was prepared similarly to the procedure described in Example 57 substituting 4-bromo-6-(trifluoromethyl)pyrimidine for 1-bromo-2-methylbenzene. MS (ESI) m/z 453 (M+H)$^+$.

Example 241

N-{trans-1-[(1-methyl-1H-imidazol-4-yl)sulfonyl]-
4-phenylpyrrolidin-3-yl}isoquinolin-7-amine The title compound was prepared similarly to the procedure described in Example 57 substituting 7-bromoisoquinoline for 1-bromo-2-methylbenzene. MS (ESI) m/z 434 (M+H)$^+$.

Example 242 trans-4-(4-fluorophenyl)-1-[(1-methyl-1H-imidazol-
4-yl)sulfonyl]-N-phenylpyrrolidine-3-carboxamide

Example 242A

A solution of (E)-methyl 3-(4-fluorophenyl)acrylate (10.52 g, 58.4 mmol) and N-benzyl-1-methoxy-N-((trimethylsilyl)methyl)methanamine (19.41 g, 81.8 mmol) in 110 mL of dichloromethane was cooled to 0° C. Trifluoroacetic acid (0.495 ml, 6.42 mmol) was slowly added under N$_2$. The reaction mixture was stirred at 0° C. for 1 hour, then stirred at room temperature for 18 hours. The reaction mixture was partitioned with saturated sodium bicarbonate. The organic fraction was collected, concentrated, and purified by flash-chromatography on silica gel (20-30% ethyl acetate in hexane) to provide the title compound. MS (ESI) m/z 314.3 (M+H)$^+$

Example 242B

Trans-methyl
4-(4-fluorophenyl)pyrrolidine-3-carboxylate

Example 242A (17.98 g, 57.4 mmol) and tetrahydrofuran (10 ml) were added to 20% Pd(OH)$_2$/C, wet (3.60 g, 25.6 mmol) in a 250 mL SS pressure bottle and stirred for 16 hours under 30 psi of hydrogen at room temperature. The mixture was filtered through a nylon membrane and concentrated to provide the title compound. MS (ESI) m/z 224.0 (M+H)$^+$.

Example 242C

Trans-methyl 4-(4-fluorophenyl)-1-(1-methyl-1H-
imidazol-4-ylsulfonyl)pyrrolidine-3-carboxylate To Example 242 B (12.74 g, 57.1 mmol) in 15 mL of dichloromethane were added triethylamine (12.13 g, 120 mmol) and 4-dimethylaminopyridine (0.35 g, 2.85 mmol). The reaction mixture was cooled to 0° C. 1-methyl-1H-imidazole-4-sulfonyl chloride (10.82 g, 59.9 mmol) was added portion wise at 0° C. The reaction mixture was slowly warmed up to room temperature and stirred for 1 hour. The reaction mixture was partitioned with dichloromethane, and water. The organic fraction was collected, washed with water, concentrated, and purified by flash-chromatography on silica gel (100% ethyl acetate) to afford the title compound. MS (ESI) m/z 368.0 (M+H)$^+$.

Example 242D

Trans-4-(4-fluorophenyl)-1-(1-methyl-1H-imidazol-
4-ylsulfonyl)pyrrolidine-3-carboxylic acid To Example 242C (3.67 g, 9.99 mmol) was added 4 mL of methanol. To this solution was added lithium hydroxide (1 M, methanol:water=5:3, 15 mL, 15 mmol). The reaction mixture was stirred at room temperature for 5 hours. The reaction mixture was concentrated, and the residue was then treated with hydrochloric acid (1 M, aq.) until pH=5. The reaction mixture was partitioned with ethyl acetate and the organic fraction was collected. The aqueous fraction was washed with ethyl acetate (3×), and the organic fractions were combined and concentrated to provide the title product. MS (ESI) m/z 354.0 (M+H)$^+$.

Example 242E

Trans-4-(4-fluorophenyl)-1-[(1-methyl-1H-imidazol-4-yl)sulfonyl]-N-phenylpyrrolidine-3-carboxamide To solution of Example 242D (150 mg, 0.42 mmol) in dimethylformamide/pyridine (1:1. mL) was added 1-(3-dimethylaminopropyl)-3-ethylcarbodiimide hydrochloride (85 mg, 0.45 mmol) and aniline (41.5 mg, 0.45 mmol). The reaction mixture was stirred at room temperature for 18 hours. The reactiom mixture was concentrated purified by HPLC to provide the title product. MS (ESI) m/z 429.1 (M+H)$^+$.

Example 243

Trans-4-(4-fluorophenyl)-1-[(1-methyl-1H-imidazol-4-yl)sulfonyl]-N-[4-(trifluoromethyl)phenyl]pyrrolidine-3-carboxamide The title compound was prepared using the same sequence of steps described in Example 242 substituting 4-(trifluoromethyl)aniline for aniline. MS (ESI) m/z 497.0 (M+H)$^+$.

Example 244

Trans-N-(3,5-dichlorophenyl)-4-(4-fluorophenyl)-1-[(1-methyl-1H-imidazol-4-yl)sulfonyl]pyrrolidine-3-carboxamide The title compound was prepared using the procedures described in Example 242 substituting 3,5-dichloroaniline for aniline. MS (ESI) m/z 497.1 (M+H)$^+$.

Example 245

4-{[trans-3-(4-fluorophenyl)-4-(phenoxymethyl)pyrrolidin-1-yl]sulfonyl}-1-methyl-1H-imidazole To a solution of Example 206 (52 mg, 0.15 mmol) in tetrahydrofuran (1 mL) was added phenol (21.6 mg, 0.23 mmol), PS-triphenylphosphine (105 mg, 0.34 mmol, 3.2 mmol/g), and ditert-butylazodicarboxylate (70.6 mg, 0.31 mmol). The reaction mixture was stirred at room temperature for 18 hours. The reaction mixture was filtered and washed with methanol. The filtrate was concentrated and purified by HPLC to provide the title compound. MS (ESI) m/z 416.1 (M+H)$^+$.

Example 246

4-{[trans-3-[(2,4-dichlorophenoxy)methyl]-4-(4-fluorophenyl)pyrrolidin-1-yl]sulfonyl}-1-methyl-1H-imidazole The title compound was prepared using the procedure described in Example 245 substituting 2,4-dichlorophenol for phenol. MS (ESI) m/z 484.1 (M+H)$^+$.

Example 247

4-{[trans-3-(4-fluorophenyl)-4-{[3-(trifluoromethoxy)phenoxy]methyl}pyrrolidin-1-yl]sulfonyl}-1-methyl-1H-imidazole The title compound was prepared using the procedure described in Example 245 substituting 3-(trifluoromethoxy)phenol for phenol. MS (ESI) m/z 500.1 (M+H)$^+$.

Example 248

4-{[trans-3-[(3-chlorophenoxy)methyl]-4-(4-fluorophenyl)pyrrolidin-1-yl]sulfonyl}-1-methyl-1H-imidazole The title compound was prepared using the procedure described in Example 245 substituting 3-chlorophenol for phenol. MS (ESI) m/z 450.1 (M+H)$^+$.

Example 249

4-{[trans-3-{[4-chloro-3-(trifluoromethyl)phenoxy]methyl}-4-(4-fluorophenyl)pyrrolidin-1-yl]sulfonyl}-1-methyl-1H-imidazole The title compound was prepared using the procedures described in Example 245 substituting 4-chloro-3-(trifluoromethyl)phenol for phenol. MS (ESI) m/z 518.2 (M+H)$^+$.

Example 250

4-{[trans-3-{[2-chloro-3-(trifluoromethyl)phenoxy]methyl}-4-(4-fluorophenyl)pyrrolidin-1-yl]sulfonyl}-1-methyl-1H-imidazole The title compound was prepared using the procedures as in Example 245 substituting 2-chloro-3-(trifluoromethyl)phenol for phenol. MS (ESI) m/z 518.1 (M+H)$^+$.

Example 251

4-{[trans-3-[(3-fluorophenoxy)methyl]-4-(4-fluorophenyl)pyrrolidin-1-yl]sulfonyl}-1-methyl-1H-imidazole The title compound was prepared using the procedure described in Example 245 substituting 3-fluorophenol for phenol. MS (ESI) m/z 434.1 (M+H)$^+$.

Example 252 trans-4-(2-chlorophenyl)-N-(3-fluorophenyl)-1-[(1-methyl-1H-imidazol-4-yl)sulfonyl]pyrrolidin-3-amine Example 252A trans-4-(2-chlorophenyl)-1-(1-methyl-1H-imidazol-4-ylsulfonyl)pyrrolidin-3-amine The title compound was prepared similarly to the procedures described in Example 2A-2F substituting (E)-1-chloro-2-(2-nitrovinyl)benzene for (E)-1-methoxy-4-(2-nitrovinyl)benzene.

Example 252B trans-4-(2-chlorophenyl)-N-(3-fluorophenyl)-1-[(1-methyl-1H-imidazol-4-yl)sulfonyl]pyrrolidin-3-amine The title compound was prepared similarly to the procedure described in Example 57 substituting Example 252A for Example 14A and substituting 1-bromo-3-fluorobenzene for 1-bromo-2-methylbenzene. MS (ESI) m/z 435 (M+H)$^+$.

Example 253 trans-4-(2-chlorophenyl)-N-(4-fluorophenyl)-1-[(1-methyl-1H-imidazol-4-yl)sulfonyl]pyrrolidin-3-amine

Example 253A trans-4-(2-chlorophenyl)-1-(1-methyl-1H-imidazol-4-ylsulfonyl)pyrrolidin-3-amine The title compound was prepared similarly to the procedure described in Example 3A substituting (E)-1-chloro-2-(2-nitrovinyl)benzene for (E)-(2-nitrovinyl)benzene.

Example 253B trans-4-(2-chlorophenyl)-N-(4-fluorophenyl)-1-[(1-methyl-1H-imidazol-4-yl)sulfonyl]pyrrolidin-3-amine The title compound was prepared similarly to the procedure described in Example 57 substituting Example 253A for Example 14A and substituting 1-bromo-4-fluorobenzene for 1-bromo-2-methylbenzene. MS (ESI) m/z 435 (M+H)$^+$.

Example 254 trans-4-(2-chlorophenyl)-N-(4-chlorophenyl)-1-[(1-methyl-1H-imidazol-4-yl)sulfonyl]pyrrolidin-3-amine The title compound was prepared similarly to the procedure described in Example 57 substituting Example 253A for Example 14A and substituting 1-bromo-4-chlorobenzene for 1-bromo-2-methylbenzene. MS (ESI) m/z 451 (M+H)$^+$.

Example 255 trans-4-(2-chlorophenyl)-1-[(1-methyl-1H-imidazol-4-yl)sulfonyl]-N-[3-(trifluoromethyl)phenyl]pyrrolidin-3-amine The title compound was prepared similarly to the procedure described in Example 57 substituting Example 253A for Example 14A and substituting 1-bromo-3-(trifluoromethyl)benzene for 1-bromo-2-methylbenzene. MS (ESI) m/z 485 (M+H)$^+$.

Example 256 trans-4-(2-chlorophenyl)-1-[(1-methyl-1H-imidazol-4-yl)sulfonyl]-N-[4-(trifluoromethyl)phenyl]pyrrolidin-3-amine The title compound was prepared similarly to the procedure described in Example 57 substituting Example 253A for Example 14A and substituting 1-bromo-4-(trifluoromethyl)benzene for 1-bromo-2-methylbenzene. MS (ESI) m/z 485 (M+H)$^+$.

Example 257 trans-N-(3-chloro-4-fluorophenyl)-4-(2-chlorophenyl)-1-[(1-methyl-1H-imidazol-4-yl)sulfonyl]pyrrolidin-3-amine The title compound was prepared similarly to the procedure described in Example 57 substituting Example 253A for Example 14A and substituting 1-bromo-3-chloro-4-fluorobenzene for 1-bromo-2-methylbenzene. MS (ESI) m/z 469 (M+H)$^+$.

Example 258 trans-4-(2-chlorophenyl)-N-[4-fluoro-3-(trifluoromethyl)phenyl]-1-[(1-methyl-1H-imidazol-4-yl)sulfonyl]pyrrolidin-3-amine The title compound was prepared similarly to the procedure described in Example 57 substituting Example 253A for Example 14A and substituting 1-bromo-4-fluoro-3-(trifluoromethyl)benzene for 1-bromo-2-methylbenzene. MS (ESI) m/z 503 (M+H)$^+$.

Example 259

N-{trans-4-(2-chlorophenyl)-1-[(1-methyl-1H-imidazol-4-yl)sulfonyl]pyrrolidin-3-yl}-2-(trifluoromethyl)pyridin-4-amine The title compound was prepared similarly to the procedure described in Example 57 substituting Example 253A for Example 14A and substituting 4-bromo-2-(trifluoromethyl)pyridine for 1-bromo-2-methylbenzene. MS (ESI) m/z 486 (M+H)$^+$.

Example 260 trans-N-(2-chlorobenzyl)-4-(4-fluorophenyl)-1-[(1-methyl-1H-imidazol-4-yl)sulfonyl]pyrrolidin-3-amine The title compound was prepared similarly to the procedure described in Example 148 substituting 2-chlorobenzaldehyde for benzaldehyde. MS (ESI) m/z 449 (M+H)$^+$.

Example 261 trans-N-(3-chlorobenzyl)-4-(4-fluorophenyl)-1-[(1-methyl-1H-imidazol-4-yl)sulfonyl]pyrrolidin-3-amine The title compound was prepared similarly to the procedure described in Example 148 substituting 3-chlorobenzaldehyde for benzaldehyde. MS (ESI) m/z 449 (M+H)$^+$.

Example 262 trans-N-(4-chlorobenzyl)-4-(4-fluorophenyl)-1-[(1-methyl-1H-imidazol-4-yl)sulfonyl]pyrrolidin-3-amine The title compound was prepared similarly to the procedure described in Example 148 substituting 4-chlorobenzaldehyde for benzaldehyde. MS (ESI) m/z 449 (M+H)$^+$.

Example 263 trans-N-(2-fluorobenzyl)-4-(4-fluorophenyl)-1-[(1-methyl-1H-imidazol-4-yl)sulfonyl]pyrrolidin-3-amine The title compound was prepared similarly to the procedure described in Example 148 substituting 2-fluorobenzaldehyde for benzaldehyde. MS (ESI) m/z 433 (M+H)$^+$.

Example 264 trans-N-(3-fluorobenzyl)-4-(4-fluorophenyl)-1-[(1-methyl-1H-imidazol-4-yl)sulfonyl]pyrrolidin-3-amine The title compound was prepared similarly to the procedure described in Example 148 substituting 3-fluorobenzaldehyde for benzaldehyde. MS (ESI) m/z 433 (M+H)$^+$.

Example 265 trans-4-(4-fluorophenyl)-1-[(1-methyl-1H-imidazol-4-yl)sulfonyl]-N-[2-(trifluoromethyl)benzyl]pyrrolidin-3-amine The title compound was prepared similarly to the procedure described in Example 148 substituting 2-(trifluoromethyl)benzaldehyde for benzaldehyde. MS (ESI) m/z 483 (M+H)$^+$.

Example 266 trans-4-(4-fluorophenyl)-1-[(1-methyl-1H-imidazol-4-yl)sulfonyl]-N-[3-(trifluoromethyl)benzyl]pyrrolidin-3-amine The title compound was prepared similarly to the procedure described in Example 148 substituting 3-(trifluoromethyl)benzaldehyde for benzaldehyde. MS (ESI) m/z 483 (M+H)$^+$.

Example 267 trans-4-(4-fluorophenyl)-1-[(1-methyl-1H-imidazol-4-yl)sulfonyl]-N-[4-(trifluoromethyl)benzyl]pyrrolidin-3-amine The title compound was prepared similarly to the procedure described in Example 148 substituting 4-(trifluoromethyl)benzaldehyde for benzaldehyde. MS (ESI) m/z 483 (M+H)$^+$.

Example 268 trans-4-(4-fluorophenyl)-1-[(1-methyl-1H-imidazol-4-yl)sulfonyl]-N-(pyridin-2-ylmethyl)pyrrolidin-3-amine The title compound was prepared similarly to the procedure described in Example 148 substituting picolinaldehyde for benzaldehyde. MS (ESI) m/z 416 (M+H)$^+$.

Example 269 trans-4-(4-fluorophenyl)-1-[(1-methyl-1H-imidazol-4-yl)sulfonyl]-N-(pyridin-3-ylmethyl)pyrrolidin-3-amine The title compound was prepared similarly to the procedure described in Example 148 substituting nicotinaldehyde for benzaldehyde. MS (ESI) m/z 416 (M+H)$^+$.

Example 270 trans-4-(4-fluorophenyl)-1-[(1-methyl-1H-imidazol-4-yl)sulfonyl]-N-(pyridin-4-ylmethyl)pyrrolidin-3-amine The title compound was prepared similarly to the procedure described in Example 148 substituting isonicotinaldehyde for benzaldehyde. MS (ESI) m/z 416 (M+H)$^+$.

Example 271

{trans-4-(4-fluorophenyl)-1-[(1-methyl-1H-imidazol-4-yl)sulfonyl]pyrrolidin-3-yl}(phenyl)methanone

Example 271A

Trans-4-(4-fluorophenyl)-N-methoxy-N-methyl-1-(1-methyl-1H-imidazol-4-ylsulfonyl)pyrrolidine-3-carboxamide To a solution of Example 242D (610 mg, 1.73 mmol) in dimethylformamide (5 mL) was added triethylamine (0.52 mL, 3.71 mmol), N,O-dimethylhydroxylamine hydrochloride (236 mg. 2.42 mmol), and 2-(1H-benzo[d][1,2,3]triazol-1-yl)-1,1,3,3-tetramethylisouronium tetrafluoroborate (665 mg, 2.07 mmol). The mixture was stirred at room temperature for 4 hours. The reaction mixture was partitioned between water and ethyl acetate. The organic fraction was collected. The aqueous fraction was washed with ethyl acetate 3 more times. The combined organic fractions were dried over sodium sulfate, concentrated, and purified by flash-chromatography on silica gel (5-10% methanol in dichloromethane (with 0.5% volume triethylamine added)) to afford the title compound. MS (ESI) m/z 397.0 (M+H)$^+$.

Example 271B

{Trans-4-(4-fluorophenyl)-1-[(1-methyl-1H-imidazol-4-yl)sulfonyl]pyrrolidin-3-yl}(phenyl)methanone To a solution of Example 271A (113 mg, 0.29 mmol) in tetrahydrofuran (0.5 mL) was added phenylmagnesium bromide (0.57 mL, 0.57 mmol, 1.0 M in tetrahydrofuran) slowly at room temperature. The solution stirred for 1 hour. The reaction mixture was partitioned with saturated ammonium chloride (aq.) and the organic fraction was collected. The organic fraction was dried over sodium sulfate, concen-

Example 272

Trans-N-[2-chloro-3-(trifluoromethyl)phenyl]-4-(4-fluorophenyl)-1-[(1-methyl-1H-imidazol-4-yl)sulfonyl]pyrrolidine-3-carboxamide The title compound was prepared using the procedure described in Example 242E substituting 2-chloro-3-(trifluoromethyl)aniline for aniline. MS (ESI) m/z 531.1 (M+H)$^+$.

Example 273

Trans-4-(4-fluorophenyl)-1-[(1-methyl-1H-imidazol-4-yl)sulfonyl]-N-[3-(trifluoromethoxy)phenyl]pyrrolidine-3-carboxamide The title compound was prepared using the procedure described in Example 242E substituting 3-(trifluoromethoxy)aniline for aniline. MS (ESI) m/z 513.1 (M+H)$^+$.

Example 274 trans-4-(4-fluorophenyl)-N-[4-fluoro-3-(trifluoromethyl)phenyl]-1-[(1-methyl-1H-imidazol-4-yl)sulfonyl]pyrrolidine-3-carboxamide The title compound was prepared similarly to the procedure described in Example 242E substituting 4-fluoro-3-(trifluoromethyl)aniline for aniline. MS (ESI) m/z 515.1 (M+H)$^+$.

Example 275 trans-N-(3-chloro-4-fluorophenyl)-4-(4-fluorophenyl)-1-[(1-methyl-1H-imidazol-4-yl)sulfonyl]pyrrolidine-3-carboxamide The title compound was prepared using the procedure described in Example 242E substituting 3-chloro-4-fluoroaniline for aniline. MS (ESI) m/z 481.1 (M+H)$^+$.

Example 276 trans-N-[3-chloro-4-(trifluoromethyl)phenyl]-4-(4-fluorophenyl)-1-[(1-methyl-1H-imidazol-4-yl)sulfonyl]pyrrolidine-3-carboxamide The title compound was prepared using the procedure described in Example 242E substituting 3-chloro-4-(trifluoromethyl)aniline for aniline. MS (ESI) m/z 531.1 (M+H)$^+$.

Example 277

1-methyl-4-[(3-phenoxy-4-phenylpyrrolidin-1-yl)sulfonyl]-1H-imidazole

To a stirred solution of tert-butyl 3-hydroxy-4-phenylpyrrolidine-1-carboxylate (200 mg, 0.76 mmol) in tetrahydrofuran (5 mL) was added (Z)-di-tert-butyl diazene-1,2-dicarboxylate (262 mg, 1.1 mmol), phenol (72 mg, 0.76 mmol), and polystyrene triphenylphosphine resin (2.37 mmol/g, 961 mg, 2.3 mmol). The reaction mixture was stirred at room temperature for 18 hours before the resin was filtered off. The filtrate was concentrated. The concentrate was dissolved in dichloromethane (2 mL) and HCl (4M in dioxane, 2 mL, 8 mmol) was added. When LCMS showed that the reaction was complete the reaction mixture was concentrated. To a stirred solution of the concentrate in pyridine (4 mL) was added 1-methyl-1H-imidazole-4-sulfonyl chloride (165 mg, 0.91 mmol). The reaction mixture was warmed to 60° C. for 18 hours. The reaction was then concentrated. Purification via HPLC provided the title compound.

Example 278 trans-4-(2-chlorophenyl)-N-(3-chlorophenyl)-1-[(1-methyl-1H-imidazol-4-yl)sulfonyl]pyrrolidin-3-amine The title compound was prepared similarly to the procedure described in Example 57 substituting Example 252A for Example 14A and substituting 1-bromo-3-chlorobenzene for 1-bromo-2-methylbenzene. MS (ESI) m/z 451 (M+H)$^+$.

Example 279 trans-N-(2,4-dichlorobenzyl)-4-(4-fluorophenyl)-1-[(1-methyl-1H-imidazol-4-yl)sulfonyl]pyrrolidin-3-amine The title compound was prepared similarly to the procedure described in Example 148 substituting 2,4-dichlorobenzaldehyde for benzaldehyde. MS (ESI) m/z 483 (M+H)$^+$.

Example 280 trans-N-(2,4-dichlorobenzyl)-1-[(1-methyl-1H-imidazol-4-yl)sulfonyl]-4-phenylpyrrolidin-3-amine The title compound was prepared similarly to the procedure described in Example 148 substituting Example 14A for Example 3A and substituting 2,4-dichlorobenzaldehyde for benzaldehyde. MS (ESI) m/z 465 (M+H)$^+$.

Example 281 trans-N-[2-chloro-4-(trifluoromethyl)benzyl]-1-[(1-methyl-1H-imidazol-4-yl)sulfonyl]-4-phenylpyrrolidin-3-amine The title compound was prepared similarly to the procedure described in Example 148 substituting Example 14A for Example 3A and substituting 2-chloro-4-(trifluoromethyl)benzaldehyde for benzaldehyde. MS (ESI) m/z 499 (M+H)$^+$.

Example 282 trans-N-(2,4-dichlorobenzyl)-4-(2-fluorophenyl)-1-[(1-methyl-1H-imidazol-4-yl)sulfonyl]pyrrolidin-3-amine

Example 282A trans-4-(2-fluorophenyl)-1-(1-methyl-1H-imidazol-4-ylsulfonyl)pyrrolidin-3-amine The title compound was prepared as the HCl salt similarly to the procedure described in Example 2A-2F substituting (E)-1-fluoro-2-(2-nitrovinyl)benzene for (E)-1-methoxy-4-(2-nitrovinyl)benzene.

Example 282B trans-N-(2,4-dichlorobenzyl)-4-(2-fluorophenyl)-1-[(1-methyl-1H-imidazol-4-yl)sulfonyl]pyrrolidin-3-amine The title compound was prepared similarly to the procedure described in Example 148 substituting Example 282A for Example 3A and substituting 2,4-dichlorobenzaldehyde for benzaldehyde. MS (ESI) m/z 483 (M+H)+.

Example 283 trans-N-[2-chloro-4-(trifluoromethyl)benzyl]-4-(2-fluorophenyl)-1-[(1-methyl-1H-imidazol-4-yl)sulfonyl]pyrrolidin-3-amine The title compound was prepared similarly to the procedure described in Example 148 substituting Example 282A for Example 3A and substituting 2-chloro-4-(trifluoromethyl)benzaldehyde for benzaldehyde. MS (ESI) m/z 517 (M+H)+.

Example 284 trans-4-(2-chlorophenyl)-N-(2,4-dichlorobenzyl)-1-[(1-methyl-1H-imidazol-4-yl)sulfonyl]pyrrolidin-3-amine The title compound was prepared similarly to the procedure described in Example 148 substituting Example 252A for Example 3A and substituting 2,4-dichlorobenzaldehyde for benzaldehyde. MS (ESI) m/z 501 (M+H)+.

Example 285 trans-4-(2-chlorophenyl)-N-[2-chloro-4-(trifluoromethyl)benzyl]-1-[(1-methyl-1H-imidazol-4-yl)sulfonyl]pyrrolidin-3-amine The title compound was prepared similarly to the procedure described in Example 148 substituting Example 252A for Example 3A and substituting 2-chloro-4-(trifluoromethyl)benzaldehyde for benzaldehyde. MS (ESI) m/z 533 (M+H)+.

Example 286 trans-N-(2,4-dichlorobenzyl)-1-[(1-methyl-1H-imidazol-4-yl)sulfonyl]-4-(pyridin-3-yl)pyrrolidin-3-amine

Example 286A trans-1-(1-methyl-1H-imidazol-4-ylsulfonyl)-4-(pyridin-3-yl)pyrrolidin-3-amine The title compound was prepared as an HCl salt similarly to the conditions described in Example 2A-2F substituting (E)-3-(2-nitrovinyl)pyridine for (E)-1-methoxy-4-(2-nitrovinyl)benzene.

Example 286B trans-N-(2,4-dichlorobenzyl)-1-[(1-methyl-1H-imidazol-4-yl)sulfonyl]-4-(pyridin-3-yl)pyrrolidin-3-amine The title compound was prepared similarly to the procedure described in Example 148 substituting 286A for Example 3A and substituting 2,4-dichlorobenzaldehyde for benzaldehyde. MS (ESI) m/z 466 (M+H)+.

Example 287

N-{trans-4-(4-fluorophenyl)-1-[(1-methyl-1H-imidazol-4-yl)sulfonyl]pyrrolidin-3-yl}-4-(trifluoromethyl)pyridin-2-amine The title compound was prepared similarly to the procedure described in Example 57 substituting Example 3A for Example 14A and substituting 2-bromo-4-(trifluoromethyl)pyridine for 1-bromo-2-methylbenzene. MS (ESI) m/z 470 (M+H)+.

Example 288

N-{trans-4-(4-fluorophenyl)-1-[(1-methyl-1H-imidazol-4-yl)sulfonyl]pyrrolidin-3-yl}-2-(trifluoromethyl)pyridin-4-amine The title compound was prepared similarly to the procedure described in Example 57 substituting Example 3A for Example 14A and substituting 4-bromo-2-(trifluoromethyl)pyridine for 1-bromo-2-methylbenzene. MS (ESI) m/z 470 (M+H)+.

Example 289

Trans-N-benzyl-4-(4-fluorophenyl)-1-[(1-methyl-1H-imidazol-4-yl)sulfonyl]pyrrolidine-3-carboxamide The title compound was prepared using the procedure described in Example 242E substituting phenylmethanamine for aniline. MS (ESI) m/z 443.1 (M+H)+.

Example 290

N-({trans-4-(4-fluorophenyl)-1-[(1-methyl-1H-imidazol-4-yl)sulfonyl]pyrrolidin-3-yl}methyl)aniline To a solution of Example 242E (106.7 mg, 0.25 mmol) in dry tetrahydrofuran (0.7 mL) under argon, was added borane dimethyl sulfide complex (0.5 mL, 1.0 mmol, 2M in tetrahydrofuran). The reaction mixture was stirred at 60° C. for 5 hours and stirred at room temperature for 18 hours. Hydrochloric acid (0.5 mL of 0.5 N HCl) was carefully added. The reaction mixture was refluxed for 2 hours, then treated with sodium hydroxide (1N) to pH=8-9. The reaction mixture was portioned with ethyl acetate. The organic fraction was collected. The aqueous fraction was washed with dichloromethane. The organic fractions were combined, dried over sodium sulfate, concentrated, and purified by HPLC to afford the title compound. MS (ESI) m/z 415.1 (M+H)+.

Example 291

N-({trans-4-(4-fluorophenyl)-1-[(1-methyl-1H-imidazol-4-yl)sulfonyl]pyrrolidin-3-yl}methyl)-4-(trifluoromethyl)aniline The title compound was prepared using the procedure described in Example 290 substituting Example 243 for Example 242E. MS (ESI) m/z 483.1 (M+H)+.

Example 292

3,5-dichloro-N-({trans-4-(4-fluorophenyl)-1-[(1-methyl-1H-imidazol-4-yl)sulfonyl]pyrrolidin-3-yl}methyl)aniline The title compound was prepared using the procedure described in Example 290 substituting Example 244 for Example 242E. MS (ESI) m/z 483.1 (M+H)$^+$.

Example 293

4-{[trans-3-(4-fluorophenyl)-4-{[3-(trifluoromethyl)phenoxy]methyl}pyrrolidin-1-yl]sulfonyl}-1-methyl-1H-imidazole The title compound was prepared similarly to the procedure described in Example 245 substituting 3-(trifluoromethyl)phenol for phenol. MS (ESI) m/z 484.1 (M+H)$^+$

Example 294

4-{[trans-3-{[2-chloro-4-(trifluoromethyl)phenoxy]methyl}-4-(4-fluorophenyl)pyrrolidin-1-yl]sulfonyl}-1-methyl-1H-imidazole The title compound was prepared similarly to the procedure described in Example 245 substituting 3-chloro-4-hydroxybenzotrifluoride for phenol. MS (ESI) m/z 518.1 (M+H)$^+$

Example 295

4-{[trans-3-(4-fluorophenyl)-4-{[4-fluoro-3-(trifluoromethyl)phenoxy]methyl}pyrrolidin-1-yl]sulfonyl}-1-methyl-1H-imidazole The title compound was prepared similarly to the procedure described in Example 245 substituting 4-fluoro-3-(trifluoromethyl)phenol for phenol. MS (ESI) m/z 502.1 (M+H)$^+$.

Example 296

4-({trans-3-(4-fluorophenyl)-4-[(3-methylphenoxy)methyl]pyrrolidin-1-yl}sulfonyl)-1-methyl-1H-imidazole The title compound was prepared similarly to the procedure described in Example 245 substituting m-cresol for phenol. MS (ESI) m/z 430.1 (M+H)$^+$.

Example 297

(3-chlorophenyl){trans-4-(4-fluorophenyl)-1-[(1-methyl-1H-imidazol-4-yl)sulfonyl]pyrrolidin-3-yl}methanone The title compound was prepared similarly to the procedure described in Example 271B substituting (3-chlorophenyl)magnesium bromide for phenylmagnesium bromide. MS (ESI) m/z 448.1 (M+H)$^+$.

Example 298 trans-N-[4-fluoro-3-(trifluoromethoxy)phenyl]-1-[(1-methyl-1H-imidazol-4-yl)sulfonyl]-4-phenylpyrrolidin-3-amine The title compound was prepared similarly to the conditions described in Example 57 substituting 1-bromo-4-fluoro-3-(trifluoromethoxy)benzene for 1-bromo-2-methylbenzene. MS (ESI) m/z 485 (M+H)$^+$.

Example 299 trans-N-[4-chloro-3-(trifluoromethoxy)phenyl]-1-[(1-methyl-1H-imidazol-4-yl)sulfonyl]-4-phenylpyrrolidin-3-amine The title compound was prepared similarly to the conditions described in Example 57 substituting 1-bromo-4-chloro-3-(trifluoromethoxy)benzene for 1-bromo-2-methylbenzene. MS (ESI) m/z 501 (M+H)$^+$.

Example 300

{trans-4-(4-fluorophenyl)-1-[(1-methyl-1H-imidazol-4-yl)sulfonyl]pyrrolidin-3-yl}(3-methylphenyl)methanone The title compound was prepared similarly to the procedure described in Example 271B substituting m-tolylmagnesium bromide for phenylmagnesium bromide. MS (ESI) m/z 428.0 (M+H)$^+$.

Example 301

(3-fluorophenyl){(trans-4-(4-fluorophenyl)-1-[(1-methyl-1H-imidazol-4-yl)sulfonyl]pyrrolidin-3-yl}methanone The title compound was prepared similarly to the procedure described in Example 271B substituting (3-fluorophenyl)magnesium bromide for phenylmagnesium bromide. MS (ESI) m/z 432.1 (M+H)$^+$.

Example 302

{trans-4-(4-fluorophenyl)-1-[(1-methyl-1H-imidazol-4-yl)sulfonyl]pyrrolidin-3-yl}[3-(trifluoromethyl)phenyl]methanone The title compound was prepared similarly to the procedure described in Example 271B substituting (3-(trifluoromethyl)phenyl)magnesium bromide for phenylmagnesium bromide. MS (ESI) m/z 482.1 (M+H)$^+$.

Example 303

(4-fluorophenyl){trans-4-(4-fluorophenyl)-1-[(1-methyl-1H-imidazol-4-yl)sulfonyl]pyrrolidin-3-y}methanone The title compound was prepared similarly to the procedure described in Example 271B substituting (4-fluorophe-

Example 304 trans-N-(3-chlorophenyl)-4-(4-fluorophenyl)-1-[(1-methyl-1H-imidazol-4-yl)sulfonyl]pyrrolidine-3-carboxamide The title compound was prepared similarly to the procedure described in Example 242E substituting 3-chloro aniline for aniline. MS (ESI) m/z 463.0 (M+H)$^+$.

Example 305 trans-4-(4-fluorophenyl)-N-[4-fluoro-3-(trifluoromethoxy)phenyl]-1-[(1-methyl-1H-imidazol-4-yl)sulfonyl]pyrrolidin-3-amine The title compound was prepared similarly to the conditions described in Example 57 substituting Example 3A For Example 14A and substituting 1-bromo-4-fluoro-3-(trifluoromethoxy)benzene for 1-bromo-2-methylbenzene. MS (ESI) m/z 503 (M+H)$^+$.

Example 306 trans-N-[4-chloro-3-(trifluoromethoxy)phenyl]-4-(4-fluorophenyl)-1-[(1-methyl-1H-imidazol-4-yl)sulfonyl]pyrrolidin-3-amine The title compound was prepared similarly to the conditions described in Example 57 substituting Example 3A For Example 14A and substituting 1-bromo-4-chloro-3-(trifluoromethoxy)benzene for 1-bromo-2-methylbenzene. MS (ESI) m/z 519 (M+H)$^+$.

Example 307 trans-N-(2,4-dichlorobenzyl)-1-[(1-methyl-1H-imidazol-4-yl)sulfonyl]-4-(pyridin-2-yl)pyrrolidin-3-amine

Example 307A (E)-2-(2-nitrovinyl)pyridine

To a stirred solution of nitromethane (15.2 mL, 280 mmol) and 2-pyridinecarboxaldeyde (8.9 mL, 93 mmol) in toluene (100 mL) at room temperature was added 1,1,2,2,tetramethylguanidine (1.2 mL, 9.3 mmol) followed by methanesulfonyl chloride (14.5 mL, 187 mmol). The reaction mixture was stirred for 5 minutes before triethylamine (26.1 mL, 187 mmol) was added. The reaction mixture was stirred for 30 minutes, then quenched with sodium bicarbonate (aq.) The organic fraction was collected. The aqueous fraction was washed with dichloromethane. All organic fractions were combined. Purification via flash chromatography provided the title compound.

Example 307B trans-1-(1-methyl-1H-imidazol-4-ylsulfonyl)-4-(pyridin-2-yl)pyrrolidin-3-amine The title compound was prepared as an HCl salt similarly to the procedures described in Example 2A-2F substituting Example 307A for (E)-1-methoxy-4-(2-nitrovinyl)benzene.

Example 307C trans-N-(2,4-dichlorobenzyl)-1-[(1-methyl-1H-imidazol-4-yl)sulfonyl]-4-(pyridin-2-yl)pyrrolidin-3-amine The title compound was prepared similarly to the procedure described in Example 148 substituting Example 307B for Example 3A and substituting 2,4-dichlorobenzaldehyde for benzaldehyde. MS (ESI) m/z 466 (M+H)$^+$.

Example 308 trans-1-[(1-methyl-1H-imidazol-4-yl)sulfonyl]-4-(pyridin-3-yl)-N-[3-(trifluoromethyl)phenyl]pyrrolidin-3-amine The title compound was prepared similarly to the procedure described in Example 57 substituting Example 286A for Example 14A and substituting 1-bromo-3-(trifluoromethyl)benzene for 1-bromo-2-methylbenzene. MS (ESI) m/z 452 (M+H)$^+$.

Example 309

4-{[3-(3-chlorobenzyl)-4-cyclopropylpyrrolidin-1-yl]sulfonyl}-1-methyl-1H-imidazole

Example 309A 2-(3-chlorobenzyl)-3-cyclopropyl-4-nitrobutanal

The title compound was prepared using the conditions described in Example 182A substituting (E)-(2-nitrovinyl)cyclopropane for (E)-1-fluoro-4-(2-nitrovinyl)benzene.

Example 309B 3-(3-chlorobenzyl)-4-cyclopropylpyrrolidine

The title compound was prepared using the conditions described in Example 182B substituting Example 309A for Example 182A.

Example 309

4-{[3-(3-chlorobenzyl)-4-cyclopropylpyrrolidin-1-yl]sulfonyl}-1-methyl-1H-imidazole The title compound was prepared using the conditions described in Example 182C substituting Example 309B for Example 182B. MS (ESI) m/z 380/382(3:1) (M+H)$^+$.

Example 310

N-[3-(difluoromethyl)-4-fluorophenyl]-4-(4-fluorophenyl)-1-[(1-methyl-1H-imidazol-4-yl)sulfonyl]pyrrolidin-3-amine To a 10 mL microwave vial was added 4-(4-fluorophenyl)-1-(1-methyl-1H-imidazol-4-ylsulfonyl)pyrrolidin-3-amine hydrochloride (100 mg, 0.277 mmol) and premixed tris(dibenzylidene-acetone)dipalladium(0)/sodium tert-butoxide/2,2'-bis(diphenylphosphino)-1,1'-binaphthyl (100 mg, 0.05:0.15:2), aldrich 715530). The solids were suspended in 1,2-dimethoxyethane, and 4-bromo-2-(difluoromethyl)-1-fluorobenzene (74.8 mg, 0.333 mmol) was added.

(nyl) magnesium bromide for phenylmagnesium bromide. MS (ESI) m/z 432.1 (M+H)$^+$.

The reaction vessel was capped and the reaction mixture was heated in a microwave (Biotage Initiator™, maximum 400 Watts) for 15 min at 130° C. The mixture was filtered through celite, concentrated, dissolved in 2 ml 50% methanol/dimethylsulfoxide, and purified by HPLC to provide the title compound. MS (ESI) m/z 469 (M+H)+.

Example 311

3-chloro-N-({trans-4-(4-fluorophenyl)-1-[(1-methyl-1H-imidazol-4-yl)sulfonyl]pyrrolidin-3-yl}methyl)-4-(trifluoromethyl)aniline The title compound was prepared similarly to the procedure described in Example 290 substituting Example 276 for Example 242E. MS (ESI) m/z 517.0 (M+H)+.

Example 312

N-({trans-4-(4-fluorophenyl)-1-[(1-methyl-1H-imidazol-4-yl)sulfonyl]pyrrolidin-3-yl} methyl)-3-(trifluoromethoxy)aniline The title compound was prepared similarly to the procedure described in Example 290 substituting Example 273 for Example 242E. MS (ESI) m/z 499 (M+H)+.

Example 313

4-fluoro-N-({trans-4-(4-fluorophenyl)-1-[(1-methyl-1-imidazol-4-yl)sulfonyl]pyrrolidin-3-yl}methyl)-3-(trifluoromethyl)aniline The title compound was prepared similarly to the procedure described in Example 290 substituting Example 274 for Example 242E. MS (ESI) m/z 501.1 (M+H)+.

Example 314

3-chloro-4-fluoro-N-({trans-4-(4-fluorophenyl)-1-[(1-methyl-1H-imidazol-4-yl)sulfonyl]pyrrolidin-3-yl}methyl)aniline The title compound was prepared similarly to the procedure described in Example 290 substituting Example 275 for Example 242E. MS (ESI) m/z 467.1 (M+H)+.

Example 315

N-benzyl-1-{trans-4-(4-fluorophenyl)-1-[(1-methyl-1H-imidazol-4-yl)sulfonyl]pyrrolidin-3-yl}methanamine The title compound was prepared similarly to the procedure described in Example 290 substituting Example 289 for Example 242E. MS (ESI) m/z 429.1 (M+H)+.

Example 316 trans-4-(4-fluorophenyl)-1-[(1-methyl-1H-imidazol-4-yl)sulfonyl]-N-(3-methylphenyl)pyrrolidine-3-carboxamide The title compound was prepared similarly to the procedure described in Example 242E substituting m-toluidine for aniline. MS (ESI) m/z 443.0 (M+H)+

Example 317

Trans-4-(4-fluorophenyl)-1-[(1-methyl-1H-imidazol-4-yl)sulfonyl]-N-[3-(trifluoromethyl)phenyl]pyrrolidine-3-carboxamide The title compound was prepared using the procedure described in Example 242E substituting 3-(trifluoromethyl)aniline for aniline. MS (ESI) m/z 497.0 (M+H)+.

Example 318

4-{[Trans-3-[(3-chloro-4-fluorophenoxy)methyl]-4-(4-fluorophenyl)pyrrolidin-1-yl]sulfonyl}-1-methyl-1H-imidazole The title compound was prepared similarly to the procedure described in Example 245 substituting 3-chloro-4-fluorophenol for phenol. MS (ESI) m/z 468.1 (M+H)+.

Example 319

(4-Chloro-3-fluorophenyl){trans-4-(4-fluorophenyl)-1-[(1-methyl-1-imidazol-4-yl)sulfonyl]pyrrolidin-3-yl}methanone The title compound was prepared similarly to the procedure described in Example 271B substituting (4-chloro-3-fluorophenyl) magnesium bromide for phenylmagnesium bromide. MS (ESI) m/z 466.1 (M+H)+.

Example 320 trans-N-[2-chloro-4-(trifluoromethyl)benzyl]-1-[(1-methyl-1H-imidazol-4-yl)sulfonyl]-4-(pyridin-2-yl)pyrrolidin-3-amine The title compound was prepared similarly to the procedure described in Example 148 substituting Example 286A for Example 3A and substituting 2-chloro-4-(trifluoromethyl)benzaldehyde for benzaldehyde. MS (ESI) m/z 500 (M+H)+.

Example 321

(3S,4R)-N-[2-chloro-4-(trifluoromethyl)benzyl]-4-(4-fluorophenyl)-1-[(1-methyl-1H-imidazol-4-yl)sulfonyl]pyrrolidin-3-amine Example 321A tert-butyl (3S,4R)-4-(4-fluorophenyl)-1-(1-methyl-1H-imidazol-4-ylsulfonyl)pyrrolidin-3-ylcarbamate The title compound was prepared similarly to the conditions described in Example 2A-2E substituting (E)-1-fluoro-4-(2-nitrovinyl)benzene for (E)-1-methoxy-4-(2-nitrovinyl)benzene. A Chiral SFC separation provided the title compound. (Instrument: SFC200 Column: AD-H, 50×250 mm, 5 μm; Column Temperature: 35° C.; Mobile Phase: CO₂/methanol/diethylamine=80/20/0.1; Flow rate: 180 g/min; Back Pressure: 100 Bar; Wavelength: 214 nm; Cycle time: 5.1 min; Injection: 2.0 mL Sample solution: 55 g in 500 mL methanol). Retention Time=4.03 minutes.

Example 321B (3S,4R)-4-(4-fluorophenyl)-1-(1-methyl-1H-imidazol-4-ylsulfonyl)pyrrolidin-3-amine The title compound was prepared as an HCl salt similarly to the procedure described in Example 2F substituting Example 321A for Example 2E.

Example 321C (3S,4R)-N-[2-chloro-4-(trifluoromethyl)benzyl]-4-(4-fluorophenyl)-1-[(1-methyl-1H-imidazol-4-yl)sulfonyl]pyrrolidin-3-amine The title compound was prepared similarly to the procedure described in Example 148 substituting Example 321B for Example 3A and substituting 2-chloro-4-(trifluoromethyl)benzaldehyde for benzaldehyde. MS (ESI) m/z 517 (M+H)$^+$.

Example 322

(3R,4S)-N-[2-chloro-4-(trifluoromethyl)benzyl]-4-(4-fluorophenyl)-1-[(1-methyl-1H-imidazol-4-yl)sulfonyl]pyrrolidin-3-amine

Example 322A tert-butyl (3R,4S)-4-(4-fluorophenyl)-1-(1-methyl-1H-imidazol-4-ylsulfonyl)pyrrolidin-3-ylcarbamate The title compound was prepared similarly to Example 321A. $R_T$=5.73 minutes.

Example 322B (3R,4S)-4-(4-fluorophenyl)-1-(1-methyl-1H-imidazol-4-ylsulfonyl)pyrrolidin-3-amine The title compound was prepared as an HCl salt similarly to the procedure described in Example 2F substituting Example 322A for Example 2E.

Example 322C (3R,4S)-N-[2-chloro-4-(trifluoromethyl)benzyl]-4-(4-fluorophenyl)-1-[(1-methyl-1H-imidazol-4-yl)sulfonyl]pyrrolidin-3-amine The title compound was prepared similarly to the procedure described in Example 148 substituting Example 322B for Example 3A and substituting 2-chloro-4-(trifluoromethyl)benzaldehyde for benzaldehyde. MS (ESI) m/z 517 (M+H)$^+$.

Example 323

(3S,4R)-4-(4-fluorophenyl)-1-[(1-methyl-1H-imidazol-4-yl)sulfonyl]-N-[3-(trifluoromethoxy)phenyl]pyrrolidin-3-amine Under nitrogen, a pressure vial was charged with Example 321B (100 mg, 0.27 mmol), 1-bromo-3-(trifluoromethoxy) benzene (67 mg, 0.27 mmol), 2'-(di-tert-butylphosphino)-N,N-dimethylbiphenyl-2-amine (9.5 mg, 0.03 mmol), tris(dibenzylidene-acetone)dipalladium(0) (13 mg, 0.014 mmol), sodium tert-butoxide (107 mg, 1.1 mmol), and dioxane (4 mL). The reaction mixture was stirred at 80° C. for 2 hours. Then, the reaction mixture was concentrated. Purification via HPLC provided the title compound. MS (ESI) m/z 485 (M+H)$^+$.

Example 324

(3S,4R)—N,4-bis(4-fluorophenyl)-1-[(1-methyl-1H-imidazol-4-yl)sulfonyl]pyrrolidin-3-amine The title compound was prepared similarly to the procedure described in Example 323 substituting 1-bromo-4-fluorobenzene for bromo-3-(trifluoromethoxy)benzene. MS (ESI) m/z 419 (M+H)$^+$.

Example 325

(3S,4R)-N-(3-chlorophenyl)-4-(4-fluorophenyl)-1-[(1-methyl-1H-imidazol-4-yl)sulfonyl]pyrrolidin-3-amine The title compound was prepared similarly to the procedure described in Example 323 substituting 1-bromo-3-chlorobenzene for bromo-3-(trifluoromethoxy)benzene. MS (ESI) m/z 435 (M+H)$^+$.

Example 326

(3S,4R)-4-(4-fluorophenyl)-1-[(1-methyl-1H-imidazol-4-yl)sulfonyl]-N-[3-(trifluoromethyl)phenyl]pyrrolidin-3-amine The title compound was prepared similarly to the procedure described in Example 323 substituting 1-bromo-3-(trifluoromethyl)benzene for bromo-3-(trifluoromethoxy)benzene. MS (ESI) m/z 469 (M+H)$^+$.

Example 327

(3R,4S)-4-(4-fluorophenyl)-1-[(1-methyl-1H-imidazol-4-yl)sulfonyl]-N-[3-(trifluoromethyl)phenyl]pyrrolidin-3-amine Under nitrogen, a pressure vial was charged with Example 322B (100 mg, 0.28 mmol), 1-bromo-3-(trifluoromethyl) benzene (62 mg, 0.28 mmol), 2'-(di-tert-butylphosphino)-N,N-dimethylbiphenyl-2-amine (9.5 mg, 0.03 mmol), tris(dibenzylidene-acetone)dipalladium(0) (13 mg, 0.014 mmol), sodium tert-butoxide (107 mg, 1.1 mmol), and dioxane (4 mL). The reaction mixture was stirred at 80° C. for 2 hours. Then, the reaction mixture was concentrated. Purification via HPLC provided the title compound. MS (ESI) m/z 469 (M+H)$^+$.

Example 328

(3R,4S)-N-(3-chlorophenyl)-4-(4-fluorophenyl)-1-[(1-methyl-1H-imidazol-4-yl)sulfonyl]pyrrolidin-3-amine The title compound was prepared similarly to the procedure described in Example 327 substituting 1-bromo-3- chlorobenzene for 1-bromo-3-(trifluoromethyl)benzene, but the reaction only stirred for 1 hour. MS (ESI) m/z 435 (M+H)⁺.

Example 329

(3R,4S)-4-(4-fluorophenyl)-1-[(1-methyl-1-imidazol-4-yl)sulfonyl]-N-[3-(trifluoromethoxy)phenyl]pyrrolidin-3-amine The title compound was prepared similarly to the procedure described in Example 327 substituting 1-bromo-3-(trifluoromethoxy)benzene for 1-bromo-3-(trifluoromethyl) benzene. MS (ESI) m/z 485 (M+H)⁺.

Example 330

(3R,4S)-N,4-bis(4-fluorophenyl)-1-[(1-methyl-1H-imidazol-4-yl)sulfonyl]pyrrolidin-3-amine The title compound was prepared similarly to the procedure described in Example 327 substituting 1-bromo-4-fluorobenzene for 1-bromo-3-(trifluoromethoxy)benzene. MS (ESI) m/z 419 (M+H)⁺.

Example 331

3-(3-chlorobenzyl)-1-[(1-methyl-1H-imidazol-4-yl)sulfonyl]-4-phenylpyrrolidin-2-one

Example 331A methyl 2-(3-chlorobenzyl)-4-nitro-3-phenylbutanoate

To a solution of diisopropylamine (210 mg, 2 mmol) in tetrahydrofurane (1 mL) at −78° C. was added butyllithium (1 mL, 2N, 2 mmol). The mixture was allowed to stir for 10 minutes. Then methyl 3-(3-chlorophenyl)propanoate in tetrahydrofurane (1 mL) was added. The mixture was allowed to stir for 30 minutes. (E)-(2-nitrovinyl)benzene in tetrahydrofuran (1 mL) was added. The mixture was allowed to stir for 1 hour, and partitioned with ammonium chloride (aq) and ethyl acetate. The organic fraction was collected and concentrated to provide the crude title compound.

Example 331B 3-(3-chlorobenzyl)-4-phenylpyrrolidin-2-one

To a solution of Example 331A in methanol (2 mL) was added an acetic acid solution (2 mL. 50% aq.), and zinc (6×130 mg, 12 mmol). The reaction mixture stirred for 2 hours. The reaction mixture was concentrated and partitioned between ethyl acetate and enough NaOH(1M aq.) to adjust the pH value to 10. The insoluble material was filtered off through celite. The organic fraction was collected, and dried over sodium hydroxide pellets for 16 hours. The mixture was washed with HCl(aq) and purified by silica gel flash chromatography (100% ethyl acetate) to afford the title compound.

Example 331C 3-(3-chlorobenzyl)-1-[(1-methyl-1H-imidazol-4-yl)sulfonyl]-4-phenylpyrrolidin-2-one To a solution of Example 331B (150 mg, 0.53 mmol) in tetrahydrofuran (1 mL) at −78° C. was added butyllithium (0.3 mL, 2 N, 0.6 mmol). The mixture was allowed to stir for 10 minutes. 1-Methyl-1H-imidazole-4-sulfonyl chloride (95 mg, 0.53 mmol) was added. The reaction stirred for 2 hours. The mixture was warmed to 20° C. and quenched with ammonium chloride (aq.) The mixture was extracted with ethyl acetate and purified by flash chromatography (10% methanol/ethyl acetate) followed by trituration in methanol. The precipitates were collected to afford the title compound. MS (ESI) m/z 430/432(3:1) (M+H)⁺.

Example 332

2-Chloro-N-({trans-4-(4-fluorophenyl)-1-[(1-methyl-1H-imidazol-4-yl)sulfonyl]pyrrolidin-3-yl}methyl)-4-(trifluoromethyl)aniline

Example 332A

Trans-4-(4-fluorophenyl)-1-(1-methyl-1H-imidazol-4-ylsulfonyl)pyrrolidine-3-carbaldehyde To a solution of Example 206 (180 mg, 0.53 mmol) in dichloromethane (2 mL) was added Dess-MartinPeriodinane (450 mg, 1.06 mmol). The reaction mixture was stirred at room temperature for 16 hours. The reaction mixture was filtered and washed with dichloromethane. The filtrate was concentrated to afford the title compound. MS (ESI) m/z 338.0 (M+H)⁺.

Example 332B

2-Chloro-N-({trans-4-(4-fluorophenyl)-1-[(1-methyl-1H-imidazol-4-yl)sulfonyl]pyrrolidin-3-yl}methyl)-4-(trifluoromethyl)aniline To Example 332A (150 mg, 0.45 mmol) in methanol acetate buffer (2 mL, made from 48 g AcOH and 30.5 g NaOAc in 1 L methanol) was added 2-chloro-4-(trifluoromethyl)aniline (104 mg, 0.53 mmol) and sodium cyanoborohydride (42 mg, 0.67 mmol). The mixture was allowed to stir overnight. It was partitioned between dichoromethane and saturated sodium bicarbonate. Purification via HPLC afford the title compound. MS (ESI) m/z 517.0 (M+H)⁺.

Example 333

3-Chloro-N-({trans-4-(4-fluorophenyl)-1-[(1-methyl-1H-imidazol-4-yl)sulfonyl]pyrrolidin-3-yl}methyl)aniline The title compound was prepared similarly to the procedure described in Example 290 substituting Example 304 for Example 242E. MS (ESI) m/z 449.1 (M+H)⁺.

Example 334

N-({Trans-4-(4-fluorophenyl)-1-[(1-methyl-1H-imidazol-4-yl)sulfonyl]pyrrolidin-3-yl}methyl)-3-methylaniline The title compound was prepared similarly to the procedure described in Example 290 substituting Example 316 for Example 242E. MS (ESI) m/z 429.1 (M+H)⁺.

Example 335

N-({Trans-4-(4-fluorophenyl)-1-[(1-methyl-1H-imidazol-4-yl)sulfonyl]pyrrolidin-3-yl}methyl)-3-(trifluoromethyl)aniline The title compound was prepared using the procedure as described in Example 290 substituting Example 317 for Example 242E. MS (ESI) m/z 483.1 (M+H)$^+$.

Example 336

4-({Trans-4-(4-fluorophenyl)-1-[(1-methyl-1H-imidazol-4-yl)sulfonyl]pyrrolidin-3-yl}methoxy)-6-(trifluoromethyl)pyrimidine The title compound was prepared using the procedure as described in Example 245 substituting 6-(trifluoromethyl)pyrimidin-4-ol for phenol. MS (ESI) m/z 486.1 (M+H)$^+$.

Example 337

Trans-4-cyclopropyl-1-[(1-methyl-1H-imidazol-4-yl)sulfonyl]-N-[3-(trifluoromethyl)phenyl]pyrrolidin-3-amine

Example 337A

Trans-1-benzyl-3-cyclopropyl-4-nitropyrrolidine

The title compound was prepared similarly to the procedure described in Example 2A substituting (E)-(2-nitrovinyl)cyclopropane for trans-4-methoxy-beta-nitrostyrene.

Example 337B

Trans-1-benzyl-4-cyclopropylpyrrolidin-3-amine

The title compound was prepared similarly to the procedure described in Example 2B substituting Example 337A for Example 2A.

Example 337C tert-butyl (trans-1-benzyl-4-cyclopropylpyrrolidin-3-yl)carbamate To a solution of Example 337B (1.0 g, 4.6 mmol) in ethyl acetate (10 mL) was added ditert-butyl dicarbonate (1.4 g, 6.4 mmol). The mixture was allowed to stir for 1 hour. The mixture was concentrated and purified by silica gel column chromatography (50% ethyl acetate/hexanes) to afford the title compound.

Example 337D tert-butyl ((trans-4-cyclopropylpyrrolidin-3-yl)carbamate

The title compound was prepared similarly to the procedure described in Example 2D substituting Example 337C for 2C.

Example 337E tert-butyl ((trans-4-cyclopropyl-1-((1-methyl-1H-imidazol-4-yl)sulfonyl)pyrrolidin-3-yl)carbamate The title compound was prepared similarly to the procedure described in Example 2E substituting Example 337D for Example 2D.

Example 337F

Trans-4-cyclopropyl-1-((1-methyl-1H-imidazol-4-yl)sulfonyl)pyrrolidin-3-amine

To Example 337E (0.82 g, 2.2 mmol) in dioxane (5 mL), was added hydrochloric acid (4N in dioxane, 3 mL). The mixture was stirred overnight, concentrated, and partitioned between ethyl acetate and sodium hydroxide (1M). The organic fraction was dried over potassium carbonate, filtered, and concentrated to provide the title compound.

Example 337G

Trans-4-cyclopropyl-1-[(1-methyl-1H-imidazol-4-yl)sulfonyl]-N-[3-(trifluoromethyl)phenyl]pyrrolidin-3-amine To a solution of Example 337F (135 mg, 0.5 mmol) in dioxane (1 mL) was added 1-bromo-3-(trifluoromethyl)benzene (101 mg, 0.5 mmol), tris(dibenzylidene-acetone)dipalladium(0) (46 mg, 0.05 mmol), dicyclohexyl(2',4',6'-triisopropyl-[1,1'-biphenyl]-2-yl)phosphine (48 gm, 0.1 mmol), and sodium 2-methylpropan-2-olate (48 mg, 0.5 mmol). The mixture was heated at 110° C. for 2 hours, partitioned between ethyl acetate and ammonium chloride (aq), and purified by HPLC to give the title compound. MS (ESI) m/z 415 (M+H)$^+$.

Example 338

Trans-N-(3-chlorophenyl)-4-cyclopropyl-1-[(1-methyl-1H-imidazol-4-yl)sulfonyl]pyrrolidin-3-amine The title compound was prepared similarly to the procedure described in Example 337G substituting 1-bromo-3-chlorobenzene for 1-bromo-3-(trifluoromethyl)benzene. MS (ESI) m/z 381/383(3:1) (M+H)$^+$.

Example 339

4-{[3-(2-chlorophenyl)-4-(4-fluorophenyl)pyrrolidin-1-yl]sulfonyl}-1-methyl-1H-imidazole

Example 339A 2-(2-chlorophenyl)acetaldehyde

To 2-(2-chlorophenyl)ethanol (1 g, 6.39 mmol) in 10 mL of dichloromethane was added Dess-MartinPeriodinane (3.52 g, 8.3 mmol) at 0° C. This mixture was stirred at 0° C.

for 1 hour. The mixture was filtered and washed with dichloromethane. The filtrate was concentrated to afford the title product.

Example 339B 2-(2-Chlorophenyl)-3-(4-fluorophenyl)-4-nitrobutanal

The title compound was prepared similarly to the procedure described in Example 182A substituting Example 339A for 3-(3-chlorophenyl)propanal.

Example 339C

Trans-3-(2-chlorophenyl)-4-(4-fluorophenyl)pyrrolidine

The title compound was prepared similarly to the procedure described in Example 182B substituting Example 339B for Example 182A.

Example 339D

4-{[3-(2-chlorophenyl)-4-(4-fluorophenyl)pyrrolidin-1-yl]sulfonyl}-1-methyl-1H-imidazole The title compound was prepared similarly to the procedure described in Example 182C substituting Example 339C for Example 182 B. MS (ESI) m/z 420.3 (M+H)$^+$.

Example 340

4-{[3-(4-chlorophenyl)-4-(4-fluorophenyl)pyrrolidin-1-yl]sulfonyl}-1-methyl-1H-imidazole

Example 340A 2-(4-Chlorophenyl)acetaldehyde

The title compound was prepared similarly to the procedure described in Example 339A substituting 2-(4-chlorophenyl)ethanol for 2-(2-chlorophenyl)ethanol.

Example 340B 2-(4-Chlorophenyl)-3-(4-fluorophenyl)-4-nitrobutanal

The title compound was prepared similarly to the procedure described in Example 182A substituting Example 340A for 3-(3-chlorophenyl)propanal.

Example 340C

The title compound was prepared similarly to the procedure described in Example 182B substituting Example 340B for Example 182A.

Example 340D

4-{[3-(4-chlorophenyl)-4-(4-fluorophenyl)pyrrolidin-1-yl]sulfonyl}-1-methyl-1H-imidazole The title compound was prepared similarly to the procedure described in Example 182C substituting Example 340C for Example 182B. MS (ESI) m/z 420.2 (M+H)$^+$.

Example 341

2-chloro-4-({trans-4-(4-fluorophenyl)-1-[(1-methyl-1H-imidazol-4-yl)sulfonyl]pyrrolidin-3-yl}amino)benzonitrile A 10 mL microwave vial was charged with Example 322B (100 mg, 0.277 mmol) and 100 mg of premixed tris(dibenzylidene-acetone)dipalladium(0)/sodium tert-butoxide/2,2'-bis(diphenylphosphino)-1,1'-binaphthyl (0.05:0.15:2), aldrich 715530). The solids were suspended in 1,2-dimethoxyethane and 4-bromo-2-chlorobenzonitrile (72.1 mg, 0.333 mmol) was added. The reaction vessel was capped and the reaction mixture heated under microwave conditions for 15 min at 130° C. The mixture was filtered through celite, concentrated, dissolved in 2 ml 50% MeOH/dimethylsulfoxide, and purified by reverse phase HPLC to obtain the title compound. MS (ESI) m/z 460 (M+H)$^+$.

Example 342

2-fluoro-4-({trans-4-(4-fluorophenyl)-1-[(1-methyl-1H-imidazol-4-yl)sulfonyl]pyrrolidin-3-yl}amino)benzonitrile The title compound was prepared similarly to the procedure described in Example 341 substituting 4-bromo-2-fluorobenzonitrile for 4-bromo-2-(difluoromethyl)benzonitrile. MS (ESI) m/z 444 (M+H)$^+$.

Example 343

3-(3-chlorobenzyl)-1-[(1-methyl-1H-imidazol-4-yl)sulfonyl]-4-phenylimidazolidin-2-one

Example 343A

N1-(3-chlorobenzyl)-1-phenylethane-1,2-diamine

To (3-chlorophenyl)methanamine (0.28 g, 2 mmol) in methanol (5 mL) was added (E)-(2-nitrovinyl)benzene (0.30 g, 2 mmol). The mixture was allowed to stir for 4 hours. A solution of acetic acid in water (50%, 2 mL) was added, followed by zinc (5×130 mg, 10 mmol). The mixture was allowed to stir for 1 hour and concentrated. NaOH(1 M) was added to adjust the pH to 10. Ethyl acetate was added and the solution partitioned. The organic fraction was collected, dried over potassium carbonate, filtered, and concentrated to provide the title compound.

Example 343B 1-(3-chlorobenzyl)-5-phenylimidazolidin-2-one

To a solution of Example 343A in dichloromethane (5 mL) at −78° C. was added triethylamine (100 mg, 1 mmol) and triphosgene (60 mg, 0.2 mmol). The reaction mixture was allowed to warm to room temperature and stir for 18 hours. The crude material was purified by flash chromatography (100% ethyl acetate) to afford the title compound.

Example 343C 3-(3-chlorobenzyl)-1-[(1-methyl-1H-imidazol-4-yl)sulfonyl]-4-phenylimidazolidin-2-one To a solution of Example 343B (60 mg, 0.2 mmol) in tetrahydrofuran (1 mL) at 0° C. was added sodium hydride (40 mg, 60%, 1 mmol) and 1-methyl-1H-imidazole-4-sulfonyl chloride (38 mg, 0.2 mmol). The mixture was stiffed for 18 hours, quenched with ammonium chloride (aq). Ethyl acetate was added then the solution partitioned. The organic fraction was collected and concentrated. Purification via HPLC provided the title compound. MS (ESI) m/z 431/433 (3:1) (M+H)$^+$.

Example 344 trans-1-[(1-methyl-1H-imidazol-4-yl)sulfonyl]-4-(pyridin-2-yl)-N-[3-(trifluoromethyl)phenyl]pyrrolidin-3-amine The title compound was prepared similarly to the procedure described in Example 337G substituting Example 307B for Example 337F. MS (ESI) m/z 452 (M+H)$^+$.

Example 345

Trans-N-(3-chlorophenyl)-1-[(1-methyl-1H-imidazol-4-yl)sulfonyl]-4-(pyridin-2-yl)pyrrolidin-3-amine The title compound was prepared similarly to the procedure described in Example 337G substituting Example 307B for Example 337F and substituting 1-bromo-3-chlorobenzene for 1-bromo-3-(trifluoromethyl)benzene. MS (ESI) m/z 418/420 (3:1) (M+H)$^+$.

Example 346

2-({Trans-4-(4-fluorophenyl)-1-[(1-methyl-1H-imidazol-4-yl)sulfonyl]pyrrolidin-3-yl}methoxy)-4-(trifluoromethyl)pyridine The title compound was prepared similarly to the procedure described in Example 245 substituting 4-(trifluoromethyl)pyridin-2-ol for phenol. MS (ESI) m/z 485.1 (M+H)$^+$.

Example 347

Trans-N-(3-cyanophenyl)-4-(4-fluorophenyl)-1-[(1-methyl-1H-imidazol-4-yl)sulfonyl]pyrrolidine-3-carboxamide The title compound was prepared similarly to the procedure described in Example 242E substituting 3-aminobenzonitrile for aniline. MS (ESI) m/z 454.1 (M+H)$^+$.

Example 348

4-{[Trans-3-[(4-fluorophenoxy)methyl]-4-(4-fluorophenyl)pyrrolidin-1-yl]sulfonyl}-1-methyl-1H-imidazole The title compound was prepared similarly to the procedure described in Example 245 substituting 4-fluorophenol for phenol. MS (ESI) m/z 434.1 (M+H)$^+$.

Example 349

4-(4-fluorophenyl)-1-[(1-methyl-1H-imidazol-4-yl)sulfonyl]-N-[3-(propan-2-yloxy)phenyl]pyrrolidin-3-amine The title compound was prepared similarly to the procedure described in Example 341 substituting 1-bromo-3-isopropoxybenzene for 4-bromo-2-(difluoromethyl)-1-fluorobenzene. MS (ESI) m/z 459 (M+H)$^+$ Example 350

N-{4-(4-fluorophenyl)-1-[(1-methyl-1H-imidazol-4-yl)sulfonyl]pyrrolidin-3-yl}pyridazin-3-amine Example 350A 6-chloro-N-(4-(4-fluorophenyl)-1-(1-methyl-1H-imidazol-4-ylsulfonyl)pyrrolidin-3-yl)pyridazin-3-amine 4-(4-fluorophenyl)-1-(1-methyl-1H-imidazol-4-ylsulfonyl)pyrrolidin-3-amine (100 mg, 0.308 mmol), 3,6-dichloropyridazine (46 mg, 0.308 mmol), N,N-diisopropylethyl amine (53.8 µl, 0.308 mmol), and 4 mL ethanol were placed in a 2-5 mL microwave vial and irradiated in a microwave (Biotage Initiator™, maximum 400 Watts) for 1 hour at 175° C. The reaction contents were concentrated, reddissolved in 2 mL 50% dimethylsulfoxide/methanol and purified via reverse phase HPLC to yield the title compound.

Example 350B

N-{4-(4-fluorophenyl)-1-[(1-methyl-1H-imidazol-4-yl)sulfonyl]pyrrolidin-3-yl}pyridazin-3-amine Example 350A (18 mg, 0.041 mmol) and methanol (4 ml) were added to 5% Pd/C, wet (4 mg, 0.940 µmol) and triethyl amine (8 mg, 0.082 mmol) in a 50 ml pressure bottle. The mixture stirred for 2 hours under 30 psi of hydrogen until HPLC indicated complete conversion. The mixtore was filtered through a nylon membrane. Purification via HPLC provided the title compound. MS (ESI) m/z 459 (M+H)$^+$.

Example 351

N-{(3R,4S)-4-(4-fluorophenyl)-1-[(1-methyl-1H-imidazol-4-yl)sulfonyl]pyrrolidin-3-yl}-6-(trifluoromethyl)pyridin-2-amine The title compound was prepared similarly to the procedure described in Example 341 substituting 2-bromo-6-(trifluoromethyl)pyridine for 4-bromo-2-(difluoromethyl)-1-fluorobenzene. MS (ESI) m/z 470 (M+H)$^+$.

Example 352

(3R,4S)-N-(3-chloro-4-fluorophenyl)-4-(4-fluorophenyl)-1-[(1-methyl-1H-imidazol-4-yl)sulfonyl]pyrrolidin-3-amine The title compound was prepared similarly to the procedure described in Example 341 substituting 4-bromo-2-chloro-1-fluorobenzene for 4-bromo-2-(difluoromethyl)-1-fluorobenzene. MS (ESI) m/z 453 (M+H)$^+$.

Example 353

(3R,4S)-N-(3-fluorophenyl)-4-(4-fluorophenyl)-1-[(1-methyl-1H-imidazol-4-yl)sulfonyl]pyrrolidin-3-amine The title compound was prepared similarly to the procedure described in Example 341 substituting 1-bromo-3- fluorobenzene for 4-bromo-2-(difluoromethyl)-1-fluorobenzene. MS (ESI) m/z 419 (M+H)+.

Example 354

Trans-N-(4-chlorobenzyl)-3-methyl-1-[(1-methyl-1H-imidazol-4-yl)sulfonyl]-4-phenylpyrrolidin-3-amine Example 354A Trans-1-benzyl-3-methyl-3-nitro-4-phenylpyrrolidine The title compound was prepared similarly to the procedure described in Example 2A substituting Example (E)-(2-nitroprop-1-en-1-yl)benzene for 4-methoxy-beta-nitrostyrene.

Example 354B

Trans-1-benzyl-3-methyl-4-phenylpyrrolidin-3-amine

The title compound was prepared similarly to the procedure described in Example 2B substituting Example 354A for Example 2A.

Example 354C

Trans-3-methyl-4-phenylpyrrolidin-3-amine

The title compound was prepared similarly to the procedure described in Example 2D substituting Example 354B for 2C.

Example 354D

Trans-3-methyl-1-((1-methyl-1H-imidazol-4-yl)sulfonyl)-4-phenylpyrrolidin-3-amine The title compound was prepared similarly to the procedure described in Example 182C substituting Example 354C for Example 182B.

Example 354E

Trans-N-(4-chlorobenzyl)-3-methyl-1-[(1-methyl-1H-imidazol-4-yl)sulfonyl]-4-phenylpyrrolidin-3-amine To a solution of Example 354D (100 mg, 0.28 mmol) in methanol acetate buffer (pH4, 1M, 1 mL, made from 48 g AcOH and 30.5 g NaOAc in 1 L methanol) was added 4-chlorobenzaldehyde (40 mg, 0.28 mmol) and sodium cyanoborohydride (40 mg, 0.65 mmol). The mixture was stirred for 18 hours and partitioned between ethyl acetate and NaOH(1 M). The organic fraction was collected, concentrated, and purified by HPLC to afford the title compound. MS (ESI) m/z 445/447 (3:1) (M+H)+.

Example 355

Trans-3-methyl-1-[(1-methyl-1H-imidazol-4-yl)sulfonyl]-4-phenyl-N-[4-(trifluoromethyl)benzyl]pyrrolidin-3-amine The title compound was prepared similarly to the procedure described in Example 354E substituting 4-(trifluoromethyl)benzaldehyde for 4-chlorobenzaldehyde. MS (ESI) m/z 479 (M+H)+.

Example 356

Trans-N-[2-chloro-4-(trifluoromethyl)benzyl]-3-methyl-1-[(1-methyl-1H-imidazol-4-yl)sulfonyl]-4-phenylpyrrolidin-3-amine The title compound was prepared similarly to the procedure described in Example 354E substituting 2-chloro-4-(trifluoromethyl)benzaldehyde for 4-chlorobenzaldehyde. MS (ESI) m/z 514/516 (3:1) (M+H)+.

Example 357

(3,4-Difluorophenyl){trans-4-(4-fluorophenyl)-1-[(1-methyl-1H-imidazol-4-yl)sulfonyl]pyrrolidin-3-yl}methanone The title compound was prepared similarly to the procedure described in Example 271B substituting (3,4-difluorophenyl)magnesium bromide for phenylmagnesium bromide. MS (ESI) m/z 450.2 (M+H)+.

Example 358

Trans-N,4-bis(4-fluorophenyl)-1-[(1-methyl-1H-imidazol-4-yl)sulfonyl]pyrrolidine-3-carboxamide The title compound was prepared similarly to the procedure described in Example 242E substituting 4-fluoroaniline for aniline. MS (ESI) m/z 447.1 (M+H)+.

Example 359

(3,4-Dichlorophenyl){trans-4-(4-fluorophenyl)-1-[(1-methyl-1H-imidazol-4-yl)sulfonyl]pyrrolidin-3-yl}methanone The title compound was prepared similarly to the procedure described in Example 271B substituting (3,4-dichlorophenyl)magnesium bromide for phenylmagnesium bromide. MS (ESI) m/z 482.1 (M+H)+.

Example 360

(3,5-Dichlorophenyl){trans-4-(4-fluorophenyl)-1-[(1-methyl-1-imidazol-4-yl)sulfonyl]pyrrolidin-3-yl}methanone The title compound was prepared similarly to the procedure described in Example 271B substituting (3,5-dichlorophenyl)magnesium bromide for phenylmagnesium bromide. MS (ESI) m/z 482.1 (M+H)⁺.

Example 361

(3-Chloro-5-fluorophenyl){trans-4-(4-fluorophenyl)-1-[(1-methyl-1H-imidazol-4-yl)sulfonyl]pyrrolidin-3-yl}methanone The title compound was prepared similarly to the procedure described in Example 271B substituting (3-chloro-5-fluorophenyl)magnesium bromide for phenylmagnesium bromide. MS (ESI) m/z 466.2 (M+H)⁺.

Example 362

{Trans-4-(4-fluorophenyl)-1-[(1-methyl-1H-imidazol-4-yl)sulfonyl]pyrrolidin-3-yl}[3-(trifluoromethoxy)phenyl]methanone The title compound was prepared similarly to the procedure described in Example 271B substituting (3-(trifluoromethoxy)phenyl)magnesium bromide for phenylmagnesium bromide. MS (ESI) m/z 498.1 (M+H)⁺.

Example 363

{Trans-4-(4-fluorophenyl)-1-[(1-methyl-1H-imidazol-4-yl)sulfonyl]pyrrolidin-3-yl}[4-(trifluoromethoxy)phenyl]methanone The title compound was prepared similarly to the procedure described in Example 271B substituting (4-(trifluoromethoxy)phenyl)magnesium bromide for phenylmagnesium bromide. MS (ESI) m/z 498.1 (M+H)⁺.

Example 364

3-[({Trans-4-(4-fluorophenyl)-1-[(1-methyl-1H-imidazol-4-yl)sulfonyl]pyrrolidin-3-yl}methyl)amino]benzamide The title compound was prepared similarly to the procedure described in Example 290 substituting Example 347 for Example 242E. MS (ESI) m/z 458.1 (M+H)⁺.

Example 365

3-(Aminomethyl)-N-({Trans-4-(4-fluorophenyl)-1-[(1-methyl-1H-imidazol-4-yl)sulfonyl]pyrrolidin-3-yl}methyl)aniline The title compound was prepared similarly to the procedure described in Example 290 substituting Example 347 for Example 242E. MS (ESI) m/z 444.1 (M+H)⁺.

Example 366

4-({Trans-4-(4-fluorophenyl)-1-[(1-methyl-1H-imidazol-4-yl)sulfonyl]pyrrolidin-3-yl}methoxy)-2-(trifluoromethyl)pyridine The title compound was prepared similarly to the procedure described in Example 245 substituting 2-(trifluoromethyl)pyridin-4-ol for phenol. MS (ESI) m/z 485.1 (M+H)⁺.

Example 367

4-Fluoro-N-({trans-4-(4-fluorophenyl)-1-[(1-methyl-1H-imidazol-4-yl)sulfonyl]pyrrolidin-3-yl}methyl)aniline The title compound was prepared similarly to the procedure described in Example 290 substituting Example 358 for Example 242E. MS (ESI) m/z 433.1 (M+H)⁺.

Example 368

N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine The title compound was prepared similarly to the procedure described in Example 327 substituting 2-bromo-4-(trifluoromethyl)benzene for 1-bromo-3-(trifluoromethoxy)benzene. MS (ESI) m/z 470 (M+H)⁺.

Example 369

Trans-4-(4-fluorophenyl)-1-[(1-methyl-1H-imidazol-4-yl)sulfonyl]-N-[4-(trifluoromethyl)pyridin-2-yl]pyrrolidine-3-carboxamide The title compound was prepared similarly to the procedure described in Example 242E substituting 4-(trifluoromethyl)pyridin-2-amine for aniline. MS (ESI) m/z 498.1 (M+H)⁺.

Example 370

Trans-4-(4-fluorophenyl)-N-[4-fluoro-3-(trifluoromethoxy)phenyl]-1-[(1-methyl-1H-imidazol-4-yl)sulfonyl]pyrrolidine-3-carboxamide The title compound was prepared similarly to the procedure described in Example 242E substituting 4-fluoro-3-(trifluoromethoxy)aniline for aniline. MS (ESI) m/z 531.1 (M+H)⁺.

Example 371

Trans-N-[4-chloro-3-(trifluoromethoxy)phenyl]-4-(4-fluorophenyl)-1-[(1-methyl-1H-imidazol-4-yl)sulfonyl]pyrrolidine-3-carboxamide The title compound was prepared similarly to the procedure described in Example 242E substituting 4-chloro-3-(trifluoromethoxy)aniline for aniline. MS (ESI) m/z 547.1 (M+H)⁺.

Example 372

N-[4-chloro-2-({Trans-4-(4-fluorophenyl)-1-[(1-methyl-1H-imidazol-4-yl)sulfonyl]pyrrolidin-3-yl}amino)phenyl]acetamide The title compound was prepared similarly to the procedure described in Example 337G substituting Example 3A for Example 337F and N-(2-bromo-4-chlorophenyl)acetamide for 1-bromo-3-(trifluoromethyl)benzene. MS (ESI) m/z 492/494 (3:1) (M+H)⁺.

Example 373

Trans-4-[(3-chlorophenyl)amino]-1-[(1-methyl-1H-imidazol-4-yl)sulfonyl]pyrrolidin-3-ol

Example 373A (trans)-tert-butyl 3-((3-chlorophenyl)amino)-4-hydroxypyrrolidine-1-carboxylate A mixture of 3-chloroaniline (0.38 g, 3 mmol) and tert-butyl 6-oxa-3-azabicyclo[3.1.0]hexane-3-carboxylate (0.56 g, 3 mmol) in ethanol (3 mL) was heated at 100° C. for 3 days. The mixture was concentrated and purified by flash chromatography (50% ethyl acetate/hexanes) to afford the title compound.

Example 373B

Trans-4((3-chlorophenyl)amino)pyrrolidin-3-ol

To a solution of Example 373A (0.97 g, 3.1 mmol) in dioxane (3 mL) at 0° C. was added hydrochloric acid (4N in dioxane, 5 mL). The mixture was allowed to stir for 5 hours. Concentration provided the title compound as the hydrochloride salt.

Example 373C

Trans-4-[(3-chlorophenyl)amino]-1-[(1-methyl-1H-imidazol-4-yl)sulfonyl]pyrrolidin To a solution of Example 373B in dichloromethane (5 mL) was added triethylamine (1 g, 10 mmol) and 1-methyl-1H-imidazole-4-sulfonyl chloride (540 mg, 3.0 mmol). The mixture was allowed to stir for 16 hours. The reaction mixture was concentrated and partitioned between ethyl acetate and NaOH(1 M). The organic fraction was collected, concentrated, and purified by flash chromatography (100% ethyl acetate) to afford the title compound. MS (ESI) m/z 357/359 (3:1) (M+H)$^+$.

Example 374

N-[Trans-1-[(1-methyl-1H-imidazol-4-yl)sulfonyl]-4-(pyridin-2-yl)pyrrolidin-3-yl]-1-(trifluoromethyl)cyclopropanecarboxamide The title compound was prepared similarly to the procedure described in Example 242E substituting Example 307B for 242D and substituting 1-(trifluoromethyl)cyclopropanecarboxylic acid for aniline. MS (ESI) m/z 444.0 (M+H)$^+$.

Example 375

N-{(3R,4S)-4-(4-fluorophenyl)-1-[(1-methyl-1H-imidazol-4-yl)sulfonyl]pyrrolidin-3-yl}-1-(trifluoromethyl)cyclopropanecarboxamide The title compound was prepared similarly to the procedure described in Example 242E substituting Example 322B for Example 242D and substituting 1-(trifluoromethyl)cyclopropanecarboxylic acid for aniline. MS (ESI) m/z 461.1 (M+H)$^+$.

Example 376

4-fluoro-N-({trans-4-(4-fluorophenyl)-1-[(1-methyl-1H-imidazol-4-yl)sulfonyl]pyrrolidin-3-yl}methyl)-3-(trifluoromethoxy)aniline The title compound was prepared similarly to the procedure described in Example 290 substituting Example 370 for Example 242E. MS (ESI) m/z 517.2 (M+H)$^+$.

Example 377

4-chloro-N-({trans-4-(4-fluorophenyl)-1-[(1-methyl-1H-imidazol-4-yl)sulfonyl]pyrrolidin-3-yl}methyl)-3-(trifluoromethoxy)aniline The title compound was prepared similarly to the procedure described in Example 290 substituting Example 371 for Example 242E. MS (ESI) m/z 533.2 (M+H)$^+$.

Example 378

Trans-N-(3-chlorophenyl)-4-(4-fluorophenoxy)-1-[(1-methyl-1H-imidazol-4-yl)sulfonyl]pyrrolidin-3-amine To a solution of Example 373 (142 mg, 0.4 mmol) in dimethylformamide (0.2 mL) was added copper(I) iodide (40 mg, 0.2 mmol), cesium carbonate (300 mg, 0.92 mmol), and 1-fluoro-4-iodobenzene (88 mg, 0.4 mmol). The mixture was stirred at 110° C. for 16 hours, then partitioned between ethyl acetate and water. The organic fraction was collected, concentrated and purified by HPLC to provide the title compound. MS (ESI) m/z 452/454 (3:1) (M+H)$^+$.

Example 379

2-({trans-4-(4-fluorophenyl)-1-[(1-methyl-1H-imidazol-4-yl)sulfonyl]pyrrolidin-3-yl}oxy)-4-(trifluoromethyl)pyridine

Example 379A

Trans-tert-butyl 3-(4-fluorophenyl)-4-hydroxypyrrolidine-1-carboxylate

To a solution of tert-butyl 6-oxa-3-azabicyclo[3.1.0]hexane-3-carboxylate (0.93 g, 5 mmol) in tetrahydrofuran (5 mL) at −78° C. was added copper(I) iodide (85 mg, 0 5 mmol) then (4-fluorophenyl)magnesium bromide (7 mL, 1 M, 7 mol). The mixture was warmed to room temperature and, allowed to stir for 3 hours. The reaction mixture was partitioned with ammonium chloride (aq). The organic fraction was collected dried over MgSO$_4$, filtered, and concentrated to provide the title compound.

Example 379B

Trans-4-(4-fluorophenyl)pyrrolidin-3-ol

The title compound was prepared as the hydrochloride salt similarly to the procedure described in Example 373B substituting Example 379A for Example 373A.

Example 379C

Trans-4-(4-fluorophenyl)-1-((1-methyl-1H-imidazol-4-yl)sulfonyl)pyrrolidin-3-ol

The title compound was prepared similarly to the procedure described in Example 373C substituting Example 379B for Example 373B.

Example 379D 2-({Trans-4-(4-fluorophenyl)-1-[(1-methyl-1H-imidazol-4-yl)sulfonyl]pyrrolidin-3-yl}oxy)-4-(trifluoromethyl)pyridine To a solution of Example 379C (110 mg, 0.34 mmol) in dimethylsulfoxide (0.3 mL) was added potassium 2-methylpropan-2-olate (50 mg, 0.45 mmol) and 2-fluoro-4-(trifluoromethyl)pyridine (70 mg, 0.43 mmol). The mixture was stirred at 100° C. for 16 hours, then partitioned between ethyl acetate and water. Purification by HPLC provided the title compound. MS (ESI) m/z 471 (M+H)$^+$.

Example 380

3-({{(3R,4S)-4-(4-fluorophenyl)-1-[(1-methyl-1H-imidazol-4-yl)sulfonyl]pyrrolidin-3-yl} amino)benzonitrile

Example 380A (3R,4S)-4-(4-fluorophenyl)-1-(1-methyl-1H-imidazol-4-ylsulfonyl)pyrrolidin-3-amine Example 322B (2.53 g, 7.03 mmol) was partitioned between ethyl acetate (25 mL) and saturated sodium bicarbonate (aq. 10 mL). The organic fraction was collected. The aqueous fraction was washed with ethyl acetate 3 times. The combined organic fractions were dried over sodium sulfate and concentrated to give the title compound. MS (ESI) m/z 325.3 (M+H)$^+$.

Example 380B 3-({{(3R,4S)-4-(4-fluorophenyl)-1-[(1-methyl-1H-imidazol-4-yl)sulfonyl]pyrrolidin-3-yl}amino)benzonitrile The title compound was prepared similarly to the procedure described in Example 337G substituting Example 380A for Example 337F and substituting 3-bromobenzonitrile for 1-bromo-3-(trifluoromethyl)benzene. MS (ESI) m/z 426.1 (M+H)$^+$.

Example 381

6-chloro-2-[Trans-1-[(1-methyl-1H-imidazol-4-yl)sulfonyl]-4-(pyridin-2-yl)pyrrolidin-3-yl]-2,3-dihydro-1H-isoindol-1-one

Example 381A

Trans-N-(2-bromo-4-chlorobenzyl)-1-((1-methyl-1H-imidazol-4-yl)sulfonyl)-4-(pyridin-2-yl)pyrrolidin-3-amine The title compound was prepared similarly to the procedure described in Example 354E substituting Example 307B for Example 354D and 2-bromo-4-chlorobenzaldehyde for 4-chlorobenzaldehyde.

Example 381B 6-chloro-2-[Trans-1-[(1-methyl-1H-imidazol-4-yl)sulfonyl]-4-(pyridin-2-yl)pyrrolidin-3-yl]-2,3-dihydro-1H-isoindol-1-one To a solution of Example 381A (500 mg, 0.98 mmol) in methanol (5 mL) in a 50 mL pressure bottle was added 1,1'-Bis(diphenylphosphino)ferrocene]dichloropalladium (II), (36 mg, 0.048 mmol) and triethylamine (0.27 mL, 2 mmol). The mixture was pressurized with Carbon Monoxide (60 psi), and stirred for 4 hours at 80° C. The insoluble materials were filtered off and the filtrate was purified by HPLC to provide the title compound. MS (ESI) m/z 458/460 (3:1) (M+H)$^+$.

Example 382

3-benzyl-4-(4-fluorophenyl)-1-[(1-methyl-1H-imidazol-4-yl)sulfonyl]pyrrolidin-3-ol

Example 382A 4-(4-fluorophenyl)-1-((1-methyl-1H-imidazol-4-yl)sulfonyl)pyrrolidin-3-one To a solution of Example 379C (0.43 g, 1.3 mmol) in dichloromethane (3 mL) was added Dess-Martin periodinane (0.67 g, 1.6 mmol). The mixture was stirred overnight and partitioned between ethyl acetate and sodium hydroxide (1M aq.). The organic fraction was collected, dried over MgSO$_4$, filtered, and concentrated to provide the title compound.

Example 382B 3-benzyl-4-(4-fluorophenyl)-1-[(1-methyl-1H-imidazol-4-yl)sulfonyl]pyrrolidin To a solution of Example 382A (50 mg) in tetrahydrofuran (0.5 mL) at −78° C. was added benzylmagnesiumbromide (1 M, 1 mL, 1 mmol). The mixture was allowed to stir at room temperature for 1 hour. The reaction mixture was partitioned between Ammonium chloride (aq) and ethyl acetate. The organic frantion was collected, concentrated, and purified by

Example 383

N-{trans-4-(4-fluorophenyl)-1-[(1-methyl-1H-imidazol-4-yl)sulfonyl]pyrrolidin-3-yl}-5-(trifluoromethyl)pyridazin-3-amine

Example 383A

Trans-6-chloro-N-(4-(4-fluorophenyl)-1-(1-methyl-1H-imidazol-4-ylsulfonyl)pyrrolidin-3-yl)-5-(trifluoromethyl)pyridazin-3-amine Example 3A (100 mg, 0.308 mmol), 3,6-dichloro-4-(trifluoromethyl)pyridazine (67 mg, 0.308 mmol), diisopropylethylamine (53.8 µl, 0.308 mmol), and ethanol (4 mL) were placed in a 2-5 mL microwave vial and irradiated for 1 hr at 175° C. The reaction contents were concentrated, reddissolved in 2 mL 50% dimethylsulfoxide/methanol and purified via HPLC to provide the title compound. MS (ESI) m/z 505 (M+H)$^+$

Example 383B

N-{(3R,4S)-4-(4-fluorophenyl)-1-[(1-methyl-1H-imidazol-4-yl)sulfonyl]pyrrolidin-3-yl}-5-(trifluoromethyl)pyridazin-3-amine The title compound was prepared similarly to the procedure described in Example 350B substituting 6-chloro-N-(4-(4-fluorophenyl)-1-(1-methyl-1H-imidazol-4-ylsulfonyl)pyrrolidin-5-yl)-4-(trifluoromethyl)pyridazin-3-amine for 6-chloro-N-(4-(4-fluorophenyl)-1-(1-methyl-1H-imidazol-4-ylsulfonyl)pyrrolidin-3-yl)-pyridazin-3-amine MS (ESI) m/z 471 (M+H)+

Example 384

N-{4-(4-fluorophenyl)-1-[(1-methyl-1H-imidazol-4-yl)sulfonyl]pyrrolidin-3-yl}-4-(trifluoromethyl)pyridazin-3-amine The title compound was prepared similarly to the procedure described in Example 350A-350B As both isomers are formed in 350A. MS (ESI) m/z 471 (M+H)+

Example 385

1-methyl-4-{[trans-3-phenyl-4-(phenylsulfonyl)pyrrolidin-1-yl]sulfonyl}-1H-imidazole

Example 385A

Trans-1-benzyl-3-phenyl-4-(phenylsulfonyl)pyrrolidine

The title compound was prepared similarly to the procedure described in Example 2A substituting phenyl trans-styryl sulfone for 4-methoxy-beta-nitrostyrene. MS (ESI) m/z 378.1 (M+H)$^+$.

Example 385B

Trans-3-phenyl-4-(phenylsulfonyl)pyrrolidine

The title compound was prepared similarly to the procedure described in Example 2D substituting Example 385A for 2C. MS (ESI) m/z 288.1 (M+H)$^+$.

Example 385C

1-Methyl-4-{trans-3-phenyl-4-(phenylsulfonyl)pyrrolidin-1-yl]sulfonyl}-1H-imidazole The title compound was prepared similarly to the procedure described in Example 2E substituting Example 385B for Example 2D. MS (ESI) m/z 432.1 (M+H)$^+$.

Example 386

(3R,4S)-4-(4-fluorophenyl)-1-[(1-methyl-1H-imidazol-4-yl)sulfonyl]-N-{[1-(trifluoromethyl)cyclopropyl]methyl}pyrrolidin-3-amine The title compound was prepared similarly to the procedure described in Example 290 substituting Example 375 for Example 242E. MS (ESI) m/z 447.1 (M+H)$^+$.

Example 387

(3S,4R)-N-(3-chloro-4-fluorophenyl)-4-(4-fluorophenyl)-1-[(1-methyl-1H-imidazol-4-yl)sulfonyl]pyrrolidin-3-amine The title compound was prepared similarly to the procedure described in Example 337G substituting Example 389A for Example 337F and 4-bromo-2-chloro-1-fluorobenzene for 1-bromo-3-(trifluoromethyl)benzene. MS (ESI) m/z 453.2 (M+H)$^+$.

Example 388

N-{Trans-3-methyl-1-[(1-methyl-1H-imidazol-4-yl)sulfonyl]-4-phenylpyrrolidin-3-yl}-4-(trifluoromethyl)pyridin-2-amine The title compound was prepared similarly to the procedure described in Example 337G substituting Example 354D for Example 337F and 2-bromo-4-(trifluoromethyl)pyridine for 1-bromo-3-(trifluoromethyl)benzene. MS (ESI) m/z 466 (M+H)$^+$.

Example 389

3-({(3S,4R)-4-(4-fluorophenyl)-1-[(1-methyl-1H-imidazol-4-yl)sulfonyl]pyrrolidin-3-yl}amino)benzonitrile

Example 389A (3S,4R)-4-(4-fluorophenyl)-1-(1-methyl-1H-imidazol-4-ylsulfonyl)pyrrolidin-3-amine The title compound was prepared similarly to the procedure described in Example 380A substituting Example 321B for Example 322B. MS (ESI) m/z 307.1 (M+H)$^+$.

Example 389B 3-({(3S,4R)-4-(4-fluorophenyl)-1-[(1-methyl-1H-imidazol-4-yl)sulfonyl]pyrrolidin-3-yl}amino)benzonitrile The title compound was prepared similarly to the procedure described in Example 337G substituting 389A for Example 337F and substituting 3-bromobenzonitrile for 1-bromo-3-(trifluoromethyl)benzene. MS (ESI) m/z 426.3 (M+H)⁺.

Example 390

N-{(3R,4S)-4-(4-fluorophenyl)-1-[(1-methyl-1H-imidazol-4-yl)sulfonyl]pyrrolidin-3-yl}-6-(trifluoromethyl)pyrimidin-4-amine The title compound was prepared similarly to the procedure described in Example 337G substituting Example 380A for Example 337F and substituting 4-bromo-6-(trifluoromethyl)pyrimidine for 1-bromo-3-(trifluoromethyl)benzene. MS (ESI) m/z 471.2 (M+H)⁺.

Example 391

(3R,4S)-4-(4-fluorophenyl)-1-[(1-methyl-1H-imidazol-4-yl)sulfonyl]-N-{[5-(trifluoromethyl)furan-2-yl]methyl}pyrrolidin-3-amine The title compound was prepared similarly to the procedure described in Example 354E substituting Example 380A for Example 354D and substituting 5-(trifluoromethyl)furan-2-carbaldehyde for 4-chlorobenzaldehyde. MS (ESI) m/z 473.1 (M+H)⁺.

Example 392

1,1,1-trifluoro-2-[3-({(3R,4S)-4-(4-fluorophenyl)-1-[(1-methyl-1H-imidazol-4-yl)sulfonyl]pyrrolidin-3-yl}amino)phenyl]propan-2-ol

Example 392A 2-(3-Bromophenyl)-1,1,1-trifluoropropan-2-ol

To 1-(3-bromophenyl)ethanone (364 mg, 1.83 mmol) and (trifluoromethyl)trimethylsilane (3 mL, 1.46 mmol, 0.5 M in tetrahydrofuran) was added tetrabutylammonium fluoride (1 M in tetrahydrofurane, 2.0 mL, 2.0 mmol) at 0° C. The reaction mixture stirred at room temperature for 3 hours. The reaction mixture was partitioned with saturated sodium carbonate (aq.) and dichloromethane. The organic fraction was collected. The aqueous fraction was washed with dichloromethane 3 times. The combined organic fractions were washed with saturated brine, dried over sodium sulfate, concentrated, and purified by flash chromatography (5:1 EtOAc/hexanes) to afford the title compound.

Example 392B 1,1,1-trifluoro-2-[3-({(3R,4S)-4-(4-fluorophenyl)-1-[(1-methyl-1H-imidazol-4-yl)sulfonyl]pyrrolidin-3-yl}amino)phenyl]propan-2-ol The title compound was prepared similarly to the procedure described in Example 337G substituting Example 380A for Example 337F and susbstituting Example 392A for 1-bromo-3-(trifluoromethyl)benzene. MS (ESI) m/z 513.3 (M+H)⁺.

Example 393

(3R,4S)-N-[(5-chlorothiophen-2-yl)methyl]-4-(4-fluorophenyl)-1-[(1-methyl-1H-imidazol-4-yl)sulfonyl]pyrrolidin-3-amine The title compound was prepared similarly to the procedure described in Example 354E substituting Example 380A for Example 354D and substituting 5-chlorothiophene-2-carbaldehyde for 4-chlorobenzaldehyde and. MS (ESI) m/z 455.3 (M+H)⁺.

Example 394

(3R,4S)-N-[2-chloro-4-(trifluoromethyl)benzyl]-1-[(1-methyl-1H-imidazol-4-yl)sulfonyl]-4-phenylpyrrolidin-3-amine The title compound was prepared similarly to the procedure described in Example 354E substituting Example 380A for Example 354D and substituting 2-chloro-4-(trifluoromethyl)benzaldehyde for 4-chlorobenzaldehyde. MS (ESI) m/z 455.3 (M+H)⁺.

Example 395

(3S,4R)-N-[2-chloro-4-(trifluoromethyl)benzyl]-1-[(1-methyl-1H-imidazol-4-yl)sulfonyl]-4-phenylpyrrolidin-3-amine

Example 395A (3S,4R)-1-(1-methyl-1H-imidazol-4-ylsulfonyl)-4-phenylpyrrolidin-3-amine hydrochloride The title compound was prepared similarly to the conditions described in Example 2A-2F substituting (E)-4-(2-nitrovinyl)benzene for (E)-1-methoxy-4-(2-nitrovinyl)benzene and separating the enantiomers produced from the procedure of Example 2C via Chiral SFC separation (SFC 200 Column: Whelk-O1, 50×250 mm, 5 µm Column Temperature: 35° C. Mobile Phase: CO₂/IPA/DEA=70/30/0.1 Flow rate: 70 g/min Back Pressure: 100 Bar Wavelength: 214 nm Cycle time: 5.0 min Injection: 4.0 mL Sample solution: 41000 mg in 250 mL methanol) RT=6.00 minutes.

Example 395B (3S,4R)-1-(1-methyl-1H-imidazol-4-ylsulfonyl)-4-phenylpyrrolidin-3-amine The title compound was prepared similarly to the procedure described in Example 380A substituting Example 395A for Example 322B. MS (ESI) m/z 307.1 (M+H)⁺.

Example 395C (3S,4R)-N-[2-chloro-4-(trifluoromethyl)benzyl]-1-[(1-methyl-1H-imidazol-4-yl)sulfonyl]-4-phenylpyrrolidin-3-amine The title compound was prepared similarly to the procedure described in Example 354E substituting Example 395B for Example 354D and substituting 2-chloro-4-(trifluoromethyl)benzaldehyde for 4-chlorobenzaldehyde. MS (ESI) m/z 499.2 (M+H)+.

Example 396

N-{(3R,4S)-1-[(1-methyl-1H-imidazol-4-yl)sulfonyl]-4-phenylpyrrolidin-3-yl}-4-(trifluoromethyl)pyridin-2-amine Example 396A N-{(3R,4S)-1-[(1-methyl-1H-imidazol-4-yl)sulfonyl]-4-phenylpyrrolidin-3-yl}-4-(trifluoromethyl)pyridin-2-amine The title compound was prepared similarly to the procedure described in Example 380A substituting Example 574A for Example 322B. MS (ESI) m/z 307.1 (M+H)+.

Example 396B

N-{(3R,4S)-1-[(1-methyl-1H-imidazol-4-yl)sulfonyl]-4-phenylpyrrolidin-3-yl}-4-(trifluoromethyl)pyridin-2-amine The title compound was prepared similarly to the procedure described in Example 337G substituting Example 396A for Example 337F and 2-bromo-4-(trifluoromethyl)pyridine for 1-bromo-3-(trifluoromethyl)benzene. MS (ESI) m/z 452.2 (M+H)+.

Example 397

(3R,4S)-1-[(1-methyl-1H-imidazol-4-yl)sulfonyl]-4-phenyl-N-[3-(trifluoromethyl)phenyl]pyrrolidin-3-amine The title compound was prepared similarly to the procedure described in Example 337G substituting Example 396A for Example 337F. MS (ESI) m/z 452.2 (M+H)+.

Example 398

(3R,4S)-1-[(1-methyl-1H-imidazol-4-yl)sulfonyl]-4-phenyl-N-[4-(trifluoromethyl)benzyl]pyrrolidin-3-amine The title compound was prepared similarly to the procedure described in Example 354E substituting 4-(trifluoromethyl)benzaldehyde for 4-chlorobenzaldehyde and Example 396A Example 354D. MS (ESI) m/z 465.1 (M+H)+.

Example 399

1,1,1-trifluoro-2-[3-({(3R,4S)-1-[(1-methyl-1H-imidazol-4-yl)sulfonyl]-4-phenylpyrrolidin-3-yl}amino)phenyl]propan-2-ol The title compound was prepared similarly to the procedure described in Example 337G substituting Example 396A for Example 337F and Example 392A for 1-bromo-3-(trifluoromethyl)benzene. MS (ESI) m/z 495.1 (M+H)+.

Example 400

Trans-4-(benzyloxy)-N-(3-chlorophenyl)-1-[(1-methyl-1H-imidazol-4-yl)sulfonyl]pyrrolidin-3-amine To a solution of Example 373C (71 mg, 0.2 mmol) in tetrahydrofuran (0.5 mL) was added potassium tert-butoxide (22 mg, 0.2 mmol) and benzyl bromide (40 mg, 0.23 mmol). The mixture was allowed to stir at room temperature for 2 hours. The reaction mixture was then partitioned with water and ethyl acetate. The organic fractin was collected, concentrate, and purified by HPLC to provide the title compound. MS (ESI) m/z 447/449 (3:1) (M+H)+.

Example 401

Trans-1-[(1-methyl-1H-imidazol-4-yl)sulfonyl]-4-phenyl-3-{[4-(trifluoromethyl)benzyl]amino}pyrrolidin-3-yl]methanol Example 401A (E)-2-nitro-3-phenylprop-2-en-1-ol To (E)-(2-nitrovinyl)benzene (1.5 g, 10 mmol) in tetrahydrofuran (10 mL) was added formaldehyde (37%, aq., 10 mL), imidazole (0.68 g, 10 mmol), and antranilic acid (14 mg, 0.1 mmol). The mixture was allowed to stir for 16 hours. The reaction mixture was partitioned between ethyl acetate and hydrochloric acid (1N). The organic fraction was collected, dried over $MgSO_4$, filtered, and concentrated to provide the title compound.

Example 401B (E)-((2-nitro-3-phenylallyl)oxy)methyl acetate

To a solution of Example 401A (900 mg, 5 mmol) in dichloromethane (5 mL) was added triethylamine (600 mg, 6 mmol) and acetyl chloride (400 mg, 5.1 mmol) at 0° C. The mixture was allowed to stir for 1 hour. Water was added and the solution partitioned. The organic fraction was collected, concentrated, and purified by flash chromatography (15% ethyl acetate/hexanes) to afford the title compound.

Example 401C ((1-benzyl-3-nitro-4-phenylpyrrolidin-3-yl)methoxy)methyl acetate

The title compound was prepared similarly to the procedure described in Example 2A substituting Example 401B for 4-methoxy-beta-nitrostyrene. Example 401D 7-benzyl-9-phenyl-3-oxa-1,7-diazaspiro[4.4]nonane The title compound was prepared similarly to the procedure described in Example 2B substituting Example 401C for Example 2A.

Example 401E tert-butyl 7-benzyl-9-phenyl-3-oxa-1,7-diazaspiro[4.4]nonane-1-carboxylate The title compound was prepared similarly to the procedure described in Example 337C substituting Example 401D for Example 337B.

Example 401F tert-butyl 9-phenyl-3-oxa-1,7-diazaspiro[4.4]
nonane-1-carboxylate The title compound was prepared similarly to the procedure described in Example 2D substituting Example 401E for 2C.

Example 401G tert-butyl 7-((1-methyl-1H-imidazol-4-yl)sulfonyl)-
9-phenyl-3-oxa-1,7-diazaspiro[4.4]nonane-1-carboxylate The title compound was prepared similarly to the procedure described in Example 373C substituting Example 401F for Example 373B.

Example 401H 7-((1-methyl-1H-imidazol-4-yl)sulfonyl)-9-phenyl-
3-oxa-1,7-diazaspiro[4.4]nonane The title compound was prepared as the hydrochloride salt similarly to the procedure described in Example 373B substituting Example 401G for Example 373A

Example 401I

[Trans-1-[(1-methyl-1H-imidazol-4-yl)sulfonyl]-4-
phenyl-3-{[4-(trifluoromethyl)benzyl]
amino}pyrrolidin-3-yl]methanol The title compound was prepared similarly to the procedure described in Example 354E substituting 4-(trifluoromethyl)benzaldehyde for 4-chlorobenzaldehyde and Example 401H for Example 354D MS (ESI) m/z 495 (M+H)+.

Example 402

Trans-N-(3-chlorophenyl)-1-[(1-methyl-1H-imida-
zol-4-yl)sulfonyl]-4-(prop-2-en-1-yloxy)pyrrolidin-
3-amine The title compound was prepared similarly to the procedure described in Example 400 substituting allyl bromide for benzyl bromide. MS (ESI) m/z 397/399 (3:1) (M+H)+.

Example 403

Trans-N-(3-chlorophenyl)-1-[(1-methyl-1H-imida-
zol-4-yl)sulfonyl]-4-[(2-methylprop-2-en-1-yl)oxy]
pyrrolidin-3-amine The title compound was prepared similarly to the procedure described in Example 400 substituting 3-bromo-2-methylprop-1-ene for benzyl bromide. MS (ESI) m/z 411/413 (3:1) (M+H)+.

Example 404

3-{Trans-1-[(1-methyl-1H-imidazol-4-yl)sulfonyl]-
4-phenylpyrrolidin-3-yl}-6-(trifluoromethyl)-3,4-
dihydroquinazolin-2(1H)-one

Example 404A

N-(Trans-1-((1-methyl-1H-imidazol-4-yl)sulfonyl)-
4-phenylpyrrolidin-3-yl)-2-nitro-5-(trifluoromethyl)
benzamide To Example 14A (140 mg, 0.4 mmol) in dimethylformamide (0.5 mL) was added 2-nitro-5-(trifluoromethyl)benzoic acid (96 mg, 0.4 mmol), triethylamine (100 mg, 1 mmol), and 0-(Benzotriazol-1-yl)-NANW-tetramethyluronium tetrafluoroborate (160 mg, 0.5 mmol). The mixture was allowed to stir overnight. Water was added and the precipitates were collected to provide the title compound.

Example 404B

Trans-N-(2-amino-5-(trifluoromethyl)benzyl)-1-((1-
methyl-1H-imidazol-4-yl)sulfonyl)-4-phenylpyrroli-
din-3-amine To a solution of Example 404A (110 mg, 0.21 mmol) in tetrahydrofuran (1 mL) was added borane dimethyl sulfide complex (2N, 1.4 mL, 2.8 mmol). The mixture was stirred at 60° C. for 2 days and quenched with hydrochloric acid (1 M aq.). The mixture was allowed to stir for 30 minutes. Sodium hydroxide (1 M, aq.) was added to adjust the pH value to 10. The mixture was partitioned with ethyl acetate. The organic fraction was collected and dried over potassium carbonate, filtered, and concentrated to provide the title compound.

Example 404C

3-{Trans-1-[(1-methyl-1H-imidazol-4-yl)sulfonyl]-
4-phenylpyrrolidin-3-yl}-6-(trifluoromethyl)-3,4-
dihydroquinazolin-2(1H)-one To a solution of Example 404B (130 mg, 0.27 mmol) in dichloromethane (10 mL) was added triethylamine (100 mg, 1 mmol) and triphosegene (28 mg, 0.094 mmol). The mixture was allowed to stir for 1 hour, and then methanol was added. The mixture was concentrated and purified by HPLC to provide the title compound. MS (ESI) m/z 506 (M+H)

Example 405

4-fluoro-N-(3R,4S)-1-[(1-methyl-1H-imidazol-4-yl)
sulfonyl]-4-phenylpyrrolidin-3-yl pyridin-2-amine The title compound was prepared similarly to the procedure described in Example 337G substituting Example 396A for Example 337F and 2-bromo-4-fluoropyridine for 1-bromo-3-(trifluoromethyl)benzene. MS (ESI) m/z 402.1 (M+H)+.

Example 406

N-{(3R,4S)-1-[(1-methyl-1H-imidazol-4-yl)sulfonyl]-4-
phenylpyrrolidin-3-yl}-7H-pyrrolo[2,3-d]pyrimidin-4-
amine The title compound was prepared similarly to the procedure described in Example 337G substituting Example 396A

Example 407

Trans-7-[(1-methyl-1H-imidazol-4-yl)sulfonyl]-9-phenyl-1-[4-(trifluoromethyl)benzyl]-3-oxa-1,7-diazaspiro[4.4]nonan-2-one The title compound was prepared similarly to the procedure described in Example 404C substituting Example 401I for Example 404B. MS (ESI) m/z 521 (M+H)+.

Example 408

3,5-difluoro-N-{(3R,4S)-1-[(1-methyl-1H-imidazol-4-yl)sulfonyl]-4-phenylpyrrolidin-3-yl}-4-(trifluoromethyl)pyridin-2-amine To Example 396A (100 mg, 0.33 mmol) in dimethylsulfoxide (0.5 mL) was added potassium tert-butoxide (50 mg, 0.45 mmol) and 2,3,5-trifluoro-4-(trifluoromethyl)pyridine (80 mg, 0.4 mmol). The mixture was stirred at 80° C. for 2 hours, and then partitioned between water and ethyl acetate. The organic fraction was collected, dried over potassium carbonate, filtered, concentrated, and purified by reversed phase HPLC to provide the title compound. MS (ESI) m/z 488 (M+H)+.

Example 409

(3R,4S)-1-[(1-methyl-1H-imidazol-4-yl)sulfonyl]-4-phenyl-N-{[5-(trifluoromethyl)pyridin-2-yl]methyl}pyrrolidin-3-amine The title compound was prepared similarly to the procedure described in Example 354E substituting Example 574A for Example 354D and substituting 5-(trifluoromethyl)picolinaldehyde for 4-chlorobenzaldehyde. MS (ESI) m/z 466.1 (M+H)+.

Example 410

5-cyclopropyl-N-{(3R,4S)-1-[(1-methyl-1H-imidazol-4-yl)sulfonyl]-4-phenylpyrrolidin-3-yl}pyrazin-2-amine The title compound was prepared similarly to the procedure described in Example 337G substituting Example 396A for Example 337F and 2-bromo-5-cyclopropylpyrazine for 1-bromo-3-(trifluoromethyl)benzene. MS (ESI) m/z 425.3 (M+H)+.

Example 411

5-cyclobutyl-N-{(3R,4S)-1-[(1-methyl-1H-imidazol-4-yl)sulfonyl]-4-phenylpyrrolidin-3-yl}pyrazin-2-amine The title compound was prepared similarly to the procedure described in Example 337G substituting Example 396A for Example 337F and 2-bromo-5-cyclobutylpyrazine for 1-bromo-3-(trifluoromethyl)benzene. MS (ESI) m/z 439.3 (M+H)+.

for Example 337F and substituting 4-bromo-7H-pyrrolo[2,3-D]pyrimidine for 1-bromo-3-(trifluoromethyl)benzene. MS (ESI) m/z 424.2 (M+H)+.

Example 412

Trans-N-(3-chlorophenyl)-1-[(1-methyl-1H-imidazol-4-yl)sulfonyl]-4-(2-methylpropoxy)pyrrolidin-3-amine To Example 403 (17 mg, 0.041 mmol) in tetrahydrofuran (4 mL) was added 5% Pt/C (20 mg, 0.041 mmol). The mixture was stirred for 45 minutes under 30 psi of hydrogen at room temperature. The mixture was filtered through a nylon membrane and purified by reversed phase HPLC to provide the title compound. MS (ESI) m/z 413/415 (3:1) (M+H)+.

Example 413

N-{(3R,4S)-1-[(1-methyl-1H-imidazol-4-yl)sulfonyl]-4-phenylpyrrolidin-3-yl}-5-(pyrrolidin-1-yl)pyrazin-2-amine The title compound was prepared similarly to the procedure described in Example 337G substituting Example 396A for Example 337F and substituting 2-bromo-5-(pyrrolidin-1-yl)pyrazine for 1-bromo-3-(trifluoromethyl)benzene. MS (ESI) m/z 454.3 (M+H)+.

Example 414

N-{(3R,4S)-1-[(1-methyl-1H-imidazol-4-yl)sulfonyl]-4-phenylpyrrolidin-3-yl}-5-(trifluoromethyl)pyrazine-2-carboxamide The title compound was prepared similarly to the procedure described in Example 242E substituting Example 574A for aniline and 5-(trifluoromethyl)pyrazine-2-carboxylic acid for Example 242D. MS (ESI) m/z 481.2 (M+H)+.

Example 415

5-chloro-N-{(3R,4S)-1-[(1-methyl-1H-imidazol-4-yl)sulfonyl]-4-phenylpyrrolidin-3-yl}pyrazine-2-carboxamide The title compound was prepared similarly to the procedure described in Example 242E substituting Example 574A for aniline and 5-chloropyrazine-2-carboxylic acid for Example 242D. MS (ESI) m/z 447.1 (M+H)+.

Example 416

(3R,4S)-N-(4-chlorobenzyl)-1-[(1-methyl-1H-imidazol-4-yl)sulfonyl]-4-phenylpyrrolidin-3-amine The title compound was prepared similarly to the procedure described in Example 354E substituting Example 574A for Example 354D. MS (ESI) m/z 431.1 (M+H)+.

Example 417

(3R,4S)-N-(3-chloro-4-fluorophenyl)-1-[(1-methyl-1H-imidazol-4-yl)sulfonyl]-4-phenylpyrrolidin-3-amine The title compound was prepared similarly to the procedure described in Example 337G substituting Example 396A for Example 337F and substituting 4-bromo-2-chloro-1-fluorobenzene for 1-bromo-3-(trifluoromethyl)benzene. MS (ESI) m/z 435.1 (M+H)+.

Example 418

(3R,4S)-N-(3,4-difluorophenyl)-4-(4-fluorophenyl)-1-[(1-methyl-1H-imidazol-4-yl)sulfonyl]pyrrolidin-3-amine The title compound was prepared similarly to the procedure described in Example 337G substituting Example 380A for Example 337F and substituting 1-bromo-3,4-difluorobenzene for 1-bromo-3-(trifluoromethyl)benzene. MS (ESI) m/z 437.1 (M+H)+.

Example 419

6-chloro-N-{(3R,4S)-1-[(1-methyl-1H-imidazol-4-yl)sulfonyl]-4-phenylpyrrolidin-3-yl}pyridazine-3-carboxamide The title compound was prepared similarly to the procedure described in Example 242E substituting Example 574A for aniline and substituting 6-chloropyridazine-3-carboxylic acid for Example 242D. MS (ESI) m/z 447.2 (M+H)+.

Example 420

N-{(3R,4S)-1-[(1-methyl-1H-imidazol-4-yl)sulfonyl]-4-phenylpyrrolidin-3-yl}-2-(morpholin-4-yl)pyrimidin-4-amine The title compound was prepared similarly to the procedure described in Example 337G substituting Example 396A for Example 337F and substituting 4-(4-bromopyrimidin-2-yl)morpholine for 1-bromo-3-(trifluoromethyl)benzene. MS (ESI) m/z 470.2 (M+H)+.

Example 421

4-({(3R,4S)-1-[(1-methyl-1H-imidazol-4-yl)sulfonyl]-4-phenylpyrrolidin-3-yl}amino)-2,3-dihydro-1H-isoindol-1-one The title compound was prepared similarly to the procedure described in Example 337G substituting Example 396A for Example 337F and substituting 4-(4-bromopyrimidin-2-yl)morpholine for 1-bromo-3-(trifluoromethyl)benzene. MS (ESI) m/z 470.2 (M+H)+.

Example 422

(3R,4S)-1-[(1-methyl-1H-imidazol-4-yl)sulfonyl]-N-[3-(methylsulfonyl)phenyl]-4-phenylpyrrolidin-3-amine The title compound was prepared similarly to the procedure described in Example 337G substituting Example 396A for Example 337F and substituting 1-bromo-3-(methylsulfonyl)benzene for 1-bromo-3-(trifluoromethyl)benzene. MS (ESI) m/z 461.2 (M+H)+.

Example 423

(3R,4S)-1-[(1-methyl-1H-imidazol-4-yl)sulfonyl]-4-phenyl-N-{[5-(trifluoromethyl)piperazin-2-yl]methyl}pyrrolidin-3-amine The title compound was prepared using the same procedures as described in Example 290 substituting Example 414 for Example 242E. MS (ESI) m/z 473.2 (M+H)+.

Example 424

5-fluoro-N-{(3R,4S)-1-[(1-methyl-1H-imidazol-4-yl)sulfonyl]-4-phenylpyrrolidin-3-yl}pyrimidin-2-amine The title compound was prepared similarly to the procedure described in Example 57 substituting 2-bromo-5-fluoropyrimidine for 1-bromo-2-methylbenzene MS (ESI) m/z 403.2 (M+H)+.

Example 425

Trans-4-cyclohexyl-1-[(1-methyl-1H-imidazol-4-yl)sulfonyl]-N-[3-(trifluoromethoxy)phenyl]pyrrolidin-3-amine Example 425A (E)-(2-nitrovinyl)cyclohexane A solution of cyclohexane carboxaldehyde (5.0 g, 44.6 mmol) and nitromethane (4.1 g, 66.9 mmol) in tetrahydrofuran (25 ml) and tert butanol (25 ml) was stirred and chilled in an ice bath under nitrogen. Potassium-t-butoxide (1.0 g, 9.0 mmol) was added as a solid in one portion and the reaction was allowed to stir and warm to room temperature over one hour. The reaction was stirred for an additional four hours and was then partitioned with a saturated solution of ammonium chloride. The organic fraction was collected, and the aqueous portion was washed with dichloromethane. The combined organic fractions were washed with brine, dried over sodium sulfate, filtered, and concentrated. The resulting liquid was dissolved in dichloromethane (100 ml) and chilled in an ice bath. Trifluoroacetic anhydride (9.8 g, 46.7 mmol) was added in one portion, and the solution stirred for five minutes. Triethylamine (9.5 g, 93.5 mmol) was added drop-wise. Stirring was continued for one hour, and then the reaction was allowed to warm to room temperature and stir for two hours. The reaction was partitioned with a solution of saturated ammonium chloride. The organic fraction was collected. The aqueous portion was washed with dichloromethane. The organic fractions were combined and washed with water and brine, and dried over sodium sulfate. The mixture was filtered, concentrated and chromatograhed on a silica gel flah column eluting with 98:2 heptane:ethyl acetate to afford 5.1 g of a slightly tinted liquid. MS (DCI) m/z 173.1 (M+NH$_4$)+

Example 425B trans-4-cyclohexyl-1-(1-methyl-1H-imidazol-4-yl-sulfonyl)pyrrolidin-3-amine The title compound was prepared as an HCl salt similarly to the procedures described in Examples 2A-2F substituting Example 425A for trans-4-methoxy-beta-nitrostyrene in Example 2A. MS (DCI) m/z 313.1 (M+H)+

Example 425C trans-4-cyclohexyl-1-[(1-methyl-1H-imidazol-4-yl)sulfonyl]-N-[3-(trifluoromethoxy)phenyl]pyrrolidin-3-amine The title compound was prepared similarly to the procedures described in Example 57 substituting Example 425B for Example 14A and substituting 1-bromo-3-(trifluoromethoxy)benzene for 1-bromo-2-methylbenzene. MS (ESI) m/z 473.2 (M+H)+.

Example 426

(3R,4S)-1-[(1-methyl-1H-imidazol-4-yl)sulfonyl]-4-phenyl-N-(4,4,4-trifluorobutyl)pyrrolidin-3-amine The title compound was prepared similarly to the procedure described in Example 354E substituting 4,4,4-trifluorobutanal for 4-chlorobenzaldehyde and substituting Example 574A for Example 354D. MS (ESI) m/z 417.0 (M+H)+

Example 427

(3R,4S)-N-(2-cyclopentylethyl)-1-[(1-methyl-1H-imidazol-4-yl)sulfonyl]-4-phenylpyrrolidin-3-amine The title compound was prepared similarly to the procedure described in Example 354E substituting 2-cyclopentylacetaldehyde for 4-chlorobenzaldehyde and substituting Example 574A for Example 354D. MS (ESI) m/z 403.0 (M+H)+

Example 428

(3R,4S)-1-[(1-methyl-1H-imidazol-4-yl)sulfonyl]-4-phenyl-N-[(5-propyl-furan-2-yl)methyl]pyrrolidin-3-amine The title compound was prepared similarly to the procedure described in Example 354E substituting 5-propyl-furan-2-carbaldehyde for 4-chlorobenzaldehyde and substituting Example 574A for Example 354D. MS (ESI) m/z 429.0 (M+H)+.

Example 429

(3R,4S)-1-[(1-methyl-1H-imidazol-4-yl)sulfonyl]-N-[(4-methyltetrahydro-2H-pyran-4-yl)methyl]-4-phenylpyrrolidin-3-amine The title compound was prepared similarly to the procedure described in Example 354E substituting 4-methyltetrahydro-2H-pyran-4-carbaldehyde for 4-chlorobenzaldehyde and substituting Example 574A for Example 354D. MS (ESI) m/z 419.0 (M+H)+.

Example 430

(3R,4S)-1-[(1-methyl-1H-imidazol-4-yl)sulfonyl]-4-phenyl-N-[(4-phenyl-1,3-thiazol-5-yl)methyl]pyrrolidin-3-amine The title compound was prepared similarly to the procedure described in Example 354E substituting 4-phenylthiazole-5-carbaldehyde for 4-chlorobenzaldehyde and substituting Example 574A for Example 354D. MS (ESI) m/z 480.0 (M+H)+

Example 431

(3R,4S)-1-[(1-methyl-1H-imidazol-4-yl)sulfonyl]-N-[(5-methyl-1,3-thiazol-2-yl)methyl]-4-phenylpyrrolidin-3-amine The title compound was prepared similarly to the procedure described in Example 354E substituting 5-methylthiazole-2-carbaldehyde for 4-chlorobenzaldehyde and substituting Example 574A for Example 354D. MS (ESI) m/z 418.0 (M+H)+

Example 432

(3R,4S)-N-[(3,5-dichloropyridin-4-yl)methyl]-1-[(1-methyl-1H-imidazol-4-yl)sulfonyl]-4-phenylpyrrolidin-3-amine The title compound was prepared similarly to the procedure described in Example 354E substituting 3,5-dichloroisonicotinaldehyde for 4-chlorobenzaldehyde and substituting Example 574A for Example 354D. MS (ESI) m/z 467.0 (M+H)+

Example 433

(3R,4S)-N-(2-ethylhexyl)-1-[(1-methyl-1H-imidazol-4-yl)sulfonyl]-4-phenylpyrrolidin-3-amine The title compound was prepared similarly to the procedure described in Example 354E substituting 2-ethylhexanal for 4-chlorobenzaldehyde and substituting Example 574A for Example 354D. MS (ESI) m/z 419.0 (M+H)+

Example 434

(3R,4S)-1-[(1-methyl-1H-imidazol-4-yl)sulfonyl]-N-[(4-methyl-1,3-thiazol-5-yl)methyl]-4-phenylpyrrolidin-3-amine The title compound was prepared similarly to the procedure described in Example 354E substituting 4-methylthiazole-5-carbaldehyde for 4-chlorobenzaldehyde and substituting Example 574A for Example 354D. MS (ESI) m/z 418.0 (M+H)+

Example 435

(3R,4S)-N-[(2,4-dichloro-1,3-thiazol-5-yl)methyl]-1-[(1-methyl-1H-imidazol-4-yl)sulfonyl]-4-phenylpyrrolidin-3-amine The title compound was prepared similarly to the procedure described in Example 354E substituting 2,4-dichlorothiazole-5-carbaldehyde for 4-chlorobenzaldehyde and substituting Example 574A for Example 354D. MS (ESI) m/z 473.0 (M+H)+

Example 436

(3R,4S)-N-(2,2-dimethylpropyl)-1-[(1-methyl-1H-imidazol-4-yl)sulfonyl]-4-phenylpyrrolidin-3-amine The title compound was prepared similarly to the procedure described in Example 354E substituting pivalaldehyde

Example 437

(3R,4S)-N-[(5-methyl-1-benzothiophen-2-yl)methyl]-1-[(1-methyl-1H-imidazol-4-yl)sulfonyl]-4-phenylpyrrolidin-3-amine The title compound was prepared similarly to the procedure described in Example 354E substituting 5-methylbenzo[b]thiophene-2-carbaldehyde for 4-chlorobenzaldehyde and substituting Example 574A for Example 354D. MS (ESI) m/z 467.0 (M+H)$^+$.

Example 438

(3R,4S)-N-[(2-bromo-1,3-thiazol-5-yl)methyl]-1-[(1-methyl-1H-imidazol-4-yl)sulfonyl]-4-phenylpyrrolidin-3-amine The title compound was prepared similarly to the procedure described in Example 354E substituting 2-bromothiazole-5-carbaldehyde for 4-chlorobenzaldehyde and substituting Example 574A for Example 354D. MS (ESI) m/z 483.0 (M+H)$^+$.

Example 439

(3R,4S)-1-[(1-methyl-1H-imidazol-4-yl)sulfonyl]-N-(2-methylpropyl)-4-phenylpyrrolidin-3-amine The title compound was prepared similarly to the procedure described in Example 354E substituting isobutyraldehyde for 4-chlorobenzaldehyde and substituting Example 574A for Example 354D. MS (ESI) m/z 363.0 (M+H)$^+$.

Example 440

(3R,4S)-N-[(3-chloro-1-benzothiophen-2-yl)methyl]-1-[(1-methyl-1H-imidazol-4-yl)sulfonyl]-4-phenylpyrrolidin-3-amine The title compound was prepared similarly to the procedure described in Example 354E substituting 3-chlorobenzo[b]thiophene-2-carbaldehyde for 4-chlorobenzaldehyde and substituting Example 574A for Example 354D. MS (ESI) m/z 487.0 (M+H)$^+$.

Example 441

(3R,4S)-N-[(2,4-dimethyl-1,3-thiazol-5-yl)methyl]-1-[(1-methyl-1H-imidazol-4-yl)sulfonyl]-4-phenylpyrrolidin-3-amine The title compound was prepared similarly to the procedure described in Example 354E substituting 2,4-dimethylthiazole-5-carbaldehyde for 4-chlorobenzaldehyde and substituting Example 574A for Example 354D. MS (ESI) m/z 432.0 (M+H)$^+$.

Example 442

(3R,4S)-1-[(1-methyl-1H-imidazol-4-yl)sulfonyl]-4-phenyl-N-(thieno[2,3-b]pyridin-2-ylmethyl)pyrrolidin-3-amine The title compound was prepared similarly to the procedure described in Example 354E substituting thieno[2,3-b]pyridine-2-carbaldehyde for 4-chlorobenzaldehyde and Example 574A for Example 354D. MS (ESI) m/z 454.0 (M+H)$^+$.

Example 443

(3R,4S)-N-[(2-methyl-1-benzofuran-3-yl)methyl]-1-[(1-methyl-1H-imidazol-4-yl)sulfonyl]-4-phenylpyrrolidin-3-amine The title compound was prepared similarly to the procedure described in Example 354E substituting 2-methylbenzofuran-3-carbaldehyde for 4-chlorobenzaldehyde and substituting Example 574A for Example 354D. MS (ESI) m/z 451.0 (M+H)$^+$.

Example 444

(3R,4S)-N-[(6-chloro-2-methylimidazo[1,2-a]pyridin-3-yl)methyl]-1-[(1-methyl-1H-imidazol-4-yl)sulfonyl]-4-phenylpyrrolidin-3-amine The title compound was prepared similarly to the procedure described in Example 354E substituting 6-chloro-2-methylimidazo[1,2-a]pyridine-3-carbaldehyde for 4-chlorobenzaldehyde and substituting Example 574A for Example 354D. MS (ESI) m/z 485.0 (M+H)$^+$.

Example 445

(3R,4S)-N-{[5-(4-fluorophenyl)pyridin-3-yl]methyl}-1-[(1-methyl-1H-imidazol-4-yl)sulfonyl]-4-phenylpyrrolidin-3-amine The title compound was prepared similarly to the procedure described in Example 354E substituting 5-(4-fluorophenyl)nicotinaldehyde for 4-chlorobenzaldehyde and substituting Example 574A for Example 354D. MS (ESI) m/z 492.0 (M+H)$^+$.

Example 446

(3R,4S)-1-[(1-methyl-1H-imidazol-4-yl)sulfonyl]-N-(2-methylpentyl)-4-phenylpyrrolidin-3-amine The title compound was prepared similarly to the procedure described in Example 354E substituting 2-methylpentanal for 4-chlorobenzaldehyde and substituting Example 574A for Example 354D. MS (ESI) m/z 391.0 (M+H)$^+$

Example 447

(3R,4S)-1-[(1-methyl-1H-imidazol-4-yl)sulfonyl]-4-phenyl-N-(tetrahydrofuran-3-ylmethyl)pyrrolidin-3-amine The title compound was prepared similarly to the procedure described in Example 354E substituting tetrahydrofuran-3-carbaldehyde for 4-chlorobenzaldehyde and substituting Example 574A for Example 354D. MS (ESI) m/z 391.0 (M+H)$^+$

Example 448

(3R,4S)-1-[(1-methyl-1H-imidazol-4-yl)sulfonyl]-N-pentyl-4-phenylpyrrolidin-3-amine The title compound was prepared similarly to the procedure described in Example 354E substituting pentanal for

Example 449

(3R,4S)-N-(2-ethylbutyl)-1-[(1-methyl-1H-imidazol-4-yl)sulfonyl]-4-phenylpyrrolidin-3-amine The title compound was prepared similarly to the procedure described in Example 354E substituting 2-ethylbutanal for 4-chlorobenzaldehyde and substituting Example 574A for Example 354D. MS (ESI) m/z 391.0 (M+H)$^+$

Example 450

(3R,4S)-N-(2,2-dimethylbutyl)-1-[(1-methyl-1H-imidazol-4-yl)sulfonyl]-4-phenylpyrrolidin-3-amine The title compound was prepared similarly to the procedure described in Example 354E substituting 2,2-dimethylbutanal for 4-chlorobenzaldehyde and substituting Example 574A for Example 354D MS (ESI) m/z 391.0 (M+H)$^+$.

Example 451

(3R,4S)-1-[(1-methyl-1H-imidazol-4-yl)sulfonyl]-N-[(2-methyl-1,3-thiazol-5-yl)methyl]-4-phenylpyrrolidin-3-amine The title compound was prepared similarly to the procedure described in Example 354E substituting 2-methylthiazole-5-carbaldehyde for 4-chlorobenzaldehyde and substituting Example 574A for Example 354D. MS (ESI) m/z 418.0 (M+H)$^+$.

Example 452

(3R,4S)-1-[(1-methyl-1H-imidazol-4-yl)sulfonyl]-4-phenyl-N-[2-(tetrahydro-2H-pyran-4-yl)ethyl]pyrrolidin-3-amine The title compound was prepared similarly to the procedure described in Example 354E substituting 2-(tetrahydro-2H-pyran-4-yl)acetaldehyde for 4-chlorobenzaldehyde and substituting Example 574A for Example 354D. MS (ESI) m/z 419.0 (M+H)$^+$.

Example 453

(3R,4S)-N-(1,3-benzothiazol-2-ylmethyl)-1-[(1-methyl-1H-imidazol-4-yl)sulfonyl]-4-phenylpyrrolidin-3-amine The title compound was prepared similarly to the procedure described in Example 354E substituting benzo[d]thiazole-2-carbaldehyde for 4-chlorobenzaldehyde and substituting Example 574A for Example 354D. MS (ESI) m/z 454.0 (M+H)$^+$.

Example 454

(3R,4S)-1-[(1-methyl-1H-imidazol-4-yl)sulfonyl]-N-[(4-methyl-1,3-thiazol-2-yl)methyl]-4-phenylpyrrolidin-3-amine The title compound was prepared similarly to the procedure described in Example 354E substituting 4-methylthiazole-2-carbaldehyde for 4-chlorobenzaldehyde and substituting Example 574A for Example 354D. MS (ESI) m/z 418.0 (M+H)$^+$.

Example 455

(3R,4S)-N-[(4,5-dimethylthiophen-2-yl)methyl]-1-[(1-methyl-1H-imidazol-4-yl)sulfonyl]-4-phenylpyrrolidin-3-amine The title compound was prepared similarly to the procedure described in Example 354E substituting 4,5-dimethylthiophene-2-carbaldehyde for 4-chlorobenzaldehyde and substituting Example 574A for Example 354D. MS (ESI) m/z 431.0 (M+H)$^+$.

Example 456

(3R,4S)-1-[(1-methyl-1H-imidazol-4-yl)sulfonyl]-4-phenyl-N-(4,5,6,7-tetrahydro-1,3-benzothiazol-2-ylmethyl)pyrrolidin-3-amine The title compound was prepared similarly to the procedure described in Example 354E substituting 4,5,6,7-tetrahydrobenzo[d]thiazole-2-carbaldehyde for 4-chlorobenzaldehyde and substituting Example 574A for Example 354D. MS (ESI) m/z 458.0 (M+H)$^+$.

Example 457

(3R,4S)-1-[(1-methyl-1H-imidazol-4-yl)sulfonyl]-4-phenyl-N-(1,3-thiazol-5-ylmethyl)pyrrolidin-3-amine The title compound was prepared similarly to the procedure described in Example 354E substituting thiazole-5-carbaldehyde for 4-chlorobenzaldehyde and substituting Example 574A for Example 354D MS (ESI) m/z 404.0 (M+H)$^+$.

Example 458

(3R,4S)-1-[(1-methyl-1H-imidazol-4-yl)sulfonyl]-4-phenyl-N-[2-(2,6,6-trimethylcyclohex-1-en-1-yl)ethyl]pyrrolidin-3-amine The title compound was prepared similarly to the procedure described in Example 354E substituting 2-(2,6,6-trimethylcyclohex-1-en-1-yl)acetaldehyde for 4-chlorobenzaldehyde and substituting Example 574A for Example 354D. MS (ESI) m/z 457.0 (M+H)$^+$.

Example 459

(3R,4S)-1-[(1-methyl-1H-imidazol-4-yl)sulfonyl]-4-phenyl-N-{[1-(propan-2-yl)piperidin-4-yl]methyl}pyrrolidin-3-amine The title compound was prepared similarly to the procedure described in Example 354E substituting 1-isopropylpiperidine-4-carbaldehyde for 4-chlorobenzaldehyde and substituting Example 574A for Example 354D. MS (ESI) m/z 446.0 (M+H)+.

Example 460

(3R,4S)-N-{[4-(4-fluorophenyl)-1,3-thiazol-2-yl]methyl}-1-[(1-methyl-1H-imidazol-4-yl)sulfonyl]-4-phenylpyrrolidin-3-amine The title compound was prepared similarly to the procedure described in Example 354E substituting 4-(4-fluorophenyl)thiazole-2-carbaldehyde for 4-chlorobenzaldehyde and substituting Example 574A for Example 354D. MS (ESI) m/z 498.0 (M+H)+.

Example 461

(3R,4S)-1-[(1-methyl-1H-imidazol-4-yl)sulfonyl]-N-[2-(4-methylphenyl)ethyl]-4-phenylpyrrolidin-3-amine The title compound was prepared similarly to the procedure described in Example 354E substituting 2-(p-tolyl)acetaldehyde for 4-chlorobenzaldehyde and substituting Example 574A for Example 354D. MS (ESI) m/z 425.0 (M+H)+.

Example 462

(3R,4S)-1-[(1-methyl-1H-imidazol-4-yl)sulfonyl]-N-[(5-methylthiophen-2-yl)methyl]-4-phenylpyrrolidin-3-amine The title compound was prepared similarly to the procedure described in Example 354E substituting 5-methylthiophene-2-carbaldehyde for 4-chlorobenzaldehyde and substituting Example 574A for Example 354D. MS (ESI) m/z 417.0 (M+H)+.

Example 463

(3R,4S)-N-(3-methylbutyl)-1-[(1-methyl-1H-imidazol-4-yl)sulfonyl]-4-phenylpyrrolidin-3-amine The title compound was prepared similarly to the procedure described in Example 354E substituting 3-methylbutanal for 4-chlorobenzaldehyde and substituting Example 574A for Example 354D. MS (ESI) m/z 377.0 (M+H)+.

Example 464

(3R,4S)-1-[(1-methyl-1H-imidazol-4-yl)sulfonyl]-4-phenyl-N-(3,5,5-trimethylhexyl)pyrrolidin-3-amine The title compound was prepared similarly to the procedure described in Example 354E substituting 3,5,5-trimethylhexanal for 4-chlorobenzaldehyde and Example 574A for Example 354D. MS (ESI) m/z 433.0 (M+H)+.

Example 465

(3R,4S)-1-[(1-methyl-1H-imidazol-4-yl)sulfonyl]-4-phenyl-N-(2-phenylpropyl)pyrrolidin-3-amine The title compound was prepared similarly to the procedure described in Example 354E substituting 2-phenylpropanal for 4-chlorobenzaldehyde and substituting Example 574A for Example 354D. MS (ESI) m/z 425.0 (M+H)+.

Example 466

(3R,4S)-N-(3,3-dimethylbutyl)-1-[(1-methyl-1H-imidazol-4-yl)sulfonyl]-4-phenylpyrrolidin-3-amine The title compound was prepared similarly to the procedure described in Example 354E substituting 3,3-dimethylbutanal for 4-chlorobenzaldehyde and substituting Example 574A for Example 354D. MS (ESI) m/z 391.0 (M+H)+.

Example 467

(3R,4S)-N-[(1-methylcyclohexyl)methyl]-1-[(1-methyl-1H-imidazol-4-yl)sulfonyl]-4-phenylpyrrolidin-3-amine The title compound was prepared similarly to the procedure described in Example 354E substituting 1-methylcyclohexanecarbaldehyde for 4-chlorobenzaldehyde and substituting Example 574A for Example 354D. MS (ESI) m/z 417.0 (M+H)+.

Example 468

(3R,4S)-N-[2-(3-chlorophenyl)ethyl]-1-[(1-methyl-1H-imidazol-4-yl)sulfonyl]-4-phenylpyrrolidin-3-amine The title compound was prepared similarly to the procedure described in Example 354E substituting 2-(3-chlorophenyl)acetaldehyde for 4-chlorobenzaldehyde and substituting Example 574A for Example 354D. MS (ESI) m/z 445.0 (M+H)+.

Example 469

(3R,4S)-N-[2-(4-tert-butylphenoxy)ethyl]-1-[(1-methyl-1H-imidazol-4-yl)sulfonyl]-4-phenylpyrrolidin-3-amine The title compound was prepared similarly to the procedure described in Example 354E substituting 2-(4-(tert-butyl)phenoxy)acetaldehyde for 4-chlorobenzaldehyde and substituting Example 574A for Example 354D. MS (ESI) m/z 483.0 (M+H)+.

Example 470

(3R,4S)-N-(2-ethyl-3-methylbutyl)-1-[(1-methyl-1H-imidazol-4-yl)sulfonyl]-4-phenylpyrrolidin-3-amine The title compound was prepared similarly to the procedure described in Example 354E substituting 2-ethyl-3-methylbutanal for 4-chlorobenzaldehyde and substituting Example 574A for Example 354D MS (ESI) m/z 405.0 (M+H)+.

Example 471

(3R,4S)-N-[3-(3-chlorophenyl)propyl]-1-[(1-methyl-1H-imidazol-4-yl)sulfonyl]-4-phenylpyrrolidin-3-amine The title compound was prepared similarly to the procedure described in Example 354E substituting 3-(3-chlorophenyl)propanal for 4-chlorobenzaldehyde and substituting Example 574A for Example 354D. MS (ESI) m/z 459.0 (M+H)⁺.

Example 472

(3R,4S)-N-[(4-bromo-1,3-thiazol-2-yl)methyl]-1-[(1-methyl-1H-imidazol-4-yl)sulfonyl]-4-phenylpyrrolidin-3-amine The title compound was prepared similarly to the procedure described in Example 354E substituting 4-bromothiazole-2-carbaldehyde for 4-chlorobenzaldehyde and substituting Example 574A for Example 354D. MS (ESI) m/z 482 (M+H)⁺.

Example 473

(3R,4S)-1-[(1-methyl-1H-imidazol-4-yl)sulfonyl]-N-[(4-methyl-2-phenyl-1,3-thiazol-5-yl)methyl]-4-phenylpyrrolidin-3-amine The title compound was prepared similarly to the procedure described in Example 354E substituting 4-methyl-2-phenylthiazole-5-carbaldehyde for 4-chlorobenzaldehyde and substituting Example 574A for Example 354D. MS (ESI) m/z 494 (M+H)⁺.

Example 474

N-(3,4-difluorophenyl)-1-[(2,4-dimethyl-1,3-thiazol-5-yl)sulfonyl]-4-phenylpyrrolidin-3-amine Example 474A N-(3,4-difluorophenyl)-4-phenylpyrrolidin-3-amine To a 100 mL round bottom flask with magnetic stir bar under argon was added cesium carbonate (28.7 g, 88 mmol)], 4-bromo-1,2-difluorobenzene (5.66 g, 29.3 mmol), 1-benzyl-4-phenylpyrrolidin-3-amine (7.4 g, 29.3 mmol), and Dichloro[1,3-bis(2,6-Di-3-pentylphenyl)imidazol-2-ylidene](3-chloropyridyl)palladium(II), (0.928 g, 1.173 mmol). 1,2-dimethoxyethane (25 mL) was added and the reaction mixture was stirred at 80° C. for 18 hours. The reaction mixture was cooled, concentrated onto celite, and purified via flash chromatography (5-50% EtOAc/Hex, 220 g column) to provide the title compound.

Example 474B

N-(3,4-difluorophenyl)-1-[(2,4-dimethyl-1,3-thiazol-5-yl)sulfonyl]-4-phenylpyrrolidin-3-amine A 4 mL vial with a magnetic stir bar was charged with Example 474A (40 mg, 0.146 mmol) and a solution of diisopropylethylamine in dichloromethane (1 mL of a 5 wt % diisopropylethylamine). A solution of 2,4-dimethylthiazole-5-sulfonyl chloride (972 µl, 0.292 mmol, 0.3 mM in 5% diisopropylethylamine in dichloromethane) was added and the reaction mixture was allowed to stir for 4 hours. The reaction was concentrated, redissolved in 2 mL of 50% dimethylsulfoxide/methanol and purified via HPLC to provide the title compound. MS (ESI) m/z 450 (M+H)⁺.

Example 475

N-(3,4-difluorophenyl)-1-{[3-methyl-1-(propan-2-yl)-1H-pyrazol-4-yl]sulfonyl}-4-phenylpyrrolidin-3-amine The title compound was prepared similarly to the procedure described in Example 474B substituting 1-isopropyl-3-methyl-1H-pyrazole-4-sulfonyl chloride for 2,4-dimethylthiazole-5-sulfonyl chloride. MS (ESI) m/z 461 (M+H)⁺.

Example 476

N-(3,4-difluorophenyl)-1-{[1-methyl-3-(trifluoromethyl)-1H-pyrazol-4-yl]sulfonyl}-4-phenylpyrrolidin-3-amine The title compound was prepared similarly to the procedure described in Example 474B substituting 1-methyl-3-(trifluoromethyl)-1H-pyrazole-4-sulfonyl chloride for 2,4-dimethylthiazole-5-sulfonyl chloride. MS (ESI) m/z 487 (M+H)⁺.

Example 477

N-(3,4-difluorophenyl)-4-phenyl-1-(pyridin-3-ylsulfonyl)pyrrolidin-3-amine

The title compound was prepared similarly to the procedure described in Example 474B substituting pyridine-3-sulfonyl chloride for 2,4-dimethylthiazole-5-sulfonyl chloride. MS (ESI) m/z 416 (M+H)⁺.

Example 478

5-({3-[(3,4-difluorophenyl)amino]-4-phenylpyrrolidin-1-yl}sulfonyl)-3,3-dimethyl-1,3-dihydro-2H-indol-2-one The title compound was prepared similarly to the procedure described in Example 474B substituting 3,3-dimethyl-2-oxoindoline-5-sulfonyl chloride for 2,4-dimethylthiazole-5-sulfonyl chloride. MS (ESI) m/z 498 (M+H)⁺.

Example 479

1-[(1-cyclopentyl-3-methyl-1H-pyrazol-4-yl)sulfonyl]-N-(3,4-difluorophenyl)-4-phenylpyrrolidin-3-amine The title compound was prepared similarly to the procedure described in Example 474B substituting 1-cyclopentyl-3-methyl-1H-pyrazole-4-sulfonyl chloride for 2,4-dimethylthiazole-5-sulfonyl chloride. MS (ESI) m/z 487 (M+H)⁺.

Example 480

6-({3-[(3,4-difluorophenyl)amino]-4-phenylpyrrolidin-1-yl}sulfonyl)quinazoline-2,4(1H,3H)dione The title compound was prepared similarly to the procedure described in Example 474B substituting 2,4-dioxo-1, 2,3,4-tetrahydroquinazoline-6-sulfonyl chloride for 2,4-dimethylthiazole-5-sulfonyl chloride. MS (ESI) m/z 499 (M+H)$^+$.

Example 481

7-({3-[(3,4-difluorophenyl)amino]-4-phenylpyrrolidin-1-yl}sulfonyl)-6-methyl-2H-1,4-benzoxazin-3(4H)-one The title compound was prepared similarly to the procedure described in Example 474B substituting 6-methyl-3-oxo-3,4-dihydro-2H-benzo[b][1,4]oxazine-7-sulfonyl chloride for 2,4-dimethylthiazole-5-sulfonyl chloride. MS (ESI) m/z 500 (M+H)$^+$.

Example 482

N-(3,4-difluorophenyl)-1-[(1,3-dimethyl-1H-pyrazol-5-yl)sulfonyl]-4-phenylpyrrolidin-3-amine The title compound was prepared similarly to the procedure described in Example 474B substituting 1,3-dimethyl-1H-pyrazole-5-sulfonyl chloride for 2,4-dimethylthiazole-5-sulfonyl chloride. MS (ESI) m/z 433 (M+H)$^+$.

Example 483

N-(3,4-difluorophenyl)-1-[(1,5-dimethyl-1H-pyrazol-4-yl)sulfonyl]-4-phenylpyrrolidin-3-amine The title compound was prepared similarly to the procedure described in Example 474B substituting 1,5-dimethyl-1H-pyrazole-4-sulfonyl chloride for 2,4-dimethylthiazole-5-sulfonyl chloride. MS (ESI) m/z 433 (M+H)$^+$.

Example 484

N-(3,4-difluorophenyl)-1-[(4-methylthiophen-2-yl)sulfonyl]-4-phenylpyrrolidin-3-amine The title compound was prepared similarly to the procedure described in Example 474B substituting 4-methylthiophene-2-sulfonyl chloride for 2,4-dimethylthiazole-5-sulfonyl chloride. MS (ESI) m/z 435 (M+H)$^+$.

Example 485

N-(3,4-difluorophenyl)-4-phenyl-1-(pyrrolidin-1-ylsulfonyl)pyrrolidin-3-amine

The title compound was prepared similarly to the procedure described in Example 474B substituting pyrrolidine-1-sulfonyl chloride for 2,4-dimethylthiazole-5-sulfonyl chloride. MS (ESI) m/z 408 (M+H)$^+$.

Example 486

1-[(5-chloro-1,3-dimethyl-1H-pyrazol-4-yl)sulfonyl]-N-(3,4-difluorophenyl)-4-phenylpyrrolidin-3-amine The title compound was prepared similarly to the procedure described in Example 474B substituting 5-chloro-1,3-dimethyl-1H-pyrazole-4-sulfonyl chloride for 2,4-dimethylthiazole-5-sulfonyl chloride. MS (ESI) m/z 467 (M+H)$^+$.

Example 487

N-(3,4-difluorophenyl)-1-[(5-methyl-1,2-oxazol-4-yl)sulfonyl]-4-phenylpyrrolidin-3-amine The title compound was prepared similarly to the procedure described in Example 474B substituting 5-methylisoxazole-4-sulfonyl chloride for 2,4-dimethylthiazole-5-sulfonyl chloride. MS (ESI) m/z 420(M+H)$^+$.

Example 488

N-(3,4-difluorophenyl)-1-[(2,5-dimethylfuran-3-yl)sulfonyl]-4-phenylpyrrolidin-3-amine The title compound was prepared similarly to the procedure described in Example 474B substituting 2,5-dimethylfuran-3-sulfonyl chloride for 2,4-dimethylthiazole-5-sulfonyl chloride. MS (ESI) m/z 433 (M+H)$^+$.

Example 489 methyl 3-({3-[(3,4-difluorophenyl)amino]-4-phenylpyrrolidin-1-yl}sulfonyl)thiophene-2-carboxylate The title compound was prepared similarly to the procedure described in Example 474B substituting methyl 3-(chlorosulfonyl)thiophene-2-carboxylate for 2,4-dimethylthiazole-5-sulfonyl chloride. MS (ESI) m/z 479 (M+H)$^+$.

Example 490

N-(3,4-difluorophenyl)-1-[(1,2-dimethyl-1H-imidazol-5-yl)sulfonyl]-4-phenylpyrrolidin-3-amine The title compound was prepared similarly to the procedure described in Example 474B substituting 1,2-dimethyl-1H-imidazole-5-sulfonyl chloride for 2,4-dimethylthiazole-5-sulfonyl chloride. MS (ESI) m/z 433 (M+H)$^+$.

Example 491 methyl 5-({3-[(3,4-difluorophenyl)amino]-4-phenylpyrrolidin-1-yl}sulfonyl)-4-methoxythiophene-3-carboxylate The title compound was prepared similarly to the procedure described in Example 474B substituting methyl 5-(chlorosulfonyl)-4-methoxythiophene-3-carboxylate for 2,4-dimethylthiazole-5-sulfonyl chloride. MS (ESI) m/z 509 (M+H)$^+$.

Example 492

N-(3,4-difluorophenyl)-1-[(5-ethylthiophen-2-yl)sulfonyl]-4-phenylpyrrolidin-3-amine The title compound was prepared similarly to the procedure described in Example 474B substituting 5-ethylthiophene-2-sulfonyl chloride for 2,4-dimethylthiazole-5-sulfonyl chloride. MS (ESI) m/z 449 (M+H)$^+$.

Example 493

N-(3,4-difluorophenyl)-1-[(4-methylpiperidin-1-yl)sulfonyl]-4-phenylpyrrolidin-3-amine The title compound was prepared similarly to the procedure described in Example 474B substituting 4-methylpiperidine-1-sulfonyl chloride for 2,4-dimethylthiazole-5-sulfonyl chloride. MS (ESI) m/z 436 (M+H)+.

Example 494

N-(3,4-difluorophenyl)-1-{[6-(morpholin-4-yl)pyridin-3-yl]sulfonyl}-4-phenylpyrrolidin-3-amine The title compound was prepared similarly to the procedure described in Example 474B substituting 6-morpholinopyridine-3-sulfonyl chloride for 2,4-dimethylthiazole-5-sulfonyl chloride. MS (ESI) m/z 501(M+H)+.

Example 495

1-(1,3-benzodioxol-5-ylsulfonyl)-N-(3,4-difluorophenyl)-4-phenylpyrrolidin-3-amine The title compound was prepared similarly to the procedure described in Example 474B substituting benzo[d][1,3]dioxole-5-sulfonyl chloride for 2,4-dimethylthiazole-5-sulfonyl chloride. MS (ESI) m/z 459 (M+H)+.

Example 496

N-(3,4-difluorophenyl)-1-(2,3-dihydro-1,4-benzodioxin-6-ylsulfonyl)-4-phenylpyrrolidin-3-amine The title compound was prepared similarly to the procedure described in Example 474B substituting 2,3-dihydrobenzo[b][1,4]dioxine-6-sulfonyl chloride for 2,4-dimethylthiazole-5-sulfonyl chloride. MS (ESI) m/z 473 (M+H)+.

Example 497

N-(3,4-difluorophenyl)-1-(6,7-dihydro-5H-pyrrolo[1,2-a]imidazol-3-ylsulfonyl)-4-phenylpyrrolidin-3-amine The title compound was prepared similarly to the procedure described in Example 474B substituting 6,7-dihydro-5H-pyrrolo[1,2-a]imidazole-3-sulfonyl chloride for 2,4-dimethylthiazole-5-sulfonyl chloride. MS (ESI) m/z 445 (M+H)+.

Example 498

N-(3,4-difluorophenyl)-4-phenyl-1-[(tetrahydro-2H-pyran-2-ylmethyl)sulfonyl]pyrrolidin-3-amine The title compound was prepared similarly to the procedure described in Example 474B substituting (tetrahydro-2H-pyran-2-yl)methanesulfonyl chloride for 2,4-dimethylthiazole-5-sulfonyl chloride. MS (ESI) m/z 437 (M+H)+.

Example 499

N-[5-({3-[(3,4-difluorophenyl)amino]-4-phenylpyrrolidin-1-yl}sulfonyl)-1,3-thiazol-2-yl]acetamide The title compound was prepared similarly to the procedure described in Example 474B substituting 2-acetamidothiazole-5-sulfonyl chloride for 2,4-dimethylthiazole-5-sulfonyl chloride. MS (ESI) m/z 479 (M+H)+.

Example 500

N-(3,4-difluorophenyl)-4-phenyl-1-{[6-(trifluoromethyl)pyridin-3-yl]sulfonyl}pyrrolidin-3-amine The title compound was prepared similarly to the procedure described in Example 474B substituting 6-(trifluoromethyl)pyridine-3-sulfonyl chloride for 2,4-dimethylthiazole-5-sulfonyl chloride. MS (ESI) m/z 484 (M+H)+.

Example 501

6-({3-[(3,4-difluorophenyl)amino]-4-phenylpyrrolidin-1-yl}sulfonyl)-1,4-dihydroquinoxaline-2,3-dione The title compound was prepared similarly to the procedure described in Example 474B substituting 2,3-dioxo-1,2,3,4-tetrahydroquinoxaline-6-sulfonyl chloride for 2,4-dimethylthiazole-5-sulfonyl chloride. MS (ESI) m/z 499 (M+H)+.

Example 502

N-(3,4-difluorophenyl)-1-[(1-methyl-1H-pyrazol-3-yl)sulfonyl]-4-phenylpyrrolidin-3-amine The title compound was prepared similarly to the procedure described in Example 474B substituting 1-methyl-1H-pyrazole-3-sulfonyl chloride for 2,4-dimethylthiazole-5-sulfonyl chloride. MS (ESI) m/z 419 (M+H)+.

Example 503

N-(3,4-difluorophenyl)-1-[(1-methyl-1H-indol-5-yl)sulfonyl]-4-phenylpyrrolidin-3-amine The title compound was prepared similarly to the procedure described in Example 474B substituting 1-methyl-1H-indole-5-sulfonyl chloride for 2,4-dimethylthiazole-5-sulfonyl chloride. MS (ESI) m/z 468 (M+H)+.

Example 504 methyl 5-({3-[(3,4-difluorophenyl)amino]-4-phenylpyrrolidin-1-yl}sulfonyl)-1-methyl-1H-pyrrole-2-carboxylate The title compound was prepared similarly to the procedure described in Example 474B substituting methyl 5-(chlorosulfonyl)-1-methyl-1H-pyrrole-2-carboxylate 2,4-dimethylthiazole-5-sulfonyl chloride. MS (ESI) m/z 476 (M+H)+.

Example 505

1-(1,2-benzoxazol-5-ylsulfonyl)-N-(3,4-difluorophenyl)-4-phenylpyrrolidin-3-amine The title compound was prepared similarly to the procedure described in Example 474B substituting benzo[d]isoxazole-5-sulfonyl chloride for 2,4-dimethylthiazole-5-sulfonyl chloride. MS (ESI) m/z 456 (M+H)+.

Example 506

5-({3-[(3,4-difluorophenyl)amino]-4-phenylpyrrolidin-1-yl}sulfonyl)-1,3-dihydro-2H-benzimidazol-2-one The title compound was prepared similarly to the procedure described in Example 474B substituting 2-oxo-2,3-dihydro-1H-benzo[d]imidazole-5-sulfonyl chloride for 2,4-dimethylthiazole-5-sulfonyl chloride. MS (ESI) m/z 471 (M+H)$^+$.

Example 507

5-({3-[(3,4-difluorophenyl)amino]-4-phenylpyrrolidin-1-yl}sulfonyl)-1,3-dihydro-2H-indol-2-one The title compound was prepared similarly to the procedure described in Example 474B substituting 2-oxoindoline-5-sulfonyl chloride for 2,4-dimethylthiazole-5-sulfonyl chloride. MS (ESI) m/z 470 (M+H)$^+$.

Example 508

N-(3,4-difluorophenyl)-4-phenyl-1-[(1,3,5-trimethyl-1H-pyrazol-4-yl)sulfonyl]pyrrolidin-3-amine The title compound was prepared similarly to the procedure described in Example 474B substituting 1,3,5-trimethyl-1H-pyrazole-4-sulfonyl chloride for 2,4-dimethylthiazole-5-sulfonyl chloride. MS (ESI) m/z 447(M+H)$^+$.

Example 509

1-(cyclobutylsulfonyl)-N-(3,4-difluorophenyl)-4-phenylpyrrolidin-3-amine

The title compound was prepared similarly to the procedure described in Example 474B substituting cyclobutanesulfonyl chloride for 2,4-dimethylthiazole-5-sulfonyl chloride. MS (ESI) m/z 393 (M+H)$^+$.

Example 510

1-(cyclohexylsulfonyl)-N-(3,4-difluorophenyl)-4-phenylpyrrolidin-3-amine

The title compound was prepared similarly to the procedure described in Example 474B substituting cyclohexanesulfonyl chloride for 2,4-dimethylthiazole-5-sulfonyl chloride. MS (ESI) m/z 421 (M+H)$^+$.

Example 511

1-[(5-chlorothiophen-2-yl)sulfonyl]-N-(3,4-difluorophenyl)-4-phenylpyrrolidin-3-amine The title compound was prepared similarly to the procedure described in Example 474B substituting 5-chlorothiophene-2-sulfonyl chloride for 2,4-dimethylthiazole-5-sulfonyl chloride. MS (ESI) m/z 455 (M+H)$^+$.

Example 512

6-({3-[(3,4-difluorophenyl)amino]-4-phenylpyrrolidin-1-yl}sulfonyl)-3,4-dihydroquinolin-2(1H)one The title compound was prepared similarly to the procedure described in Example 474B substituting 2-oxo-1,2,3,4-tetrahydroquinoline-6-sulfonyl chloride for 2,4-dimethylthiazole-5-sulfonyl chloride. MS (ESI) m/z 484 (M+H)$^+$.

Example 513

N-(3,4-difluorophenyl)-1-[(3,5-dimethyl-1,2-oxazol-4-yl)sulfonyl]-4-phenylpyrrolidin-3-amine The title compound was prepared similarly to the procedure described in Example 474B substituting 3,5-dimethylisoxazole-4-sulfonyl chloride for 2,4-dimethylthiazole-5-sulfonyl chloride. MS (ESI) m/z 434 (M+H)$^+$.

Example 514

5-({3-[(3,4-difluorophenyl)amino]-4-phenylpyrrolidin-1-yl}sulfonyl)-1,3-benzoxazol-2(3H)-one The title compound was prepared similarly to the procedure described in Example 474B substituting 2-oxo-2,3-dihydrobenzo[d]oxazole-5-sulfonyl chloride for 2,4-dimethylthiazole-5-sulfonyl chloride. MS (ESI) m/z 472 (M+H)$^+$.

Example 515

N-(3,4-difluorophenyl)-1-(isoquinolin-5-ylsulfonyl)-4-phenylpyrrolidin-3-amine

The title compound was prepared similarly to the procedure described in Example 474B substituting isoquinoline-5-sulfonyl chloride for 2,4-dimethylthiazole-5-sulfonyl chloride. MS (ESI) m/z 466 (M+H)$^+$.

Example 516

N-(3,4-difluorophenyl)-1-[(1-methyl-1H-pyrazol-5-yl)sulfonyl]-4-phenylpyrrolidin-3-amine The title compound was prepared similarly to the procedure described in Example 474B substituting 1-methyl-1H-pyrazole-5-sulfonyl chloride for 2,4-dimethylthiazole-5-sulfonyl chloride. MS (ESI) m/z 419 (M+H)$^+$.

Example 517

N-(3,4-difluorophenyl)-1-[(2,5-dimethylthiophen-3-yl)sulfonyl]-4-phenylpyrrolidin-3-amine The title compound was prepared similarly to the procedure described in Example 474B substituting 2,5-dimethylthiophene-3-sulfonyl chloride for 2,4-dimethylthiazole-5-sulfonyl chloride. MS (ESI) m/z 449 (M+H)$^+$.

Example 518

N-(3,4-difluorophenyl)-1-[(5-methylthiophen-2-yl)sulfonyl]-4-phenylpyrrolidin-3-amine The title compound was prepared similarly to the procedure described in Example 474B substituting 5-methylthiophene-2-sulfonyl chloride for 2,4-dimethylthiazole-5-sulfonyl chloride. MS (ESI) m/z 435 (M+H)$^+$.

Example 519

N-(3,4-difluorophenyl)-1-(2,3-dihydro-1-benzofuran-5-ylsulfonyl)-4-phenylpyrrolidin-3-amine The title compound was prepared similarly to the procedure described in Example 474B substituting 2,3-dihydrobenzofuran-5-sulfonyl chloride for 2,4-dimethylthiazole-5-sulfonyl chloride. MS (ESI) m/z 457 (M+H)+.

Example 520

1-[(6-chloroimidazo[2,1-b][1,3]thiazol-5-yl)sulfonyl]-N-(3,4-difluorophenyl)-4-phenylpyrrolidin-3-amine The title compound was prepared similarly to the procedure described in Example 474B substituting 6-chloroimidazo[2,1-b]thiazole-5-sulfonyl chloride for 2,4-dimethylthiazole-5-sulfonyl chloride. MS (ESI) m/z 495 (M+H)+.

Example 521

N-(3,4-difluorophenyl)-1-(morpholin-4-ylsulfonyl)-4-phenylpyrrolidin-3-amine

The title compound was prepared similarly to the procedure described in Example 474B substituting morpholine-4-sulfonyl chloride for 2,4-dimethylthiazole-5-sulfonyl chloride. MS (ESI) m/z 424 (M+H)+.

Example 522

1-[5-({3-[(3,4-difluorophenyl)amino]-4-phenylpyrrolidin-1-yl}sulfonyl)-2,3-dihydro-1H-indol-1-yl]ethanone The title compound was prepared similarly to the procedure described in Example 474B substituting 1-acetylindoline-5-sulfonyl chloride for 2,4-dimethylthiazole-5-sulfonyl chloride. MS (ESI) m/z 498 (M+H)+.

Example 523 tert-butyl {trans-1-[(2-cyanophenyl)sulfonyl]-4-phenylpyrrolidin-3-yl}carbamate

Example 523A

Tert-butyl-trans-4-phenylpyrrolidin-3-ylcarbamate

The title compound was prepared similarly to the procedures described in Example 2A-2D substituting (E)-(2-nitrovinyl)benzene for trans-4-methoxy-beta-nitrostyrene.

Example 523B

Tert-butyl {trans-1-[(2-cyanophenyl)sulfonyl]-4-phenylpyrrolidin-3-yl}carbamate

The title compound was prepared similarly to the procedure described in Example 2E substituting Example 523A for Example 2D and substituting 2-cyanobenzene-1-sulfonyl chloride for 1-methyl-1H-imidazole-4-sulfonyl chloride. MS (DCI) m/z 444.8 (M+NH4)+.

Example 524 tert-butyl [trans-1-[(2-cyanophenyl)sulfonyl]-4-(4-fluorophenyl)pyrrolidin-3-yl]carbamate

Example 524A

Tert-butyl-trans-4-(4-fluorophenyl)pyrrolidin-3-yl-carbamate

The title compound was prepared similarly to the procedures described in Example 2A-2D substituting (E)-1-fluoro-4-(2-nitrovinyl)benzene for trans-4-methoxy-beta-nitrostyrene.

Example 524B

Tert-butyl [trans-1-[(2-cyanophenyl)sulfonyl]-4-(4-fluorophenyl)pyrrolidin-3-yl]carbamate The title compound was prepared similarly to the procedure described in Example 2E substituting Example 524A for Example 2D and substituting 2-cyanobenzene-1-sulfonyl chloride for 1-methyl-1H-imidazole-4-sulfonyl chloride. MS (DCI) m/z 444.4 (M−H)−.

Example 525

2-{[trans-3-phenyl-4-{[4-(trifluoromethyl)pyridin-2-yl]amino}pyrrolidin-1-yl]sulfonyl}benzonitrile The title compound was prepared similarly to the procedure described in Example 337G substituting Example 527 for Example 337F and substituting 2-bromo-4-(trifluoromethyl)pyridine for 1-bromo-3-(trifluoromethyl)benzene. MS (ESI) m/z 473.2 (M+H)+.

Example 526

2-{[trans-3-phenyl-4-{[4-(trifluoromethyl)pyridin-2-yl]amino}pyrrolidin-1-yl]sulfonyl}benzamide The title compound was prepared similarly to the procedure described in Example 337G substituting Example 527 for Example 337F and substituting 2-bromo-4-(trifluoromethyl)pyridine for 1-bromo-3-(trifluoromethyl)benzene. MS (ESI) m/z 491.2 (M+H)+.

Example 527

2-(Trans-3-amino-4-phenylpyrrolidin-1-ylsulfonyl)benzonitrile

The title compound was prepared similarly to the procedure described in Example 380A substituting Example 523 for Example 322B. MS (ESI) MS m/z 328.2 (M+H)+.

Example 528

2-({Trans-3-[(3-chlorophenyl)amino]-4-phenylpyrrolidin-1-yl}sulfonyl)benzonitrile The title compound was prepared similarly to the procedure described in Example 337G substituting Example 527 for Example 337F and substituting 1-bromo-3-chlorobenzene for 1-bromo-3-(trifluoromethyl)benzene. MS (ESI) m/z 438.2 (M+H)+.

Example 529

2-({Trans-3-[(4-fluorophenyl)amino]-4-phenylpyrrolidin-1-yl}sulfonyl)benzonitrile The title compound was prepared similarly to the procedure described in Example 337G substituting Example 527 for Example 337F and substituting 1-bromo-4-fluorobenzene for 1-bromo-3-(trifluoromethyl)benzene. MS (ESI) m/z 422.2 (M+H)$^+$.

Example 530

Trans-N-(3-chlorophenyl)-4-(cyclopropylmethoxy)-1-[(1-methyl-1H-imidazol-4-yl)sulfonyl]pyrrolidin-3-amine The title compound was prepared similarly to the procedure described in Example 400 substituting (bromomethyl)cyclopropane for benzyl bromide. MS (ESI) m/z 411/413 (3:1) (M+H)$^+$.

Example 531

N-{trans-4-cyclohexyl-1-[(1-methyl-1H-imidazol-4-yl)sulfonyl]pyrrolidin-3-yl}-6-(trifluoromethyl)pyrimidin-4-amine The title compound was prepared similarly to the procedure described in Example 425C substituting 4-bromo-6-trifluoromethylpyrimidine for 1-bromo-3-trifluoromethylbenzene. MS (ESI) m/z 459.4 (M+H)$^+$.

Example 532

2-methoxy-N-{(3R,4S)-1-[(1-methyl-1H-imidazol-4-yl)sulfonyl]-4-phenylpyrrolidin-3-yl}pyrimidin-4-amine The title compound was prepared similarly to the procedure described in Example 337G substituting Example 396A for Example 337F and substituting 4-bromo-2-methoxypyrimidine for 1-bromo-3-(trifluoromethyl)benzene. MS (ESI) m/z 415.2 (M+H)$^+$.

Example 533

(3R,4S)-1-[(1-methyl-1H-imidazol-4-yl)sulfonyl]-N-[(2-methyl-1,3-thiazol-4-yl)methyl]-4-phenylpyrrolidin-3-amine The title compound was prepared similarly to the procedure described in Example 354E substituting 2-methylthiazole-4-carbaldehyde for 4-chlorobenzaldehyde and substituting Example 574A for Example 354D. MS (ESI) m/z 418 (M+H)$^+$.

Example 534

(3R,4S)-N-[(2-ethyl-1-benzofuran-3-yl)methyl]-1-[(1-methyl-1H-imidazol-4-yl)sulfonyl]-4-phenylpyrrolidin-3-amine The title compound was prepared similarly to the procedure described in Example 354E substituting 2-ethylbenzofuran-3-carbaldehyde for 4-chlorobenzaldehyde and substituting Example 574A for Example 354D. MS (ESI) m/z 465 (M+H)$^+$.

Example 535

(3R,4S)-N-(imidazo[1,2-a]pyridin-8-ylmethyl)-1-[(1-methyl-1H-imidazol-4-yl)sulfonyl]-4-phenylpyrrolidin-3-amine The title compound was prepared similarly to the procedure described in Example 354E substituting imidazo[1,2-a]pyridine-8-carbaldehyde for 4-chlorobenzaldehyde and substituting Example 574A for Example 354D. MS (ESI) m/z 437 (M+H)$^+$.

Example 536

(3R,4S)-1-[(1-methyl-1H-imidazol-4-yl)sulfonyl]-N-[(5-methylpyridin-2-yl)methyl]-4-phenylpyrrolidin-3-amine The title compound was prepared similarly to the procedure described in Example 354E substituting 5-methylpicolinaldehyde for 4-chlorobenzaldehyde and substituting Example 574A for Example 354D. MS (ESI) m/z 412 (M+H)$^+$.

Example 537

(3R,4S)-1-[(1-methyl-1H-imidazol-4-yl)sulfonyl]-4-phenyl-N-(pyrazolo[1,5-a]pyridin-3-ylmethyl)pyrrolidin-3-amine The title compound was prepared similarly to the procedure described in Example 354E substituting pyrazolo[1,5-a]pyridine-3-carbaldehyde for 4-chlorobenzaldehyde and substituting Example 574A for Example 354D. MS (ESI) m/z 437 (M+H)$^+$.

Example 538

N-{Trans-4-hydroxy-1-[(1-methyl-1H-imidazol-4-yl)sulfonyl]-4-phenylpyrrolidin-3-yl}-4-(trifluoromethyl)benzamide

Example 538A

Trans-tert-butyl 3-hydroxy-4-(4-(trifluoromethyl)benzamido)pyrrolidine-1-carboxylate To a solution of trans-tert-butyl 3-amino-4-hydroxypyrrolidine-1-carboxylate (600 mg, 3 mmol) in dichloromethane (10 mL) at 0° C. was added triethylamine (350 mg, 3.5 mmol) and 4-(trifluoromethyl)benzoyl chloride (620 mg, 3 mmol). The mixture was allowed to stir for 16 hours. The mixture was concentrated and dissolved in methanol (5 mL). Sodium methoxide (21% in methanol, 0.5 mL) was added. The mixture was stirred for 6 hours, concentrated, and partitioned between ethyl acetate and water. The organic fractions were collected, dried over MgSO$_4$, filtered, and concentrated to provide the title compound.

Example 538B

N-(trans-4-hydroxypyrrolidin-3-yl)-4-(trifluoromethyl)benzamide

The title compound was prepared as the hydrochloride salt similarly to the procedure described in Example 373B substituting Example 538A for Example 373A.

Example 538C

N-(trans-4-hydroxy-1-((1-methyl-1H-imidazol-4-yl)sulfonyl)pyrrolidin-3-yl)-4-(trifluoromethyl)benzamide The title compound was prepared similarly to the procedure described in Example 373C substituting Example 538B for Example 373B.

Example 538D

N-(1-((1-methyl-1H-imidazol-4-yl)sulfonyl)-4-oxopyrrolidin-3-yl)-4-(trifluoromethyl)benzamide The title compound was prepared similarly to the procedure described in Example 382A substituting Example 538C for Example 379C.

Example 538E

N-{Trans-4-hydroxy-1-[(1-methyl-1H-imidazol-4-yl)sulfonyl]-4-phenylpyrrolidin-3-yl}-4-(trifluoromethyl)benzamide The title compound was prepared similarly to the procedure described in Example 382B substituting Example 538D for Example 382A and phenylmagnesium bromide for benzylmagnesium bromide. MS (ESI) m/z 495 (M+H)$^+$.

Example 539

1-[(1-methyl-1H-imidazol-4-yl)sulfonyl]-3-phenyl-4-{[4-(trifluoromethyl)benzyl]amino}pyrrolidin-3-ol The title compound was prepared similarly to the procedure described in Example 404B substituting Example 538E for Example 404A. MS (ESI) m/z 481 (M+H)$^+$.

Example 540

(3R,4S)-N-[4-chloro-3-(trifluoromethyl)phenyl]-4-(4-fluorophenyl)-1-[(1-methyl-1H-imidazol-4-yl)sulfonyl]pyrrolidin-3-amine The title compound was prepared similarly to the procedure described in Example 327 substituting 1-bromo-4-chloro-3-(trifluoromethyl)benzene for 1-bromo-3-(trifluoromethoxy)benzene, but only heating for 1 hour. MS (ESI) m/z 503 (M+H)$^+$.

Example 541 ethyl {(3R,4S)-1-[(1-methyl-1H-imidazol-4-yl)sulfonyl]-4-phenylpyrrolidin-3-yl}carbamate To Example 396A (50 mg, 0.16 mmol) in dichloromethane (0.5 mL) was added triethylamine (20 mg, 0.2 mmol) and ethyl chloroformate (22 mg, 0.2 mmol). The mixture was stirred for 1 hour, concentrated, and purified by HPLC to provide the title compound. MS (ESI) m/z 379 (M+H)$^+$.

Example 542 propyl {(3R,4S)-1-[(1-methyl-1H-imidazol-4-yl)sulfonyl]-4-phenylpyrrolidin-3-yl}carbamate The title compound was prepared similarly to the procedure described in Example 541 substituting propyl chloroformate for ethyl chloroformate. MS (ESI) m/z 393 (M+H)$^+$.

Example 543

2-methylpropyl {(3R,4S)-1-[(1-methyl-1H-imidazol-4-yl)sulfonyl]-4-phenylpyrrolidin-3-yl}carbamate The title compound was prepared similarly to the procedure described in Example 541 substituting isobutyl chloroformate for ethyl chloroformate. MS (ESI) m/z 407 (M+H)$^+$.

Example 544 butyl {(3R,4S)-1-[(1-methyl-1H-imidazol-4-yl)sulfonyl]-4-phenylpyrrolidin-3-yl}carbamate The title compound was prepared similarly to the procedure described in Example 541 substituting butyl chloroformate for ethyl chloroformate. MS (ESI) m/z 407 (M+H)$^+$.

Example 545

(3R,4S)-N-(2-cyclopropylethyl)-1-[(1-methyl-1H-imidazol-4-yl)sulfonyl]-4-phenylpyrrolidin-3-amine The title compound was prepared similarly to the procedure described in Example 404B substituting Example 546 for Example 404A. MS (ESI) m/z 375 (M+H)$^+$.

Example 546

2-cyclopropyl-N-{(3R,4S)-1-[(1-methyl-1H-imidazol-4-yl)sulfonyl]-4-phenylpyrrolidin-3-yl}acetamide The title compound was prepared similarly to the procedure described in Example 404A substituting Example 396A for Example 14A and substituting 2-cyclopropylacetic acid for 2-nitro-5-(trifluoromethyl)benzoic acid. MS (ESI) m/z 388 (M+H)$^+$.

Example 547

(3R,4S)-N-[(2E)-hex-2-en-1-yl]-1-[(1-methyl-1H-imidazol-4-yl)sulfonyl]-4-phenylpyrrolidin-3-amine The title compound was prepared similarly to the procedure described in Example 354E substituting (E)-hex-2-enal for 4-chlorobenzaldehyde and substituting Example 396A

Example 548

(3R,4S)-N-hexyl-1-[(1-methyl-1H-imidazol-4-yl)sulfonyl]-4-phenylpyrrolidin-3-amine The title compound was prepared similarly to the procedure described in Example 354E substituting (E)-hex-2-enal for 4-chlorobenzaldehyde and Example 396A for Example 354D. Both Example 547 and Example 548 were isolated. MS (ESI) m/z 391 (M+H)+.

Example 549

N-{(3R,4S)-1-[(1-methyl-1H-imidazol-4-yl)sulfonyl]-4-phenylpyrrolidin-3-yl}pentanamide The title compound was prepared similarly to the procedure described in Example 404A substituting Example 396A for Example 14A and pentanoic acid for 2-nitro-5-(trifluoromethyl)benzoic acid. MS (ESI) m/z 391 (M+H)+.

Example 550

N-{(3R,4S)-1-[(1-methyl-1H-imidazol-4-yl)sulfonyl]-4-phenylpyrrolidin-3-yl}hexanamide The title compound was prepared similarly to the procedure described in Example 404A substituting Example 396A for Example 14A and substituting hexanoic acid for 2-nitro-5-(trifluoromethyl)benzoic acid. MS (ESI) m/z 405 (M+H)+.

Example 551

(3R,4S)-N-(2-{[tert-butyl(dimethyl)silyl]oxy}ethyl)-1-[(1-methyl-1H-imidazol-4-yl)sulfonyl]-4-phenylpyrrolidin-3-amine The title compound was prepared similarly to the procedure described in Example 354E substituting (tert-butyldimethylsilyloxy)acetaldehyde for 4-chlorobenzaldehyde and substituting Example 396A for Example 354D. MS (ESI) m/z 465.2 (M+H)+.

Example 552

(3R,4S)-1-[(1-methyl-1H-imidazol-4-yl)sulfonyl]-4-phenyl-N-{[6-(trifluoromethyl)pyridin-2-yl]methyl}pyrrolidin-3-amine The title compound was prepared similarly to the procedure described in Example 354E substituting 6-(trifluoromethyl)picolinaldehyde for 4-chlorobenzaldehyde and substituting Example 574A for Example 354D. MS (ESI) m/z 466 (M+H)+.

Example 553

(3R,4S)-N-[(3-chlorothiophen-2-yl)methyl]-1-[(1-methyl-1H-imidazol-4-yl)sulfonyl]-4-phenylpyrrolidin-3-amine The title compound was prepared similarly to the procedure described in Example 354E substituting 3-chlorothiophene-2-carbaldehyde for 4-chlorobenzaldehyde and substituting Example 574A for Example 354D. MS (ESI) m/z 437 (M+H)+.

Example 554

(3R,4S)-N-[(4,4-difluorocyclohexyl)methyl]-1-[(1-methyl-1H-imidazol-4-yl)sulfonyl]-4-phenylpyrrolidin-3-amine The title compound was prepared similarly to the procedure described in Example 354E substituting 4,4-difluorocyclohexanecarbaldehyde for 4-chlorobenzaldehyde and substituting Example 574A for Example 354D. MS (ESI) m/z 439 (M+H)+.

Example 555

(3R,4S)-1-[(1-methyl-1H-imidazol-4-yl)sulfonyl]-4-phenyl-N-(pyrazolo[1,5-a]pyridin-7-ylmethyl)pyrrolidin-3-amine The title compound was prepared similarly to the procedure described in Example 354E substituting pyrazolo[1,5-a]pyridine-7-carbaldehyde for 4-chlorobenzaldehyde and Example 574A for Example 354D. MS (ESI) m/z 437 (M+H)+.

Example 556

(3R,4S)-1-[(1-methyl-1H-imidazol-4-yl)sulfonyl]-4-phenyl-N-{[4-(propan-2-yl)-1,3-thiazol-2-yl]methyl}pyrrolidin-3-amine The title compound was prepared similarly to the procedure described in Example 354E substituting 4-isopropylthiazole-2-carbaldehyde for 4-chlorobenzaldehyde and substituting Example 574A for Example 354D. MS (ESI) m/z 446 (M+H)+.

Example 557

(3R,4S)-N-[(2,2-dimethyltetrahydro-2H-pyran-4-yl)methyl]-1-[(1-methyl-1H-imidazol-4-yl)sulfonyl]-4-phenylpyrrolidin-3-amine The title compound was prepared similarly to the procedure described in Example 354E substituting 2,2-dimethyltetrahydro-2H-pyran-4-carbaldehyde for 4-chlorobenzaldehyde and substituting Example 574A for Example 354D. MS (ESI) m/z 433 (M+H)+.

Example 558

(3R,4S)-1-[(1-methyl-1H-imidazol-4-yl)sulfonyl]-4-phenyl-N-{[5-(tetrahydro-2H-pyran-2-yl)thiophen-2-yl]methyl}pyrrolidin-3-amine The title compound was prepared similarly to the procedure described in Example 354E substituting 5-(tetrahydro-2H-pyran-2-yl)thiophene-2-carbaldehyde for 4-chlorobenzaldehyde and substituting Example 574A for Example 354D. MS (ESI) m/z 487 (M+H)$^+$.

Example 559

(3R,4S)-N-[(5-bromo-4-methyl-1,3-thiazol-2-yl)methyl]-1-[(1-methyl-1H-imidazol-4-yl)sulfonyl]-4-phenylpyrrolidin-3-amine The title compound was prepared similarly to the procedure described in Example 354E substituting 5-bromo-4-methylthiazole-2-carbaldehyde for 4-chlorobenzaldehyde and substituting Example 574A for Example 354D. MS (ESI) m/z 497 (M+H)$^+$.

Example 560

(3R,4S)-N-(imidazo[1,5-a]pyridin-5-ylmethyl)-1-[(1-methyl-1H-imidazol-4-yl)sulfonyl]-4-phenylpyrrolidin-3-amine The title compound was prepared similarly to the procedure described in Example 354E substituting imidazo[1,5-a]pyridine-5-carbaldehyde for 4-chlorobenzaldehyde and substituting Example 574A for Example 354D. MS (ESI) m/z 437 (M+H)$^+$.

Example 561

(3R,4S)-N-(2,3-dimethylpentyl)-1-[(1-methyl-1H-imidazol-4-yl)sulfonyl]-4-phenylpyrrolidin-3-amine The title compound was prepared similarly to the procedure described in Example 354E substituting 2,3-dimethylpentanal for 4-chlorobenzaldehyde and substituting Example 574A for Example 354D. MS (ESI) m/z 405 (M+H)$^+$.

Example 562

(3R,4S)-N-[(2-chloro-1,3-thiazol-4-yl)methyl]-1-[(1-methyl-1H-imidazol-4-yl)sulfonyl]-4-phenylpyrrolidin-3-amine The title compound was prepared similarly to the procedure described in Example 354E substituting 2-chlorothiazole-4-carbaldehyde for 4-chlorobenzaldehyde and substituting Example 574A for Example 354D. MS (ESI) m/z 438 (M+H)$^+$.

Example 563

(3R,4S)-1-[(1-methyl-1H-imidazol-4-yl)sulfonyl]-N-[(5-methylimidazo[1,2-a]pyridin-3-yl)methyl]-4-phenylpyrrolidin-3-amine The title compound was prepared similarly to the procedure described in Example 354E substituting 5-methylimidazo[1,2-a]pyridine-3-carbaldehyde for 4-chlorobenzaldehyde and substituting Example 574A for Example 354D. MS (ESI) m/z 451 (M+H)$^+$.

Example 564

(3R,4S)-1-[(1-methyl-1H-imidazol-4-yl)sulfonyl]-4-phenyl-N-[(2-phenylcyclopropyl)methyl]pyrrolidin-3-amine The title compound was prepared similarly to the procedure described in Example 354E substituting 2-phenylcyclopropanecarbaldehyde for 4-chlorobenzaldehyde and substituting Example 574A for Example 354D. MS (ESI) m/z 437 (M+H)$^+$.

Example 565

(3R,4S)-N-[(4-chloro-1,3-thiazol-5-yl)methyl]-1-[(1-methyl-1H-imidazol-4-yl)sulfonyl]-4-phenylpyrrolidin-3-amine The title compound was prepared similarly to the procedure described in Example 354E substituting 4-chlorothiazole-5-carbaldehyde for 4-chlorobenzaldehyde and substituting Example 574A for Example 354D. MS (ESI) m/z 438 (M+H)$^+$.

Example 566

(3R,4S)-1-[(1-methyl-1H-imidazol-4-yl)sulfonyl]-4-phenyl-N-(3,3,3-trifluoro-2-methylpropyl)pyrrolidin-3-amine The title compound was prepared similarly to the procedure described in Example 354E substituting 3,3,3-trifluoro-2-methylpropanal for 4-chlorobenzaldehyde and substituting Example 574A for Example 354D. MS (ESI) m/z 417 (M+H)$^+$.

Example 567

(3R,4S)-N-[(2-chloro-3-fluoropyridin-4-yl)methyl]-1-[(1-methyl-1H-imidazol-4-yl)sulfonyl]-4-phenylpyrrolidin-3-amine The title compound was prepared similarly to the procedure described in Example 354E substituting 2-chloro-3-fluoroisonicotinaldehyde for 4-chlorobenzaldehyde and substituting Example 574A for Example 354D. MS (ESI) m/z 450 (M+H)$^+$.

Example 568

(3R,4S)-N-[(5-fluoro-1-benzothiophen-2-yl)methyl]-1-[(1-methyl-1H-imidazol-4-yl)sulfonyl]-4-phenylpyrrolidin-3-amine The title compound was prepared similarly to the procedure described in Example 354E substituting 5-fluorobenzo[b]thiophene-2-carbaldehyde for 4-chlorobenzaldehyde and substituting Example 574A for Example 354D. MS (ESI) m/z 471 (M+H)$^+$.

Example 569

(3R,4S)-N-[5-chloro-2-(difluoromethoxy)benzyl]-1-[(1-methyl-1H-imidazol-4-yl)sulfonyl]-4-phenylpyrrolidin-3-amine The title compound was prepared similarly to the procedure described in Example 354E substituting 5-chloro-2-

(difluoromethoxy)benzaldehyde for 4-chlorobenzaldehyde and substituting Example 574A for Example 354D. MS (ESI) m/z 497 (M+H)+.

Example 570

(3R,4S)-N-[(2,5-dichlorothiophen-3-yl)methyl]-1-[(1-methyl-1H-imidazol-4-yl)sulfonyl]-4-phenylpyrrolidin-3-amine The title compound was prepared similarly to the procedure described in Example 354E substituting 2,5-dichlorothiophene-3-carbaldehyde for 4-chlorobenzaldehyde and substituting Example 574A for Example 354D. MS (ESI) m/z 471 (M+H)+.

Example 571

(3R,4S)-N-{[2-(4-fluorophenyl)pyridin-3-yl]methyl}-1-[(1-methyl-1H-imidazol-4-yl)sulfonyl]-4-phenylpyrrolidin-3-amine The title compound was prepared similarly to the procedure described in Example 354E substituting 2-(4-fluorophenyl)nicotinaldehyde for 4-chlorobenzaldehyde and substituting Example 574A for Example 354D. MS (ESI) m/z 492 (M+H)+.

Example 572

(3R,4S)-1-[(1-methyl-1H-imidazol-4-yl)sulfonyl]-N-{[2-(4-methylphenyl)-1,3-thiazol-5-yl]methyl}-4-phenylpyrrolidin-3-amine The title compound was prepared similarly to the procedure described in Example 354E substituting 2-(p-tolyl)thiazole-5-carbaldehyde for 4-chlorobenzaldehyde and substituting Example 574A for Example 354D. MS (ESI) m/z 494 (M+H)+.

Example 573

(3R,4S)-N-(3-cyclopropylpropyl)-1-[(1-methyl-1H-imidazol-4-yl)sulfonyl]-4-phenylpyrrolidin-3-amine

Example 573A 3-cyclopropyl-N-((3R,4S)-1-((1-methyl-1H-imidazol-4-yl)sulfonyl)-4-phenylpyrrolidin-3-yl)propanamide The title compound was prepared similarly to the procedure described in Example 404A substituting Example 396A for Example 14A and substituting 3-cyclopropylpropanoic acid for 2-nitro-5-(trifluoromethyl)benzoic acid.

Example 573B (3R,4S)-N-(3-cyclopropylpropyl)-1-[(1-methyl-1H-imidazol-4-yl)sulfonyl]-4-phenylpyrrolidin-3-amine The title compound was prepared similarly to the procedure described in Example 404B substituting Example 573A for Example 404A. MS (ESI) m/z 389 (M+H)+.

Example 574

5-fluoro-4-methyl-N-{(3R,4S)-1-[(1-methyl-1H-imidazol-4-yl)sulfonyl]-4-phenylpyrrolidin-3-yl}pyridin-2-amine

Example 574A (3R,4S)-1-(1-methyl-1H-imidazol-4-ylsulfonyl)-4-phenylpyrrolidin-3-amine The title compound was prepared as an HCl salt similarly to the conditions described in Example 2A-2F substituting (E)-4-(2-nitrovinyl)benzene for (E)-1-methoxy-4-(2-nitrovinyl)benzene and separating the enantiomers produced from the procedure of Example 2C via Chiral SFC separation (SFC 200 Column: Whelk-O1, 50×250 mm, 5 μm Column Temperature: 35° C. Mobile Phase: $CO_2$/IPA/DEA=70/30/0.1 Flow rate: 70 g/min Back Pressure: 100 Bar Wavelength: 214 nm Cycle time: 5.0 min Injection: 4.0 mL Sample solution: 41000 mg in 250 mL methanol) The enantiomer with a retention time of 4.41 minutes was used to make the title compound.

Example 574B 5-fluoro-4-methyl-N-{(3R,4S)-1-[(1-methyl-1H-imidazol-4-yl)sulfonyl]-4-phenylpyrrolidin-3-yl}pyridin-2-amine The title compound was prepared similarly to the procedure described in Example 327 substituting Example 574A for Example 322B and substituting 2-bromo-4-methyl-5-fluoropyridine for 1-bromo-3-(trifluoromethoxy)benzene. MS (APCI) m/z 416 (M+H)+.

Example 575

1,5-dimethyl-N-(3R,4S)-1-[(1-methyl-1H-imidazol-4-yl)sulfonyl]-4-phenylpyrrolidin-3-yl-1H-1,2,4-triazol-3-amine The title compound was prepared similarly to the procedure described in Example 327 substituting Example 574A for Example 322B and substituting 3-bromo-1,5-dimethyl-1H-1,2,4-triazole for 1-bromo-3-(trifluoromethoxy)benzene. MS (ESI) m/z 402 (M+H)+.

Example 576

1,5-dimethyl-4-({(3R,4S)-1-[(1-methyl-1H-imidazol-4-yl)sulfonyl]-4-phenylpyrrolidin-3-yl}amino)-1H-pyrrole-2-carbonitrile The title compound was prepared similarly to the procedure described in Example 327 substituting Example 574A for Example 322B and substituting 4-bromo-1,5-dimethyl-1H-pyrrole-2-carbonitrile for 1-bromo-3-(trifluoromethoxy)benzene. MS (APCI) m/z 425 (M+H)+.

Example 577

(3S,4R)-4-(4-fluorophenyl)-1-[(1-methyl-1H-imidazol-4-yl)sulfonyl]-N-[3-(propan-2-yloxy)propyl]pyrrolidine-3-carboxamide The title compound was prepared similarly to the procedure described in Example 242E substituting 3-isopropoxypropylamine for aniline. MS (ESI) m/z 453.2 (M+H)+.

Example 578

(3S,4R)-N-(3-ethoxypropyl)-4-(4-fluorophenyl)-1-[(1-methyl-1H-imidazol-4-yl)sulfonyl]pyrrolidine-3-carboxamide The title compound was prepared similarly to the procedure described in Example 242E substituting 3-ethoxypropylamine for aniline. MS (ESI) m/z 439.2 (M+H)$^+$.

Example 579

(3S,4R)-4-(4-fluorophenyl)-N-(2-methoxyethyl)-1-[(1-methyl-1H-imidazol-4-yl)sulfonyl]pyrrolidine-3-carboxamide The title compound was prepared similarly to the procedure described in Example 242E substituting 2-methoxyethylamine for aniline. MS (ESI) m/z 411.2 (M+H)$^+$.

Example 580

(3S,4R)-4-(4-fluorophenyl)-1-[(1-methyl-1H-imidazol-4-yl)sulfonyl]-N-propylpyrrolidine-3-carboxamide The title compound was prepared similarly to the procedure described in Example 242E substituting propylamine for aniline. MS (ESI) m/z 395.2 (M+H)$^+$.

Example 581

(3S,4R)-N-butyl-4-(4-fluorophenyl)-1-[(1-methyl-1H-imidazol-4-yl)sulfonyl]pyrrolidine-3-carboxamide The title compound was prepared similarly to the procedure described in Example 242E substituting butylamine for aniline. MS (ESI) m/z 409.2 (M+H)$^+$.

Example 582

(3S,4R)-4-(4-fluorophenyl)-N-[1-methoxypropan-2-yl]-1-[(1-methyl-1H-imidazol-4-yl)sulfonyl]pyrrolidine-3-carboxamide The title compound was prepared similarly to the procedure described in Example 242E substituting 2-methoxyisopropylamine for aniline. MS (ESI) m/z 425.2 (M+H)$^+$.

Example 583

(3R,4S)-4-(4-fluorophenyl)-N-(3-methoxypropyl)-1-[(1-methyl-1H-imidazol-4-yl)sulfonyl]pyrrolidine-3-carboxamide The title compound was prepared similarly to the procedure described in Example 242E substituting 3-methoxypropylamine for aniline. MS (ESI) m/z 425.2 (M+H)$^+$.

Example 584

(3S,4R)-N-(2-ethoxyethyl)-4-(4-fluorophenyl)-1-[(1-methyl-1H-imidazol-4-yl)sulfonyl]pyrrolidine-3-carboxamide The title compound was prepared similarly to the procedure described in Example 242E substituting 2-ethoxyethylamine for aniline. MS (ESI) m/z 425.2 (M+H)$^+$.

Example 585

(3R,4S)-N-[4-chloro-3-(trifluoromethoxy)phenyl]-4-(4-fluorophenyl)-1-[(1-methyl-1H-imidazol-4-yl)sulfonyl]pyrrolidin-3-amine The title compound was prepared similarly to Example 327 substituting 1-bromo-4-chloro-3-(trifluoromethoxy)benzene for 1-bromo-3-(trifluoromethyl)benzene, but the reaction mixture was only heated for 1 hour. MS (APCI) m/z 519 (M+H)$^+$.

Example 586

(3S,4R)-N-(cyclopropylmethyl)-4-(4-fluorophenyl)-1-[(1-methyl-1H-imidazol-4-yl)sulfonyl]pyrrolidine-3-carboxamide The title compound was prepared similarly to the procedure described in Example 242E substituting cyclopropylmethylamine for aniline. MS (ESI) m/z 407.1 (M+H)$^+$.

Example 587

(3S,4R)-4-(4-fluorophenyl)-1-[(1-methyl-1H-imidazol-4-yl)sulfonyl]-N-[2-(propan-2-yloxy)ethyl]pyrrolidine-3-carboxamide The title compound was prepared similarly to the procedure described in Example 242E substituting 2-isopropoxyethylamine for aniline. MS (ESI) m/z 439.1 (M+H)$^+$.

Example 588

(3R,4S)-N-(3-methoxypropyl)-1-[(1-methyl-1H-imidazol-4-yl)sulfonyl]-4-phenylpyrrolidin-3-amine

Example 588A (3R,4S)-N-(3-(benzyloxy)propyl)-1-((1-methyl-1H-imidazol-4-yl)sulfonyl)-4-phenylpyrrolidin-3-amine The title compound was prepared similarly to the procedure described in Example 354E substituting Example 396A for Example 354D and substituting 3-(benzyloxy)propanal for 4-chlorobenzaldehyde.

Example 588B tert-butyl (3-(benzyloxy)propyl)((3R,4S)-1-((1-methyl-1H-imidazol-4-yl)sulfonyl)-4-phenylpyrrolidin-3-yl)carbamate The title compound was prepared similarly to the procedure described in Example 337C substituting Example 588A for Example 337B.

Example 588C tert-butyl (3-hydroxypropyl)((3R,4S)-1-((1-methyl-1H-imidazol-4-yl)sulfonyl)-4-phenylpyrrolidin-3-yl)carbamate To Example 588B (200 mg, 0.36 mmol) in tetrahydrofuran (10 mL) was added 20% palladium hydroxide on carbon, (80 mg, 0.058 mmol). The mixture was allowed to stir under 30 psi of hydrogen at 50° C. for 16 hours. The

Example 588D (3R,4S)-N-(3-methoxypropyl)-1-[(1-methyl-1H-imidazol-4-yl)sulfonyl]-4-phenylpyrrolidin-3-amine To Example 588C (60 mg, 0.13 mmol) in tetrahydrofuran (0.5 mL) was added iodomethane (70 mg, 0.5 mmol) and sodium hydride (60%, 20 mg, 0.5 mmol). The mixture was stirred at 60° C. for 2 hours. Hydrochloric acid (4N in dioxane, 1 mL) was added. The mixture was stirred for 2 hours, concentrated, and partitioned between ethyl acetate and NaOH (1 M aq). The organic fraction was collected, concentrated, and purified HPLC to provide the title compound. MS (ESI) m/z 379 (M+H)$^+$.

Example 589

(3R,4S)-N-(3-ethoxypropyl)-1-[(1-methyl-1H-imidazol-4-yl)sulfonyl]-4-phenylpyrrolidin-3-amine The title compound was prepared similarly to the procedure described in Example 588D substituting iodoethane for ioidomethane. MS (ESI) m/z 393 (M+H)$^+$.

Example 590

(3R,4S)-N-{[1-(methoxymethyl)cyclopropyl]methyl}-1-[(1-methyl-1H-imidazol-4-yl)sulfonyl]-4-phenylpyrrolidin-3-amine

Example 590A 1-(methoxymethyl)-N-((3R,4S)-1-((1-methyl-1H-imidazol-4-yl)sulfonyl)-4-phenylpyrrolidin-3-yl)cyclopropane carboxamide The title compound was prepared similarly to the procedure described in Example 404A substituting Example 396A for Example 14A and substituting 1-(methoxymethyl)cyclopropanecarboxylic acid for 2-nitro-5-(trifluoromethyl)benzoic acid.

Example 590

(3R,4S)-N-{[1-(methoxymethyl)cyclopropyl]methyl}-1-[(1-methyl-1H-imidazol-4-yl)sulfonyl]-4-phenylpyrrolidin-3-amine The title compound was prepared similarly to the procedure described in Example 404B substituting Example 590A for Example 404A. MS (ESI) m/z 405 (M+H)$^+$.

Example 591

N-({trans-4-(4-fluorophenyl)-1-[(1-methyl-1H-imidazol-4-yl)sulfonyl]pyrrolidin-3-yl}methyl)-3-(propan-2-yloxy)propan-1-amine The title compound was prepared similarly to the procedure described in Example 290 substituting Example 577 for Example 242E. MS (ESI) m/z 439.1 (M+H)$^+$.

Example 592

3-ethoxy-N-({trans-4-(4-fluorophenyl)-1-[(1-methyl-1H-imidazol-4-yl)sulfonyl]pyrrolidin-3-yl}methyl)propan-1-amine The title compound was prepared similarly to the procedure described in Example 290 substituting Example 578 for Example 242E. MS (ESI) m/z 425.1 (M+H)$^+$.

Example 593

N-({trans-4-(4-fluorophenyl)-1-[(1-methyl-1H-imidazol-4-yl)sulfonyl]pyrrolidin-3-yl}methyl)-2-methoxyethanamine The title compound was prepared similarly to the procedure described in Example 290 substituting Example 579 for Example 242E. MS (ESI) m/z 397.1 (M+H)$^+$.

Example 594

N-({trans-4-(4-fluorophenyl)-1-[(1-methyl-1H-imidazol-4-yl)sulfonyl]pyrrolidin-3-yl}methyl)propan-1-amine The title compound was prepared similarly to the procedure described in Example 290 substituting Example 580 for Example 242E. MS (ESI) m/z 381.1 (M+H)$^+$.

Example 595

N-({trans-4-(4-fluorophenyl)-1-[(1-methyl-1H-imidazol-4-yl)sulfonyl]pyrrolidin-3-yl}methyl)butan-1-amine The title compound was prepared similarly to the procedure described in Example 290 substituting Example 581 for Example 242E. MS (ESI) m/z 394.1 (M+H)$^+$.

Example 596

(2S)-N-({trans-4-(4-fluorophenyl)-1-[(1-methyl-1H-imidazol-4-yl)sulfonyl]pyrrolidin-3-yl}methyl)-1-methoxypropan-2-amine The title compound was prepared similarly to the procedure described in Example 290 substituting Example 582 for Example 242E. MS (ESI) m/z 411.1 (M+H)$^+$.

Example 597

N-({trans-4-(4-fluorophenyl)-1-[(1-methyl-1H-imidazol-4-yl)sulfonyl]pyrrolidin-3-yl}methyl)-3-methoxypropan-1-amine The title compound was prepared similarly to the procedure described in Example 290 substituting Example 583 for Example 242E. MS (ESI) m/z 411.1 (M+H)$^+$.

Example 598

2-ethoxy-N-({trans-4-(4-fluorophenyl)-1-[(1-methyl-1H-imidazol-4-yl)sulfonyl]pyrrolidin-3-yl}methyl)ethanamine The title compound was prepared similarly to the procedure described in Example 290 substituting Example 584 for Example 242E. MS (ESI) m/z 411.1 (M+H)$^+$.

(Note: page begins with) mixture was filtered through a nylon membrane and concentrated to provide the title compound.

Example 599

N-({trans-4-(4-fluorophenyl)-1-[(1-methyl-1H-imidazol-4-yl)sulfonyl]pyrrolidin-3-yl}methyl)-2-(propan-2-yloxy)ethanamine The title compound was prepared similarly to the procedure described in Example 290 substituting Example 587 for Example 242E. MS (ESI) m/z 425.1 (M+H)$^+$.

Example 600

(3R,4S)-N-(2-methoxyethyl)-1-[(1-methyl-1H-imidazol-4-yl)sulfonyl]-4-phenylpyrrolidin-3-amine

Example 600A

Tert-butyl 2-(tert-butyldimethylsilyloxy)ethyl((3R,4S)-1-(1-methyl-1H-imidazol-4-ylsulfonyl)-4-phenylpyrrolidin-3-yl)carbamate To a solution of Example 551 (686 mg, 1.48 mmol) in ethyl acetate (7 mL), was added ditert-butyldicarbonate (644 mg, 2.95 mmol). This solution was stirred at room temperature for 16 hours. The solution was then concentrated and purified by flash-chromatography (30-50% ethyl acetate/heptanes) to provide the title compound. MS (ESI) m/z 565.0 (M+H)$^+$.

Example 600B

Tert-butyl 2-hydroxyethyl((3R,4S)-1-(1-methyl-1H-imidazol-4-ylsulfonyl)-4-phenylpyrrolidin-3-yl)carbamate To a solution of Example 600A (626 mg, 1.11 mmol) in 8 mL of dichloromethane (5 mL) was added tetrabutylammonium fluoride hydrate (620 mg, 2.22 mmol). This solution was stirred at room temperature for 16 hours, concentrated, and purified by flash-chromatography (5% methanol/dichloromethane with 0.5% triethylamine added) to provide the title compound. MS (ESI) m/z 450.8 (M+H)$^+$.

Example 600C (3R,4S)-N-(2-methoxyethyl)-1-[(1-methyl-1H-imidazol-4-yl)sulfonyl]-4-phenylpyrrolidin-3-amine Powdered potassium hydroxide (30 mg, 0.53 mmol) was added dimethylsulfoxide (7 mL) and the mixture was stirred for 2 minutes. To this solution was added Example 600 B (60 mg, 0.13 mmol) and iodomethane (66.2 mg, 0.47 mmol). This mixture was stirred at room temperature for 16 hours then partitioned between ethyl acetate and water, The organic fraction was collected, and the aqueous fraction was washed with ethyl acetate 3 times. All organic fractions were combined and concentrated. To this concentrate was added dichloromethane (1 mL) and trifluoroacetic acid (0.3 mL), and the solution stirred at room temperature for 2 hours. The mixture was concentrated and purified by HPLC to provide the title compound. MS (ESI) m/z 365.1 (M+H)$^+$.

Example 601

1-[(1-methyl-1H-imidazol-4-yl)sulfonyl]-4-(tetrahydrofuran-2-yl)-N-[3-(trifluoromethoxy)phenyl]pyrrolidin-3-amine

Example 601A (E)-2-(2-nitrovinyl)tetrahydrofuran

A solution of terahydrofuran-2-carboxaldehyde (2.0 g, 20.0 mmol) and nitromethane (3.66 g, 60.0 mmol) in tetrahydrofuran (20 ml) was stirred at room temperature under nitrogen and 1,1,3,3-tetramethylguanidine (230 mg, 2.0 mmol) was added in one portion. The reaction mixture was stirred for thirty minutes. The mixture was then chilled in an ice bath to 0° C. Trifluoroacetic anhydride (5.25 g, 25 mmol) was added in one portion. The reaction mixture was stirred for thirty minutes after which time triethylamine (5.06 g, 50.0 mmol) was added dropwise. The reaction was stirred for 30 minutes and then partitioned between ethyl acetate and a saturated solution of ammonium chloride. The organic fraction was collected, and the aqueous portion was washed with additional ethyl acetate. The combined organic extracts were dried over sodium sulfate, filtered, concentrated, and purified via flash column (1:2 ethyl acetate:heptanes) to afford the title compound.

Examample 601B 1-(1-methyl-1H-imidazol-4-ylsulfonyl)-4-((S)-tetrahydrofuran-2-yl)pyrrolidin-3-amine The title compound was prepared similarly to the procedures described in Example 2A-2F substituting Example 601A for trans-4-methoxy-beta nitrostyrene.

Example 601C

1-[(1-methyl-1H-imidazol-4-yl)sulfonyl]-4-(tetrahydrofuran-2-yl)-N-[3-(trifluoromethoxy)phenyl]pyrrolidin-3-amine The title compound was prepared similarly to the procedure described in Example 57 substituting Example 601B for Example 14A. Purification via flash chromatography (4:1 ethyl acetate:heptanes) provided the title compound. MS (ESI) m/z 461.1 (M+H)$^+$.

Example 602

1-[(1-methyl-1H-imidazol-4-yl)sulfonyl]-4-(tetrahydrofuran-2-yl)-N-[3-(trifluoromethoxy)phenyl]pyrrolidin-3-amine The title compound was prepared similarly to the procedure described in Example 57 substituting Example 601B for Example 14A. Purification via flash chromatography (4:1 ethyl acetate:heptanes) provided the title compound. MS (ESI) m/z 461.1 (M+H)$^+$.

Example 603

1-[(1-methyl-1H-imidazol-4-yl)sulfonyl]-4-(tetrahydrofuran-2-yl)-N-[3-(trifluoromethyl)phenyl]pyrrolidin-3-amine The title compound was prepared similarly to the procedure described in Example 57 substituting Example 601B for Example 14A and substituting 1-bromo-3-trifluoromethylbenzene for 1-bromo-2-methylbenzene. Purification via flash chromatography (3:1 ethyl acetate:heptane) provided the title compound. MS (ESI) m/z 445.1 (M+H)$^+$.

Example 604

(3R,4S)-1-[(1-methyl-1H-imidazol-4-yl)sulfonyl]-4-(tetrahydrofuran-2-yl)-N-[3-(trifluoromethyl)phenyl]pyrrolidin-3-amine The title compound was prepared similarly to the procedure described in Example 57 substituting Example 601B for Example 14A and substituting 1-bromo-3-trifluoromethylbenzene for 1-bromo-2-methylbenzene. Purification via flash chromatography (3:1 ethyl acetate:heptane) provided the title compound. MS (ESI) m/z 445.1 (M+H)$^+$.

Example 605

2-methoxy-N-{(3R,4S)-1-[(1-methyl-1H-imidazol-4-yl)sulfonyl]-4-phenylpyrrolidin-3-yl}-6-(trifluoromethyl)pyrimidin-4-amine

Example 605A

N-((3R,4S)-1-((1-methyl-1H-imidazol-4-yl)sulfonyl)-4-phenylpyrrolidin-3-yl)-2-(methylthio)-6-(trifluoromethyl)pyrimidin-4-amine To Example 396A (80 mg, 0.26 mmol) in dimethylsulfoxide (0.3 mL) was added 4-chloro-2-(methylthio)-6-(trifluoromethyl)pyrimidine (80 mg, 0.35 mmol) and cesium carbonate (120 mg, 0.37). The mixture was stirred at 120° C. for 4 hours and then partitioned between ethyl acetate and water. The organic fraction was dried over MgSO$_4$, filtered, and concentrated to provide the crude title compound.

Example 605B

N-((3R,4S)-1-((1-methyl-1H-imidazol-4-yl)sulfonyl)-4-phenylpyrrolidin-3-yl)-2-(methylsulfonyl)-6-(trifluoromethyl)pyrimidin-4-amine To Example 605A in dichloromethane (1 mL) was added meta-chloroperbenzoic acid (<77%, 320 mg, 1.4 mmol). The mixture was allowed to stir for 3 days. Then the mixture was partition between sodium metabisulfite (aq.) and ethyl acetate. The organic fraction was collected, dried over MgSO$_4$, filtered, and concentrated to provide the crude title compound.

Example 605C 2-methoxy-N-{(3R,4S)-1-[(1-methyl-1H-imidazol-4-yl)sulfonyl]-4-phenylpyrrolidin-3-yl}-6-(trifluoromethyl)pyrimidin-4-amine To a solution of Example 605B (0.19 g, 0.36 mmol) in methanol (1 mL) was added sodium methoxide (21% in methanol, 1 mL). The mixture was stirred at 100° C. for 2 hours and, partitioned between ethyl acetate and water. The organic fraction was collected, concentrated, and purified by HPLC to provide the title compound. MS (ESI) m/z 483 (M+H)$^+$.

Example 606

6-chloro-N-{(3R,4S)-1-[(1-methyl-1H-imidazol-4-yl)sulfonyl]-4-phenylpyrrolidin-3-yl}pyrimidin-4-amine To a solution of Example 574A (586 mg, 1.85 mmol) in methanol (10 mL) was added 4,6-dichloropyrimidine (829 mg, 5.6 mmol) and triethylamine (0.52 mL, 3.7 mmol). The reaction heated at 50 C for 1 hour. More 4,6-dichloropyrimidine (800 mg) was added and the reaction stirred for 18 hours. The reaction mixture was concentrated. Purification via flash chromatography (0-100% EtOAc/Hexanes) provided the title compound. MS (ESI) m/z 419 (M+H)$^+$.

Example 607

1-cyclopropyl-N-({(3R,4R)-4-(4-fluorophenyl)-1-[(1-methyl-1H-imidazol-4-yl)sulfonyl]pyrrolidin-3-yl}methyl)methanamine The title compound was prepared similarly to the procedure described in Example 290 substituting Example 586 for Example 242E. MS (ESI) m/z 393.1 (M+H)$^+$.

Example 608

(3R,4S)-N-(2-ethoxyethyl)-1-[(1-methyl-1H-imidazol-4-yl)sulfonyl]-4-phenylpyrrolidin-3-amine To a solution of Example 600B (70 mg, 0.16 mmol) in tetrahydrofuran (7 ml) under nitrogen was added iodoethane (43.6 mg, 0.28 mmol) and sodium hydride (18.6 mg, 0.47 mmol). This solution was stirred at 60° C. for 1 hour, and then it was cooled to room temperature. To the reaction mixture was added hydrochloric acid (4N in dioxane 0.7 mL) and the solution stirred at room temperature for 1 hour. The reaction mixture was then concentrated and partitioned between ethyl acetate and saturated sodium bicarbonate (aq.). The organic fraction was collected, concentrated, and purified by HPLC to afford the title product. MS (ESI) m/z 379.1 (M+H)$^+$.

Example 609

(3R,4S)-1-[(1-methyl-1H-imidazol-4-yl)sulfonyl]-4-phenyl-N-(2-propoxyethyl)pyrrolidin-3-amine

Example 609A

Tert-butyl 2-(allyloxy)ethyl((3R,4S)-1-(1-methyl-1H-imidazol-4-ylsulfonyl)-4-phenylpyrrolidin-3-yl) carbamate To a solution of Example 600B (73 mg, 0.16 mmol) in dimethylformamide (0.5 mL) under nitrogen at 0° C. was added allyl bromide (98 mg, 0.81 mmol) and sodium hydride (19.44 mg, 0.49 mmol). This mixture was stirred at 0° C. for 30 minutes, partitioned between ethyl acetate and water. The organic fraction was collected and concentrated to afford the title compound. MS (ESI) m/z 491.3 (M+H)$^+$.

Example 609B (3R,4S)-1-[(1-methyl-1H-imidazol-4-yl)sulfonyl]-4-phenyl-N-(2-propoxyethyl)pyrrolidin-3-amine To a solution of Example 609A (79 mg, 0.161 mmol) in tetrahydrofuran (15 ml) in a 50 ml pressure bottle was added 5% Pd/C, wet (8 mg, 1.879 µmol). The solution was stirred for 30 minutes under 50 psi of hydrogen at room temperature. The mixture was filtered through a nylon membrane and concentrated. The concentrate was dissolved in dichloromethane (0.5 mL) and trifluoroacetic acid (0.3 mL) was added. This solution was stirred at room temperature for 1 hour, concentrated, and purified via HPLC to afford the title compound. MS (ESI) m/z 393.1 (M+H)$^+$.

Example 610

N-(3,4-difluorophenyl)-1-[(1-methyl-1H-imidazol-4-yl)sulfonyl]-4-[-tetrahydrofuran-2-yl]pyrrolidin-3-amine The title compound was prepared similarly to the procedure described in Example 57 substituting Example 601B for Example 14A and substituting 3,4-difluoro-1-bromobenzene for 1-bromo-2-methylbenzene. Purification via flash chromatography (100% ethyl acetate) provided the title compound. MS (ESI) m/z 413.0 (M+H)$^+$.

Example 611

N-(3,4-difluorophenyl)-1-[(1-methyl-1H-imidazol-4-yl)sulfonyl]-4-(tetrahydrofuran-2-yl)pyrrolidin-3-amine The title compound was prepared similarly to the procedure described in Example 57 substituting Example 601B for Example 14A and substituting 3,4-difluoro-1-bromobenzene for 1-bromo-2-methylbenzene. Purification via flash chromatography (100% ethyl acetate) provided the title compound. MS (ESI) m/z 413.0 (M+H)$^+$.

Example 612

6-cyclopropyl-N-{(3R,4S)-1-[(1-methyl-1H-imidazol-4-yl)sulfonyl]-4-phenylpyrrolidin-3-yl}pyrimidin-4-amine The title compound was prepared similarly to the procedure described in Example 327 substituting Example 574A for Example 322B and substituting 4-bromo-6-cyclopropylpyrimidine for 1-bromo-3-(trifluoromethyl)benzene. MS (ESI) m/z 425 (M+H)$^+$.

Example 613

6-ethyl-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 337G substituting Example 380A for Example 337F and substituting 4-bromo-6-ethylpyrimidine for 1-bromo-3-(trifluoromethyl)benzene. MS (ESI) m/z 431.1 (M+H)$^+$.

Example 614

N-{(3R,4S)-4-(4-fluorophenyl)-1-[(1-methyl-1H-imidazol-4-yl)sulfonyl]pyrrolidin-3-yl}-6-(propan-2-yl)pyrimidin-4-amine The title compound was prepared similarly to the procedure described in Example 337G substituting Example 380A for Example 337F and substituting 4-bromo-6-isopropylpyrimidine for 1-bromo-3-(trifluoromethyl)benzene. MS (ESI) m/z 445.1 (M+H)$^+$.

Example 615

N-{(3R,4S)-4-(4-fluorophenyl)-1-[(1-methyl-1H-imidazol-4-yl)sulfonyl]pyrrolidin-3-yl}-2-methyl-6-(trifluoromethyl)pyrimidin-4-amine The title compound was prepared similarly to the procedure described in Example 605A substituting Example 380A for Example 396A and substituting 4-chloro-2-methyl-6-(trifluoromethyl)pyrimidine for 4-chloro-2-(methylthio)-6-(trifluoromethyl)pyrimidine. MS (ESI) m/z 485 (M+H)$^+$.

Example 616

N-{(3R,4S)-4-(4-fluorophenyl)-1-[(1-methyl-1H-imidazol-4-yl)sulfonyl]pyrrolidin-3-yl}-6-propylpyrimidin-4-amine The title compound was prepared similarly to the procedure described in Example 605A substituting Example 380A for Example 396A and substituting 4-chloro-6-propylpyrimidine for 4-chloro-2-(methylthio)-6-(trifluoromethyl)pyrimidine. MS (ESI) m/z 445 (M+H)$^+$.

Example 617

5-chloro-N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine The title compound was prepared similarly to the procedure described in Example 605A substituting Example 380A for Example 396A and substituting 2,5-dichloro-4-(trifluoromethyl)pyridine for 4-chloro-2-(methylthio)-6-(trifluoromethyl)pyrimidine. MS (ESI) m/z 504/506 (3:1) (M+H)+.

Example 618

(3S,4R)-N-[4-chloro-3-(trifluoromethyl)phenyl]-1-[(1-methyl-1H-imidazol-4-yl)sulfonyl]-4-(tetrahydrofuran-2-yl)pyrrolidin-3-amine The title compound was prepared similarly to the procedure described in Example 57 substituting Example 601B for Example 14A and substituting 1-bromo-4-chloro-3-trifluoromethylbenzene for 1-bromo-2-methylbenzene. Purification via flash chromatography (3:1 ethyl acetate:heptane) provided the title compound. MS (ESI) m/z 479.3 (M+H)+.

Example 619

(3R,4S)-N-[4-chloro-3-(trifluoromethyl)phenyl]-1-[(1-methyl-1H-imidazol-4-yl)sulfonyl]-4-(tetrahydrofuran-2-yl)pyrrolidin-3-amine The title compound was prepared similarly to the procedure described in Example 57 substituting Example 601B for Example 14A and substituting 1-bromo-4-chloro-3-trifluoromethylbenzene for 1-bromo-2-methylbenzene. Purification via flash chromatography (3:1 ethyl acetate:heptane) provided the title compound. MS (ESI) m/z 479.3 (M+H)+.

Example 620

6-ethoxy-N-{(3R,4S)-1-[(1-methyl-1H-imidazol-4-yl)sulfonyl]-4-phenylpyrrolidin-3-yl}pyrimidin-4-amine A microwave vial was charged with Example 606 (100 mg, 0.24 mmol), ethanol (2 mL), and sodium tert-butoxide (115 mg, 1.2 mmol). The reaction mixture was heated in a microwave (Biotage Initiator™, maximum 400 Watts) at 120° C. for 10 minutes. Purification via HPLC provided the title compound. MS (ESI) m/z 429 (M+H)+.

Example 621

6-methoxy-N-{(3R,4S)-1-[(1-methyl-1H-imidazol-4-yl)sulfonyl]-4-phenylpyrrolidin-3-yl}pyrimidin-4-amine The title compound was prepared similarly to Example 620 substituting methanol for ethanol. MS (ESI) m/z 415 (M+H)+.

Example 622

N-{(3R,4S)-1-[(1-methyl-1H-imidazol-4-yl)sulfonyl]-4-phenylpyrrolidin-3-yl}-6-propoxypyrimidin-4-amine The title compound was prepared similarly to Example 620 substituting propanol for ethanol. MS (ESI) m/z 443 (M+H)+.

Example 623

6-butoxy-N-{(3R,4S)-1-[(1-methyl-1H-imidazol-4-yl)sulfonyl]-4-phenylpyrrolidin-3-yl}pyrimidin-4-amine The title compound was prepared similarly to Example 620 substituting butanol for ethanol. MS (ESI) m/z 457 (M+H)+.

Example 624

N-{(3R,4S)-1-[(1-methyl-1H-imidazol-4-yl)sulfonyl]-4-phenylpyrrolidin-3-yl}-6-(2-methylpropoxy)pyrimidin-4-amine The title compound was prepared similarly to Example 620 substituting isobutanol for ethanol. MS (ESI) m/z 457 (M+H)+.

Example 625

4-{[(3S,4R)-3-(4-fluorophenyl)-4-(hexyloxy)pyrrolidin-1-yl]sulfonyl}-1-methyl-1H-imidazole

Example 625A

Trans-tert-butyl 3-(4-fluorophenyl)-4-(hexyloxy)pyrrolidine-1-carboxylate

To Example 379A (140 mg, 0.5 mmol) in dimethylformamide (0.5 mL) was added sodium hydride (35 mg, 60%, 0.9 mmol) and 1-bromohexane (150 mg, 0.91 mmol). The mixture was stirred at 100° C. for 2 hours. The mixture was partitioned between ethyl acetate and water. The organic fraction was collected, and the aqueous fraction was washed with ethyl acetate 3 time. The organic fractions were combined, dried over MgSO4, filtered, and concentrated to provide the title compound.

Example 625B

Trans-3-(4-fluorophenyl)-4-(hexyloxy)pyrrolidine

The title compound was prepared as the hydrochloride salt similarly to the procedure described in Example 373B substituting Example 625A for Example 373A.

Example 625C

4-{[Trans-3-(4-fluorophenyl)-4-(hexyloxy)pyrrolidin-1-yl]sulfonyl}-1-methyl-1H-imidazole The title compound was prepared similarly to the procedure described in Example 373C substituting Example 625B for Example 373B. MS (ESI) m/z 410 (M+H)+.

Example 626

Trans-4-(4-fluorophenyl)-1-[(1-methyl-1H-imidazol-4-yl)sulfonyl]-N-pentylpyrrolidine-3-carboxamide The title compound was prepared similarly to the procedure described in Example 242E substituting pentan-1-amine for aniline. MS (ESI) m/z 423.1 (M+H)+.

Example 627

Trans-4-(4-fluorophenyl)-N-hexyl-1-[(1-methyl-1H-imidazol-4-yl)sulfonyl]pyrrolidine-3-carboxamide The title compound was prepared similarly to the procedure described in Example 242E substituting hexan-1-amine for aniline. MS (ESI) m/z 437.1 (M+H)$^+$.

Example 628

Trans-N-(3-chlorobenzyl)-4-(4-fluorophenyl)-1-[(1-methyl-1H-imidazol-4-yl)sulfonyl]pyrrolidine-3-carboxamide The title compound was prepared similarly to the procedure described in Example 242E substituting 3-chlorobenzylamine for aniline. MS (ESI) m/z 477.2 (M+H)$^+$.

Example 629

Trans-N-(4-chlorobenzyl)-4-(4-fluorophenyl)-1-[(1-methyl-1H-imidazol-4-yl)sulfonyl]pyrrolidine-3-carboxamide The title compound was prepared similarly to the procedure described in Example 242E substituting 4-chlorobenzylamine for aniline. MS (ESI) m/z 477.2 (M+H)$^+$.

Example 630

Trans-N-(4-fluorobenzyl)-4-(4-fluorophenyl)-1-[(1-methyl-1H-imidazol-4-yl)sulfonyl]pyrrolidine-3-carboxamide The title compound was prepared similarly to the procedure described in Example 242E substituting 4-fluorobenzylamine for aniline. MS (ESI) m/z 461 (M+H)$^+$.

Example 631

Trans-N-(3,4-difluorobenzyl)-4-(4-fluorophenyl)-1-[(1-methyl-1H-imidazol-4-yl)sulfonyl]pyrrolidine-3-carboxamide The title compound was prepared similarly to the procedure described in Example 242E substituting (3,4-difluorophenyl)methanamine for aniline. MS (ESI) m/z 479.3 (M+H)$^+$.

Example 632

Trans-4-(4-fluorophenyl)-1-[(1-methyl-1H-imidazol-4-yl)sulfonyl]-N-[3-(trifluoromethyl)benzyl]pyrrolidine-3-carboxamide The title compound was prepared similarly to the procedure described in Example 242E substituting (3-(trifluoromethyl)phenyl)methanamine for aniline. 45 mg (31%) of the product was obtained. MS (ESI) m/z 511.3 (M+H)$^+$.

Example 633

Trans-N-[2-chloro-5-(trifluoromethyl)benzyl]-4-(4-fluorophenyl)-1-[(1-methyl-1H-imidazol-4-yl)sulfonyl]pyrrolidine-3-carboxamide The title compound was prepared similarly to the procedure described in Example 242E substituting (2-chloro-5-(trifluoromethyl)phenyl)methanamine for aniline. MS (ESI) m/z 545.3 (M+H)$^+$.

Example 634

Trans-4-(4-fluorophenyl)-1-[(1-methyl-1H-imidazol-4-yl)sulfonyl]-N-(pyridin-2-ylmethyl)pyrrolidine-3-carboxamide The title compound was prepared similarly to the procedure described in Example 242E substituting pyridin-2-ylmethanamine for aniline. MS (ESI) m/z 444.2 (M+H)$^+$.

Example 635

Trans-4-(4-fluorophenyl)-1-[(1-methyl-1H-imidazol-4-yl)sulfonyl]-N-{[4-(trifluoromethyl)pyridin-2-yl]methyl}pyrrolidine-3-carboxamide The title compound was prepared similarly to the procedure described in Example 242E substituting (4-(trifluoromethyl)pyridin-2-yl)methanamine hydrochloride for aniline. MS (ESI) m/z 512.2 (M+H)$^+$.

Example 636

Trans-N,N-dibutyl-4-(4-fluorophenyl)-1-[(1-methyl-1H-imidazol-4-yl)sulfonyl]pyrrolidine-3-carboxamide The title compound was prepared similarly to the procedure described in Example 242E substituting dibutylamine for aniline. MS (ESI) m/z 465.2 (M+H)$^+$.

Example 637

6-methyl-N-{(3R,4S)-1-[(1-methyl-1H-imidazol-4-yl)sulfonyl]-4-phenylpyrrolidin-3-yl}pyrimidin-4-amine The title compound was prepared similarly to the procedure described in Example 327 substituting Example 574A for Example 322B and substituting 4-bromo-6-methylpyrimidine for 1-bromo-3-(trifluoromethyl)benzene. MS (ESI) m/z 399 (M+H)$^+$.

Example 638

(3R,4S)-4-(4-fluorophenyl)-1-[(1-methyl-1H-imidazol-4-yl)sulfonyl]-N-[4-methyl-3-(trifluoromethyl)phenyl]pyrrolidin-3-amine The title compound was prepared similarly to the procedure described in Example 327 substituting 1-bromo-4- methyl-3-(trifluoromethyl)benzene for 1-bromo-3-(trifluoromethyl)benzene. MS (ESI) m/z 483 (M+H)+.

Example 639

4-({(3R,4S)-4-(4-fluorophenyl)-1-[(1-methyl-1H-imidazol-4-yl)sulfonyl]pyrrolidin-3-yl}amino)-2-(trifluoromethyl)benzonitrile The title compound was prepared similarly to the procedure described in Example 327 substituting 4-bromo-2-(trifluoromethyl)benzonitrile for 1-bromo-3-(trifluoromethyl)benzene. MS (ESI) m/z 494 (M+H)+.

Example 640

4-{(3R,4S)-4-(4-fluorophenyl)-1-[(1-methyl-1H-imidazol-4-yl)sulfonyl]pyrrolidin-3-yl}-1-propyl-1H-1,2,3-triazole

Example 640A 4-((trans-3-(2,2-dibromovinyl)-4-(4-fluorophenyl)pyrrolidin-1-yl)sulfonyl)-1-methyl-1H-imidazole To a solution of Example 332A (0.39 g, 1.2 mmol) in dichloromethane (10 mL) was added carbon tetrabromide (0.38 g, 1.2 mmol) and triphenylphosphine (0.61 g, 2.3 mmol) in portions. The mixture was stirred for 2 hours, concentrated, and purified by flash chromatography (100% ethyl acetate) to afford the title compound.

Example 640B 4-(((3S,4S)-3-ethynyl-4-(4-fluorophenyl)pyrrolidin-1-yl)sulfonyl)-1-methyl-1H-imidazole To a solution of Example 640A (0.24 g, 0.49 mmol) in tetrahydrofuran (1 mL) at −78° C. was added butyllithium (2N, 0.5 mL, 1 mmol). The mixture was stirred for 1 hour and then warmed to room temperature. The mixture was stirred for 1 hour at room temperature, and then partitioned between ammonium chloride (aq.) and ethyl acetate. The organic fraction was collected, dried over MgSO4, filtered, and concentrated to provide the title compound.

Example 640C 1-azidopropane

To a solution of 1-bromo propane (2.4 g, 20 mmol) in tetrahydrofuran (15 mL) was added sodium azide (1.3 g, 20 mmol) and water (1 mL). The mixture was stirred at 70° C. for 2 hours and this solution containing the title compound was used for Example 604D.

Example 640D

4-{Trans-4-(4-fluorophenyl)-1-[(1-methyl-1H-imidazol-4-yl)sulfonyl]pyrrolidin-3-yl}-1-propyl-1H-1,2,3-triazole To Example 640B (0.18 g, 0.54 mmol) in half of Example 604C solution was added CuI (90 mg, 0.5 mmol). The mixture was heated at 70° C. for 5 hours, concentrated, and partitioned between ethyl acetate and water. The organic fraction was collected, concentrated, and purified by HPLC to provide the title compound. MS (ESI) m/z 419 (M+H)+.

Example 641

4-[1-cyclopropylpiperidin-3-yl]-1-[(1-methyl-1H-imidazol-4-yl)sulfonyl]-N-[3-(trifluoromethoxy)phenyl]pyrrolidin-3-amine

Example 641A tert-Butyl (−1-benzyl-4-(pyridin-3-yl)pyrrolidin-3-yl)carbamate The title compound was prepared in similarly to the procedures described in Example 2A-2C substituting 3-(2-nitroethenyl)pyridine for trans-4-methoxy-beta-nitrostyrene. MS (DCI) m/z 354.2 (+H)+.

Example 641B tert-butyl 1-benzyl-4-(piperidin-3-yl)pyrrolidin-3-ylcarbamate

A solution of Example 641A (3.9 g, 11.03 mmol) in acetic acid (80 mL) was added to 5% platinum on carbon (50% water, 1.1 g) in a stainless steel pressure bottle. The vessel was pressureized with 30 psi of hydrogen and shaken for 8 hours at room temperature. The mixture was filtered through a nylon membrane and concentrated to provide the title compound.

Example 641C tert-butyl 1-benzyl-4-(1-cyclopropylpiperidin-3-yl)pyrrolidin-3-ylcarbamate 641B (1.0 g, 2.78 mmol), 1-ethoxycyclopropoxy-trimethylsilane (1.16 g, 6.68 mmol) and sodium cyanoborohydride (327 mg, 5.2 mmol) in methanol (10 ml) was stirred and heated to 60° C. under nitrogen for six hours. The reaction was then concentrated and the residue was taken up in ethyl acetate. The organic solution was washed with water, brine, and dried over sodium sulfate. The organic mixture was filtered, concentrated, and purified via flash chromatography (97.5:2.5 dichloromethane:2N ammonia in methanol) to afford the title compound.

Example 641D 4-(1-cyclopropylpiperidin-3-yl)-1-(1-methyl-1H-1,2,3-triazol-4-ylsulfonyl)pyrrolidin-3-amine The title compound was prepared similarly to the procedures described in Examples 2D-2F substituting the 641C for Example 2C.

Example 641E

4-[-1-cyclopropylpiperidin-3-yl]-1-[(1-methyl-1H-imidazol-4-yl)sulfonyl]-N-[3-(trifluoromethoxy)phenyl]pyrrolidin-3-amine The title compound was prepared similarly to the procedure described in Example 57 substituting Example 641D for Example 14A and substituting 1-bromo-3-trifluoromethylbenzene for 1-bromo-2-methylbenzene. MS (ESI) m/z 514.2 (M+H)$^+$.

Example 642

Trans-N-(3-chloro-4-fluorobenzyl)-4-(4-fluorophenyl)-1-[(1-methyl-1H-imidazol-4-yl)sulfonyl]pyrrolidine-3-carboxamide The title compound was prepared similarly to the procedure described in Example 242E substituting (3-chloro-4-fluorophenyl)methanamine for aniline. MS (ESI) m/z 495.2 (M+H)$^+$.

Example 643

Trans-4-(4-fluorophenyl)-N-(6-methylheptyl)-1-[(1-methyl-1H-imidazol-4-yl)sulfonyl]pyrrolidine-3-carboxamide The title compound was prepared similarly to the procedure described in Example 242E substituting 6-methylheptan-1-amine for aniline. MS (ESI) m/z 465.2 (M+H)$^+$.

Example 644

2-(4-fluorophenoxy)-N-{(3R,4S)-4-(4-fluorophenyl)-1-[(1-methyl-1H-imidazol-4-yl)sulfonyl]pyrrolidin-3-yl}acetamide The title compound was prepared similarly to the procedure described in Example 242E substituting Example 380A for aniline and substituting 4-fluorophenoxyacetic acid for Example 242D. MS (ESI) m/z 477.5 (M+H)$^+$.

Example 645

(3R,4S)-N-[4-fluoro-3-(trifluoromethyl)phenyl]-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 4-bromo-1-fluoro-2-(trifluoromethyl)benzene for 1-bromo-3-(trifluoromethyl)benzene. MS (ESI) m/z 469 (M+H)$^+$.

Example 646

(3R,4S)-N-[4-fluoro-3-(trifluoromethoxy)phenyl]-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 4-bromo-1-fluoro-2-(trifluoromethoxy)benzene for 1-bromo-3-(trifluoromethyl)benzene. MS (ESI) m/z 485 (M+H)$^+$.

Example 647

(3R,4S)-N-(4-methoxybutyl)-1-[(1-methyl-1H-imidazol-4-yl)sulfonyl]-4-phenylpyrrolidin-3-amine Example 647A methyl 4-(((3R,4S)-1-((1-methyl-1H-imidazol-4-yl)sulfonyl)-4-phenylpyrrolidin-3-yl)amino)butanoate The title compound was prepared similarly to the procedure described in Example 354E substituting methyl 4-oxobutanoate for 4-chlorobenzaldehyde and substituting Example 396A for Example 354D.

Example 647B methyl 4-((tert-butoxycarbonyl)((3R,4S)-1-((1-methyl-1H-imidazol-4-yl)sulfonyl)-4-phenylpyrrolidin-3-yl)amino)butanoate The title compound was prepared similarly to the procedure described in Example 337C substituting Example 647A for Example 337B.

Example 647C tert-butyl (4-hydroxybutyl)((3R,4S)-1-((1-methyl-1H-imidazol-4-yl)sulfonyl)-4-phenylpyrrolidin-3-yl)carbamate To a solution of Example 647B (140 mg, 0.28 mmol) in dichloromethane (1 mL) at −78° C. was added diisobutylaluminum hydride (0.5 mL, 1N in hexanes, 0.5 mmol). The mixture was allowed to stir for 45 minutes. The mixture was quenched and partitioned with ethyl acetate and sodium hydride CO$_3$(aq). The organic fraction was collected, dried over MgSO$_4$, filtered, and concentrated to provide the crude title compound.

Example 647D (3R,4S)-N-(4-methoxybutyl)-1-[(1-methyl-1H-imidazol-4-yl)sulfonyl]-4-phenylpyrrolidin-3-amine The title compound was prepared similarly to the procedure described in Example 588D substituting Example 647C for Example 588C. MS (ESI) m/z 393 (M+H)$^+$.

Example 648

(3R,4S)-N-(4-methoxyhexyl)-1-[(1-methyl-1H-imidazol-4-yl)sulfonyl]-4-phenylpyrrolidin-3-amine Example 648A tert-butyl ((3R,4S)-1-((1-methyl-1H-imidazol-4-yl)sulfonyl)-4-phenylpyrrolidin-3-yl)(4-oxobutyl)carbamate To a solution of Example 647B (140 mg, 0.28 mmol) in dichloromethane (1 mL) at −78° C. was added Diisobutylaluminum hydride (0.5 mL, 1N in hexanes, 0.5 mmol). The mixture was stirred for 45 minutes, and then quenched with ethyl acetate and sodium bicarbonate. The organic fraction was collected, dried over MgSO$_4$, filtered, and concentrated to provide the crude title compound.

Example 648B tert-butyl(4-hydroxyhexyl)((3R,4S)-1-((1-methyl-1H-imidazol-4-yl)sulfonyl)-4-phenylpyrrolidin-3-yl)carbamate The title compound was prepared similarly to the procedure described in Example 382B substituting Example 648A for Example 382A and substituting EtMgBr for BnMgBr.

Example 648C (3R,4S)-N-(4-methoxyhexyl)-1-[(1-methyl-1H-imidazol-4-yl)sulfonyl]-4-phenylpyrrolidin-3-amine The title compound was prepared similarly to the procedure described in Example 588D substituting Example 648B for Example 588C. MS (ESI) m/z 421 (M+H)$^+$.

Example 649

(3R,4S)-1-[(1-methyl-1H-imidazol-4-yl)sulfonyl]-4-phenyl-N-[(2-propylcyclopropyl)methyl]pyrrolidin-3-amine

Example 649A

Cis-2-propylcyclopropyl)methanol

To a solution of (Z)-hex-2-en-1-ol (200 mg, 2 mmol) in dichloromethane (4 mL) was added diiodomethane (0.66 g, 2.5 mmol), then diethylzinc (4 mL, 1N), 4 mmol) dropwise under nitrogen. The mixture was allowed to stir for 16 hours, and was then quenched with ammonium chloride (aq) hydrochloric acid (aq). Ethyl acetate was added and the mixture partitioned. The organic fraction was collected, dried over MgSO$_4$, filtered, and concentrated to provide the title compound.

Example 649B

Cis-2-propylcyclopropanecarbaldehyde

To a solution of Example 649A (200 mg, 1.75 mmol) in dichloromethane (1 mL) was added Dess-Martin periodinane (424 mg, 1 mmol). The mixture was stirred for 1 hour, and then quenched with sodium bisulfite (aq), and extracted with dichloromethane. The organic extracts were dried over MgSO$_4$, filtered, and concentrated to nearly dry to provide a concentrated dichloromethane solution of the title compound.

Example 649C (3R,4S)-1-[(1-methyl-1H-imidazol-4-yl)sulfonyl]-4-phenyl-N-[(2-propylcyclopropyl)methyl]pyrrolidin-3-amine The title compound was prepared similarly to the procedure described in Example 354E substituting Example 649B for 4-chlorobenzaldehyde and Example 396A for Example 354D. MS (ESI) m/z 403 (M+H)$^+$.

Example 650

(3R,4S)-1-[(1-methyl-1H-imidazol-4-yl)sulfonyl]-4-phenyl-N-[(2-propylcyclopropyl)methyl]pyrrolidin-3-amine

Example 650A (Trans-2-propylcyclopropyl)methanol

The title compound was prepared similarly to the procedure described in Example 649A substituting (E)-hex-2-en-1-ol for (Z)-hex-2-en-1-ol.

Example 650B

Trans-2-propylcyclopropanecarbaldehyde

The title compound was prepared similarly to the procedure described in Example 649B substituting Example 650A for Example 649A.

Example 650C (3R,4S)-1-[(1-methyl-1H-imidazol-4-yl)sulfonyl]-4-phenyl-N-[(2-propylcyclopropyl)methyl]pyrrolidin-3-amine The title compound was prepared similarly to the procedure described in Example 354E substituting Example 650B for 4-chlorobenzaldehyde and substituting Example 396A for Example 354D. MS (ESI) m/z 403 (M+H)$^+$

Example 651

(3R,4S)-4-(4-fluorophenyl)-N-[4-fluoro-3-(trifluoromethoxy)phenyl]-1-[(1-methyl-1H-imidazol-4-yl)sulfonyl]pyrrolidin-3-amine The title compound was prepared similarly to the procedure described in Example 327 substituting 4-bromo-1-fluoro-2-(trifluoromethoxy)benzene for 1-bromo-3-(trifluoromethyl)benzene. MS (ESI) m/z 503 (M+H)$^+$.

Example 652

(3R,4S)-4-(4-fluorophenyl)-N-[4-fluoro-3-(trifluoromethyl)phenyl]-1-[(1-methyl-1H-imidazol-4-yl)sulfonyl]pyrrolidin-3-amine The title compound was prepared similarly to the procedure described in Example 327 substituting 4-bromo-1-fluoro-2-(trifluoromethyl)benzene for 1-bromo-3-(trifluoromethyl)benzene. MS (ESI) m/z 503 (M+H)$^+$.

Example 653

(3R,4S)-N-[4-methoxy-3-(trifluoromethyl)phenyl]-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 4-bromo-1-methoxy-2-(trifluoromethyl)benzene for 1-bromo-3-(trifluoromethyl)benzene. MS (ESI) m/z 481 (M+H)$^+$.

Example 654

(3R,4S)-N-(1-benzothiophen-5-yl)-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 5-bromobenzo[b]thiophene for 1-bromo-3-(trifluoromethyl)benzene. MS (ESI) m/z 439 (M+H)+.

Example 655

(3R,4S)-N-(2,3-dihydro-1H-inden-5-yl)-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 5-bromo-2,3-dihydro-1H-indene for 1-bromo-3-(trifluoromethyl)benzene. MS (ESI) m/z 423 (M+H)+.

Example 656

(3R,4S)-N-[3,4-bis(trifluoromethyl)phenyl]-1-[(1-methyl-1H-imidazol-4-4-yl)sulfonyl]-4-phenylpyrrolidin-3-amine The title compound was prepared similarly to the procedure described in Example 327 substituting Example 574A for Example 322B and substituting 1-bromo-3,4-bis(trifluoromethyl)benzene for 1-bromo-3-(trifluoromethyl)benzene. MS (ESI) m/z 519 (M+H)+.

Example 657

(3R,4S)-1-[(1-methyl-1H-imidazol-4-yl)sulfonyl]-4-phenyl-N-(5,6,7,8-tetrahydronaphthalen-2-yl)pyrrolidin-3-amine The title compound was prepared similarly to the procedure described in Example 327 substituting Example 574A for Example 322B and substituting 6-bromo-1,2,3,4-tetrahydronaphthalene for 1-bromo-3-(trifluoromethyl)benzene. MS (ESI) m/z 437 (M+H)+.

Example 658

(3R,4S)-N-(3,4-dihydro-2H-chromen-6-yl)-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 6-bromochroman for 1-bromo-3-(trifluoromethyl)benzene. MS (ESI) m/z 439 (M+H)+.

Example 659

4-({(3S,4R)-1-[(1-methyl-1H-imidazol-4-yl)sulfonyl]-4-phenylpyrrolidin-3-yl}methyl)-1-propyl-1H-1,2,3-triazole

Example 659A 1-benzyl-4-phenylpyrrolidin-2-one

To a solution of 4-phenylpyrrolidin-2-one (1 g, 6.2 mmol) in tetrahydrofuran (6 mL) was added sodium hydride (60%, 280 mg, 7 mmol). Benzylbromide was added after 10 minutes. The mixture was allowed to stir at. 65° C. for 2 hours. The reaction mixture was, quenched with ammonium chloride (aq) and partitioned with ethyl acetate. The organic fraction was collected, dried over MgSO$_4$, filtered, and concentrated to provide the title compound.

Example 659B

Trans-1-benzyl-4-phenyl-3-(prop-2-yn-1-yl)pyrrolidin-2-one

To a solution of diisopropylamine (700 mg, 7 mmol) in tetrahydrofuran (7 mL) at −78° C. was added butyllithium (2N, 3.1 mL, 6.2 mmol). The mixture was allowed to stir for 10 minutes. Example 659A (1.56 g, 6.2 mmol) in tetrahydrofuran (5 mL) was added. The mixture was allowed to stir for 30 minutes. Propargyl bromide (0.7 mL, 80% toluene solution, 6.2 mmol) in tetrahydrofuran (3 mL) was added. The mixture was allowed to stir for 1 hour, quenched with ammonium chlorid (aq), and partitioned with ethyl acetate. The organic fraction was collected, concentrated, and purified via flash chromatography (50% ethyl acetate/hexanes) to afford the title compound.

Example 659C

Trans-1-benzyl-4-phenyl-3-((1-propyl-1H-1,2,3-triazol-4-yl)methyl)pyrrolidin-2-one The title compound was prepared similarly to the procedure described in Example 640D substituting Example 659B for Example 640B.

Example 659D 4-((trans-1-benzyl-4-phenylpyrrolidin-3-yl)methyl)-1-propyl-1H-1,2,3-triazole To a solution of Example 659C (0.32 g, 0.86 mmol) in tetrahydrofuran (3 mL) was added lithium aluminumhydride in tetrahydrofuran (2N, 1 mL, 2 mmol). The mixture was allowed to stir for 3 hours. It was then quenched with methanol, followed by sodium bicarbonate (aq). The mixture was partitioned with ethyl acetate. The organic fraction was dried over potassium carbonate, filtered, and concentrated to provide the title compound.

Example 659E 4-((trans-4-phenylpyrrolidin-3-yl)methyl)-1-propyl-1H-1,2,3-triazole The title compound was prepared similarly to the procedure described in Example 2D substituting Example 659D for Example 2C.

Example 659F 4-({Trans-1-[(1-methyl-1H-imidazol-4-yl)sulfonyl]-4-phenylpyrrolidin-3-yl}methyl)-1-propyl-1H-1,2,3-triazole The title compound was prepared similarly to the procedure described in Example 373C substituting Example 659E for Example 373B. MS (ESI) m/z 415 (M+H)+.

Example 660

(3R,4S)-N-(1-benzofuran-5-yl)-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 5-bromobenzofuran for 1-bromo-3-(trifluoromethyl)benzene. MS (ESI) m/z 423 (M+H)$^+$.

Example 661

Trans-4-(4-fluorophenyl)-1-[(1-methyl-1H-imidazol-4-yl)sulfonyl]-N-[3-(trifluoromethoxy)benzyl]pyrrolidine-3-carboxamide The title compound was prepared similarly to the procedure described in Example 242E substituting (3-(trifluoromethoxy)phenyl)methanamine for aniline. MS (ESI) m/z 527.2 (M+H)$^+$.

Example 662 methyl 5-({(3R,4S)-4-(4-fluorophenyl)-1-[(1-methyl-1H-imidazol-4-yl)sulfonyl]pyrrolidin-3-yl}amino)-5-oxopentanoate The title compound was prepared similarly to the procedure described in Example 242E substituting Example 380A for aniline, methyl hydrogen glutarate for Example 242D. MS (ESI) m/z 453.3 (M+H)$^+$.

Example 663

(3R,4S)-N-[2-chloro-4-(trifluoromethyl)benzyl]-4-(4-fluorophenyl)-1-[(1-methyl-1H-imidazol-4-yl)sulfonyl]pyrrolidine-3-carboxamide The title compound was prepared similarly to the procedure described in Example 242E substituting (2-chloro-4-(trifluoromethyl)phenyl)methanamine for aniline. MS (ESI) m/z 545.3 (M+H)$^+$.

Example 664

(3R,4S)-4-(4-fluorophenyl)-1-[(1-methyl-1H-imidazol-4-4-yl)sulfonyl]-N-pentylpyrrolidin-3-amine The title compound was prepared similarly to the procedure described in Example 354E substituting valeraldehyde for 4-chlorobenzaldehyde and substituting Example 380A for Example 354D. MS (ESI) m/z 395.2 (M+H)$^+$.

Example 665

(3R,4S)-4-(4-fluorophenyl)-N-hexyl-1-[(1-methyl-1H-imidazol-4-yl)sulfonyl]pyrrolidin-3-amine The title compound was prepared similarly to the procedure described in Example 354E substituting hexanal for 4-chlorobenzaldehyde and substituting Example 380A for Example 354D. MS (ESI) m/z 409.2 (M+H)$^+$.

Example 666

(3R,4S)-N-[2-(2-methoxyethoxy)ethyl]-1-[(1-methyl-1H-imidazol-4-yl)sulfonyl]-4-phenylpyrrolidin-3-amine

Example 666A 2-(2-methoxyethoxy)-N-((3R,4S)-1-((1-methyl-1H-imidazol-4-yl)sulfonyl)-4-phenylpyrrolidin-3-yl)acetamide The title compound was prepared similarly to the procedure described in Example 404A substituting Example 396A for Example 14A and substituting 2-(2-methoxyethoxy)acetic acid for 2-nitro-5-(trifluoromethyl)benzoic acid.

Example 666B (3R,4S)-N-[2-(2-methoxyethoxy)ethyl]-1-[(1-methyl-1H-imidazol-4-yl)sulfonyl]-4-phenylpyrrolidin-3-amine The title compound was prepared similarly to the procedure described in Example 404B substituting Example 666A for Example 404A. MS (ESI) m/z 409 (M+H)$^+$.

Example 667

(3R,4S)-N-[2-(4-fluorophenoxy)ethyl]-4-(4-fluorophenyl)-1-[(1-methyl-1H-imidazol-4-yl)sulfonyl]pyrrolidin-3-amine The title compound was prepared similarly to the procedure described in Example 290 substituting Example 644 for Example 242E. MS (ESI) m/z 463.1 (M+H)$^+$.

Example 668

4-butyl-1-{(3R,4S)-1-[(1-methyl-1H-imidazol-4-yl)sulfonyl]-4-phenylpyrrolidin-3-yl}-1H-1,2,3-triazole

Example 668A

Ethyl 2-(4-butyl-1H-1,2,3-triazol-1-yl)acetate

The title compound was prepared similarly to the procedure described in Example 640D substituting hex-1-yne for Example 640B and substituting ethyl 2-azidoacetate for Example 640C.

Example 668B ethyl 2(4-butyl-1H-1,2,3-triazol-1-yl)-4-nitro-3-phenylbutanoate The title compound was prepared similarly to the procedure described in Example 331A substituting Example 668A for methyl 3-(3-chlorophenyl)propanoate.

Example 668C

Trans-3(4-butyl-1H-1,2,3-triazol-1-yl)-4-phenylpyrrolidin-2-one

To Example 668B (530 mg, 1.5 mmol) in ethanol (10 mL) was added Raney nickel, water slurry (616 mg, 10.5 mmol)

in a 20 mL pressure bottle. The mixture was stirred under 60 psi of hydrogen at room temperate for 2 days. The mixture was filtered through a polypropylene membrane and concentrated to provide the title compound.

Example 668D

4-Butyl-1-(Trans-4-phenylpyrrolidin-3-yl)-1H-1,2,3-triazole

The title compound was prepared similarly to the procedure described in Example 404B substituting Example 668C for Example 404A.

Example 668E 4-butyl-1-{Trans-1-[(1-methyl-1H-imidazol-4-yl)sulfonyl]-4-phenylpyrrolidin-3-yl}-1H-1,2,3-triazole The title compound was prepared similarly to the procedure described in Example 373C substituting Example 668D for Example 373B. MS (ESI) m/z 375 (M+H)$^+$. MS (ESI) m/z 415 (M+H)$^+$.

Example 669

(3R,4S)-N-(4-chloro-3-methylphenyl)-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 1-bromo-4-chloro-3-methylbenzene for 1-bromo-3-(trifluoromethyl)benzene. MS (APCI) m/z 431 (M+H)$^+$.

Example 670

(3R,4S)-1-[(1-methyl-1H-imidazol-4-yl)sulfonyl]-4-phenyl-N-[3-(2,2,2-trifluoroethoxy)phenyl]pyrrolidin-3-amine The title compound was prepared similarly to the procedure described in Example 327 substituting Example 574A for Example 322B and substituting 1-bromo-3-(2,2,2-trifluoroethoxy)benzene for 1-bromo-3-(trifluoromethyl)benzene. MS (ESI) m/z 481 (M+H)$^+$.

Example 671

(3R,4S)-N-(2,3-dihydro-1-benzofuran-5-yl)-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 5-bromo-2,3-dihydrobenzofuran for 1-bromo-3-(trifluoromethyl)benzene. MS (ESI) m/z 425 (M+H)$^+$.

Example 672

(3R,4S)-N-(4,4-dimethyl-3,4-dihydro-2H-chromen-6-yl)-4-(4-fluorophenyl)-1-[(1-methyl-1H-imidazol-4-yl)sulfonyl]pyrrolidin-3-amine The title compound was prepared similarly to the procedure described in Example 327 substituting 6-bromo-4,4-dimethylchroman for 1-bromo-3-(trifluoromethyl)benzene. MS (ESI) m/z 485 (M+H)$^+$.

Example 673

N-{(3R,4S)-4-(4-fluorophenyl)-1-[(1-methyl-1H-imidazol-4-yl)sulfonyl]pyrrolidin-3-yl}-2-hydroxyhexanamide The title compound was prepared similarly to the procedure described in Example 242E substituting Example 380A for aniline and substituting DL-alpha-hydroxycaproic acid for Example 242D. MS (ESI) m/z 439.2 (M+H)$^+$.

Example 674

(3R,4S)-N-(3-methoxyhexyl)-1-[(1-methyl-1H-imidazol-4-yl)sulfonyl]-4-phenylpyrrolidin-3-amine Example 674A tert-butyl (3-hydroxyhexyl)((3R,4S)-1-((1-methyl-1H-imidazol-4-yl)sulfonyl)-4-phenylpyrrolidin-3-yl)carbamate A mixture of hex-1-en-3-one (38 mg, 0.4 mmol) and Example 396A (120 mg, 0.4 mmol) in methanol (0.5 mL) was allowed to stir overnight. Sodium borohydride (15 mg, 0.4 mmol) was added to the solution. The mixture was stirred for 30 minutes, di-tert-butyl dicarbonate (100 mg, 0.45 mmol) was added. The mixture was stirred for 2 hours and partitioned between ethyl acetate and water. The organic fraction was collected, concentrated, and purified by flash chromatography (100% ethyl acetate).to afford the title compound.

Example 674B (3R,4S)-N-(3-methoxyhexyl)-1-[(1-methyl-1H-imidazol-4-yl)sulfonyl]-4-phenylpyrrolidin-3-amine The title compound was prepared similarly to the procedure described in Example 588D substituting Example 674A for Example 588C. MS (ESI) m/z 421 (M+H)$^+$.

Example 675

(3R,4S)-N-[4-chloro-3-(propan-2-yl)phenyl]-4-(4-fluorophenyl)-1-[(1-methyl-1H-imidazol-4-yl)sulfonyl]pyrrolidin-3-amine The title compound was prepared similarly to the procedure described in Example 327 substituting 4-bromo-1-chloro-2-isopropylbenzene for 1-bromo-3-(trifluoromethyl)benzene. MS (ESI) m/z 477 (M+H)$^+$.

Example 676

(3R,4S)-4-(4-fluorophenyl)-1-[(1-methyl-1H-imidazol-4-yl)sulfonyl]-N-[3-methyl-4-(trifluoromethyl)phenyl]pyrrolidin-3-amine The title compound was prepared similarly to the procedure described in Example 327 substituting 4-bromo-3-methyl-1-(trifluoromethyl)benzene for 1-bromo-3-(trifluoromethyl)benzene. MS (ESI) m/z 483 (M+H)$^+$.

Example 677

(3R,4S)-N-(1-benzothiophen-6-yl)-4-(4-fluorophenyl)-1-[(1-methyl-1H-imidazol-4-yl)sulfonyl]pyrrolidin-3-amine The title compound was prepared similarly to the procedure described in Example 327 substituting 6-bromobenzo[b]thiophene for 1-bromo-3-(trifluoromethyl)benzene. MS (ESI) m/z 457 (M+H)$^+$.

Example 678

-4-(1-cyclopropylpiperidin-4-yl)-1-[(1-methyl-1H-imidazol-4-yl)sulfonyl]-N-[3-(trifluoromethoxy)phenyl]pyrrolidin-3-amine

Example 678A (E)-tert-butyl 4-(2-nitrovinyl)piperidine-1-carboxylate

The title compound was prepared similarly to the procedure described in Example 601A substituting 4-formylpiperidine-1-carboxylic acid-t-butyl ester for tetrahydrofuran-2-carboxaldehyde. MS (DCI) m/z 274.1 (M+NH$_4$)$^+$

Example 678B 4-(1-cyclopropylpiperidin-4-yl)-1-(1-methyl-1H-1,2,3-triazol-4-ylsulfonyl)pyrrolidin-3-amine The title compound was prepared similarly to the procedures described in Example 2A-2F substituting Example 678A for (E)-1-methoxy-4-(2-nitrovinyl)benzene.

Example 678C

-4-(1-cyclopropylpiperidin-4-yl)-1-[(1-methyl-1H-imidazol-4-yl)sulfonyl]-N-[3-(trifluoromethoxy)phenyl]pyrrolidin-3-amine The title compound was prepared similarly to the procedure described in Example 57 substituting 1-bromo-3-(trifluoromethoxy)benzene for 1-bromo-2-methylbenzene. MS (ESI) m/z 514.2 (M+H)+

Example 679

(3R,4S)-N-hexyl-1-[(1-methyl-1H-imidazol-4-yl)sulfonyl]-4-(tetrahydro-2H-pyran-2-yl)pyrrolidin-3-amine

Example 679A tetrahydro-2H-pyran-2-carbaldehyde

To a solution of oxalyl chloride (1.3 g, 10 mmol) in dichloromethane (20 mL) at −78° C. was added dimethylsufoxide (1.3 g, 17 mmol). The mixture was stirred for 10 minutes. A solution of (tetrahydro-2H-pyran-2-yl)methanol (1.2 g, 10 mmol) in dichloromethane (20 mL) was added. The mixture was stirred for 15 minutes at room temperature. The mixture was washed with water. The organic fraction was dried over MgSO$_4$, filtered, and concentrated to provide the title compound.

Example 679B (E)-2-(2-nitrovinyl)tetrahydro-2H-pyran

To a solution of Example 679A (1.2 g, 10 mmol) in nitromethane (5 mL) was added pyrrolidine (100 mL). The mixture was allowed to stir overnight and concentrated to afford the title compound.

Example 679C

Trans-1-benzyl-3-nitro-4-(-tetrahydro-2H-pyran-2-yl)pyrrolidine

The title compound was prepared similarly to the procedure described in Example 2A substituting Example 679B for 4-methoxy-beta-nitrostyrene.

Example 679D

Trans-1-benzyl-4-(tetrahydro-2H-pyran-2-yl)pyrrolidin-3-amine

The title compound was prepared similarly to the procedure described in Example 2B substituting Example 679C for Example 2A

Example 679E tert-butyl (trans-1-benzyl-4-(tetrahydro-2H-pyran-2-yl)pyrrolidin-3-yl)carbamate The title compound was prepared similarly to the procedure described in Example 337C substituting Example 679D for Example 337B.

Example 679F tert-butyl (trans-4-(tetrahydro-2H-pyran-2-yl)pyrrolidin-3-yl)carbamate The title compound was prepared similarly to the procedure described in Example 2D substituting Example 679E for 2C

Example 679G tert-butyl (trans-1-((1-methyl-1H-imidazol-4-yl)sulfonyl)-4-(tetrahydro-2H-pyran-2-yl)pyrrolidin-3-yl)carbamate The title compound was prepared similarly to the procedure described in Example 373C substituting Example 679F for Example 373B

Example 679H

Trans-1-((1-methyl-1H-imidazol-4-yl)sulfonyl)-4-(tetrahydro-2H-pyran-2-yl)pyrrolidin-3-amine The title compound was prepared similarly to the procedure described in Example 337F substituting Example 679G for Example 337E.

Example 679I

Trans-N-hexyl-1-[(1-methyl-1H-imidazol-4-yl)sulfonyl]-4-(tetrahydro-2H-pyran-2-yl)pyrrolidin-3-amine The title compound was prepared similarly to the procedure described in Example 354E substituting hexanal for 4-chlorobenzaldehyde and substituting Example 679H for Example 354D. MS (ESI) m/z 399 (M+H)+.

Example 680

Trans-N-[2-chloro-4-(trifluoromethyl)benzyl]-1-[(1-methyl-1H-imidazol-4-yl)sulfonyl]-4-(tetrahydro-2H-pyran-2-yl)pyrrolidin-3-amine The title compound was prepared similarly to the procedure described in Example 354E substituting 2-chloro-4-(trifluoromethyl)benzaldehyde for 4-chlorobenzaldehyde and substituting Example 679H for Example 354D. MS (ESI) m/z 507/509 (3:1) (M+H)+.

Example 681

Trans-1-[(1-methyl-1H-imidazol-4-yl)sulfonyl]-4-(tetrahydro-2H-pyran-2-yl)-N-[3-(trifluoromethyl)phenyl]pyrrolidin-3-amine The title compound was prepared similarly to the procedure described in Example 337G substituting Example 679H for Example 337F. MS (ESI) m/z 459 (M+H)+.

Example 682

N-{Trans-1-[(1-methyl-1H-imidazol-4-yl)sulfonyl]-4-[tetrahydro-2H-pyran-2-yl]pyrrolidin-3-yl}-4-(trifluoromethyl)pyridin-2-amine The title compound was prepared similarly to the procedure described in Example 337G substituting Example 679H for Example 337F and substituting 2-bromo-4-(trifluoromethyl)pyridine for 1-bromo-3-(trifluoromethyl)benzene. MS (ESI) m/z 460 (M+H)+.

Example 683

N-{Trans-1-[(1-methyl-1H-imidazol-4-yl)sulfonyl]-4-[tetrahydro-2H-pyran-2-yl]pyrrolidin-3-yl}-4-(trifluoromethyl)pyridin-2-amine The title compound was prepared similarly to the procedure described in Example 337G substituting Example 679H for Example 337F and substituting 2-bromo-4-(trifluoromethyl)pyridine for 1-bromo-3-(trifluoromethyl)benzene. MS (ESI) m/z 460 (M+H)+.

Example 684

(3R,4S)-N-[4-(4,4-dimethyl-1,3-dioxan-2-yl)butyl]-4-(4-fluorophenyl)-1-[(1-methyl-1H-imidazol-4-yl)sulfonyl]pyrrolidin-3-amine The title compound was prepared similarly to the procedure described in Example 354E substituting 5,5-dimethyl-2-(3'-formylpropyl)-1,3-dioxane for 4-chlorobenzaldehyde and substituting Example 380A for Example 354D. MS (ESI) m/z 495.1 (M+H)+.

Example 685

Trans-1-[(1-methyl-1H-imidazol-4-yl)sulfonyl]-4-(tetrahydro-2H-pyran-2-yl)-N-[3-(trifluoromethoxy)phenyl]pyrrolidin-3-amine The title compound was prepared similarly to the procedure described in Example 337G substituting Example 679H for Example 337F and substituting 1-bromo-3-(trifluoromethoxy)benzene for 1-bromo-3-(trifluoromethyl)benzene. MS (ESI) m/z 475 (M+H)+.

Example 686

Trans-1-[(1-methyl-1H-imidazol-4-yl)sulfonyl]-4-[tetrahydro-2H-pyran-2-yl]-N-[3-(trifluoromethoxy)phenyl]pyrrolidin-3-amine The title compound was prepared similarly to the procedure described in Example 337G substituting Example 679H for Example 337F and substituting 1-bromo-3-(trifluoromethoxy)benzene for 1-bromo-3-(trifluoromethyl)benzene. MS (ESI) m/z 475 (M+H)+.

Example 687

N-[Trans-1-[(1-methyl-1H-imidazol-4-yl)sulfonyl]-4-(tetrahydro-2H-pyran-2-yl)pyrrolidin-3-yl]-6-(trifluoromethyl)pyrimidin-4-amine The title compound was prepared similarly to the procedure described in Example 337G substituting Example 679H for Example 337F and substituting 4-bromo-6-(trifluoromethyl)pyrimidine for 1-bromo-3-(trifluoromethyl)benzene. MS (ESI) m/z 461 (M+H)+.

Example 688

N-[2-({Trans-4-(4-fluorophenyl)-1-[(1-methyl-1H-imidazol-4-yl)sulfonyl]pyrrolidin-3-yl}oxy)ethyl]propan-1-amine The title compound was prepared similarly to the procedure described in Example 404B substituting Example 689E for Example 404A. MS (ESI) m/z 411 (M+H)+.

Example 689

2-({Trans-4-(4-fluorophenyl)-1-[(1-methyl-1H-imidazol-4-yl)sulfonyl]pyrrolidin-3-yl}oxy)-N-propylacetamide

Example 689A

Trans-tert-butyl 3-(4-fluorophenyl)-4-(2-methoxy-2-oxoethoxy)pyrrolidine-1-carboxylate To a solution of Example 379A (0.56 g, 2 mmol) in dimethylformamide (2 mL) was added methyl 2-bromoacetate (0.38 g, 2.5 mmol) and sodium hydride (60%, 120 mg, 3 mmol). The mixture was stirred at 80° C. for 4 hours. The mixture was partitioned with water and ethyl acetate. The organic fraction was collected, concentrated, and purified by flash chromatography (50% ethyl acetate/hexanes) to afford the title compound.

Example 689B methyl 2-((trans-4-(4-fluorophenyl)pyrrolidin-3-yl)oxy)acetate

The title compound was prepared as the hydrochloride salt similarly to the procedure described in Example 373B substituting Example 689A for Example 373A.

Example 689C methyl 2-((trans-4-(4-fluorophenyl)-1-((1-methyl-1H-imidazol-4-yl)sulfonyl)pyrrolidin-3-yl)oxy)acetate The title compound was prepared similarly to the procedure described in Example 373C substituting Example 689B for Example 373B.

Example 689D 2-((Trans-4-(4-fluorophenyl)-1-((1-methyl-1H-imidazol-4-yl)sulfonyl)pyrrolidin-3-yl)oxy)acetic acid Example 689C (0.11 g, 0.28 mmol) was dissolved in a solution of litium hydroxide (methanol:water. 5:3, 1N, 3 mL). The mixture was stirred for 2 hours. Hydrochloric acid (aq) was added to adjust the pH value to 2. The mixture was partitioned with ethyl acetate. The organic fraction was collected, dried over $MgSO_4$, filtered, and concentrated to provide the title compound.

Example 689E 2-({Trans-4-(4-fluorophenyl)-1-[(1-methyl-1H-imidazol-4-yl)sulfonyl]pyrrolidin-3-yl}oxy)-N-propylacetamide The title compound was prepared similarly to the procedure described in Example 404A substituting propyl amine for Example 14A and Example 689D for 2-nitro-5-(trifluoromethyl)benzoic acid. MS (ESI) m/z 425 (M+H)+.

Example 690

6-chloro-N-{(3R,4S)-4-(4-fluorophenyl)-1-[(1-methyl-1H-imidazol-4-yl)sulfonyl]pyrrolidin-3-yl}-2-methylpyrimidin-4-amine The title compound was prepared similarly to the procedure described in Example 606 substituting Example 322B for Example 574A and substituting 4,6-dichloro-2-methylpyrimidine for 4,6-dichloropyrimidine. MS (ESI) m/z 451 (M+H)+.

Example 691

6-chloro-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 606 substituting Example 322B for Example 574A but heated at 120° C. for 10 minutes in a microwave (Biotage Initiator™, maximum 400 Watts). MS (ESI) m/z 437 (M+H)+.

Example 692

1-{(3R,4S)-4-(4-fluorophenyl)-1-[(1-methyl-1H-imidazol-4-yl)sulfonyl]pyrrolidin-3-yl}-3-phenylurea A microwave vial was charged with Example 322B (50 mg, 0.15 mmol), isocyanatobenzene (20 mg, 0.17 mmol), triethylamine (65 µL, 0.46 mmol) and tetrahydrofuran (2 mL). The reaction mixture was heated in a microwave (Biotage Initiator™, maximum 400 Watts) at 100° C. for 10 minutes. Purification via HPLC provided the title compound. MS (ESI) m/z 444 (M+H)+.

Example 693 phenyl {(3R,4S)-4-(4-fluorophenyl)-1-[(1-methyl-1H-imidazol-4-yl)sulfonyl]pyrrolidin-3-yl}carbamate The title compound was prepared similarly to Example 692 substituting phenyl carbonochloridate for isocyanatobenzene. MS (ESI) m/z 445 (M+H)+.

Example 694

1-(2-chlorophenyl)-3-{(3R,4S)-4-(4-fluorophenyl)-1-[(1-methyl-1-imidazol-4-yl)sulfonyl]pyrrolidin-3-yl}urea The title compound was prepared similarly to Example 692 substituting 1-chloro-2-isocyanatobenzene for isocyanatobenzene. MS (ESI) m/z 478 (M+H)+.

Example 695

N-{(3R,4S)-4-(4-fluorophenyl)-1-[(1-methyl-1H-imidazol-4-yl)sulfonyl]pyrrolidin-3-yl}-5-oxohexanamide The title compound was prepared similarly to the procedure described in Example 242E substituting Example 380A for aniline and substituting 4-acetylbutyric acid for Example 242D. MS (ESI) m/z 437.1 (M+H)+.

Example 696

N-{(3R,4S)-4-(4-fluorophenyl)-1-[(1-methyl-1H-imidazol-4-yl)sulfonyl]pyrrolidin-3-yl}-4-(trifluoromethyl)cyclohexanecarboxamide The title compound was prepared similarly to the procedure described in Example 242E substituting Example 380A for aniline and substituting 4-(trifluoromethyl)cyclohexanecarboxylic acid for Example 242D. MS (ESI) m/z 503.3 (M+H)+.

Example 697 butyl (3S,4R)-4-(4-fluorophenyl)-1-[(1-methyl-1H-imidazol-4-yl)sulfonyl]pyrrolidin-3-yl carbonate

Example 697A

Trans-tert-butyl 3-(butoxycarbonyloxy)-4-(4-fluorophenyl)pyrrolidine-1-carboxylate The title compound was prepared similarly to the procedure described in Example 699A substituting butyl carbonochloridate for 1-isocyanatobutane.

Example 697B

Butyl-trans-4-(4-fluorophenyl)pyrrolidin-3-yl carbonate

The title compound was prepared similarly to the procedure described in Example 699B substituting Example 697A for Example 699A.

Example 697C

Butyl-trans-4-(4-fluorophenyl)-1-[(1-methyl-1H-imidazol-4-yl)sulfonyl]pyrrolidin-3-yl carbonate The title compound was prepared similarly to the procedure described in Example 699C substituting Example 697B for Example 699B. MS (ESI) m/z 426.0 (M+H)$^+$.

Example 698

5,5,5-trifluoro-N-{(3R,4S)-4-(4-fluorophenyl)-1-[(1-methyl-1H-imidazol-4-yl)sulfonyl]pyrrolidin-3-yl}pentanamide The title compound was prepared similarly to the procedure described in Example 242E substituting Example 380A for aniline and substituting 5,5,5-trifluoropentanoic acid for Example 242D. MS (ESI) m/z 463.1 (M+H)$^+$.

Example 699

(3S,4R)-4-(4-fluorophenyl)-1-[(1-methyl-1H-imidazol-4-yl)sulfonyl]pyrrolidin-3-yl butylcarbamate

Example 699A

Trans-tert-butyl 3-(butylcarbamoyloxy)-4-(4-fluorophenyl)pyrrolidine-1-carboxylate To a solution of Example 379A (155 mg, 0.55 mmol) in dichloromethane (1.5 mL) was added triethylamine (167 mg, 1.65 mmol) and 1-isocyanatobutane (109 mg, 1.10 mmol). The solution was stirred at room temperature for 16 hours. The mixture was partitioned between dichloromethane and water. The organic fraction was collected, dried over sodium sulfate, concentrated, and purified by flash chromatography (25% ethyl acetate/hexanes) to provide the title compound.

Example 699B

Trans-4-(4-fluorophenyl)pyrrolidin-3-yl butylcarbamate

To a solution of Example 699A (85.5 mg, 0.23 mmol) in dichloromethane (1 mL) was added trifluoroacetic acid (0.4 mL). The mixture was stirred at room temperature for 1 hour, and was then concentrated to afford title compound.

Example 699C

Trans-4-(4-fluorophenyl)-1-[(1-methyl-1H-imidazol-4-yl)sulfonyl]pyrrolidin-3-yl butylcarbamate To a solution of Example 699B (63 mg, 0.23 mmol) in dichloromethane (1 mL) was added triethylamine (68.2 mg, 0.67 mmol) and 4-dimethylaminopyridine (1.4 mg, 0.011 mmol). The solution was cooled 0° C. To the chilled solution was added 1-methyl-1H-imidazole-4-sulfonyl chloride (42.6 mg, 0.24 mmol) portionwise. This mixture was slowly warmed up to room temperature over 1 hour and stirred at room temperature for 1 hour. The reaction mixture was partitioned with dichloromethane and water. The organic layer was collected, concentrated, and purified via HPLC to provide the title compound. MS (ESI) m/z 425.1 (M+H)$^+$.

Example 700

2,2-difluoro-N-{(3R,4S)-4-(4-fluorophenyl)-1-[(1-methyl-1H-imidazol-4-yl)sulfonyl]pyrrolidin-3-yl}pentanamide The title compound was prepared similarly to the procedure described in Example 242E substituting Example 380A for aniline and substituting 2,2-difluorohexanoic acid for Example 242D. MS (ESI) m/z 459.2 (M+H)$^+$.

Example 701

1-(4-chlorophenyl)-3-{(3R,4S)-4-(4-fluorophenyl)-1-[(1-methyl-1H-imidazol-4-yl)sulfonyl]pyrrolidin-3-yl}urea The title compound was prepared similarly to Example 692 substituting 1-chloro-4-isocyanatobenzene for isocyanatobenzene. MS (ESI) m/z 478 (M+H)$^+$.

Example 702

1-(2-fluorophenyl)-3-{(3R,4S)-4-(4-fluorophenyl)-1-[(1-methyl-1H-imidazol-4-yl)sulfonyl]pyrrolidin-3-yl}urea The title compound was prepared similarly to Example 692 substituting 1-fluoro-2-isocyanatobenzene for isocyanatobenzene. MS (ESI) m/z 462 (M+H)$^+$.

Example 703

1-(3-fluorophenyl)-3-{(3R,4S)-4-(4-fluorophenyl)-1-[(1-methyl-1H-imidazol-4-yl)sulfonyl]pyrrolidin-3-yl}urea The title compound was prepared similarly to Example 692 substituting 1-fluoro-3-isocyanatobenzene for isocyanatobenzene. MS (ESI) m/z 462 (M+H)$^+$.

Example 704

1-(4-fluorophenyl)-3-{(3R,4S)-4-(4-fluorophenyl)-1-[(1-methyl-1H-imidazol-4-yl)sulfonyl]pyrrolidin-3-yl}urea The title compound was prepared similarly to Example 692 substituting 1-fluoro-4-isocyanatobenzene for isocyanatobenzene. MS (ESI) m/z 462 (M+H)$^+$.

Example 705

1-(2-chlorobenzyl)-3-{(3R,4S)-4-(4-fluorophenyl)-1-[(1-methyl-1H-imidazol-4-yl)sulfonyl]pyrrolidin-3-yl}urea The title compound was prepared similarly to Example 692 substituting 1-chloro-2-(isocyanatomethyl)benzene for isocyanatobenzene. MS (ESI) m/z 492 (M+H)$^+$.

Example 706

4,5-dichloro-N-{(3R,4S)-4-(4-fluorophenyl)-1-[(1-methyl-1H-imidazol-4-yl)sulfonyl]pyrrolidin-3-yl}pyridin-2-amine To a stirred solution of Example 322B (100 mg, 0.31 mmol) in dimethylsulfoxide (4 mL) was added 2,4,5-trichloropyridine (112 mg, 0.62 mmol) and sodium tert-butoxide (59 mg, 0.062 mmol). The reaction mixture was heated at 90° C. for 18 hours, then concentrated. Purification via HPLC provided the title compound. MS (ESI) m/z 470.5 (M+H)$^+$.

Example 707

(3R,4S)-4-(4-fluorophenyl)-1-[(1-methyl-1H-imidazol-4-yl)sulfonyl]-N-{[4-(trifluoromethyl)cyclohexyl]methyl}pyrrolidin-3-amine The title compound was prepared similarly to the procedure described in Example 290 substituting Example 696 for Example 242E. MS (ESI) m/z 489.1 (M+H)$^+$.

Example 708

2,2-difluoro-N-{(3R,4S)-4-(4-fluorophenyl)-1-[(1-methyl-1H-imidazol-4-yl)sulfonyl]pyrrolidin-3-yl}hexanamide The title compound was prepared similarly to the procedure described in Example 242E substituting Example 380A for aniline and substituting 2,2-difluorohexanoic acid for Example 242D. MS (ESI) m/z 459.2 (M+H)$^+$.

Example 709

Trans-N-[3,4-difluorophenyl]-1-[(1-methyl-1H-imidazol-4-yl)sulfonyl]-4-(1,3-oxazol-2-yl)pyrrolidin-3-amine

Example 709A (E)-2-(2-nitrovinyl)oxazole

The title compound was prepared similarly to the procedure described in Example 601A substituting oxazole-2-carboxaldehyde for tetrahydrofuran-2-carboxaldehyde. MS (DCI) m/z 141.0 (M+H)$^+$

Example 709B (3R,4S)-1-(1-methyl-1H-imidazol-4-ylsulfonyl)-4-(oxazol-2-yl)pyrrolidin-3-amine The title compound was prepared similarly to the procedures described in Examples 2A-2F substituting Example 709A for (E)-1-methoxy-4-(2-nitrovinyl)benzene.

Example 709C

Trans-N-[3,4-difluorophenyl]-1-[(1-methyl-1H-imidazol-4-yl)sulfonyl]-4-(1,3-oxazol-2-yl)pyrrolidin-3-amine The title compound was prepared similarly to the procedure described in Example 57 substituting Example 709C for Example 14A and substituting 1-bromo-3,4-difluorobenzene for 1-bromo-2-methylbenzene. MS (ESI) m/z 410.1 (M+H)$^+$.

Example 710

N-[4-chloro-3-(trifluoromethyl)phenyl]-1-[(1-methyl-1H-imidazol-4-yl)sulfonyl]-4-(1,3-oxazol-2-yl)pyrrolidin-3-amine The title compound was prepared as described in Example 709C substituting 1-bromo-4-chloro-3-(trifluoromethyl)benzene for 1-bromo-3,4-difluorobenzene. MS (ESI) m/z 476.0 (M+H)$^+$

Example 711

4-{[trans-3-[(4-fluorobenzyl)oxy]-4-(4-fluorophenyl)pyrrolidin-1-yl]sulfonyl}-1-methyl-1H-imidazole The title compound was prepared similarly to the procedure described in Example 625A substituting Example 379C for Example 379A and substituting 4-fluorobenzyl bromide for 1-bromohexane. MS (ESI) m/z 434 (M+H)$^+$.

Example 712

4-{[trans-3-[(3-fluorobenzyl)oxy]-4-(4-fluorophenyl)pyrrolidin-1-yl]sulfonyl}-1-methyl-1H-imidazole The title compound was prepared similarly to the procedure described in Example 625A substituting Example 379C for Example 379A and substituting 3-fluorobenzyl bromide for 1-bromohexane. MS (ESI) m/z 434 (M+H)$^+$.

Example 713

4-{[trans-3-(4-fluorophenyl)-4-{[4-(methylsulfonyl)benzyl]oxy}pyrrolidin-1-yl]sulfonyl}-1-methyl-1H-imidazole The title compound was prepared similarly to the procedure described in Example 625A substituting Example 379C

Example 714

4-{[trans-3-(4-fluorophenyl)-4-{[3-(methylsulfonyl)benzyl]oxy}pyrrolidin-1-yl]sulfonyl}-1-methyl-1H-imidazole The title compound was prepared similarly to the procedure described in Example 625A substituting Example 379C for Example 379A and substituting 3-methylsulfonylbenzyl bromide for 1-bromohexane. MS (ESI) m/z 494 (M+H)+.

Example 715

6-ethoxy-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 620 substituting Example 691 for Example 606. MS (ESI) m/z 447 (M+H)+.

Example 716

N-{(3R,4S)-4-(4-fluorophenyl)-1-[(1-methyl-1H-imidazol-4-yl)sulfonyl]pyrrolidin-3-yl}-6-(propan-2-yloxy)pyrimidin-4-amine The title compound was prepared similarly to the procedure described in Example 620 substituting Example 691 for Example 606 and substituting isopropanol for ethanol. MS (ESI) m/z 461 (M+H)+.

Example 717

6-butoxy-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 620 substituting Example 691 for Example 606 and substituting n-butanol for ethanol. MS (ESI) m/z 473 (M+H)+.

Example 718

N-{(3R,4S)-4-(4-fluorophenyl)-1-[(1-methyl-1H-imidazol-4-yl)sulfonyl]pyrrolidin-3-yl}-6-(2-methylpropoxy)pyrimidin-4-amine The title compound was prepared similarly to the procedure described in Example 620 substituting Example 691 for Example 606 and substituting iso-butanol for ethanol. MS (ESI) m/z 473 (M+H)+.

Example 719

6-(cyclobutyloxy)-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 620 substituting Example 691 for Example 606 and substituting cyclobutanol for ethanol. MS (ESI) m/z 473 (M+H)+.

Example 720

6-(cyclopentyloxy)-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 620 substituting Example 691 for Example 606 and substituting cyclopentanol for ethanol. MS (ESI) m/z 487 (M+H)+.

Example 721

6-(cyclohexyloxy)-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 620 substituting Example 691 for Example 606 and substituting cyclohexanol for ethanol. MS (ESI) m/z 487 (M+H)+.

Example 722

N-{(3R,4S)-4-(4-fluorophenyl)-1-[(1-methyl-1H-imidazol-4-yl)sulfonyl]pyrrolidin-3-yl}-6-phenylpyrimidin-4-amine A microwave vial was charged with Example 722 (50 mg, 0.11 mmol), phenylboronic acid (14 mg, 0.12 mmol), dicyclohexyl(2',6'-dimethoxy-[1,1'-biphenyl]-2-yl)phosphine (4.7 mg, 11 µmol), potassium carbonate (2M, 57 µL, 0.14 mmol)), palladium(II) acetate (1.3 mg, 5.7 µmol), and 1,2-dimethoxyethane (2 mL). The reaction mixture was heated to 100° C. in a microwave (Biotage Initiator™, maximum 400 Watts) for 10 minutes. The reaction mixture was concentrated. Purification via HPLC provided the title compound. MS (ESI) m/z 479 (M+H)+.

Example 723

N-{(3R,4S)-4-(4-fluorophenyl)-1-[(1-methyl-1H-imidazol-4-yl)sulfonyl]pyrrolidin-3-yl}-6-(2-methylphenyl)pyrimidin-4-amine The title compound was prepared similarly to the procedure described in Example 722 substituting o-tolylboronic acid for phenylboronic acid. MS (ESI) m/z 493 (M+H)+.

Example 724

N-{(3R,4S)-4-(4-fluorophenyl)-1-[(1-methyl-1H-imidazol-4-yl)sulfonyl]pyrrolidin-3-yl}-6-(3-methylphenyl)pyrimidin-4-amine The title compound was prepared similarly to the procedure described in Example 722 substituting m-tolylboronic acid for phenylboronic acid. MS (ESI) m/z 493 (M+H)+.

Example 725

N-{(3R,4S)-4-(4-fluorophenyl)-1-[(1-methyl-1H-imidazol-4-yl)sulfonyl]pyrrolidin-3-yl}-6-(4-methylphenyl)pyrimidin-4-amine The title compound was prepared similarly to the procedure described in Example 722 substituting p-tolylboronic acid for phenylboronic acid. MS (ESI) m/z 493 (M+H)+.

Example 726

6-(2-fluorophenyl)-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 722 substituting 2-(fluorophenyl)boronic acid for phenylboronic acid. MS (ESI) m/z 497 (M+H)$^+$.

Example 727

6-(3-fluorophenyl)-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 722 substituting 3-(fluorophenyl)boronic acid for phenylboronic acid. MS (ESI) m/z 497 (M+H)$^+$.

Example 728

6-(4-fluorophenyl)-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 722 substituting 4-(fluorophenyl)boronic acid for phenylboronic acid. MS (ESI) m/z 497 (M+H)$^+$.

Example 729

6-(3-chlorophenyl)-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 722 substituting 3-(chlorophenyl)boronic acid for phenylboronic acid. MS (ESI) m/z 513 (M+H)$^+$.

Example 730

6-(4-chlorophenyl)-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 722 substituting 4-(chlorophenyl)boronic acid for phenylboronic acid. MS (ESI) m/z 513 (M+H)$^+$.

Example 731

4-({(3S,4R)-3-(4-fluorophenyl)-4-[(4-methylbenzyl)oxy]pyrrolidin-1-yl}sulfonyl)-1-methyl-1H-imidazole The title compound was prepared similarly to the procedure described in Example 625A substituting Example 379C for Example 379A and substituting 4-methylbenzyl bromide for 1-bromohexane. MS (ESI) m/z 430 (M+H)$^+$.

Example 732

(3R,4S)-4-(4-fluorophenyl)-1-[(1-methyl-1H-imidazol-4-yl)sulfonyl]-N-(5,5,5-trifluoropentyl)pyrrolidin-3-amine The title compound was prepared similarly to the procedure described in Example 290 substituting Example 698 for Example 242E. MS (ESI) m/z 449.1 (M+H)$^+$.

Example 733

(3R,4S)-N-(2,2-difluorohexyl)-4-(4-fluorophenyl)-1-[(1-methyl-1H-imidazol-4-yl)sulfonyl]pyrrolidin-3-amine The title compound was prepared similarly to the procedure described in Example 290 substituting Example 700 for Example 242E. MS (ESI) m/z 445.1 (M+H)$^+$.

Example 734

(3R,4S)-N-(2,2-difluoropentyl)-4-(4-fluorophenyl)-1-[(1-methyl-1H-imidazol-4-yl)sulfonyl]pyrrolidin-3-amine The title compound was prepared similarly to the procedure described in Example 290 substituting Example 700 for Example 242E. MS (ESI) m/z 431.1 (M+H)$^+$.

Example 735

5,5-difluoro-N-{(3R,4S)-4-(4-fluorophenyl)-1-[(1-methyl-1H-imidazol-4-yl)sulfonyl]pyrrolidin-3-yl}hexanamide To a solution of Example 695 (200 mg, 0.46 mmol) in dichloromethane (2.5 mL) at 0° C. was added diethylaminosulfur trifluoride (258 mg, 1.60 mmol). The reaction mixture stirred at 0° C. for 1 hour and then room tomoperature for 2 days. The reaction mixture was partitioned between dichloromethane and aqueous sodium bicarbonate. The organic fraction was collected, washed with water, concentrated, and purified by HPLC to provide the title compound. MS (ESI) m/z 459.1 (M+H)$^+$.

Example 736

4-fluoro-N-{(3R,4S)-4-(4-fluorophenyl)-1-[(1-methyl-1H-imidazol-4-yl)sulfonyl]pyrrolidin-3-yl}pyridin-2-amine The title compound was prepared similarly to the procedure described in Example 327 substituting 2-chloro-4-fluoropyridine for 1-bromo-3-(trifluoromethyl)benzene. MS (DCI) m/z 420.1 (M+H)$^+$.

Example 737

5-fluoro-N-{(3R,4S)-4-(4-fluorophenyl)-1-[(1-methyl-1H-imidazol-4-yl)sulfonyl]pyrrolidin-3-yl}pyridin-2-amine The title compound was prepared similarly to the procedure described in Example 327 substituting 2-chloro-5-fluoropyridine for 1-bromo-3-(trifluoromethyl)benzene. MS (DCI) m/z 420 (M+H)$^+$.

Example 738

N-{(3R,4S)-4-(4-fluorophenyl)-1-[(1-methyl-1H-imidazol-4-yl)sulfonyl]pyrrolidin-3-yl}-4-oxopentanamide The title compound was prepared similarly to the procedure described in Example 242E substituting Example 380A for aniline and substituting 4-oxopentanoic acid for Example 242D. MS (ESI) m/z 423.0 (M+H)$^+$.

Example 739

(3R,4S)-N-(5,5-difluorohexyl)-4-(4-fluorophenyl)-1-[(1-methyl-1H-imidazol-4-yl)sulfonyl]pyrrolidin-3-amine The title compound was prepared similarly to the procedure described in Example 290 substituting Example 735 for Example 242E. MS (ESI) m/z 445.2 (M+H)$^+$

Example 740

4-chloro-N-[2-({(3R,4S)-4-(4-fluorophenyl)-1-[(1-methyl-1H-imidazol-4-yl)sulfonyl]pyrrolidin-3-yl}oxy)ethyl]aniline

Example 740A

N-(4-fluorophenyl)-2-((trans-4-(4-fluorophenyl)-1-((1-methyl-1H-imidazol-4-yl)sulfonyl)pyrrolidin-3-yl)oxy)acetamide The title compound was prepared similarly to the procedure described in Example 404A substituting 4-fluoroaniline for Example 14A and substituting Example 689D for 2-nitro-5-(trifluoromethyl)benzoic acid.

Example 740B 4-chloro-N-[2-({Trans-4-(4-fluorophenyl)-1-[(1-methyl-1H-imidazol-4-yl)sulfonyl]pyrrolidin-3-yl}oxy)ethyl]aniline The title compound was prepared similarly to the procedure described in Example 404B substituting Example 740A for Example 404A. MS (ESI) m/z 479/481 (3:1) (M+H)$^+$.

Example 741

(3S,4R)-N-[4-fluoro-3-(trifluoromethoxy)phenyl]-1-[(1-methyl-1H-imidazol-4-yl)sulfonyl]-4-(tetrahydro-2H-pyran-2-yl)pyrrolidin-3-amine The title compound was prepared similarly to the procedure described in Example 337G substituting Example 679H for Example 337F and substituting 4-bromo-1-fluoro-2-(trifluoromethoxy)benzene for 1-bromo-3-(trifluoromethyl)benzene. MS (ESI) m/z 493 (M+H)$^+$.

Example 742

1-benzyl-3-{(3R,4S)-4-(4-fluorophenyl)-1-[(1-methyl-1H-imidazol-4-yl)sulfonyl]pyrrolidin-3-yl}urea The title compound was prepared similarly to the procedure described in Example 692 substituting (isocyanatomethyl)benzene for isocyanatobenzene. MS (ESI) m/z 458 (M+H)$^+$.

Example 743

(3R,4S)-N-(4-chloro-3-methylphenyl)-4-(4-fluorophenyl)-1-[(1-methyl-1H-imidazol-4-yl)sulfonyl]pyrrolidin-3-amine The title compound was prepared similarly to Example 327 substituting 1-bromo-4-chloro-3-methylbenzene for 1-bromo-3-(trifluoromethyl)benzene. MS (ESI) m/z 449 (M+H)$^+$.

Example 744

(3R,4S)-4-(4-fluorophenyl)-1-[(1-methyl-1H-imidazol-4-yl)sulfonyl]-N-[3-(2,2,2-trifluoroethoxy)phenyl]pyrrolidin-3-amine The title compound was prepared similarly to Example 327 substituting 1-bromo-3-(2,2,2-trifluoroethoxy)benzene for 1-bromo-3-(trifluoromethyl)benzene. MS (ESI) m/z 499 (M+H)$^+$.

Example 745

(3R,4S)-4-(4-fluorophenyl)-N-[4-fluoro-3-(pyridin-3-yl)phenyl]-1-[(1-methyl-1H-imidazol-4-yl)sulfonyl]pyrrolidin-3-amine A solution of Example 352 (100 mg, 0.22 mmol), pyridine-3-ylboronic acid (41 mg, 0.33 mmol), tricyclohexylphosphine (6.2 mg, 22 µmol), potassium phosphate (1.2 M (aq.), 0.36 mL, 442 mmol)) and palladium(II) acetate (10 mg, 11 µmol) in dioxane (2 mL) was stirred at 100° C. for 18 hours. The reaction mixture was concentrated. Purification via HPLC provided the title compound. MS (ESI) m/z 496 (M+H)$^+$.

Example 746

(3R,4S)-4-(4-fluorophenyl)-N-[4-fluoro-3-(pyridin-4-yl)phenyl]-1-[(1-methyl-1H-imidazol-4-yl)sulfonyl]pyrrolidin-3-amine The title compound was prepared similarly to the procedure described in Example 745 substituting pyridin-4-ylboronic acid for pyridine-3-ylboronic acid. MS (ESI) m/z 496 (M+H)$^+$.

Example 747

(3R,4S)-N-(4-fluoro-3-methylphenyl)-4-(4-fluorophenyl)-1-[(1-methyl-1H-imidazol-4-yl)sulfonyl]pyrrolidin-3-amine The title compound was prepared similarly to the procedure described in Example 327 substituting 1-bromo-4- fluoro-3-methylbenzene for 1-bromo-3-(trifluoromethyl)benzene. MS (ESI) m/z 433 (M+H)⁺.

Example 748

5-fluoro-N-{(3R,4S)-4-(4-fluorophenyl)-1-[(1-methyl-1H-imidazol-4-yl)sulfonyl]pyrrolidin-3-yl}-4-methylpyridin-2-amine The title compound was prepared similarly to the procedure described in Example 327 substituting 2-bromo-5-fluoro-4-methylpyridine for 1-bromo-3-(trifluoromethyl)benzene. MS (ESI) m/z 434 (M+H)⁺.

Example 749

(3R,4S)-4-(4-fluorophenyl)-N-[4-fluoro-3-(pyrimidin-5-yl)phenyl]-1-[(1-methyl-1H-imidazol-4-yl)sulfonyl]pyrrolidin-3-amine The title compound was prepared similarly to the procedure described in Example 745 substituting pyrimidin-5-ylboronic acid for pyridine-3-ylboronic acid. MS (ESI) m/z 497 (M+H)⁺.

Example 750

N-{(3R,4S)-4-(4-fluorophenyl)-1-[(1-methyl-1H-imidazol-4-yl)sulfonyl]pyrrolidin-3-yl}-3,4'-bipyridin-2'-amine The title compound was prepared similarly to the procedure described in Example 745 substituting Example 759 for Example 352. MS (ESI) m/z 479 (M+H)⁺.

Example 751

N-{(3R,4S)-4-(4-fluorophenyl)-1-[(1-methyl-1H-imidazol-4-yl)sulfonyl]pyrrolidin-3-yl}-4,4'-bipyridin-2-amine The title compound was prepared similarly to the procedure described in Example 745 substituting Example 759 for Example 352 and substituting pyridin-4-ylboronic acid for pyridine-3-ylboronic acid. MS (ESI) m/z 479 (M+H)⁺.

Example 752

4-({(3S,4R)-4-(4-fluorophenyl)-1-[(1-methyl-1H-imidazol-4-yl)sulfonyl]pyrrolidin-3-yl}oxy)-6-(trifluoromethyl)pyrimidine The title compound was prepared similarly to the procedure described in Example 379D substituting 4-bromo-6-(trifluoromethyl)pyrimidine for 2-fluoro-4-(trifluoromethyl)pyridine. MS (ESI) m/z 472 (M+H)⁺.

Example 753

N-[(3R,4S)-4-chloro-3-(trifluoromethyl)phenyl]-1-[(1-methyl-1H-imidazol-4-yl)sulfonyl]-4-(1,3-oxazol-4-yl)pyrrolidin-3-amine Example 753A (E)-4-(2-nitrovinyl)oxazole The title compound was prepared similarly to the procedure described in Example 601A substituting 4-oxazolecarboxaldehyde for tetrahydrofuran-2-carboxaldehyde.

Example 753B (trans)-1-(1-methyl-1H-imidazol-4-ylsulfonyl)-4-(oxazol-4-yl)pyrrolidin-3-amine The title compound was prepared similarly to the procedures described in Example 2A-2F substituting Example 753A for (E)-1-methoxy-4-(2-nitrovinyl)benzene.

Example 753C

N-[(3R,4S)-4-chloro-3-(trifluoromethyl)phenyl]-1-[(1-methyl-1H-imidazol-4-yl)sulfonyl]-4-(1,3-oxazol-4-yl)pyrrolidin-3-amine The title compound was prepared similarly to the procedure described in Example 57 substituting Example 753B for Example 14a and substituting 1-bromo-4-chloro-3-(trifluoromethyl)benzene for 1-bromo-2-methylbenzene. MS (ESI) m/z 476.0 (M+H)⁺.

Example 754

4,4-difluoro-N-{(3R,4S)-4-(4-fluorophenyl)-1-[(1-methyl-1H-imidazol-4-yl)sulfonyl]pyrrolidin-3-yl}pentanamide The title compound was prepared similarly to the procedure described in Example 735 substituting Example 738 for Example 695. MS (ESI) m/z 445.1 (M+H)⁺.

Example 755

(3R,4S)-N-(3,4-difluorophenyl)-1-[(1,2-dimethyl-1H-imidazol-4-yl)sulfonyl]-4-(4-fluorophenyl)pyrrolidin-3-amine Example 755A (3R,4S)-1-(1,2-dimethyl-1H-imidazol-4-ylsulfonyl)-4-(4-fluorophenyl)pyrrolidin-3-amine hydrochloride The title compound was prepared similarly to the procedures described in Example 2A-2F substituting (E)-1-fluoro-4-(2-nitrovinyl)benzene for (E)-1-methoxy-4-(2-nitrovinyl)benzene and substituting 1,2-dimethyl-1H-imidazole-4-sulfonyl chloride for 1-methyl-1H-imidazole-4-sulfonyl chloride.

Example 755B (3R,4S)-1-(1,2-dimethyl-1H-imidazol-4-ylsulfonyl)-4-(4-fluorophenyl)pyrrolidin-3-amine The title compound was prepared similarly to the procedure described in Example 380A substituting Example 755A for Example 322B. MS (ESI) m/z 339.1 (M+H)⁺.

Example 755C (3R,4S)-N-(3,4-difluorophenyl)-1-[(1,2-dimethyl-1H-imidazol-4-yl)sulfonyl]-4-(4-fluorophenyl)pyrrolidin-3-amine The title compound was prepared similarly to the procedure described in Example 337G substituting Example 755B for Example 337F and substituting 4-bromo-1,2-difluorobenzene for 1-bromo-3-(trifluoromethyl)benzene. MS (ESI) m/z 451.2 (M+H)+.

Example 756

(3R,4S)-1-[(1,2-dimethyl-1H-imidazol-4-yl)sulfonyl]-4-(4-fluorophenyl)-N-[4-fluoro-3-(trifluoromethyl)phenyl]pyrrolidin-3-amine The title compound was prepared similarly to the procedure described in Example 337G substituting Example 755B for Example 337F and substituting 4-bromo-1-fluoro-2-(trifluoromethyl)benzene for 1-bromo-3-(trifluoromethyl)benzene. MS (ESI) m/z 501.1 (M+H)+.

Example 757

(3R,4S)-N-(3,4-difluorophenyl)-1-[(1,2-dimethyl-1H-imidazol-5-yl)sulfonyl]-4-(4-fluorophenyl)pyrrolidin-3-amine

Example 757A (3R,4S)-1-(1,2-dimethyl-1H-imidazol-5-ylsulfonyl)-4-(4-fluorophenyl)pyrrolidin-3-amine hydrochloride The title compound was prepared similarly to the conditions described in Example 2A-2F substituting (E)-1-fluoro-4-(2-nitrovinyl)benzene for (E)-1-methoxy-4-(2-nitrovinyl)benzene and substituting 1,2-dimethyl-1H-imidazole-5-sulfonyl chloride for 1-methyl-1H-imidazole-4-sulfonyl chloride.

Example 757B (3R,4S)-1-(1,2-dimethyl-1H-imidazol-5-ylsulfonyl)-4-(4-fluorophenyl)pyrrolidin-3-amine The title compound was prepared similarly to the procedure described in Example 380A substituting Example 757A for Example 322B. MS (ESI) m/z 339.1 (M+H)+.

Example 757C (3R,4S)-N-(3,4-difluorophenyl)-1-[(1,2-dimethyl-1H-imidazol-5-yl)sulfonyl]-4-(4-fluorophenyl)pyrrolidin-3-amine The title compound was prepared similarly to the procedure described in Example 337G substituting Example 757B for Example 337F and substituting 4-bromo-1,2-difluorobenzene for 1-bromo-3-(trifluoromethyl)benzene. MS (ESI) m/z 451.2 (M+H)+

Example 758

(3R,4S)-1-[(1,2-dimethyl-1H-imidazol-5-yl)sulfonyl]-4-(4-fluorophenyl)-N-[4-fluoro-3-(trifluoromethyl)phenyl]pyrrolidin-3-amine The title compound was prepared similarly to the procedure described in Example 337G substituting Example 757B for Example 337F and substituting 4-bromo-1-fluoro-2-(trifluoromethyl)benzene for 1-bromo-3-(trifluoromethyl)benzene. MS (ESI) m/z 501.1 (M+H)+

Example 759

4-chloro-N-{(3R,4S)-4-(4-fluorophenyl)-1-[(1-methyl-1H-imidazol-4-yl)sulfonyl]pyrrolidin-3-yl}pyridin-2-amine The title compound was prepared similarly to the procedure described in Example 327 substituting 2-bromo-4-chloropyrdine for 1-bromo-3-(trifluoromethyl)benzene. MS (ESI) m/z 436 (M+H)+.

Example 760

5-chloro-N-[(3R,4S)-1-[(1,2-dimethyl-1H-imidazol-4-yl)sulfonyl]-4-(4-fluorophenyl)pyrrolidin-3-yl]-4-(trifluoromethyl)pyridin-2-amine The title compound was prepared similarly to the procedure described in Example 848 substituting Example 755B for Example 679H. MS (ESI) m/z 518.1 (M+H)+

Example 761

Trans-chloro-4-(trifluoromethyl)benzyl]-4-(3-fluoropyridin-2-yl)-1-[(1-methyl-1H-imidazol-4-yl)sulfonyl]pyrrolidin-3-amine

Example 761A

Trans-4-(3-fluoropyridin-2-yl)-1-(1-methyl-1H-imidazol-4-ylsulfonyl)pyrrolidin-3-amine hydrochloride The title compound was prepared similarly to the procedures described in Examples 2A-2F substituting (E)-3-fluoro-2-(2-nitrovinyl)pyridine for (E)-1-methoxy-4-(2-nitrovinyl)benzene.

Example 761B

Trans-4-(3-fluoropyridin-2-yl)-1-(1-methyl-1H-imidazol-4-ylsulfonyl)pyrrolidin-3-amine The title compound was prepared similarly to the procedure described in Example 380A substituting Example 761A for Example 322B.

Example 761C

Trans-N-[2-chloro-4-(trifluoromethyl)benzyl]-4-(3-fluoropyridin-2-yl)-1-[(1-methyl-1H-imidazol-4-yl)sulfonyl]pyrrolidin-3-amine The title compound was prepared similarly to the procedure described in Example 354E substituting 2-chloro-4-(trifluoromethyl)benzaldehyde for 4-chlorobenzaldehyde, Example 761 A for 354D amine. MS (ESI) m/z 517.9 (M+H)+

Example 762

Trans-4-(3-fluoropyridin-2-yl)-N-hexyl-1-[(1-methyl-1H-imidazol-4-yl)sulfonyl]pyrrolidin-3-amine The title compound was prepared similarly to the procedure described in Example 354E substituting hexanal for 4-chlorobenzaldehyde and substituting Example 761 A for 354D amine. MS (ESI) m/z 410.1 (M+H)+.

Example 763

Trans-4-(3-fluoropyridin-2-yl)-N,N-dihexyl-1-[(1-methyl-1H-imidazol-4-yl)sulfonyl]pyrrolidin-3-amine The title compound was prepared similarly to the procedure described in Example 354E substituting hexanal for 4-chlorobenzaldehyde and substituting Example 761A for 354D. MS (ESI) m/z 494.1 (M+H)+

Example 764

Trans-4-(3-fluoropyridin-2-yl)-1-[(1-methyl-1H-imidazol-4-yl)sulfonyl]-N,N-dipentylpyrrolidin-3-amine The title compound was prepared similarly to the procedure described in Example 354E substituting pentanal for 4-chlorobenzaldehyde and substituting Example 761 A for 354D. MS (ESI) m/z 466.1 (M+H)+

Example 765

Trans-4-(3-fluoropyridin-2-yl)-1-[(1-methyl-1H-imidazol-4-yl)sulfonyl]-N-pentylpyrrolidin-3-amine The title compound was prepared similarly to the procedure described in Example 354E substituting pentanal for 4-chlorobenzaldehyde and substituting Example 761 A for 354D. MS (ESI) m/z 396.1 (M+H)+

Example 766

Trans-N-(3,4-difluorophenyl)-4-(3-fluoropyridin-2-yl)-1-[(1-methyl-1H-imidazol-4-yl)sulfonyl]pyrrolidin-3-amine The title compound was prepared similarly to the procedure described in Example 337G substituting Example 761 B for Example 337F and substituting 4-bromo-1,2-difluorobenzene for 1-bromo-3-(trifluoromethyl)benzene. MS (ESI) m/z 438.0 (M+H)+

Example 767

Trans-4-(3-fluoropyridin-2-yl)-N-[4-fluoro-3-(trifluoromethyl)phenyl]-1-[(1-methyl-1H-imidazol-4-yl)sulfonyl]pyrrolidin-3-amine The title compound was prepared similarly to the procedure described in Example 337G substituting Example 761B for Example 337F and substituting 4-bromo-1-fluoro-2-(trifluoromethyl)benzene for 1-bromo-3-(trifluoromethyl) benzene. MS (ESI) m/z 488.0 (M+H)+

Example 768

Trans-4-(3-fluoropyridin-2-yl)-N-[4-fluoro-3-(trifluoromethoxy)phenyl]-1-[(1-methyl-1H-imidazol-4-yl)sulfonyl]pyrrolidin-3-amine The title compound was prepared similarly to the procedure described in Example 337G substituting Example 761B for Example 337F and substituting 4-bromo-1-fluoro-2-(trifluoromethoxy)benzene for 1-bromo-3-(trifluoromethyl) benzene. MS (ESI) m/z 504.0 (M+H)+

Example 769

5-fluoro-N-{trans-4-(3-fluoropyridin-2-yl)-1-[(1-methyl-1H-imidazol-4-yl)sulfonyl]pyrrolidin-3-yl}-4-methylpyridin-2-amine The title compound was prepared similarly to the procedure described in Example 337G substituting Example 761B for Example 337F and 2-bromo-5-fluoro-4-methylpyridine for 1-bromo-3-(trifluoromethyl)benzene. MS (ESI) m/z 435.1 (M+H)+

Example 770

N-{Trans-4-(3-fluoropyridin-2-yl)-1-[(1-methyl-1H-imidazol-4-yl)sulfonyl]pyrrolidin-3-yl}-6-(trifluoromethyl)pyrimidin-4-amine The title compound was prepared similarly to the procedure described in Example 337G substituting Example 761B for Example 337F and substituting 4-bromo-6-(trifluoromethyl)pyrimidine for 1-bromo-3-(trifluoromethyl)benzene. MS (ESI) m/z 472.0 (M+H)+

Example 771

Trans-N-(3-chloro-4-fluorophenyl)-4-(3-fluoropyridin-2-yl)-1-[(1-methyl-1H-imidazol-4-yl)sulfonyl]pyrrolidin-3-amine The title compound was prepared similarly to the procedure described in Example 337G substituting Example 761B for Example 337F and substituting 4-bromo-2-chloro-1-fluorobenzene for 1-bromo-3-(trifluoromethyl)benzene. MS (ESI) m/z 453.9 (M+H)+

Example 772

6-chloro-N-{trans-4-(3-fluoropyridin-2-yl)-1-[(1-methyl-1H-imidazol-4-yl)sulfonyl]pyrrolidin-3-yl}pyrimidin-4-amine To a microwave vial charged with Example 761B (100 mg, 0.31 mmol) and methanol (1 mL) was added triethylamine (62.2 mg, 0.62 mmol) and 4,6-dichloropyrimidine (137 mg, 0.93 mmol). The reaction mixture was stirred in a microwave at 120° C. for 1 hour. The mixture was concentrated and purified via HPLC to afford the title compound. MS (ESI) m/z 438.0 (M+H)+

Example 773

(3R,4S)-N-[3-(benzyloxy)phenyl]-1-[(1-methyl-1H-imidazol-4-yl)sulfonyl]-4-phenylpyrrolidin-3-amine The title compound was prepared similarly to the procedure described in Example 327 substituting Example 574A for Example 322B and substituting 1-(benzyloxy)-3-bromobenzene for 1-bromo-3-(trifluoromethyl)benzene. MS (APCI) m/z 489 (M+H)+.

Example 774

6-(benzyloxy)-N-{(3R,4S)-4-(4-fluorophenyl)-1-[(1-methyl-1H-imidazol-4-yl)sulfonyl]pyrrolidin-3-yl}pyrimidin-4-amine The title compound was prepared similarly to the procedure described in Example 327 substituting 4-(benzyloxy)-6-bromopyrimidine for 1-bromo-3-(trifluoromethyl)benzene. MS (ESI) m/z 509 (M+H)+.

Example 775

Trans-N-(4-fluoro-3-methylphenyl)-4-(3-fluoropyridin-2-yl)-1-[(1-methyl-1H-imidazol-4-yl)sulfonyl] pyrrolidin-3-amine The title compound was prepared similarly to the procedure described in Example 337G substituting Example 761B for Example 337F and substituting 4-bromo-1-fluoro-2-methylbenzene for 1-bromo-3-(trifluoromethyl)benzene. MS (ESI) m/z 434.0 (M+H)+

Example 776

4-(benzyloxy)-5-fluoro-N-{(3R,4S)-1-[(1-methyl-1H-imidazol-4-yl)sulfonyl]-4-phenylpyrrolidin-3-yl}pyridin-2-amine Example 776A 4-(benzyloxy)-2-bromo-5-fluoropyridine To a stirred solution of 2-bromo-5-fluoropyridin-4-ol (100 mg, 0.52 mmol) in dimethylformamide (4 mL) was added (bromomethyl)benzene (89 mg, 0.52 mmol) and potassium carbonate (144 mg, 1.0 mmol). The reaction mixture was stirred at 60° C. for 3 hours. Water and EtOAc were added. The organic fraction was collected and concentrated. Purification via flash chromatography (0-50% EtOAc/heptanes) provided the title compound.

Example 776B 4-(benzyloxy)-5-fluoro-N-{(3R,4S)-1-[(1-methyl-1H-imidazol-4-yl)sulfonyl]-4-phenylpyrrolidin-3-yl}pyridin-2-amine The title compound was prepared similarly to the procedure described in Example 327 substituting Example 574A for Example 322B and substituting Example 776A for 1-bromo-3-(trifluoromethyl)benzene. MS (ESI) m/z 508 (M+H)+.

Example 777

(3R,4S)-1-[(1-methyl-1H-imidazol-4-yl)sulfonyl]-4-phenyl-N-[3-(piperidin-4-yl)phenyl]pyrrolidin-3-amine The title compound was prepared similarly to the procedure described in Example 327 substituting Example 574A for Example 322B and substituting tert-butyl 4-(3-bromophenyl)piperidine-1-carboxylate for 1-bromo-3-(trifluoromethyl)benzene followed by dissolving the crude mixture in dichloromethane (5 mL) and treating the crude mixture with HCl (4 M, 3 mL) and purifying via HPLC. MS (APCI) m/z 466 (M+H)+.

Example 778

6-(azetidin-3-ylmethoxy)-N-{(3R,4S)-4-(4-fluorophenyl)-1-[(1-methyl-1H-imidazol-4-yl)sulfonyl] pyrrolidin-3-yl}pyrimidin-4-amine Tert-butyl 3-((6-((3R,4S)-4-(4-fluorophenyl)-1-(1-methyl-1H-imidazol-4-ylsulfonyl)pyrrolidin-3-ylamino)pyrimidin-4-yloxy)methyl)azetidine-1-carboxylate was prepared similarly to the procedure described in Example 691 substituting Example 606 for Example 691 and substituting tert-butyl 3-(hydroxymethyl)azetidine-1-carboxylate (3 eq.) for ethanol and adding tert-butanol (5 mL). The reaction mixture was concentrated, dissolved in dichloromethane, and treated with HCl (4 M, 10 eq.). Purification via HPLC provided the title compound. MS (ESI) m/z 488 (M+H)+.

Example 779

N-{(3R,4S)-4-(4-fluorophenyl)-1-[(1-methyl-1H-imidazol-4-yl)sulfonyl]pyrrolidin-3-yl}-6-(pyrrolidin-3-ylmethoxy)pyrimidin-4-amine The title compound was prepared similarly to the procedure described in Example 778 substituting tert-butyl-3-hydroxymethyl-pyrrolidine-1-carboxylate for tert-butyl 3-(hydroxymethyl)azetidine-1-carboxylate. MS (ESI) m/z 502 (M+H)+.

Example 780

N-{(3R,4S)-4-(4-fluorophenyl)-1-[(1-methyl-1H-imidazol-4-yl)sulfonyl]pyrrolidin-3-yl}-6-(pyrrolidin-2-ylmethoxy)pyrimidin-4-amine The title compound was prepared similarly to the procedure described in Example 778 substituting tert-butyl 2-(hydroxymethyl)pyrrolidine-1-carboxylate for tert-butyl 3-(hydroxymethyl)azetidine-1-carboxylate. MS (ESI) m/z 502 (M+H)+.

Example 781 trans-1-[(1-methyl-1H-imidazol-4-yl)sulfonyl]-N-(3-methylphenyl)-4-(tetrahydro-2H-pyran-3-yl)pyrrolidin-3-amine Example 781A (E)-3-(2-nitrovinyl)tetrahydro-2H-pyran The title compound was prepared similarly to the procedure described in Example 307A substituting tetrahydropyran-3-carbaldehyde for 2-pyridinecarboxaldeyde.

Example 781B trans-1-(1-methyl-1H-imidazol-4-ylsulfonyl)-4-((S)-tetrahydro-2H-pyran-3-yl)pyrrolidin-3-amine The title compound was prepared as an HCl salt similarly to the procedures described in Examples 2A-2F substituting Example 781A for (E)-1-methoxy-4-(2-nitrovinyl)benzene.

Example 781C trans-1-[(1-methyl-1H-imidazol-4-yl)sulfonyl]-N-(3-methylphenyl)-4-(tetrahydro-2H-pyran-3-yl)pyrrolidin-3-amine The title compound was prepared similarly to the procedure described in Example 327 substituting Example 781B for Example 322B and substituting 1-bromo-3-methylbenzene for 1-bromo-3-(trifluoromethyl)benzene. MS (ESI) m/z 405 (M+H)$^+$.

Example 782 trans-1-[(1-methyl-1H-imidazol-4-yl)sulfonyl]-4-(tetrahydro-2H-pyran-3-yl)-N-[3-(trifluoromethyl)phenyl]pyrrolidin-3-amine The title compound was prepared similarly to the procedure described in Example 327 substituting Example 781B for Example 322B. MS (ESI) m/z 459 (M+H)$^+$.

Example 783 trans-N-(3-chlorophenyl)-1-[(1-methyl-1H-imidazol-4-yl)sulfonyl]-4-(tetrahydro-2H-pyran-3-yl)pyrrolidin-3-amine The title compound was prepared similarly to the procedure described in Example 327 substituting Example 781B for Example 322B and substituting 1-bromo-3-chlorobenzene for 1-bromo-3-(trifluoromethyl)benzene. MS (ESI) m/z 425 (M+H)$^+$.

Example 784 trans-1-[(1-methyl-1H-imidazol-4-yl)sulfonyl]-4-[(3S)-tetrahydro-2H-pyran-3-yl]-N-[3-(trifluoromethoxy)phenyl]pyrrolidin-3-amine The title compound was prepared similarly to the procedure described in Example 327 substituting Example 781B for Example 322B and substituting 1-bromo-3-(trifluoromethoxy)benzene for 1-bromo-3-(trifluoromethyl)benzene. MS (ESI) m/z 475 (M+H)$^+$.

Example 785 trans-1-[(1-methyl-1H-imidazol-4-yl)sulfonyl]-4-[(3S)-tetrahydro-2H-pyran-3-yl]-N-[3-(2,2,2-trifluoroethoxy)phenyl]pyrrolidin-3-amine The title compound was prepared similarly to the procedure described in Example 327 substituting Example 781B for Example 322B and substituting 1-bromo-3-(2,2,2-trifluoroethoxy)benzene for 1-bromo-3-(trifluoromethyl)benzene. MS (ESI) m/z 489 (M+H)$^+$.

Example 786 trans-1-[(1-methyl-1H-imidazol-4-yl)sulfonyl]-N-(3-phenoxyphenyl)-4-[(3S)-tetrahydro-2H-pyran-3-yl]pyrrolidin-3-amine The title compound was prepared similarly to the procedure described in Example 327 substituting Example 781B for Example 322B and substituting 1-bromo-3-phenoxybenzene for 1-bromo-3-(trifluoromethyl)benzene. MS (ESI) m/z 483 (M+H)$^+$.

Example 787 trans-N-(biphenyl-3-yl)-1-[(1-methyl-1H-imidazol-4-yl)sulfonyl]-4-[(3S)-tetrahydro-2H-pyran-3-yl]pyrrolidin-3-amine The title compound was prepared similarly to the procedure described in Example 327 substituting Example 781B for Example 322B and substituting 3-bromo-1,1'-biphenyl for 1-bromo-3-(trifluoromethyl)benzene. MS (ESI) m/z 467 (M+H)$^+$.

Example 788

Trans-N-[4-fluoro-3-(trifluoromethoxy)phenyl]-1-[(1-methyl-1H-imidazol-4-yl)sulfonyl]-4-[(3S)-tetrahydro-2H-pyran-3-yl]pyrrolidin-3-amine The title compound was prepared similarly to the procedure described in Example 327 substituting Example 781B for Example 322B and substituting 4-bromo-1-fluoro-2-(trifluoromethoxy)benzene for 1-bromo-3-(trifluoromethyl)benzene. MS (ESI) m/z 493 (M+H)$^+$.

Example 789

Trans-N-(3-chloro-4-fluorophenyl)-1-[(1-methyl-1H-imidazol-4-yl)sulfonyl]-4-[(3S)-tetrahydro-2H-pyran-3-yl]pyrrolidin-3-amine The title compound was prepared similarly to the procedure described in Example 327 substituting Example 781B for Example 322B and substituting 4-bromo-1-fluoro-2-chlorobenzene for 1-bromo-3-(trifluoromethyl)benzene. MS (ESI) m/z 443 (M+H)$^+$.

Example 790

Trans-N-(4-fluoro-3-methylphenyl)-1-[(1-methyl-1H-imidazol-4-yl)sulfonyl]-4-[(3S)-tetrahydro-2H-pyran-3-yl]pyrrolidin-3-amine The title compound was prepared similarly to the procedure described in Example 327 substituting Example 781B for Example 322B and substituting 4-bromo-1-fluoro-2-methylbenzene for 1-bromo-3-(trifluoromethyl)benzene. MS (ESI) m/z 423 (M+H)$^+$.

Example 791

Trans-N-[4-fluoro-3-(trifluoromethyl)phenyl]-1-[(1-methyl-1H-imidazol-4-yl)sulfonyl]-4-[(3S)-tetrahydro-2H-pyran-3-yl]pyrrolidin-3-amine The title compound was prepared similarly to the procedure described in Example 327 substituting Example 781B for Example 322B and substituting 4-bromo-1-fluoro-2-

Example 792

Trans-N-[4-chloro-3-(trifluoromethyl)phenyl]-1-[(1-methyl-1H-imidazol-4-yl)sulfonyl]-4-[(3S)-tetrahydro-2H-pyran-3-yl]pyrrolidin-3-amine The title compound was prepared similarly to the procedure described in Example 327 substituting Example 781B for Example 322B and substituting 4-bromo-1-chloro-2-(trifluoromethyl)benzene for 1-bromo-3-(trifluoromethyl)benzene. MS (ESI) m/z 509 (M+H)$^+$.

Example 793

Trans-N-[4-chloro-3-(trifluoromethoxy)phenyl]-1-[(1-methyl-1H-imidazol-4-yl)sulfonyl]-4-[(3S)-tetrahydro-2H-pyran-3-yl]pyrrolidin-3-amine The title compound was prepared similarly to the procedure described in Example 327 substituting Example 781B for Example 322B and substituting 4-bromo-1-chloro-2-(trifluoromethoxy)benzene for 1-bromo-3-(trifluoromethyl)benzene. MS (ESI) m/z 497 (M+H)$^+$.

Example 794

Trans-N-[3-(benzyloxy)phenyl]-1-[(1-methyl-1H-imidazol-4-yl)sulfonyl]-4-[(3S)-tetrahydro-2H-pyran-3-yl]pyrrolidin-3-amine The title compound was prepared similarly to the procedure described in Example 327 substituting Example 781B for Example 322B and substituting 1-(benzyloxy)-3-bromobenzene for 1-bromo-3-(trifluoromethyl)benzene. MS (ESI) m/z 497 (M+H)$^+$.

Example 795

5-fluoro-N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine To a solution of Example 368 (0.12 g, 0.26 mmol) in dimethylformamide (0.4 mL) was added 1-(chloromethyl)-4-fluoro-1,4-diazabicyclo[2.2.2]octane-1,4-diium tetrafluoroborate (SelectFluo, 91 mg, 0.26 mmol). The mixture was stirred at room temperature for 16 hours. More 1-(chloromethyl)-4-fluoro-1,4-diazabicyclo[2.2.2]octane-1,4-diium tetrafluoroborate (60 mg) was added. The mixture was stirred at room temperature for another 16 hours, concentrated, and purified by HPLC to afford the title compound. MS (ESI) m/z 488 (M+H)$^+$.

Example 796

3-fluoro-N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine To a solution of Example 368 (0.12 g, 0.26 mmol) in dimethylformamide (0.4 mL) was added 1-(chloromethyl)-4-fluoro-1,4-diazabicyclo[2.2.2]octane-1,4-diium tetrafluoroborate (SelectFluo, 91 mg, 0.26 mmol). The mixture was stirred at room temperature for 16 hours. More 1-(chloromethyl)-4-fluoro-1,4-diazabicyclo[2.2.2]octane-1,4-diium tetrafluoroborate (60 mg) was added. The mixture was stirred at room temperature for another 16 hours, concentrated, and purified by HPLC to afford the title compound. MS (ESI) m/z 488 (M+H)$^+$.

Example 797

N-(2,2-difluoroethyl)-2-({(3R,4S)-4-(4-fluorophenyl)-1-[(1-methyl-1H-imidazol-4-yl)sulfonyl]pyrrolidin-3-yl}oxy)acetamide The title compound was prepared similarly to the procedure described in Example 242E substituting 2,2-difluoroethanamine for aniline and substituting Example 689D for Example 242D. MS (ESI) m/z 447.0 (M+H)$^+$

Example 798

Trans-4-(3-fluoropyridin-2-yl)-1-[(1-methyl-1H-imidazol-4-yl)sulfonyl]-N-[3-(trifluoromethyl)phenyl]pyrrolidin-3-amine The title compound was prepared similarly to the procedure described in Example 337G substituting Example 761B for Example 337F. MS (ESI) m/z 470.0 (M+H)$^+$

Example 799

Trans-4-(3-fluoropyridin-2-yl)-1-[(1-methyl-1H-imidazol-4-yl)sulfonyl]-N-[3-(trifluoromethoxy)phenyl]pyrrolidin-3-amine The title compound was prepared similarly to the procedure described in Example 337G substituting Example 761B for Example 337F and substituting 1-bromo-3-(trifluoromethoxy)benzene for 1-bromo-3-(trifluoromethyl)benzene. MS (ESI) m/z 486.0 (M+H)$^+$

Example 800

Trans-4-(3-fluoropyridin-2-yl)-1-[(1-methyl-1H-imidazol-4-yl)sulfonyl]-N-[3-(2,2,2-trifluoroethoxy)phenyl]pyrrolidin-3-amine The title compound was prepared similarly to the procedure described in Example 337G substituting Example 761B for Example 337F and substituting 1-bromo-3-(2,2,2-trifluoroethoxy)benzene for 1-bromo-3-(trifluoromethyl)benzene. MS (ESI) m/z 500.0 (M+H)$^+$

Example 801

(3R,4S)-4-(4-fluorophenyl)-1-[(1-methyl-1H-imidazol-4-yl)sulfonyl]-N-[3-(pyridin-2-yl)phenyl]pyrrolidin-3-amine The title compound was prepared similarly to Example 327 substituting 2-(3-bromophenyl)pyridine for 1-bromo-3-(trifluoromethyl)benzene. MS (ESI) m/z 478 (M+H)$^+$.

Example 802

(3R,4S)-1-[(1-methyl-1H-imidazol-4-yl)sulfonyl]-4-phenyl-N-[3-(pyridin-2-yl)phenyl]pyrrolidin-3-amine The title compound was prepared similarly to Example 327 substituting Example 574A for Example 322B and substituting 2-(3-bromophenyl)pyridine. MS (ESI) m/z 460 (M+H)$^+$.

Example 803

5-fluoro-N-{(3R,4S)-1-[(1-methyl-1H-imidazol-4-yl)sulfonyl]-4-phenylpyrrolidin-3-yl}-4-(2,2,2-trifluoroethoxy)pyridin-2-amine

Example 803A 2-bromo-5-fluoro-4-(2,2,2-trifluoroethoxy)pyridine

A microwave vial was charged with 2-bromo-5-fluoropyridin-4-ol (1 g, 5.2 mmol), 1,1,1-trifluoro-2-iodoethane (3.3 g, 15.6 mmol), potassium carbonate (1.44 g, 10.4 mmol), and dimethylsulfoxide (10 mL). The reaction mixture was stirred in a microwave (Biotage Initiator™, maximum 400 Watts) at 150° C. for 1 hour. The reaction mixture was partitioned between water and EtOAc. The organic fraction was collected and concentrated. Flash chromatography (0-50% EtOAc/heptanes) provided the title compound.

Example 803B 5-fluoro-N-{(3R,4S)-1-[(1-methyl-1H-imidazol-4-yl)sulfonyl]-4-phenylpyrrolidin-3-yl}-4-(2,2,2-trifluoroethoxy)pyridin-2-amine The title compound was prepared similarly to the procedure described in Example 327 substituting Example 574A for Example 322B and substituting Example 803A for 1-bromo-3-(trifluoromethyl)benzene. MS (ESI) m/z 500 (M+H)$^+$.

Example 804

5-Chloro-N-{trans-4-(3-fluoropyridin-2-yl)-1-[(1-methyl-1H-imidazol-4-yl)sulfonyl]pyrrolidin-3-yl}-4-(trifluoromethyl)pyridin-2-amine The title compound was prepared as described in Example 848 substituting Example 761B for Example 679H. MS (ESI) m/z 505.0 (M+H)$^+$

Example 805

Trans-N-(3-fluorophenyl)-4-(3-fluoropyridin-2-yl)-1-[(1-methyl-1H-imidazol-4-yl)sulfonyl]pyrrolidin-3-amine The title compound was prepared similarly to the procedure described in Example 337G substituting Example 761B for Example 337F and substituting 1-bromo-3-fluorobenzene for 1-bromo-3-(trifluoromethyl)benzene. MS (ESI) m/z 420.0 (M+H)$^+$

Example 806

5-chloro-N-{(3R,4S)-4-(4-fluorophenyl)-1-[(1-methyl-1H-imidazol-4-yl)sulfonyl]pyrrolidin-3-yl}-4-(2,2,2-trifluoroethoxy)pyridin-2-amine

Example 806A 2-bromo-5-chloro-4-(2,2,2-trifluoroethoxy)pyridine

The title compound was prepared similarly to Example 803A substituting 2-bromo-5-chloropyridin-4-ol for 2-bromo-5-fluoropyridin-4-ol.

Example 806B 5-chloro-N-{(3R,4S)-4-(4-fluorophenyl)-1-[(1-methyl-1H-imidazol-4-yl)sulfonyl]pyrrolidin-3-yl}-4-(2,2,2-trifluoroethoxy)pyridin-2-amine The title compound was prepared similarly to the procedure described in Example 327 substituting Example 806A for 1-bromo-3-(trifluoromethyl)benzene. MS (ESI) m/z 534 (M+H)$^+$.

Example 807

N-{(3R,4S)-4-(4-fluorophenyl)-1-[(1-methyl-1H-imidazol-4-yl)sulfonyl]pyrrolidin-3-yl}-4-(2,2,2-trifluoroethoxy)pyridin-2-amine

Example 807A 2-bromo-4-(2,2,2-trifluoroethoxy)pyridine

The title compound was prepared similarly to the procedure described in Example 803A substituting 2-bromopyridin-4-ol for 2-bromo-5-fluoropyridin-4-ol.

Example 807B

N-{(3R,4S)-4-(4-fluorophenyl)-1-[(1-methyl-1H-imidazol-4-yl)sulfonyl]pyrrolidin-3-yl}-4-(2,2,2-trifluoroethoxy)pyridin-2-amine The title compound was prepared similarly to the procedure described in Example 327 substituting Example 807A for 1-bromo-3-(trifluoromethyl)benzene. MS (ESI) m/z 500 (M+H)$^+$.

Example 808

5-chloro-N-{(3R,4S)-1-[(1-methyl-1H-imidazol-4-yl)sulfonyl]-4-phenylpyrrolidin-3-yl}-4-(2,2,2-trifluoroethoxy)pyridin-2-amine The title compound was prepared similarly to the procedure described in Example 327 substituting Example 574A for Example 322B and substituting Example 806A for 1-bromo-3-(trifluoromethyl)benzene. MS (ESI) m/z 516 (M+H)$^+$.

Example 809

N-{(3R,4S)-1-[(1-methyl-1H-imidazol-4-yl)sulfonyl]-4-phenylpyrrolidin-3-yl}-4-(2,2,2-trifluoroethoxy)pyridin-2-amine The title compound was prepared similarly to the procedure described in Example 327 substituting Example 574A

Example 810

5-fluoro-N-{(3R,4S)-4-(4-fluorophenyl)-1-[(1-methyl-1H-imidazol-4-yl)sulfonyl]pyrrolidin-3-yl}-4-(2,2,2-trifluoroethoxy)pyridin-2-amine The title compound was prepared similarly to the procedure described in Example 327 substituting Example 803A for 1-bromo-3-(trifluoromethyl)benzene. MS (ESI) m/z 518 (M+H)+.

Example 811

Trans-4-(3-fluoropyridin-2-yl)-N-hexyl-1-[(1-methyl-1H-1,2,3-triazol-4-yl)sulfonyl]pyrrolidin-3-amine

Example 811A

Trans-4-(3-fluoropyridin-2-yl)-1-(1-methyl-1H-1,2,3-triazol-4-ylsulfonyl)pyrrolidin-3-amine hydrochloride The title compound was prepared similarly to the conditions described in Example 2A-2F substituting (E)-3-fluoro-2-(2-nitrovinyl)pyridine for (E)-1-methoxy-4-(2-nitrovinyl)benzene and 1-methyl-1H-1,2,3-triazole-4-sulfonyl chloride for 1-methyl-1H-imidazole-4-sulfonyl chloride.

Example 811B

Trans-4-(3-fluoropyridin-2-yl)-N-hexyl-1-[(1-methyl-1H-1,2,3-triazol-4-yl)sulfonyl]pyrrolidin-3-amine The title compound was prepared similarly to the procedure described in Example 354E substituting hexanal for 4-chlorobenzaldehyde and substituting Example 811 A for 354D. MS (ESI) m/z 411.0 (M+H)+

Example 812

N-{(3R,4S)-4-(4-fluorophenyl)-1-[(1-methyl-1H-imidazol-4-yl)sulfonyl]pyrrolidin-3-yl}-4-(propan-2-yl)pyridin-2-amine The title compound was prepared similarly to the procedure described in Example 327 substituting 2-bromo-4-isopropylpyridine for 1-bromo-3-(trifluoromethyl)benzene. MS (ESI) m/z 444 (M+H)+.

Example 813

N-{(3R,4S)-1-[(1-methyl-1H-imidazol-4-yl)sulfonyl]-4-phenylpyrrolidin-3-yl}-4-(propan-2-yl)pyridin-2-amine The title compound was prepared similarly to the procedure described in Example 327 substituting Example 574A for Example 322B and substituting 2-bromo-4-isopropylpyridine for 1-bromo-3-(trifluoromethyl)benzene. MS (ESI) m/z 426 (M+H)+.

Example 814

2,2,2-trifluoro-N-[2-({trans-4-(4-fluorophenyl)-1-[(1-methyl-1H-imidazol-4-yl)sulfonyl]pyrrolidin-3-yl}oxy)ethyl]ethanamine The title compound was prepared similarly to the procedure described in Example 290 substituting Example 797 for Example 242E. MS (ESI) m/z 451.1 (M+H)+

Example 815

Trans-N-(3-chloro-4-fluorophenyl)-1-[(1-methyl-1H-imidazol-4-yl)sulfonyl]-4-(tetrahydro-2H-pyran-2-yl)pyrrolidin-3-amine The title compound was prepared similarly to the procedure described in Example 337G substituting Example 679H for Example 337F and substituting 4-bromo-2-chloro-1-fluorobenzene for 1-bromo-3-trifluoromethylbenzene. MS (ESI) m/z 443.0 (M+H)+

Example 816

Trans-1-[(1-methyl-1H-imidazol-4-yl)sulfonyl]-4-(tetrahydro-2H-pyran-2-yl)-N-[3-(2,2,2-trifluoroethoxy)phenyl]pyrrolidin-3-amine The title compound was prepared similarly to the procedure described in Example 337G substituting Example 679H for Example 337F and substituting 1-bromo-3-(2,2,2-trifluoroethoxy)benzene for 1-bromo-3-trifluoromethylbenzene. MS (ESI) m/z 489.1 (M+H)+

Example 817

2-({1-[(1-methyl-1H-imidazol-4-yl)sulfonyl]-4-phenylpyrrolidin-3-yl}methyl)-4-(trifluoromethyl)pyridine

Example 817A (E)-ethyl 3-(4-(trifluoromethyl)pyridin-2-yl)acrylate

To a solution of ethyl 2-(diethoxyphosphoryl)acetate (0.45 g, 2 mmol) in tetrahydrofuran (3 mL) at −20° C. was added sodium hydride (100 mg, 60%, 2.5 mmol) followed by the addition of 4-(trifluoromethyl)picolinaldehyde in tetrahydrofuran (1 mL). The mixture was warmed to room temperature over 1 hour. Aqueous ammonium chloride was added and the solution was partitioned with ethyl acetate. The organic fraction was collected, concentrated, and purified by flash chromatography (25% ethyl acetate/hexanes) to afford the title compound.

Example 817B ethyl 3-(4-(trifluoromethyl)pyridin-2-yl)propanoate

To a solution of Example 817A (460 mg, 1.8 mmol) in ethanol (20 mL) in a 50 mL pressure bottle was added 5% palladium on carbon, (95 mg, 0.022 mmol). The mixture was stirred for 2 hours under 30 psi of hydrogen at room temperature. The mixture was filtered through a nylon membrane and concentrated to afford the title compound.

Example 817C ethyl 4-nitro-3-phenyl-2-((4-(trifluoromethyl)pyridin-2-yl)methyl)butanoate The title compound was prepared similarly to the procedure described in Example 331A substituting Example 817B for methyl 3-(3-chlorophenyl)propanoate.

Example 817D 4-phenyl-34(4-(trifluoromethyl)pyridin-2-yl)methyl)pyrrolidin-2-one The title compound was prepared similarly to the procedure described in Example 331B substituting Example 817C for Example 331A.

Example 817E 2-((4-phenylpyrrolidin-3-yl)methyl)-4-(trifluoromethyl)pyridine To a solution of Example 817D (450 mg, 1.4 mmol) in tetrahydrofuran (3 mL) was added lithiumaluminum hydride (2N, 1.5 mL, 3 mmol). The mixture was stirred for 16 hours. Aqueous sodium bicarbonate followed by ethyl acetate was added. The organic fraction was collected, dried over potassium carbonate, filtered, and concentrated to provide the title compound.

Example 817F 2-({1-[(1-methyl-1H-imidazol-4-yl)sulfonyl]-4-phenylpyrrolidin-3-yl}methyl)-4-(trifluoromethyl)pyridine The title compound was prepared similarly to the procedure described in Example 182C substituting Example 817E for Example 182B. MS (ESI) m/z 451 (M+H)$^+$.

Example 818

Trans-N-[2-chloro-4-(trifluoromethyl)benzyl]-4-(3-fluoropyridin-2-yl)-1-[(1-methyl-1H-1,2,3-triazol-4-yl)sulfonyl]pyrrolidin-3-amine The title compound was prepared similarly to the procedure described in Example 354E substituting 2-chloro-4-(trifluoromethyl)benzaldehyde for 4-chlorobenzaldehyde and substituting example 811A for 354D. MS (ESI) m/z 519.0 (M+H)$^+$

Example 819

Trans-1-[(1-methyl-1H-imidazol-4-yl)sulfonyl]-4-(tetrahydrofuran-2-yl)-N-[3-(2,2,2-trifluoroethoxy)phenyl]pyrrolidin-3-amine The title compound was prepared as described in Example 603 substituting 1-bromo-3-(2,2,2-trifluoroethoxy)benzene for 1-bromo-3-trifluoromethylbenzene. MS (ESI) m/z 475.1 (M+H)$^+$

Example 820

N-Hexyl-1-[(1-methyl-1H-imidazol-4-yl)sulfonyl]-4-[(2R)-tetrahydrofuran-2-yl]pyrrolidin-3-amine The title compound was prepared similarly to the procedure described in Example 354E substituting hexanal for 4-chlorobenzaldehyde and substituting example 601B for 354D. MS (ESI) m/z 385.2 (M+H)$^+$.

Example 821

N-hexyl-1-[(1-methyl-1H-imidazol-4-yl)sulfonyl]-4-[(2S)-tetrahydrofuran-2-yl]pyrrolidin-3-amine The title compound was prepared similarly to the procedure described in Example 354E substituting hexanal for 4-chlorobenzaldehyde and substituting example 601B for 354D. MS (ESI) m/z 385.2 (M+H)$^+$.

Example 822

Trans-N-[2-chloro-4-(trifluoromethyl)benzyl]-1-[(1-methyl-1H-imidazol-4-yl)sulfonyl]-4-(tetrahydrofuran-2-yl)pyrrolidin-3-amine The title compound was prepared similarly to the procedure described in Example 354E substituting 2-chloro-4-(trifluoromethyl)benzaldehyde for 4-chlorobenzaldehyde and substituting example 601B for 354D. MS (ESI) m/z 493.1 (M+H)$^+$.

Example 823

N-[2-chloro-4-(trifluoromethyl)benzyl]-1-[(1-methyl-1H-imidazol-4-yl)sulfonyl]-4-[(2S)-tetrahydrofuran-2-yl]pyrrolidin-3-amine The title compound was prepared similarly to the procedure described in Example 354E substituting 2-chloro-4-(trifluoromethyl)benzaldehyde for 4-chlorobenzaldehyde and substituting example 601B for 354D. MS (ESI) m/z 493.1 (M+H)$^+$.

Example 824

Trans-N-(3-chloro-4-fluorophenyl)-1-[(1-methyl-1H-imidazol-4-yl)sulfonyl]-4-(tetrahydrofuran-2-yl)pyrrolidin-3-amine The title compound was prepared as described in Example 603 substituting 4-bromo-2-chloro-1-fluorobenzene for 1-bromo-3-trifluoromethylbenzene. MS (ESI) m/z 429.1 (M+H)$^+$

Example 825

N-(3-chloro-4-fluorophenyl)-1-[(1-methyl-1H-imidazol-4-yl)sulfonyl]-4-[(2S)-tetrahydrofuran-2-yl]pyrrolidin-3-amine The title compound was prepared as described in Example 603 substituting 4-bromo-2-chloro-1-fluorobenzene for 1-bromo-3-trifluoromethylbenzene. MS (ESI) m/z 429.1 (M+H)$^+$

Example 826

1-benzyl-N-{(3R,4S)-1-[(1-methyl-1H-imidazol-4-yl)sulfonyl]-4-phenylpyrrolidin-3-yl}-2,3-dihydro-1H-indol-6-amine

Example 826A 1-benzyl-6-bromoindoline

To a stirred solution of 6-bromoindoline (100 mg, 0.50 mmol) in dimethylformamide (5 mL) was added (bromomethyl)benzene (95 mg, 0.55 mmol) and potassium carbonate (140 mg, 1.0 mmol). The reaction was stirred at 60° C. for 18 hours. The reaction mixture was partitioned between water and ethyl acetate. The organic fraction was collected, washed with brine, dried with magnesium sulfate, and concentrated to provide the title compound.

Example 826B 1-benzyl-N-{(3R,4S)-1-[(1-methyl-1H-imidazol-4-yl)sulfonyl]-4-phenylpyrrolidin-3-yl}-2,3-dihydro-1H-indol-6-amine The title compound was prepared similarly to the procedure described in Example 327 substituting Example 574A for Example 322B and substituting Example 826A for 1-bromo-3-(trifluoromethyl)benzene. MS (ESI) m/z 514 (M+H)$^+$.

Example 827 trans-1-[(1-methyl-1H-imidazol-4-yl)sulfonyl]-4-(tetrahydrofuran-3-yl)-N-[3-(trifluoromethyl)phenyl]pyrrolidin-3-amine

Example 827A (E)-3-(2-nitrovinyl)tetrahydrofuran

To a solution of oxalyl chloride (5.1 mL, 60 mmol) in dichloromethane (100 mL) under a nitrogen atmosphere at −78° C. was added dropwise dimethylsulfoxide (4.6 mL, 65 mmol) in dichloromethane (10 mL). The reaction mixture stirred for 10 minutes. Tetrahydro-3-furan methanol (5.5 g, 54 mmol) was added in dichloromethane (20 mL) over several minutes, and the reaction mixture was stirred for 10 minutes. Triethylamine (17.4 mL, 125 mmol) was added drop wise. The reaction mixture was allowed to warm to room temperature. Diethyl ether was added and the solution was filtered. The filtrate was concentrated to provide crude tetrahydrofuran-3-carbaldehyde.

To a stirred solution of this crude tetrahydrofuran-3-carbaldehyde in tetrahydrofuran (50 mL) under a nitrogen atmosphere was added nitromethane (8.1 mL, 150 mmol), 1,1,2,2-tetramethyl guanidine (0.69 mL, 5.5 mmol). The reaction was stirred at room temperature for 1 hour. The reaction mixture was then cooled to 0° C. and trifluoroacetic anhydride (6.3 mL, 100 mmol) was added. The reaction mixture stirred for 15 minutes. Triethylamine (13.9 mL, 100 mmol) was added dropwise and the reaction mixture stirred for 1 hour. The reaction mixture was concentrated and partitioned between ethyl acetate and water. The organic fraction was collected, washed with brine, and concentrated. Purification via flash chromatography (40% EtOAc/heptanes) provided the title compound.

Example 827B trans-1-(1-methyl-1H-imidazol-4-ylsulfonyl)-4-((S)-tetrahydrofuran-3-yl)pyrrolidin-3-amine The title compound was prepare as an HCl salt similarly to the procedures described in Example 2A-2F substituting Example 827A for (E)-1-methoxy-4-(2-nitrovinyl)benzene.

Example 827C trans-1-[(1-methyl-1H-imidazol-4-yl)sulfonyl]-4-(tetrahydrofuran-3-yl)-N-[3-(trifluoromethyl)phenyl]pyrrolidin-3-amine The title compound was prepared similarly to the procedure described in Example 327 substituting Example 827B for Example 322B. MS (ESI) m/z 445 (M+H)$^+$.

Example 828 trans-1-[(1-methyl-1H-imidazol-4-yl)sulfonyl]-N-(3-methylphenyl)-4-(tetrahydrofuran-3-yl)pyrrolidin-3-amine The title compound was prepared similarly to the procedure described in Example 327 substituting Example 827B for Example 322B and substituting 1-bromo-3-methylbenzene for 1-bromo-3-(trifluoromethyl)benzene. MS (ESI) m/z 391 (M+H)$^+$.

Example 829 trans-N-(3-chlorophenyl)-1-[(1-methyl-1H-imidazol-4-yl)sulfonyl]-4-(tetrahydrofuran-3-yl)pyrrolidin-3-amine The title compound was prepared similarly to the procedure described in Example 327 substituting Example 827B for Example 322B and substituting 1-bromo-3-chlorobenzene for 1-bromo-3-(trifluoromethyl)benzene. MS (ESI) m/z 411 (M+H)$^+$.

Example 830 trans-N-(3-chloro-4-fluorophenyl)-1-[(1-methyl-1H-imidazol-4-yl)sulfonyl]-4-(tetrahydrofuran-3-yl)pyrrolidin-3-amine The title compound was prepared similarly to the procedure described in Example 327 substituting Example 827B for Example 322B and substituting 1-bromo-3-chloro-4-fluorobenzene for 1-bromo-3-(trifluoromethyl)benzene, but only stirring for 1 hour. MS (APCI) m/z 429 (M+H)$^+$.

Example 831 trans-N-[4-fluoro-3-(trifluoromethoxy)phenyl]-1-[(1-methyl-1H-imidazol-4-yl)sulfonyl]-4-(tetrahydrofuran-3-yl)pyrrolidin-3-amine The title compound was prepared similarly to the procedure described in Example 327 substituting Example 827B for Example 322B and substituting 1-bromo-4-fluoro-3-

(trifluoromethoxy)benzene for 1-bromo-3-(trifluoromethyl) benzene. MS (ESI) m/z 479 (M+H)+.

Example 832 trans-N-[4-fluoro-3-(trifluoromethyl)phenyl]-1-[(1-methyl-1H-imidazol-4-yl)sulfonyl]-4-(tetrahydrofuran-3-yl)pyrrolidin-3-amine The title compound was prepared similarly to the procedure described in Example 327 substituting Example 827B for Example 322B and substituting 1-bromo-4-fluoro-3-(trifluoromethyl)benzene for 1-bromo-3-(trifluoromethyl)benzene. MS (APCI) m/z 463 (M+H)+.

Example 833 trans-N-[4-chloro-3-(trifluoromethyl)phenyl]-1-[(1-methyl-1H-imidazol-4-yl)sulfonyl]-4-(tetrahydrofuran-3-yl)pyrrolidin-3-amine The title compound was prepared similarly to the procedure described in Example 327 substituting Example 827B for Example 322B and substituting 1-bromo-4-chloro-3-(trifluoromethyl)benzene for 1-bromo-3-(trifluoromethyl)benzene. MS (ESI) m/z 479 (M+H)+.

Example 834 trans-1-[(1-methyl-1H-imidazol-4-yl)sulfonyl]-4-(tetrahydrofuran-3-yl)-N-[3-(2,2,2-trifluoroethoxy)phenyl]pyrrolidin-3-amine The title compound was prepared similarly to the procedure described in Example 327 substituting Example 827B for Example 322B and substituting 1-bromo-3-(2,2,2-trifluoroethoxy)benzene for 1-bromo-3-(trifluoromethyl)benzene. MS (ESI) m/z 475 (M+H)+.

Example 835 trans-1-[(1-methyl-1H-imidazol-4-yl)sulfonyl]-4-(tetrahydrofuran-3-yl)-N-[3-(trifluoromethoxy)phenyl]pyrrolidin-3-amine The title compound was prepared similarly to the procedure described in Example 327 substituting Example 827B for Example 322B and substituting 1-bromo-3-(trifluoromethoxy)benzene for 1-bromo-3-(trifluoromethyl)benzene. MS (ESI) m/z 461 (M+H)+.

Example 836 trans-4-(4-fluorophenyl)-1-[(1-methyl-1H-1,2,3-triazol-4-yl)sulfonyl]-N-[3-(2,2,2-trifluoroethoxy)phenyl]pyrrolidin-3-amine

Example 836A 1-methyl-1H-1,2,3-triazole-4-sulfonyl chloride

To an ice-cooled solution of sodium 1H-1,2,3-triazole-4-thiolate (34.5 g, 280 mmol) in ethanol (400 mL) was added benzylbromide (18.8 mL, 158 mmol) drop-wise. The mixture stirred at 25° C. for 2 hours, and was then diluted with EtOAc (600 mL), washed with water (500 mL), brine (500 mL), dried over sodium sulfate filtered, and concentrated under reduced pressure to afford 4-(benzylthio)-1H-1,2,3-triazole.

To a solution of 4-(benzylthio)-1H-1,2,3-triazole (55.0 g, 288 mmol) in dimethylformamide (550 mL) at 0° C. was added potassium carbonate (87.0 g, 630 mmol) followed by dimethyl sulfate (55.0 mL, 575 mmol) dropwise. Then the reaction mixture was stirred at 20° C. for 16 hours. After the reaction was completed, the reaction mixture was concentrated under reduced pressure. The residue was dissolved in dichloromethane (500 mL) and washed with water (500 mL). The organic fraction was dried with sodium sulfate, and concentrated. The residue was purified via flash chromatography (Petroleum ether:EtOAc=1:0, 10:1, 5:1 to 3:1) to afford 4-(benzylthio)-1-methyl-1H-1,2,3-triazole.

1,3-dichloro-5,5-dimethylimidazolidine-2,4-dione (40.3 g, 205 mmol) was added portion wise to a mixture of 4-(benzylthio)-1-methyl-1H-1,2,3-triazole (28.0 g, 137 mmol) in acetonitrile (1200 mL), AcOH (50 mL) and water (34 mL), which had been cooled to 0° C. The addition was slow enough to maintain the internal temperature of the reaction mixture below 5° C. Upon complete addition, the mixture stirred for an additional 2 hours at 0° C. The reaction mixture was then quenched slowly with aqueous sodium hydride CO$_3$ solution (5%, 700 mL). The resulting mixture was stirred for 15 minutes and then diluted with dichloromethane (2000 mL). The organic fraction was collected, washed with brine (1000 mL), dried over sodiumsulfate, filtered and concentrated under reduced pressure. The residue was purified by flash column chromatography (petroleum ether/EtOAc=1:0 to 5:1) to afford the title compound.

Example 836B trans-4-(4-fluorophenyl)-1-(1-methyl-1H-1,2,3-triazol-4-ylsulfonyl)pyrrolidin-3-amine The title compound was prepared as an HCl salt similarly to the procedures described in Examples 2A-2F substituting (E)-1-fluoro-4-(2-nitrovinyl)benzene for (E)-1-methoxy-4-(2-nitrovinyl)benzene and substituting 1-methyl-1H-1,2,3-triazole-4-sulfonyl chloride for 1-methyl-1H-imidazole-4-sulfonyl chloride.

Example 836C trans-4-(4-fluorophenyl)-1-[(1-methyl-1H-1,2,3-triazol-4-yl)sulfonyl]-N-[3-(2,2,2-trifluoroethoxy)phenyl]pyrrolidin-3-amine The title compound was prepared similarly to the procedure described in Example 327 substituting Example 836B for Example 322B and substituting 1-bromo-3-(2,2,2-trifluoroethoxy)benzene for 1-bromo-3-(trifluoromethyl)benzene. MS (ESI) m/z 500 (M+H)+.

Example 837

(3R,4S)-4-(4-fluorophenyl)-1-[(1-methyl-1H-1,2,3-triazol-4-yl)sulfonyl]-N-[3-(trifluoromethoxy)phenyl]pyrrolidin-3-amine The title compound was prepared similarly to the procedure described in Example 327 substituting Example 836B for Example 322B and substituting 1-bromo-3-(trifluoromethoxy)benzene for 1-bromo-3-(trifluoromethyl)benzene. MS (ESI) m/z 486 (M+H)+.

Example 838

(3R,4S)-4-(4-fluorophenyl)-N-[4-fluoro-3-(trifluoromethoxy)phenyl]-1-[(1-methyl-1H-1,2,3-triazol-4-yl)sulfonyl]pyrrolidin-3-amine The title compound was prepared similarly to the procedure described in Example 327 substituting Example 836B for Example 322B and substituting 1-bromo-4-fluoro-3-(trifluoromethoxy)benzene for 1-bromo-3-(trifluoromethyl)benzene. MS (ESI) m/z 504 (M+H)+.

Example 839

(3R,4S)-4-(4-fluorophenyl)-1-[(1-methyl-1H-1,2,3-triazol-4-yl)sulfonyl]-N-[3-(trifluoromethyl)phenyl]pyrrolidin-3-amine The title compound was prepared similarly to the procedure described in Example 327 substituting Example 836B for Example 322B and substituting 1-bromo-3-(trifluoromethyl)benzene for 1-bromo-3-(trifluoromethyl)benzene. MS (ESI) m/z 470 (M+H)+.

Example 840

(3R,4S)-4-(4-fluorophenyl)-N-[4-fluoro-3-(trifluoromethyl)phenyl]-1-[(1-methyl-1H-1,2,3-triazol-4-yl)sulfonyl]pyrrolidin-3-amine The title compound was prepared similarly to the procedure described in Example 327 substituting Example 836B for Example 322B and substituting 1-bromo-4-fluoro-3-(trifluoromethyl)benzene for 1-bromo-3-(trifluoromethyl)benzene. MS (ESI) m/z 488 (M+H)+.

Example 841

(3R,4S)-N-(3-chlorophenyl)-4-(4-fluorophenyl)-1-[(1-methyl-1H-1,2,3-triazol-4-yl)sulfonyl]pyrrolidin-3-amine The title compound was prepared similarly to the procedure described in Example 327 substituting Example 836B for Example 322B and substituting 1-bromo-3-chlorobenzene for 1-bromo-3-(trifluoromethyl)benzene. MS (ESI) m/z 436 (M+H)+.

Example 842

(3R,4S)-N-(3-chloro-4-fluorophenyl)-4-(4-fluorophenyl)-1-[(1-methyl-1H-1,2,3-triazol-4-yl)sulfonyl]pyrrolidin-3-amine The title compound was prepared similarly to the procedure described in Example 327 substituting Example 836B for Example 322B and substituting 1-bromo-3-chloro-4-fluorobenzene for 1-bromo-3-(trifluoromethyl)benzene, but only stirring for 1 hour. MS (ESI) m/z 454 (M+H)+.

Example 843

Trans-N-[4-fluoro-3-(trifluoromethyl)phenyl]-1-[(1-methyl-1H-imidazol-4-yl)sulfonyl]-4-(tetrahydrofuran-2-yl)pyrrolidin-3-amine The title compound was prepared similarly to the procedure described in Example 603 substituting 4-bromo-1-fluoro-2-(trifluoromethyl)benzene for 1-bromo-3-trifluoromethylbenzene. MS (ESI) m/z 463.1 (M+H)+

Example 844

5-Chloro-N-[trans-1-[(1-methyl-1H-imidazol-4-yl)sulfonyl]-4-(tetrahydrofuran-2-yl)pyrrolidin-3-yl]-4-(trifluoromethyl)pyridin-2-amine The title compound was prepared similarly to the procedure in Example 848 substituting Example 601B for Example 679H. MS (ESI) m/z 480.1 (M+H)+

Example 845

Trans-N-(4-fluoro-3-methylphenyl)-1-[(1-methyl-1H-imidazol-4-yl)sulfonyl]-4-(tetrahydrofuran-2-yl)pyrrolidin-3-amine The title compound was prepared similarly to the procedure described in Example 603 substituting 4-bromo-1-fluoro-2-methylbenzene for 1-bromo-3-trifluoromethylbenzene. MS (ESI) m/z 409.1 (M+H)+

Example 846

Trans-N-[4-fluoro-3-(trifluoromethyl)phenyl]-1-[(1-methyl-1H-imidazol-4-yl)sulfonyl]-4-(tetrahydro-2H-pyran-2-yl)pyrrolidin-3-amine The title compound was prepared similarly to the procedure described in Example 337G substituting Example 679H for Example 337F and substituting 4-bromo-1-fluoro-2-(trifluoromethyl)benzene for 1-bromo-3-trifluoromethylbenzene. MS (ESI) m/z 477.1 (M+H)+

Example 847

Trans-N-(4-fluoro-3-methylphenyl)-1-[(1-methyl-1H-imidazol-4-yl)sulfonyl]-4-(tetrahydro-2H-pyran-2-yl)pyrrolidin-3-amine The title compound was prepared similarly to the procedure described in Example 337G substituting Example 679H for Example 337F and substituting 4-bromo-1-fluoro-2-methylbenzene for 1-bromo-3-trifluoromethylbenzene. MS (ESI) m/z 423.1 (M+H)+

Example 848

5-Chloro-N-[trans-1-[(1-methyl-1H-imidazol-4-yl)sulfonyl]-4-(tetrahydro-2H-pyran-2-yl)pyrrolidin-3-yl]-4-(trifluoromethyl)pyridin-2-amine To a microwave vial charged with Example 679H (80 mg, 0.254 mmol) and N-methyl-2-pyrrolidone (0.5 mL) was added cesium carbonate (141 mg, 0.43 mmol) and 2,5-dichloro-4-(trifluoromethyl)pyridine (71.4 mg, 0.33 mmol) under Argon. This mixture was stirred at 120° C. for 5 hours. The mixture was then partitioned between water and ethyl acetate. The organic fraction was collected, concentrated, and purified by flash chromatography to provide the title compound. MS (ESI) m/z 494.1 (M+H)$^+$ Example 849

Trans-N-(3-chlorophenyl)-1-[(1-methyl-1H-imidazol-4-yl)sulfonyl]-4-(tetrahydro-2H-pyran-2-yl)pyrrolidin-3-amine The title compound was prepared similarly to the procedure described in Example 337G substituting Example 679H for Example 337F and substituting 1-bromo-3-chlorobenzene for 1-bromo-3-trifluoromethylbenzene. MS (ESI) m/z 425.1 (M+H)$^+$ Example 850

Trans-N-(3-chlorophenyl)-1-[(1-methyl-1H-imidazol-4-yl)sulfonyl]-4-(tetrahydrofuran-2-yl)pyrrolidin-3-amine The title compound was prepared similarly to the procedure described in Example 603 substituting 1-bromo-3-chlorobenzene for 1-bromo-3-trifluoromethylbenzene. MS (ESI) m/z 411.1 (M+H)$^+$ Example 851

5-Fluoro-4-methyl-N-[trans-1-[(1-methyl-1H-imidazol-4-yl)sulfonyl]-4-(tetrahydrofuran-2-yl)pyrrolidin-3-yl]pyridin-2-amine The title compound was prepared similarly to the procedure described in Example 603 substituting 2-bromo-5-fluoro-4-methylpyridine for 1-bromo-3-trifluoromethylbenzene. MS (ESI) m/z 410.2 (M+H)$^+$ Example 852

5-Fluoro-4-methyl-N-[trans-1-[(1-methyl-1H-imidazol-4-yl)sulfonyl]-4-(tetrahydro-2H-pyran-2-yl)pyrrolidin-3-yl]pyridin-2-amine The title compound was prepared similarly to the procedure described in Example 337G substituting Example 679H for Example 337F and substituting 2-bromo-5-fluoro-4-methylpyridine for 1-bromo-3-trifluoromethylbenzene. MS (ESI) m/z 424.2 (M+H)$^+$ Example 853

N-[Trans-1-[(1-methyl-1H-imidazol-4-yl)sulfonyl]-4-(tetrahydrofuran-2-yl)pyrrolidin-3-yl]-6-(trifluoromethyl)pyrimidin-4-amine The title compound was prepared similarly to the procedure described in Example 603 substituting 4-bromo-6-(trifluoromethyl)pyrimidine for 1-bromo-3-trifluoromethylbenzene. MS (ESI) m/z 447.1 (M+H)$^+$ Example 854

(3R,4S)-N-cyclohexyl-4-(4-fluorophenyl)-1-(1-methyl-1H-imidazol-4-ylsulfonyl)pyrrolidin-3-amine The title compound was prepared similarly to the procedure described in Example 148 substituting Example 322B for Example 3A and substituting cyclohexanone for benzaldehyde. MS (ESI) m/z 407 (M+H)$^+$.

Example 855

(3R,4S)-N-(3,3-dimethylcyclohexyl)-4-(4-fluorophenyl)-1-(1-methyl-1H-imidazol-4-ylsulfonyl)pyrrolidin-3-amine The title compound was prepared similarly to the procedure described in Example 148 substituting Example 322B for Example 3A and substituting 3,3-dimethylcyclohexanone for benzaldehyde. MS (ESI) m/z 435 (M+H)$^+$.

Example 856

(3R,4S)-N-(4,4-dimethylcyclohexyl)-4-(4-fluorophenyl)-1-(1-methyl-1H-imidazol-4-ylsulfonyl)pyrrolidin-3-amine The title compound was prepared similarly to the procedure described in Example 148 substituting Example 322B for Example 3A and substituting 4,4-dimethylcyclohexanone for benzaldehyde. MS (ESI) m/z 435 (M+H)$^+$.

Example 857

(3R,4S)-N-cyclopentyl-4-(4-fluorophenyl)-1-(1-methyl-1H-imidazol-4-ylsulfonyl)pyrrolidin-3-amine The title compound was prepared similarly to the procedure described in Example 148 substituting Example 322B for Example 3A and substituting cyclopentanone for benzaldehyde. MS (ESI) m/z 393 (M+H)$^+$.

Example 858

(3R,4S)-N-(3,3-dimethylcyclopentyl)-4-(4-fluorophenyl)-1-(1-methyl-1H-imidazol-4-ylsulfonyl)pyrrolidin-3-amine The title compound was prepared similarly to the procedure described in Example 148 substituting Example 322B for Example 3A and substituting 3,3-dimethylcyclopentanone for benzaldehyde. MS (ESI) m/z 421 (M+H)$^+$.

Example 859

(3R,4S)-N-(1-(2,4-dichlorophenyl)ethyl)-4-(4-fluorophenyl)-1-(1-methyl-1H-imidazol-4-ylsulfonyl)pyrrolidin-3-amine The title compound was prepared similarly to the procedure described in Example 148 substituting Example 322B for Example 3A and substituting 1-(2,4-dichlorophenyl)ethanone for benzaldehyde. MS (ESI) m/z 497 (M+H)$^+$.

Example 860

(3R,4S)-N-(2,3-dihydro-1H-inden-1-yl)-4-(4-fluorophenyl)-1-(1-methyl-1H-imidazol-4-ylsulfonyl)pyrrolidin-3-amine The title compound was prepared similarly to the procedure described in Example 148 substituting Example 322B for Example 3A and substituting 2,3-dihydro-1H-inden-1-one for benzaldehyde. MS (ESI) m/z 441 (M+H)$^+$.

Example 861

(3R,4S)-N-(5-chloro-2,3-dihydro-1H-inden-1-yl)-4-(4-fluorophenyl)-1-(1-methyl-1H-imidazol-4-ylsulfonyl)pyrrolidin-3-amine The title compound was prepared similarly to the procedure described in Example 148 substituting Example 322B for Example 3A and substituting 5-chloro-2,3-dihydro-1H-inden-1-one for benzaldehyde. MS (ESI) m/z 475 (M+H)$^+$.

Example 862

N-(4-chlorobenzyl)-N-((3R,4S)-4-(4-fluorophenyl)-1-(1-methyl-1H-imidazol-4-ylsulfonyl)pyrrolidin-3-yl)acetamide

Example 862A (3R,4S)-N-(4-chlorobenzyl)-4-(4-fluorophenyl)-1-(1-methyl-1H-imidazol-4-ylsulfonyl)pyrrolidin-3-amine The title compound was prepared similarly to the procedure described in Example 148 substituting Example 322B for Example 3A and substituting 4-chlorobenzaldehyde for benzaldehyde.

Example 862B

N-(4-chlorobenzyl)-N-((3R,4S)-4-(4-fluorophenyl)-1-(1-methyl-1H-imidazol-4-ylsulfonyl)pyrrolidin-3-yl)acetamide The title compound was prepared similarly to the procedure described in Example 4C substituting Example 862A for Example 4B and substituting acetic acid for 2-chloro-3-(trifluoromethyl)benzoic acid. MS (ESI) m/z 491 (M+H)$^+$.

Example 863

5-butyl-3-{(3R,4S)-4-(4-fluorophenyl)-1-[(1-methyl-1H-imidazol-4-yl)sulfonyl]pyrrolidin-3-yl}-1,3-oxazolidin-2-one

Example 863A

N-((3R,4S)-4-(4-fluorophenyl)-1-((1-methyl-1H-imidazol-4-yl)sulfonyl)pyrrolidin-3-yl)-2-hydroxyhexanamide The title compound was prepared according to the procedure outlined in Example 242 E by substituting Example 380A for aniline and 2-hydroxyhexanoic acid for Example 242D. MS (ESI) m/z 439.4 (M+H)$^+$.

Example 863B 1-(((3R,4S)-4-(4-fluorophenyl)-1-((1-methyl-1H-imidazol-4-yl)sulfonyl)pyrrolidin-3-yl)amino)hexan-2-ol The title compound was prepared according to the procedure outlined in Example 290 by substituting Example 863A for Example 242E. MS (ESI) m/z 425.4 (M+H)$^+$.

Example 863C tert-butyl ((3R,4S)-4-(4-fluorophenyl)-1-((1-methyl-1H-imidazol-4-yl)sulfonyl)pyrrolidin-3-yl)(2-hydroxyhexyl)carbamate To Example 863B (140 mg, 0.33 mmol) in dry tetrahydrofuran (3 mL) was added diisopropylethylamine (0.1 mL, 0.56 mmol), followed by di-tert-butyl dicarbonate (94 mg, 0.43 mmol) at 0° C. This was stirred at 0° C. for 3 hours. Then ice bath was removed and stirred was continued at room temperature for 30 minutes. The reaction mixture was concentrated, and the residue obtained was dissolved in ethyl acetate (30 mL), and then washed with H$_2$O, and separated. The organic layer was dried over Na$_2$SO$_4$ and concentrated down to give the title product. MS (ESI) m/z 525.4 (M+H)$^+$.

Example 863D 5-butyl-3-{(3R,4S)-4-(4-fluorophenyl)-1-[(1-methyl-1H-imidazol-4-yl)sulfonyl]pyrrolidin-3-yl}-1,3-oxazolidin-2-one To Example 863C (174 mg, 0.33 mmol) was added 1.5 mL of dry tetrahydrofuran under N$_2$, then were added NaH (26.5 mg, 0.66 mmol, 60% dispersion in mineral oil) and MeI (70.6 mg, 0.49 mmol). The reaction mixture was heated up to 60° C. for 1 hour, then quenched with H$_2$O, and extracted with ethyl acetate. The organic layer was concentrated down and purified by reverse phase HPLC column to provide the title product. MS (ESI) m/z 451.2 (M+H)$^+$.

Example 864

4-{(3R,4S)-4-(4-fluorophenyl)-1-[(1-methyl-1H-imidazol-4-yl)sulfonyl]pyrrolidin-3-yl}thiomorpholine 1,1-dioxide In a 5 mL microwave vial was added (3R,4S)-4-(4-fluorophenyl)-1-((1-methyl-1H-imidazol-4-yl)sulfonyl)pyrrolidin-3-amine (100 mg, 0.308 mmol) and (vinylsulfonyl)ethene (36.4 mg, 0.308 mmol) in 3 mL THF. The vial was stirred with the cap off for 30 seconds and then capped and reacted in the microwave at 100° C. for 10 minutes. The reaction mixture was dried under nitrogen, was taken up in 2 mL 50% MeOH/DMSO, and was then purified by reverse phase HPLC to provide the desired compound. MS (ESI) m/z 443 (M+H)$^+$

Example 865

5-fluoro-N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine The title compound was prepared according to the procedure outlined in Example 327 substituting 2-bromo-5- fluoro-4-(trifluoromethyl)pyridine for 1-bromo-3-(trifluoromethyl)benzene. MS (ESI) m/z 488 (M+H)+.

Example 866

(3R,4S)-1-[(1-methyl-1H-imidazol-4-yl)sulfonyl]-4-[(2R)-tetrahydro-2H-pyran-2-yl]-N-[3-(trifluoromethoxy)phenyl]pyrrolidin-3-amine

Example 866 A

Tetrahydro-2H-pyran-2-carbaldehyde

To a solution of oxalyl dichloride (131 g, 1.03 mol) in dichloromethane (700 mL) was added dimethyl sulfoxide (87 g, 1.12 mol) slowly at −78° C., the reaction was kept at −78° C. for 10 min, then (tetrahydro-2H-pyran-2-yl)methanol (100 g, 0.86 mol) was added dropwise and the reaction kept at −78° C. for another 10 min when the addition was completed. Then at −78° C. was added triethylamine (226 g, 2.24 mol) dropwise and the reaction was allowed to come to room temperature for 30 min. Three additional vials were set up as described above. All three reaction mixtures were combined and the mixture was diluted with dichloromethane and filtered through a pad of celite. The filtrate was concentrated with no heat to afford the title product which was used in next step without further purification.

Example 866 B (E)-2-(2-nitrovinyl)tetrahydro-2H-pyran

Example 866A (350 g, 3.07 mol) was dissolved in tetrahydrofuran (1000 mL) under $N_2$ atmosphere, and nitromethane (374 g, 6.13 mol) was added in one portion. To the stirred solution was added 1,1,3,3-tetramethylguanidine (17.66 g, 0.15 mol), and a mild exothermo reaction ensued. The reaction was stirred for 2.5 hrs at 20° C., then concentrated and purified by silica gel to provide the intermediate. The intermediate was dissolved in tetrahydrofuran (500 mL) under $N_2$ atmosphere at chilled ice bath, and 2,2,2-trifluoroacetic anhydride (644 g, 3.07 mol) was added rapidly. The reaction was kept for 15 min, then triethylamine (621 g, 6.13 mmol) was added dropwise and the reaction was kept for another 15 min. The reaction mixture was then extracted by ethyl acetate and water, the organic layers were combined and concentrated, and the residue obtained was purified by silica gel to provide the title product.

Example 866 C 1-benzyl-3-nitro-4-(tetrahydro-2H-pyran-2-yl)pyrrolidine

The title compound was prepared according to the procedure outlined in Example 2A substituting Example 866B for 4-methoxy-beta-nitrostyrene.

Example 866 D 1-benzyl-4-(tetrahydro-2H-pyran-2-yl)pyrrolidin-3-amine

The title compound was prepared according to the procedure outlined in Example 2B substituting Example 866C for Example 2A.

Example 866 E tert-butyl (1-benzyl-4-(tetrahydro-2H-pyran-2-yl)pyrrolidin-3-yl)carbamate The title compound was prepared according to the procedure outlined in Example 337C substituting Example 866D for Example 337B.

Example 866 F tert-butyl (4-(tetrahydro-2H-pyran-2-yl)pyrrolidin-3-yl)carbamate The title compound was prepared according to the procedure outlined in Example 2D substituting Example 866E for 2C.

Example 866 G tert-butyl (1-((1-methyl-1H-imidazol-4-yl)sulfonyl)-4-(tetrahydro-2H-pyran-2-yl)pyrrolidin-3-yl)carbamate The title compound was prepared according to the procedure outlined in Example 373C substituting Example 866F for Example 373B.

Example 866 H tert-butyl ((3R,4S)-1-((1-methyl-1H-imidazol-4-yl)sulfonyl)-4-((R)-tetrahydro-2H-pyran-2-yl)pyrrolidin-3-yl)carbamate Example 866 G (22 g, 53.1 mmol) was dissolved in methanol (500 ml) keeping the concentration at 44 mg/ml and then chirally separated using the following conditions: {Column: Chiralpak AD-H, 3 cm ID×25 cm, Mobile Phase SFC $CO_2$, Back pressure: 100 Bar, Pressure drop: 81 Bar, Modifier: methanol 12%. Flow Rate: 100 gm/min, Detector: UV 224 nm Sample concentration: 40 mg/mL in Methanol, Sample load: 2 mL (80 mg)}

The title product was detected by LCMS at $t_R$=2.801 min, 100% purity, m/z=415.2 (M+H)+ Method: LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% trifluoroacetic acid in water, mobile phase B was 0.018% trifluoroacetic acid in acetonitrile. The column used for the chromatography was a 2.1×50 mm Venusil XBP-C18 column (5 μm particles). Detection methods are diode array (DAD) and evaporative light scattering (ELSD) detection as well as positive/negative electrospray ionization.

Example 866 I (3R,4S)-1-((1-methyl-1H-imidazol-4-yl)sulfonyl)-4-((R)-tetrahydro-2H-pyran-2-yl)pyrrolidin-3-amine The title compound was prepared as the hydrochloride salt according to the procedure outlined in Example 373B substituting Example 866 H for Example 373A. The compound thus obtained was free based according to the procedure outlined in Example 380A substituting the hydrochloride salt of Example 866I for Example 322B.

Example 866 J (3R,4S)-1-[(1-methyl-1H-imidazol-4-yl)sulfonyl]-4-[(2R)-tetrahydro-2H-pyran-2-yl]-N-[3-(trifluoromethoxy)phenyl]pyrrolidin-3-amine The titled compound was prepared according to the procedure outlined in Example 337G substituting Example 866I for Example 337F and 1-bromo-3-(trifluoromethoxy)benzene for 1-bromo-3-(trifluoromethyl)benzene. MS (ESI) m/z 475.1 (M+H)+

Example 867

(3R,4S)-4-(4-fluorophenyl)-1-[(1-methyl-1H-imidazol-4-yl)sulfonyl]-N-[2-methyl-5-(prop-1-en-2-yl)cyclohexyl]pyrrolidin-3-amine In a 4 mL vial was added (3R,4S)-4-(4-fluorophenyl)-14(1-methyl-1H-imidazol-4-yl)sulfonyl)pyrrolidin-3-amine (40 mg, 0.123 mmol) and 2-methyl-5-(prop-1-en-2-yl)cyclohexanone (21 mg, 0.135 mmol). Then a buffer pH=4 solution (2 mL, made from 48 g AcOH and 30.5 g NaOAc in 1 L methanol) was added followed by the addition of Si-cyanoborohydride (350 mg, 0.311 mmol, load capacity: 0.89 mmol/g, Silicycle Catalog number: R66730B). The vial was capped and reacted for 16 hours. The reaction mixture was then filtered and purified by reverse phase HPLC to afford the title compound. MS (ESI) m/z 461 (M+H)+

Example 868

(3R,4S)-4-(4-fluorophenyl)-1-[(1-methyl-1H-imidazol-4-yl)sulfonyl]-N-(2,2,2-trifluoro-1-phenylethyl)pyrrolidin-3-amine To a solution of Example 322B (100 mg, 0.3 mmol) in dichloromethane (5 mL) was added 2,2,2-trifluoro-1-phenylethanone (53.7 mg, 0.3 mmol) followed by trimethyl aluminum (617 uL, 1 M in heptane). The mixture was stirred for 3 hours, and Borane-dimethylsulfide complex (308 uL, 2 M in tetrahydrofuran) was added. The mixture was stirred 2 hours. Then the reaction was partitioned between sodium hydroxide (1 M, aq) and dichloromethane. The organic fraction was collected, and purification via HPLC afforded the title compound. MS (DCI) m/z 483 (M+H)+.

Example 869

N-[2-chloro-4-(trifluoromethyl)benzyl]-2-[(1-methyl-1H-imidazol-4-yl)sulfonyl]octahydro-3aH-isoindol-3a-amine

Example 869A tert-butyl trans-2-benzyloctahydro-1H-isoindol-3a-ylcarbamate

The title compound was prepared according to the procedure outlined in Example 337C substituting trans-2-benzyloctahydro-1H-isoindol-3α-amine for Example 337B.

Example 869B tert-butyl trans-octahydro-1H-isoindol-3a-ylcarbamate

The title compound was prepared according to the procedure outlined in Example 2D substituting Example 869A for 2C.

Example 869C tert-butyl trans-2-(1-methyl-1H-imidazol-4-ylsulfonyl)octahydro-1H-isoindol-3a-ylcarbamate The title compound was prepared according to the procedure outlined in Example 373C substituting Example 869B for Example 373B.

Example 869D

Trans-2(1-methyl-1H-imidazol-4-ylsulfonyl)octahydro-1H-isoindol-3a-amine

The title compound was prepared as the hydrochloride salt according to the procedure outlined in Example 373B substituting Example 869C for Example 373A.

Example 869E

Trans-N-[2-chloro-4-(trifluoromethyl)benzyl]-2-[(1-methyl-1H-imidazol-4-yl)sulfonyl]octahydro-3aH-isoindol-3a-amine The title compound was prepared according to the procedure outlined in Example 354E substituting 2-chloro-4-(trifluoromethyl)benzaldehyde for 4-chlorobenzaldehyde and substituting Example 869D for Example 354D. MS (ESI) m/z 477/479 (3:1) (M+H)+.

Example 870

2-chloro-N-{2-[(1-methyl-1H-imidazol-4-yl)sulfonyl]octahydro-3aH-isoindol-3a-yl}-3-(trifluoromethyl)benzamide The title compound was prepared similarly to the procedure described in Example 404A substituting Example 869D for Example 14A and substituting 2-chloro-3-(trifluoromethyl)benzoic acid for 2-nitro-5-(trifluoromethyl)benzoic acid. MS (ESI) m/z 491/493 (3:1) (M+H)+.

Example 871

2,4-dichloro-N-{2-[(1-methyl-1H-imidazol-4-yl)sulfonyl]octahydro-3aH-isoindol-3a-yl}benzamide The title compound was prepared similarly to the procedure described in Example 404A substituting Example 869D for Example 14A and substituting 2,4-dichloro-3-benzoic acid for 2-nitro-5-(trifluoromethyl)benzoic acid. MS (ESI) m/z 457/459/461 (9:6:1) (M+H)+.

Example 872

1-hexyl-6-[(1-methyl-1H-imidazol-4-yl)sulfonyl]
octahydro-1H-pyrrolo[3, 4-1)]pyridine

Example 872A tert-butyl 6-(1-methyl-1H-imidazol-4-ylsulfonyl)
octahydro-1H-pyrrolo[3,4-b]pyridine-1-carboxylate The title compound was prepared according to the procedure outlined in Example 373C substituting tert-butyl octahydro-1H-pyrrolo[3,4-b]pyridine-1-carboxylate for Example 373B.

Example 872B 6-(1-methyl-1H-imidazol-4-ylsulfonyl)octahydro-
1H-pyrrolo[3,4-b]pyridine The title compound was prepared as the hydrochloride salt according to the procedure outlined in Example 373B substituting Example 872A for Example 373A.

Example 872C 1-hexyl-6-[(1-methyl-1H-imidazol-4-yl)sulfonyl]
octahydro-1H-pyrrolo[3,4-b]pyridine The title compound was prepared according to the procedure outlined in Example 354E substituting hexanal for 4-chlorobenzaldehyde and substituting Example 872B for Example 354D. MS (ESI) m/z 355 (M+H)$^+$.

Example 873

(2,4-dichlorophenyl){6-[(1-methyl-1H-imidazol-4-
yl)sulfonyl]octahydro-1H-pyrrolo[3,4-b]pyridin-1-
yl}methanone The title compound was prepared similarly to the procedure described in Example 404A substituting Example 872B for Example 14A and substituting 2,4-dichlorobenzoic acid for 2-nitro-5-(trifluoromethyl)benzoic acid. MS (ESI) m/z 443/445/447 (9:6:1) (M+H)$^+$.

Example 874

[2-chloro-3-(trifluoromethyl)phenyl]{6-[(1-methyl-
1H-imidazol-4-yl)sulfonyl]octahydro-1H-pyrrolo[3,
4-b]pyridin-1-yl}methanone The title compound was prepared similarly to the procedure described in Example 404A substituting Example 872B for Example 14A and substituting 2-chloro-3-(trifluoromethyl)benzoic acid for 2-nitro-5-(trifluoromethyl)benzoic acid. MS (ESI) m/z 477/479 (3:1) (M+H)$^+$.

Example 875

(3R,4S)-4-(4-fluorophenyl)-1-[(1-methyl-1H-imida-
zol-4-yl)sulfonyl]-N-[2,2,2-trifluoro-1-(3-methyl-
phenyl)ethyl]pyrrolidin-3-amine The title compound was prepared similarly to the procedure described in Example 868 substituting 2,2,2-trifluoro-1-(m-tolyl)ethanone for 2,2,2-trifluoro-1-phenylethanone. MS (ESI) m/z 497 (M+H)$^+$.

Example 876

(3R,4S)-4-(4-fluorophenyl)-1-[(1-methyl-1H-imida-
zol-4-yl)sulfonyl]-N-[2,2,2-trifluoro-1-(4-methyl-
phenyl)ethyl]pyrrolidin-3-amine The title compound was prepared similarly to the procedure described in Example 868 substituting 2,2,2-trifluoro-1-(p-tolyl)ethanone for 2,2,2-trifluoro-1-phenylethanone. MS (ESI) m/z 497 (M+H)$^+$.

Example 877

(1R,2R,3R,4S)-3-(4-fluorophenyl)-N-[4-fluoro-3-
(trifluoromethyl)phenyl]-7-[(1-methyl-1H-imidazol-
4-yl)sulfonyl]-7-azabicyclo[2.2.1]heptan-2-amine

Example 877A tert-butyl 2-(trimethylsilyl)pyrrolidine-1-carboxylate

A solution of tert-butyl pyrrolidine-1-carboxylate (6.84 g, 39.9 mmol) in dry Ether (40 mL) charged into a 250 mL flask equipped with a magnetic stirring bar and argon gas balloon, was cooled to –78° C. Tetramethylethylenediamine (7.23 mL, 47.9 mmol) followed by sec-butyl lithium (36.9 mL, 47.9 mmol) (1.3 M solution in hexane) was introduced. The mixture was allowed to stir for 2 hours at –78° C. Trimethylsilyl chloride (6.13 mL, 47.9 mmol) was added dropwise. After addition, the reaction mixture was allowed to warm to room temperature gradually and then diluted with 15 mL of saturated aqueous ammonium chloride solution. The organic layer was separated, and the aqueous layer was extracted with ethyl acetate (2×30 mL). The combined extracts were dried over sodium sulfate, filtered and concentrated. The crude oily residue, obtained after the concentration, was purified by fractional distillation (bp 55° C./0.5 mm) to give Example 877A as a colorless oil. MS (ESI) m/z 188 [M-C$_4$H$_8$+1]$^+$.

Example 877B tert-butyl
2,5-bis(trimethylsilyl)pyrrolidine-1-carboxylate

A 250 mL three-neck flask, equipped with a magnetic stirring bar and argon gas balloon, was charged with a solution of Example 877A (4.86 g, 20.0 mmol) in dry Ether (30 mL) and was cooled to –45° C. Tetramethylethylenediamine (6.03 mL, 39.9 mmol) followed by sec-butyl lithium (30.7 mL, 39.9 mmol) (1.3 M in hexane) was added to the flask dropwise while stirring. After 15 minutes of stirring at –45° C., the temperature was raised to –30° C. After 30 minutes, it was re-cooled to –45° C. and afterward trimethylsilyl chloride (5.10 mL, 39.9 mmol) was added drop-wise. The reaction mixture was allowed to warm to room temperature (about 25° C.), and diluted with 10 mL of saturated aqueous ammonium chloride solution. The solution was extracted with ethyl acetate (30 mL×3). The combined organic layers were dried over sodium sulfate, filtered and concentrated. The resulting mixture was deposited onto silica gel, loaded onto a silica gel column and eluted with petroleum ether/ethyl acetate (100:1) to give Example 877B as a pale yellow oil. MS (ESI) m/z 260 [M-C$_4$H$_8$+1]$^+$.

Example 877C benzyl-2,5-bis(trimethylsilyl)pyrrolidine

A stirring solution of Example 877B (16.1 g, 51.0 mmol) in DCM (160 mL) was cooled to 0° C. and was treated with trifluoroacetic acid (32 mL) drop-wise. The mixture was allowed to warm to room temperature (about 25° C.), and stirring was continued for an additional 2 hours. The reaction mixture was re-cooled to 0° C. and basified with 20% aqueous sodium hydroxide solution to pH=10. The organic layer was separated, and the aqueous layer was extracted with $CH_2Cl_2$ (2×60 ml). The combined extracts were washed with brine, dried over $Na_2SO_4$, and concentrated to give 13 g of crude amine (contain some salt) which was utilized for the next step directly without further purification. To a 260 mL solution of the crude amine (13 g, 51 mmol) in acetonitrile, were added potassium carbonate (8.47 g, 61.3 mmol) and benzyl bromide (7.86 g, 45.9 mmol). The resultant suspension was stirred at room temperature for 16 hours. The mixture was filtered, and the solvent was evaporated under vacuum. The crude yellow oil was purified by silica gel column chromatography, eluting with ethyl acetate/petroleum ether (0:1 to 1:50), to obtain Example 877C as a pale yellow oil. MS (ESI) m/z 306 [M+1]$^+$.

Example 877D 7-benzyl-2-(4-fluorophenyl)-3-nitro-7-azabicyclo[2.2.1]heptane (E)-1-fluoro-4-(2-nitrovinyl)benzene (3.95 g, 23.65 mmol) and Example 877C (6.49 ml, 19.71 mmol) were dissolved in 75 mL acetonitrile under an argon atomosphere. Silver(I) fluoride (5 g, 39.4 mmol) was added in a single portion and the reactoin was allowed to proceed overnight. At this time, LC/MS indicated an excess of nitrostyrene present. An additional 0.5 eq of 1-benzyl-2,5-bis(trimethylsilyl)pyrrolidine (3.25 mL, 9.85 mmol) and NaF (2.5 g, 19.7 mmol) were added. The reaction proceeded further to 85% conversion. The contents were concentrated, taken up in ethyl acetate, washed with sodium bicarbonate, water, and brine. The crude material was purified via FLASH 0-50% ethyl acetate/hexane (120 g column) to yield Example 877D as a yellow oil. MS (APCI) m/z 327 [M+1]$^+$.

Example 877E 7-benzyl-2-(4-fluorophenyl)-3-nitro-7-azabicyclo[2.2.1]heptane

Example 877D (850 mg, 2.60 mmol) and tetrahydrofuran (10 ml) were added to a Raney Nickel 2800 water slurry (900 mg, 6.90 mmol) in a 50 ml pressure bottle. The contents were stirred for 16 hr under 30 psi hydrogen gas. The mixture was filtered through a nylon membrane and concentrated to yield Example 877E. MS (DCI) m/z 297 (M+H)$^+$.

Example 877F tert-butyl 7-benzyl-3-(4-fluorophenyl)-7-azabicyclo[2.2.1]heptan-2-ylcarbamate In a 100 mL round bottom flask were added 15 mL dichloromethane and Example 877E. BOC-Anhydride (1116 µl, 4.81 mmol) was dissolved in 5 mL DCM and added dropwise via an addition funnel. The reaction was allowed to proceed for 2 hr. The contents were dried by rotovap and purified by FLASH chromatography (0-50% ethyl acetate/heptane) to yield Example 877F. MS (APCI) m/z 397 (M+H)$^+$.

Example 877G tert-butyl 3-(4-fluorophenyl)-7-azabicyclo[2.2.1]heptan-2-ylcarbamate Example 877F (1.07 g, 2.70 mmol) and tetrahydrofuran (25 ml) were added to wet 20% Palladium Hydroxide on carbon (0.25 g, 0.182 mmol) in a 50 ml pressure bottle. The contents were stirred for 32 hr under 30 psi hydrogen gas at room temperature. The mixture was filtered through a nylon membrane and concentrated to yield Example 877G. MS (DCI) m/z 307 (M+H)$^+$.

Example 877H 3-(4-fluorophenyl)-7-((1-methyl-1H-imidazol-4-yl)sulfonyl)-7-azabicyclo[2.2.1]heptan-2-amine hydrochloride In a 20 mL scintillation vial were added 5 mL dichloromethane and Example 877G. To this solution was added 1-methyl-1H-imidazole-4-sulfonyl chloride (749 mg, 4.15 mmol) followed by DIEA (966 µl, 5.53 mmol). The reaction was allowed to proceed for 3 hours and the contents were then concentrated and purified via FLASH chromatography (30-100% ethyl acetate/heptane). The collected fractions were combined and dried. The solid was dissolved in 5 mL dichloromethane and then 5 mL of a 4 N hydrochloric acid solution in dioxane was added. The reaction was allowed to proceed for 72 hour and then the white precipitate was collected by filtration to yield Example 877H as a white powder. MS (APCI) m/z 351 (M+H)$^+$.

Example 877I

N-(4-fluoro-3-(trifluoromethyl)phenyl)-3-(4-fluorophenyl)-7-((1-methyl-1H-imidazol-4-yl)sulfonyl)-7-azabicyclo[2.2.1]heptan-2-amine In a 10 mL microwave vial was added Example 877H (30 mg, 0.086 mmol), 4-bromo-1-fluoro-2-(trifluoromethyl)benzene (20.80 mg, 0.086 mmol), sodium ter-butoxide (16.46 mg, 0.171 mmol), BINAP (2.67 mg, 4.28 µmol) and bis(dibenzylideneacetone)palladium (1.231 mg, 2.140 µmol) followed by the addition of 2 mL dimethoxyethane. The reaction vessel was capped and the reaction mixture was heated under microwave conditions for 15 min at 130° C. Upon completion, the mixture was filtered through celite, concentrated, dissolved in 2 ml 50% MeOH/DMSO, and purified by reverse phase HPLC to obtain the title compound as one of the two products. MS (ESI) m/z 512 (M+H)$^+$

Example 878

3-(4-fluorophenyl)-N-[4-fluoro-3-(trifluoromethyl)phenyl]-7-[(1-methyl-1H-imidazol-4-yl)sulfonyl]-7-azabicyclo[2.2.1]heptan-2-amine The desired compound was obtained as described in Example 877 as the second product from the reverse phase HPLC purification. MS (ESI) m/z 512 (M+H)$^+$

Example 879

1-[2-chloro-4-(trifluoromethyl)benzyl]-6-[(1-methyl-1H-imidazol-4-yl)sulfonyl]octahydro-1H-pyrrolo[3,4-b]pyridine The title compound was prepared according to the procedure outlined in Example 354E substituting 2-chloro-4-(trifluoromethyl)benzaldehyde for 4-chlorobenzaldehyde and substituting Example 872B for Example 354D. MS (ESI) m/z 463/465 (3:1) (M+H)$^+$.

Example 880

[2-chloro-4-(trifluoromethyl)phenyl]{6-[(1-methyl-1H-imidazol-4-yl)sulfonyl]octahydro-1H-pyrrolo[3,4-b]pyridin-1-yl}methanone The title compound was prepared similarly to the procedure described in Example 404A substituting Example 872B for Example 14A and substituting 2-chloro-4-(trifluoromethyl)benzoic acid for 2-nitro-5-(trifluoromethyl)benzoic acid. MS (ESI) m/z 477/479 (3:1) (M+H)$^+$.

Example 881

N-(3-chloro-4-fluorobenzyl)-2-[(1-methyl-1H-imidazol-4-yl)sulfonyl]-2-azaspiro[4.5]decane-4-carboxamide

Example 881A

Ethyl 2-benzyl-2-azaspiro[4.5]decane-4-carboxylate

The title compound was prepared according to the procedure outlined in Example 2A substituting ethyl 2-cyclohexylideneacetate for 4-methoxy-beta-nitrostyrene.

Example 881B

Ethyl 2-azaspiro[4.5]decane-4-carboxylate

The title compound was prepared according to the procedure outlined in Example 2D substituting Example 881A for 2C.

Example 881C

Ethyl 2-(1-methyl-1H-imidazol-4-ylsulfonyl)-2-azaspiro[4.5]decane-4-carboxylate
The title compound was prepared according to the procedure outlined in Example 373C substituting Example 881B for Example 373B.

Example 881D 2-(1-methyl-1H-imidazol-4-ylsulfonyl)-2-azaspiro[4.5]decane-4-carboxylic acid The title compound was prepared according to the procedure outlined in Example 242D substituting Example 881C for 242C.

Example 881E

N-(3-chloro-4-fluorobenzyl)-2-[(1-methyl-1H-imidazol-4-yl)sulfonyl]-2-azaspiro[4.5]decane-4-carboxamide The title compound was prepared similarly to the procedure described in Example 404A substituting 3-chloro-4-fluoro-benzyl amine for Example 14A and substituting Example 881D for 2-nitro-5-(trifluoromethyl)benzoic acid. MS (ESI) m/z 469/471 (3:1) (M+H)$^+$.

Example 882

N-(3,4-difluorobenzyl)-2-[(1-methyl-1H-imidazol-4-yl)sulfonyl]-2-azaspiro[4.5]decane-4-carboxamide The title compound was prepared similarly to the procedure described in Example 404A substituting 3,4-difluoro-benzyl amine for Example 14A and substituting Example 881D for 2-nitro-5-(trifluoromethyl)benzoic acid. MS (ESI) m/z 453 (M+H)$^+$.

Example 883

1-{(3R,4S)-4-(4-fluorophenyl)-1-[(1-methyl-1H-imidazol-4-yl)sulfonyl]pyrrolidin-3-yl}-1,3-dihydro-2H-indol-2-one

Example 883A 2-(2-bromophenyl)-N-((3R,4S)-4-(4-fluorophenyl)-1-(1-methyl-1H-imidazol-4-ylsulfonyl)pyrrolidin-3-yl)acetamide To a solution of Example 322B (200 mg, 0.62 mmol) in a 1:1 dichloromethane:dimethylformamide solution (6 mL) was added 2-(2-bromophenyl)acetic acid (159 mg, 0.74 mmol) and N1-((ethylimino)methylene)-N3,N3-dimethylpropane-1,3-diamine hydrochloride (177 mg, 0.93 mmol). The solution was stirred for 16 hours. Brine and EtOAc were added and the organic fraction was collected. The organic fraction was washed with brine and 1 M HCl (aq). Purification via flash chromatography (0-100% EtOAc/heptanes) afforded the title compound.

Example 883B

1-{(3R,4S)-4-(4-fluorophenyl)-1-[(1-methyl-1H-imidazol-4-yl)sulfonyl]pyrrolidin-3-yl}-1,3-dihydro-2H-indol-2-one Example 883A (254 mg, 0.49 mmol) was dissolved in hot tert-butanol (15 mL) and added to a vial containing dicyclohexyl(2',4',6'-triisopropyl-[1,1'-biphenyl]-2-yl)phosphine (17.4 mg, 0.04 mmol), phenylboronic acid (4.5 mg, 0.04 mmol), diacetoxypalladium (3.3 mg, 0.02 mmol), and potassium carbonate (168 mg, 1.2 mmol). The vial was sealed and stirred at 90° C. for 14 hours. Concentration followed by purification via HPLC afforded the title compound. MS (ESI) m/z 441 (M+H)$^+$.

Example 884

2-[(1-methyl-1H-imidazol-4-yl)sulfonyl]-N-[4-(trifluoromethyl)benzyl]octahydro-3aH-isoindol-3a-amine

Example 884A tert-butyl (2-benzyloctahydro-1H-isoindol-3a-yl)carbamate

To 2-benzyloctahydro-1H-isoindol-3a-amine (3.08 g, 13.4 mmol) in 30 mL of ethyl acetate was added di-tert-butyl dicarbonate (3.27 g, 15.0 mmol). This was stirred at room temperature overnight. Then water (30 mL) was added, separated, and the organic layer was washed with water one more time. The organic layer was dried over $Na_2SO_4$, concentrated down and purified by flash-chromatography on silica gel with 0-7% methanol in dichloromethane to provide the title product MS (ESI) m/z 331.2 $(M+H)^+$.

Example 884B tert-butyl (octahydro-1H-isoindol-3a-yl)carbamate

To Example 884A (4.13 g, 12.50 mmol) in 80 ml of tetrahydrofuran was added 20% $Pd(OH)_2$/C, wet (0.85 g, 0.617 mmol) in a 250 mL SS pressure bottle. This was stirred for 15 hours at 30 psi and 50° C. The mixture was filtered through a nylon membrane. The obtained solution was concentrated down to afford the title product. MS (ESI) m/z 241.0 $(M+H)^+$.

Example 884C tert-butyl (2-((1-methyl-1H-imidazol-4-yl)sulfonyl) octahydro-1H-isoindol-3a-yl)carbamate The title compound was prepared using the same sequence of steps as described in Example 182C by substituting Example 884B for Example 182 B. MS (ESI) m/z 385.4 $(M+H)^+$.

Example 884D 2-((1-methyl-1H-imidazol-4-yl)sulfonyl)octahydro-1H-isoindol-3a-amine The title compound was prepared as the hydrochloride salt according to the procedure outlined in Example 373B substituting Example 884C for Example 373A. Then it was free based according to the procedure outlined in Example 380A substituting Example 884D HCl for Example 322B.

Example 884E

2-[(1-methyl-1H-imidazol-4-yl)sulfonyl]-N-[4-(trifluoromethyl)benzyl]octahydro-3aH-isoindol-3a-amine The title compound was prepared according to the procedure outlined in Example 354E substituting 4-(trifluoromethyl)benzaldehyde for 4-chlorobenzaldehyde and substituting Example 884D for Example 354D. MS (ESI) m/z 443.1 $(M+H)^+$.

Example 885 trans-N-[2-chloro-4-(trifluoromethyl)benzyl]-2-[(1-methyl-1H-imidazol-4-yl)sulfonyl]-2,3,3a,8-tetrahydroindeno[1,2-c]pyrrol-8a(1H)-amine

Example 885A 2-nitro-1H-indene

To indene (5 g, 43 mmol) in THF (100 mL) was added $NaNO_2$ (5.44 g, 118 mmol) then $I_2$ (18.7 g, 74 mmol) in portions at r.t. The mixture was stirred for 2 h and $Na_2S_2O_5$ (aq) was added until the color mostly faded. THF was removed, the residue extracted with ethyl acetate, and the crude material was purified by silica gel column chromatography eluting with hexanes and ethyl acetate (20:1) to afford the title compound.

Example 885B 2-benzyl-8a-nitro-1,2,3,3a,8,8a-hexahydroindeno[2,1-c]pyrrole

The title compound was prepared according to the procedure outlined in Example 2A substituting Example 885A for 4-methoxy-beta-nitrostyrene.

Example 885C 2-benzyl-1,2,3,3a,8,8a-hexahydroindeno[2,1-c]pyrrol-8a-amine

The title compound was prepared according to the procedure outlined in Example 2B substituting Example 885B for Example 2A.

Example 885D tert-butyl 2-benzyl-1,2,3,3a,8,8a-hexahydroindeno[2,1-c]pyrrol-8a-ylcarbamate The title compound was prepared according to the procedure outlined in Example 337C substituting Example 885C for Example 337B.

Example 885E tert-butyl 1,2,3,3a,8,8a-hexahydroindeno[2,1-c]pyrrol-8a-ylcarbamate The title compound was prepared according to the procedure outlined in Example 2D substituting Example 885D for 2C.

Example 885F tert-butyl 2-(1-methyl-1H-imidazol-4-ylsulfonyl)-1,2,3,3a,8,8a-hexahydroindeno[2,1-c]pyrrol-8a-ylcarbamate The title compound was prepared according to the procedure outlined in Example 373C substituting Example 885E for Example 373B.

Example 885G 2-(1-methyl-1H-imidazol-4-ylsulfonyl)-1,2,3,3a,8,8a-hexahydroindeno[2,1-c]pyrrol-8a-amine The title compound was prepared as the hydrochloride salt according to the procedure outlined in Example 373B substituting Example 885F for Example 373A.

Example 885H trans-N-[2-chloro-4-(trifluoromethyl)benzyl]-2-[(1-methyl-1H-imidazol-4-yl)sulfonyl]-2,3,3a,8-tetrahydroindeno[1,2-c]pyrrol-8a(1H)-amine The title compound was prepared according to the procedure outlined in Example 354E substituting 3-chloro-4-(trifluoromethyl)benzaldehyde for 4-chlorobenzaldehyde and substituting Example 885G for Example 354D. MS (ESI) m/z 511/513 (3:1) (M+H)$^+$.

Example 886

2-{4-[(4-fluorophenoxy)methyl]-1-[(1-methyl-1H-imidazol-4-yl)sulfonyl]pyrrolidin-3-yl}pyridine Methyl 1-((1-methyl-1H-imidazol-4-yl)sulfonyl)-4-(pyridin-2-yl)pyrrolidine-3-carboxylate

Example 886 A

The title compound was prepared according to the procedures outlined in Example 242A to 242C substituting (E)-methyl 3-(pyridin-2-yl)acrylate for (E)-methyl 3-(4-fluorophenyl)acrylate.

Example 886 B 1-((1-methyl-1H-imidazol-4-yl)sulfonyl)-4-(pyridin-2-yl)pyrrolidin-3-yl)methanol The title compound was prepared according to the procedure outlined in Example 206 substituting Example 886A for Example 242 C. MS (ESI) m/z 323.1 (M+H)$^+$.

Example 886 C

2-{4-[(4-fluorophenoxy)methyl]-1-[(1-methyl-1H-imidazol-4-yl)sulfonyl]pyrrolidin-3-yl}pyridine The title compound was prepared according to the procedure outlined in Example 245 substituting Example 886B for Example 206 C and substituting 4-fluorophenol for phenol MS (ESI) m/z 417.1 (M+H)$^+$.

Example 887

1-[(1-methyl-1H-imidazol-4-yl)sulfonyl]-N-[3-(trifluoromethoxy)phenyl]-2,3-dihydro-1H-indol-3-amine

Example 887A tert-butyl (1-((1-methyl-1H-imidazol-4-yl)sulfonyl)indolin-3-yl)carbamate The title compound was prepared according to the procedures outlined in Example 1C substituting tert-butyl indolin-3-ylcarbamate for Example 1B.

Example 887B 1-((1-methyl-1H-imidazol-4-yl)sulfonyl)indolin-3-amine

The title compound was prepared according to the procedures outlined in Example 1A substituting Example 887A for Example 1A.

Example 887C 1-((1-methyl-1H-imidazol-4-yl)sulfonyl)-N-(3-(trifluoromethoxy)phenyl)indolin-3-amine The title compound was prepared according to the procedures outlined in Example 29 substituting Example 887B for Example 14A and substituting 1-bromo-3-(trifluoromethoxy)benzene for bromobenzene.

Example 888

2-[(1-methyl-1H-imidazol-4-yl)sulfonyl]-3a-{[6-(trifluoromethyl)pyrimidin-4-yl]oxy}-2,3,3a,4,5,9b-hexahydro-1H-benzo[e]isoindole

Example 888A 3-nitro-1,2-dihydronaphthalene

The title compound was prepared according to the procedure outlined in Example 885A substituting 1,2-dihydronaphthalene for indene.

Example 888B 2-benzyl-3a-nitro-2,3,3a,4,5,9b-hexahydro-1H-benzo[e]isoindole

The title compound was prepared according to the procedure outlined in Example 2A substituting Example 888A for 4-methoxy-beta-nitrostyrene.

Example 888C 2-benzyl-2,3,3a,4,5,9b-hexahydro-1H-benzo[e]isoindol-3a-amine

The title compound was prepared according to the procedure outlined in Example 2B substituting Example 888B for Example 2A.

Example 888D tert-butyl 2-benzyl-2,3,3a,4,5,9b-hexahydro-1H-benzo[e]isoindol-3a-ylcarbamate The title compound was prepared according to the procedure outlined in Example 337C substituting Example 888C for Example 337B.

Example 888E tert-butyl 2,3,3a,4,5,9b-hexahydro-1H-benzo[e]
isoindol-3a-ylcarbamate The title compound was prepared according to the procedure outlined in Example 2D substituting Example 888D for 2C.

Example 888F tert-butyl 2-(1-methyl-1H-imidazol-4-ylsulfonyl)-2,
3,3a,4,5,9b-hexahydro-1H-benzo[e]isoindol-3a-yl-carbamate The title compound was prepared according to the procedure outlined in Example 373C substituting Example 888E for Example 373B.

Example 888G 2-(1-methyl-1H-imidazol-4-ylsulfonyl)-2,3,3a,4,5,
9b-hexahydro-1H-benzo[e]isoindol-3a-amine The title compound was prepared as the hydrochloride salt according to the procedure outlined in Example 373B substituting Example 888F for Example 373A.

Example 888H

2-[(1-methyl-1H-imidazol-4-yl)sulfonyl]-3a-{[6-(trifluoromethyl)pyrimidin-4-yl]oxy}-2,3,3a,4,5,9b-hexahydro-1H-benzo[e]isoindole The title compound was prepared according to the procedure outlined in Example 337G substituting Example 888G for Example 337F and substituting 4-bromo-6-(trifluoromethyl)pyrimidine for 1-bromo-3-(trifluoromethyl)benzene. MS (ESI) m/z 480 (M+H)$^+$.

Example 889

N-(4-fluorobenzyl)-2-[(1-methyl-1H-imidazol-4-yl)sulfonyl]-1,2,3,4,5,9b-hexahydro-3aH-benzo[e]isoindol-3a-amine The title compound was prepared according to the procedure outlined in Example 354E substituting 4-fluorobenzaldehyde for 4-chlorobenzaldehyde and substituting Example 888G for Example 354D. MS (ESI) m/z 441 (M+H)$^+$.

Example 890

N-[2-chloro-4-(trifluoromethyl)benzyl]-2-[(1-methyl-1H-imidazol-4-yl)sulfonyl]-1,2,3,4,5,9b-hexahydro-3aH-benzo[e]isoindol-3α-amine The title compound was prepared according to the procedure outlined in Example 354E substituting 3-chloro-4-trifluoromethylbenzaldehyde for 4-chlorobenzaldehyde and substituting Example 888G for Example 354D. MS (ESI) m/z 525/527 (3:1) (M+H)$^+$.

Example 891

2-[(1-methyl-1H-1,2,3-triazol-4-yl)sulfonyl]-N-[6-(trifluoromethyl)pyrimidin-4-yl]-2,3,3a,8-tetrahydroindeno[1,2-c]pyrrol-8a(1H)-amine The title compound was prepared according to the procedure outlined in Example 337G substituting Example 885G for Example 337F and substituting 4-bromo-6-(trifluoromethyl)pyrimidine for 1-bromo-3-(trifluoromethyl)benzene. MS (ESI) m/z 466 (M+H)$^+$.

Example 892

2-[(1-methyl-1H-imidazol-4-yl)sulfonyl]-N-[4-(trifluoromethyl)pyridin-2-yl]-2,3,3a,8-tetrahydroindeno[1,2-c]pyrrol-8a(1H)-amine The title compound was prepared according to the procedure outlined in Example 337G substituting Example 885G for Example 337F and substituting 4-bromo-6-(trifluoromethyl)pyrimidine for 1-bromo-3-(trifluoromethyl)benzene. MS (ESI) m/z 466 (M+H)$^+$.

Example 893

N-(2,3-dihydro-1H-inden-1-yl)-1-[(1-methyl-1H-imidazol-4-yl)sulfonyl]-4-(1-methylpiperidin-2-yl)pyrrolidin-3-amine

Example 893A tert-butyl (trans)-1-(1-methyl-1H-imidazol-4-ylsulfonyl)-4-(pyridin-2-yl)pyrrolidin-3-ylcarbamate The title compound was prepared similarly to the procedures described in Example 2A-2E substituting Example 307A for (E)-1-methoxy-4-(2-nitrovinyl)benzene.

Example 893B tert-butyl (trans)-1-(1-methyl-1H-imidazol-4-ylsulfonyl)-4-((R)-1-methylpiperidin-2-yl)pyrrolidin-3-ylcarbamate To a solution of Example 893A (2 g, 4.91 mmol) in acetic acid (20 ml) in a 50 ml pressure bottle was added 5% Pt/C (wet, 0.4 g, 0.843 mmol) and the solution was shaken for 3 days under hydrogen (30 psi) at 50° C. and 1 day at room temperature. During this time 50 wt % platinum dioxide was added. Concentration afforded crude tert-butyl (trans)-1-(1-methyl-1H-imidazol-4-ylsulfonyl)-4-((R)-piperidin-2-yl)pyrrolidin-3-ylcarbamate. The title compound was obtained by following the procedure described in Example 3A substituting this crude for Example 3A and substituting formaldehyde for benzaldehyde.

Example 893C (trans)-1-(1-methyl-1H-imidazol-4-ylsulfonyl)-4-((R)-1-methylpiperidin-2-yl)pyrrolidin-3-amine The title compound was prepared as an HCl salt similarly to the procedure described in Example 2F substituting Example 893B for Example 2E.

Example 893D (trans)-N-(2,3-dihydro-1H-inden-1-yl)-1-[(1-methyl-1H-imidazol-4-yl)sulfonyl]-4-(1-methylpiperidin-2-yl)pyrrolidin-3-amine The title compound was prepared similarly to the procedure described in Example 148 substituting Example 893C for Example 3A and substituting 2,3-dihydro-1H-inden-1-one for benzaldehyde. MS (ESI) m/z 444 (M+H)$^+$.

Example 894

1-[(1-methyl-1H-imidazol-4-yl)sulfonyl]-4-(1-methylpiperidin-2-yl)-N-[3-(2,2,2-trifluoroethoxy)phenyl]pyrrolidin-3-amine The title compound was prepared similarly to the procedure described in Example 327 substituting Example 893C for Example 322B and substituting 1-bromo-3-(2,2,2-trifluoroethoxy)benzene for 1-bromo-3-(trifluoromethyl)benzene. MS (ESI) m/z 502 (M+H)$^+$.

Example 895

4-(5-fluoropyridin-2-yl)-1-[(1-methyl-1H-imidazol-4-yl)sulfonyl]-N-[3-(trifluoromethoxy)phenyl]pyrrolidin-3-amine

Example 895A (trans)-4-(5-fluoropyridin-2-yl)-1-(1-methyl-1H-imidazol-4-ylsulfonyl)pyrrolidin-3-amine The title compound was prepared similarly to the procedures described in Examples 307A-307B substituting 5-fluoropicolinaldehyde for 2-pyridinecarboxaldeyde.

Example 895B (trans)-4-(5-fluoropyridin-2-yl)-1-[(1-methyl-1H-imidazol-4-yl)sulfonyl]-N-[3-(trifluoromethoxy)phenyl]pyrrolidin-3-amine The title compound was prepared similarly to the procedure described in Example 327 substituting Example 895A for Example 322B and substituting 1-bromo-3-(trifluoromethoxy)benzene for 1-bromo-3-(trifluoromethyl)benzene. MS (ESI) m/z 486 (M+H)$^+$.

Example 896

(3R,4S)-4-(1,3-dioxan-2-yl)-1-[(1-methyl-1H-1,2,3-triazol-4-yl)sulfonyl]-N-[3-(trifluoromethoxy)phenyl]pyrrolidin-3-amine

Example 896A (E)-3,3-dimethoxy-1-nitroprop-1-ene

To 2,2-dimethoxyacetaldehyde (4 mL 60%) in nitromethane (10 mL) was added potassium carbonate (338 mg). The mixture was allowed to stir for 2 h, ethyl acetate was added, and water was drained. The crude intermediate was dissolved in dichloromethane (30 mL), triethyl amine (6.1 g, 60 mmol) and trifluoroacetic anhydride (6.3 g, 30 mmol) were added at −20° C. The mixture was allowed to stir at −20° C. for 10 min and at r.t for 1 h. Dichloromethane was removed, ethyl acetate was added and the organic extract was washed with water to afford the title compound.

Example 896B

Trans-1-benzyl-3-(dimethoxymethyl)-4-nitropyrrolidine

The title compound was prepared according to the procedure outlined in Example 2A substituting Example 896A for 4-methoxy-beta-nitrostyrene.

Example 896C (3R,4R)-1-benzyl-3-(dimethoxymethyl)-4-nitropyrrolidine

A solution of D-tartaric acid (26.8 g, 178 mmol) in 250 mL ethanol was added in a thin stream to a stirring solution of Example 896B (50 g, 178 mmol) in 250 mL ethanol. Solids began to crash out before the addition was complete. The suspension was stirred overnight, filtered, and washed with ethanol. The crude material was recrystallized from ethanol to afford the title compound.

Example 896D (3R,4R)-1-benzyl-4-(dimethoxymethyl)pyrrolidin-3-amine

The title compound was prepared according to the procedure outlined in Example 2B substituting Example 896C for Example 2A.

Example 896E tert-butyl (3R,4R)-1-benzyl-4-(dimethoxymethyl)pyrrolidin-3-ylcarbamate The title compound was prepared according to the procedure outlined in Example 337C substituting Example 896D for Example 337B.

Example 896F tert-butyl (3R,4R)-4-(dimethoxymethyl)pyrrolidin-3-ylcarbamate

The title compound was prepared according to the procedure outlined in Example 2D substituting Example 896E for 2C.

Example 896G tert-butyl (3R,4R)-4-(dimethoxymethyl)-1-(1-methyl-1H-1,2,3-triazol-4-ylsulfonyl)pyrrolidin-3-ylcarbamate The title compound was prepared according to the procedure outlined in Example 373C substituting Example 896F for Example 373B and substituting 1-methyl-1H-1,2,3-triazole-4-sulfonyl chloride for 1-methyl-1H-imidazole-4-sulfonyl chloride.

Example 896H tert-butyl (3R,4R)-4-(1,3-dioxan-2-yl)-1-(1-methyl-1H-1,2,3-triazol-4-ylsulfonyl)pyrrolidin-3-ylcarbamate To Example 896G (2 g, 4.9 mmol) in toluene (10 mL) was added propane-1,3-diol (1.5 g, 20 mmol) and toluenesulfonic acid (20 mg, 0.1 mmol). The mixture was heated at 80° C. for 3 h. Volatiles were removed to afford the title compound.

Example 896I (3R,4R)-4-(1,3-dioxan-2-yl)-1-(1-methyl-1H-1,2,3-triazol-4-ylsulfonyl)pyrrolidin-3-amine The title compound was prepared as the hydrochloride salt according to the procedure outlined in Example 373B substituting Example 896H for Example 373A.

Example 896J (3R,4S)-4-(1,3-dioxan-2-yl)-1-[(1-methyl-1H-1,2,3-triazol-4-yl)sulfonyl]-N-[3-(trifluoromethoxy)phenyl]pyrrolidin-3-amine The title compound was prepared according to the procedure outlined in Example 337G substituting Example 896I for Example 337F and 1-bromo-3-(trifluoromethoxy)benzene for 1-bromo-3-(trifluoromethyl)benzene. MS (ESI) m/z 478 (M+H)$^+$.

Example 897

(3R,4S)-4-(1,3-dioxan-2-yl)-1-[(1-methyl-1H-imidazol-4-yl)sulfonyl]-N-[3-(trifluoromethoxy)phenyl]pyrrolidin-3-amine

Example 897A tert-butyl (3R,4R)-4-(dimethoxymethyl)-1-(1-methyl-1H-imidazol-4-ylsulfonyl)pyrrolidin-3-ylcarbamate The title compound was prepared according to the procedure outlined in Example 373C substituting Example 896F for Example 373B.

Example 897B tert-butyl (3R,4R)-4-(1,3-dioxan-2-yl)-1-(1-methyl-1H-imidazol-4-ylsulfonyl)pyrrolidin-3-ylcarbamate The title compound was prepared according to the procedure outlined in Example 896H substituting Example 897A for Example 896G.

Example 897C (3R,4R)-4-(1,3-dioxan-2-yl)-1-(1-methyl-1H-imidazol-4-ylsulfonyl)pyrrolidin-3-amine The title compound was prepared as the hydrochloride salt according to the procedure outlined in Example 373B substituting Example 897B for Example 373A.

Example 897D (3R,4S)-4-(1,3-dioxan-2-yl)-1-[(1-methyl-1H-imidazol-4-yl)sulfonyl]-N-[3-(trifluoromethoxy)phenyl]pyrrolidin-3-amine The title compound was prepared according to the procedure outlined in Example 337G substituting Example 897C for Example 337F and 1-bromo-3-(trifluoromethoxy)benzene for 1-bromo-3-(trifluoromethyl)benzene. MS (ESI) m/z 477 (M+H)$^+$.

Example 898

1-[(1-methyl-1H-imidazol-4-yl)sulfonyl]-4-(1-methylpiperidin-2-yl)-N-[3-(trifluoromethoxy)phenyl]pyrrolidin-3-amine The title compound was prepared similarly to the procedure described in Example 327 substituting Example 893C for Example 322B and substituting 1-bromo-3-(trifluoromethoxy)benzene for 1-bromo-3-(trifluoromethyl)benzene. MS (ESI) m/z 488 (M+H)$^+$.

Example 899

(3R,4S)-4-(1,3-dioxan-2-yl)-1-[(1-methyl-1H-imidazol-4-yl)sulfonyl]-N-[3-(2,2,2-trifluoroethoxy)phenyl]pyrrolidin-3-amine The title compound was prepared according to the procedure outlined in Example 337G substituting Example 897C for Example 337F and 1-bromo-3-(trifluoroethoxy)benzene for 1-bromo-3-(trifluoromethyl)benzene. MS (ESI) m/z 491 (M+H)$^+$.

Example 900

(3R,4S)-4-(5,5-dimethyl-1,3-dioxan-2-yl)-1-[(1-methyl-1H-imidazol-4-yl)sulfonyl]-N-[3-(trifluoromethoxy)phenyl]pyrrolidin-3-amine

Example 900A (3R,4R)-4-(dimethoxymethyl)-1-(1-methyl-1H-imidazol-4-ylsulfonyl)pyrrolidin-3-amine The title compound was prepared as the hydrochloride salt according to the procedure outlined in Example 373B substituting Example 897A for Example 373A.

Example 900B (3R,4R)-4-(dimethoxymethyl)-1-(1-methyl-1H-imidazol-4-ylsulfonyl)-N-(3-(trifluoromethoxy)phenyl)pyrrolidin-3-amine The title compound was prepared according to the procedure outlined in Example 337G substituting Example 900A for Example 337F and substituting 1-bromo-3-(trifluoromethoxy)benzene for 1-bromo-3-(trifluoromethyl)benzene.

Example 900C (3R,4S)-4-(5,5-dimethyl-1,3-dioxan-2-yl)-1-[(1-methyl-1H-imidazol-4-yl)sulfonyl]-N-[3-(trifluoromethoxy)phenyl]pyrrolidin-3-amine The title compound was prepared according to the procedure outlined in Example 896H substituting Example 900B for Example 896G and substituting 2,2-dimethylpropane-1,3-diol for propane-1,3-diol. MS (ESI) m/z 505 (M+H)$^+$.

Example 901

(3R,4S)-4-(1,3-dioxepan-2-yl)-1-[(1-methyl-1H-imidazol-4-yl)sulfonyl]-N-[3-(trifluoromethoxy)phenyl]pyrrolidin-3-amine The title compound was prepared according to the procedure outlined in Example 896H substituting Example 900B for Example 896G and substituting butane-1,4-diol for propane-1,3-diol. MS (ESI) m/z 491(M+H)$^+$.

Example 902

(3R,4S)-4-(1,3-dioxolan-2-yl)-1-[(1-methyl-1H-imidazol-4-yl)sulfonyl]-N-[3-(trifluoromethoxy)phenyl]pyrrolidin-3-amine The title compound was prepared according to the procedure outlined in Example 896H substituting Example 900B for Example 896G and substituting ethane-1,2-diol for propane-1,3-diol. MS (ESI) m/z 491(M+H)$^+$. MS (ESI) m/z 463 (M+H)$^+$.

Example 903

(3R,4S)-N-(2,3-dihydro-1H-inden-1-yl)-4-(1,3-dioxan-2-yl)-1-[(1-methyl-1H-imidazol-4-yl)sulfonyl]pyrrolidin-3-amine The title compound was prepared according to the procedure outlined in Example 354E substituting Example 897C for Example 354D and 2,3-dihydro-1H-inden-1-one for 4-chlorobenzaldehyde. MS (ESI) m/z 433 (M+H)$^+$.

Example 904

(3R,4S)-N-[2-chloro-4-(trifluoromethyl)benzyl]-4-(1,3-dioxan-2-yl)-1-[(1-methyl-1H-imidazol-4-yl)sulfonyl]pyrrolidin-3-amine The title compound was prepared according to the procedure outlined in Example 354E substituting Example 897C for Example 354D and 2-chloro-4-(trifluoromethyl)benzaldehyde for 4-chlorobenzaldehyde. MS (ESI) m/z 509/511 (3:1) (M+H)$^+$.

Example 905

(3R,4S)-4-(1,3-dioxan-2-yl)-1-[(1-methyl-1H-imidazol-4-yl)sulfonyl]-N-[3-(trifluoromethoxy)benzyl]pyrrolidin-3-amine The title compound was prepared according to the procedure outlined in Example 354E substituting Example 897C for Example 354D and 3-(trifluoromethoxy)benzaldehyde for 4-chlorobenzaldehyde. MS (ESI) m/z 491 (M+H)$^+$.

Example 906

(3R,4S)-4-(1,3-dioxan-2-yl)-N-(4-fluorobenzyl)-1-[(1-methyl-1H-imidazol-4-yl)sulfonyl]pyrrolidin-3-amine The title compound was prepared according to the procedure outlined in Example 354E substituting Example 897C for Example 354D and 4-trifluorobenzaldehyde for 4-chlorobenzaldehyde. MS (ESI) m/z 425 (M+H)$^+$.

Example 907

(3R,4S)-4-(1,3-dioxan-2-yl)-N-methyl-1-[(1-methyl-1H-imidazol-4-yl)sulfonyl]-N-pentylpyrrolidin-3-amine

Example 907A (3R,4R)-4-(1,3-dioxan-2-yl)-1-(1-methyl-1H-imidazol-4-ylsulfonyl)-N-pentylpyrrolidin-3-amine The title compound was prepared according to the procedure outlined in Example 354E substituting Example 897C for Example 354D and pentanal for 4-chlorobenzaldehyde.

Example 907B (3R,4S)-4-(1,3-dioxan-2-yl)-N-methyl-1-[(1-methyl-1H-imidazol-4-yl)sulfonyl]-N-pentylpyrrolidin-3-amine The title compound was prepared according to the procedure outlined in Example 354E substituting Example 907A for Example 354D and formaldehyde for 4-chlorobenzaldehyde. MS (ESI) m/z 401 (M+H)$^+$.

Example 908

(3R,4S)-4-(1,3-dioxan-2-yl)-1-[(1-methyl-1H-imidazol-4-yl)sulfonyl]-N,N-dipentylpyrrolidin-3-amine The title compound was prepared according to the procedure outlined in Example 354E substituting Example 897C for Example 354D and pentanal for 4-chlorobenzaldehyde. MS (ESI) m/z 457 (M+H)$^+$.

Example 909

(3R,4S)-4-(1,3-dioxan-2-yl)-N,N-dihexyl-1-[(1-methyl-1H-imidazol-4-yl)sulfonyl]pyrrolidin-3-amine The title compound was prepared according to the procedure outlined in Example 354E substituting Example 897C for Example 354D and hexanal for 4-chlorobenzaldehyde. MS (ESI) m/z 599 (M+H)$^+$.

Example 910

(3R,4S)-4-(1,3-dioxan-2-yl)-N-hexyl-1-[(1-methyl-1H-imidazol-4-yl)sulfonyl]pyrrolidin-3-amine The title compound was prepared according to the procedure outlined in Example 354E substituting Example 897C for Example 354D and hexanal for 4-chlorobenzaldehyde. MS (ESI) m/z 401 (M+H)$^+$.

Example 911

5-chloro-N-{(3R,4S)-4-(1,3-dioxan-2-yl)-1-[(1-methyl-1H-imidazol-4-yl)sulfonyl]pyrrolidin-3-yl}-4-(trifluoromethyl)pyridin-2-amine The title compound was prepared similarly to the procedure described in Example 605A substituting Example 897C for Example 396A and substituting 2,5-dichloro-4-(trifluoromethyl)pyridine for 4-chloro-2-(methylthio)-6-(trifluoromethyl)pyrimidine. MS (ESI) m/z 496/498 (3:1) (M+H)$^+$.

Example 912

(3R,4S)-4-(1,3-dioxan-2-yl)-N-[4-fluoro-3-(trifluoromethyl)phenyl]-1-[(1-methyl-1H-imidazol-4-yl)sulfonyl]pyrrolidin-3-amine The title compound was prepared according to the procedure outlined in Example 337G substituting Example 897C for Example 337F and 4-bromo-1-fluoro-2-(trifluoromethyl)benzene for 1-bromo-3-(trifluoromethyl)benzene. MS (ESI) m/z 479.0 (M+H)$^+$.

Example 913

1-[(1-methyl-1H-imidazol-4-yl)sulfonyl]-4-(piperidin-1-yl)-N-[3-(trifluoromethoxy)phenyl]pyrrolidin-3-amine Example 913A trans-tert-butyl 3-hydroxy-4-(3-(trifluoromethoxy)phenylamino)pyrrolidine-1-carboxylate The title compound was prepared according to the procedure outlined in Example 373A substituting 3-trifluoromethoxyaniline for 3-chloroaniline.

Example 913B tert-butyl 6-(3-(trifluoromethoxy)phenyl)-3,6-diazabicyclo[3.1.0]hexane-3-carboxylate To a solution of Example 913A (2.9 g, 8 mmol) and 4-methylbenezenesulfonyl chloride (1.5 g, 8 mmol) in toluene (10 mL) was added tetrabutylammonium hydrogensulfate (0.54 g, 1.6 mmol) followed by 50% NaOH(aq) (1 mL). The mixture was stirred over night. Ethyl acetate was added, and the organic phase washed with water and then brine. The crude material was purified by silica gel column chromatography eluting with hexanes and ethyl acetate (2:1) to afford the title compound.

Example 913C trans-tert-butyl 3-(piperidin-1-yl)-4-(3-(trifluoromethoxy)phenylamino)pyrrolidine-1-carboxylate A mixture of Example 913B (2 g, 5.8 mmol) and LiBr (20 mg, 0.22 mmol) in piperidine (5 mL) was heated at 120° C. for 3 days, then concentrated and purified by silica gel column chromatography eluting with hexanes and ethyl acetate (1:1) to afford the title compound.

Example 913D trans-4-(piperidin-1-yl)-N-(3-(trifluoromethoxy)phenyl)pyrrolidin-3-amine The title compound was prepared as the hydrochloride salt according to the procedure outlined in Example 373B substituting Example 913C for Example 373A.

Example 913E trans-1-[(1-methyl-1H-imidazol-4-yl)sulfonyl]-4-(piperidin-1-yl)-N-[3-(trifluoromethoxy)phenyl]pyrrolidin-3-amine The title compound was prepared according to the procedure outlined in Example 373C substituting Example 913D for Example 373B. MS (ESI) m/z 474 (M+H)$^+$.

Example 914

(3R,4S)-N-(3-chlorophenyl)-4-(1,3-dioxan-2-yl)-1-[(1-methyl-1H-imidazol-4-yl)sulfonyl]pyrrolidin-3-amine The title compound was prepared according to the procedure outlined in Example 337G substituting Example 897C for Example 337F and 1-bromo-3-chlorobenzene for 1-bromo-3-(trifluoromethyl)benzene. MS (ESI) m/z 427.0 (M+H)$^+$.

Example 915

(3R,4S)-4-(1,3-dioxan-2-yl)-1-[(1-methyl-1H-imidazol-4-yl)sulfonyl]-N-[3-(trifluoromethyl)phenyl]pyrrolidin-3-amine The title compound was prepared according to the procedure outlined in Example 337G substituting Example 897C for Example 337F. MS (ESI) m/z 461.0 (M+H)$^+$.

Example 916

(3R,4S)-N-(3-chloro-4-fluorophenyl)-4-(1,3-dioxan-2-yl)-1-[(1-methyl-1H-imidazol-4-yl)sulfonyl]pyrrolidin-3-amine The title compound was prepared according to the procedure outlined in Example 337G substituting Example 897C for Example 337F and 4-bromo-2-chloro-1-fluorobenzene for 1-bromo-3-(trifluoromethyl)benzene. MS (ESI) m/z 445.0 (M+H)$^+$.

Example 917

(3R,4S)-4-(1,3-dioxan-2-yl)-1-[(1-methyl-1H-imidazol-4-yl)sulfonyl]-N-(3-methylphenyl)pyrrolidin-3-amine The title compound was prepared according to the procedure outlined in Example 337G substituting Example 897C for Example 337F and 1-bromo-3-methylbenzene for 1-bromo-3-(trifluoromethyl)benzene. MS (ESI) m/z 407.0 (M+H)+.

Example 918

4-({3-(1,3-dioxan-2-yl)-4-[3-(trifluoromethyl)benzyl]pyrrolidin-1-yl}sulfonyl)-1-methyl-1H-imidazole

Example 918A 4,4-dimethoxy-3-(nitromethyl)-2-(3-(trifluoromethyl)benzyl)butanal The title compound was prepared according to the procedure outlined in Example 182A substituting Example 896A for (E)-1-fluoro-4-(2-nitrovinyl)benzene and substituting 3-(3-(trifluoromethyl)phenyl)propanal for 3-(3-chlorophenyl)propanal.

Example 918B 3-(dimethoxymethyl)-4-(3-(trifluoromethyl)benzyl)pyrrolidine

The title compound was prepared according to the procedure outlined in Example 182B substituting Example 918A for Example 182A.

Example 918C 4-(3-(dimethoxymethyl)-4-(3-(trifluoromethyl)benzyl)pyrrolidin-1-ylsulfonyl)-1-methyl-1H-imidazole The title compound was prepared according to the procedure outlined in Example 373C substituting Example 918B for Example 373B.

Example 918D 4-({trans-3-(1,3-dioxan-2-yl)-4-[3-(trifluoromethyl)benzyl]pyrrolidin-1-yl}sulfonyl)-1-methyl-1H-imidazole The title compound was prepared according to the procedure outlined in Example 896H substituting Example 918C for Example 896G. MS (ESI) m/z 460 (M+H)+.

Example 919

4-({3-(1,3-dioxan-2-yl)-4-[3-(trifluoromethyl)benzyl]pyrrolidin-1-yl}sulfonyl)-1-methyl-1H-1,2,3-triazole

Example 919A 4-(3-(dimethoxymethyl)-4-(3-(trifluoromethyl)benzyl)pyrrolidin-1-ylsulfonyl)-1-methyl-1H-1,2,3-triazole The title compound was prepared according to the procedure outlined in Example 373C substituting Example 918B for Example 373B and 1-methyl-1H-1,2,3-triazole-4-sulfonyl chloride for 1-methyl-1H-imidazole-4-sulfonyl chloride.

Example 919B 4-({3-(1,3-dioxan-2-yl)-4-[3-(trifluoromethyl)benzyl]pyrrolidin-1-yl}sulfonyl)-1-methyl-1H-1,2,3-triazole The title compound was prepared according to the procedure outlined in Example 896H substituting Example 919A for Example 896G. MS (ESI) m/z 461 (M+H)+.

Example 920

(3R,4S)-4-(5,7-dioxaspiro[2.5]oct-6-yl)-1-[(1-methyl-1H-imidazol-4-yl)sulfonyl]-N-[3-(trifluoromethoxy)phenyl]pyrrolidin-3-amine The title compound was prepared according to the procedure outlined in Example 896H substituting Example 900B for Example 896G and substituting cyclopropane-1,1-diyldimethanol for propane-1,3-diol. MS (ESI) m/z 503 (M+H)+.

Example 921

(3R,4S)-4-[(4R,6R)-4,6-dimethyl-1,3-dioxan-2-yl]-1-[(1-methyl-1H-imidazol-4-yl)sulfonyl]-N-[3-(trifluoromethoxy)phenyl]pyrrolidin-3-amine The title compound was prepared according to the procedure outlined in Example 896H substituting Example 900B for Example 896G and substituting (2R,4R)-pentane-2,4-diol for propane-1,3-diol. MS (ESI) m/z 505 (M+H)+.

Example 922

(3R,4S)-4-[(4S,6S)-4,6-dimethyl-1,3-dioxan-2-yl]-1-[(1-methyl-1H-imidazol-4-yl)sulfonyl]-N-[3-(trifluoromethoxy)phenyl]pyrrolidin-3-amine The title compound was prepared according to the procedure outlined in Example 896H substituting Example 900B for Example 896G and substituting (2S,4S)-pentane-2,4-diol for propane-1,3-diol. MS (ESI) m/z 505 (M+H)+.

Example 923

(3R,4S)-4-(1,3-dioxan-2-yl)-N-(4-fluoro-3-methylphenyl)-1-[(1-methyl-1H-imidazol-4-yl)sulfonyl]pyrrolidin-3-amine The title compound was prepared according to the procedure outlined in Example 337G substituting Example 897C for Example 337F and 4-bromo-1-fluoro-2-methylbenzene for 1-bromo-3-(trifluoromethyl)benzene. MS (ESI) m/z 425.0 (M+H)+.

Example 924

(3R,4S)-4-(1,3-dioxan-2-yl)-N-[4-fluoro-3-(trifluoromethoxy)phenyl]-1-[(1-methyl-1H-imidazol-4-yl)sulfonyl]pyrrolidin-3-amine The title compound was prepared according to the procedure outlined in Example 337G substituting Example 897C for Example 337F and 4-bromo-1-fluoro-2-(trifluoromethoxy)benzene for 1-bromo-3-(trifluoromethyl)benzene. MS (ESI) m/z 495.0 (M+H)$^+$.

Example 925

(3R,4S)-N-[3-(difluoromethoxy)phenyl]-4-(1,3-dioxan-2-yl)-1-[(1-methyl-1H-imidazol-4-yl)sulfonyl]pyrrolidin-3-amine The title compound was prepared according to the procedure outlined in Example 337G substituting Example 897C for Example 337F and 1-bromo-3-(difluoromethoxy)benzene for 1-bromo-3-(trifluoromethyl)benzene. MS (ESI) m/z 459.0 (M+H)$^+$.

Example 926

(3R,4S)-4-(1,3-dioxan-2-yl)-1-[(1-methyl-1H-imidazol-4-yl)sulfonyl]-N-[3-(propan-2-yl)phenyl]pyrrolidin-3-amine The title compound was prepared according to the procedure outlined in Example 337G substituting Example 897C for Example 337F and 1-bromo-3-isopropylbenzene for 1-bromo-3-(trifluoromethyl)benzene. MS (ESI) m/z 435.1 (M+H)$^+$.

Example 927

4-(5-fluoropyridin-2-yl)-N-[4-fluoro-3-(trifluoromethyl)phenyl]-1-[(1-methyl-1H-imidazol-4-yl)sulfonyl]pyrrolidin-3-amine The title compound was prepared similarly to the procedure described in Example 327 substituting Example 895A for Example 322B and substituting 4-bromo-1-fluoro-2-(trifluoromethyl)benzene for 1-bromo-3-(trifluoromethyl)benzene. MS (ESI) m/z 488 (M+H)$^+$.

Example 928

(3R,4S)-N-[3-(2,2-difluoro ethoxy)phenyl]-4-(1,3-dioxan-2-yl)-1-[(1-methyl-1H-imidazol-4-yl)sulfonyl]pyrrolidin-3-amine The title compound was prepared according to the procedure outlined in Example 337G substituting Example 897C for Example 337F and 1-bromo-3-(2,2-difluoroethoxy)benzene for 1-bromo-3-(trifluoromethyl)benzene. MS (ESI) m/z 473.0 (M+H)$^+$.

Further examplary compounds include:
1-(Trans-1-((1-methyl-1H-imidazol-4-yl)sulfonyl)-4-((6-(trifluoromethyl)pyrimidin-4-yl)oxy)pyrrolidin-3-yl)azepane;
4-(Trans-1-((1-methyl-1H-imidazol-4-yl)sulfonyl)-4-((6-(trifluoromethyl)pyrimidin-4-yl)oxy)pyrrolidin-3-yl)morpholine;
4-((Trans-1-((1-methyl-1H-imidazol-4-yl)sulfonyl)-4-(2-methylpiperidin-1-yl)pyrrolidin-3-yl)oxy)-6-(trifluoromethyl)pyrimidine;
4-((Trans-1-((1-methyl-1H-imidazol-4-yl)sulfonyl)-4-(3-methylpiperidin-1-yl)pyrrolidin-3-yl)oxy)-6-(trifluoromethyl)pyrimidine;
4-((Trans-1-((1-methyl-1H-imidazol-4-yl)sulfonyl)-4-(4-methylpiperidin-1-yl)pyrrolidin-3-yl)oxy)-6-(trifluoromethyl)pyrimidine;
4-((Trans-4-(4-fluoropiperidin-1-yl)-1-((1-methyl-1H-imidazol-4-yl)sulfonyl)pyrrolidin-3-yl)oxy)-6-(trifluoromethyl)pyrimidine;
4-((Trans-4-(4,4-difluoropiperidin-1-yl)-1-((1-methyl-1H-imidazol-4-yl)sulfonyl)pyrrolidin-3-yl)oxy)-6-(trifluoromethyl)pyrimidine;
4-((Trans-4-(3-fluoroazetidin-1-yl)-1-((1-methyl-1H-imidazol-4-yl)sulfonyl)pyrrolidin-3-yl)oxy)-6-(trifluoromethyl)pyrimidine;
4-((Trans-1-((1-methyl-1H-imidazol-4-yl)sulfonyl)-4-(piperidin-1-yl)pyrrolidin-3-yl)oxy)-6-(trifluoromethyl)pyrimidine;
Trans-1'-((1-methyl-1H-imidazol-4-yl)sulfonyl)-4'-((6-(trifluoromethyl)pyrimidin-4-yl)oxy)-1,3'-bipyrrolidine;
Trans-3-((3-chlorophenyl)amino)-4-(4-fluorophenyl)-1-((1-methyl-1H-imidazol-4-yl)sulfonyl)pyrrolidin-2-one;
Trans-3-((3-chloro-4-fluorophenyl)amino)-4-(4-fluorophenyl)-1-((1-methyl-1H-imidazol-4-yl)sulfonyl)pyrrolidin-2-one;
Trans-4-(4-fluorophenyl)-1-((1-methyl-1H-imidazol-4-yl)sulfonyl)-3-((3-(trifluoromethyl)phenyl)amino)pyrrolidin-2-one;
Trans-3-((4-fluoro-3-(trifluoromethoxy)phenyl)amino)-4-(4-fluorophenyl)-1-((1-methyl-1H-imidazol-4-yl)sulfonyl)pyrrolidin-2-one;
3-(Trans-4-(4-fluorophenyl)-1-((1-methyl-1H-imidazol-4-yl)sulfonyl)pyrrolidin-3-yl)-5-(4-(trifluoromethyl)phenyl)-4,5-dihydroisoxazole;
2-(Trans-4-(4-fluorophenyl)-1-((1-methyl-1H-imidazol-4-yl)sulfonyl)pyrrolidin-3-yl)-5-(4-(trifluoromethyl)phenyl)oxazole;
5-(3-Chlorophenyl)-2-(trans-4-(4-fluorophenyl)-1-((1-methyl-1H-imidazol-4-yl)sulfonyl)pyrrolidin-3-yl)-1H-imidazole;
4-((Trans-3-(4-fluoro-3-(trifluoromethyl)phenoxy)-4-(4-fluorophenyl)pyrrolidin-1-yl)sulfonyl)-1-methyl-1H-imidazole;
Trans-4-(4-fluorophenyl)-1-((1-methyl-1H-imidazol-4-yl)sulfonyl)-N-(3-(trifluoromethyl)cyclohexyl)pyrrolidin-3-amine;
N-(Trans-4-(4-fluorophenyl)-1-((1-methyl-1H-imidazol-4-yl)sulfonyl)pyrrolidin-3-yl)-1-isopropylpiperidin-4-amine;
Trans-4-(4-fluorophenyl)-1-((1-methyl-1H-imidazol-4-yl)sulfonyl)-N-(2-methyltetrahydrofuran-3-yl)pyrrolidin-3-amine;
1-Ethyl-N-(Trans-4-(4-fluorophenyl)-1-((1-methyl-1H-imidazol-4-yl)sulfonyl)pyrrolidin-3-yl)piperidin-3-amine.

Biological Testing

1. [$^3$H]-Glycine uptake into recombinant CHO cells expressing human GlyT1: Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays the culture medium was aspirated and the cells were washed once with 100 µl HBSS (Gibco BRL, #14025-050) with 5 mM L-Alanine (Merck #1007). 80 µl HBSS buffer were added, followed by 10 µl inhibitor or vehicle (10% DMSO) and 10 µl [$^3$H]-glycine (TRK71, Amersham Biosciences) to a final concentration of 200 nM for initiation of glycine uptake. The plates were placed in a Wallac Microbeta (PerkinElmer) and continuously counted by solid phase scintillation spectrometry during up to 3 hours. Nonspecific uptake was determined in the presence of 10 µM Org24598. IC$_{50}$ calculations were made by four-parametric logistic nonlinear regression analysis (GraphPad Prism) using determinations within the range of linear increase of [$^3$H]-glycine incorporation between 60 and 120 min.

2. Radioligand binding assays using recombinant CHO cell membranes expressing human GlyT1:

Radioligand binding to human GlyT1c transporter-expressing membranes was determined as described in Mezler et al., Molecular Pharmacology 74:1705-1715, 2008.

The following results were obtained with the compounds disclosed in the examples:

| Ex. | Ki [μM] |
|---|---|
| 1 | — |
| 2 | ≤1 |
| 3 | ≤0.1 |
| 4 | ≥10 |
| 13 | ≤1 |
| 14 | ≤1 |
| 15 | ≤10 |
| 16 | ≤1 |
| 17 | ≤10 |
| 18 | ≤10 |
| 19 | ≤10 |
| 20 | ≤10 |
| 21 | ≤10 |
| 22 | ≤10 |
| 23 | ≤10 |
| 24 | ≤10 |
| 25 | ≤10 |
| 26 | ≤1 |
| 27 | ≤1 |
| 29 | ≤1 |
| 30 | ≤10 |
| 31 | ≤1 |
| 32 | ≤10 |
| 33 | ≤10 |
| 34 | ≤10 |
| 35 | ≤10 |
| 36 | ≤1 |
| 37 | ≤1 |
| 38 | ≤10 |
| 39 | ≤10 |
| 40 | ≥10 |
| 41 | ≤10 |
| 42 | ≤10 |
| 43 | ≤10 |
| 44 | ≤10 |
| 45 | ≥10 |
| 46 | ≥10 |
| 47 | ≥10 |
| 48 | ≤10 |
| 49 | ≤10 |
| 50 | ≤10 |
| 51 | ≤0.1 |
| 52 | ≤10 |
| 53 | ≤10 |
| 54 | ≤1 |
| 55 | ≤1 |
| 56 | ≤1 |
| 57 | ≤10 |
| 58 | ≤0.1 |
| 59 | ≤10 |
| 60 | ≤0.1 |
| 61 | ≤1 |
| 62 | ≤0.1 |
| 63 | ≤0.1 |
| 64 | ≤0.1 |
| 65 | ≤1 |
| 66 | ≤10 |
| 67 | ≤0.01 |
| 68 | ≤1 |
| 69 | ≤10 |
| 70 | ≤1 |
| 71 | ≤1 |
| 72 | — |
| 73 | ≤10 |
| 74 | ≤0.1 |
| 75 | ≤1 |
| 76 | ≤10 |
| 77 | ≤1 |
| 78 | ≤1 |
| 79 | ≤1 |
| 80 | ≤1 |
| 81 | ≤10 |
| 82 | ≤10 |
| 83 | ≤1 |
| 84 | ≤1 |
| 85 | ≤0.01 |
| 86 | ≤1 |
| 87 | ≤10 |
| 88 | ≤0.01 |
| 89 | ≤0.1 |
| 90 | ≤1 |
| 91 | ≤0.1 |
| 92 | ≤0.1 |
| 93 | ≤1 |
| 94 | ≤0.01 |
| 95 | ≤1 |
| 100 | ≤10 |
| 101 | ≤1 |
| 102 | ≤1 |
| 115 | ≤0.1 |
| 122 | ≤10 |
| 123 | ≤10 |
| 124 | ≤10 |
| 125 | >10 |
| 126 | ≤10 |
| 127 | ≤10 |
| 128 | ≤10 |
| 129 | >10 |
| 130 | >10 |
| 131 | >10 |
| 132 | ≤10 |
| 133 | ≤10 |
| 134 | ≤10 |
| 135 | >10 |
| 136 | ≤10 |
| 137 | ≤10 |
| 142 | ≤10 |
| 143 | ≤10 |
| 144 | >10 |
| 145 | ≤0.1 |
| 148 | ≤10 |
| 149 | ≤0.1 |
| 150 | ≤0.001 |
| 151 | ≤0.1 |
| 152 | ≤1 |
| 153 | ≤1 |
| 154 | ≤0.1 |
| 155 | ≤0.1 |
| 156 | ≤0.1 |
| 157 | ≤10 |
| 158 | ≤0.1 |
| 159 | ≤0.01 |
| 160 | ≤0.01 |
| 161 | ≤1 |
| 162 | ≤1 |
| 163 | ≤1 |
| 164 | ≤10 |
| 165 | ≤1 |
| 166 | ≤1 |
| 167 | ≤0.1 |
| 168 | ≤0.1 |
| 169 | ≤10 |
| 170 | ≤0.1 |
| 171 | ≤0.1 |
| 172 | ≤0.1 |
| 173 | ≤1 |
| 174 | ≤1 |
| 175 | ≤1 |
| 176 | ≤0.01 |
| 177 | ≤10 |
| 178 | ≤1 |
| 179 | ≤10 |

| Ex. | Ki [μM] |
|---|---|
| 180 | ≤1 |
| 181 | ≤10 |
| 182 | ≤0.1 |
| 183 | ≤10 |
| 184 | ≤10 |
| 185 | ≤10 |
| 186 | ≤1 |
| 187 | ≤10 |
| 188 | ≤0.1 |
| 189 | ≤0.1 |
| 190 | ≤1 |
| 191 | ≤10 |
| 192 | ≤1 |
| 193 | ≤10 |

| Ex. | Ki [μM] |
|---|---|
| 194 | ≤0.1 |
| 195 | ≤10 |
| 196 | ≤10 |
| 197 | ≤1 |
| 198 | ≤1 |
| 199 | ≤1 |
| 200 | ≤1 |
| 201 | ≤0.1 |
| 202 | ≤1 |
| 203 | ≤10 |
| 204 | ≤0.1 |
| 205 | ≤1 |
| 206 | ≤10 |
| 207 | ≤10 |
| 208 | ≤10 |
| 209 | ≤10 |
| 210 | ≤10 |
| 211 | ≤1 |
| 212 | ≤0.10 |
| 213 | ≤1 |
| 214 | ≤0.1 |
| 215 | ≤0.1 |
| 216 | ≤1 |
| 217 | ≤1 |
| 218 | ≤1 |
| 219 | ≤10 |
| 220 | ≤0.01 |
| 221 | ≤1 |
| 222 | ≤1 |
| 223 | ≤0.1 |
| 224 | ≤1 |
| 225 | ≤10 |
| 226 | ≤0.01 |
| 227 | ≤10 |
| 228 | ≤10 |
| 229 | ≤10 |
| 230 | ≤10 |
| 231 | ≤1 |
| 232 | ≤10 |
| 233 | ≤10 |
| 234 | ≤1 |
| 235 | ≤10 |
| 236 | ≤10 |
| 237 | ≤10 |
| 238 | ≤10 |
| 239 | ≤10 |
| 240 | ≤0.1 |
| 241 | ≤10 |
| 242 | ≤10 |
| 243 | ≤1 |
| 244 | ≤1 |
| 245 | ≤0.1 |
| 246 | ≤0.1 |
| 247 | ≤0.01 |
| 248 | ≤1 |
| 249 | ≤1 |
| 250 | ≤10 |

| Ex. | Ki [μM] |
|---|---|
| 251 | ≤0.1 |
| 252 | ≤1 |
| 253 | ≤1 |
| 254 | ≤10 |
| 255 | ≤0.1 |
| 256 | ≤1 |
| 257 | ≤0.1 |
| 258 | ≤1 |
| 259 | ≤1 |
| 260 | ≤0.1 |
| 261 | ≤1 |
| 262 | ≤0.01 |
| 263 | ≤0.1 |
| 264 | ≤1 |
| 265 | ≤1 |
| 266 | ≤1 |
| 267 | ≤0.01 |
| 268 | ≤10 |
| 269 | ≤10 |
| 270 | ≤10 |
| 271 | ≤1 |
| 272 | ≤1 |
| 273 | ≤1 |
| 274 | ≤0.1 |
| 275 | ≤1 |
| 276 | ≤1 |
| 277 | ≤10 |
| 278 | ≤0.1 |
| 279 | ≤10 |
| 280 | ≤0.01 |
| 281 | ≤0.01 |
| 282 | ≤0.1 |
| 283 | ≤0.1 |
| 284 | ≤0.1 |
| 285 | ≤0.1 |
| 286 | ≤10 |
| 287 | ≤0.01 |
| 288 | ≤1 |
| 289 | ≤1 |
| 290 | ≤10 |
| 291 | ≤0.1 |
| 292 | ≤1 |
| 293 | ≤0.1 |
| 294 | ≤0.01 |
| 295 | ≤0.1 |
| 296 | ≤0.1 |
| 297 | ≤0.01 |
| 298 | ≤0.01 |
| 299 | ≤1 |
| 300 | ≤1 |
| 301 | ≤1 |
| 302 | ≤0.1 |
| 303 | ≤10 |
| 304 | ≤1 |
| 305 | ≤0.01 |
| 306 | ≤0.1 |
| 307 | ≤0.1 |
| 308 | ≤1 |
| 309 | ≤1 |
| 310 | ≤0.1 |
| 311 | ≤1 |
| 312 | ≤0.1 |
| 313 | ≤1 |
| 314 | ≤1 |
| 315 | ≤1 |
| 316 | ≤1 |
| 317 | ≤1 |
| 318 | ≤1 |
| 319 | ≤0.1 |
| 320 | ≤0.01 |
| 321 | ≤1 |
| 322 | ≤0.01 |
| 323 | ≤1 |
| 324 | ≤10 |
| 325 | ≤1 |
| 326 | ≤1 |
| 327 | ≤0.01 |

| Ex. | Ki [μM] |
|---|---|
| 328 | ≤0.1 |
| 329 | ≤0.01 |
| 329 | ≤0.01 |
| 330 | ≤0.1 |
| 330 | ≤0.1 |
| 331 | ≤1 |
| 332 | ≤0.1 |
| 333 | ≤1 |
| 334 | ≤1 |
| 335 | ≤1 |
| 336 | ≤1 |
| 337 | ≤1 |
| 338 | ≤1 |
| 339 | ≤10 |
| 340 | ≤1 |
| 341 | ≤10 |
| 342 | ≤10 |
| 343 | ≤10 |
| 344 | ≤0.1 |
| 345 | ≤0.1 |
| 346 | ≤1 |
| 347 | ≤10 |

| Ex. | Ki [μM] |
|---|---|
| 348 | ≤0.1 |
| 349 | ≤0.1 |
| 350 | >10 |
| 351 | ≤1 |
| 352 | ≤0.01 |
| 353 | ≤0.1 |
| 354 | ≤1 |
| 355 | ≤1 |
| 356 | ≤0.1 |
| 357 | ≤1 |
| 358 | ≤0.1 |
| 359 | ≤1 |
| 360 | ≤0.1 |
| 361 | ≤1 |
| 362 | ≤0.1 |
| 363 | ≤0.1 |
| 364 | ≤10 |
| 365 | ≤10 |
| 366 | ≤0.1 |
| 367 | ≤0.1 |
| 368 | ≤0.01 |
| 369 | ≤1 |
| 370 | ≤1 |
| 371 | ≤1 |
| 372 | ≤10 |
| 373 | ≤10 |
| 374 | ≥10 |
| 375 | ≥10 |
| 376 | ≤1 |
| 377 | ≤1 |
| 378 | ≤10 |
| 379 | ≤0.1 |
| 380 | ≤0.1 |
| 381 | ≤10 |
| 382 | ≤0.1 |
| 383 | ≤1 |
| 384 | ≤10 |
| 385 | ≤10 |
| 386 | ≤1 |
| 387 | ≤10 |
| 388 | ≤0.1 |
| 389 | ≤10 |
| 390 | ≤0.01 |
| 390 | ≤0.01 |
| 391 | ≤0.1 |
| 392 | ≤0.1 |
| 393 | ≤0.01 |
| 394 | ≤0.01 |
| 395 | ≤1 |

| Ex. | Ki [μM] |
|---|---|
| 396 | ≤0.01 |
| 397 | ≤0.01 |
| 398 | ≤0.01 |
| 399 | ≤0.1 |
| 400 | ≤10 |
| 401 | ≤10 |
| 402 | ≤10 |
| 403 | ≤0.1 |
| 404 | ≤10 |
| 405 | ≤1 |
| 406 | ≤10 |
| 407 | ≤10 |
| 408 | ≤10 |
| 409 | ≤0.1 |
| 410 | ≤10 |
| 411 | ≤10 |
| 412 | ≤1 |
| 413 | ≤10 |
| 414 | ≤10 |
| 415 | ≤10 |
| 416 | — |
| 417 | ≤0.01 |
| 418 | ≤0.1 |
| 419 | ≥10 |
| 420 | ≤10 |
| 421 | ≤10 |
| 422 | ≤1 |
| 423 | ≤10 |
| 424 | ≤1 |
| 425 | ≤0.01 |
| 426 | ≤1 |
| 427 | ≤0.1 |
| 428 | ≤0.1 |
| 429 | >10 |
| 430 | >10 |
| 431 | ≤10 |
| 432 | ≤10 |
| 433 | ≤0.1 |
| 434 | ≤10 |
| 435 | ≤0.1 |
| 436 | ≤1 |
| 437 | ≤0.1 |
| 438 | ≤1 |
| 439 | ≤1 |
| 440 | ≤0.1 |
| 441 | ≤10 |
| 442 | ≤1 |
| 443 | ≤1 |
| 444 | — |
| 445 | ≤1 |
| 446 | ≤0.1 |
| 447 | ≤10 |
| 448 | ≤0.1 |
| 449 | ≤1 |
| 450 | ≤1 |
| 451 | — |
| 452 | — |
| 453 | ≤1 |
| 454 | ≤10 |
| 455 | ≤0.1 |
| 456 | ≤1 |
| 457 | ≤10 |
| 458 | ≤10 |
| 459 | ≤10 |
| 460 | ≤10 |
| 461 | ≤1 |
| 462 | ≤0.1 |
| 463 | ≤1 |
| 464 | ≤1 |
| 465 | ≤1 |
| 466 | — |
| 467 | ≤1 |
| 468 | ≤0.1 |
| 469 | ≤1 |
| 470 | ≤10 |
| 471 | ≤0.1 |
| 472 | ≤1 |

| Ex. | Ki [μM] |
|---|---|
| 473 | ≤0.1 |
| 474 | ≤10 |
| 475 | ≤10 |
| 476 | ≤10 |
| 477 | ≤10 |
| 478 | ≤10 |
| 479 | >10 |
| 480 | >10 |
| 481 | ≤10 |
| 482 | ≤10 |
| 483 | ≤10 |
| 484 | ≤10 |
| 485 | ≤10 |
| 486 | ≤10 |
| 487 | ≤10 |
| 488 | ≤10 |
| 489 | ≤10 |
| 490 | ≤10 |
| 491 | ≤10 |
| 492 | ≥10 |
| 493 | ≤10 |
| 494 | ≤10 |
| 495 | >10 |
| 496 | ≥10 |
| 497 | ≤10 |
| 498 | ≤10 |
| 499 | ≥10 |
| 500 | ≤10 |
| 501 | ≤10 |
| 502 | ≤10 |

| Ex. | Ki [μM] |
|---|---|
| 503 | ≥10 |
| 504 | ≤10 |
| 505 | — |
| 506 | ≤10 |
| 507 | ≤10 |
| 508 | ≤10 |
| 509 | ≤10 |
| 510 | ≤10 |
| 511 | ≤10 |
| 512 | ≤10 |
| 513 | >10 |
| 514 | ≤10 |
| 515 | ≤10 |
| 516 | ≤10 |
| 517 | ≤10 |
| 518 | >10 |
| 519 | >10 |
| 520 | ≤10 |
| 521 | ≤10 |
| 522 | — |
| 523 | ≤10 |
| 524 | ≤10 |
| 525 | ≤10 |
| 526 | ≤10 |
| 527 | ≤10 |
| 528 | >10 |
| 529 | ≤10 |
| 530 | ≤1 |
| 531 | ≤0.1 |
| 532 | ≤10 |
| 533 | ≤10 |
| 534 | ≤1 |
| 535 | ≤10 |
| 536 | ≤1 |
| 537 | ≤10 |
| 538 | ≤10 |
| 539 | ≤10 |
| 540 | ≤0.1 |
| 540 | ≤0.1 |
| 541 | ≤10 |
| 542 | ≤10 |
| 543 | ≤10 |
| 544 | ≤10 |
| 545 | ≤1 |
| 546 | ≥10 |
| 547 | ≤0.1 |
| 548 | ≤0.01 |
| 549 | ≤10 |
| 550 | ≤10 |
| 551 | ≤10 |
| 552 | ≤10 |
| 553 | ≤1 |
| 554 | ≤1 |
| 555 | ≤10 |
| 556 | ≤10 |
| 557 | ≤10 |
| 558 | ≤10 |
| 559 | ≤1 |
| 560 | ≥10 |
| 561 | ≤1 |
| 562 | ≤10 |
| 563 | ≤10 |
| 564 | ≤1 |
| 565 | ≤10 |
| 566 | ≤10 |
| 567 | ≤1 |
| 568 | ≤0.1 |
| 569 | ≤1 |
| 570 | ≤0.01 |
| 571 | ≤10 |
| 572 | ≤1 |
| 573 | ≤0.1 |
| 574 | ≤0.1 |
| 575 | ≤10 |
| 576 | — |
| 577 | >10 |
| 578 | ≤10 |
| 579 | ≤10 |
| 580 | ≤1 |
| 581 | ≤0.1 |
| 582 | ≤10 |
| 583 | ≤10 |
| 584 | ≤10 |
| 585 | ≤0.1 |
| 586 | ≤1 |
| 587 | ≤10 |
| 588 | ≤10 |
| 589 | ≤1 |
| 590 | ≤10 |
| 591 | ≤10 |
| 592 | ≤10 |
| 593 | ≤10 |
| 594 | ≤10 |
| 595 | ≤10 |
| 596 | ≤10 |
| 597 | ≤10 |
| 598 | ≤10 |
| 599 | ≤10 |
| 600 | ≤10 |
| 601 | ≤0.1 |
| 602 | ≤1 |
| 603 | ≤0.1 |
| 604 | ≤0.1 |
| 605 | ≤1 |
| 606 | ≤0.1 |
| 607 | ≤10 |
| 608 | ≤10 |
| 609 | ≤1 |
| 610 | ≤10 |
| 611 | ≤10 |
| 612 | ≤1 |
| 613 | ≤1 |
| 614 | ≤1 |
| 615 | ≤1 |
| 616 | ≤1 |
| 617 | ≤0.01 |
| 618 | ≤1 |
| 619 | ≤1 |

| Ex. | Ki [μM] |
|---|---|
| 620 | ≤1 |
| 621 | ≤10 |
| 622 | ≤0.1 |
| 623 | ≤0.1 |
| 624 | ≤1 |
| 625 | ≤0.01 |
| 626 | ≤1 |
| 627 | ≤1 |
| 628 | ≤0.01 |
| 629 | ≤1 |
| 630 | ≤0.1 |
| 631 | ≤0.01 |
| 632 | ≤1 |
| 633 | ≤1 |
| 634 | ≤10 |
| 635 | ≤1 |
| 636 | ≤1 |
| 637 | ≤10 |
| 638 | ≤1 |
| 639 | ≤10 |
| 640 | ≤1 |
| 641 | ≤0.1 |
| 642 | ≤0.01 |
| 643 | ≤10 |
| 644 | ≤10 |
| 645 | ≤0.01 |
| 646 | ≤0.01 |
| 647 | ≤10 |
| 648 | ≤10 |
| 649 | ≤0.1 |
| 650 | ≤1 |
| 651 | ≤0.01 |
| 651 | ≤0.01 |
| 652 | ≤0.01 |
| 653 | ≤10 |
| 654 | ≤1 |
| 655 | ≤1 |
| 656 | ≤1 |

| Ex. | Ki [μM] |
|---|---|
| 657 | ≤1 |
| 658 | ≤1 |
| 659 | ≤10 |
| 660 | ≤1 |
| 661 | ≤1 |
| 662 | ≤10 |
| 663 | ≤0.1 |
| 664 | ≤0.1 |
| 665 | ≤0.01 |
| 666 | 10 |
| 667 | ≤0.1 |
| 668 | ≤10 |
| 669 | ≤0.1 |
| 670 | ≤0.01 |
| 671 | ≤1 |
| 672 | ≤1 |
| 673 | ≤1 |
| 674 | ≤1 |
| 675 | ≤1 |
| 676 | ≤1 |
| 677 | ≤1 |
| 678 | ≤1 |
| 679 | ≤1 |
| 680 | ≤0.1 |
| 681 | ≤0.01 |
| 682 | ≤0.1 |
| 683 | ≤0.1 |
| 684 | ≤1 |
| 685 | ≤0.01 |
| 686 | ≤0.01 |
| 687 | ≤0.1 |
| 688 | ≤1 |
| 689 | ≤1 |

| Ex. | Ki [μM] |
|---|---|
| 690 | ≤1 |
| 691 | ≤0.1 |
| 692 | ≤1 |
| 693 | ≤10 |
| 694 | ≤1 |
| 695 | ≤10 |
| 696 | ≤10 |
| 697 | ≤1 |
| 698 | ≤1 |
| 699 | ≤1 |
| 700 | ≤10 |
| 701 | ≤1 |
| 702 | ≤10 |
| 703 | ≤1 |
| 704 | ≤1 |
| 705 | ≤1 |
| 706 | ≤10 |
| 707 | ≤1 |
| 708 | ≤10 |
| 709 | ≤10 |
| 710 | ≤1 |
| 711 | — |
| 712 | ≤1 |
| 713 | >10 |
| 714 | ≤10 |
| 715 | ≤1 |
| 716 | ≤0.1 |
| 717 | ≤0.1 |
| 718 | ≤0.1 |
| 719 | ≤0.1 |
| 720 | ≤0.1 |
| 721 | ≤0.1 |
| 722 | ≤0.01 |
| 723 | ≤0.1 |
| 724 | ≤0.1 |
| 725 | ≤0.01 |
| 726 | ≤0.1 |
| 727 | ≤0.01 |
| 728 | ≤0.01 |
| 729 | ≤0.01 |
| 730 | ≤0.01 |
| 731 | ≤0.1 |
| 732 | ≤0.1 |
| 733 | ≤0.01 |
| 734 | ≤0.1 |
| 735 | ≤10 |
| 736 | ≤1 |
| 737 | ≤0.1 |
| 738 | >10 |
| 739 | ≤0.1 |
| 740 | ≤10 |
| 741 | ≤0.1 |
| 742 | ≤1 |
| 743 | ≤0.1 |
| 744 | ≤0.01 |
| 745 | ≤0.01 |
| 746 | ≤0.01 |
| 747 | ≤0.01 |
| 748 | ≤0.01 |
| 749 | ≤0.01 |
| 750 | ≤0.1 |
| 751 | ≤0.1 |
| 752 | ≤0.1 |
| 753 | ≤1 |
| 754 | ≤10 |
| 755 | ≥10 |
| 756 | ≤10 |
| 757 | ≤10 |
| 758 | ≤10 |
| 759 | ≤0.01 |
| 760 | >10 |
| 761 | ≤0.1 |
| 762 | ≤0.1 |
| 763 | ≤1 |
| 764 | ≤1 |
| 765 | ≤1 |
| 766 | ≤1 |

| Ex. | Ki [μM] |
|---|---|
| 767 | ≤0.1 |
| 768 | ≤0.1 |
| 769 | ≤1 |
| 770 | ≤1 |
| 771 | ≤0.1 |
| 772 | ≤10 |
| 773 | ≤0.1 |
| 774 | ≤0.1 |
| 775 | ≤1 |
| 776 | ≤0.01 |
| 777 | >10 |
| 778 | >10 |
| 779 | ≤10 |
| 780 | ≤10 |
| 781 | ≤10 |
| 782 | ≤1 |
| 783 | ≤1 |
| 784 | ≤0.1 |
| 785 | ≤0.1 |
| 786 | ≤1 |
| 787 | ≤1 |
| 788 | ≤1 |
| 789 | ≤1 |
| 790 | ≤1 |
| 791 | ≤1 |
| 792 | ≤10 |
| 793 | ≤10 |
| 794 | ≤1 |
| 795 | ≤0.01 |
| 796 | ≤0.1 |
| 797 | ≤10 |
| 798 | ≤0.1 |
| 799 | ≤0.1 |
| 800 | ≤0.01 |
| 801 | ≤0.01 |
| 802 | ≤0.1 |
| 803 | ≤0.01 |
| 804 | — |
| 805 | ≤1 |
| 806 | ≤0.01 |
| 807 | ≤0.01 |
| 808 | ≤0.01 |
| 809 | ≤0.01 |
| 810 | ≤0.01 |
| 811 | ≤0.1 |
| 812 | — |

| Ex. | Ki [μM] |
|---|---|
| 813 | ≤0.1 |
| 814 | ≤1 |
| 815 | ≤0.1 |
| 816 | ≤0.01 |
| 817 | ≤1 |
| 818 | ≤0.01 |
| 819 | ≤0.1 |
| 820 | ≤10 |
| 821 | ≤10 |
| 822 | ≤1 |
| 823 | ≤1 |
| 824 | ≤1 |
| 825 | ≤1 |
| 826 | ≤10 |
| 827 | ≤1 |
| 828 | ≤10 |
| 829 | ≤10 |
| 830 | ≤10 |
| 831 | ≤1 |
| 832 | ≤1 |
| 833 | ≤10 |
| 834 | ≤1 |
| 835 | ≤1 |
| 836 | ≤0.01 |
| 837 | ≤0.01 |
| 838 | ≤0.01 |
| 839 | ≤0.01 |
| 840 | ≤0.01 |
| 841 | ≤0.01 |
| 842 | ≤0.01 |
| 843 | ≤0.1 |
| 844 | ≤1 |
| 845 | ≤1 |
| 846 | ≤0.1 |
| 847 | ≤0.1 |
| 848 | ≤1 |
| 849 | ≤0.1 |
| 850 | ≤1 |
| 851 | ≤10 |
| 852 | ≤1 |
| 853 | ≤ |
| 854 | — |
| 855 | — |
| 856 | — |
| 857 | — |
| 858 | — |
| 859 | — |
| 860 | — |
| 861 | — |
| 862 | — |
| 863 | ≤1 |
| 864 | ≤10 |
| 865 | ≤0.01 |
| 866 | ≤0.01 |
| 867 | ≤0.1 |
| 868 | ≤10 |
| 869 | ≤0.01 |
| 870 | ≤0.1 |
| 871 | ≤0.1 |
| 872 | >10 |
| 873 | ≤10 |
| 874 | ≤10 |
| 875 | ≤10 |
| 876 | ≤1 |
| 877 | ≤10 |
| 878 | ≤10 |
| 879 | ≤1 |
| 880 | ≤1 |
| 881 | ≤1 |
| 882 | ≤1 |
| 883 | ≤10 |
| 884 | ≤0.1 |
| 885 | ≤0.1 |
| 886 | ≤1 |
| 887 | ≤0.1 |
| 888 | ≤1 |
| 889 | ≤0.1 |
| 890 | ≤0.1 |
| 891 | ≤0.1 |
| 892 | ≤0.1 |
| 893 | ≤0.1 |
| 894 | ≤0.01 |
| 895 | ≤0.01 |
| 896 | ≤0.01 |
| 897 | ≤0.01 |
| 898 | ≤0.01 |
| 899 | ≤0.1 |
| 900 | ≤1 |
| 901 | ≤0.01 |
| 902 | ≤1 |
| 903 | ≤0.01 |
| 904 | ≤0.01 |
| 905 | ≤1 |
| 906 | ≤1 |
| 907 | ≤1 |
| 908 | ≤10 |
| 909 | ≤1 |
| 910 | ≤0.1 |
| 911 | ≤0.01 |
| 912 | ≤0.01 |

-continued

| Ex. | Ki [μM] |
|---|---|
| 913 | ≤0.01 |
| 914 | ≤0.01 |
| 915 | ≤0.01 |
| 916 | ≤0.1 |
| 917 | ≤0.1 |
| 918 | ≤1 |
| 919 | ≤10 |
| 920 | ≤0.01 |
| 921 | ≤0.1 |
| 922 | ≤0.01 |
| 923 | ≤0.1 |
| 924 | ≤0.01 |
| 925 | ≤0.01 |
| 926 | ≤0.01 |
| 927 | ≤0.01 |
| 928 | ≤0.01 |

3. Metabolic stability

Metabolic stability was determined as follows:

0.5 μM test substance was preincubated together with human liver microsomes (0.25 mg of microsomal protein/ml) in 0.05 M potassium phosphate buffer of pH 7.4 in microtiter plates at 37° C. for 5 min. The reaction was started by adding NADPH (1.0 mM). After 0, 5, 10, 15, 20 and 30 min the reaction was stopped and cooled with twice the amount of quench solution consisting of acetonitrile/methanol 1:1, and containing 0.2 μM carbutamide. The samples were frozen until analyzed. The remaining concentration of undegraded test substance was determined by LC MSMS. The half-life (T½) was determined from the gradient of the signal of test substance/unit time plot, allowing to calculate the half-life of the test substance, assuming first order kinetics, from the decrease in the concentration of the compound with time. The microsomal clearance (mClint) was calculated as follows: mClint=((ln(2)/t ½)/Microsomal Protein Concentration (mg/ml))*1000, leading to the unit of uL/min/mg. The scaled clearance (mClin_scaled) was calculated as mCLint scaled=m CLint*(Microsomal Yield (mg/kg BW))/1000000*60, leading to the units L/hr/kg. The Microsomal Yield is defined by the specifics of the used microsomes. Calculations were modified from references: Di, The Society for Biomolecular Screening, 2003, 453-462; Obach, DMD, 1999 vol 27. N 11, 1350-1359.

4. Determination of efflux ratio using Madin-Darby Canine Kidney Type II cells

Bidirectional transport experiments were performed on Madin-Darby Canine Kidney Type II cells over-expressing multidrug resistance protein 1 (MDR$^1$-MDCK) to evaluate the compounds as potential P-gp substrates.

Compounds were added at 1 μM in HBSS-pH 7.4 (hanks balanced salt solution) to either the apical or basolateral side of MDR1-MDCK cell monolayers grown on Millicell 96-Cell polycarbonate filters. Samples were collected from both apical and basolateral sides at time 0 and after 1 h incubation at 37C, compounds concentrations were measured by HPLC/MS/MS and permeability coefficients were then determined in both transport directions. The efflux ratio was subsequently calculated from the permeability coefficient.

We claim:
1. A compound of the formula (I)

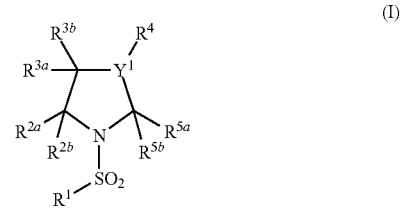

wherein
$R^1$ is a 5-membered heterocyclic ring selected from the group consisting of pyrazolyl, imidazolyl and triazolyl, which is optionally substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxycarbonyl and $C_1$-$C_6$-alkylkcarbonylamino;
$R^{2a}$, $R^{2b}$
are independently hydrogen, halogen, or $C_1$-$C_3$-alkyl, or
$R^{2a}$, $R^{2b}$
together with the carbon atom to which they are bound may form a C=O;
$R^{3a}$ is $C_3$-$C_{12}$-cycloalkyl, optionally substituted $C_6$-$C_{12}$-aryl, hydroxy, $C_1$-$C_6$-alkoxy, halogenated $C_1$-$C_6$-alkoxy, $C_3$-$C_{12}$-cycloalkyl-$C_1$-$C_4$-alkoxy, $C_2$-$C_6$-alkenyloxy, $C_6$-$C_{12}$-aryl-$C_1$-$C_4$-alkoxy, $C_3$-$C_{12}$-heterocyclyl-$C_1$-$C_4$-alkoxy, optionally substituted $C_6$-$C_{12}$-aryloxy, $C_3$-$C_{12}$-heterocyclyloxy, or optionally substituted $C_3$-$C_{12}$-heterocyclyl;
$R^{3b}$ is hydrogen, $C_1$-$C_6$-alkyl, or hydroxyl; or
$R^{3a}$ and $R^{3b}$
together are optionally substituted $C_2$-$C_5$-alkylene;
$Y^1$ is >$CR^6$— or >N—;
$R^6$ is hydrogen, $C_1$-$C_6$-alkyl, halogenated $C_1$-$C_6$-alkyl, (optionally substituted $C_6$-$C_{12}$-aryl)-$C_1$-$C_4$-alkyl, hydroxy-$C_1$-$C_6$-alkyl, $C_1$-$C_4$-alkoxy-$C_1$-$C_6$-alkyl, or hydroxyl, or
$R^6$ and $R^{3a}$ or $R^{3b}$
together are optionally substituted $C_1$-$C_5$-alkylene, or
$R^6$ is $C_1$-$C_4$-alkylene that is bound to a carbon atom in $R^{3a}$, and $R^{3a}$ is an optionally substituted $C_6$-$C_{12}$-aryl or an optionally substituted $C_3$-$C_{12}$-heterocyclyl;
$R^4$ is —$NR^{8a}(CR^{9a}R^{9b})_{n4}R^{13}$, —$(CR^{7a}R^{7b})_{n1}OR^{10}$, —$(CR^{7c}R^{7d})_{n2}NR^{11a}R^{11b}$, —$(CR^{7e}R^{7f})_{n3}R^{12}$, optionally substituted $C_6$-$C_{12}$-aryl, —$NR^{8b}COR^{14}$, —$NR^{8c}COOR^{15}$, —$NR^{8d}CONR^{16a}R^{16b}$, —$NR^{8e}SO_2R^{17}$, —$O(CR^{9c}R^{9d})_{n5}R^{18}$, —$COR^{19}$, —$CONR^{20a}R^{20b}$, —$SO_2R^{21}$, or optionally substituted $C_3$-$C_{12}$-heterocyclyl;
$R^{7a}$, $R^{7b}$
are independently hydrogen or $C_1$-$C_6$-alkyl;
n1 is 1, 2, 3, or 4;
$R^{10}$ is hydrogen, optionally substituted $C_6$-$C_{12}$-aryl, or optionally substituted $C_3$-$C_{12}$-heterocyclyl;
$R^{7c}$, $R^{7d}$
are independently hydrogen or $C_1$-$C_6$-alkyl;
n2 is 1, 2, 3, or 4;
$R^{11a}$ is $C_1$-$C_8$-alkyl, (optionally substituted $C_3$-$C_{12}$-cycloalkyl)-$C_1$-$C_4$-alkyl, $C_1$-$C_6$-alkoxy -$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{11b}$
is hydrogen or $C_2$-$C_6$ alkyl;

$R^{7e}$, $R^{7f}$
are independently hydrogen or $C_1$-$C_6$-alkyl;

n3 is 1, 2, 3, or 4;

$R^{12}$
is optionally substituted $C_6$-$C_{12}$-aryl or optionally substituted $C_3$-$C_{12}$-heterocyclyl;

$R^{8a}$, $R^{8b}$, $R^{8c}$, $R^{8d}$, $R^{8e}$
are independently hydrogen, $C_1$-$C_6$-alkyl, or $C_1$-$C_6$-alkylcarbonyl, or $R^6$ and one of $R^{8a}$, $R^{8b}$, $R^{8c}$, $R^{8d}$, or $R^{8e}$
together are optionally substituted $C_1$-$C_5$-alkylene, wherein one or more —$CH_2$— of $C_1$-$C_5$-alkylene may be independently replaced by a an oxygen atom or C=O, or $R^{3a}$ and one of $R^{8a}$ or $R^{8b}$
together are optionally substituted $C_1$-$C_5$-alkylene;

$R^{9a}$, $R^{9b}$
are independently hydrogen, halogen, $C_1$-$C_6$-alkyl, halogenated $C_1$-$C_6$-alkyl, hydroxyl, or $C_1$-$C_6$-alkoxy;

n4 is 0, 1, 2, 3, or 4;

$R^{13}$ is $C_2$-$C_8$-alkyl, halogenated $C_1$-$C_6$-alkyl, (optionally substituted $C_3$-$C_{12}$-cycloalkyl)-$C_1$-$C_4$-alkyl, $C_1$-$C_6$-alkoxy-$C_1$-$C_6$-alkyl, optionally substituted $C_3$-$C_{12}$-cycloalkyl, $C_2$-$C_6$-alkenyl, optionally substituted $C_3$-$C_6$-cycloalkenyl, optionally substituted $C_6$-$C_{12}$-aryl, hydroxy, $C_1$-$C_6$-alkoxy, $C_1$-$C_6$-alkoxy-$C_1$-$C_4$-alkoxy, optionally substituted $C_6$-$C_{12}$-aryloxy, optionally substituted $C_3$-$C_{12}$-heterocyclyloxy, optionally substituted $C_3$-$C_{12}$-heterocyclyl, or tri-($C_1$-$C_4$-alkyl)-silyloxy;

$R^{14}$ is $C_2$-$C_6$-alkyl, halogenated $C_1$-$C_6$-alkyl, (optionally substituted $C_3$-$C_{12}$-cycloalkyl)-$C_1$-$C_4$-alkyl, (optionally substituted $C_6$-$C_{12}$-aryl)-$C_1$-$C_4$-alkyl, hydroxy-$C_1$-$C_6$-alkyl, $C_1$-$C_6$-alkoxy-$C_1$-$C_6$-alkyl, (optionally substituted $C_6$-$C_{12}$-aryloxy)-$C_1$-$C_4$-alkyl, $C_1$-$C_6$-alkylcarbonyl-$C_1$-$C_4$-alkyl, $C_1$-$C_6$-alkoxycarbonyl-$C_1$-$C_4$-alkyl, $C_1$-$C_6$-alkylaminocarbonyl-$C_1$-$C_4$-alkyl, optionally substituted ($C_3$-$C_{12}$-heterocyclyl)-$C_1$-$C_4$-alkyl, optionally substituted $C_3$-$C_{12}$-cycloalkyl, optionally substituted $C_6$-$C_{12}$-aryl, or optionally substituted $C_3$-$C_{12}$-heterocyclyl;

$R^{15}$ is $C_1$-$C_8$-alkyl, optionally substituted $C_6$-$C_{12}$-aryl, or optionally substituted $C_3$-$C_{12}$-heterocyclyl;

$R^{16a}$ is (optionally substituted $C_6$-$C_{12}$-aryl)-$C_1$-$C_4$-alkyl, optionally substituted ($C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{16b}$ is hydrogen or $C_1$-$C_6$-alkyl;

$R^{17}$ is (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{9c}$, $R^{9d}$
are independently hydrogen, halogen, or $C_1$-$C_6$-alkyl;

n5 is 0, 1, 2, 3, or 4;

$R^{18}$ is hydrogen, $C_1$-$C_8$-alkyl, optionally substituted $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, $C_1$-$C_6$-alkylaminocarbonyl, (halogenated $C_1$-$C_4$-alkyl)aminocarbonyl, $C_6$-$C_{12}$-arylaminocarbonyl, optionally substituted $C_6$-$C_{12}$-aryl, $C_1$-$C_6$-alkylamine, ($C_3$-$C_{12}$-cycloalkyl-$C_1$-$C_4$-alkyl) amino, (halogenated $C_1$-$C_6$-alkyl)amino, ($C_1$-$C_6$-alkoxy-$C_1$-$C_6$-alkyl)amino, ($C_6$-$C_{12}$-aryl-$C_1$-$C_4$-alkyl) amino, $C_1$-$C_6$-dialkylamine, optionally substituted $C_6$-$C_{12}$-arylamine, or optionally substituted $C_3$-$C_{12}$-heterocyclyl;

$R^{19}$ is optionally substituted $C_6$-$C_{12}$-aryl or optionally substituted $C_3$-$C_{12}$-heterocyclyl;

$R^{20a}$ is $C_1$-$C_8$-alkyl, (optionally substituted $C_3$-$C_{12}$-cycloalkyl)-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{20b}$ is hydrogen or $C_1$-$C_8$-alkyl;

$R^{21}$ is optionally substituted $C_6$-$C_{12}$-aryl, or optionally substituted $C_3$-$C_{12}$-heterocyclyl; and $R^{5a}$, $R^{5b}$
are independently hydrogen, halogen, or $C_1$-$C_3$-alkyl, or $R^{5a}$, $R^{5b}$
together with the carbon atom to which they are bound may form a C=O, or one of $R^{2a}$ or $R^{2b}$ and one of $R^{5a}$ or $R^{5b}$
together are optionally substituted $C_1$-$C_5$-alkylene;

or a physiologically tolerated salt thereof;

provided that the following compounds are excluded: compounds of formula (II) and the physiologically tolerated salts thereof:

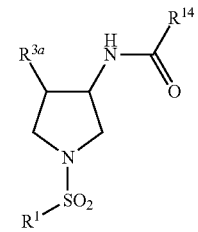

(II)

wherein $R^1$, $R^{3a}$ and $R^{14}$ are as defined in the following table

| $R^1$ | $R^{3a}$ | $R^{14}$ |
|---|---|---|
| imidazolyl | tetrahydrofuranyl | 4-F—Ph |
| imidazolyl | tetrahydrofuranyl | 4-CF$_3$—Ph |
| imidazolyl | tetrahydrofuranyl | 2-OMe—Ph |

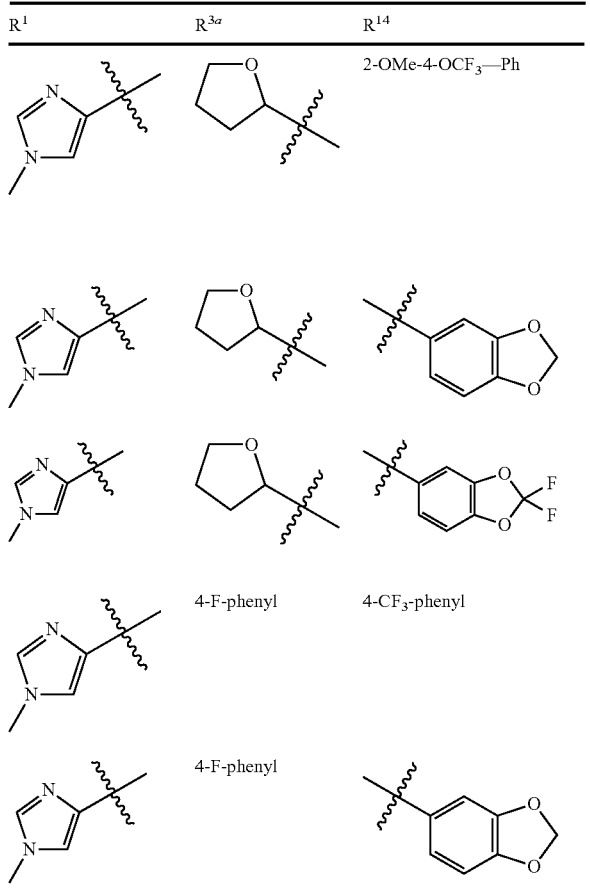

compounds of formula (II')

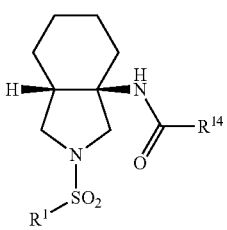
(II'')

wherein $R^1$ and $R^{14}$ are defined in the following table

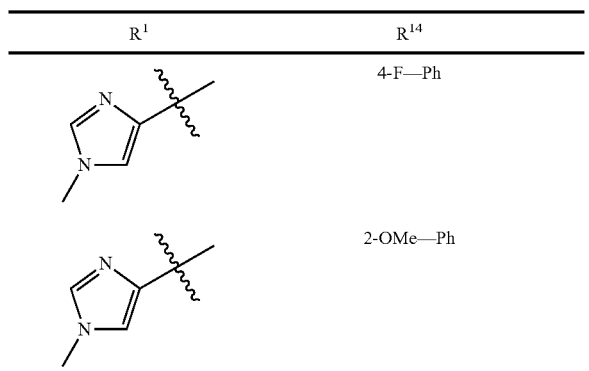

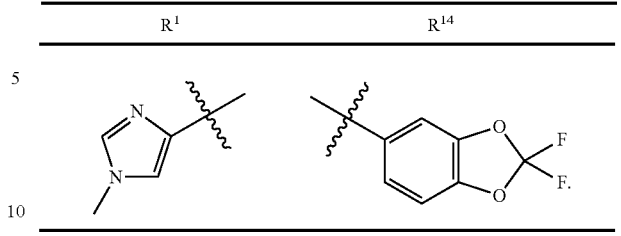

2. The compound as claimed in claim 1, wherein $R^1$ is optionally substituted 1,3-diazolyl or optionally substituted 1,2,3-triazolyl.

3. The compound as claimed in claim 1, wherein $R^1$ is 1,2-diazol-4-yl, 1-methyl-1,2-diazol-4-yl, 1-methyl-1,2-diazol-3-yl, 1-methyl-1,3-diazol-4-yl, 1-methyl-1,2-diazol-5-yl, 1,5-dimethyl-1,2-diazol-4-yl, 1,3-dimethyl-1,2-diazol-4-yl, 1,5-dimethyl-1,2-diazol-4-yl, 1,3-dimethyl-1,2-diazol-4-yl, 1,3-dimethyl-1,2-diazol-5-yl, 1,3-dimethyl-5-Cl-1,2-diazol-4-yl, 1-iso-propyl-3-methyl-1,2-diazol-4-yl, 1-Me-3-CF$_3$-1,2-diazol-4-yl, 1-cyclopentyl-3-Me-1,2-diazol-4-yl, 1,3,5-trimethyl-1,2-diazol-4-yl, 1-CHF$_2$-3,5-dimethyl-1,2-diazol-4-yl, 1,2-dimethyl-1,3-diazol-4-yl, 1,2-dimethyl-1,3-diazol-5-yl, 1-methyl-5-Cl-1,3-diazol-4-yl, 1-Me-1,2,3-triazol-4-yl, 1-ethyl-1,3-diazol-4-yl, or 1-methyl-1,2,4-triazol-3-yl.

4. The compound as claimed in claims 1, wherein $R^{2a}$ is hydrogen, halogen or $C_1$-$C_3$-alkyl, and $R^{2b}$ is hydrogen.

5. The compound as claimed in claim 1, wherein $R^{3a}$ is $C_6$-$C_{12}$-aryl optionally substituted with 1, 2, or 3 substituents independently selected from the group consisting of halogen, $C_1$-$C_4$-alkyl and $C_1$-$C_4$-alkoxy.

6. The compound as claimed in claim 1, wherein $R^{3a}$ is $C_3$-$C_{12}$-heterocyclyl optionally substituted with 1, 2, or 3 substituents independently selected from the group consisting of halogen, $C_1$-$C_4$-alkyl and $C_3$-$C_6$-cycloalkyl.

7. The compound as claimed in claim 1, wherein $R^{3b}$ is hydrogen.

8. The compound as claimed in claim 1, wherein $Y^1$ is >CR$^6$— and $R^6$ is hydrogen, methyl, benzyl, hydroxymethyl, or hydroxy.

9. The compound as claimed in claims 1, wherein $R^{5a}$ is hydrogen, halogen or $C_1$-$C_3$-alkyl, and $R^{5b}$ is hydrogen.

10. The compound as claimed in claim 1, having formula (Ia)

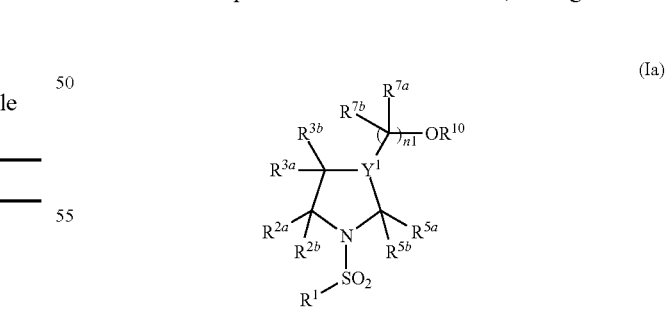

wherein $R^{7a}$, $R^{7b}$ are independently hydrogen or $C_1$-$C_6$-alkyl;

n1 is 1, 2, 3, or 4; and $R^{10}$ is hydrogen, optionally substituted $C_6$-$C_{12}$-aryl, or optionally substituted $C_3$-$C_{12}$-heterocyclyl.

11. The compound as claimed in claim 1, having formula

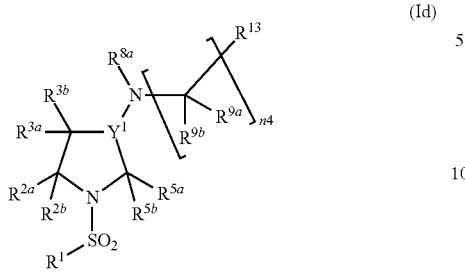
(Id)

wherein
R$^{8a}$ is hydrogen, C$_1$-C$_6$-alkyl, or C$_1$-C$_6$-alkylcarbonyl, or
R$^6$, R$^{8a}$
together are optionally substituted C$_1$-C$_5$-alkylene, wherein one or more —CH$_2$— of C$_1$-C$_5$-alkylene may be independently replaced by a an oxygen atom or C=O;
R$^{9a}$, R$^{9b}$
are independently hydrogen, halogen, C$_1$-C$_6$-alkyl, hydroxy, or C$_1$-C$_6$-alkoxy;
n4 is 0, 1, 2, 3, or 4; and
R$^{13}$ is C$_2$-C$_8$-alkyl, halogenated C$_1$-C$_6$-alkyl, (optionally substituted C$_3$-C$_{12}$-cycloalkyl)-C$_1$-C$_4$-alkyl, C$_1$-C$_6$-alkoxy-C$_1$-C$_6$-alkyl, optionally substituted C$_3$-C$_{12}$-cycloalkyl, C$_2$-C$_6$-alkenyl, optionally substituted C$_3$-C$_6$-cycloalkenyl, optionally substituted C$_6$-C$_{12}$-aryl, hydroxy, C$_1$-C$_6$-alkoxy, C$_1$-C$_6$-alkoxy-C$_1$-C$_4$-alkoxy, optionally substituted C$_6$-C$_{12}$-aryloxy, optionally substituted C$_3$-C$_{12}$-heterocyclyloxy, optionally substituted C$_3$-C$_{12}$-heterocyclyl, or tri-(C$_1$-C$_4$-alkyl)-silyloxy.

12. The compound as claimed in claim 11, wherein
R$^1$ is a 5-membered heterocyclic ring selected from the group consisting of pyrazolyl, imidazolyl and triazolyl, which is optionally substituted with 1, 2 or 3 substituents independently selected from the group consisting of halogen, C$_1$-C$_6$-alkyl, halogenated C$_1$-C$_6$-alkyl, C$_3$-C$_6$-cycloalkyl, C$_1$-C$_4$-alkoxycarbonyl, and C$_1$-C$_6$-alkycarbonylamino;
R$^{2a}$, R$^{2b}$
are hydrogen;
R$^{3a}$ is C$_3$-C$_{12}$-cycloalkyl, optionally substituted C$_6$-C$_{12}$-aryl, hydroxy, C$_1$-C$_6$-alkoxy, C$_3$-C$_{12}$-cycloalkyl-C$_1$-C$_4$-alkoxy, C$_2$-C$_6$-alkenyloxy, C$_6$-C$_{12}$-aryl-C$_1$-C$_4$-alkoxy, optionally substituted C$_6$-C$_{12}$-aryloxy, or optionally substituted C$_3$-C$_{12}$-heterocyclyl;
R$^{3b}$ is hydrogen or hydroxy;
Y$^1$ is >CR$^6$;
R$^6$ is hydrogen, C$_1$-C$_6$-alkyl, or hydroxy-C$_1$-C$_6$-alkyl,
R$^{8a}$ is hydrogen, C$_1$-C$_6$-alkyl, or C$_1$-C$_6$-alkylcarbonyl, or
R$^6$,R$^{8a}$
are together optionally substituted C$_1$-C$_5$-alkylene, wherein one or more —CH$_2$— of C$_1$-C$_5$-alkylene may be independently replaced by a an oxygen atom or C=O;
R$^{9a}$ is hydrogen, halogen, C$_1$-C$_6$-alkyl, or C$_1$-C$_6$-alkoxy;
R$^{9b}$ is hydrogen;
n4 is 0, 1, 2, 3, or 4;
R$^{13}$ is C$_2$-C$_8$-alkyl, halogenated C$_1$-C$_6$-alkyl, C$_1$-C$_6$-alkoxy-C$_1$-C$_6$-alkyl, optionally substituted C$_3$-C$_{12}$-cycloalkyl, C$_2$-C$_6$-alkenyl, optionally substituted C$_6$-C$_{12}$-aryl, C$_1$-C$_6$-alkoxy, C$_1$-C$_6$-alkoxy-C$_1$-C$_4$-alkoxy, optionally substituted C$_6$-C$_{12}$-aryloxy optionally substituted C$_3$-C$_{12}$-heterocyclyl, or tri-(C$_1$-C$_4$-alkyl)-silyloxy; and
R$^{5a}$, R$^{5b}$
are hydrogen.

13. The compound as claimed in claim 11, wherein
R$^1$ is 1,3-diazolyl optionally substituted with halogen or C$_1$-C$_4$-alkyl, or 1,2,3-triazolyl optionally substituted with C$_1$-C$_4$-alkyl;
R$^{2a}$, R$^{2b}$
are hydrogen;
R$^{3a}$ is C$_3$-C$_{12}$-cycloalkyl, C$_6$-C$_{12}$-aryl optionally substituted with 1, 2, or 3 substituents independently selected from the group consisting of halogen and C$_1$-C$_4$-alkyl, or hydroxy, C$_1$-C$_6$-alkoxy, C$_3$-C$_{12}$-cycloalkyl-C$_1$-C$_4$-alkoxy, C$_2$-C$_6$-alkenyloxy, C$_6$-C$_{12}$-aryl-C$_1$-C$_4$-alkoxy, C$_6$-C$_{12}$-aryloxy optionally substituted with 1, 2, or 3 substituents independently selected from the group consisting of halogen and C$_1$-C$_4$-alkyl, or C$_3$-C$_{12}$-heterocyclyl optionally substituted with 1, 2, or 3 substituents independently selected from the group consisting of halogen, C$_1$-C$_4$-alkyl and C$_3$-C$_6$-cycloalkyl;
R$^{3b}$ is hydrogen or hydroxy;
Y$^1$ is >CR$^6$;
R$^6$ is hydrogen, C$_1$-C$_6$-alkyl, or hydroxy-C$_1$-C$_6$-alkyl,
R$^{8a}$ is hydrogen, C$_1$-C$_6$-alkyl, or C$_1$-C$_6$-alkylcarbonyl, or
R$^6$,R$^{8a}$
are together optionally substituted C$_1$-C$_5$-alkylene, wherein one or more —CH$_2$— of C$_1$-C$_5$-alkylene may be independently replaced by a an oxygen atom or C=O;
R$^{9a}$ is hydrogen, halogen, C$_1$-C$_6$-alkyl, or C$_1$-C$_6$-alkoxy;
R$^{9b}$ is hydrogen;
n4 is 0, 1, 2, 3, or 4;
R$^{13}$ is C$_2$-C$_8$-alkyl, halogenated C$_1$-C$_6$-alkyl, C$_1$-C$_6$-alkoxy-C$_1$-C$_6$-alkyl, C$_3$-C$_{12}$-cycloalkyl optionally substituted with 1, 2, or 3 substituents independently selected from the group consisting of halogen, C$_1$-C$_4$-alkyl, halogenated C$_1$-C$_4$-alkyl, C$_1$-C$_4$-alkoxy-C$_1$-C$_4$-alkyl and C$_6$-C$_{12}$-aryl, or C$_2$-C$_6$-alkenyl, C$_3$-C$_6$-cycloalkenyl optionally substituted with 1, 2, or 3 substituents independently selected from the group consisting of C$_1$-C$_4$-alkyl, or C$_6$-C$_{12}$-aryl optionally substituted with 1, 2, or 3 substituents independently selected from the group consisting of halogen, C$_1$-C$_4$-alkyl, halogenated C$_1$-C$_4$-alkyl, hydroxy-(halogenated C$_1$-C$_4$-alkyl), CN, C$_6$-C$_{12}$-aryl, C$_1$-C$_4$-alkoxy, halogenated C$_1$-C$_4$-alkoxy, C$_6$-C$_{12}$ aryl-C$_1$-C$_4$-alkoxy, C$_6$-C$_{12}$-aryloxy, C$_1$-C$_4$-alkyl-sulfonyl, C$_1$-C$_4$-alkylcarbonylamino and C$_3$-C$_{12}$-heterocyclyl, or C$_1$-C$_6$-alkoxy, C$_1$-C$_6$-alkoxy-C$_1$-C$_4$-alkoxy, C$_6$-C$_{12}$-aryloxy optionally substituted with 1, 2, or 3 substituents independently selected from the group consisting of halogen and C$_1$-C$_4$-alkyl, or C$_3$-C$_{12}$-heterocyclyl optionally substituted with 1, 2, or 3 substituents independently selected from the group consisting of halogen, C$_1$-C$_4$-alkyl, halogenated C$_1$-C$_4$-alkyl, C$_6$-C$_{12}$-aryl-C$_1$-C$_6$-alkyl, C$_3$-C$_6$-cycloalkyl, hydroxy, CN, C$_6$-C$_{12}$-aryl optionally substituted with halogen and C$_1$-C$_4$-alkyl, C$_1$-C$_4$-alkoxy, halogenated C$_1$-C$_4$-alkoxy, C$_3$-C$_6$-cycloalkoxy, C$_6$-C$_{12}$aryl-C$_1$-C$_4$-alkoxy, C$_3$-C$_{12}$-heterocyclyl-C$_1$-C$_4$-alkoxy and C$_3$-C$_{12}$-heterocyclyl, or tri-(C$_1$-C$_4$-alkyl)-silyloxy; and
R$^{5a}$, R$^{5b}$
are hydrogen.

14. The compound as claimed in claim 11, wherein $R^{13}$ is a group of the formula (Id1):

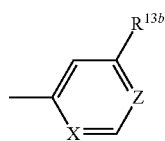

(Id1)

wherein

X is >CH— or >N—;

Z is >C—$R^{13c}$ or >N—;

$R^{13b}$ is halogen, $C_1$-$C_4$-alkyl, halogenated $C_1$-$C_4$-alkyl, hydroxy-(halogenated $C_1$-$C_4$-alkyl), $C_6$-$C_{12}$-aryl-$C_1$-$C_4$-alkyl, $C_3$-$C_6$-cycloalkyl, CN, $C_6$-$C_{12}$-aryl optionally substituted with halogen or $C_1$-$C_4$-alkyl, $C_1$-$C_4$-alkoxy, halogenated $C_1$-$C_4$-alkoxy, $C_3$-$C_6$-cycloalkoxy, $C_6$-$C_{12}$ aryl-$C_1$-$C_4$-alkoxy, $C_3$-$C_{12}$-heterocyclyl-$C_1$-$C_4$-alkoxy, $C_6$-$C_{12}$-aryloxy, $C_1$-$C_4$-alkyl-sulfonyl, $C_1$-$C_4$-alkyl-carbonylamino or $C_3$-$C_{12}$-heterocyclyl; and $R^{13c}$ is hydrogen or halogen.

15. The compound as claimed in claim 14, wherein $R^{8a}$ is hydrogen.

16. The compound as claimed in claim 1, having formula

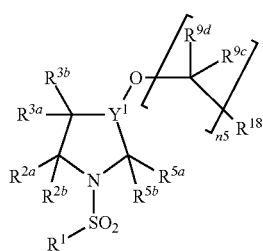

(Ih)

wherein $R^{9c}$, $R^{9d}$ are independently hydrogen, halogen, or $C_1$-$C_6$-alkyl;

n5 is 0, 1, 2, 3, or 4; and $R^{18}$ is hydrogen, optionally substituted $C_1$-$C_8$-alkyl, optionally substituted $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, $C_1$-$C_6$-alkylaminocarbonyl, (halogenated $C_1$-$C_4$-alkyl) aminocarbonyl, $C_6$-$C_{12}$-arylaminocarbonyl, optionally substituted $C_6$-$C_{12}$-aryl, $C_1$-$C_6$-alkylamine, ($C_3$-$C_{12}$-cycloalkyl-$C_1$-$C_4$-alkyl)amino, (halogenated $C_1$-$C_6$-alkyl)amino, ($C_1$-$C_6$-alkoxy-$C_1$-$C_6$-alkyl)amino, ($C_6$-$C_{12}$-aryl-$C_1$-$C_4$-alkyl)amino, $C_1$-$C_6$-dialkylamine, optionally substituted $C_6$-$C_{12}$-arylamine, or optionally substituted $C_3$-$C_{12}$-heterocyclyl.

17. The compound as claimed in claim 1, wherein $R^1$ is a 5-membered heterocyclic ring selected from the group consisting of pyrazolyl, imidazolyl and triazolyl, which is optionally substituted with 1, 2 or 3 substituents independently selected from the group consisting of halogen, $C_1$-$C_6$-alkyl, halogenated $C_1C_6$-alkyl, $C_3$-$C_6$-cycloalkyl, $C_1$-$C_4$-alkoxycarbonyl, and $C_1$-$C_6$-alkylcarbonylamino;

$R^{2a}$, $R^{2b}$ are hydrogen;

$R^{3a}$ is $C_3$-$C_{12}$-cycloalkyl, optionally substituted $C_6$-$C_{12}$-aryl, hydroxy, $C_1$-$C_6$-alkoxy, $C_3$-$C_{12}$-cycloalkyl-$C_1$-$C_4$-alkoxy, $C_2$-$C_6$-alkenyloxy, $C_6$-$C_{12}$-aryl-$C_1$-$C_4$-alkoxy, optionally substituted $C_6$-$C_{12}$-aryloxy, or optionally substituted $C_3$-$C_{12}$-heterocyclyl;

$R^{3b}$ is hydrogen or hydroxy;

$Y^1$ is >$CR^6$— or >N—;

$R^6$ is hydrogen, $C_1$-$C_6$-alkyl, ($C_6$-$C_{12}$-aryl)-$C_1$-$C_4$-alkyl, hydroxy-$C_1$-$C_6$-alkyl, or hydroxy;

$R^4$ is —$(CR^{7a}R^{7b})_{n1}OR^{10}$, —$(CR^{7c}R^{7d})_{n2}NR^{11a}R^{11b}$, —$(CR^{7e}R^{7f})_{n3}R^{12}$, optionally substituted $C_6$-$C_{12}$-aryl, —$NR^{8a}(CR^{9a}R^{9b})_{n4}R^{13}$, —$NR^{8b}COR^{14}$, —$NR^{8c}COOR^{15}$, —$NR^{8d}CONR^{16a}R^{16b}$, —$O(CR^{9c}R^{9d})_{n5}R^{18}$, —$COR^{19}$, —$CONR^{20a}R^{20b}$, —$SO_2R^{21}$, or optionally substituted $C_3$-$C_{12}$-heterocyclyl;

$R^{7a}$, $R^{7b}$ are hydrogen;

n1 is 1;

$R^{10}$ is hydrogen, optionally substituted $C_6$-$C_{12}$-aryl, or optionally substituted $C_3$-$C_{12}$-heterocyclyl;

$R^{7c}$, $R^{7d}$ are hydrogen;

n2 is 1;

$R^{11a}$ is $C_1$-$C_6$-alkyl, $C_3$-$C_{12}$-cycloalkyl-$C_1$-$C_4$-alkyl, $C_1$-$C_6$-alkoxy-$C_1$-$C_6$-alkyl, $C_6$-$C_{12}$-aryl-$C_1$-$C_4$-alkyl, or optionally substituted $C_6$-$C_{12}$-aryl;

$R^{11b}$ is hydrogen;

$R^{7e}$, $R^{7f}$ are hydrogen, n3 is 1;

$R^{12}$ is optionally substituted $C_6$-$C_{12}$-aryl or optionally substituted $C_3$-$C_{12}$-heterocyclyl;

$R^{8a}$, $R^{8b}$, $R^{8c}$, $R^{8d}$, $R^{8e}$ are independently hydrogen or $C_1$-$C_6$-alkyl, or $R^6$ and one of $R^{8a}$, $R^{8b}$, $R^{8c}$, $R^{8d}$, or $R^{8e}$ together are optionally substituted $C_1$-$C_5$-alkylene, wherein one or more —$CH_2$— of $C_1$-$C_5$-alkylene may be independently replaced by a an oxygen atom or C=O;

$R^{9a}$, $R^{9b}$ are independently hydrogen, halogen, $C_1$-$C_6$-alkyl, or $C_1$-$C_6$-alkoxy;

n4 is 0, 1, 2, 3, or 4;

$R^{13}$ is $C_2$-$C_8$-alkyl, halogenated $C_1$-$C_6$-alkyl, $C_1$-$C_6$-alkoxy-$C_1$-$C_6$-alkyl, optionally substituted $C_3$-$C_{12}$-cycloalkyl, $C_2$-$C_6$-alkenyl, optionally substituted $C_3$-$C_6$-cycloalkenyl, optionally substituted $C_6$-$C_{12}$-aryl, $C_1$-$C_6$-alkoxy, $C_1$-$C_6$-alkoxy-$C_1$-$C_4$-alkoxy, optionally substituted $C_6$-$C_{12}$-aryloxy, optionally substituted $C_3$-$C_{12}$-heterocyclyl, or tri-($C_1$-$C_4$-alkyl)-silyloxy;

$R^{14}$ is $C_2$-$C_6$ alkyl, halogenated $C_1$-$C_6$-alkyl, $C_3$-$C_{12}$-cycloalkyl-$C_1$-$C_4$-alkyl, hydroxy-$C_1$-$C_6$-alkyl, (optionally substituted $C_6$-$C_{12}$-aryloxy)-$C_1$-$C_4$-alkyl, $C_1$-$C_6$-alkylcarbonyl-$C_1$-$C_4$-alkyl, $C_1$-$C_6$-alkoxycarbonyl-$C_1$-$C_4$-alkyl, optionally substituted $C_3$-$C_{12}$-cycloalkyl, optionally substituted $C_6$-$C_{12}$-aryl, or optionally substituted $C_3$-$C_{12}$-heterocyclyl;

$R^{15}$ is $C_1$-$C_8$-alkyl, $C_6$-$C_{12}$-aryl, or optionally substituted $C_3$-$C_{12}$-heterocyclyl;

$R^{16a}$ is (optionally substituted $C_6$-$C_{12}$-aryl)-$C_1$-$C_4$-alkyl or optionally substituted $C_6$-$C_{12}$-aryl;

$R^{16b}$ is hydrogen;

$R^{9c}$, $R^{9d}$ are hydrogen;

n5 is 0, 1, or 2;

$R^{18}$ is hydrogen, $C_1$-$C_8$-alkyl, $C_1$-$C_6$-alkoxycarbonyl, $C_1$-$C_6$-alkylaminocarbonyl, (halogenated $C_1$-$C_4$-alkyl) aminocarbonyl, optionally substituted $C_6$-$C_{12}$-aryl, $C_1$-$C_6$-alkylamine, (halogenated $C_1$-$C_6$-alkyl)amino, optionally substituted $C_6$-$C_{12}$-arylamine, or optionally substituted $C_3$-$C_{12}$-heterocyclyl;

$R^{19}$ is optionally substituted $C_6$-$C_{12}$-aryl;

$R^{20a}$ is $C_1$-$C_8$-alkyl, $C_3$-$C_{12}$-cycloalkyl-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{20b}$ is hydrogen or $C_1$-$C_8$-alkyl;

$R^{21}$ is $C_6$-$C_{12}$-aryl; and $R^{5a}$, $R^{5b}$ are hydrogen, or $R^{5a}$, $R^{5b}$ together with the carbon atom to which they are bound may form a C=O.

18. The compound as claimed in claim 1 which is:

2-chloro-N-{trans-1-[(1-methyl-1H-imidazol-4-yl)sulfonyl]-4-phenylpyrrolidin-3-yl}-3-(trifluoromethyl)benzamide;

2-chloro-N-{trans-4-(4-methoxyphenyl)-1-[(1-methyl-1H-imidazol-4-yl)sulfonyl]pyrrolidin-3-yl}-3-(trifluoromethyl)benzamide;

2-chloro-N-{trans-4-(4-fluorophenyl)-1-[(1-methyl-1H-imidazol-4-yl)sulfonyl]pyrrolidin-3-yl}-3-(trifluoromethyl)benzamide;

2-chloro-N-{trans-1-[(1-methyl-1H-imidazol-4-yl)sulfonyl]-4-phenylpyrrolidin-3-yl}-3-(trifluoromethyl)benzamide;

2-chloro-N-{trans-4-(4-chlorophenyl)-1-[(1-methyl-1H-imidazol-4-yl)sulfonyl]pyrrolidin-3-yl}-3-(trifluoromethyl)benzamide;

2-chloro-N-{trans-1-[(1-methyl-1H-imidazol-4-yl)sulfonyl]-4-phenylpyrrolidin-3-yl}benzamide;

3-chloro-N-{trans-1-[(1-methyl-1H-imidazol-4-yl)sulfonyl]-4-phenylpyrrolidin-3-yl}benzamide;

4-chloro-N-{trans-1-[(1-methyl-1H-imidazol-4-yl)sulfonyl]-4-phenylpyrrolidin-3-yl}benzamide;

2-fluoro-N-{trans-1-[(1-methyl-1H-imidazol-4-yl)sulfonyl]-4-phenylpyrrolidin-3-yl}benzamide;

3-fluoro-N-{trans-1-[(1-methyl-1H-imidazol-4-yl)sulfonyl]-4-phenylpyrrolidin-3-yl}benzamide;

4-fluoro-N-{trans-1-[(1-methyl-1H-imidazol-4-yl)sulfonyl]-4-phenylpyrrolidin-3-yl}benzamide;

2-methoxy-N-{trans-1-[(1-methyl-1H-imidazol-4-yl)sulfonyl]-4-phenylpyrrolidin-3-yl}benzamide;

3-methoxy-N-{trans-1-[(1-methyl-1H-imidazol-4-yl)sulfonyl]-4-phenylpyrrolidin-3-yl}benzamide;

2-methyl-N-{trans-1-[(1-methyl-1H-imidazol-4-yl)sulfonyl]-4-phenylpyrrolidin-3-yl}benzamide;

3-methyl-N-{trans-1-[(1-methyl-1H-imidazol-4-yl)sulfonyl]-4-phenylpyrrolidin-3-yl}benzamide;

4-methyl-N-{trans-1-[(1-methyl-1H-imidazol-4-yl)sulfonyl]-4-phenylpyrrolidin-3-yl}benzamide;

N-{trans-1-[(1-methyl-1H-imidazol-4-yl)sulfonyl]-4-phenylpyrrolidin-3-yl}benzamide;

2,4-dichloro-N-{trans-1-[(1-methyl-1H-imidazol-4-yl)sulfonyl]-4-phenylpyrrolidin-3-yl}benzamide;

2-chloro-4-fluoro-N-{trans-1-[(1-methyl-1H-imidazol-4-yl)sulfonyl]-4-phenylpyrrolidin-3-yl}benzamide;

trans-1-[(1-methyl-1H-imidazol-4-yl)sulfonyl]-N,4-diphenylpyrrolidin-3-amine;

3,5-dichloro-N-{trans-1-[(1-methyl-1H-imidazol-4-yl)sulfonyl]-4-phenylpyrrolidin-3-yl}benzamide;

2,3-dichloro-N-{trans-1-[(1-methyl-1H-imidazol-4-yl)sulfonyl]-4-phenylpyrrolidin-3-yl}benzamide;

2-cyano-N-{trans-1-[(1-methyl-1H-imidazol-4-yl)sulfonyl]-4-phenylpyrrolidin-3-yl}benzamide;

3-cyano-N-{trans-1-[(1-methyl-1H-imidazol-4-yl)sulfonyl]-4-phenylpyrrolidin-3-yl}benzamide;

4-cyano-N-{trans-1-[(1-methyl-1H-imidazol-4-yl)sulfonyl]-4-phenylpyrrolidin-3-yl}benzamide;

N-{trans-1-[(1-methyl-1H-imidazol-4-yl)sulfonyl]-4-phenylpyrrolidin-3-yl}-2-(trifluoromethyl)benzamide;

N-{trans-1-[(1-methyl-1H-imidazol-4-yl)sulfonyl]-4-phenylpyrrolidin-3-yl}-3-(trifluoromethyl)benzamide;

N-{trans-1-[(1-methyl-1H-imidazol-4-yl)sulfonyl]-4-phenylpyrrolidin-3-yl}-4-(trifluoromethyl)benzamide;

2-chloro-N-[trans-1-{[1-methyl-3-(trifluoromethyl)-1H-pyrazol-4-yl]sulfonyl}-4-phenylpyrrolidin-3-yl]-3-(trifluoromethyl)benzamide;

2-chloro-N-[trans-1-{[1-(difluoromethyl)-3,5-dimethyl-1H-pyrazol-4-yl]sulfonyl}-4-phenylpyrrolidin-3-yl]-3-(trifluoromethyl)benzamide;

2-chloro-N-{trans-1-[(5-chloro-1,3-dimethyl-1H-pyrazol-4-yl)sulfonyl]-4-phenylpyrrolidin-3-yl}-3-(trifluoromethyl)benzamide;

2-chloro-N-{trans-1-[(1,5-dimethyl-1H-pyrazol-4-yl)sulfonyl]-4-phenylpyrrolidin-3-yl}-3-(trifluoromethyl)benzamide;

2-chloro-N-{trans-1-[(1,3-dimethyl-1H-pyrazol-4-yl)sulfonyl]-4-phenylpyrrolidin-3-yl}-3-(trifluoromethyl)benzamide;

2-chloro-N-{trans-1-[(1-methyl-1H-pyrazol-4-yl)sulfonyl]-4-phenylpyrrolidin-3-yl}-3-(trifluoromethyl)benzamide;

2-chloro-N-[trans-4-phenyl-1-(1H-pyrazol-4-ylsulfonyl)pyrrolidin-3-yl]-3-(trifluoromethyl)benzamide;

2-chloro-N-{trans-1-[(1-methyl-1H-pyrazol-5-yl)sulfonyl]-4-phenylpyrrolidin-3-yl}-3-(trifluoromethyl)benzamide;

2-chloro-N-{trans-1-[(5-chloro-1-methyl-1H-imidazol-4-yl)sulfonyl]-4-phenylpyrrolidin-3-yl}-3-(trifluoromethyl)benzamide;

2-chloro-N-{trans-1-[(1-methyl-1H-pyrazol-3-yl)sulfonyl]-4-phenylpyrrolidin-3-yl}-3-(trifluoromethyl)benzamide;

trans-N-(4-methoxyphenyl)-1-[(1-methyl-1H-imidazol-4-yl)sulfonyl]-4-phenylpyrrolidin-3-amine;

3-({trans-1-[(1-methyl-1H-imidazol-4-yl)sulfonyl]-4-phenylpyrrolidin-3-yl}amino)benzonitrile;

4-({trans-1-[(1-methyl-1H-imidazol-4-yl)sulfonyl]-4-phenylpyrrolidin-3-yl}amino)benzonitrile;

3-fluoro-4-({trans-1-[(1-methyl-1H-imidazol-4-yl)sulfonyl]-4-phenylpyrrolidin-3-yl}amino)benzonitrile;

2-chloro-N-{trans-4-(2-fluorophenyl)-1-[(1-methyl-1H-imidazol-4-yl)sulfonyl]pyrrolidin-3-yl}-3-(trifluoromethyl)benzamide;

2-chloro-N-{trans-4-(3-fluorophenyl)-1-[(1-methyl-1H-imidazol-4-yl)sulfonyl]pyrrolidin-3-yl}-3-(trifluoromethyl)benzamide;

2-chloro-N-{trans-4-(3-chlorophenyl)-1-[(1-methyl-1H-imidazol-4-yl)sulfonyl]pyrrolidin-3-yl}-3-(trifluoromethyl)benzamide;

trans-1-[(1-methyl-1H-imidazol-4-yl)sulfonyl]-N-(2-methylphenyl)-4-phenylpyrrolidin-3-amine;

trans-1-[(1-methyl-1H-imidazol-4-yl)sulfonyl]-N-(3-methylphenyl)-4-phenylpyrrolidin-3-amine;

trans-1-[(1-methyl-1H-imidazol-4-yl)sulfonyl]-N-(4-methylphenyl)-4-phenylpyrrolidin-3-amine;
2-chloro-N-{trans-1-[(1-methyl-1H-imidazol-4-yl)sulfonyl]-4-phenylpyrrolidin-3-yl}-4-(trifluoromethyl)benzamide;
3-chloro-N-{trans-1-[(1-methyl-1H-imidazol-4-yl)sulfonyl]-4-phenylpyrrolidin-3-yl}-4-(trifluoromethyl)benzamide;
2-chloro-N-{trans-4-(4-fluorophenyl)-1-[(1-methyl-1H-imidazol-4-yl)sulfonyl]pyrrolidin-3-yl}-4-(trifluoromethyl)benzamide;
3-chloro-N-{trans-4-(4-fluorophenyl)-1-[(1-methyl-1H-imidazol-4-yl)sulfonyl]pyrrolidin-3-yl}-4-(trifluoromethyl)benzamide;
N-{trans-4-(4-fluorophenyl)-1-[(1-methyl-1H-imidazol-4-yl)sulfonyl]pyrrolidin-3-yl}-4-(trifluoromethyl)benzamide;
3,5-dichloro-N-{trans-4-(4-fluorophenyl)-1-[(1-methyl-1H-imidazol-4-yl)sulfonyl]pyrrolidin-3-yl}benzamide;
trans-1-[(1-methyl-1H-imidazol-4-yl)sulfonyl]-4-phenyl-N-[2-(trifluoromethyl)phenyl]pyrrolidin-3-amine;
trans-1-[(1-methyl-1H-imidazol-4-yl)sulfonyl]-4-phenyl-N-[3-(trifluoromethyl)phenyl]pyrrolidin-3-amine;
trans-1-[(1-methyl-1H-imidazol-4-yl)sulfonyl]-4-phenyl-N-[4-(trifluoromethyl)phenyl]pyrrolidin-3-amine;
trans-N-(2-fluorophenyl)-1-[(1-methyl-1H-imidazol-4-yl)sulfonyl]-4-phenylpyrrolidin-3-amine;
trans-N-(3-fluorophenyl)-1-[(1-methyl-1H-imidazol-4-yl)sulfonyl]-4-phenylpyrrolidin-3-amine;
trans-N-(4-fluorophenyl)-1-[(1-methyl-1H-imidazol-4-yl)sulfonyl]-4-phenylpyrrolidin-3-amine;
3-({trans-4-(4-fluorophenyl)-1-[(1-methyl-1H-imidazol-4-yl)sulfonyl]pyrrolidin-3-yl}amino)benzonitrile;
trans-N-(2-chlorophenyl)-1-[(1-methyl-1H-imidazol-4-yl)sulfonyl]-4-phenylpyrrolidin-3-amine;
trans-N-(3-chlorophenyl)-1-[(1-methyl-1H-imidazol-4-yl)sulfonyl]-4-phenylpyrrolidin-3-amine;
trans-N-(4-chlorophenyl)-1-[(1-methyl-1H-imidazol-4-yl)sulfonyl]-4-phenylpyrrolidin-3-amine;
4-fluoro-3-({trans-1-[(1-methyl-1H-imidazol-4-yl)sulfonyl]-4-phenylpyrrolidin-3-yl}amino)benzonitrile;
2-fluoro-3-({trans-1-[(1-methyl-1H-imidazol-4-yl)sulfonyl]-4-phenylpyrrolidin-3-yl}amino)benzonitrile;
3-fluoro-5-({trans-1-[(1-methyl-1H-imidazol-4-yl)sulfonyl]-4-phenylpyrrolidin-3-yl}amino)benzonitrile;
2-chloro-5-({trans-1-[(1-methyl-1H-imidazol-4-yl)sulfonyl]-4-phenylpyrrolidin-3-yl}amino)benzonitrile;
3-chloro-5-({trans-1-[(1-methyl-1H-imidazol-4-yl)sulfonyl]-4-phenylpyrrolidin-3-yl}amino)benzonitrile;
4-chloro-3-({trans-1-[(1-methyl-1H-imidazol-4-yl)sulfonyl]-4-phenylpyrrolidin-3-yl}amino)benzonitrile;
4-methyl-3-({trans-1-[(1-methyl-1H-imidazol-4-yl)sulfonyl]-4-phenylpyrrolidin-3-yl}amino)benzonitrile;
2-methyl-3-({trans-1-[(1-methyl-1H-imidazol-4-yl)sulfonyl]-4-phenylpyrrolidin-3-yl}amino)benzonitrile;
trans-4-(4-fluorophenyl)-1-[(1-methyl-1H-imidazol-4-yl)sulfonyl]-N-(2-methylphenyl)pyrrolidin-3-amine;
trans-4-(4-fluorophenyl)-1-[(1-methyl-1H-imidazol-4-yl)sulfonyl]-N-(3-methylphenyl)pyrrolidin-3-amine;
trans-4-(4-fluorophenyl)-1-[(1-methyl-1H-imidazol-4-yl)sulfonyl]-N-(4-methylphenyl)pyrrolidin-3-amine;
trans-4-(4-fluorophenyl)-1-[(1-methyl-1H-imidazol-4-yl)sulfonyl]-N-[2-(trifluoromethyl)phenyl]pyrrolidin-3-amine;
trans-4-(4-fluorophenyl)-1-[(1-methyl-1H-imidazol-4-yl)sulfonyl]-N-[3-(trifluoromethyl)phenyl]pyrrolidin-3-amine;
trans-4-(4-fluorophenyl)-1-[(1-methyl-1H-imidazol-4-yl)sulfonyl]-N-[4-(trifluoromethyl)phenyl]pyrrolidin-3-amine;
trans-N-(2-fluorophenyl)-4-(4-fluorophenyl)-1-[(1-methyl-1H-imidazol-4-yl)sulfonyl]pyrrolidin-3-amine;
trans-N-(3-fluorophenyl)-4-(4-fluorophenyl)-1-[(1-methyl-1H-imidazol-4-yl)sulfonyl]pyrrolidin-3-amine;
trans-N,4-bis(4-fluorophenyl)-1-[(1-methyl-1H-imidazol-4-yl)sulfonyl]pyrrolidin-3-amine;
trans-N-(2-chlorophenyl)-4-(4-fluorophenyl)-1-[(1-methyl-1H-imidazol-4-yl)sulfonyl]pyrrolidin-3-amine;
trans-N-(3-chlorophenyl)-4-(4-fluorophenyl)-1-[(1-methyl-1H-imidazol-4-yl)sulfonyl]pyrrolidin-3-amine;
trans-N-(4-chlorophenyl)-4-(4-fluorophenyl)-1-[(1-methyl-1H-imidazol-4-yl)sulfonyl]pyrrolidin-3-amine;
2-methoxy-5-({trans-1-[(1-methyl-1H-imidazol-4-yl)sulfonyl]-4-phenylpyrrolidin-3-yl}amino)benzonitrile;
3-methyl-5-({trans-1-[(1-methyl-1H-imidazol-4-yl)sulfonyl]-4-phenylpyrrolidin-3-yl}amino)benzonitrile;
5-({trans-1-[(1-methyl-1H-imidazol-4-yl)sulfonyl]-4-phenylpyrrolidin-3-yl}amino)-2-(trifluoromethoxy)benzonitrile;
2-chloro-N-{trans-4-(2-chlorophenyl)-1-[(1-methyl-1H-imidazol-4-yl)sulfonyl]pyrrolidin-3-yl}-3-(trifluoromethyl)benzamide;
4-{[trans-3-benzyl-4-phenylpyrrolidin-1-yl]sulfonyl}-1-methyl-1H-imidazole; p1 trans-N-benzyl-4-(4-fluorophenyl)-1-[(1-methyl-1H-imidazol-4-yl)sulfonyl]pyrrolidin-3-amine; trans-N-[2-chloro-3-(trifluoromethyl)benzyl]-4-(4-fluorophenyl)-1-[(1-methyl-1H-imidazol-4-yl)sulfonyl]pyrrolidin-3-amine;
trans-N-[2-chloro-4-(trifluoromethyl)benzyl]-4-(4-fluorophenyl)-1-[(1-methyl-1H-imidazol-4-yl)sulfonyl]pyrrolidin-3-amine;
trans-N-[2-chloro-4-(trifluoromethyl)benzyl]-4-(4-fluorophenyl)-1-[(1-methyl-1H-imidazol-4-yl)sulfonyl]pyrrolidin-3-amine;
3-[({trans-4-(4-fluorophenyl)-1-[(1-methyl-1H-imidazol-4-yl)sulfonyl]pyrrolidin-3-yl}amino)methyl]benzonitrile;
trans-4-(4-fluorophenyl)-N-(2-methylbenzyl)-1-[(1-methyl-1H-imidazol-4-yl)sulfonyl]pyrrolidin-3-amine;
trans-4-(4-fluorophenyl)-N-(3-methylbenzyl)-1-[(1-methyl-1H-imidazol-4-yl)sulfonyl]pyrrolidin-3-amine;
trans-4-(4-fluorophenyl)-N-(4-methylbenzyl)-1-[(1-methyl-1H-imidazol-4-yl)sulfonyl]pyrrolidin-3-amine;
trans-N-(4-fluorobenzyl)-4-(4-fluorophenyl)-1-[(1-methyl-1H-imidazol-4-yl)sulfonyl]pyrrolidin-3-amine;
(cis)-N-benzyl-1-[(1-methyl-1H-imidazol-4-yl)sulfonyl]-4-phenylpyrrolidin-3-amine;
trans-N-(3,4-difluorophenyl)-4-(4-fluorophenyl)-1-[(1-methyl-1H-imidazol-4-yl)sulfonyl]pyrrolidin-3-amine;
trans-4-(4-fluorophenyl)-N-[4-fluoro-3-(trifluoromethyl)phenyl]-1-[(1-methyl-1H-imidazol-4-yl)sulfonyl]pyrrolidin-3-amine;
trans-N-(3-chloro-4-fluorophenyl)-4-(4-fluorophenyl)-1-[(1-methyl-1H-imidazol-4-yl)sulfonyl]pyrrolidin-3-amine;
trans-N-(3,4-dichlorophenyl)-4-(4-fluorophenyl)-1-[(1-methyl-1H-imidazol-4-yl)sulfonyl]pyrrolidin-3-amine;
trans-N-(4-chloro-3-fluorophenyl)-4-(4-fluorophenyl)-1-[(1-methyl-1H-imidazol-4-yl)sulfonyl]pyrrolidin-3-amine;
trans-N-(2,3-difluorophenyl)-4-(4-fluorophenyl)-1-[(1-methyl-1H-imidazol-4-yl)sulfonyl]pyrrolidin-3-amine;
trans-N-(2,5-difluorophenyl)-4-(4-fluorophenyl)-1-[(1-methyl-1H-imidazol-4-yl)sulfonyl]pyrrolidin-3-amine;

trans-N-(2,4-difluorophenyl)-4-(4-fluorophenyl)-1-[(1-methyl-1H-imidazol-4-yl)sulfonyl]pyrrolidin-3-amine;
trans-4-(4-fluorophenyl)-1-[(1-methyl-1H-imidazol-4-yl)sulfonyl]-N-(2,3,4-trifluorophenyl)pyrrolidin-3-amine;
trans-4-(4-fluorophenyl)-N-[2-fluoro-3-(trifluoromethyl)phenyl]-1-[(1-methyl-1H-imidazol-4-yl)sulfonyl]pyrrolidin-3-amine;
trans-4-(4-fluorophenyl)-N-[3-fluoro-5-(trifluoromethyl)phenyl]-1-[(1-methyl-1H-imidazol-4-yl)sulfonyl]pyrrolidin-3-amine;
trans-4-(4-fluorophenyl)-N-[2-fluoro-5-(trifluoromethyl)phenyl]-1-[(1-methyl-1H-imidazol-4-yl)sulfonyl]pyrrolidin-3-amine;
trans-4-(4-fluorophenyl)-1-[(1-methyl-1H-imidazol-4-yl)sulfonyl]-N-[3-(propan-2-yl)phenyl]pyrrolidin-3-amine;
trans-N-(3-tert-butylphenyl)-4-(4-fluorophenyl)-1-[(1-methyl-1H-imidazol-4-yl)sulfonyl]pyrrolidin-3-amine;
trans-N-[4-chloro-3-(trifluoromethyl)phenyl]-4-(4-fluorophenyl)-1-[(1-methyl-1H-imidazol-4-yl)sulfonyl]pyrrolidin-3-amine;
trans-N-[3-chloro-4-(trifluoromethyl)phenyl]-4-(4-fluorophenyl)-1-[(1-methyl-1H-imidazol-4-yl)sulfonyl]pyrrolidin-3-amine;
trans-N-(3-chloro-5-fluorophenyl)-4-(4-fluorophenyl)-1-[(1-methyl-1H-imidazol-4-yl)sulfonyl]pyrrolidin-3-amine;
trans-N-(3-chloro-4,5-difluorophenyl)-4-(4-fluorophenyl)-1-[(1-methyl-1H-imidazol-4-yl)sulfonyl]pyrrolidin-3-amine;
trans-4-(4-fluorophenyl)-1-[(1-methyl-1H-imidazol-4-yl)sulfonyl]-N-[3-(trifluoromethoxy)phenyl]pyrrolidin-3-amine;
N-{trans-4-(4-fluorophenyl)-1-[(1-methyl-1H-imidazol-4-yl)sulfonyl]pyrrolidin-3-yl}pyridin-4-amine;
N-{trans-4-(4-fluorophenyl)-1-[(1-methyl-1H-imidazol-4-yl)sulfonyl]pyrrolidin-3-yl}pyridin-2-amine;
N-{trans-4-(4-fluorophenyl)-1-[(1-methyl-1H-imidazol-4-yl)sulfonyl]pyrrolidin-3-yl}pyridin-3-amine;
N-{trans-4-(4-fluorophenyl)-1-[(1-methyl-1H-imidazol-4-yl)sulfonyl]pyrrolidin-3-yl}-6-(trifluoromethyl)pyridin-2-amine;
N-{trans-4-(4-fluorophenyl)-1-[(1-methyl-1H-imidazol-4-yl)sulfonyl]pyrrolidin-3-yl}-5-(trifluoromethyl)pyridin-3-amine;
4-{[3-(3-chlorobenzyl)-4-(4-fluorophenyl)pyrrolidin-1-yl]sulfonyl}-1-methyl-1H-imidazole;
2-chloro-N-{(cis)-1-[(1-methyl-1H-imidazol-4-yl)sulfonyl]-4-phenylpyrrolidin-3-yl}-3-(trifluoromethyl)benzamide;
2-chloro-N-{(cis)-1-[(1-methyl-1H-imidazol-4-yl)sulfonyl]-4-phenylpyrrolidin-3-yl}-3-(trifluoromethyl)benzamide;
trans-4-(3-fluorophenyl)-1-[(1-methyl-1H-imidazol-4-yl)sulfonyl]-N-phenylpyrrolidin-3-amine;
trans-N,4-bis(3-fluorophenyl)-1-[(1-methyl-1H-imidazol-4-yl)sulfonyl]pyrrolidin-3-amine;
trans-4-(3-fluorophenyl)-N-(4-fluorophenyl)-1-[(1-methyl-1H-imidazol-4-yl)sulfonyl]pyrrolidin-3-amine;
trans-N-(3-chlorophenyl)-4-(3-fluorophenyl)-1-[(1-methyl-1H-imidazol-4-yl)sulfonyl]pyrrolidin-3-amine;
trans-4-(3-fluorophenyl)-1-[(1-methyl-1H-imidazol-4-yl)sulfonyl]-N-[3-(trifluoromethyl)phenyl]pyrrolidin-3-amine;
trans-4-(3-fluorophenyl)-1-[(1-methyl-1H-imidazol-4-yl)sulfonyl]-N-[4-(trifluoromethyl)phenyl]pyrrolidin-3-amine;
N-{trans-4-(3-fluorophenyl)-1-[(1-methyl-1H-imidazol-4-yl)sulfonyl]pyrrolidin-3-yl}pyridin-4-amine;
trans-N-(3,4-dichlorophenyl)-4-(3-fluorophenyl)-1-[(1-methyl-1H-imidazol-4-yl)sulfonyl]pyrrolidin-3-amine;
trans-N-(4-chloro-3-fluorophenyl)-4-(3-fluorophenyl)-1-[(1-methyl-1H-imidazol-4-yl)sulfonyl]pyrrolidin-3-amine;
trans-N-(3-chloro-4-fluorophenyl)-4-(3-fluorophenyl)-1-[(1-methyl-1H-imidazol-4-yl)sulfonyl]pyrrolidin-3-amine;
N-{trans-4-(3-fluorophenyl)-1-[(1-methyl-1H-imidazol-4-yl)sulfonyl]pyrrolidin-3-yl}-6-(trifluoromethyl)pyridin-2-amine;
N-{trans-4-(3-fluorophenyl)-1-[(1-methyl-1H-imidazol-4-yl)sulfonyl]pyrrolidin-3-yl}-5-(trifluoromethyl)pyridin-3-amine;
trans-N-(3,4-difluorophenyl)-4-(3-fluorophenyl)-1-[(1-methyl-1H-imidazol-4-yl)sulfonyl]pyrrolidin-3-amine;
trans-4-(2-fluorophenyl)-1-[(1-methyl-1H-imidazol-4-yl)sulfonyl]-N-phenylpyrrolidin-3-amine;
trans-4-(2-fluorophenyl)-N-(3-fluorophenyl)-1-[(1-methyl-1H-imidazol-4-yl)sulfonyl]pyrrolidin-3-amine;
trans-4-(2-fluorophenyl)-N-(4-fluorophenyl)-1-[(1-methyl-1H-imidazol-4-yl)sulfonyl]pyrrolidin-3-amine;
trans-N-(3-chlorophenyl)-4-(2-fluorophenyl)-1-[(1-methyl-1H-imidazol-4-yl)sulfonyl]pyrrolidin-3-amine;
trans-N-(4-chlorophenyl)-4-(2-fluorophenyl)-1-[(1-methyl-1H-imidazol-4-yl)sulfonyl]pyrrolidin-3-amine;
N-{trans-4-(2-fluorophenyl)-1-[(1-methyl-1H-imidazol-4-yl)sulfonyl]pyrrolidin-3-yl}-6-(trifluoromethyl)pyridin-2-amine;
N-{trans-4-(2-fluorophenyl)-1-[(1-methyl-1H-imidazol-4-yl)sulfonyl]pyrrolidin-3-yl}-2-(trifluoromethyl)pyridin-4-amine;
4-{[3-(2-bromobenzyl)-4-(2-bromophenyl)pyrrolidin-1-yl]sulfonyl}-1-methyl-1H-imidazole;
{Trans-4-(4-fluorophenyl)-1-[(1-methyl-1H-imidazol-4-yl)sulfonyl]pyrrolidin-3-yl}methanol;
N-{trans-1-[(1-methyl-1H-imidazol-4-yl)sulfonyl]-4-phenylpyrrolidin-3-yl}pyridin-2-amine;
N-{trans-1-[(1-methyl-1H-imidazol-4-yl)sulfonyl]-4-phenylpyrrolidin-3-yl}pyridin-3-amine;
N-{trans-1-[(1-methyl-1H-imidazol-4-yl)sulfonyl]-4-phenylpyrrolidin-3-yl}pyridin-4-amine;
N-{trans-1-[(1-methyl-1H-imidazol-4-yl)sulfonyl]-4-phenylpyrrolidin-3-yl}-6-(trifluoromethyl)pyridin-2-amine;
N-{trans-1-[(1-methyl-1H-imidazol-4-yl)sulfonyl]-4-phenylpyrrolidin-3-yl}-2-(trifluoromethyl)pyridin-4-amine;
N-{trans-1-[(1-methyl-1H-imidazol-4-yl)sulfonyl]-4-phenylpyrrolidin-3-yl}-4-(trifluoromethyl)pyridin-2-amine;
N-{trans-1-[(1-methyl-1H-imidazol-4-yl)sulfonyl]-4-phenylpyrrolidin-3-yl}-5-(trifluoromethyl)pyridin-3-amine;
trans-N-[4-fluoro-3-(trifluoromethyl)phenyl]-1-[(1-methyl-1H-imidazol-4-yl)sulfonyl]-4-phenylpyrrolidin-3-amine;
trans-N-(3-chloro-4-fluorophenyl)-1-[(1-methyl-1H-imidazol-4-yl)sulfonyl]-4-phenylpyrrolidin-3-amine;
trans-N-(3,4-difluorophenyl)-1-[(1-methyl-1H-imidazol-4-yl)sulfonyl]-4-phenylpyrrolidin-3-amine;
trans-N-[4-chloro-3-(trifluoromethyl)phenyl]-1-[(1-methyl-1H-imidazol-4-yl)sulfonyl]-4-phenylpyrrolidin-3-amine;

trans-N-(3,4-dichlorophenyl)-1-[(1-methyl-1H-imidazol-4-yl)sulfonyl]-4-phenylpyrrolidin-3-amine;
trans-N-(3-chloro-4,5-difluorophenyl)-1-[(1-methyl-1H-imidazol-4-yl)sulfonyl]-4-phenylpyrrolidin-3-amine;
trans-1-[(1-methyl-1H-imidazol-4-yl)sulfonyl]-4-phenyl-N-[3-(propan-2-yl)phenyl]pyrrolidin-3-amine;
trans-N-(3-tert-butylphenyl)-1-[(1-methyl-1H-imidazol-4-yl)sulfonyl]-4-phenylpyrrolidin-3-amine;
trans-N-[2-fluoro-3-(trifluoromethyl)phenyl]-1-[(1-methyl-1H-imidazol-4-yl)sulfonyl]-4-phenylpyrrolidin-3-amine;
trans-N-[3-fluoro-5-(trifluoromethyl)phenyl]-1-[(1-methyl-1H-imidazol-4-yl)sulfonyl]-4-phenylpyrrolidin-3-amine;
trans-N-[2-fluoro-5-(trifluoromethyl)phenyl]-1-[(1-methyl-1H-imidazol-4-yl)sulfonyl]-4-phenylpyrrolidin-3-amine;
trans-N-(3-chloro-5-fluorophenyl)-1-[(1-methyl-1H-imidazol-4-yl)sulfonyl]-4-phenylpyrrolidin-3-amine;
trans-1-[(1-methyl-1H-imidazol-4-yl)sulfonyl]-4-phenyl-N-[3-(trifluoromethoxy)phenyl]pyrrolidin-3-amine;
N-{trans-1-[(1-methyl-1H-imidazol-4-yl)sulfonyl]-4-phenylpyrrolidin-3-yl}-4-(trifluoromethyl)pyrimidin-2-amine;
N-{trans-1-[(1-methyl-1H-imidazol-4-yl)sulfonyl]-4-phenylpyrrolidin-3-yl}quinolin-7-amine;
N-{trans-1-[(1-methyl-1H-imidazol-4-yl)sulfonyl]-4-phenylpyrrolidin-3-yl}quinolin-6-amine;
N-{trans-1-[(1-methyl-1H-imidazol-4-yl)sulfonyl]-4-phenylpyrrolidin-3-yl}isoquinolin-6-amine;
trans-N-(2,3-difluorophenyl)-1-[(1-methyl-1H-imidazol-4-yl)sulfonyl]-4-phenylpyrrolidin-3-amine;
trans-N-(2,5-difluorophenyl)-1-[(1-methyl-1H-imidazol-4-yl)sulfonyl]-4-phenylpyrrolidin-3-amine;
trans-N-(2,4-difluorophenyl)-1-[(1-methyl-1H-imidazol-4-yl)sulfonyl]-4-phenylpyrrolidin-3-amine;
trans-1-[(1-methyl-1H-imidazol-4-yl)sulfonyl]-4-phenyl-N-(2,3,4-trifluorophenyl)pyrrolidin-3-amine;
6-fluoro-N-{trans-1-[(1-methyl-1H-imidazol-4-yl)sulfonyl]-4-phenylpyrrolidin-3-yl}pyridin-2-amine;
2-fluoro-N-{trans-1-[(1-methyl-1H-imidazol-4-yl)sulfonyl]-4-phenylpyrrolidin-3-yl}pyridin-4-amine;
5-fluoro-N-{trans-1-[(1-methyl-1H-imidazol-4-yl)sulfonyl]-4-phenylpyrrolidin-3-yl}pyridin-3-amine;
6-fluoro-N-{trans-4-(4-fluorophenyl)-1-[(1-methyl-1-imidazol-4-yl)sulfonyl]pyrrolidin-3-yl}pyridin-2-amine;
2-fluoro-N-{trans-4-(4-fluorophenyl)-1-[(1-methyl-1-imidazol-4-yl)sulfonyl]pyrrolidin-3-yl}pyridin-4-amine;
N-{trans-1-[(1-methyl-1H-imidazol-4-yl)sulfonyl]-4-phenylpyrrolidin-3-yl}-6-(trifluoromethyl)pyrimidin-4-amine;
N-{trans-1-[(1-methyl-1H-imidazol-4-yl)sulfonyl]-4-phenylpyrrolidin-3-yl}isoquinolin-7-amine;
trans-4-(4-fluorophenyl)-1-[(1-methyl-1H-imidazol-4-yl)sulfonyl]-N-phenylpyrrolidine-3-carboxamide;
Trans-4-(4-fluorophenyl)-1-[(1-methyl-1H-imidazol-4-yl)sulfonyl]-N-[4-(trifluoromethyl)phenyl]pyrrolidine-3-carboxamide;
Trans-N-(3,5-dichlorophenyl)-4-(4-fluorophenyl)-1-[(1-methyl-1H-imidazol-4-yl)sulfonyl]pyrrolidine-3-carboxamide;
4-{[trans-3-(4-fluorophenyl)-4-(phenoxymethyl)pyrrolidin-1-yl]sulfonyl}-1-methyl-1H-imidazole;
4-{[trans-3-[(2,4-dichlorophenoxy)methyl]-4-(4-fluorophenyl)pyrrolidin-1-yl]sulfonyl}-1-methyl-1H-imidazole;
4-{[trans-3-(4-fluorophenyl)-4-{[3-(trifluoromethoxy)phenoxy]methyl}pyrrolidin-1-yl]sulfonyl}-1-methyl-1H-imidazole;
4-{[trans-3-[(3-chlorophenoxy)methyl]-4-(4-fluorophenyl)pyrrolidin-1-yl]sulfonyl}-1-methyl-1H-imidazole;
4-{[trans-3-{[4-chloro-3-(trifluoromethyl)phenoxy]methyl}-4-(4-fluorophenyl)pyrrolidin-1-yl]sulfonyl}-1-methyl-1H-imidazole;
4-{[trans-3-{[2-chloro-3-(trifluoromethyl)phenoxy]methyl}-4-(4-fluorophenyl)pyrrolidin-1-yl]sulfonyl}-1-methyl-1H-imidazole;
4-{[trans-3-[(3-fluorophenoxy)methyl]-4-(4-fluorophenyl)pyrrolidin-1-yl]sulfonyl}-1-methyl-1H-imidazole;
trans-4-(2-chlorophenyl)-N-(3-fluorophenyl)-1-[(1-methyl-1H-imidazol-4-yl)sulfonyl]pyrrolidin-3-amine;
trans-4-(2-chlorophenyl)-N-(4-fluorophenyl)-1-[(1-methyl-1H-imidazol-4-yl)sulfonyl]pyrrolidin-3-amine;
trans-4-(2-chlorophenyl)-N-(4-chlorophenyl)-1-[(1-methyl-1H-imidazol-4-yl)sulfonyl]pyrrolidin-3-amine;
trans-4-(2-chlorophenyl)-1-[(1-methyl-1H-imidazol-4-yl)sulfonyl]-N-[3-(trifluoromethyl)phenyl]pyrrolidin-3-amine;
trans-4-(2-chlorophenyl)-1-[(1-methyl-1H-imidazol-4-yl)sulfonyl]-N-[4-(trifluoromethyl)phenyl]pyrrolidin-3-amine;
trans-N-(3-chloro-4-fluorophenyl)-4-(2-chlorophenyl)-1-[(1-methyl-1H-imidazol-4-yl)sulfonyl]pyrrolidin-3-amine;
trans-4-(2-chlorophenyl)-N-[4-fluoro-3-(trifluoromethyl)phenyl]-1-[(1-methyl-1H-imidazol-4-yl)sulfonyl]pyrrolidin-3-amine;
N-{trans-4-(2-chlorophenyl)-1-[(1-methyl-1H-imidazol-4-yl)sulfonyl]pyrrolidin-3-yl}-2-(trifluoromethyl)pyridin-4-amine;
trans-N-(2-chlorobenzyl)-4-(4-fluorophenyl)-1-[(1-methyl-1H-imidazol-4-yl)sulfonyl]pyrrolidin-3-amine;
trans-N-(3-chlorobenzyl)-4-(4-fluorophenyl)-1-[(1-methyl-1H-imidazol-4-yl)sulfonyl]pyrrolidin-3-amine;
trans-N-(4-chlorobenzyl)-4-(4-fluorophenyl)-1-[(1-methyl-1H-imidazol-4-yl)sulfonyl]pyrrolidin-3-amine;
trans-N-(2-fluorobenzyl)-4-(4-fluorophenyl)-1-[(1-methyl-1H-imidazol-4-yl)sulfonyl]pyrrolidin-3-amine;
trans-N-(3-fluorobenzyl)-4-(4-fluorophenyl)-1-[(1-methyl-1H-imidazol-4-yl)sulfonyl]pyrrolidin-3-amine;
trans-4-(4-fluorophenyl)-1-[(1-methyl-1H-imidazol-4-yl)sulfonyl]-N-[2-(trifluoromethyl)benzyl]pyrrolidin-3-amine;
trans-4-(4-fluorophenyl)-1-[(1-methyl-1H-imidazol-4-yl)sulfonyl]-N-[3-(trifluoromethyl)benzyl]pyrrolidin-3-amine;
trans-4-(4-fluorophenyl)-1-[(1-methyl-1H-imidazol-4-yl)sulfonyl]-N-[4-(trifluoromethyl)benzyl]pyrrolidin-3-amine;
trans-4-(4-fluorophenyl)-1-[(1-methyl-1H-imidazol-4-yl)sulfonyl]-N-(pyridin-2-ylmethyl)pyrrolidin-3-amine;
trans-4-(4-fluorophenyl)-1-[(1-methyl-1H-imidazol-4-yl)sulfonyl]-N-(pyridin-3-ylmethyl)pyrrolidin-3-amine;
trans-4-(4-fluorophenyl)-1-[(1-methyl-1H-imidazol-4-yl)sulfonyl]-N-(pyridin-4-ylmethyl)pyrrolidin-3-amine;
{trans-4-(4-fluorophenyl)-1-[(1-methyl-1H-imidazol-4-yl)sulfonyl]pyrrolidin-3-yl}(phenyl)methanone;
Trans-N-[2-chloro-3-(trifluoromethyl)phenyl]-4-(4-fluorophenyl)-1-[(1-methyl-1H-imidazol-4-yl)sulfonyl]pyrrolidine-3-carboxamide;

Trans-4-(4-fluorophenyl)-1-[(1-methyl-1H-imidazol-4-yl)sulfonyl]-N-[3-(trifluoromethoxy)phenyl]pyrrolidine-3-carboxamide;

trans-4-(4-fluorophenyl)-N-[4-fluoro-3-(trifluoromethyl)phenyl]-1-[(1-methyl-1H-imidazol-4-yl)sulfonyl]pyrrolidine-3-carboxamide;

trans-N-(3-chloro-4-fluorophenyl)-4-(4-fluorophenyl)-1-[(1-methyl-1H-imidazol-4-yl)sulfonyl]pyrrolidine-3-carboxamide;

trans-N-[3-chloro-4-(trifluoromethyl)phenyl]-4-(4-fluorophenyl)-1-[(1-methyl-1H-imidazol-4-yl)sulfonyl]pyrrolidine-3-carboxamide;

1-methyl-4-[(3-phenoxy-4-phenylpyrrolidin-1-yl)sulfonyl]-1H-imidazole;

trans-4-(2-chlorophenyl)-N-(3-chlorophenyl)-1-[(1-methyl-1H-imidazol-4-yl)sulfonyl]pyrrolidin-3-amine;

trans-N-(2,4-dichlorobenzyl)-4-(4-fluorophenyl)-1-[(1-methyl-1H-imidazol-4-yl)sulfonyl]pyrrolidin-3-amine;

trans-N-(2,4-dichlorobenzyl)-1-[(1-methyl-1H-imidazol-4-yl)sulfonyl]-4-phenylpyrrolidin-3-amine;

trans-N-[2-chloro-4-(trifluoromethyl)benzyl]-1-[(1-methyl-1H-imidazol-4-yl)sulfonyl]-4-phenylpyrrolidin-3-amine;

trans-N-(2,4-dichlorobenzyl)-4-(2-fluorophenyl)-1-[(1-methyl-1H-imidazol-4-yl)sulfonyl]pyrrolidin-3-amine;

trans-N-[2-chloro-4-(trifluoromethyl)benzyl]-4-(2-fluorophenyl)-1-[(1-methyl-1H-imidazol-4-yl)sulfonyl]pyrrolidin-3-amine;

trans-4-(2-chlorophenyl)-N-(2,4-dichlorobenzyl)-1-[(1-methyl-1H-imidazol-4-yl)sulfonyl]pyrrolidin-3-amine;

trans-4-(2-chlorophenyl)-N-[2-chloro-4-(trifluoromethyl)benzyl]-1-[(1-methyl-1H-imidazol-4-yl)sulfonyl]pyrrolidin-3-amine;

trans-N-(2,4-dichlorobenzyl)-1-[(1-methyl-1H-imidazol-4-yl)sulfonyl]-4-(pyridin-3-yl)pyrrolidin-3-amine;

N-{trans-4-(4-fluorophenyl)-1-[(1-methyl-1-imidazol-4-yl)sulfonyl]pyrrolidin-3-yl}-4-(trifluoromethyl)pyridin-2-amine;

N-{trans-4-(4-fluorophenyl)-1-[(1-methyl-1-imidazol-4-yl)sulfonyl]pyrrolidin-3-yl}-2-(trifluoromethyl)pyridin-4-amine;

Trans-N-benzyl-4-(4-fluorophenyl)-1-[(1-methyl-1H-imidazol-4-yl)sulfonyl]pyrrolidine-3-carboxamide;

N-({trans-4-(4-fluorophenyl)-1-[(1-methyl-1H-imidazol-4-yl)sulfonyl]pyrrolidin-3-yl}methyl)aniline;

N-({trans-4-(4-fluorophenyl)-1-[(1-methyl-1H-imidazol-4-yl)sulfonyl]pyrrolidin-3-yl}methyl)-4-(trifluoromethyl)aniline;

3,5-dichloro-N-({trans-4-(4-fluorophenyl)-1-[(1-methyl-1H-imidazol-4-yl)sulfonyl]pyrrolidin-3-yl}methyl)aniline;

4-{[trans-3-(4-fluorophenyl)-4-{[3-(trifluoromethyl)phenoxy]methyl}pyrrolidin-1-yl]sulfonyl}-1-methyl-1H-imidazole;

4-{[trans-3-{[2-chloro-4-(trifluoromethyl)phenoxy]methyl}-4-(4-fluorophenyl)pyrrolidin-1-yl]sulfonyl}-1-methyl-1H-imidazole;

4-{[trans-3-(4-fluorophenyl)-4-{[4-fluoro-3-(trifluoromethyl)phenoxy]methyl}pyrrolidin-1-yl]sulfonyl}-1-methyl-1H-imidazole;

4-({trans-3-(4-fluorophenyl)-4-[(3-methylphenoxy)methyl]pyrrolidin-1-yl}sulfonyl)-1-methyl-1H-imidazole;

3-chlorophenyl){trans-4-(4-fluorophenyl)-1-[(1-methyl-1H-imidazol-4-yl)sulfonyl]pyrrolidin-3-yl}methanone;

trans-N-[4-fluoro-3-(trifluoromethoxy)phenyl]-1-[(1-methyl-1H-imidazol-4-yl)sulfonyl]-4-phenylpyrrolidin-3-amine;

trans-N-[4-chloro-3-(trifluoromethoxy)phenyl]-1-[(1-methyl-1H-imidazol-4-yl)sulfonyl]-4-phenylpyrrolidin-3-amine;

{trans-4-(4-fluorophenyl)-1-[(1-methyl-1H-imidazol-4-yl)sulfonyl]pyrrolidin-3-yl}(3-methylphenyl)methanone;

(3-fluorophenyl){trans-4-(4-fluorophenyl)-1-[(1-methyl-1H-imidazol-4-yl)sulfonyl]pyrrolidin-3-yl}methanone;

{trans-4-(4-fluorophenyl)-1-[(1-methyl-1H-imidazol-4-yl)sulfonyl]pyrrolidin-3-yl}[3-(trifluoromethyl)phenyl]methanone;

(4-fluorophenyl){trans-4-(4-fluorophenyl)-1-[(1-methyl-1H-imidazol-4-yl)sulfonyl]pyrrolidin-3-yl}methanone;

trans-N-(3-chlorophenyl)-4-(4-fluorophenyl)-1-[(1-methyl-1H-imidazol-4-yl)sulfonyl]pyrrolidine-3-carboxamide;

trans-4-(4-fluorophenyl)-N-[4-fluoro-3-(trifluoromethoxy)phenyl]-1-[(1-methyl-1H-imidazol-4-yl)sulfonyl]pyrrolidin-3-amine;

trans-N-[4-chloro-3-(trifluoromethoxy)phenyl]-4-(4-fluorophenyl)-1-[(1-methyl-1H-imidazol-4-yl)sulfonyl]pyrrolidin-3-amine;

trans-N-(2,4-dichlorobenzyl)-1-[(1-methyl-1H-imidazol-4-yl)sulfonyl]-4-(pyridin-2-yl)pyrrolidin-3-amine;

trans-1-[(1-methyl-1H-imidazol-4-yl)sulfonyl]-4-(pyridin-3-yl)-N-[3-(trifluoromethyl)phenyl]pyrrolidin-3-amine;

4-{[3-(3-chlorobenzyl)-4-cyclopropylpyrrolidin-1-yl]sulfonyl}-1-methyl-1H-imidazole;

N-[3-(difluoromethyl)-4-fluorophenyl]-4-(4-fluorophenyl)-1-[(1-methyl-1H-imidazol-4-yl)sulfonyl]pyrrolidin-3-amine;

3-chloro-N-({trans-4-(4-fluorophenyl)-1-[(1-methyl-1H-imidazol-4-yl)sulfonyl]pyrrolidin-3-yl}methyl)-4-(trifluoromethyl)aniline;

N-({trans-4-(4-fluorophenyl)-1-[(1-methyl-1H-imidazol-4-yl)sulfonyl]pyrrolidin-3-y}methyl)-3-(trifluoromethoxy)aniline;

4-fluoro-N-({trans-4-(4-fluorophenyl)-1-[(1-methyl-1H-imidazol-4-yl)sulfonyl]pyrrolidin-3-yl}methyl)-3-(trifluoromethyl)aniline;

3-chloro-4-fluoro-N-({trans-4-(4-fluorophenyl)-1-[(1-methyl-1H-imidazol-4-yl)sulfonyl]pyrrolidin-3-yl}methyl)aniline;

N-benzyl-1-{trans-4-(4-fluorophenyl)-1-[(1-methyl-1H-imidazol-4-yl)sulfonyl]pyrrolidin-3-yl}methanamine;

trans-4-(4-fluorophenyl)-1-[(1-methyl-1H-imidazol-4-yl)sulfonyl]-N-(3-methylphenyl)pyrrolidine-3-carboxamide;

Trans-4-(4-fluorophenyl)-1-[(1-methyl-1H-imidazol-4-yl)sulfonyl]-N-[3-(trifluoromethyl)phenyl]pyrrolidine-3-carboxamide;

4-{[Trans-3-[(3-chloro-4-fluorophenoxy)methyl]-4-(4-fluorophenyl)pyrrolidin-1-yl]sulfonyl}-1-methyl-1H-imidazole;

(4-Chloro-3-fluorophenyl){trans-4-(4-fluorophenyl)-1-[(1-methyl-1H-imidazol-4-yl)sulfonyl]pyrrolidin-3-yl}methanone;

trans-N-[2-chloro-4-(trifluoromethyl)benzyl]-1-[(1-methyl-1H-imidazol-4-yl)sulfonyl]-4-(pyridin-2-yl)pyrrolidin-3-amine;

(3S,4R)-N-[2-chloro-4-(trifluoromethyl)benzyl]-4-(4-fluorophenyl)-1-[(1-methyl-1H-imidazol-4-yl)sulfonyl]pyrrolidin-3-amine;

(3R,4S)-N-[2-chloro-4-(trifluoromethyl)benzyl]-4-(4-fluorophenyl)-1-[(1-methyl-1H-imidazol-4-yl)sulfonyl]pyrrolidin-3-amine;

(3S,4R)-4-(4-fluorophenyl)-1-[(1-methyl-1H-imidazol-4-yl)sulfonyl]-N-[3-(trifluoromethoxy)phenyl]pyrrolidin-3-amine;

(3S,4R)-N,4-bis(4-fluorophenyl)-1-[(1-methyl-1H-imidazol-4-yl)sulfonyl]pyrrolidin-3-amine;

(3S,4R)-N-(3-chlorophenyl)-4-(4-fluorophenyl)-1-[(1-methyl-1H-imidazol-4-yl)sulfonyl]pyrrolidin-3-amine;

(3S,4R)-4-(4-fluorophenyl)-1-[(1-methyl-1H-imidazol-4-yl)sulfonyl]-N-[3-(trifluoromethyl)phenyl]pyrrolidin-3-amine;

(3R,4S)-4-(4-fluorophenyl)-1-[(1-methyl-1H-imidazol-4-yl)sulfonyl]-N-[3-(trifluoromethyl)phenyl]pyrrolidin-3-amine;

(3R,4S)-N-(3-chlorophenyl)-4-(4-fluorophenyl)-1-[(1-methyl-1H-imidazol-4-yl)sulfonyl]pyrrolidin-3-amine;

(3R,4S)-4-(4-fluorophenyl)-1-[(1-methyl-1H-imidazol-4-yl)sulfonyl]-N-[3-(trifluoromethoxy)phenyl]pyrrolidin-3-amine;

(3R,4S)-N,4-bis(4-fluorophenyl)-1-[(1-methyl-1H-imidazol-4-yl)sulfonyl]pyrrolidin-3-amine;

3-(3-chlorobenzyl)-1-[(1-methyl-1H-imidazol-4-yl)sulfonyl]-4-phenylpyrrolidin-2-one;

2-Chloro-N-({trans-4-(4-fluorophenyl)-1-[(1-methyl-1-imidazol-4-yl)sulfonyl]pyrrolidin-3-yl}methyl)-4-(trifluoromethyl)aniline;

3-Chloro-N-({trans-4-(4-fluorophenyl)-1-[(1-methyl-1-imidazol-4-yl)sulfonyl]pyrrolidin-3-yl}methyl)aniline;

N-({Trans-4-(4-fluorophenyl)-1-[(1-methyl-1H-imidazol-4-yl)sulfonyl]pyrrolidin-3-yl}methyl)-3-methylaniline;

N-({Trans-4-(4-fluorophenyl)-1-[(1-methyl-1H-imidazol-4-yl)sulfonyl]pyrrolidin-3-yl}methyl)-3-(trifluoromethyl)aniline;

4-({Trans-4-(4-fluorophenyl)-1-[(1-methyl-1H-imidazol-4-yl)sulfonyl]pyrrolidin-3-yl}methoxy)-6-(trifluoromethyl)pyrimidine;

Trans-4-cyclopropyl-1-[(1-methyl-1H-imidazol-4-yl)sulfonyl]-N-[3-(trifluoromethyl)phenyl]pyrrolidin-3-amine;

Trans-N-(3-chlorophenyl)-4-cyclopropyl-1-[(1-methyl-1H-imidazol-4-yl)sulfonyl]pyrrolidin-3-amine;

4-{[3-(2-chlorophenyl)-4-(4-fluorophenyl)pyrrolidin-1-yl]sulfonyl}-1-methyl-1H-imidazole;

4-{[3-(4-chlorophenyl)-4-(4-fluorophenyl)pyrrolidin-1-yl]sulfonyl}-1-methyl-1H-imidazole;

2-chloro-4-({trans-4-(4-fluorophenyl)-1-[(1-methyl-1H-imidazol-4-yl)sulfonyl]pyrrolidin-3-yl}amino)benzonitrile;

2-fluoro-4-({trans-4-(4-fluorophenyl)-1-[(1-methyl-1H-imidazol-4-yl)sulfonyl]pyrrolidin-3-yl}amino)benzonitrile;

3-(3-chlorobenzyl)-1-[(1-methyl-1H-imidazol-4-yl)sulfonyl]-4-phenylimidazolidin-2-one;

trans-1-[(1-methyl-1H-imidazol-4-yl)sulfonyl]-4-(pyridin-2-yl)-N-[3-(trifluoromethyl)phenyl]pyrrolidin-3-amine;

Trans-N-(3-chlorophenyl)-1-[(1-methyl-1H-imidazol-4-yl)sulfonyl]-4-(pyridin-2-yl)pyrrolidin-3-amine;

2-({Trans-4-(4-fluorophenyl)-1-[(1-methyl-1H-imidazol-4-yl)sulfonyl]pyrrolidin-3-yl}methoxy)-4-(trifluoromethyl)pyridine;

Trans-N-(3-cyanophenyl)-4-(4-fluorophenyl)-1-[(1-methyl-1H-imidazol-4-yl)sulfonyl]pyrrolidine-3-carboxamide;

4-{[Trans-3-[(4-fluorophenoxy)methyl]-4-(4-fluorophenyl)pyrrolidin-1-yl]sulfonyl}-1-methyl-1H-imidazole;

4-(4-fluorophenyl)-1-[(1-methyl-1H-imidazol-4-yl)sulfonyl]-N-[3-(propan-2-yloxy)phenyl]pyrrolidin-3-amine;

N-{4-(4-fluorophenyl)-1-[(1-methyl-1H-imidazol-4-yl)sulfonyl]pyrrolidin-3-yl}pyridazin-3-amine;

N-{(3R,4S)-4-(4-fluorophenyl)-1-[(1-methyl-1H-imidazol-4-yl)sulfonyl]pyrrolidin-3-yl}-6-(trifluoromethyl)pyridin-2-amine;

3R,4S)-N-(3-chloro-4-fluorophenyl)-4-(4-fluorophenyl)-1-[(1-methyl-1H-imidazol-4-yl)sulfonyl]pyrrolidin-3-amine;

(3R,4S)-N-(3-fluorophenyl)-4-(4-fluorophenyl)-1-[(1-methyl-1H-imidazol-4-yl)sulfonyl]pyrrolidin-3-amine;

Trans-N-(4-chlorobenzyl)-3-methyl-1-[(1-methyl-1H-imidazol-4-yl)sulfonyl]-4-phenylpyrrolidin-3-amine;

Trans-3-methyl-1-[(1-methyl-1H-imidazol-4-yl)sulfonyl]-4-phenyl-N-[4-(trifluoromethyl)benzyl]pyrrolidin-3-amine;

Trans-N-[2-chloro-4-(trifluoromethyl)benzyl]-3-methyl-1-[(1-methyl-1H-imidazol-4-yl)sulfonyl]-4-phenylpyrrolidin-3-amine;

(3,4-Difluorophenyl){trans-4-(4-fluorophenyl)-1-[(1-methyl-1H-imidazol-4-yl)sulfonyl]pyrrolidin-3-yl}methanone;

Trans-N,4-bis(4-fluorophenyl)-1-[(1-methyl-1H-imidazol-4-yl)sulfonyl]pyrrolidine-3-carboxamide;

(3,4-Dichlorophenyl){trans-4-(4-fluorophenyl)-1-[(1-methyl-1H-imidazol-4-yl)sulfonyl]pyrrolidin-3-yl}methanone;

(3,5-Dichlorophenyl){trans-4-(4-fluorophenyl)-1-[(1-methyl-1H-imidazol-4-yl)sulfonyl]pyrrolidin-3-yl}methanone;

(3-Chloro-5-fluorophenyl){trans-4-(4-fluorophenyl)-1-[(1-methyl-1H-imidazol-4-yl)sulfonyl]pyrrolidin-3-yl}methanone;

{Trans-4-(4-fluorophenyl)-1-[(1-methyl-1H-imidazol-4-yl)sulfonyl]pyrrolidin-3-yl}[3-(trifluoromethoxy)phenyl]methanone;

{Trans-4-(4-fluorophenyl)-1-[(1-methyl-1H-imidazol-4-yl)sulfonyl]pyrrolidin-3-yl}[4-(trifluoromethoxy)phenyl]methanone;

3-[({Trans-4-(4-fluorophenyl)-1-[(1-methyl-1H-imidazol-4-yl)sulfonyl]pyrrolidin-3-yl}methyl)amino]benzamide;

3-(Aminomethyl)-N-({Trans-4-(4-fluorophenyl)-1-[(1-methyl-1H-imidazol-4-yl)sulfonyl]pyrrolidin-3-yl}methyl)aniline;

4-({Trans-4-(4-fluorophenyl)-1-[(1-methyl-1H-imidazol-4-yl)sulfonyl]pyrrolidin-3-yl}methoxy)-2-(trifluoromethyl)pyridine;

4-Fluoro-N-({trans-4-(4-fluorophenyl)-1-[(1-methyl-1H-imidazol-4-yl)sulfonyl]pyrrolidin-3-yl}methyl)aniline;

N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine;

Trans-4-(4-fluorophenyl)-1-[(1-methyl-1H-imidazol-4-yl)sulfonyl]-N-[4-(trifluoromethyl)pyridin-2-yl]pyrrolidine-3-carboxamide;

Trans-4-(4-fluorophenyl)-N-[4-fluoro-3-(trifluoromethoxy)phenyl]-1-[(1-methyl-1H-imidazol-4-yl)sulfonyl]pyrrolidine-3-carboxamide;

Trans-N-[4-chloro-3-(trifluoromethoxy)phenyl]-4-(4-fluorophenyl)-1-[(1-methyl-1H-imidazol-4-yl)sulfonyl]pyrrolidine-3-carboxamide;

N-[4-chloro-2-({Trans-4-(4-fluorophenyl)-1-[(1-methyl-1H-imidazol-4-yl)sulfonyl]pyrrolidin-3-yl}amino)phenyl]acetamide;

Trans-4-[(3-chlorophenyl)amino]-1-[(1-methyl-1H-imidazol-4-yl)sulfonyl]pyrrolidin-3-ol;

N-[Trans-1-[(1-methyl-1H-imidazol-4-yl)sulfonyl]-4-(pyridin-2-yl)pyrrolidin-3-yl]-1-(trifluoromethyl)cyclopropanecarboxamide;

N-{(3R,4S)-4-(4-fluorophenyl)-1-[(1-methyl-1H-imidazol-4-yl)sulfonyl]pyrrolidin-3-yl}-1-(trifluoromethyl)cyclopropanecarboxamide;

4-fluoro-N-({trans-4-(4-fluorophenyl)-1-[(1-methyl-1H-imidazol-4-yl)sulfonyl]pyrrolidin-3-yl}methyl)-3-(trifluoromethoxy)aniline;

4-chloro-N-({trans-4-(4-fluorophenyl)-1-[(1-methyl-1H-imidazol-4-yl)sulfonyl]pyrrolidin-3-yl}methyl)-3-(trifluoromethoxy)aniline;

Trans-N-(3-chlorophenyl)-4-(4-fluorophenoxy)-1-[(1-methyl-1H-imidazol-4-yl)sulfonyl]pyrrolidin-3-amine;

2-({trans-4-(4-fluorophenyl)-1-[(1-methyl-1H-imidazol-4-yl)sulfonyl]pyrrolidin-3-yl}oxy)-4-(trifluoromethyl)pyridine;

3-({(3R,4S)-4-(4-fluorophenyl)-1-[(1-methyl-1H-imidazol-4-yl)sulfonyl]pyrrolidin-3-yl}amino)benzonitrile;

6-chloro-2-[Trans-1-[(1-methyl-1H-imidazol-4-yl)sulfonyl]-4-(pyridin-2-yl)pyrrolidin-3-yl]-2,3-dihydro-1H-isoindol-1-one;

3-benzyl-4-(4-fluorophenyl)-1-[(1-methyl-1H-imidazol-4-yl)sulfonyl]pyrrolidin-3-ol;

N-{trans-4-(4-fluorophenyl)-1-[(1-methyl-1-imidazol-4-yl)sulfonyl]pyrrolidin-3-yl}-5-(trifluoromethyl)pyridazin-3-amine;

N-{4-(4-fluorophenyl)-1-[(1-methyl-1H-imidazol-4-yl)sulfonyl]pyrrolidin-3-yl}-4-(trifluoromethyl)pyridazin-3-amine;

1-methyl-4-{[trans-3-phenyl-4-(phenylsulfonyl)pyrrolidin-1-yl]sulfonyl}-1H-imidazole;

(3R,4S)-4-(4-fluorophenyl)-1-[(1-methyl-1H-imidazol-4-yl)sulfonyl]-N-{[1-(trifluoromethyl)cyclopropyl]methyl}pyrrolidin-3-amine;

(3S,4R)-N-(3-chloro-4-fluorophenyl)-4-(4-fluorophenyl)-1-[(1-methyl-1H-imidazol-4-yl)sulfonyl]pyrrolidin-3-amine;

N-{Trans-3-methyl-1-[(1-methyl-1H-imidazol-4-yl)sulfonyl]-4-phenylpyrrolidin-3-yl}-4-(trifluoromethyl)pyridin-2-amine;

3-({(3S,4R)-4-(4-fluorophenyl)-1-[(1-methyl-1H-imidazol-4-yl)sulfonyl]pyrrolidin-3-yl}amino)benzonitrile;

N-{(3R,4S)-4-(4-fluorophenyl)-1-[(1-methyl-1H-imidazol-4-yl)sulfonyl]pyrrolidin-3-yl}-6-(trifluoromethyl)pyrimidin-4-amine;

(3R,4S)-4-(4-fluorophenyl)-1-[(1-methyl-1H-imidazol-4-yl)sulfonyl]-N-{[5-(trifluoromethyl)furan-2-yl]methyl}pyrrolidin-3-amine;

1,1,1-trifluoro-2-[3-({(3R,4S)-4-(4-fluorophenyl)-1-[(1-methyl-1H-imidazol-4-yl)sulfonyl]pyrrolidin-3-yl}amino)phenyl]propan-2-ol;

(3R,4S)-N-[(5-chlorothiophen-2-yl)methyl]-4-(4-fluorophenyl)-1-[(1-methyl-1H-imidazol-4-yl)sulfonyl]pyrrolidin-3-amine;

(3R,4S)-N-[2-chloro-4-(trifluoromethyl)benzyl]-1-[(1-methyl-1H-imidazol-4-yl)sulfonyl]-4-phenylpyrrolidin-3-amine;

(3S,4R)-N-[2-chloro-4-(trifluoromethyl)benzyl]-1-[(1-methyl-1H-imidazol-4-yl)sulfonyl]-4-phenylpyrrolidin-3-amine;

N-{(3R,4S)-1-[(1-methyl-1H-imidazol-4-yl)sulfonyl]-4-phenylpyrrolidin-3-yl}-4-(trifluoromethyl)pyridin-2-amine;

(3R,4S)-1-[(1-methyl-1H-imidazol-4-yl)sulfonyl]-4-phenyl-N-[3-(trifluoromethyl)phenyl]pyrrolidin-3-amine;

(3R,4S)-1-[(1-methyl-1H-imidazol-4-yl)sulfonyl]-4-phenyl-N-[4-(trifluoromethyl)benzyl]pyrrolidin-3-amine;

1,1,1-trifluoro-2-[3-({(3R,4S)-1-[(1-methyl-1H-imidazol-4-yl)sulfonyl]-4-phenylpyrrolidin-3-yl}amino)phenyl]propan-2-ol;

Trans-4-(benzyloxy)-N-(3-chlorophenyl)-1-[(1-methyl-1H-imidazol-4-yl)sulfonyl]pyrrolidin-3-amine;

Trans-1-[[(1-methyl-1H-imidazol-4-yl)sulfonyl]-4-phenyl-3-{[4-(trifluoromethyl)benzyl]amino}pyrrolidin-3-yl]methanol;

Trans-N-(3-chlorophenyl)-1-[(1-methyl-1H-imidazol-4-yl)sulfonyl]-4-(prop-2-en-1-yloxy)pyrrolidin-3-amine;

Trans-N-(3-chlorophenyl)-1-[(1-methyl-1H-imidazol-4-yl)sulfonyl]-4-[(2-methylprop-2-en-1-yl)oxy]pyrrolidin-3-amine;

3-{Trans-1-[(1-methyl-1H-imidazol-4-yl)sulfonyl]-4-phenylpyrrolidin-3-yl}-6-(trifluoromethyl)-3,4-dihydroquinazolin-2(1H)-one;

4-fluoro-N-{(3R,4S)-1-[(1-methyl-1H-imidazol-4-yl)sulfonyl]-4-phenylpyrrolidin-3-yl}pyridin-2-amine;

N-{(3R,4S)-1-[(1-methyl-1H-imidazol-4-yl)sulfonyl]-4-phenylpyrrolidin-3-yl}-7H-pyrrolo[2,3-d]pyrimidin-4-amine;

Trans-7-[(1-methyl-1H-imidazol-4-yl)sulfonyl]-9-phenyl-1-[4-(trifluoromethyl)benzyl]-3-oxa-1,7-diazaspiro[4.4]nonan-2-one;

3,5-difluoro-N-{(3R,4S)-1-[(1-methyl-1H-imidazol-4-yl)sulfonyl]-4-phenylpyrrolidin-3-yl}-4-(trifluoromethyl)pyridin-2-amine;

(3R,4S)-1-[(1-methyl-1H-imidazol-4-yl)sulfonyl]-4-phenyl-N-{[5-(trifluoromethyl)pyridin-2-yl]methyl}pyrrolidin-3-amine;

5-cyclopropyl-N-{(3R,4S)-1-[(1-methyl-1H-imidazol-4-yl)sulfonyl]-4-phenylpyrrolidin-3-yl}pyrazin-2-amine;

5-cyclobutyl-N-{(3R,4S)-1-[(1-methyl-1H-imidazol-4-yl)sulfonyl]-4-phenylpyrrolidin-3-yl}pyrazin-2-amine;

Trans-N-(3-chlorophenyl)-1-[(1-methyl-1H-imidazol-4-yl)sulfonyl]-4-(2-methylpropoxy)pyrrolidin-3-amine;

N-{(3R,4S)-1-[(1-methyl-1H-imidazol-4-yl)sulfonyl]-4-phenylpyrrolidin-3-yl}-5-(pyrrolidin-1-yl)pyrazin-2-amine;

N-{(3R,4S)-1-[(1-methyl-1H-imidazol-4-yl)sulfonyl]-4-phenylpyrrolidin-3-yl}-5-(trifluoromethyl)pyrazine-2-carboxamide;

5-chloro-N-{(3R,4S)-1-[(1-methyl-1H-imidazol-4-yl)sulfonyl]-4-phenylpyrrolidin-3-yl}pyrazine-2-carboxamide;

3R,4S)-N-(4-chlorobenzyl)-1-[(1-methyl-1H-imidazol-4-yl)sulfonyl]-4-phenylpyrrolidin-3-amine;

(3R,4S)-N-(3-chloro-4-fluorophenyl)-1-[(1-methyl-1H-imidazol-4-yl)sulfonyl]-4-phenylpyrrolidin-3-amine;

(3R,4S)-N-(3,4-difluorophenyl)-4-(4-fluorophenyl)-1-[(1-methyl-1H-imidazol-4-yl)sulfonyl]pyrrolidin-3-amine;

6-chloro-N-{(3R,4S)-1-[(1-methyl-1H-imidazol-4-yl)sulfonyl]-4-phenylpyrrolidin-3-yl}pyridazine-3-carboxamide;

N-{(3R,4S)-1-[(1-methyl-1H-imidazol-4-yl)sulfonyl]-4-phenylpyrrolidin-3-yl}-2-(morpholin-4-yl)pyrimidin-4-amine;

4-({(3R,4S)-1-[(1-methyl-1H-imidazol-4-yl)sulfonyl]-4-phenylpyrrolidin-3-yl}amino)-2,3-dihydro-1H-isoindol-1-one;

(3R,4S)-1-[(1-methyl-1H-imidazol-4-yl)sulfonyl]-N-[3-(methylsulfonyl)phenyl]-4-phenylpyrrolidin-3-amine;

(3R,4S)-1-[(1-methyl-1H-imidazol-4-yl)sulfonyl]-4-phenyl-N-{[5-(trifluoromethyl)piperazin-2-yl]methyl}pyrrolidin-3-amine;

5-fluoro-N-{(3R,4S)-1-[(1-methyl-1H-imidazol-4-yl)sulfonyl]-4-phenylpyrrolidin-3-yl}pyrimidin-2-amine;

Trans-4-cyclohexyl-1-[(1-methyl-1H-imidazol-4-yl)sulfonyl]-N-[3-(trifluoromethoxy)phenyl]pyrrolidin-3-amine;

(3R,4S)-1-[(1-methyl-1H-imidazol-4-yl)sulfonyl]-4-phenyl-N-(4,4,4-trifluorobutyl)pyrrolidin-3-amine;

(3R,4S)-N-(2-cyclopentylethyl)-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-4-phenyl-N-[(5-propyl-furan-2-yl)methyl]pyrrolidin-3-amine;

(3R,4S)-1-[(1-methyl-1H-imidazol-4-yl)sulfonyl]-N-[(4-methyltetrahydro-2H-pyran-4-yl)methyl]-4-phenylpyrrolidin-3-amine;

(3R,4S)-1-[(1-methyl-1H-imidazol-4-yl)sulfonyl]-4-phenyl-N-[(4-phenyl-1,3-thiazol-5-yl)methyl]pyrrolidin-3-amine;

(3R,4S)-1-[(1-methyl-1H-imidazol-4-yl)sulfonyl]-N-[(5-methyl-1,3-thiazol-2-yl)methyl]-4-phenylpyrrolidin-3-amine;

(3R,4S)-N-[(3,5-dichloropyridin-4-yl)methyl]-1-[(1-methyl-1H-imidazol-4-yl)sulfonyl]-4-phenylpyrrolidin-3-amine;

(3R,4S)-N-(2-ethylhexyl)-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-N-[(4-methyl-1,3-thiazol-5-yl)methyl]-4-phenylpyrrolidin-3-amine;

(3R,4S)-N-[(2,4-dichloro-1,3-thiazol-5-yl)methyl]-1-[(1-methyl-1H-imidazol-4-yl)sulfonyl]-4-phenylpyrrolidin-3-amine;

(3R,4S)-N-(2,2-dimethylpropyl)-1-[(1-methyl-1H-imidazol-4-yl)sulfonyl]-4-phenylpyrrolidin-3-amine;

(3R,4S)-N-[(5-methyl-1-benzothiophen-2-yl)methyl]-1-[(1-methyl-1H-imidazol-4-yl)sulfonyl]-4-phenylpyrrolidin-3-amine;

(3R,4S)-N-[(2-bromo-1,3-thiazol-5-yl)methyl]-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-N-(2-methylpropyl)-4-phenylpyrrolidin-3-amine;

(3R,4S)-N-[(3-chloro-1-benzothiophen-2-yl)methyl]-1-[(1-methyl-1H-imidazol-4-yl)sulfonyl]-4-phenylpyrrolidin-3-amine;

(3R,4S)-N-[(2,4-dimethyl-1,3-thiazol-5-yl)methyl]-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-4-phenyl-N-(thieno[2,3-b]pyridin-2-ylmethyl)pyrrolidin-3-amine;

(3R,4S)-N-[(2-methyl-1-benzofuran-3-yl)methyl]-1-[(1-methyl-1H-imidazol-4-yl)sulfonyl]-4-phenylpyrrolidin-3-amine;

(3R,4S)-N-[(6-chloro-2-methylimidazo[1,2-a]pyridin-3-yl)methyl]-1-[(1-methyl-1H-imidazol-4-yl)sulfonyl]-4-phenylpyrrolidin-3-amine;

(3R,4S)-N-{[5-(4-fluorophenyl)pyridin-3-yl]methyl}-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-N-(2-methylpentyl)-4-phenylpyrrolidin-3-amine;

(3R,4S)-1-[(1-methyl-1H-imidazol-4-yl)sulfonyl]-4-phenyl-N-(tetrahydrofuran-3-ylmethyl)pyrrolidin-3-amine;

(3R,4S)-1-[(1-methyl-1H-imidazol-4-yl)sulfonyl]-N-pentyl-4-phenylpyrrolidin-3-amine;

(3R,4S)-N-(2-ethylbutyl)-1-[(1-methyl-1H-imidazol-4-yl)sulfonyl]-4-phenylpyrrolidin-3-amine;

(3R,4S)-N-(2,2-dimethylbutyl)-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-N-[(2-methyl-1,3-thiazol-5-yl)methyl]-4-phenylpyrrolidin-3-amine;

(3R,4S)-1-[(1-methyl-1H-imidazol-4-yl)sulfonyl]-4-phenyl-N-[2-(tetrahydro-2H-pyran-4-yl)ethyl]pyrrolidin-3-amine;

(3R,4S)-N-(1,3-benzothiazol-2-ylmethyl)-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-N-[(4-methyl-1,3-thiazol-2-yl)methyl]-4-phenylpyrrolidin-3-amine;

(3R,4S)-N-[(4,5-dimethylthiophen-2-yl)methyl]-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-4-phenyl-N-(4,5,6,7-tetrahydro-1,3-benzothiazol-2-ylmethyl)pyrrolidin-3-amine;

(3R,4S)-1-[(1-methyl-1H-imidazol-4-yl)sulfonyl]-4-phenyl-N-(1,3-thiazol-5-ylmethyl)pyrrolidin-3-amine;

(3R,4S)-1-[(1-methyl-1H-imidazol-4-yl)sulfonyl]-4-phenyl-N-[2-(2,6,6-trimethylcyclohex-1-en-1-yl)ethyl]pyrrolidin-3-amine;

(3R,4S)-1-[(1-methyl-1H-imidazol-4-yl)sulfonyl]-4-phenyl-N-{[1-(propan-2-yl)piperidin-4-yl]methyl}pyrrolidin-3-amine;

(3R,4S)-N-{[4-(4-fluorophenyl)-1,3-thiazol-2-yl]methyl}-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-N-[2-(4-methylphenyl)ethyl]-4-phenylpyrrolidin-3-amine;

(3R,4S)-1-[(1-methyl-1H-imidazol-4-yl)sulfonyl]-N-[(5-methylthiophen-2-yl)methyl]-4-phenylpyrrolidin-3-amine;

(3R,4S)-N-(3-methylbutyl)-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-4-phenyl-N-(3,5,5-trimethylhexyl)pyrrolidin-3-amine;

(3R,4S)-1-[(1-methyl-1H-imidazol-4-yl)sulfonyl]-4-phenyl-N-(2-phenylpropyl)pyrrolidin-3-amine;

(3R,4S)-N-(3,3-dimethylbutyl)-1-[(1-methyl-1H-imidazol-4-yl)sulfonyl]-4-phenylpyrrolidin-3-amine;

(3R,4S)-N-[(1-methylcyclohexyl)methyl]-1-[(1-methyl-1H-imidazol-4-yl)sulfonyl]-4-phenylpyrrolidin-3-amine;

(3R,4S)-N-[2-(3-chlorophenyl)ethyl]-1-[(1-methyl-1H-imidazol-4-yl)sulfonyl]-4-phenylpyrrolidin-3-amine;

(3R,4S)-N-[2-(4-tert-butylphenoxy)ethyl]-1-[(1-methyl-1H-imidazol-4-yl)sulfonyl]-4-phenylpyrrolidin-3-amine;

(3R,4S)-N-(2-ethyl-3-methylbutyl)-1-[(1-methyl-1H-imidazol-4-yl)sulfonyl]-4-phenylpyrrolidin-3-amine;
(3R,4S)-N-[3-(3-chlorophenyl)propyl]-1-[(1-methyl-1H-imidazol-4-yl)sulfonyl]-4-phenylpyrrolidin-3-amine;
(3R,4S)-N-[(4-bromo-1,3-thiazol-2-yl)methyl]-1-[(1-methyl-1H-imidazol-4-yl)sulfonyl]-4-phenylpyrrolidin-3-amine;
(3R,4S)-1-[(1-methyl-1H-imidazol-4-yl)sulfonyl]-N-[(4-methyl-2-phenyl-1,3-thiazol-5-yl)methyl]-4-phenylpyrrolidin-3-amine;
N-(3,4-difluorophenyl)-1-{[3-methyl-1-(propan-2-yl)-1H-pyrazol-4-yl]sulfonyl}-4-phenylpyrrolidin-3-amine;
N-(3,4-difluorophenyl)-1-{[1-methyl-3-(trifluoromethyl)-1H-pyrazol-4-yl]sulfonyl}-4-phenylpyrrolidin-3-amine;
1-[(1-cyclopentyl-3-methyl-1H-pyrazol-4-yl)sulfonyl]-N-(3,4-difluorophenyl)-4-phenylpyrrolidin-3-amine;
N-(3,4-difluorophenyl)-1-[(1,3-dimethyl-1H-pyrazol-5-yl)sulfonyl]-4-phenylpyrrolidin-3-amine;
N-(3,4-difluorophenyl)-1-[(1,5-dimethyl-1H-pyrazol-4-yl)sulfonyl]-4-phenylpyrrolidin-3-amine;
1-[(5-chloro-1,3-dimethyl-1H-pyrazol-4-yl)sulfonyl]-N-(3,4-difluorophenyl)-4-phenylpyrrolidin-3-amine;
N-(3,4-difluorophenyl)-1-[(1,2-dimethyl-1H-imidazol-5-yl)sulfonyl]-4-phenylpyrrolidin-3-amine;
N-(3,4-difluorophenyl)-1-[(1-methyl-1H-pyrazol-3-yl)sulfonyl]-4-phenylpyrrolidin-3-amine;
N-(3,4-difluorophenyl)-4-phenyl-1-[(1,3,5-trimethyl-1H-pyrazol-4-yl)sulfonyl]pyrrolidin-3-amine;
N-(3,4-difluorophenyl)-1-[(1-methyl-1H-pyrazol-5-yl)sulfonyl]-4-phenylpyrrolidin-3-amine;
Trans-N-(3-chlorophenyl)-4-(cyclopropylmethoxy)-1-[(1-methyl-1H-imidazol-4-yl)sulfonyl]pyrrolidin-3-amine;
N-{trans-4-cyclohexyl-1-[(1-methyl-1H-imidazol-4-yl)sulfonyl]pyrrolidin-3-yl}-6-(trifluoromethyl)pyrimidin-4-amine;
2-methoxy-N-{(3R,4S)-1-[(1-methyl-1H-imidazol-4-yl)sulfonyl]-4-phenylpyrrolidin-3-yl}pyrimidin-4-amine;
(3R,4S)-1-[(1-methyl-1H-imidazol-4-yl)sulfonyl]-N-[(2-methyl-1,3-thiazol-4-yl)methyl]-4-phenylpyrrolidin-3-amine;
(3R,4S)-N-[(2-ethyl-1-benzofuran-3-yl)methyl]-1-[(1-methyl-1H-imidazol-4-yl)sulfonyl]-4-phenylpyrrolidin-3-amine;
(3R,4S)-N-(imidazo[1,2-a]pyridin-8-ylmethyl)-1-[(1-methyl-1H-imidazol-4-yl)sulfonyl]-4-phenylpyrrolidin-3-amine;
(3R,4S)-1-[(1-methyl-1H-imidazol-4-yl)sulfonyl]-N-[(5-methylpyridin-2-yl)methyl]-4-phenylpyrrolidin-3-amine;
(3R,4S)-1-[(1-methyl-1H-imidazol-4-yl)sulfonyl]-4-phenyl-N-(pyrazolo[1,5-a]pyridin-3-ylmethyl)pyrrolidin-3-amine;
N-{Trans-4-hydroxy-1-[(1-methyl-1H-imidazol-4-yl)sulfonyl]-4-phenylpyrrolidin-3-yl}-4-(trifluoromethyl)benzamide;
1-[(1-methyl-1H-imidazol-4-yl)sulfonyl]-3-phenyl-4-{[4-(trifluoromethyl)benzyl]amino}pyrrolidin-3-ol;
(3R,4S)-N-[4-chloro-3-(trifluoromethyl)phenyl]-4-(4-fluorophenyl)-1-[(1-methyl-1H-imidazol-4-yl)sulfonyl]pyrrolidin-3-amine;
ethyl {(3R,4S)-1-[(1-methyl-1H-imidazol-4-yl)sulfonyl]-4-phenylpyrrolidin-3-yl}carbamate;
propyl {(3R,4S)-1-[(1-methyl-1H-imidazol-4-yl)sulfonyl]-4-phenylpyrrolidin-3-yl}carbamate;
2-methylpropyl {(3R,4S)-1-[(1-methyl-1H-imidazol-4-yl)sulfonyl]-4-phenylpyrrolidin-3-yl}carbamate;
butyl {(3R,4S)-1-[(1-methyl-1H-imidazol-4-yl)sulfonyl]-4-phenylpyrrolidin-3-yl}carbamate;
(3R,4S)-N-(2-cyclopropylethyl)-1-[(1-methyl-1H-imidazol-4-yl)sulfonyl]-4-phenylpyrrolidin-3-amine;
2-cyclopropyl-N-{(3R,4S)-1-[(1-methyl-1H-imidazol-4-yl)sulfonyl]-4-phenylpyrrolidin-3-yl}acetamide;
(3R,4S)-N-[(2E)-hex-2-en-1-yl]-1-[(1-methyl-1H-imidazol-4-yl)sulfonyl]-4-phenylpyrrolidin-3-amine;
(3R,4S)-N-hexyl-1-[(1-methyl-1H-imidazol-4-yl)sulfonyl]-4-phenylpyrrolidin-3-amine;
N-{(3R,4S)-1-[(1-methyl-1H-imidazol-4-yl)sulfonyl]-4-phenylpyrrolidin-3-yl}pentanamide;
N-{(3R,4S)-1-[(1-methyl-1H-imidazol-4-yl)sulfonyl]-4-phenylpyrrolidin-3-yl}hexanamide;
(3R,4S)-N-(2-{[tert-butyl(dimethyl)silyl]oxy}ethyl)-1-[(1-methyl-1H-imidazol-4-yl)sulfonyl]-4-phenylpyrrolidin-3-amine;
(3R,4S)-1-[(1-methyl-1H-imidazol-4-yl)sulfonyl]-4-phenyl-N-{[6-(trifluoromethyl)pyridin-2-yl]methyl}pyrrolidin-3-amine;
(3R,4S)-N-[(3-chlorothiophen-2-yl)methyl]-1-[(1-methyl-1H-imidazol-4-yl)sulfonyl]-4-phenylpyrrolidin-3-amine;
(3R,4S)-N-[(4,4-difluorocyclohexyl)methyl]-1-[(1-methyl-1H-imidazol-4-yl)sulfonyl]-4-phenylpyrrolidin-3-amine;
(3R,4S)-1-[(1-methyl-1H-imidazol-4-yl)sulfonyl]-4-phenyl-N-(pyrazolo[1,5-a]pyridin-7-ylmethyl)pyrrolidin-3-amine;
(3R,4S)-1-[(1-methyl-1H-imidazol-4-yl)sulfonyl]-4-phenyl-N-{[4-(propan-2-yl)-1,3-thiazol-2-yl]methyl}pyrrolidin-3-amine;
(3R,4S)-N-[(2,2-dimethyltetrahydro-2H-pyran-4-yl)methyl]-1-[(1-methyl-1H-imidazol-4-yl)sulfonyl]-4-phenylpyrrolidin-3-amine;
(3R,4S)-1-[(1-methyl-1H-imidazol-4-yl)sulfonyl]-4-phenyl-N-{[5-(tetrahydro-2H-pyran-2-yl)thiophen-2-yl]methyl}pyrrolidin-3-amine;
(3R,4S)-N-[(5-bromo-4-methyl-1,3-thiazol-2-yl)methyl]-1-[(1-methyl-1H-imidazol-4-yl)sulfonyl]-4-phenylpyrrolidin-3-amine;
(3R,4S)-N-(imidazo[1,5-a]pyridin-5-ylmethyl)-1-[(1-methyl-1H-imidazol-4-yl)sulfonyl]-4-phenylpyrrolidin-3-amine;
(3R,4S)-N-(2,3-dimethylpentyl)-1-[(1-methyl-1H-imidazol-4-yl)sulfonyl]-4-phenylpyrrolidin-3-amine;
(3R,4S)-N-[(2-chloro-1,3-thiazol-4-yl)methyl]-1-[(1-methyl-1H-imidazol-4-yl)sulfonyl]-4-phenylpyrrolidin-3-amine;
(3R,4S)-1-[(1-methyl-1H-imidazol-4-yl)sulfonyl]-N-[(5-methylimidazo[1,2-a]pyridin-3-yl)methyl]-4-phenylpyrrolidin-3-amine;
(3R,4S)-1-[(1-methyl-1H-imidazol-4-yl)sulfonyl]-4-phenyl-N-[(2-phenylcyclopropyl)methyl]pyrrolidin-3-amine;
(3R,4S)-N-[(4-chloro-1,3-thiazol-5-yl)methyl]-1-[(1-methyl-1H-imidazol-4-yl)sulfonyl]-4-phenylpyrrolidin-3-amine;
(3R,4S)-1-[(1-methyl-1H-imidazol-4-yl)sulfonyl]-4-phenyl-N-(3,3,3-trifluoro-2-methylpropyl)pyrrolidin-3-amine;
(3R,4S)-N-[(2-chloro-3-fluoropyridin-4-yl)methyl]-1-[(1-methyl-1H-imidazol-4-yl)sulfonyl]-4-phenylpyrrolidin-3-amine;

(3R,4S)-N-[(5-fluoro-1-benzothiophen-2-yl)methyl]-1-[(1-methyl-1H-imidazol-4-yl)sulfonyl]-4-phenylpyrrolidin-3-amine;

(3R,4S)-N-[5-chloro-2-(difluoromethoxy)benzyl]-1-[(1-methyl-1H-imidazol-4-yl)sulfonyl]-4-phenylpyrrolidin-3-amine;

(3R,4S)-N-[(2,5-dichlorothiophen-3-yl)methyl]-1-[(1-methyl-1H-imidazol-4-yl)sulfonyl]-4-phenylpyrrolidin-3-amine;

(3R,4S)-N-{[2-(4-fluorophenyl)pyridin-3-yl]methyl}-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-N-{[2-(4-methylphenyl)-1,3-thiazol-5-yl]methyl}-4-phenylpyrrolidin-3-amine;

(3R,4S)-N-(3-cyclopropylpropyl)-1-[(1-methyl-1H-imidazol-4-yl)sulfonyl]-4-phenylpyrrolidin-3-amine;

5-fluoro-4-methyl-N-{(3R,4S)-1-[(1-methyl-1H-imidazol-4-yl)sulfonyl]-4-phenylpyrrolidin-3-yl}pyridin-2-amine;

1,5-dimethyl-N-{(3R,4S)-1-[(1-methyl-1H-imidazol-4-yl)sulfonyl]-4-phenylpyrrolidin-3-yl}-1H-1,2,4-triazol-3-amine;

1,5-dimethyl-4-({(3R,4S)-1-[(1-methyl-1H-imidazol-4-yl)sulfonyl]-4-phenylpyrrolidin-3-yl}amino)-1H-pyrrole-2-carbonitrile;

(3S,4R)-4-(4-fluorophenyl)-1-[(1-methyl-1H-imidazol-4-yl)sulfonyl]-N-[3-(propan-2-yloxy)propyl]pyrrolidine-3-carboxamide;

(3S,4R)-N-(3-ethoxypropyl)-4-(4-fluorophenyl)-1-[(1-methyl-1H-imidazol-4-yl)sulfonyl]pyrrolidine-3-carboxamide;

(3S,4R)-4-(4-fluorophenyl)-N-(2-methoxyethyl)-1-[(1-methyl-1H-imidazol-4-yl)sulfonyl]pyrrolidine-3-carboxamide;

(3S,4R)-4-(4-fluorophenyl)-1-[(1-methyl-1H-imidazol-4-yl)sulfonyl]-N-propylpyrrolidine-3-carboxamide;

(3S,4R)-N-butyl-4-(4-fluorophenyl)-1-[(1-methyl-1H-imidazol-4-yl)sulfonyl]pyrrolidine-3-carboxamide;

(3S,4R)-4-(4-fluorophenyl)-N-[1-methoxypropan-2-yl]-1-[(1-methyl-1H-imidazol-4-yl)sulfonyl]pyrrolidine-3-carboxamide;

(3R,4S)-4-(4-fluorophenyl)-N-(3-methoxypropyl)-1-[(1-methyl-1H-imidazol-4-yl)sulfonyl]pyrrolidine-3-carboxamide;

(3S,4R)-N-(2-ethoxyethyl)-4-(4-fluorophenyl)-1-[(1-methyl-1H-imidazol-4-yl)sulfonyl]pyrrolidine-3-carboxamide;

(3R,4S)-N-[4-chloro-3-(trifluoromethoxy)phenyl]-4-(4-fluorophenyl)-1-[(1-methyl-1H-imidazol-4-yl)sulfonyl]pyrrolidin-3-amine;

(3S,4R)-N-(cyclopropylmethyl)-4-(4-fluorophenyl)-1-[(1-methyl-1H-imidazol-4-yl)sulfonyl]pyrrolidine-3-carboxamide;

(3S,4R)-4-(4-fluorophenyl)-1-[(1-methyl-1H-imidazol-4-yl)sulfonyl]-N-[2-(propan-2-yloxy)ethyl]pyrrolidine-3-carboxamide;

(3R,4S)-N-(3-methoxypropyl)-1-[(1-methyl-1H-imidazol-4-yl)sulfonyl]-4-phenylpyrrolidin-3-amine;

(3R,4S)-N-(3-ethoxypropyl)-1-[(1-methyl-1H-imidazol-4-yl)sulfonyl]-4-phenylpyrrolidin-3-amine;

(3R,4S)-N-{[1-(methoxymethyl)cyclopropyl]methyl}-1-[(1-methyl-1H-imidazol-4-yl)sulfonyl]-4-phenylpyrrolidin-3-amine;

N-({trans-4-(4-fluorophenyl)-1-[(1-methyl-1H-imidazol-4-yl)sulfonyl]pyrrolidin-3-yl}methyl)-3-(propan-2-yloxy)propan-1-amine;

3-ethoxy-N-({trans-4-(4-fluorophenyl)-1-[(1-methyl-1H-imidazol-4-yl)sulfonyl]pyrrolidin-3-yl}methyl)propan-1-amine;

N-({trans-4-(4-fluorophenyl)-1-[(1-methyl-1H-imidazol-4-yl)sulfonyl]pyrrolidin-3-yl}methyl)-2-methoxyethanamine;

N-({trans-4-(4-fluorophenyl)-1-[(1-methyl-1H-imidazol-4-yl)sulfonyl]pyrrolidin-3-yl}methyl)propan-1-amine;

N-({trans-4-(4-fluorophenyl)-1-[(1-methyl-1H-imidazol-4-yl)sulfonyl]pyrrolidin-3-yl}methyl)butan-1-amine;

(2S)-N-({trans-4-(4-fluorophenyl)-1-[(1-methyl-1H-imidazol-4-yl)sulfonyl]pyrrolidin-3-yl}methyl)-1-methoxypropan-2-amine;

N-({trans-4-(4-fluorophenyl)-1-[(1-methyl-1H-imidazol-4-yl)sulfonyl]pyrrolidin-3-yl}methyl)-3-methoxypropan-1-amine;

2-ethoxy-N-({trans-4-(4-fluorophenyl)-1-[(1-methyl-1H-imidazol-4-yl)sulfonyl]pyrrolidin-3-yl}methyl)ethanamine;

N-({trans-4-(4-fluorophenyl)-1-[(1-methyl-1H-imidazol-4-yl)sulfonyl]pyrrolidin-3-yl}methyl)-2-(propan-2-yloxy)ethanamine;

(3R,4S)-N-(2-methoxyethyl)-1-[(1-methyl-1H-imidazol-4-yl)sulfonyl]-4-phenylpyrrolidin-3-amine;

1-[(1-methyl-1H-imidazol-4-yl)sulfonyl]-4-(tetrahydrofuran-2-yl)-N-[3-(trifluoromethoxy)phenyl]pyrrolidin-3-amine;

1-[(1-methyl-1H-imidazol-4-yl)sulfonyl]-4-(tetrahydrofuran-2-yl)-N-[3-(trifluoromethoxy)phenyl]pyrrolidin-3-amine;

1-[(1-methyl-1H-imidazol-4-yl)sulfonyl]-4-(tetrahydrofuran-2-yl)-N-[3-(trifluoromethyl)phenyl]pyrrolidin-3-amine;

(3R,4S)-1-[(1-methyl-1H-imidazol-4-yl)sulfonyl]-4-(tetrahydrofuran-2-yl)-N-[3-(trifluoromethyl)phenyl]pyrrolidin-3-amine;

2-methoxy-N-{(3R,4S)-1-[(1-methyl-1H-imidazol-4-yl)sulfonyl]-4-phenylpyrrolidin-3-yl}-6-(trifluoromethyl)pyrimidin-4-amine;

6-chloro-N-{(3R,4S)-1-[(1-methyl-1H-imidazol-4-yl)sulfonyl]-4-phenylpyrrolidin-3-yl}pyrimidin-4-amine;

1-cyclopropyl-N-({(3R,4R)-4-(4-fluorophenyl)-1-[(1-methyl-1H-imidazol-4-yl)sulfonyl]pyrrolidin-3-yl}methyl)methanamine;

(3R,4S)-N-(2-ethoxyethyl)-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-4-phenyl-N-(2-propoxyethyl)pyrrolidin-3-amine;

N-(3,4-difluorophenyl)-1-[(1-methyl-1H-imidazol-4-yl)sulfonyl]-4-[-tetrahydrofuran-2-yl]pyrrolidin-3-amine;

N-(3,4-difluorophenyl)-1-[(1-methyl-1H-imidazol-4-yl)sulfonyl]-4-(tetrahydrofuran-2-yl)pyrrolidin-3-amine;

6-cyclopropyl-N-{(3R,4S)-1-[(1-methyl-1H-imidazol-4-yl)sulfonyl]-4-phenylpyrrolidin-3-yl}pyrimidin-4-amine;

6-ethyl-N-{(3R,4S)-4-(4-fluorophenyl)-1-[(1-methyl-1H-imidazol-4-yl)sulfonyl]pyrrolidin-3-yl}pyrimidin-4-amine;

N-{(3R,4S)-4-(4-fluorophenyl)-1-[(1-methyl-1H-imidazol-4-yl)sulfonyl]pyrrolidin-3-yl}-6-(propan-2-yl)pyrimidin-4-amine;

N-{(3R,4S)-4-(4-fluorophenyl)-1-[(1-methyl-1H-imidazol-4-yl)sulfonyl]pyrrolidin-3-yl}-2-methyl-6-(trifluoromethyl)pyrimidin-4-amine;

N-{(3R,4S)-4-(4-fluorophenyl)-1-[(1-methyl-1H-imidazol-4-yl)sulfonyl]pyrrolidin-3-yl}-6-propylpyrimidin-4-amine;

5-chloro-N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine;

(3S,4R)-N-[4-chloro-3-(trifluoromethyl)phenyl]-1-[(1-methyl-1H-imidazol-4-yl)sulfonyl]-4-(tetrahydrofuran-2-yl)pyrrolidin-3-amine;

(3R,4S)-N-[4-chloro-3-(trifluoromethyl)phenyl]-1-[(1-methyl-1H-imidazol-4-yl)sulfonyl]-4-(tetrahydrofuran-2-yl)pyrrolidin-3-amine;

6-ethoxy-N-{(3R,4S)-1-[(1-methyl-1H-imidazol-4-yl)sulfonyl]-4-phenylpyrrolidin-3-yl}pyrimidin-4-amine;

6-methoxy-N-{(3R,4S)-1-[(1-methyl-1H-imidazol-4-yl)sulfonyl]-4-phenylpyrrolidin-3-yl}pyrimidin-4-amine;

N-{(3R,4S)-1-[(1-methyl-1H-imidazol-4-yl)sulfonyl]-4-phenylpyrrolidin-3-yl}-6-propoxypyrimidin-4-amine;

6-butoxy-N-{(3R,4S)-1-[(1-methyl-1H-imidazol-4-yl)sulfonyl]-4-phenylpyrrolidin-3-yl}pyrimidin-4-amine;

N-{(3R,4S)-1-[(1-methyl-1H-imidazol-4-yl)sulfonyl]-4-phenylpyrrolidin-3-yl}-6-(2-methylpropoxy)pyrimidin-4-amine;

4-{[(3S,4R)-3-(4-fluorophenyl)-4-(hexyloxy)pyrrolidin-1-yl]sulfonyl}-1-methyl-1H-imidazol;

Trans-4-(4-fluorophenyl)-1-[(1-methyl-1H-imidazol-4-yl)sulfonyl]-N-pentylpyrrolidine-3-carboxamide;

Trans-4-(4-fluorophenyl)-N-hexyl-1-[(1-methyl-1H-imidazol-4-yl)sulfonyl]pyrrolidine-3-carboxamide;

Trans-N-(3-chlorobenzyl)-4-(4-fluorophenyl)-1-[(1-methyl-1H-imidazol-4-yl)sulfonyl]pyrrolidine-3-carboxamide;

Trans-N-(4-chlorobenzyl)-4-(4-fluorophenyl)-1-[(1-methyl-1H-imidazol-4-yl)sulfonyl]pyrrolidine-3-carboxamide;

Trans-N-(4-fluorobenzyl)-4-(4-fluorophenyl)-1-[(1-methyl-1H-imidazol-4-yl)sulfonyl]pyrrolidine-3-carboxamide;

Trans-N-(3,4-difluorobenzyl)-4-(4-fluorophenyl)-1-[(1-methyl-1H-imidazol-4-yl)sulfonyl]pyrrolidine-3-carboxamide;

Trans-4-(4-fluorophenyl)-1-[(1-methyl-1H-imidazol-4-yl)sulfonyl]-N-[3-(trifluoromethyl)benzyl]pyrrolidine-3-carboxamide;

Trans-N-[2-chloro-5-(trifluoromethyl)benzyl]-4-(4-fluorophenyl)-1-[(1-methyl-1H-imidazol-4-yl)sulfonyl]pyrrolidine-3-carboxamide;

Trans-4-(4-fluorophenyl)-1-[(1-methyl-1H-imidazol-4-yl)sulfonyl]-N-(pyridin-2-ylmethyl)pyrrolidine-3-carboxamide;

Trans-4-(4-fluorophenyl)-1-[(1-methyl-1H-imidazol-4-yl)sulfonyl]-N-{[4-(trifluoromethyl)pyridin-2-yl]methyl}pyrrolidine-3-carboxamide;

Trans-N,N-dibutyl-4-(4-fluorophenyl)-1-[(1-methyl-1H-imidazol-4-yl)sulfonyl]pyrrolidine-3-carboxamide;

6-methyl-N-{(3R,4S)-1-[(1-methyl-1H-imidazol-4-yl)sulfonyl]-4-phenylpyrrolidin-3-yl}pyrimidin-4-amine;

(3R,4S)-4-(4-fluorophenyl)-1-[(1-methyl-1H-imidazol-4-yl)sulfonyl]-N-[4-methyl-3-(trifluoromethyl)phenyl]pyrrolidin-3-amine;

4-({(3R,4S)-4-(4-fluorophenyl)-1-[(1-methyl-1H-imidazol-4-yl)sulfonyl]pyrrolidin-3-yl}amino)-2-(trifluoromethyl)benzonitrile;

4-{Trans-4-(4-fluorophenyl)-1-[(1-methyl-1H-imidazol-4-yl)sulfonyl]pyrrolidin-3-yl}-1-propyl-1H-1,2,3-triazole;

4-[-1-cyclopropylpiperidin-3-yl]-1-[(1-methyl-1H-imidazol-4-yl)sulfonyl]-N-[3-(trifluoromethoxy)phenyl]pyrrolidin-3-amine;

Trans-N-(3-chloro-4-fluorobenzyl)-4-(4-fluorophenyl)-1-[(1-methyl-1H-imidazol-4-yl)sulfonyl]pyrrolidine-3-carboxamide;

Trans-4-(4-fluorophenyl)-N-(6-methylheptyl)-1-[(1-methyl-1H-imidazol-4-yl)sulfonyl]pyrrolidine-3-carboxamide;

2-(4-fluorophenoxy)-N-{(3R,4S)-4-(4-fluorophenyl)-1-[(1-methyl-1H-imidazol-4-yl)sulfonyl]pyrrolidin-3-yl}acetamide;

(3R,4S)-N-[4-fluoro-3-(trifluoromethyl)phenyl]-1-[(1-methyl-1H-imidazol-4-yl)sulfonyl]-4-phenylpyrrolidin-3-amine;

(3R,4S)-N-[4-fluoro-3-(trifluoromethoxy)phenyl]-1-[(1-methyl-1H-imidazol-4-yl)sulfonyl]-4-phenylpyrrolidin-3-amine;

(3R,4S)-N-(4-methoxybutyl)-1-[(1-methyl-1H-imidazol-4-yl)sulfonyl]-4-phenylpyrrolidin-3-amine;

(3R,4S)-N-(4-methoxyhexyl)-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-4-phenyl-N-[(2-propylcyclopropyl)methyl]pyrrolidin-3-amine;

(3R,4S)-1-[(1-methyl-1H-imidazol-4-yl)sulfonyl]-4-phenyl-N-[(2-propylcyclopropyl)methyl]pyrrolidin-3-amine;

(3R,4S)-4-(4-fluorophenyl)-N-[4-fluoro-3-(trifluoromethoxy)phenyl]-1-[(1-methyl-1H-imidazol-4-yl)sulfonyl]pyrrolidin-3-amine;

(3R,4S)-4-(4-fluorophenyl)-N-[4-fluoro-3-(trifluoromethyl)phenyl]-1-[(1-methyl-1H-imidazol-4-yl)sulfonyl]pyrrolidin-3-amine;

(3R,4S)-N-[4-methoxy-3-(trifluoromethyl)phenyl]-1-[(1-methyl-1H-imidazol-4-yl)sulfonyl]-4-phenylpyrrolidin-3-amine;

(3R,4S)-N-(1-benzothiophen-5-yl)-1-[(1-methyl-1H-imidazol-4-yl)sulfonyl]-4-phenylpyrrolidin-3-amine;

(3R,4S)-N-(2,3-dihydro-1H-inden-5-yl)-1-[(1-methyl-1H-imidazol-4-yl)sulfonyl]-4-phenylpyrrolidin-3-amine;

(3R,4S)-N-[3,4-bis(trifluoromethyl)phenyl]-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-4-phenyl-N-(5,6,7,8-tetrahydronaphthalen-2-yl)pyrrolidin-3-amine;

(3R,4S)-N-(3,4-dihydro-2H-chromen-6-yl)-1-[(1-methyl-1H-imidazol-4-yl)sulfonyl]-4-phenylpyrrolidin-3-amine;

4-({Trans-1-[(1-methyl-1H-imidazol-4-yl)sulfonyl]-4-phenylpyrrolidin-3-yl}methyl)-1-propyl-1H-1,2,3-triazole;

(3R,4S)-N-(1-benzofuran-5-yl)-1-[(1-methyl-1H-imidazol-4-yl)sulfonyl]-4-phenylpyrrolidin-3-amine;

Trans-4-(4-fluorophenyl)-1-[(1-methyl-1H-imidazol-4-yl)sulfonyl]-N-[3-(trifluoromethoxy)benzyl]pyrrolidine-3-carboxamide;

methyl 5-({(3R,4S)-4-(4-fluorophenyl)-1-[(1-methyl-1H-imidazol-4-yl)sulfonyl]pyrrolidin-3-yl}amino)-5-oxopentanoate;

(3R,4S)-N-[2-chloro-4-(trifluoromethyl)benzyl]-4-(4-fluorophenyl)-1-[(1-methyl-1H-imidazol-4-yl)sulfonyl]pyrrolidine-3-carboxamide;

(3R,4S)-4-(4-fluorophenyl)-1-[(1-methyl-1H-imidazol-4-yl)sulfonyl]-N-pentylpyrrolidin-3-amine;

(3R,4S)-4-(4-fluorophenyl)-N-hexyl-1-[(1-methyl-1H-imidazol-4-yl)sulfonyl]pyrrolidin-3-amine;

(3R,4S)-N-[2-(2-methoxyethoxy)ethyl]-1-[(1-methyl-1H-imidazol-4-yl)sulfonyl]-4-phenylpyrrolidin-3-amine;

(3R,4S)-N-[2-(4-fluorophenoxy)ethyl]-4-(4-fluorophenyl)-1-[(1-methyl-1H-imidazol-4-yl)sulfonyl]pyrrolidin-3-amine;

4-butyl-1-{Trans-1-[(1-methyl-1H-imidazol-4-yl)sulfonyl]-4-phenylpyrrolidin-3-yl}-1H-1,2,3-triazole;

(3R,4S)-N-(4-chloro-3-methylphenyl)-1-[(1-methyl-1H-imidazol-4-yl)sulfonyl]-4-phenylpyrrolidin-3-amine;

(3R,4S)-1-[(1-methyl-1H-imidazol-4-yl)sulfonyl]-4-phenyl-N-[3-(2,2,2-trifluoroethoxy)phenyl]pyrrolidin-3-amine;

(3R,4S)-N-(2,3-dihydro-1-benzo furan-5-yl)-1-[(1-methyl-1H-imidazol-4-yl)sulfonyl]-4-phenylpyrrolidin-3-amine;

(3R,4S)-N-(4,4-dimethyl-3,4-dihydro-2H-chromen-6-yl)-4-(4-fluorophenyl)-1-[(1-methyl-1H-imidazol-4-yl)sulfonyl]pyrrolidin-3-amine;

N-{(3R,4S)-4-(4-fluorophenyl)-1-[(1-methyl-1H-imidazol-4-yl)sulfonyl]pyrrolidin-3-yl}-2-hydroxyhexanamide;

(3R,4S)-N-(3-methoxyhexyl)-1-[(1-methyl-1H-imidazol-4-yl)sulfonyl]-4-phenylpyrrolidin-3-amine;

(3R,4S)-N-[4-chloro-3-(propan-2-yl)phenyl]-4-(4-fluorophenyl)-1-[(1-methyl-1H-imidazol-4-yl)sulfonyl]pyrrolidin-3-amine;

(3R,4S)-4-(4-fluorophenyl)-1-[(1-methyl-1H-imidazol-4-yl)sulfonyl]-N-[3-methyl-4-(trifluoromethyl)phenyl]pyrrolidin-3-amine;

(3R,4S)-N-(1-benzothiophen-6-yl)-4-(4-fluorophenyl)-1-[(1-methyl-1H-imidazol-4-yl)sulfonyl]pyrrolidin-3-amine;

-4-(1-cyclopropylpiperidin-4-yl)-1-[(1-methyl-1H-imidazol-4-yl)sulfonyl]-N-[3-(trifluoromethoxy)phenyl]pyrrolidin-3-amine;

Trans-N-hexyl-1-[(1-methyl-1H-imidazol-4-yl)sulfonyl]-4-(tetrahydro-2H-pyran-2-yl)pyrrolidin-3-amine;

Trans-N-[2-chloro-4-(trifluoromethyl)benzyl]-1-[(1-methyl-1H-imidazol-4-yl)sulfonyl]-4-(tetrahydro-2H-pyran-2-yl)pyrrolidin-3-amine;

Trans-1-[(1-methyl-1H-imidazol-4-yl)sulfonyl]-4-(tetrahydro-2H-pyran-2-yl)-N-[3-(trifluoromethyl)phenyl]pyrrolidin-3-amine;

N-{Trans-1-[(1-methyl-1H-imidazol-4-yl)sulfonyl]-4-[tetrahydro-2H-pyran-2-yl]pyrrolidin-3-yl}-4-(trifluoromethyl)pyridin-2-amine;

N-{Trans-1-[(1-methyl-1H-imidazol-4-yl)sulfonyl]-4-[tetrahydro-2H-pyran-2-yl]pyrrolidin-3-yl}-4-(trifluoromethyl)pyridin-2-amine;

(3R,4S)-N-[4-(4,4-dimethyl-1,3-dioxan-2-yl)butyl]-4-(4-fluorophenyl)-1-[(1-methyl-1H-imidazol-4-yl)sulfonyl]pyrrolidin-3-amine;

Trans-1-[(1-methyl-1H-imidazol-4-yl)sulfonyl]-4-(tetrahydro-2H-pyran-2-yl)-N-[3-(trifluoromethoxy)phenyl]pyrrolidin-3-amine;

Trans-1-[(1-methyl-1H-imidazol-4-yl)sulfonyl]-4-[tetrahydro-2H-pyran-2-yl]-N-[3-(trifluoromethoxy)phenyl]pyrrolidin-3-amine;

N-[Trans-1-[(1-methyl-1H-imidazol-4-yl)sulfonyl]-4-(tetrahydro-2H-pyran-2-yl)pyrrolidin-3-yl]-6-(trifluoromethyl)pyrimidin-4-amine;

N-[2-({Trans-4-(4-fluorophenyl)-1-[(1-methyl-1H-imidazol-4-yl)sulfonyl]pyrrolidin-3-yl}oxy)ethyl]propan-1-amine;

2-({Trans-4-(4-fluorophenyl)-1-[(1-methyl-1H-imidazol-4-yl)sulfonyl]pyrrolidin-3-yl}oxy)N-propylacetamide;

6-chloro-N-{(3R,4S)-4-(4-fluorophenyl)-1-[(1-methyl-1H-imidazol-4-yl)sulfonyl]pyrrolidin-3-yl}-2-methylpyrimidin-4-amine;

6-chloro-N-{(3R,4S)-4-(4-fluorophenyl)-1-[(1-methyl-1H-imidazol-4-yl)sulfonyl]pyrrolidin-3-yl}pyrimidin-4-amine;

1-{(3R,4S)-4-(4-fluorophenyl)-1-[(1-methyl-1H-imidazol-4-yl)sulfonyl]pyrrolidin-3-yl}-3-phenylurea;

phenyl {(3R,4S)-4-(4-fluorophenyl)-1-[(1-methyl-1H-imidazol-4-yl)sulfonyl]pyrrolidin-3-yl}carbamate;

1-(2-chlorophenyl)-3-{(3R,4S)-4-(4-fluorophenyl)-1-[(1-methyl-1H-imidazol-4-yl)sulfonyl]pyrrolidin-3-yl}urea;

N-{(3R,4S)-4-(4-fluorophenyl)-1-[(1-methyl-1H-imidazol-4-yl)sulfonyl]pyrrolidin-3-yl}-5-oxohexanamide;

N-{(3R,4S)-4-(4-fluorophenyl)-1-[(1-methyl-1H-imidazol-4-yl)sulfonyl]pyrrolidin-3-yl}-4-(trifluoromethyl)cyclohexanecarboxamide;

Butyl-trans-4-(4-fluorophenyl)-1-[(1-methyl-1H-imidazol-4-yl)sulfonyl]pyrrolidin-3-yl carbonate;

5,5,5-trifluoro-N-{(3R,4S)-4-(4-fluorophenyl)-1-[(1-methyl-1H-imidazol-4-yl)sulfonyl]pyrrolidin-3-yl}pentanamide;

(3S,4R)-4-(4-fluorophenyl)-1-[(1-methyl-1H-imidazol-4-yl)sulfonyl]pyrrolidin-3-yl butylcarbamate;

2,2-difluoro-N-{(3R,4S)-4-(4-fluorophenyl)-1-[(1-methyl-1H-imidazol-4-yl)sulfonyl]pyrrolidin-3-yl}pentanamide;

1-(4-chlorophenyl)-3-{(3R,4S)-4-(4-fluorophenyl)-1-[(1-methyl-1H-imidazol-4-yl)sulfonyl]pyrrolidin-3-yl}urea;

1-(2-fluorophenyl)-3-{(3R,4S)-4-(4-fluorophenyl)-1-[(1-methyl-1H-imidazol-4-yl)sulfonyl]pyrrolidin-3-yl}urea;

1-(3-fluorophenyl)-3-{(3R,4S)-4-(4-fluorophenyl)-1-[(1-methyl-1H-imidazol-4-yl)sulfonyl]pyrrolidin-3-yl}urea;

1-(4-fluorophenyl)-3-{(3R,4S)-4-(4-fluorophenyl)-1-[(1-methyl-1H-imidazol-4-yl)sulfonyl]pyrrolidin-3-yl}urea;

1-(2-chlorobenzyl)-3-{(3R,4S)-4-(4-fluorophenyl)-1-[(1-methyl-1H-imidazol-4-yl)sulfonyl]pyrrolidin-3-yl}urea;

4,5-dichloro-N-{(3R,4S)-4-(4-fluorophenyl)-1-[(1-methyl-1H-imidazol-4-yl)sulfonyl]pyrrolidin-3-yl}pyridin-2-amine;

(3R,4S)-4-(4-fluorophenyl)-1-[(1-methyl-1H-imidazol-4-yl)sulfonyl]-N-{[4-(trifluoromethyl)cyclohexyl]methyl}pyrrolidin-3-amine;

2,2-difluoro-N-{(3R,4S)-4-(4-fluorophenyl)-1-[(1-methyl-1H-imidazol-4-yl)sulfonyl]pyrrolidin-3-yl}hexanamide;

Trans-N-[3,4-difluorophenyl]-1-[(1-methyl-1H-imidazol-4-yl)sulfonyl]-4-(1,3-oxazol-2-yl)pyrrolidin-3-amine;

N-[4-chloro-3-(trifluoromethyl)phenyl]-1-[(1-methyl-1H-imidazol-4-yl)sulfonyl]-4-(1,3-oxazol-2-yl)pyrrolidin-3-amine;

4-{[trans-3-[(4-fluorobenzyl)oxy]-4-(4-fluorophenyl)pyrrolidin-1-yl]sulfonyl}-1-methyl-1H-imidazole;

4-{[trans-3-[(3-fluorobenzyl)oxy]-4-(4-fluorophenyl)pyrrolidin-1-yl]sulfonyl}-1-methyl-1H-imidazole;

4-{[trans-3-(4-fluorophenyl)-4-{[4-(methylsulfonyl)benzyl]oxy}pyrrolidin-1-yl]sulfonyl}-1-methyl-1H-imidazole;

4-{[trans-3-(4-fluorophenyl)-4-{[3-(methylsulfonyl)benzyl]oxy}pyrrolidin-1-yl]sulfonyl}-1-methyl-1H-imidazole; 6-ethoxy-N-{(3R,4S)-4-(4-fluorophenyl)-1-[(1-methyl-1H-imidazol-4-yl)sulfonyl]pyrrolidin-3-yl}pyrimidin-4-amine;

N-{(3R,4S)-4-(4-fluorophenyl)-1-[(1-methyl-1H-imidazol-4-yl)sulfonyl]pyrrolidin-3-yl}-6-(propan-2-yloxy)pyrimidin-4-amine;

6-butoxy-N-{(3R,4S)-4-(4-fluorophenyl)-1-[(1-methyl-1H-imidazol-4-yl)sulfonyl]pyrrolidin-3-yl}pyrimidin-4-amine;

N-{(3R,4S)-4-(4-fluorophenyl)-1-[(1-methyl-1H-imidazol-4-yl)sulfonyl]pyrrolidin-3-yl}-6-(2-methylpropoxy)pyrimidin-4-amine;

6-(cyclobutyloxy)-N-{(3R,4S)-4-(4-fluorophenyl)-1-[(1-methyl-1H-imidazol-4-yl)sulfonyl]pyrrolidin-3-yl}pyrimidin-4-amine;

6-(cyclopentyloxy)-N-{(3R,4S)-4-(4-fluorophenyl)-1-[(1-methyl-1H-imidazol-4-yl)sulfonyl]pyrrolidin-3-yl}pyrimidin-4-amine;

6-(cyclohexyloxy)-N-{(3R,4S)-4-(4-fluorophenyl)-1-[(1-methyl-1H-imidazol-4-yl)sulfonyl]pyrrolidin-3-yl}pyrimidin-4-amine;

N-{(3R,4S)-4-(4-fluorophenyl)-1-[(1-methyl-1H-imidazol-4-yl)sulfonyl]pyrrolidin-3-yl}-6-phenylpyrimidin-4-amine;

N-{(3R,4S)-4-(4-fluorophenyl)-1-[(1-methyl-1H-imidazol-4-yl)sulfonyl]pyrrolidin-3-yl}-6-(2-methylphenyl)pyrimidin-4-amine;

N-{(3R,4S)-4-(4-fluorophenyl)-1-[(1-methyl-1H-imidazol-4-yl)sulfonyl]pyrrolidin-3-yl}-6-(3-methylphenyl)pyrimidin-4-amine;

N-{(3R,4S)-4-(4-fluorophenyl)-1-[(1-methyl-1H-imidazol-4-yl)sulfonyl]pyrrolidin-3-yl}-6-(4-methylphenyl)pyrimidin-4-amine;

6-(2-fluorophenyl)-N-{(3R,4S)-4-(4-fluorophenyl)-1-[(1-methyl-1H-imidazol-4-yl)sulfonyl]pyrrolidin-3-yl}pyrimidin-4-amine;

6-(3-fluorophenyl)-N-{(3R,4S)-4-(4-fluorophenyl)-1-[(1-methyl-1H-imidazol-4-yl)sulfonyl]pyrrolidin-3-yl}pyrimidin-4-amine;

6-(4-fluorophenyl)-N-{(3R,4S)-4-(4-fluorophenyl)-1-[(1-methyl-1H-imidazol-4-yl)sulfonyl]pyrrolidin-3-yl}pyrimidin-4-amine;

6-(3-chlorophenyl)-N-{(3R,4S)-4-(4-fluorophenyl)-1-[(1-methyl-1H-imidazol-4-yl)sulfonyl]pyrrolidin-3-yl}pyrimidin-4-amine;

6-(4-chlorophenyl)-N-{(3R,4S)-4-(4-fluorophenyl)-1-[(1-methyl-1H-imidazol-4-yl)sulfonyl]pyrrolidin-3-yl}pyrimidin-4-amine;

4-({(3S,4R)-3-(4-fluorophenyl)-4-[(4-methylbenzyl)oxy]pyrrolidin-1-yl}sulfonyl)-1-methyl-1H-imidazole;

(3R,4S)-4-(4-fluorophenyl)-1-[(1-methyl-1H-imidazol-4-yl)sulfonyl]-N-(5,5,5-trifluoropentyl)pyrrolidin-3-amine;

(3R,4S)-N-(2,2-difluorohexyl)-4-(4-fluorophenyl)-1-[(1-methyl-1H-imidazol-4-yl)sulfonyl]pyrrolidin-3-amine;

(3R,4S)-N-(2,2-difluoropentyl)-4-(4-fluorophenyl)-1-[(1-methyl-1H-imidazol-4-yl)sulfonyl]pyrrolidin-3-amine;

5,5-difluoro-N-{(3R,4S)-4-(4-fluorophenyl)-1-[(1-methyl-1-imidazol-4-yl)sulfonyl]pyrrolidin-3-yl}hexanamide;

4-fluoro-N-{(3R,4S)-4-(4-fluorophenyl)-1-[(1-methyl-1H-imidazol-4-yl)sulfonyl]pyrrolidin-3-yl}pyridin-2-amine;

5-fluoro-N-{(3R,4S)-4-(4-fluorophenyl)-1-[(1-methyl-1H-imidazol-4-yl)sulfonyl]pyrrolidin-3-yl}pyridin-2-amine;

N-{(3R,4S)-4-(4-fluorophenyl)-1-[(1-methyl-1H-imidazol-4-yl)sulfonyl]pyrrolidin-3-yl}-4-oxopentanamide;

(3R,4S)-N-(5,5-difluorohexyl)-4-(4-fluorophenyl)-1-[(1-methyl-1H-imidazol-4-yl)sulfonyl]pyrrolidin-3-amine;

4-chloro-N-[2-({Trans-4-(4-fluorophenyl)-1-[(1-methyl-1H-imidazol-4-yl)sulfonyl]pyrrolidin-3-yl}oxy)ethyl]aniline;

(3S,4R)-N-[4-fluoro-3-(trifluoromethoxy)phenyl]-1-[(1-methyl-1H-imidazol-4-yl)sulfonyl]-4-(tetrahydro-2H-pyran-2-yl)pyrrolidin-3-amine;

1-benzyl-3-{(3R,4S)-4-(4-fluorophenyl)-1-[(1-methyl-1H-imidazol-4-yl)sulfonyl]pyrrolidin-3-yl}urea;

(3R,4S)-N-(4-chloro-3-methylphenyl)-4-(4-fluorophenyl)-1-[(1-methyl-1H-imidazol-4-yl)sulfonyl]pyrrolidin-3-amine;

(3R,4S)-4-(4-fluorophenyl)-1-[(1-methyl-1H-imidazol-4-yl)sulfonyl]-N-[3-(2,2,2-trifluoroethoxy)phenyl]pyrrolidin-3-amine;

(3R,4S)-4-(4-fluorophenyl)-N-[4-fluoro-3-(pyridin-3-yl)phenyl]-1-[(1-methyl-1H-imidazol-4-yl)sulfonyl]pyrrolidin-3-amine;

(3R,4S)-4-(4-fluorophenyl)-N-[4-fluoro-3-(pyridin-4-yl)phenyl]-1-[(1-methyl-1H-imidazol-4-yl)sulfonyl]pyrrolidin-3-amine;

(3R,4S)-N-(4-fluoro-3-methylphenyl)-4-(4-fluorophenyl)-1-[(1-methyl-1H-imidazol-4-yl)sulfonyl]pyrrolidin-3-amine;

5-fluoro-N-{(3R,4S)-4-(4-fluorophenyl)-1-[(1-methyl-1H-imidazol-4-yl)sulfonyl]pyrrolidin-3-yl}-4-methylpyridin-2-amine;

(3R,4S)-4-(4-fluorophenyl)-N-[4-fluoro-3-(pyrimidin-5-yl)phenyl]-1-[(1-methyl-1H-imidazol-4-yl)sulfonyl]pyrrolidin-3-amine;

N-{(3R,4S)-4-(4-fluorophenyl)-1-[(1-methyl-1H-imidazol-4-yl)sulfonyl]pyrrolidin-3-yl}-3,4'-bipyridin-2'-amine;

N-{(3R,4S)-4-(4-fluorophenyl)-1-[(1-methyl-1H-imidazol-4-yl)sulfonyl]pyrrolidin-3-yl}-4,4'-bipyridin-2-amine;

4-({(3S,4R)-4-(4-fluorophenyl)-1-[(1-methyl-1H-imidazol-4-yl)sulfonyl]pyrrolidin-3-yl}oxy)-6-(trifluoromethyl)pyrimidine;

N-[(3R,4S)-4-chloro-3-(trifluoromethyl)phenyl]-1-[(1-methyl-1H-imidazol-4-yl)sulfonyl]-4-(1,3-oxazol-4-yl)pyrrolidin-3-amine;

4,4-difluoro-N-{(3R,4S)-4-(4-fluorophenyl)-1-[(1-methyl-1H-imidazol-4-yl)sulfonyl]pyrrolidin-3-yl}pentanamide;

(3R,4S)-N-(3,4-difluorophenyl)-1-[(1,2-dimethyl-1H-imidazol-4-yl)sulfonyl]-4-(4-fluorophenyl)pyrrolidin-3-amine;

(3R,4S)-1-[(1,2-dimethyl-1H-imidazol-4-yl)sulfonyl]-4-(4-fluorophenyl)-N-[4-fluoro-3-(trifluoromethyl)phenyl]pyrrolidin-3-amine;

(3R,4S)-N-(3,4-difluorophenyl)-1-[(1,2-dimethyl-1H-imidazol-5-yl)sulfonyl]-4-(4-fluorophenyl)pyrrolidin-3-amine;

(3R,4S)-1-[(1,2-dimethyl-1H-imidazol-5-yl)sulfonyl]-4-(4-fluorophenyl)-N-[4-fluoro-3-(trifluoromethyl)phenyl]pyrrolidin-3-amine;

4-chloro-N-{(3R,4S)-4-(4-fluorophenyl)-1-[(1-methyl-1H-imidazol-4-yl)sulfonyl]pyrrolidin-3-yl}pyridin-2-amine;

5-chloro-N-[(3R,4S)-1-[(1,2-dimethyl-1H-imidazol-4-yl)sulfonyl]-4-(4-fluorophenyl)pyrrolidin-3-yl]-4-(trifluoromethyl)pyridin-2-amine;

Trans-N-[2-chloro-4-(trifluoromethyl)benzyl]-4-(3-fluoropyridin-2-yl)-1-[(1-methyl-1H-imidazol-4-yl)sulfonyl]pyrrolidin-3-amine;
Trans-4-(3-fluoropyridin-2-yl)-N-hexyl-1-[(1-methyl-1H-imidazol-4-yl)sulfonyl]pyrrolidin-3-amine;
Trans-4-(3-fluoropyridin-2-yl)-N,N-dihexyl-1-[(1-methyl-1H-imidazol-4-yl)sulfonyl]pyrrolidin-3-amine;
Trans-4-(3-fluoropyridin-2-yl)-1-[(1-methyl-1H-imidazol-4-yl)sulfonyl]-N,N-dipentylpyrrolidin-3-amine;
Trans-4-(3-fluoropyridin-2-yl)-1-[(1-methyl-1H-imidazol-4-yl)sulfonyl]-N-pentylpyrrolidin-3-amine;
Trans-N-(3,4-difluorophenyl)-4-(3-fluoropyridin-2-yl)-1-[(1-methyl-1H-imidazol-4-yl)sulfonyl]pyrrolidin-3-amine;
Trans-4-(3-fluoropyridin-2-yl)-N-[4-fluoro-3-(trifluoromethyl)phenyl]-1-[(1-methyl-1H-imidazol-4-yl)sulfonyl]pyrrolidin-3-amine;
Trans-4-(3-fluoropyridin-2-yl)-N-[4-fluoro-3-(trifluoromethoxy)phenyl]-1-[(1-methyl-1H-imidazol-4-yl)sulfonyl]pyrrolidin-3-amine;
5-fluoro-N-{trans-4-(3-fluoropyridin-2-yl)-1-[(1-methyl-1H-imidazol-4-yl)sulfonyl]pyrrolidin-3-yl}-4-methylpyridin-2-amine;
N-{Trans-4-(3-fluoropyridin-2-yl)-1-[(1-methyl-1H-imidazol-4-yl)sulfonyl]pyrrolidin-3-yl}-6-(trifluoromethyl)pyrimidin-4-amine;
Trans-N-(3-chloro-4-fluorophenyl)-4-(3-fluoropyridin-2-yl)-1-[(1-methyl-1H-imidazol-4-yl)sulfonyl]pyrrolidin-3-amine;
6-chloro-N-{trans-4-(3-fluoropyridin-2-yl)-1-[(1-methyl-1H-imidazol-4-yl)sulfonyl]pyrrolidin-3-yl}pyrimidin-4-amine;
(3R,4S)-N-[3-(benzyloxy)phenyl]-1-[(1-methyl-1H-imidazol-4-yl)sulfonyl]-4-phenylpyrrolidin-3-amine;
6-(benzyloxy)-N-{(3R,4S)-4-(4-fluorophenyl)-1-[(1-methyl-1H-imidazol-4-yl)sulfonyl]pyrrolidin-3-yl}pyrimidin-4-amine;
Trans-N-(4-fluoro-3-methylphenyl)-4-(3-fluoropyridin-2-yl)-1-[(1-methyl-1H-imidazol-4-yl)sulfonyl]pyrrolidin-3-amine;
4-(benzyloxy)-5-fluoro-N-{(3R,4S)-1-[(1-methyl-1H-imidazol-4-yl)sulfonyl]-4-phenylpyrrolidin-3-yl}pyridin-2-amine;
(3R,4S)-1-[(1-methyl-1H-imidazol-4-yl)sulfonyl]-4-phenyl-N-[3-(piperidin-4-yl)phenyl]pyrrolidin-3-amine;
6-(azetidin-3-ylmethoxy)-N-{(3R,4S)-4-(4-fluorophenyl)-1-[(1-methyl-1H-imidazol-4-yl)sulfonyl]pyrrolidin-3-yl}pyrimidin-4-amine;
N-{(3R,4S)-4-(4-fluorophenyl)-1-[(1-methyl-1H-imidazol-4-yl)sulfonyl]pyrrolidin-3-yl}-6-(pyrrolidin-3-ylmethoxy)pyrimidin-4-amine;
N-{(3R,4S)-4-(4-fluorophenyl)-1-[(1-methyl-1H-imidazol-4-yl)sulfonyl]pyrrolidin-3-yl}-6-(pyrrolidin-2-ylmethoxy)pyrimidin-4-amine;
trans-1-[(1-methyl-1H-imidazol-4-yl)sulfonyl]-N-(3-methylphenyl)-4-(tetrahydro-2H-pyran-3-yl)pyrrolidin-3-amine;
trans-1-[(1-methyl-1H-imidazol-4-yl)sulfonyl]-4-(tetrahydro-2H-pyran-3-yl)-N-[3-(trifluoromethyl)phenyl]pyrrolidin-3-amine;
trans-N-(3-chlorophenyl)-1-[(1-methyl-1H-imidazol-4-yl)sulfonyl]-4-(tetrahydro-2H-pyran-3-yl)pyrrolidin-3-amine;
trans-1-[(1-methyl-1H-imidazol-4-yl)sulfonyl]-4-[(3S)-tetrahydro-2H-pyran-3-yl]-N-[3-(trifluoromethoxy)phenyl]pyrrolidin-3-amine;
trans-1-[(1-methyl-1H-imidazol-4-yl)sulfonyl]-4-[(3S)-tetrahydro-2H-pyran-3-yl]-N-[3-(2,2,2-trifluoroethoxy)phenyl]pyrrolidin-3-amine;
trans-1-[(1-methyl-1H-imidazol-4-yl)sulfonyl]-N-(3-phenoxyphenyl)-4-[(3S)-tetrahydro-2H-pyran-3-yl]pyrrolidin-3-amine;
trans-N-(biphenyl-3-yl)-1-[(1-methyl-1H-imidazol-4-yl)sulfonyl]-4-[(3S)-tetrahydro-2H-pyran-3-yl]pyrrolidin-3-amine;
Trans-N-[4-fluoro-3-(trifluoromethoxy)phenyl]-1-[(1-methyl-1H-imidazol-4-yl)sulfonyl]-4-[(3S)-tetrahydro-2H-pyran-3-yl]pyrrolidin-3-amine;
Trans-N-(3-chloro-4-fluorophenyl)-1-[(1-methyl-1H-imidazol-4-yl)sulfonyl]-4-[(3S)-tetrahydro-2H-pyran-3-yl]pyrrolidin-3-amine;
Trans-N-(4-fluoro-3-methylphenyl)-1-[(1-methyl-1H-imidazol-4-yl)sulfonyl]-4-[(3S)-tetrahydro-2H-pyran-3-yl]pyrrolidin-3-amine;
Trans-N-[4-fluoro-3-(trifluoromethyl)phenyl]-1-[(1-methyl-1H-imidazol-4-yl)sulfonyl]-4-[(3S)-tetrahydro-2H-pyran-3-yl]pyrrolidin-3-amine;
Trans-N-[4-chloro-3-(trifluoromethyl)phenyl]-1-[(1-methyl-1H-imidazol-4-yl)sulfonyl]-4-[(3S)-tetrahydro-2H-pyran-3-yl]pyrrolidin-3-amine;
Trans-N-[4-chloro-3-(trifluoromethoxy)phenyl]-1-[(1-methyl-1H-imidazol-4-yl)sulfonyl]-4-[(3S)-tetrahydro-2H-pyran-3-yl]pyrrolidin-3-amine;
Trans-N[3-(benzyloxy)phenyl]-1-[(1-methyl-1H-imidazol-4-yl)sulfonyl]-4-[(3S)-tetrahydro-2H-pyran-3-yl]pyrrolidin-3-amine;
5-fluoro-N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine;
3-fluoro-N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine;
N-(2,2-difluoroethyl)-2-({(3R,4S)-4-(4-fluorophenyl)-1-[(1-methyl-1H-imidazol-4-yl)sulfonyl]pyrrolidin-3-yl}oxy)acetamide;
Trans-4-(3-fluoropyridin-2-yl)-1-[(1-methyl-1H-imidazol-4-yl)sulfonyl]-N-[3-(trifluoromethyl)phenyl]pyrrolidin-3-amine;
Trans-4-(3-fluoropyridin-2-yl)-1-[(1-methyl-1H-imidazol-4-yl)sulfonyl]-N-[3-(trifluoromethoxy)phenyl]pyrrolidin-3-amine;
Trans-4-(3-fluoropyridin-2-yl)-1-[(1-methyl-1H-imidazol-4-yl)sulfonyl]-N-[3-(2,2,2-trifluoroethoxy)phenyl]pyrrolidin-3-amine;
(3R,4S)-4-(4-fluorophenyl)-1-[(1-methyl-1H-imidazol-4-yl)sulfonyl]-N-[3-(pyridin-2-yl)phenyl]pyrrolidin-3-amine;
(3R,4S)-1-[(1-methyl-1H-imidazol-4-yl)sulfonyl]-4-phenyl-N-[3-(pyridin-2-yl)phenyl]pyrrolidin-3-amine;
5-fluoro-N-{(3R,4S)-1-[(1-methyl-1H-imidazol-4-yl)sulfonyl]-4-phenylpyrrolidin-3-yl}-4-(2,2,2-trifluoroethoxy)pyridin-2-amine;
5-Chloro-N-{trans-4-(3-fluoropyridin-2-yl)-1-[(1-methyl-1H-imidazol-4-yl)sulfonyl]pyrrolidin-3-yl}-4-(trifluoromethyl)pyridin-2-amine;
Trans-N-(3-fluorophenyl)-4-(3-fluoropyridin-2-yl)-1-[(1-methyl-1H-imidazol-4-yl)sulfonyl]pyrrolidin-3-amine;
5-chloro-N-{(3R,4S)-4-(4-fluorophenyl)-1-[(1-methyl-1H-imidazol-4-yl)sulfonyl]pyrrolidin-3-yl}-4-(2,2,2-trifluoro ethoxy)pyridin-2-amine;
N-{(3R,4S)-4-(4-fluorophenyl)-1-[(1-methyl-1H-imidazol-4-yl)sulfonyl]pyrrolidin-3-yl}-4-(2,2,2-trifluoro ethoxy)pyridin-2-amine;

5-chloro-N-{(3R,4S)-1-[(1-methyl-1H-imidazol-4-yl)sulfonyl]-4-phenylpyrrolidin-3-yl}-4-(2,2,2-trifluoro ethoxy)pyridin-2-amine;

N-{(3R,4S)-1-[(1-methyl-1H-imidazol-4-yl)sulfonyl]-4-phenylpyrrolidin-3-yl}-4-(2,2,2-trifluoro ethoxy)pyridin-2-amine;

5-fluoro-N-{(3R,4S)-4-(4-fluorophenyl)-1-[(1-methyl-1H-imidazol-4-yl)sulfonyl]pyrrolidin-3-yl}-4-(2,2,2-trifluoro ethoxy)pyridin-2-amine;

Trans-4-(3-fluoropyridin-2-yl)-N-hexyl-1-[(1-methyl-1H-1,2,3-triazol-4-yl)sulfonyl]pyrrolidin-3-amine;

N-{(3R,4S)-4-(4-fluorophenyl)-1-[(1-methyl-1H-imidazol-4-yl)sulfonyl]pyrrolidin-3-yl}-4-(propan-2-yl)pyridin-2-amine;

N-{(3R,4S)-1-[(1-methyl-1H-imidazol-4-yl)sulfonyl]-4-phenylpyrrolidin-3-yl}-4-(propan-2-yl)pyridin-2-amine;

(2,2,2-trifluoro-N-[2-({trans-4-(4-fluorophenyl)-1-[(1-methyl-1H-imidazol-4-yl)sulfonyl]pyrrolidin-3-yl}oxy)ethyl]ethanamine;

Trans-N-(3-chloro-4-fluorophenyl)-1-[(1-methyl-1H-imidazol-4-yl)sulfonyl]-4-(tetrahydro-2H-pyran-2-yl)pyrrolidin-3-amine;

Trans-1-[(1-methyl-1H-imidazol-4-yl)sulfonyl]-4-(tetrahydro-2H-pyran-2-yl)-N-[3-(2,2,2-trifluoroethoxy)phenyl]pyrrolidin-3-amine;

2-({1-[(1-methyl-1H-imidazol-4-yl)sulfonyl]-4-phenylpyrrolidin-3-yl}methyl)-4-(trifluoromethyl)pyridine;

Trans-N-[2-chloro-4-(trifluoromethyl)benzyl]-4-(3-fluoropyridin-2-yl)-1-[(1-methyl-1H-1,2,3-triazol-4-yl)sulfonyl]pyrrolidin-3-amine;

Trans-1-[(1-methyl-1H-imidazol-4-yl)sulfonyl]-4-(tetrahydrofuran-2-yl)-N-[3-(2,2,2-trifluoroethoxy)phenyl]pyrrolidin-3-amine;

N-Hexyl-1-[(1-methyl-1H-imidazol-4-yl)sulfonyl]-4-[(2R)-tetrahydrofuran-2-yl]pyrrolidin-3-amine;

N-hexyl-1-[(1-methyl-1H-imidazol-4-yl)sulfonyl]-4-[(2S)-tetrahydrofuran-2-yl]pyrrolidin-3-amine;

Trans-N-[2-chloro-4-(trifluoromethyl)benzyl]-1-[(1-methyl-1H-imidazol-4-yl)sulfonyl]-4-(tetrahydrofuran-2-yl)pyrrolidin-3-amine;

N-[2-chloro-4-(trifluoromethyl)benzyl]-1-[(1-methyl-1H-imidazol-4-yl)sulfonyl]-4-[(2S)-tetrahydrofuran-2-yl]pyrrolidin-3-amine;

Trans-N-(3-chloro-4-fluorophenyl)-1-[(1-methyl-1H-imidazol-4-yl)sulfonyl]-4-(tetrahydrofuran-2-yl)pyrrolidin-3-amine;

N-(3-chloro-4-fluorophenyl)-1-[(1-methyl-1H-imidazol-4-yl)sulfonyl]-4-[(2S)-tetrahydrofuran-2-yl]pyrrolidin-3-amine;

1-benzyl-N-{(3R,4S)-1-[(1-methyl-1H-imidazol-4-yl)sulfonyl]-4-phenylpyrrolidin-3-yl}-2,3-dihydro-1H-indol-6-amine;

trans-1-[(1-methyl-1H-imidazol-4-yl)sulfonyl]-4-(tetrahydrofuran-3-yl)-N-[3-(trifluoromethyl)phenyl]pyrrolidin-3-amine;

trans-1-[(1-methyl-1H-imidazol-4-yl)sulfonyl]-N-(3-methylphenyl)-4-(tetrahydrofuran-3-yl)pyrrolidin-3-amine;

trans-N-(3-chlorophenyl)-1-[(1-methyl-1H-imidazol-4-yl)sulfonyl]-4-(tetrahydrofuran-3-yl)pyrrolidin-3-amine;

trans-N-(3-chloro-4-fluorophenyl)-1-[(1-methyl-1H-imidazol-4-yl)sulfonyl]-4-(tetrahydrofuran-3-yl)pyrrolidin-3-amine;

trans-N-[4-fluoro-3-(trifluoromethoxy)phenyl]-1-[(1-methyl-1H-imidazol-4-yl)sulfonyl]-4-(tetrahydrofuran-3-yl)pyrrolidin-3-amine;

trans-N-[4-fluoro-3-(trifluoromethyl)phenyl]-1-[(1-methyl-1H-imidazol-4-yl)sulfonyl]-4-(tetrahydrofuran-3-yl)pyrrolidin-3-amine;

trans-N-[4-chloro-3-(trifluoromethyl)phenyl]-1-[(1-methyl-1H-imidazol-4-yl)sulfonyl]-4-(tetrahydrofuran-3-yl)pyrrolidin-3-amine;

trans-1-[(1-methyl-1H-imidazol-4-yl)sulfonyl]-4-(tetrahydrofuran-3-yl)-N-[3-(2,2,2-trifluoroethoxy)phenyl]pyrrolidin-3-amine;

trans-1-[(1-methyl-1H-imidazol-4-yl)sulfonyl]-4-(tetrahydrofuran-3-yl)-N-[3-(trifluoromethoxy)phenyl]pyrrolidin-3-amine;

trans-4-(4-fluorophenyl)-1-[(1-methyl-1H-1,2,3-triazol-4-yl)sulfonyl]-N-[3-(2,2,2-trifluoroethoxy)phenyl]pyrrolidin-3-amine;

(3R,4S)-4-(4-fluorophenyl)-1-[(1-methyl-1H-1,2,3-triazol-4-yl)sulfonyl]-N-[3-(trifluoromethoxy)phenyl]pyrrolidin-3-amine;

(3R,4S)-4-(4-fluorophenyl)-N-[4-fluoro-3-(trifluoromethoxy)phenyl]-1-[(1-methyl-1H-1,2,3-triazol-4-yl)sulfonyl]pyrrolidin-3-amine;

(3R,4S)-4-(4-fluorophenyl)-1-[(1-methyl-1H-1,2,3-triazol-4-yl)sulfonyl]-N-[3-(trifluoromethyl)phenyl]pyrrolidin-3-amine;

(3R,4S)-4-(4-fluorophenyl)-N-[4-fluoro-3-(trifluoromethyl)phenyl]-1-[(1-methyl-1H-1,2,3-triazol-4-yl)sulfonyl]pyrrolidin-3-amine;

(3R,4S)-N-(3-chlorophenyl)-4-(4-fluorophenyl)-1-[(1-methyl-1H-1,2,3-triazol-4-yl)sulfonyl]pyrrolidin-3-amine;

(3R,4S)-N-(3-chloro-4-fluorophenyl)-4-(4-fluorophenyl)-1-[(1-methyl-1H-1,2,3-triazol-4-yl)sulfonyl]pyrrolidin-3-amine;

Trans-N-[4-fluoro-3-(trifluoromethyl)phenyl]-1-[(1-methyl-1H-imidazol-4-yl)sulfonyl]-4-(tetrahydrofuran-2-yl)pyrrolidin-3-amine;

5-Chloro-N-[trans-1-[(1-methyl-1H-imidazol-4-yl)sulfonyl]-4-(tetrahydrofuran-2-yl)pyrrolidin-3-yl]-4-(trifluoromethyl)pyridin-2-amine;

Trans-N-(4-fluoro-3-methylphenyl)-1-[(1-methyl-1H-imidazol-4-yl)sulfonyl]-4-(tetrahydrofuran-2-yl)pyrrolidin-3-amine;

Trans-N-[4-fluoro-3-(trifluoromethyl)phenyl]-1-[(1-methyl-1H-imidazol-4-yl)sulfonyl]-4-(tetrahydro-2H-pyran-2-yl)pyrrolidin-3-amine;

Trans-N-(4-fluoro-3-methylphenyl)-1-[(1-methyl-1H-imidazol-4-yl)sulfonyl]-4-(tetrahydro-2H-pyran-2-yl)pyrrolidin-3-amine;

5-Chloro-N-[trans-1-[(1-methyl-1H-imidazol-4-yl)sulfonyl]-4-(tetrahydro-2H-pyran-2-yl)pyrrolidin-3-yl]-4-(trifluoromethyl)pyridin-2-amine;

Trans-N-(3-chlorophenyl)-1-[(1-methyl-1H-imidazol-4-yl)sulfonyl]-4-(tetrahydro-2H-pyran-2-yl)pyrrolidin-3-amine;

Trans-N-(3-chlorophenyl)-1-[(1-methyl-1H-imidazol-4-yl)sulfonyl]-4-(tetrahydrofuran-2-yl)pyrrolidin-3-amine;

5-Fluoro-4-methyl-N-[trans-1-[(1-methyl-1H-imidazol-4-yl)sulfonyl]-4-(tetrahydrofuran-2-yl)pyrrolidin-3-yl]pyridin-2-amine;

5-Fluoro-4-methyl-N-[trans-1-[(1-methyl-1H-imidazol-4-yl)sulfonyl]-4-(tetrahydro-2H-pyran-2-yl)pyrrolidin-3-yl]pyridin-2-amine;

N-[Trans-1-[(1-methyl-1H-imidazol-4-yl)sulfonyl]-4-(tetrahydrofuran-2-yl)pyrrolidin-3-yl]-6-(trifluoromethyl)pyrimidin-4-amine;
(3R,4S)-N-cyclohexyl-4-(4-fluorophenyl)-1-(1-methyl-1H-imidazol-4-ylsulfonyl)pyrrolidin-3-amine;
(3R,4S)-N-(3,3-dimethylcyclohexyl)-4-(4-fluorophenyl)-1-(1-methyl-1H-imidazol-4-ylsulfonyl)pyrrolidin-3-amine;
(3R,4S)-N-(4,4-dimethylcyclohexyl)-4-(4-fluorophenyl)-1-(1-methyl-1H-imidazol-4-ylsulfonyl)pyrrolidin-3-amine;
(3R,4S)-N-cyclopentyl-4-(4-fluorophenyl)-1-(1-methyl-1H-imidazol-4-ylsulfonyl)pyrrolidin-3-amine;
(3R,4S)-N-(3,3-dimethylcyclopentyl)-4-(4-fluorophenyl)-1-(1-methyl-1H-imidazol-4-ylsulfonyl)pyrrolidin-3-amine;
(3R,4S)-N-(1-(2,4-dichlorophenyl)ethyl)-4-(4-fluorophenyl)-1-(1-methyl-1H-imidazol-4-ylsulfonyl)pyrrolidin-3-amine;
(3R,4S)-N-(2,3-dihydro-1H-inden-1-yl)-4-(4-fluorophenyl)-1-(1-methyl-1H-imidazol-4-ylsulfonyl)pyrrolidin-3-amine;
(3R,4S)-N-(5-chloro-2,3-dihydro-1H-inden-1-yl)-4-(4-fluorophenyl)-1-(1-methyl-1H-imidazol-4-ylsulfonyl)pyrrolidin-3-amine;
N-(4-chlorobenzyl)-N-((3R,4S)-4-(4-fluorophenyl)-1-(1-methyl-1H-imidazol-4-ylsulfonyl)pyrrolidin-3-yl)acetamide;
5-butyl-3-{(3R,4S)-4-(4-fluorophenyl)-1-[(1-methyl-1H-imidazol-4-yl)sulfonyl]pyrrolidin-3-yl}-1,3-oxazolidin-2-one;
4-{(3R,4S)-4-(4-fluorophenyl)-1-[(1-methyl-1H-imidazol-4-yl)sulfonyl]pyrrolidin-3-yl}thiomorpholine 1,1-dioxide;
5-fluoro-N-{(3R,4S)-4-(4-fluorophenyl)-1-[(1-methyl-1H-imidazol-4-yl)sulfonyl]pyrrolidin-3-yl}-4-(trifluoromethyl)pyridin-2-amine;
(3R,4S)-1-[(1-methyl-1H-imidazol-4-yl)sulfonyl]-4-[(2R)-tetrahydro-2H-pyran-2-yl]-N-[3-(trifluoromethoxy)phenyl]pyrrolidin-3-amine;
(3R,4S)-4-(4-fluorophenyl)-1-[(1-methyl-1H-imidazol-4-yl)sulfonyl]-N-[2-methyl-5-(prop-1-en-2-yl)cyclohexyl]pyrrolidin-3-amine;
(3R,4S)-4-(4-fluorophenyl)-1-[(1-methyl-1H-imidazol-4-yl)sulfonyl]-N-(2,2,2-trifluoro-1-phenylethyl)pyrrolidin-3-amine;
N-[2-chloro-4-(trifluoromethyl)benzyl]-2-[(1-methyl-1H-imidazol-4-yl)sulfonyl]octahydro-3aH-isoindol-3a-amine;
2-chloro-N-{2-[(1-methyl-1H-imidazol-4-yl)sulfonyl]octahydro-3aH-isoindol-3a-yl}-3-(trifluoromethyl)benzamide;
2,4-dichloro-N-{2-[(1-methyl-1H-imidazol-4-yl)sulfonyl]octahydro-3aH-isoindol-3a-yl}benzamide;
1-hexyl-6-[(1-methyl-1H-imidazol-4-yl)sulfonyl]octahydro-1H-pyrrolo[3,4-b]pyridine;
(2,4-dichlorophenyl){6-[(1-methyl-1H-imidazol-4-yl)sulfonyl]octahydro-1H-pyrrolo[3,4-b]pyridin-1-yl}methanone;
[2-chloro-3-(trifluoromethyl)phenyl]{6-[(1-methyl-1H-imidazol-4-yl)sulfonyl]octahydro-1H-pyrrolo[3,4-b]pyridin-1-yl}methanone;
(3R,4S)-4-(4-fluorophenyl)-1-[(1-methyl-1H-imidazol-4-yl)sulfonyl]-N-[2,2,2-trifluoro-1-(3-methylphenyl)ethyl]pyrrolidin-3-amine;
(3R,4S)-4-(4-fluorophenyl)-1-[(1-methyl-1H-imidazol-4-yl)sulfonyl]-N-[2,2,2-trifluoro-1-(4-methylphenyl)ethyl]pyrrolidin-3-amine;
(1R,2R,3R,4S)-3-(4-fluorophenyl)-N-[4-fluoro-3-(trifluoromethyl)phenyl]-7-[(1-methyl-1H-imidazol-4-yl)sulfonyl]-7-azabicyclo[2.2.1]heptan-2-amine;
3-(4-fluorophenyl)-N-[4-fluoro-3-(trifluoromethyl)phenyl]-7-[(1-methyl-1H-imidazol-4-yl)sulfonyl]-7-azabicyclo[2.2.1]heptan-2-amine;
1-[2-chloro-4-(trifluoromethyl)benzyl]-6-[(1-methyl-1H-imidazol-4-yl)sulfonyl]octahydro-1H-pyrrolo[3,4-b]pyridine;
[2-chloro-4-(trifluoromethyl)phenyl]{6-[(1-methyl-1H-imidazol-4-yl)sulfonyl]octahydro-1H-pyrrolo[3,4-b]pyridin-1-yl}methanone;
N-(3-chloro-4-fluorobenzyl)-2-[(1-methyl-1H-imidazol-4-yl)sulfonyl]-2-azaspiro[4.5]decane-4-carboxamide;
N-(3,4-difluorobenzyl)-2-[(1-methyl-1H-imidazol-4-yl)sulfonyl]-2-azaspiro[4.5]decane-4-carboxamide;
1-{(3R,4S)-4-(4-fluorophenyl)-1-[(1-methyl-1H-imidazol-4-yl)sulfonyl]pyrrolidin-3-yl}-1,3-dihydro-2H-indol-2-one;
2-[(1-methyl-1H-imidazol-4-yl)sulfonyl]-N-[4-(trifluoromethyl)benzyl]octahydro-3aH-isoindol-3a-amine;
trans-N-[2-chloro-4-(trifluoromethyl)benzyl]-2-[(1-methyl-1H-imidazol-4-yl)sulfonyl]-2,3,3a,8-tetrahydroindeno[1,2-c]pyrrol-8a(1H)-amine;
2-{4-[(4-fluorophenoxy)methyl]-1-[(1-methyl-1H-imidazol-4-yl)sulfonyl]pyrrolidin-3-yl}pyridine;
2-[(1-methyl-1H-imidazol-4-yl)sulfonyl]-3a-{[6-(trifluoromethyl)pyrimidin-4-yl]oxy}-2,3,3a,4,5,9b-hexahydro-1H-benzo[e]isoindole;
N-(4-fluorobenzyl)-2-[(1-methyl-1H-imidazol-4-yl)sulfonyl]-1,2,3,4,5,9b-hexahydro-3aH-benzo[e]isoindol-3a-amine;
N-[2-chloro-4-(trifluoromethyl)benzyl]-2-[(1-methyl-1H-imidazol-4-yl)sulfonyl]-1,2,3,4,5,9b-hexahydro-3aH-benzo[e]isoindol-3a-amine;
2-[(1-methyl-1H-1,2,3-triazol-4-yl)sulfonyl]-N-[6-(trifluoromethyl)pyrimidin-4-yl]-2,3,3a,8-tetrahydroindeno[1,2-c]pyrrol-8a(1H)-amine;
2-[(1-methyl-1H-imidazol-4-yl)sulfonyl]-N-[4-(trifluoromethyl)pyridin-2-yl]-2,3,3a,8-tetrahydroindeno[1,2-c]pyrrol-8a(1H)-amine;
N-(2,3-dihydro-1H-inden-1-yl)-1-[(1-methyl-1H-imidazol-4-yl)sulfonyl]-4-(1-methylpiperidin-2-yl)pyrrolidin-3-amine;
1-[(1-methyl-1H-imidazol-4-yl)sulfonyl]-4-(1-methylpiperidin-2-yl)-N-[3-(2,2,2-trifluoroethoxy)phenyl]pyrrolidin-3-amine;
4-(5-fluoropyridin-2-yl)-1-[(1-methyl-1H-imidazol-4-yl)sulfonyl]-N-[3-(trifluoromethoxy)phenyl]pyrrolidin-3-amine;
(3R,4S)-4-(1,3-dioxan-2-yl)-1-[(1-methyl-1H-1,2,3-triazol-4-yl)sulfonyl]-N-[3-(trifluoromethoxy)phenyl]pyrrolidin-3-amine;
(3R,4S)-4-(1,3-dioxan-2-yl)-1-[(1-methyl-1H-imidazol-4-yl)sulfonyl]-N-[3-(trifluoromethoxy)phenyl]pyrrolidin-3-amine;
1-[(1-methyl-1H-imidazol-4-yl)sulfonyl]-4-(1-methylpiperidin-2-yl)-N-[3-(trifluoromethoxy)phenyl]pyrrolidin-3-amine;
(3R,4S)-4-(1,3-dioxan-2-yl)-1-[(1-methyl-1H-imidazol-4-yl)sulfonyl]-N-[3-(2,2,2-(trifluoromethoxy)phenyl]pyrrolidin-3-amine;

(3R,4S)-4-(5,5-dimethyl-1,3-dioxoan-2-yl)-1-[(1-methyl-1H-imidazol-4-yl)sulfonyl]-N-[3-(trifluoromethoxy)phenyl]pyrrolidin-3-amine;

(3R,4S)-4-(1,3-dioxepan-2-yl)-1-[(1-methyl-1H-imidazol-4-yl)sulfonyl]-N-[3-(trifluoromethoxy)phenyl]pyrrolidin-3-amine;

(3R,4S)-4-(1,3-dioxolan-2-yl)-1-[(1-methyl-1H-imidazol-4-yl)sulfonyl]-N-[3-(trifluoromethoxy)phenyl]pyrrolidin-3-amine;

(3R,4S)-N-(2,3-dihydro-1H-inden-1-yl)-4-(1,3-dioxan-2-yl)-1-[(1-methyl-1H-imidazol-4-yl)sulfonyl]pyrrolidin-3-amine;

(3R,4S)-N-[2-chloro-4-(trifluoromethyl)benzyl]-4-(1,3-dioxan-2-yl)-1-[(1-methyl-1H-imidazol-4-yl)sulfonyl]pyrrolidin-3-amine;

(3R,4S)-4-(1,3-dioxan-2-yl)-1-[(1-methyl-1H-imidazol-4-yl)sulfonyl]-N-[3-(trifluoromethoxy)benzyl]pyrrolidin-3-amine;

(3R,4S)-4-(1,3-dioxan-2-yl)-N-(4-fluorobenzyl)-1-[(1-methyl-1H-imidazol-4-yl)sulfonyl]pyrrolidin-3-amine;

(3R,4S)-4-(1,3-dioxan-2-yl)-N-methyl-1-[(1-methyl-1H-imidazol-4-yl)sulfonyl]-N-pentylpyrrolidin-3-amine;

(3R,4S)-4-(1,3-dioxan-2-yl)-1-[(1-methyl-1H-imidazol-4-yl)sulfonyl]-N,N-dipentylpyrrolidin-3-amine;

(3R,4S)-4-(1,3-dioxan-2-yl)-N,N-dihexyl-1-[(1-methyl-1H-imidazol-4-yl)sulfonyl]pyrrolidin-3-amine;

(3R,4S)-4-(1,3-dioxan-2-yl)-N-hexyl-1-[(1-methyl-1H-imidazol-4-yl)sulfonyl]pyrrolidin-3-amine;

5-chloro-N-{(3R,4S)-4-(1,3-dioxan-2-yl)-1-[(1-methyl-1H-imidazol-4-yl)sulfonyl]pyrrolidin-3-yl}-4-(trifluoromethyl)pyridin-2-amine;

(3R,4S)-4-(1,3-dioxan-2-yl)-N-[4-fluoro-3-(trifluoromethyl)phenyl]-1-[(1-methyl-1H-imidazol-4-yl)sulfonyl]pyrrolidin-3-amine;

1-[(1-methyl-1H-imidazol-4-yl)sulfonyl]-4-(piperidin-1-yl)-N-[3-(trifluoromethoxy)phenyl]pyrrolidin-3-amine;

(3R,4S)-N-(3-chlorophenyl)-4-(1,3-dioxan-2-yl)-1-[(1-methyl-1H-imidazol-4-yl)sulfonyl]pyrrolidin-3-amine;

(3R,4S)-4-(1,3-dioxan-2-yl)-1-[(1-methyl-1H-imidazol-4-yl)sulfonyl]-N-[3-(trifluoromethyl)phenyl]pyrrolidin-3-amine;

(3R,4S)-N-(3-chloro-4-fluorophenyl)-4-(1,3-dioxan-2-yl)-1-[(1-methyl-1H-imidazol-4-yl)sulfonyl]pyrrolidin-3-amine;

(3R,4S)-4-(1,3-dioxepan-2-yl)-1-[(1-methyl-1H-imidazol-4-yl)sulfonyl]-N-(3-methylphenyl)pyrrolidin-3-amine;

4-({3-(1,3-dioxan-2-yl)-4-[3-(trifluoromethyl)benzyl]pyrrolidin-1-yl}sulfonyl)-1-methyl-1H-imidazole;

4-({3-(1,3-dioxan-2-yl)-4-[3-(trifluoromethyl)benzyl]pyrrolidin-1-yl}sulfonyl)-1-methyl-1H-1,2,3-triazole;

(3R,4S)-4-(5,7-dioxaspiro[2.5]oct-6-yl)-1-[(1-methyl-1H-imidazol-4-yl)sulfonyl]-N-[3-(trifluoromethoxy)phenyl]pyrrolidin-3-amine;

(3R,4S)-4-[(4R,6R)-4,6-dimethyl-1,3-dioxan-2-yl]-1-[(1-methyl-1H-imidazol-4-yl)sulfonyl]-N-[3-(trifluoromethoxy)phenyl]pyrrolidin-3-amine;

(3R,4S)-4-[(4S,6S)-4,6-dimethyl-1,3-dioxan-2-yl]-1-[(1-methyl-1H-imidazol-4-yl)sulfonyl]-N-[3-(trifluoromethoxy)phenyl]pyrrolidin-3-amine;

(3R,4S)-4-(1,3-dioxan-2-yl)-N-(4-fluoro-3-methylphenyl)-1-[(1-methyl-1H-imidazol-4-yl)sulfonyl]pyrrolidin-3-amine;

(3R,4S)-4-(1,3-dioxan-2-yl)-N-[4-fluoro-3-(trifluoromethoxy)phenyl]-1-[(1-methyl-1H-imidazol-4-yl)sulfonyl]pyrrolidin-3-amine;

(3R,4S)-N-[3-(difluoromethoxy)phenyl]-4-(1,3-dioxan-2-yl)-1-[(1-methyl-1H-imidazol-4-yl)sulfonyl]pyrrolidin-3-amine;

(3R,4S)-4-(1,3-dioxan-2-yl)-1-[(1-methyl-1H-imidazol-4-yl)sulfonyl]-N-[3-(propan-2-yl)phenyl]pyrrolidin-3-amine;

4-(5-fluoropyridin-2-yl)-N-[4-fluoro-3-(trifluoromethyl)phenyl]-1-[(1-methyl-1H-imidazol-4-yl)sulfonyl]pyrrolidin-3-amine; or (3R,4S)-N-[3-(2,2-difluoroethoxy)phenyl]-4-(1,3-dioxan-2-yl)-1-[(1-methyl-1H-imidazol-4-yl)sulfonyl]pyrrolidin-3-amine;

or a physiologically tolerated salt thereof.

19. A pharmaceutical composition which comprises a carrier and a compound of the formula (I)

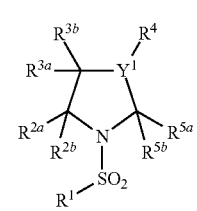

(I)

wherein $R^1$ is a 5-membered heterocyclic ring selected from the group consisting of pyrazolyl, imidazolyl and triaolyl, which is optionally substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxycarbonyl and $C_1$-$C_6$-alkylcarbonylamino;

$R^{2a}$, $R^{2b}$ are independently hydrogen, halogen, or $C_1$-$C_3$-alkyl, or $R^{2a}$, $R^{2b}$ together with the carbon atom to which they are bound may form a C=O;

$R^{3a}$ is $C_3$-$C_{12}$-cycloalkyl, optionally substituted $C_6$-$C_{12}$-aryl, hydroxy, $C_1$-$C_6$-alkoxy, halogenated $C_1$-$C_6$-alkoxy, $C_3$-$C_{12}$-cycloalkyl-$C_1$-$C_4$-alkoxy, $C_2$-$C_6$-alkenyloxy, $C_6$-$C_{12}$-aryl-$C_1$-$C_4$-alkoxy, $C_3$-$C_{12}$-heterocyclyl-$C_1$-$C_4$-alkoxy, optionally substituted $C_6$-$C_{12}$-aryloxy, $C_3$-$C_{12}$-heterocyclyloxy, or optionally substituted $C_3$-$C_{12}$-heterocyclyl;

$R^{3b}$ is hydrogen, $C_1$-$C_6$-alkyl, or hydroxyl; or $R^{3a}$ and $R^{3b}$ together are optionally substituted $C_2$-$C_5$-alkylene;

$Y^1$ is >CR$^6$— or >N—;

$R^6$ is hydrogen, $C_1$-$C_6$-alkyl, halogenated $C_1$-$C_6$-alkyl, (optionally substituted $C_6$-$C_{12}$-aryl)-$C_1$-$C_4$-alkyl, hydroxy-$C_1$-$C_6$-alkyl, $C_1$-$C_4$-alkoxy-$C_1$-$C_6$-alkyl, or hydroxyl; or $R^6$ and $R^{3a}$ or $R^{3b}$ together are optionally substituted $C_1$-$C_5$-alkylene; or $R^6$ is $C_1$-$C_4$-alkylene that is bound to a carbon atom in $R^{3a}$, and $R^{3a}$ is an optionally substituted $C_6$-$C_{12}$-aryl or an optionally substituted $C_3$-$C_{12}$-heterocyclyl;

$R^4$ is —(CR$^{7a}$R$^{7b}$)$_{n1}$OR$^{10}$, —(CR$^{7c}$R$^{7d}$)$_{n2}$NR$^{11a}$R$^{11b}$, —(CR$^{7e}$R$^{7f}$)$_{n3}$R$^{12}$, optionally substituted $C_6$-$C_{12}$-aryl, —NR$^{8a}$(CR$^{9a}$R$^{9b}$)$_{n4}$R$^{13}$, —NR$^{8b}$COR$^{14}$, —NR$^{8c}$COOR$^{15}$, —NR$^{8d}$CONR$^{16a}$R$^{16b}$, —$NR^{8e}SO_2R^{17}$, —$O(CR^{9c}R^{9d})_{n5}R^{18}$, —$COR^{19}$, —$CONR^{20a}R^{20b}$, —$SO_2R^{21}$, or optionally substituted $C_3$-$C_{12}$-heterocyclyl;

$R^{7a}$, $R^{7b}$
are independently hydrogen or $C_1$-$C_6$-alkyl;

n1 is 1, 2, 3, or 4;

$R^{10}$ is hydrogen, optionally substituted $C_6$-$C_{12}$-aryl, or optionally substituted $C_3$-$C_{12}$-heterocyclyl;

$R^{7c}$, $R^{7d}$
are independently hydrogen or $C_1$-$C_6$-alkyl;

n2 is 1, 2, 3, or 4;

$R^{11a}$ is $C_1$-$C_6$-alkyl, (optionally substituted $C_3$-$C_{12}$-cycloalkyl)-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{11b}$
is hydrogen or $C_2$-$C_6$-alkyl;

$R^{7e}$, $R^{7f}$
are independently hydrogen or $C_1$-$C_6$-alkyl;

n3 is 1, 2, 3, or 4;

$R^{12}$
is optionally substituted $C_6$-$C_{12}$-aryl or optionally substituted $C_3$-$C_{12}$-heterocyclyl;

$R^{8a}$, $R^{8b}$, $R^{8c}$, $R^{8d}$, $R^{8e}$
are independently hydrogen, $C_1$-$C_6$-alkyl, or $C_1$-$C_6$-alkylcarbonyl, or $R^6$ and one of $R^{8a}$, $R^{8b}$, $R^{8c}$, $R^{8d}$, or $R^{8e}$
together are optionally substituted $C_1$-$C_5$-alkylene, wherein one or more —$CH_2$— of $C_1$-$C_5$-alkylene may be independently replaced by a an oxygen atom or $C=O$; or $R^{3a}$ and one of $R^{8a}$ or $R^{8b}$
together are optionally substituted $C_1$-$C_5$-alkylene;

$R^{9a}$, $R^{9b}$
are independently hydrogen, halogen, $C_1$-$C_6$-alkyl, halogenated $C_1$-$C_6$-alkyl, hydroxyyl, or $C_1$-$C_6$-alkoxy;

n4 is 0, 1, 2, 3, or 4;

$R^{13}$ is $C_2$-$C_8$-alkyl, halogenated $C_1$-$C_6$-alkyl, (optionally substituted $C_3$-$C_{12}$-cycloalkyl)-$C_1$-$C_4$-alkyl, $C_1$-$C_6$-alkoxy-$C_1$-$C_6$-alkyl, optionally substituted $C_3$-$C_{12}$-cycloalkyl, $C_2$-$C_6$-alkenyl, optionally substituted $C_3$-$C_6$-cycloalkenyl, optionally substituted $C_6$-$C_{12}$-aryl, hydroxy, $C_1$-$C_6$-alkoxy, $C_1$-$C_6$-alkoxy-$C_1$-$C_4$-alkoxy, optionally substituted $C_6$-$C_{12}$-aryloxy, optionally substituted $C_3$-$C_{12}$-heterocyclyloxy, optionally substituted $C_3$-$C_{12}$-heterocyclyl, or tri-($C_1$-$C_4$-alkyl)-silyloxy;

$R^{14}$ is $C_2$-$C_6$-alkyl, halogenated $C_1$-$C_6$-alkyl, (optionally substituted $C_3$-$C_{12}$-cycloalkyl)-$C_1$-$C_4$-alkyl, (optionally substituted $C_6$-$C_{12}$-aryl)-$C_1$-$C_4$-alkyl, hydroxy-$C_1$-$C_6$-alkyl, $C_1$-$C_6$-alkoxy-$C_1$-$C_6$-alkyl, (optionally substituted $C_6$-$C_{12}$-aryloxy)-$C_1$-$C_4$-alkyl, $C_1$-$C_6$-alkylcarbonyl-$C_1$-$C_4$-alkyl, $C_1$-$C_6$-alkoxycarbonyl-$C_1$-$C_4$-alkyl, $C_1$-$C_6$-alkylaminocarbonyl-$C_1$-$C_4$-alkyl, optionally substituted ($C_3$-$C_{12}$-heterocyclyl)-$C_1$-$C_4$-alkyl, optionally substituted $C_3$-$C_{12}$-cycloalkyl, optionally substituted $C_6$-$C_{12}$-aryl, or optionally substituted $C_3$-$C_{12}$-heterocyclyl;

$R^{15}$ is $C_1$-$C_8$-alkyl, optionally substituted $C_6$-$C_{12}$-aryl, or optionally substituted $C_3$-$C_{12}$-heterocyclyl;

$R^{16a}$ is (optionally substituted $C_6$-$C_{12}$-aryl)-$C_1$-$C_4$-alkyl, optionally substituted ($C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{16b}$ is hydrogen or $C_1$-$C_6$-alkyl;

$R^{17}$ is (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{9c}$, $R^{9d}$
are independently hydrogen, halogen, or $C_1$-$C_6$-alkyl;

n5 is 0, 1, 2, 3, or 4;

$R^{18}$ is hydrogen, $C_1$-$C_8$-alkyl, optionally substituted $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, $C_1$-$C_6$-alkylaminocarbonyl, (halogenated $C_1$-$C_4$-alkyl)aminocarbonyl, $C_6$-$C_{12}$-arylaminocarbonyl, optionally substituted $C_6$-$C_{12}$-aryl, $C_1$-$C_6$-alkylamine, ($C_3$-$C_{12}$-cycloalkyl-$C_1$-$C_4$-alkyl)amino, (halogenated $C_1$-$C_6$-alkyl)amino, ($C_1$-$C_6$-alkoxy-$C_1$-$C_6$-alkyl)amino, ($C_6$-$C_{12}$-aryl-$C_1$-$C_4$-alkyl)amino, $C_1$-$C_6$-dialkylamine, optionally substituted $C_6$-$C_{12}$-arylamine, or optionally substituted $C_3$-$C_{12}$-heterocyclyl;

$R^{19}$ is optionally substituted $C_6$-$C_{12}$-aryl or optionally substituted $C_3$-$C_{12}$-heterocyclyl;

$R^{20a}$ is $C_1$-$C_8$-alkyl, (optionally substituted $C_3$-$C_{12}$-cycloalkyl)-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{20b}$ is hydrogen or $C_1$-$C_8$-alkyl;

$R^{21}$ is optionally substituted $C_6$-$C_{12}$-aryl, or optionally substituted $C_3$-$C_{12}$-heterocyclyl; and $R^{5a}$, $R^{5b}$
are independently hydrogen, halogen, or $C_1$-$C_3$-alkyl, or $R^{5a}$, $R^{5b}$
together with the carbon atom to which they are bound may form a $C=O$; or one of $R^{2a}$ or $R^{2b}$ and one of $R^{5a}$ or $R^{5b}$
together are optionally substituted $C_1$-$C_5$-alkylene;

or a physiologically tolerated salt thereof.

20. A method for treating a neurologic or psychiatric disorder or pain in a mammalian patient in need thereof which comprises administering to the patient a therapeutically effective amount of compound of the formula (I)

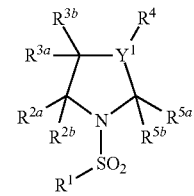

wherein $R^1$ is a 5-membered heterocyclic ring selected from the group consisting of pyrazolyl, imidazolyl and triazolyl, which is optionally substituted with 1, 2 or 3 substituents independently selected from the group consisting of halogen, $C_1$-$C_6$-alkyl, halogenated $C_1$-$C_6$-alkyl, $C_3$-$C_6$-cycloalkyl, $C_1$-$C_4$-alkoxycarbonyl and $C_1$-$C_6$-alkylcarbonylamino;

$R^{2a}$, $R^{2b}$
are independently hydrogen, halogen, or $C_1$-$C_3$-alkyl, or $R^{2a}$, $R^{2b}$
together with the carbon atom to which they are bound may form a $C=O$;

$R^{3a}$
is $C_3$-$C_{12}$-cycloalkyl, optionally substituted $C_6$-$C_{12}$-aryl, hydroxy, $C_1$-$C_6$-alkoxy, halogenated $C_1$-$C_6$-alkoxy, $C_3$-$C_{12}$-cycloalkyl-$C_1$-$C_4$-alkoxy, $C_2$-$C_6$-alkenyloxy, $C_6$-$C_{12}$-aryl-$C_1$-$C_4$-alkoxy, $C_3$-$C_{12}$-heterocyclyl-$C_1$-$C_4$-alkoxy, optionally substituted $C_6$-$C_{12}$-aryloxy, $C_3$-$C_{12}$-heterocyclyloxy, or optionally substituted $C_3$-$C_{12}$-heterocyclyl;

$R^{3b}$ is hydrogen, $C_1$-$C_6$-alkyl, or hydroxyl, or $R^{3a}$ and $R^{3b}$
together are optionally substituted $C_2$-$C_5$-alkylene;

$Y^1$ is >$CR^6$— or >N—;

$R^6$ is hydrogen, $C_1$-$C_6$-alkyl, halogenated $C_1$-$C_6$-alkyl, (optionally substituted $C_6$-$C_{12}$-aryl)-$C_1$-$C_4$-alkyl, hydroxy-$C_1$-$C_6$-alkyl, $C_1$-$C_4$-alkoxy-$C_1$-$C_6$-alkyl, or hydroxyl, or $R^6$ and $R^{3a}$ or $R^{3b}$
together are optionally substituted $C_1$-$C_5$-alkylene, or $R^6$
is $C_1$-$C_4$-alkylene that is bound to a carbon atom in $R^{3a}$, and $R^{3a}$ is an optionally substituted $C_6$-$C_{12}$-aryl or an optionally substituted $C_3$-$C_{12}$-heterocyclyl;

$R^4$ is —$(CR^{7a}R^{7b})_{n1}OR^{10}$, —$(CR^{7c}R^{7d})_{n2}NR^{11a}R^{11b}$, —$(CR^{7e}R^{7f})_{n3}R^{12}$, optionally substituted $C_6$-$C_{12}$-aryl, —$NR^{8a}(CR^{9a}R^{9b})_{n4}R^{13}$, —$NR^{8b}COR^{14}$, —$NR^{8c}COOR^{15}$, —$NR^{8d}CONR^{16a}R^{16b}$, —$NR^{8e}SO_2R^{17}$, —$O(CR^{9c}R^{9d})_{n5}R^{18}$, —$COR^{19}$, —$CONR^{20a}R^{20b}$, —$SO_2R^{21}$, or optionally substituted $C_3$-$C_{12}$-heterocyclyl;

$R^{7a}$, $R^{7b}$
are independently hydrogen or $C_1$-$C_6$-alkyl;

n1 is 1, 2, 3, or 4;

$R^{10}$ is hydrogen, optionally substituted $C_6$-$C_{12}$-aryl, or optionally substituted $C_3$-$C_{12}$-heterocyclyl;

$R^{7c}$, $R^{7d}$
are independently hydrogen or $C_1$-$C_6$-alkyl, n2 is 1, 2, 3, or 4;

$R^{11a}$ is $C_1$-$C_6$-alkyl, (optionally substituted $C_3$-$C_{12}$-cycloalkyl)-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{11b}$
is hydrogen or $C_2$-$C_6$-alkyl;

$R^{7e}$, $R^{7f}$
are independently hydrogen or $C_1$-$C_6$-alkyl;

n3 is 1, 2, 3, or 4;

$R^{12}$
is optionally substituted $C_6$-$C_{12}$-aryl or optionally substituted $C_3$-$C_{12}$-heterocyclyl;

$R^{8a}$, $R^{8b}$, $R^{8c}$, $R^{8d}$, $R^{8e}$
are independently hydrogen, $C_1$-$C_6$-alkyl, or $C_1$-$C_6$-alkylcarbonyl, or $R^6$ and one of $R^{8a}$, $R^{8b}$, $R^{8c}$, $R^{8d}$, or $R^{8e}$
together are optionally substituted $C_1$-$C_5$-alkylene, wherein one or more —$CH_2$— of $C_1$-$C_5$-alkylene may be independently replaced by a an oxygen atom or C=O, or $R^{3a}$ and one of $R^{8a}$ or $R^{8b}$
together are optionally substituted $C_1$-$C_5$-alkylene;

$R^{9a}$, $R^{9b}$
are independently hydrogen, halogen, $C_1$-$C_6$-alkyl, halogenated $C_1$-$C_6$-alkyl, hydroxyyl, or $C_1$-$C_6$-alkoxy;

n4 is 0, 1, 2, 3, or 4;

$R^{13}$ is hydrogen, $C_1$-$C_8$-alkyl, halogenated $C_1$-$C_6$-alkyl, (optionally substituted $C_3$-$C_{12}$-cycloalkyl)-$C_1$-$C_4$-alkyl, $C_1$-$C_6$-alkoxy-$C_1$-$C_6$-alkyl, optionally substituted $C_3$-$C_{12}$-cycloalkyl, $C_2$-$C_6$-alkenyl, optionally substituted $C_3$-$C_6$-cycloalkenyl, optionally substituted $C_6$-$C_{12}$-aryl, hydroxy, $C_1$-$C_6$-alkoxy, $C_1$-$C_6$-alkoxy-$C_1$-$C_4$-alkoxy, optionally substituted $C_6$-$C_{12}$-aryloxy, optionally substituted $C_3$-$C_{12}$-heterocyclyloxy, optionally substituted $C_3$-$C_{12}$-heterocyclyl, or tri-($C_1$-$C_4$-alkyl)-silyloxy;

$R^{14}$ is $C_2$-$C_6$-alkyl, halogenated $C_1$-$C_6$-alkyl, (optionally substituted $C_3$-$C_{12}$-cycloalkyl)-$C_1$-$C_4$-alkyl, (optionally substituted $C_6$-$C_{12}$-aryl)-$C_1$-$C_4$-alkyl, hydroxy-$C_1$-$C_6$-alkyl, $C_1$-$C_6$-alkoxy-$C_1$-$C_6$-alkyl, (optionally substituted $C_6$-$C_{12}$-aryloxy)-$C_1$-$C_4$-alkyl, $C_1$-$C_6$-alkylcarbonyl-$C_1$-$C_4$-alkyl, $C_1$-$C_6$-alkoxycarbonyl-$C_1$-$C_4$-alkyl, $C_1$-$C_6$-alkylaminocarbonyl-$C_1$-$C_4$-alkyl, optionally substituted ($C_3$-$C_{12}$-heterocyclyl)-$C_1$-$C_4$-alkyl, optionally substituted $C_3$-$C_{12}$-cycloalkyl, optionally substituted $C_6$-$C_{12}$-aryl, or optionally substituted $C_3$-$C_{12}$-heterocyclyl;

$R^{15}$ is $C_1$-$C_8$-alkyl, optionally substituted $C_6$-$C_{12}$-aryl, or optionally substituted $C_3$-$C_{12}$-heterocyclyl;

$R^{16a}$ is (optionally substituted $C_6$-$C_{12}$-aryl)-$C_1$-$C_4$-alkyl, optionally substituted ($C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{16b}$ is hydrogen or $C_1$-$C_6$-alkyl;

$R^{17}$ is (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{9c}$, $R^{9d}$
are independently hydrogen, halogen, or $C_1$-$C_6$-alkyl;

n5 is 0, 1, 2, 3, or 4;

$R^{18}$ is hydrogen, $C_1$-$C_8$-alkyl, optionally substituted $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, $C_1$-$C_6$-alkylaminocarbonyl, (halogenated $C_1$-$C_4$-alkyl)aminocarbonyl, $C_6$-$C_{12}$-arylaminocarbonyl, optionally substituted $C_6$-$C_{12}$-aryl, $C_1$-$C_6$-alkylamine, ($C_3$-$C_{12}$-cycloalkyl-$C_1$-$C_4$-alkyl)amino, (halogenated $C_1$-$C_6$-alkyl)amino, ($C_1$-$C_6$-alkoxy-$C_1$-$C_6$-alkyl)amino, ($C_6$-$C_{12}$-aryl-$C_1$-$C_4$-alkyl)amino, $C_1$-$C_6$-dialkylamine, optionally substituted $C_6$-$C_{12}$-arylamine, or optionally substituted $C_3$-$C_{12}$-heterocyclyl;

$R^{19}$ is optionally substituted $C_6$-$C_{12}$-aryl or optionally substituted $C_3$-$C_{12}$-heterocyclyl;

$R^{20a}$ is $C_1$-$C_8$-alkyl, (optionally substituted $C_3$-$C_{12}$-cycloalkyl)-$C_1$-$C_4$-alkyl, $C_1$-$C_6$-alkoxy-$C_1$-$C_6$-alkyl, (optionally substituted $C_6$-$C_{12}$-aryl)-$C_1$-$C_4$-alkyl, (optionally substituted $C_3$-$C_{12}$-heterocyclyl)-$C_1$-$C_4$-alkyl, optionally substituted $C_6$-$C_{12}$-aryl, or optionally substituted $C_3$-$C_{12}$-heterocyclyl;

$R^{20b}$ is hydrogen or $C_1$-$C_8$-alkyl;

$R^{21}$ is optionally substituted $C_6$-$C_{12}$-aryl, or optionally substituted $C_3$-$C_{12}$-heterocyclyl; and $R^{5a}$, $R^{5b}$
are independently hydrogen, halogen, or $C_1$-$C_3$-alkyl, or $R^{5a}$, $R^{5b}$
together with the carbon atom to which they are bound may form a C=O, or one of $R^{2a}$ or $R^{2b}$ and one of $R^{5a}$ or $R^{5b}$
together are optionally substituted $C_1$-$C_5$-alkylene;

or a physiologically tolerated salt thereof.

* * * * *